(12) United States Patent
Leach et al.

(10) Patent No.: US 8,562,528 B2
(45) Date of Patent: Oct. 22, 2013

(54) ANALYTE SENSOR

(75) Inventors: Jacob S. Leach, San Diego, CA (US);
Peter C. Simpson, Encinitas, CA (US);
Richard C. Yang, Carlsbad, CA (US);
Mark Brister, Encinitas, CA (US)

(73) Assignee: Dexcom, Inc., San Diego, CA (US)

( * ) Notice: Subject to any disclaimer, the term of this patent is extended or adjusted under 35 U.S.C. 154(b) by 1377 days.

(21) Appl. No.: 12/267,548

(22) Filed: Nov. 7, 2008

(65) Prior Publication Data

US 2009/0131769 A1 May 21, 2009

Related U.S. Application Data

(60) Continuation-in-part of application No. 12/055,114, filed on Mar. 25, 2008, now Pat. No. 8,364,231, and a continuation-in-part of application No. 12/055,149, filed on Mar. 25, 2008, now abandoned, and a continuation-in-part of application No. 12/055,203, filed on Mar. 25, 2008, now Pat. No. 8,425,416, and a continuation-in-part of application No. 12/055,227, filed on Mar. 25, 2008, now Pat. No. 8,364,230, which is a continuation-in-part of application No. 11/691,466, filed on Mar. 26, 2007, now Pat. No. 7,615,007, and a continuation-in-part of application No. 11/691,424, filed on Mar. 26, 2007, and a continuation-in-part of application No. 11/691,432, filed on Mar. 26, 2007, now Pat. No. 7,775,975, and a continuation-in-part of application No. 11/691,426, filed on Mar. 26, 2007, said application No. 12/055,203 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,149 is a continuation-in-part of application No. 11/691,466, and a continuation-in-part of application No. 11/691,424, and a continuation-in-part of application No. 11/691,432, and a continuation-in-part of application No. 11/691,426, said application No. 12/055,114 is a continuation-in-part of application No. 11/691,466, filed on Mar. 26, 2007, now Pat. No. 7,615,007, and a continuation-in-part of application No. 11/691,424, filed on Mar. 26, 2007, and a continuation-in-part of application No. 11/691,432, and a continuation-in-part of application No. 11/691,426, said application No. 11/691,466 is a continuation-in-part of application No. 11/543,396, filed on Oct. 4, 2006, and a continuation-in-part of application No. 11/543,490, filed on Oct. 4, 2006, and a continuation-in-part of application No. 11/543,404, filed on Oct. 4, 2006, now Pat. No. 8,532,730, said application No. 11/691,432 is a continuation-in-part of application No. 11/543,396, and a continuation-in-part of application No. 11/543,490, filed on Oct. 4, 2006, and a division of application No. 11/543,404, filed on Oct. 4, 2006, now Pat. No. 8,532,730, said application No. 11/691,426 is a continuation-in-part of application No. 11/543,396, and a continuation-in-part of application No. 11/543,490, and a continuation-in-part of application No. 11/543,404, said application No. 11/691,424 is a continuation-in-part of application No. 11/543,396, and a continuation-in-part of application No. 11/543,490, and a continuation-in-part of application No. 11/543,404.

(51) Int. Cl.
*A61B 5/00* (2006.01)

(52) U.S. Cl.
USPC ........... 600/309; 600/345; 600/347; 600/365; 600/348; 600/364

(58) Field of Classification Search
USPC .................................. 600/347, 365
See application file for complete search history.

(56) References Cited

U.S. PATENT DOCUMENTS 3,506,032 A     4/1970    Eveleigh et al.
3,556,950 A     1/1971    Dahms (Continued)

FOREIGN PATENT DOCUMENTS

| | | |
|---|---|---|
| EP | 0 098 592 | 1/1984 |
| EP | 0 127 958 | 12/1984 |

(Continued)

OTHER PUBLICATIONS

Abel et al. 2002. Biosensors for in vivo glucose measurement: can we cross the experimental stage. Biosens Bioelectron 17:1059-1070.

(Continued)

*Primary Examiner* — Michael Kahelin
*Assistant Examiner* — Karen Toth

(57) ABSTRACT

Systems and methods of use for continuous analyte measurement of a host's vascular system are provided. In some embodiments, a continuous glucose measurement system includes a vascular access device, a sensor and sensor electronics, the system being configured for insertion into communication with a host's circulatory system.

14 Claims, 56 Drawing Sheets

(56) References Cited

U.S. PATENT DOCUMENTS

| | | | |
|---|---|---|---|
| 3,610,226 A | 10/1971 | Albisser |
| 3,610,230 A | 10/1971 | Andersen |
| 3,837,339 A | 9/1974 | Aisenberg |
| 3,838,682 A | 10/1974 | Clark et al. |
| 3,874,850 A | 4/1975 | Sorensen et al. |
| 3,898,984 A | 8/1975 | Mandel et al. |
| 3,910,256 A | 10/1975 | Clark et al. |
| 3,933,593 A | 1/1976 | Sternberg |
| 3,943,918 A | 3/1976 | Lewis |
| 4,008,717 A | 2/1977 | Kowarski |
| 4,016,866 A | 4/1977 | Lawton |
| 4,030,640 A * | 6/1977 | Citrin et al. ............... 222/207 |
| 4,055,175 A | 10/1977 | Clemens et al. |
| 4,109,505 A | 8/1978 | Clark et al. |
| 4,119,406 A | 10/1978 | Clemens |
| 4,151,845 A | 5/1979 | Clemens |
| 4,176,659 A | 12/1979 | Rolfe |
| 4,197,852 A | 4/1980 | Schindler et al. |
| 4,206,755 A | 6/1980 | Klein |
| 4,240,438 A | 12/1980 | Updike et al. |
| 4,253,469 A | 3/1981 | Aslan |
| 4,265,249 A | 5/1981 | Schindler et al. |
| 4,300,572 A | 11/1981 | Knighton |
| 4,366,040 A | 12/1982 | Marsoner et al. |
| 4,369,785 A | 1/1983 | Rehkopf et al. |
| 4,403,984 A | 9/1983 | Ash et al. |
| 4,407,298 A | 10/1983 | Lentz et al. |
| 4,432,366 A | 2/1984 | Margules |
| 4,448,188 A | 5/1984 | Loeb |
| 4,457,339 A | 7/1984 | Juan et al. |
| 4,478,222 A | 10/1984 | Koning et al. |
| 4,486,290 A | 12/1984 | Cahalan et al. |
| 4,492,575 A | 1/1985 | Mabille |
| 4,494,950 A | 1/1985 | Fischell |
| 4,496,454 A | 1/1985 | Berger |
| 4,519,973 A | 5/1985 | Cahalan et al. |
| 4,526,569 A | 7/1985 | Bernardi |
| 4,534,825 A | 8/1985 | Koning et al. |
| 4,535,786 A | 8/1985 | Kater |
| 4,554,927 A | 11/1985 | Fussell |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,592,824 A | 6/1986 | Smith et al. |
| 4,600,495 A | 7/1986 | Fogt |
| 4,613,328 A | 9/1986 | Boyd |
| 4,614,514 A | 9/1986 | Carr et al. |
| 4,626,104 A | 12/1986 | Pointon et al. |
| 4,655,880 A | 4/1987 | Liu |
| 4,670,007 A | 6/1987 | Wheeldon et al. |
| 4,671,288 A | 6/1987 | Gough |
| 4,672,970 A | 6/1987 | Uchida et al. |
| 4,685,463 A | 8/1987 | Williams |
| 4,685,912 A * | 8/1987 | Jones ............................ 604/247 |
| 4,694,861 A | 9/1987 | Goodale et al. |
| 4,703,756 A | 11/1987 | Gough et al. |
| 4,705,503 A | 11/1987 | Dorman et al. |
| 4,731,726 A | 3/1988 | Allen |
| 4,736,748 A * | 4/1988 | Nakamura et al. ............ 600/352 |
| 4,747,822 A | 5/1988 | Peabody |
| 4,755,168 A | 7/1988 | Romanelli et al. |
| 4,757,022 A | 7/1988 | Shults et al. |
| 4,763,648 A | 8/1988 | Wyatt |
| 4,777,953 A | 10/1988 | Ash et al. |
| 4,784,157 A | 11/1988 | Halls et al. |
| 4,786,394 A | 11/1988 | Enzer et al. |
| 4,789,467 A | 12/1988 | Lindsay et al. |
| 4,791,932 A | 12/1988 | Margules |
| 4,800,495 A | 1/1989 | Smith |
| 4,805,625 A | 2/1989 | Wyler |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,813,423 A | 3/1989 | Miyasaka et al. |
| 4,815,471 A | 3/1989 | Stobie |
| 4,820,281 A | 4/1989 | Lawler |
| 4,822,336 A | 4/1989 | DiTraglia |
| 4,828,544 A | 5/1989 | Lane et al. |
| 4,830,013 A | 5/1989 | Maxwell |
| 4,832,005 A | 5/1989 | Takamiya et al. |
| 4,834,101 A | 5/1989 | Collison et al. |
| 4,838,281 A | 6/1989 | Rogers et al. |
| 4,841,974 A | 6/1989 | Gumbrecht et al. |
| 4,852,573 A | 8/1989 | Kennedy |
| 4,854,322 A | 8/1989 | Ash et al. |
| 4,867,741 A | 9/1989 | Portnoy |
| 4,874,363 A | 10/1989 | Abell |
| 4,883,467 A | 11/1989 | Franetzki et al. |
| 4,889,528 A | 12/1989 | Nadai et al. |
| 4,900,305 A | 2/1990 | Smith et al. |
| 4,907,857 A | 3/1990 | Giuliani et al. |
| 4,909,786 A | 3/1990 | Gijselhart et al. |
| 4,919,649 A | 4/1990 | Timothy et al. |
| 4,921,477 A | 5/1990 | Davis |
| 4,921,480 A | 5/1990 | Sealfon |
| 4,923,819 A | 5/1990 | Fernandez et al. |
| 4,925,444 A | 5/1990 | Orkin et al. |
| 4,928,694 A | 5/1990 | Maxwell |
| 4,934,369 A | 6/1990 | Maxwell |
| 4,934,375 A | 6/1990 | Cole et al. |
| 4,946,439 A | 8/1990 | Eggers |
| 4,951,669 A | 8/1990 | Maxwell et al. |
| 4,953,552 A | 9/1990 | DeMarzo |
| 4,957,483 A | 9/1990 | Gonser et al. |
| 4,963,131 A | 10/1990 | Wortrich |
| 4,966,579 A | 10/1990 | Polaschegg |
| 4,967,940 A | 11/1990 | Blette |
| 4,974,592 A | 12/1990 | Branco |
| 4,976,687 A | 12/1990 | Martin |
| 4,979,509 A | 12/1990 | Hakky |
| 4,994,026 A | 2/1991 | Fecondini |
| 4,997,627 A | 3/1991 | Bergkuist et al. |
| 5,000,419 A * | 3/1991 | Palmer et al. ..................... 251/9 |
| 5,002,055 A | 3/1991 | Merki et al. |
| 5,006,050 A | 4/1991 | Cooke et al. |
| 5,006,111 A | 4/1991 | Inokuchi et al. |
| 5,009,251 A | 4/1991 | Pike et al. |
| 5,026,348 A | 6/1991 | Venegas |
| 5,030,199 A | 7/1991 | Barwick et al. |
| 5,034,112 A | 7/1991 | Murase et al. |
| 5,041,092 A | 8/1991 | Barwick |
| 5,045,057 A | 9/1991 | Van et al. |
| 5,046,496 A | 9/1991 | Betts et al. |
| 5,048,525 A | 9/1991 | Maxwell |
| 5,050,612 A | 9/1991 | Matsumura |
| 5,055,198 A | 10/1991 | Shettigar |
| 5,088,981 A | 2/1992 | Howson et al. |
| 5,089,421 A | 2/1992 | Dieffenbach |
| 5,096,669 A | 3/1992 | Lauks et al. |
| 5,098,377 A | 3/1992 | Borsanyi et al. |
| 5,109,850 A | 5/1992 | Blanco et al. |
| 5,112,301 A | 5/1992 | Fenton et al. |
| 5,116,313 A | 5/1992 | Mcgregor |
| 5,137,028 A | 8/1992 | Nishimura |
| 5,145,565 A | 9/1992 | Kater et al. |
| 5,152,746 A | 10/1992 | Atkinson et al. |
| 5,161,532 A | 11/1992 | Joseph |
| 5,165,406 A | 11/1992 | Wong et al. |
| 5,165,407 A | 11/1992 | Wilson et al. |
| 5,174,291 A | 12/1992 | Schoonen et al. |
| 5,176,632 A | 1/1993 | Bernardi |
| 5,176,658 A | 1/1993 | Ranford |
| 5,178,142 A | 1/1993 | Harjunmaa et al. |
| 5,182,004 A | 1/1993 | Kohno |
| 5,188,591 A | 2/1993 | Dorsey |
| 5,195,963 A | 3/1993 | Yafuso et al. |
| 5,220,917 A | 6/1993 | Cammilli et al. |
| 5,220,920 A | 6/1993 | Gharib |
| 5,224,929 A | 7/1993 | Remiszewski |
| 5,225,063 A | 7/1993 | Gumbrecht et al. |
| 5,232,434 A | 8/1993 | Inagaki et al. |

(56) References Cited

U.S. PATENT DOCUMENTS

| | | |
|---|---|---|
| 5,243,982 A | 9/1993 | Mostl et al. |
| 5,254,102 A | 10/1993 | Ogawa |
| 5,264,104 A | 11/1993 | Gregg et al. |
| 5,265,594 A | 11/1993 | Olsson et al. |
| 5,269,891 A | 12/1993 | Colin |
| 5,271,815 A | 12/1993 | Wong et al. |
| 5,275,169 A | 1/1994 | Afromowitz et al. |
| 5,279,294 A | 1/1994 | Anderson et al. |
| 5,284,570 A | 2/1994 | Savage et al. |
| 5,298,022 A | 3/1994 | Bernardi |
| 5,299,571 A | 4/1994 | Mastrototaro |
| 5,302,093 A | 4/1994 | Owens et al. |
| 5,307,263 A | 4/1994 | Brown |
| 5,310,469 A | 5/1994 | Cunningham et al. |
| 5,311,908 A | 5/1994 | Barone et al. |
| 5,315,993 A | 5/1994 | Alcala |
| 5,316,008 A | 5/1994 | Suga et al. |
| 5,316,452 A | 5/1994 | Bogen et al. |
| 5,318,511 A | 6/1994 | Riquier et al. |
| 5,326,449 A | 7/1994 | Cunningham |
| 5,330,634 A | 7/1994 | Wong et al. |
| 5,331,555 A | 7/1994 | Hashimoto et al. |
| 5,335,658 A | 8/1994 | Bedingham |
| 5,337,747 A | 8/1994 | Neftel |
| 5,342,789 A | 8/1994 | Chick et al. |
| 5,345,932 A | 9/1994 | Yafuso et al. |
| 5,352,348 A | 10/1994 | Young et al. |
| 5,354,272 A | 10/1994 | Swendson et al. |
| 5,356,375 A | 10/1994 | Higley |
| 5,356,378 A | 10/1994 | Doan |
| 5,368,562 A | 11/1994 | Blomquist et al. |
| 5,372,135 A | 12/1994 | Mendelson et al. |
| 5,372,709 A | 12/1994 | Hood |
| 5,378,229 A | 1/1995 | Layer et al. |
| 5,380,268 A | 1/1995 | Wheeler |
| 5,380,491 A | 1/1995 | Carver et al. |
| 5,380,665 A | 1/1995 | Cusack et al. |
| 5,390,671 A | 2/1995 | Lord et al. |
| 5,409,666 A | 4/1995 | Nagel et al. |
| 5,411,052 A | 5/1995 | Murray |
| 5,411,551 A | 5/1995 | Winston et al. |
| 5,417,206 A | 5/1995 | Kaneyoshi |
| 5,421,328 A | 6/1995 | Bedingham |
| 5,423,738 A | 6/1995 | Robinson et al. |
| 5,423,749 A | 6/1995 | Merte et al. |
| 5,425,375 A | 6/1995 | Chin et al. |
| 5,429,485 A | 7/1995 | Dodge |
| 5,429,602 A | 7/1995 | Hauser |
| 5,431,174 A | 7/1995 | Knute |
| 5,437,635 A | 8/1995 | Fields et al. |
| 5,445,610 A | 8/1995 | Evert |
| 5,462,051 A | 10/1995 | Oka et al. |
| 5,482,446 A | 1/1996 | Williamson et al. |
| 5,484,404 A | 1/1996 | Schulman et al. |
| 5,494,562 A | 2/1996 | Maley et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,509,888 A | 4/1996 | Miller |
| 5,512,046 A | 4/1996 | Pusinelli et al. |
| 5,512,248 A | 4/1996 | Van |
| 5,513,636 A | 5/1996 | Palti |
| 5,514,253 A | 5/1996 | Davis et al. |
| 5,515,851 A | 5/1996 | Goldstein |
| 5,531,679 A | 7/1996 | Schulman et al. |
| 5,531,878 A | 7/1996 | Vadgama et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |
| 5,551,850 A | 9/1996 | Williamson et al. |
| 5,554,339 A | 9/1996 | Cozzette |
| 5,562,614 A | 10/1996 | O'Donnell |
| 5,562,615 A | 10/1996 | Nassif |
| 5,568,806 A | 10/1996 | Cheney, II et al. |
| 5,569,186 A | 10/1996 | Lord et al. |
| 5,569,188 A | 10/1996 | Mackool |
| 5,569,219 A | 10/1996 | Hakki et al. |
| 5,577,499 A | 11/1996 | Teves |
| 5,582,184 A | 12/1996 | Ericson et al. |
| 5,582,593 A | 12/1996 | Hultman |
| 5,586,553 A | 12/1996 | Halili et al. |
| 5,609,572 A | 3/1997 | Lang |
| 5,624,409 A | 4/1997 | Seale |
| 5,626,563 A | 5/1997 | Dodge et al. |
| 5,628,619 A | 5/1997 | Wilson |
| 5,628,890 A | 5/1997 | Carter et al. |
| 5,637,083 A | 6/1997 | Bertrand et al. |
| 5,640,470 A | 6/1997 | Iyer et al. |
| 5,643,195 A | 7/1997 | Drevet et al. |
| 5,651,767 A | 7/1997 | Schulman et al. |
| 5,658,250 A | 8/1997 | Blomquist et al. |
| 5,660,163 A | 8/1997 | Schulman et al. |
| 5,665,061 A | 9/1997 | Antwiler |
| 5,665,065 A | 9/1997 | Colman et al. |
| 5,667,504 A | 9/1997 | Baumann et al. |
| 5,676,651 A | 10/1997 | Larson et al. |
| 5,688,239 A | 11/1997 | Walker |
| 5,688,244 A | 11/1997 | Lang |
| 5,695,623 A | 12/1997 | Michel et al. |
| 5,697,366 A | 12/1997 | Kimball et al. |
| 5,697,899 A | 12/1997 | Hillman et al. |
| 5,704,354 A | 1/1998 | Preidel et al. |
| 5,743,262 A | 4/1998 | Lepper, Jr. et al. |
| 5,749,832 A | 5/1998 | Vadgama et al. |
| 5,755,692 A | 5/1998 | Manicom |
| 5,758,643 A | 6/1998 | Wong et al. |
| 5,763,760 A | 6/1998 | Gumbrecht et al. |
| 5,779,665 A | 7/1998 | Mastrototaro et al. |
| 5,791,344 A | 8/1998 | Schulman et al. |
| 5,791,880 A | 8/1998 | Wilson |
| 5,800,383 A | 9/1998 | Chandler et al. |
| 5,800,420 A | 9/1998 | Gross |
| 5,804,048 A | 9/1998 | Wong et al. |
| 5,806,517 A | 9/1998 | Gerhardt et al. |
| 5,807,274 A | 9/1998 | Henning et al. |
| 5,807,312 A | 9/1998 | Dzwonkiewicz |
| 5,807,375 A | 9/1998 | Gross et al. |
| 5,810,770 A | 9/1998 | Chin et al. |
| 5,820,589 A | 10/1998 | Torgerson et al. |
| 5,837,454 A | 11/1998 | Cozzette et al. |
| 5,840,026 A | 11/1998 | Uber et al. |
| 5,873,862 A | 2/1999 | Lopez |
| 5,897,525 A | 4/1999 | Dey et al. |
| 5,904,666 A | 5/1999 | Dedecker et al. |
| 5,911,219 A | 6/1999 | Aylsworth et al. |
| 5,921,951 A | 7/1999 | Morris |
| 5,928,155 A | 7/1999 | Eggers et al. |
| 5,928,182 A | 7/1999 | Kraus et al. |
| 5,928,189 A | 7/1999 | Phillips et al. |
| 5,928,195 A | 7/1999 | Malamud et al. |
| 5,931,814 A | 8/1999 | Alex et al. |
| 5,932,175 A | 8/1999 | Knute et al. |
| 5,938,636 A | 8/1999 | Kramer et al. |
| 5,947,911 A * | 9/1999 | Wong et al. .................. 600/573 |
| 5,957,854 A | 9/1999 | Besson et al. |
| 5,961,451 A | 10/1999 | Reber et al. |
| 5,964,993 A | 10/1999 | Blubaugh et al. |
| 5,976,085 A | 11/1999 | Kimball et al. |
| 5,995,208 A | 11/1999 | Sarge et al. |
| 6,014,577 A | 1/2000 | Henning et al. |
| 6,024,720 A | 2/2000 | Chandler et al. |
| 6,027,445 A | 2/2000 | Von Bahr |
| 6,027,479 A | 2/2000 | Alei et al. |
| 6,032,059 A | 2/2000 | Henning et al. |
| 6,032,667 A | 3/2000 | Heinonen |
| 6,059,946 A | 5/2000 | Yukawa et al. |
| 6,064,900 A | 5/2000 | Vadgama et al. |
| 6,066,088 A | 5/2000 | Davis |
| 6,071,391 A | 6/2000 | Gotoh et al. |
| 6,077,299 A | 6/2000 | Adelberg et al. |
| 6,080,583 A | 6/2000 | Von Bahr |
| 6,081,736 A | 6/2000 | Colvin et al. |

(56) References Cited

U.S. PATENT DOCUMENTS

| | | | |
|---|---|---|---|
| 6,088,608 A | 7/2000 | Schulman et al. | |
| 6,090,087 A | 7/2000 | Tsukada et al. | |
| 6,091,975 A | 7/2000 | Daddona et al. | |
| 6,093,172 A | 7/2000 | Funderburk et al. | |
| 6,099,511 A | 8/2000 | Devos et al. | |
| 6,117,290 A * | 9/2000 | Say et al. | 600/352 |
| 6,122,536 A | 9/2000 | Sun et al. | |
| 6,123,827 A | 9/2000 | Wong et al. | |
| 6,128,519 A * | 10/2000 | Say | 600/345 |
| 6,134,461 A | 10/2000 | Say et al. | |
| 6,159,186 A | 12/2000 | Wickham et al. | |
| 6,162,201 A | 12/2000 | Cohen et al. | |
| 6,164,921 A | 12/2000 | Moubayed et al. | |
| 6,165,154 A | 12/2000 | Gray et al. | |
| 6,171,276 B1 | 1/2001 | Lippe et al. | |
| 6,175,752 B1 | 1/2001 | Say et al. | |
| 6,183,437 B1 | 2/2001 | Walker | |
| 6,191,860 B1 | 2/2001 | Klinger et al. | |
| 6,213,739 B1 | 4/2001 | Phallen et al. | |
| 6,233,471 B1 | 5/2001 | Berner et al. | |
| 6,248,067 B1 | 6/2001 | Causey, III et al. | |
| 6,248,077 B1 | 6/2001 | Elson et al. | |
| 6,248,093 B1 | 6/2001 | Moberg | |
| 6,254,586 B1 | 7/2001 | Mann et al. | |
| 6,263,222 B1 | 7/2001 | Diab et al. | |
| 6,270,478 B1 | 8/2001 | Mern et al. | |
| 6,275,717 B1 | 8/2001 | Gross et al. | |
| 6,280,408 B1 | 8/2001 | Sipin | |
| 6,299,583 B1 | 10/2001 | Eggers et al. | |
| 6,309,375 B1 * | 10/2001 | Glines et al. | 604/187 |
| 6,329,161 B1 | 12/2001 | Heller et al. | |
| 6,358,225 B1 | 3/2002 | Butterfield | |
| 6,391,019 B1 | 5/2002 | Ito | |
| 6,402,703 B1 | 6/2002 | Kensey et al. | |
| 6,403,944 B1 | 6/2002 | Mackenzie et al. | |
| 6,424,847 B1 | 7/2002 | Mastrototaro et al. | |
| 6,430,437 B1 | 8/2002 | Marro | |
| 6,461,496 B1 | 10/2002 | Feldman et al. | |
| 6,464,849 B1 | 10/2002 | Say et al. | |
| 6,467,480 B1 | 10/2002 | Meier et al. | |
| 6,474,360 B1 | 11/2002 | Ito | |
| 6,484,045 B1 | 11/2002 | Holker et al. | |
| 6,485,449 B2 | 11/2002 | Ito | |
| 6,488,652 B1 | 12/2002 | Weijand et al. | |
| 6,494,879 B2 | 12/2002 | Lennox et al. | |
| 6,498,941 B1 | 12/2002 | Jackson | |
| 6,501,976 B1 | 12/2002 | Sohrab | |
| 6,514,718 B2 | 2/2003 | Heller et al. | |
| 6,517,508 B1 | 2/2003 | Utterberg et al. | |
| 6,520,477 B2 | 2/2003 | Trimmer | |
| 6,520,937 B2 | 2/2003 | Hart et al. | |
| 6,536,433 B1 | 3/2003 | Cewers | |
| 6,544,212 B2 | 4/2003 | Galley et al. | |
| 6,551,494 B1 | 4/2003 | Heller et al. | |
| 6,554,805 B2 | 4/2003 | Hiejima | |
| 6,554,822 B1 | 4/2003 | Holschneider et al. | |
| 6,558,347 B1 | 5/2003 | Jhuboo et al. | |
| 6,558,351 B1 | 5/2003 | Steil et al. | |
| 6,560,471 B1 | 5/2003 | Heller et al. | |
| 6,565,509 B1 | 5/2003 | Say et al. | |
| 6,565,535 B2 | 5/2003 | Zaias et al. | |
| 6,565,807 B1 | 5/2003 | Patterson et al. | |
| 6,572,579 B1 | 6/2003 | Raghavan et al. | |
| 6,579,257 B1 | 6/2003 | Elgas et al. | |
| 6,585,675 B1 | 7/2003 | O'Mahony et al. | |
| 6,589,229 B1 | 7/2003 | Connelly et al. | |
| 6,594,514 B2 | 7/2003 | Berner et al. | |
| 6,595,756 B2 | 7/2003 | Gray et al. | |
| 6,595,919 B2 | 7/2003 | Berner et al. | |
| 6,600,940 B1 | 7/2003 | Fein et al. | |
| 6,602,221 B1 | 8/2003 | Saravia et al. | |
| 6,609,071 B2 | 8/2003 | Shapiro et al. | |
| 6,613,379 B2 | 9/2003 | Ward et al. | |
| 6,615,061 B1 | 9/2003 | Khalil et al. | |
| 6,618,603 B2 | 9/2003 | Varalli et al. | |
| 6,656,157 B1 | 12/2003 | Duchon et al. | |
| 6,679,865 B2 | 1/2004 | Shekalim | |
| 6,679,872 B2 | 1/2004 | Turovskiy et al. | |
| 6,684,904 B2 | 2/2004 | Ito | |
| 6,685,668 B1 | 2/2004 | Cho et al. | |
| 6,689,089 B1 | 2/2004 | Tiedtke et al. | |
| 6,689,265 B2 | 2/2004 | Heller et al. | |
| 6,695,860 B1 | 2/2004 | Ward et al. | |
| 6,702,249 B2 | 3/2004 | Ito | |
| 6,711,424 B1 | 3/2004 | Fine et al. | |
| 6,712,796 B2 | 3/2004 | Fentis et al. | |
| 6,723,086 B2 | 4/2004 | Bassuk et al. | |
| 6,736,783 B2 | 5/2004 | Blake et al. | |
| 6,749,587 B2 | 6/2004 | Flaherty | |
| 6,770,030 B1 | 8/2004 | Schaupp et al. | |
| 6,770,067 B2 | 8/2004 | Lorenzen et al. | |
| 6,780,297 B2 | 8/2004 | Matsumoto et al. | |
| 6,801,041 B2 | 10/2004 | Karinka et al. | |
| 6,802,957 B2 | 10/2004 | Jung et al. | |
| 6,804,002 B2 | 10/2004 | Fine et al. | |
| 6,805,693 B2 | 10/2004 | Gray et al. | |
| 6,811,548 B2 | 11/2004 | Jeffrey | |
| 6,850,790 B2 | 2/2005 | Berner et al. | |
| 6,858,020 B2 | 2/2005 | Rusnak | |
| 6,862,465 B2 | 3/2005 | Shults et al. | |
| 6,887,228 B2 | 5/2005 | Mckay | |
| 6,895,263 B2 | 5/2005 | Shin et al. | |
| 6,895,265 B2 | 5/2005 | Silver | |
| 6,902,544 B2 | 6/2005 | Ludin et al. | |
| 6,926,691 B2 | 8/2005 | Miethke | |
| 6,931,327 B2 | 8/2005 | Goode et al. | |
| 6,932,584 B2 | 8/2005 | Gray et al. | |
| 6,936,006 B2 | 8/2005 | Sabra | |
| 6,945,965 B2 | 9/2005 | Whiting | |
| 6,948,492 B2 | 9/2005 | Wermeling et al. | |
| 6,954,662 B2 | 10/2005 | Freger et al. | |
| 6,960,192 B1 | 11/2005 | Flaherty et al. | |
| 6,965,791 B1 | 11/2005 | Hitchcock et al. | |
| 6,966,325 B2 | 11/2005 | Erickson | |
| 6,975,893 B2 | 12/2005 | Say et al. | |
| 6,979,315 B2 | 12/2005 | Rogers et al. | |
| 6,989,891 B2 | 1/2006 | Braig et al. | |
| 6,997,921 B2 | 2/2006 | Gray et al. | |
| 7,022,219 B2 | 4/2006 | Mansouri et al. | |
| 7,025,727 B2 | 4/2006 | Brockway et al. | |
| 7,048,727 B1 | 5/2006 | Moss | |
| 7,061,593 B2 | 6/2006 | Braig et al. | |
| 7,063,086 B2 | 6/2006 | Shahbazpour et al. | |
| 7,066,884 B2 | 6/2006 | Custer et al. | |
| 7,070,577 B1 | 7/2006 | Haller et al. | |
| 7,097,775 B2 | 8/2006 | Greenberg et al. | |
| 7,098,803 B2 | 8/2006 | Mann et al. | |
| 7,100,628 B1 | 9/2006 | Izenson et al. | |
| 7,120,483 B2 | 10/2006 | Russell et al. | |
| 7,131,967 B2 | 11/2006 | Gray et al. | |
| 7,136,689 B2 | 11/2006 | Shults et al. | |
| 7,146,202 B2 | 12/2006 | Ward et al. | |
| 7,150,741 B2 | 12/2006 | Erickson et al. | |
| 7,162,290 B1 | 1/2007 | Levin | |
| 7,168,597 B1 | 1/2007 | Jones et al. | |
| 7,184,810 B2 | 2/2007 | Caduff et al. | |
| 7,207,968 B1 | 4/2007 | Harcinske | |
| 7,211,074 B2 | 5/2007 | Sansoucy | |
| 7,221,970 B2 | 5/2007 | Parker | |
| 7,223,253 B2 | 5/2007 | Hogendijk | |
| 7,228,162 B2 | 6/2007 | Ward et al. | |
| 7,238,165 B2 | 7/2007 | Vincent et al. | |
| 7,247,138 B2 | 7/2007 | Reghabi et al. | |
| 7,254,450 B2 | 8/2007 | Christopherson et al. | |
| 7,255,690 B2 | 8/2007 | Gray et al. | |
| 7,258,681 B2 | 8/2007 | Houde | |
| 7,266,400 B2 | 9/2007 | Fine et al. | |
| 7,276,029 B2 | 10/2007 | Goode et al. | |
| 7,288,085 B2 | 10/2007 | Olsen | |
| 7,311,690 B2 | 12/2007 | Burnett | |
| 7,313,425 B2 | 12/2007 | Finarov et al. | |
| 7,314,452 B2 | 1/2008 | Madonia | |
| 7,315,767 B2 | 1/2008 | Caduff et al. | |
| 7,316,662 B2 | 1/2008 | Delnevo et al. | |

(56) References Cited

U.S. PATENT DOCUMENTS

| | | | |
|---|---|---|---|
| 7,317,939 B2 | 1/2008 | Fine et al. | |
| 7,318,814 B2 | 1/2008 | Levine et al. | |
| 7,327,273 B2 | 2/2008 | Hung et al. | |
| 7,329,234 B2 | 2/2008 | Sansoucy | |
| 7,334,594 B2 | 2/2008 | Ludin | |
| 7,335,179 B2 | 2/2008 | Burnett | |
| 7,335,195 B2 | 2/2008 | Mehier | |
| 7,338,464 B2 | 3/2008 | Blischak et al. | |
| 7,354,420 B2 | 4/2008 | Steil et al. | |
| 7,361,155 B2 | 4/2008 | Sage et al. | |
| 7,364,562 B2 | 4/2008 | Braig et al. | |
| 7,367,942 B2 | 5/2008 | Grage et al. | |
| 7,396,353 B2 | 7/2008 | Lorenzen et al. | |
| 7,615,007 B2 | 11/2009 | Shults et al. | |
| 7,775,975 B2 | 8/2010 | Brister et al. | |
| 2001/0021817 A1 | 9/2001 | Brugger et al. | |
| 2001/0039053 A1 | 11/2001 | Liseo et al. | |
| 2001/0041831 A1 | 11/2001 | Starkweather et al. | |
| 2002/0065454 A1 | 5/2002 | Lebel et al. | |
| 2002/0071776 A1 | 6/2002 | Bandis et al. | |
| 2002/0161288 A1 | 10/2002 | Shin et al. | |
| 2003/0028089 A1 | 2/2003 | Galley et al. | |
| 2003/0034305 A1* | 2/2003 | Luehmann et al. | 210/646 |
| 2003/0130616 A1 | 7/2003 | Steil et al. | |
| 2003/0143746 A1 | 7/2003 | Sage | |
| 2003/0153821 A1 | 8/2003 | Berner | |
| 2003/0235817 A1 | 12/2003 | Bartkowiak et al. | |
| 2004/0054352 A1 | 3/2004 | Adames et al. | |
| 2004/0078219 A1 | 4/2004 | Kaylor | |
| 2004/0152187 A1 | 8/2004 | Haight et al. | |
| 2004/0193025 A1 | 9/2004 | Steil et al. | |
| 2004/0204687 A1 | 10/2004 | Morgensen | |
| 2005/0027182 A1 | 2/2005 | Siddiqui et al. | |
| 2005/0054905 A1 | 3/2005 | Corl et al. | |
| 2005/0065464 A1 | 3/2005 | Talbot et al. | |
| 2005/0131305 A1 | 6/2005 | Danielson et al. | |
| 2005/0154271 A1 | 7/2005 | Rasdal et al. | |
| 2005/0183954 A1 | 8/2005 | Hitchcock et al. | |
| 2005/0197612 A1 | 9/2005 | Levin et al. | |
| 2005/0288596 A1 | 12/2005 | Eigler et al. | |
| 2006/0015024 A1 | 1/2006 | Brister et al. | |
| 2006/0052745 A1 | 3/2006 | Van Antwerp et al. | |
| 2006/0079809 A1 | 4/2006 | Goldberger et al. | |
| 2006/0094946 A1 | 5/2006 | Kellogg et al. | |
| 2006/0178617 A1 | 8/2006 | Adams et al. | |
| 2006/0183984 A1 | 8/2006 | Dobbles et al. | |
| 2006/0183985 A1 | 8/2006 | Brister et al. | |
| 2006/0189863 A1 | 8/2006 | Peyser et al. | |
| 2006/0189925 A1 | 8/2006 | Gable et al. | |
| 2006/0224141 A1 | 10/2006 | Rush et al. | |
| 2006/0229533 A1 | 10/2006 | Hoenes et al. | |
| 2006/0253085 A1 | 11/2006 | Geismar et al. | |
| 2006/0263839 A1 | 11/2006 | Ward et al. | |
| 2006/0272652 A1 | 12/2006 | Stocker et al. | |
| 2006/0293576 A1 | 12/2006 | Van Antwerp et al. | |
| 2007/0085995 A1 | 4/2007 | Pesach et al. | |
| 2007/0116600 A1 | 5/2007 | Kochar et al. | |
| 2007/0129619 A1 | 6/2007 | Ward et al. | |
| 2007/0129621 A1 | 6/2007 | Kellogg et al. | |
| 2007/0135699 A1 | 6/2007 | Ward et al. | |
| 2007/0142584 A1 | 6/2007 | Schorzman et al. | |
| 2007/0151869 A1 | 7/2007 | Heller et al. | |
| 2007/0173706 A1 | 7/2007 | Neinast et al. | |
| 2007/0179436 A1 | 8/2007 | Braig et al. | |
| 2007/0197889 A1 | 8/2007 | Brister et al. | |
| 2007/0203407 A1 | 8/2007 | Hoss et al. | |
| 2007/0206193 A1 | 9/2007 | Pesach | |
| 2007/0218097 A1 | 9/2007 | Heller et al. | |
| 2007/0219441 A1 | 9/2007 | Carlin | |
| 2007/0225675 A1 | 9/2007 | Robinson et al. | |
| 2007/0240497 A1 | 10/2007 | Robinson et al. | |
| 2007/0244381 A1 | 10/2007 | Robinson et al. | |
| 2007/0244382 A1 | 10/2007 | Robinson et al. | |
| 2007/0249916 A1 | 10/2007 | Pesach et al. | |
| 2008/0029390 A1 | 2/2008 | Roche | |
| 2008/0029391 A1 | 2/2008 | Mao et al. | |
| 2008/0039702 A1 | 2/2008 | Hayter et al. | |
| 2008/0071157 A1 | 3/2008 | Mcgarraugh et al. | |
| 2008/0071158 A1 | 3/2008 | Mcgarraugh et al. | |
| 2008/0072663 A1 | 3/2008 | Keenan et al. | |
| 2008/0086040 A1 | 4/2008 | Heller et al. | |
| 2008/0086041 A1 | 4/2008 | Heller et al. | |
| 2008/0086042 A1 | 4/2008 | Brister et al. | |
| 2008/0086043 A1 | 4/2008 | Heller et al. | |
| 2008/0086044 A1 | 4/2008 | Brister et al. | |
| 2008/0086273 A1 | 4/2008 | Shults et al. | |
| 2008/0091094 A1 | 4/2008 | Heller et al. | |
| 2008/0091095 A1 | 4/2008 | Heller et al. | |
| 2008/0097197 A1 | 4/2008 | Kalafut et al. | |
| 2008/0108942 A1 | 5/2008 | Brister et al. | |
| 2008/0119703 A1 | 5/2008 | Brister et al. | |
| 2008/0119704 A1 | 5/2008 | Brister et al. | |
| 2008/0119706 A1 | 5/2008 | Brister et al. | |
| 2008/0125751 A1 | 5/2008 | Fjield | |
| 2008/0197024 A1 | 8/2008 | Simpson et al. | |
| 2008/0200788 A1 | 8/2008 | Brister et al. | |
| 2008/0200789 A1 | 8/2008 | Brister et al. | |
| 2008/0200791 A1 | 8/2008 | Simpson et al. | |
| 2009/0018424 A1 | 1/2009 | Kamath et al. | |
| 2009/0124964 A1 | 5/2009 | Leach et al. | |
| 2009/0131768 A1 | 5/2009 | Simpson et al. | |
| 2009/0131776 A1 | 5/2009 | Simpson et al. | |
| 2009/0131777 A1 | 5/2009 | Simpson et al. | |
| 2009/0137886 A1 | 5/2009 | Shariati et al. | |
| 2009/0137887 A1 | 5/2009 | Shariati et al. | |
| 2009/0143659 A1 | 6/2009 | Li et al. | |
| 2009/0204340 A1 | 8/2009 | Feldman et al. | |
| 2009/0287074 A1 | 11/2009 | Shults et al. | |
| 2010/0023270 A1 | 1/2010 | Heller et al. | |
| 2010/0081910 A1 | 4/2010 | Brister et al. | |
| 2010/0298684 A1 | 11/2010 | Leach et al. | |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 441 394 | 8/1991 |
| EP | 1 266 607 | 12/2002 |
| GB | 2149918 | 6/1985 |
| WO | WO 89/02720 | 4/1989 |
| WO | WO 91/16416 | 10/1991 |
| WO | WO 93/14693 | 8/1993 |
| WO | WO 93/23744 | 11/1993 |
| WO | WO 96/14026 | 5/1996 |
| WO | WO 96/25089 | 8/1996 |
| WO | WO 97/01986 | 1/1997 |
| WO | WO 97/06727 | 2/1997 |
| WO | WO 99/56613 | 4/1999 |
| WO | WO 00/59373 | 10/2000 |
| WO | WO 00/74753 | 12/2000 |
| WO | WO 01/58348 A2 | 8/2001 |
| WO | WO 2005/026689 | 10/2005 |
| WO | WO 2007/002209 | 1/2007 |
| WO | WO 2007/097754 | 8/2007 |
| WO | WO 2007/137286 | 11/2007 |
| WO | WO 2008/001091 | 1/2008 |

OTHER PUBLICATIONS

Alcock & Turner. 1994. Continuous Analyte Monitoring to Aid Clinical Practice. IEEE Engineering in Med. & Biol. Mag. 13:319-325.

Aussedat et al. 1997. A user-friendly method for calibrating a subcutaneous glucose sensor-based hypoglycaemic alarm. Biosensors & Bioelectronics 12(11):1061-1071.

Freedman et al. 1991. Statistics, Second Edition, W.W. Norton & Company, p. 74.

Hamilton Syringe Selection Guide. 2006. Syringe Selection. www.hamiltoncompany.com.

Hoel, Paul G. 1976. Elementary Statistics, Fourth Edition. John Wiley & Sons, Inc.. pp. 113-114.

Jablecki et al. 2000. Simulations of the frequency response of implantable glucose sensors. Analytical Chemistry 72:1853-1859.

(56) References Cited

OTHER PUBLICATIONS

Jaffari et al. 1995. Recent advances in amperometric glucose biosensors for in vivo monitoring, Physiol. Meas. 16: 1-15.
Kerner et al. 1988. A potentially implantable enzyme electrode for amperometric measurement of glucose, Horm Metab Res Suppl. 20:8-13.
Kost et al. 1985. Glucose-sensitive membranes containing glucose oxidase: activity, swelling, and permeability studies, Journal of Biomedical Materials Research 19:1117-1133.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Marena et al. 1993. The artificial endocrine pancreas in clinical practice and research. Panminerva Medica 35(2): 67-74.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al. Jun. 1994. Reduction of acetaminophen interference in glucose sensors by a composite Nafion membrane: demonstration in rats and man, Diabetologia 37(6):610-616.
Mosbach et al. 1975. Determination of heat changes in the proximity of immobilized enzymes with an enzyme thermistor and its use for the assay of metabolites, Biochim. Biophys. Acta. 403:256-265.
Motonaka et al. 1993. Determination of cholesterol and cholesterol ester with novel enzyme microsensors, Anal. Chem. 65:3258-3261.
Muslu. 1991. Trickling filter performance. Applied Biochem. Biotech. 37:211-224.
Pickup et al. 1993. Developing glucose sensors for in vivo use. Elsevier Science Publishers Ltd (UK), TIBTECH vol. 11: 285-291.
Rabah et al., 1991. Electrochemical wear of graphite anodes during electrolysis of brine, Carbon, 29(2):165-171.
Rebrin et al. 1992. Subcutaneous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diab. Thechnol. & Therapeut., 10(3):194-199.
Samuels, M.P. 2004. The effects of flight and altitude. Arch Dis Child. 89: 448-455.
Schmidtke et al. Jan. 1998. Measurement and modeling of the transient difference between blood and subcutaneous glucose concentrations in the rat after injection of insulin. *Proc Natl Acad Sci U S A*, 95:294-299.
Shichiri et al. 1985. Needle-type Glucose Sensor for Wearable Artificial Endocrine Pancreas in Implantable Sensors 197-210.
Takegami et al. 1992. Pervaporation of ethanol water mixtures using novel hydrophobic membranes containing polydimethylsiloxane, Journal of Membrane Science, 75: 93-105.
Tierney et al. 2000. Effect of acetaminophen on the accuracy of glucose measurements obtained with the GlucoWatch biographer. Diabetes Technol Ther 2(2):199-207.
Thome et al. 1995. Abstract: Can the decrease in subcutaneous glucose concentration precede the decrease in blood glucose level? Proposition for a push-pull kinetics hypothesis, Horm. Metab. Res. 27:53.
Updike et al. 2000. A subcutaneous glucose sensor with improved longevity, dynamic range, and stability of calibration. Diabetes Care 23(2):208-214.
Vadgama. 1988. Diffusion limited enzyme electrodes. NATO ASI Series: Series C, Math and Phys. Sci. 226:359-377.
Ward et al. 2000. Understanding Spontaneous Output Fluctuations of an Amperometric Glucose Sensor: Effect of Inhalation Anesthesia and use of a Nonenzyme Containing Electrode. ASAIO Journal 540-546.
Ward et al. 2004. A wire-based dual-analyte sensor for Glucose and Lactate: in Vitro and in Vivo Evaluation, Diab Tech Therapeut. 6(3): 389-401.
Wiley Electrical and Electronics Engineering Dictionary. 2004. John Wiley & Sons, Inc. pp. 141, 142, 548, 549.
Wilkins et al. 1995. Integrated implantable device for long-term glucose monitoring. Biosens. Bioelectron 10:485-494.
Ye et al. 1993. High Current Density 'Wired' Quinoprotein Glucose Dehydrogenase Electrode. Anal. Chem. 65:238-241.
Zhang et al. 1993. In vitro and in vivo evaluation of oxygen effects on a glucose oxidase based implantable glucose sensor. Analytica Chimica Acta, 281:513-520.
Zhu et al. 2002 Planar amperometric glucose sensor based on glucose oxidase immobilized by chitosan film on prussian blue layer. Sensors, 2:127-136.
Ziaie et al. 1997. A single-channel implantable microstimulator for functional neuromuscular stimulation. IEEE Transactions on Biomedical Engineering 44(10):909-920.
IPRP dated Sep. 28, 2010 for PCT/US2008/082870, filed Nov. 7, 2008.
IPRP dated Sep. 28, 2010 for PCT/US2008/082905, filed Nov. 7, 2008.
EPO Communication dated Aug. 18, 011 for Application No. 07843011.3, filed Apr. 10, 2008.
EFS File History for U.S. Appl. No. 11/543,396, filed Oct. 4, 2006 containing Office Actions dated Dec. 8, 2010, Mar. 3, 2011 and Aug. 2, 2011 and Applicant Responses filed Dec. 13, 2010, Jun. 3, 2011 and Sep. 23, 2011 as of Oct. 6, 2011.
EFS File History for U.S. Appl. No. 11/543,490, filed Oct. 4, 2006 containing Office Actions dated Jan. 3, 2011, Mar. 11, 2011 and Oct. 12, 2011 and Applicant Responses filed Feb. 3, 2011 and Jul. 11, 2011 as of Oct. 14, 2011.
EFS File History for U.S. Appl. No. 11/543,404, filed Oct. 4, 2006 containing Office Actions dated Jun. 29, 2011 and Aug. 19, 2011 and Applicant Response(s) filed Jul. 29, 1922 as of Oct. 17, 2011.
EFS File History for U.S. Appl. No. 11/691,432, filed Mar. 26, 2007 (now USP 7,775,975, issued Aug. 17, 2010) containing Office Action(s) dated Jul. 28, 2008, Sep. 19, 2008, Mar. 4, 2009, Jun. 10, 2009, Nov. 30, 2009, Feb. 18, 2010, Apr. 2, 2010 and Jun. 16, 2010 and Applicant Response(s) filed Aug. 12, 2008, Nov. 26, 2008, Mar. 12, 2009, Jul. 22, 2009 and Jan. 29, 2010, Feb. 26, 2010 and Apr. 9, 2010.
EFS File History for U.S. Appl. No. 11/691,424, filed Mar. 26, 2007 containing Office Action(s) dated Sep. 25, 2008, Feb. 18, 2009, Jun. 11, 2009, Nov. 12, 2009 and Dec. 8, 2009 and Applicant Response(s) filed Nov. 24, 2008, Feb. 18, 2009, Mar. 4, 2009, Jul. 9, 2009, Nov. 19, 2009 and Feb. 8, 2010 as of Oct. 17, 2011.
EFS File History for U.S. Appl. No. 11/691,466, filed Mar. 26, 2007 (USP 7,615,007, issued Nov. 10, 2009) containing Office Action(s) dated Oct. 3, 2008, Apr. 17, 2009 and Jul. 17, 2009 and Applicant Response(s) filed Dc. 3, 2008 and Jun. 17, 2009.
EFS File History for U.S. Appl. No. 12/055,149, filed Mar. 25, 2008 containing Office Action(s) dated Jun. 13, 2011 and Applicant Response(s) filed Oct. 13, 2011 as of Oct. 17, 2011.
EFS File History for U.S. Appl. No. 12/055,227, filed Mar. 25, 2008 containing Office Action(s) dated Sep. 9, 2011 and Applicant Response(s) filed Oct. 11, 2011 as of Oct. 17, 2011.
EFS File History for U.S. Appl. No. 12/267,547, filed Nov. 7, 2008 containing Office Action(s) dated Sep. 13, 2011 as of Oct. 17, 2011.
EFS File History for U.S. Appl. No. 12/267,546, filed Nov. 7, 2008 containing Office Action(s) dated Sep. 12, 2011 as of Oct. 17, 2011.
EFS File History for U.S. Appl. No. 12/267,545, filed Nov. 7, 2008 containing Office Action(s) dated Sep. 7, 2011 as of Oct. 17, 2011.
Armour et al. Dec. 1990. Application of Chronic Intravascular Blood Glucose Sensor in Dogs. Diabetes 39:1519-1526.
Bode, B. W. 2000. Clinical utility of the continuous glucose monitoring system. Diabetes Technol Ther, 2(Suppl 1):S35-41.
Chia et al. 2004. Glucose sensors: toward closed loop insulin delivery. Endocrinol Metab Clin North Am 33:175-95.

(56) References Cited

OTHER PUBLICATIONS

Edwards Lifesciences. Accuracy for your and your patients. Marketing materials, 4 pp. 2002.

Frost et al. 2002. Implantable chemical sensors for real-time clinical monitoring: Progress and challenges. Current Opinion in Chemical Biology 6:633-641.

Kiechle, F.L. 2001. The impact of continuous glucose monitoring on hospital point-of-care testing programs. Diabetes Technol Ther 3:647-649.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

Rivers et al., Central venous oxygen saturation monitoring in the critically ill patient, Current Opinion in Critical Care, 7:204-211, 2001.

Shichiri et al. 1983. Glycaemic Control in Pancreatectomized Dogs with a Wearable Artificial Endocrine Pancreas. Diabetologia 24:179-184.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Skyler, J. S. 2000. The economic burden of diabetes and the benefits of improved glycemic control: The potential role of a continuous glucose monitoring system. Diabetes Technology & Therapeutics 2 Suppl 1:S7-12.

Thompson et al., In Vivo Probes: Problems and Perspectives, Department of Chemistry, University of Toronto, Canada, pp. 255-261, 1986.

Turner, A.P.F. 1988. Amperometric biosensor based on mediator-modified electrodes. Methods in Enzymology 137:90-103.

Unger et al. 2004. Glucose control in the hospitalized patient. Emerg Med 36(9):12-18.

Updike et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Utah Medical Products Inc., Blood Pressure Tranducers product specifications. 6 pp. 2003-2006, 2003.

Van den Berghe 2004. Tight blood glucose control with insulin in "real-life" intensive care. Mayo Clin Proc 79(8):977-978.

Velho et al. 1989. Strategies for calibrating a subcutaneous glucose sensor. Biomed Biochim Acta 48(11/12):957-964, 1989.

"Intravenous therapy," http://en.wikipedia.org/wiki/Intravenous_therapy, Aug. 15, 2006, 6 pp.

Zamzow et al. Development and evaluation of a wearable blood glucose monitor. pp. M588-M591, 1990.

Office Action dated Sep. 19, 2008 in U.S. Appl. No. 11/691,432.

Office Action dated Sep. 25, 2008 in U.S. Appl. No. 11/691,424.

Office Action dated Oct. 3, 2008 in U.S. Appl. No. 11/691,466.

Invitation to Pay Additional Fees for PCT/US07/079220, filed Sep. 21, 2007.

ISR and WO for PCT/US07/079220, filed Sep. 21, 2007.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1991. Design and In Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Brooks et al. "Development of an on-line glucose sensor for fermentation monitoring," Biosensors, 3:45-56 (1987/88).

Cass et al. "Ferrocene-mediated enzyme electrodes for amperometric determination of glucose," Anal. Chem., 36:667-71 (1984).

Davies, et al. 1992. Polymer membranes in clinical sensor applications. I. An overview of membrane function, Biomaterials, 13(14):971-978.

Fahy et al., An analysis: hyperglycemic intensive care patients need continuous glocuse monitoring—easier said than done, Journal of Diabetese Science and Technology, 2(2):201-204, Mar. 2008.

Ganesh et al., Evaluation of the VIA® blood chemistry monitor for glucose in healthy and diabetic volunteers, Journal of Diabetese Science and Technology, 2(2):182-193, Mar. 2008.

Heller, "Electrical wiring of redox enzymes," *Acc. Chem. Res.*, 23:128-134 (1990).

Heller, A. 1992. Electrical Connection of Enzyme Redox Centers to Electrodes. J. Phys. Chem. 96:3579-3587.

Hicks, 1985. In Situ Monitoring, Clinical Chemistry, 31(12):1931-1935.

Hu, et al. 1993. A needle-type enzyme-based lactate sensor for in vivo monitoring, Analytica Chimica Acta, 281:503-511.

Johnson (1991). "Reproducible electrodeposition of biomolecules for the fabrication of miniature electroenzymatic biosensors," *Sensors and Actuators B*, 5:85-89.

Johnson et al. 1992. In vivo evaluation of an electroenzymatic glucose sensor implanted in subcutaneous tissue. Biosensors & Bioelectronics, 7:709-714.

Kawagoe et al. 1991. Enzyme-modified organic conducting salt microelectrode, Anal. Chem. 63:2961-2965.

Kunjan et al., Automated blood sampling and glocuse sensing in critical care settings, Journal of Diabetes Science and Technology 2(3):194-200, Mar. 2008.

Maidan et al. 1992. Elimination of Electrooxidizable Interferent-Produced Currents in Amperometric Biosensors, Analytical Chemistry, 64:2889-2896.

Mastrototaro et al. "An electroenzymatic glucose sensor fabricated on a flexible substrate," Sensors and Actuators B, 5:139-44 (1991).

McKean, et al. Jul. 7, 1988. A Telemetry Instrumentation System for Chronically Implanted Glucose and Oxygen Sensors. Transactions on Biomedical Engineering 35:526-532.

Moatti-Sirat et al. 1992. Towards continuous glucose monitoring: in vivo evaluation of a miniaturized glucose sensor implanted for several days in rat subcutaneous tissue. Diabetologia 35:224-230.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Pickup et al. "Implantable glucose sensors: choosing the appropriate sensing strategy," Biosensors, 3:335-346 (1987/88).

Pickup et al. "In vivo, molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Poitout, et al. 1991. In Vitro and in Vivo Evaluation in Dogs of a Miniaturized Glucose Sensor, ASAIO Transactions, 37:M298-M300.

Reach et al. 1992. Can continuous glucose monitoring be used for the treatment of diabetes? Analytical Chemistry 64(5):381-386.

Rebrin et al. "Automated feedback control of subcutaneous glucose concentration in diabetic dogs," Diabetologia, 32:573-76 (1989).

Sakakida et al. 1993. Ferrocene-Mediated Needle Type Glucose Sensor Covered with Newly Designed Biocompatible Membran, Sensors and Actuators B 13-14:319-322.

Shaw et al. "In vitro testing of a simply constructed, highly stable glucose sensor suitable for implantation in diabetic patients," Biosensors & Bioelectronics, 6:401-406 (1991).

Shichiri et al. 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sternberg et al. 1988. Study and Development of Multilayer Needle-type Enzyme-based Glucose Microsensors. Biosensors 4:27-40.

(56) References Cited

OTHER PUBLICATIONS

Torjman et al., Glucose monitoring in acute care: technologies on the horizon, Journal of Deabetes Science and Technology, 2(2):178-181, Mar. 2008.
von Woedtke et al. 1989. In situ calibration of implanted electrochemical glucose sensors. Biomed Biochim. Acta 48(11/12):943-952.
Wilson et al. 1992. Progress toward the development of an implantable sensor for glucose. Clin. Chem. 38(9):1613-1617.
Worsley et al., Measurement of glucose in blood with a phenylboronic acid optical sensor, Journal of Diabetes Science and Technology, 2(2):213-220, Mar. 2008.
Yang et al (1996). "A glucose biosensor based on an oxygen electrode: In-vitro performances in a model buffer solution and in blood plasma," Biomedical Instrumentation & Technology, 30:55-61.
IPRP for PCT/US07/079220, filed Sep. 21, 2007.
ISR and WO for PCT/US08/082905, filed Nov. 7, 2008.
ISR and WO for PCT/US08/82870, filed Nov. 7, 2008.
Office Action dated Mar. 31, 2008 in U.S. Appl. No. 11/077,759.
Office Action dated Jul. 10, 2008 in U.S. Appl. No. 11/077,759.
Office Action dated Aug. 11, 2008 in U.S. Appl. No. 11/360,819.
Office Action dated Dec. 26, 2008 in U.S. Appl. No. 11/360,819.
Office Action dated May 26, 2009 in U.S. Appl. No. 11/077,759.
Office Action dated Jun. 10, 2009 in U.S. Appl. No. 11/691,432.
Office Action dated Jun. 11, 2009 in U.S. Appl. No. 11/691,424.
European Response submitted Feb. 27, 2012 for Application No. 07843011.3, filed Sep. 21, 2007.
Leonhardt et al., The Potential use of silicon compounds as oxygen carriers for free and immobilized cells containing L-amino acid oxidase, Appl Microbiol Biotechnol. (1985) 21: 162-166.

* cited by examiner

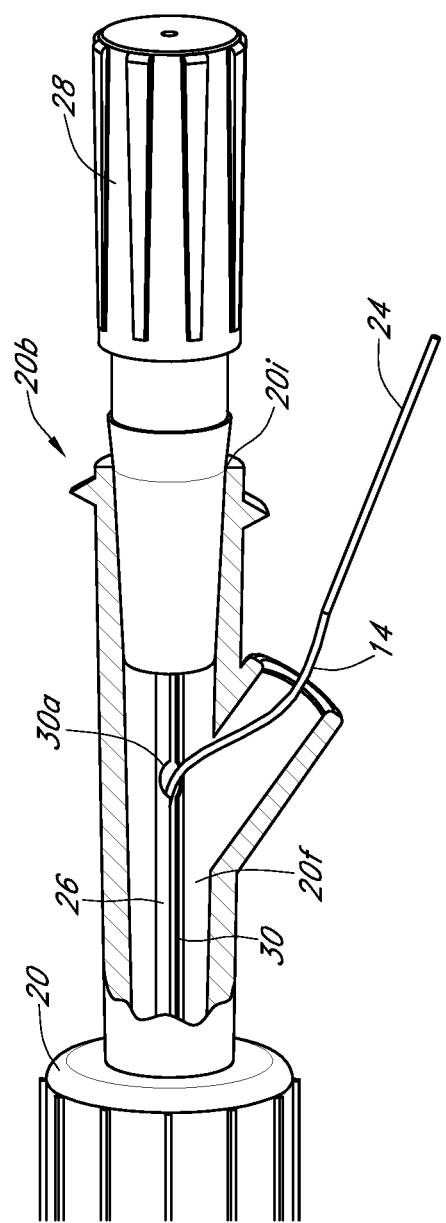
FIG. 1C₁

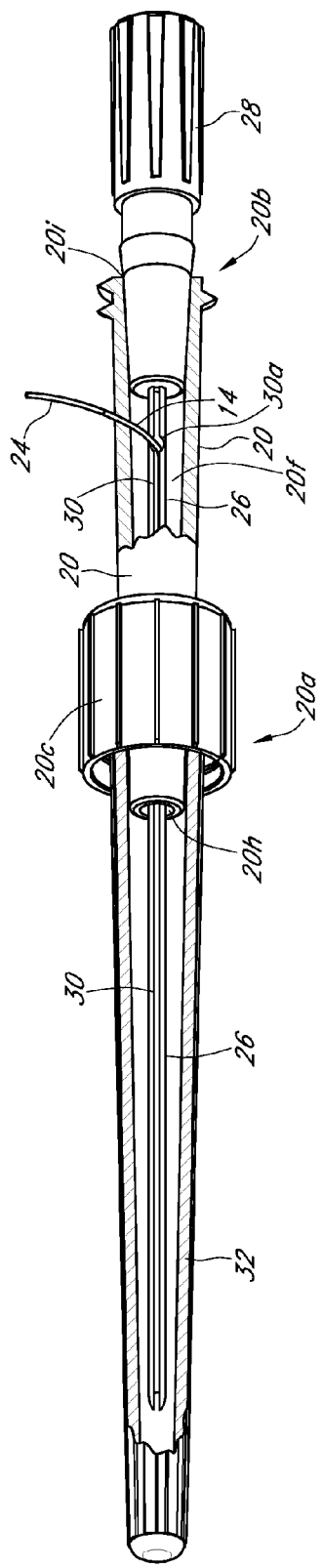
FIG. 1C₂

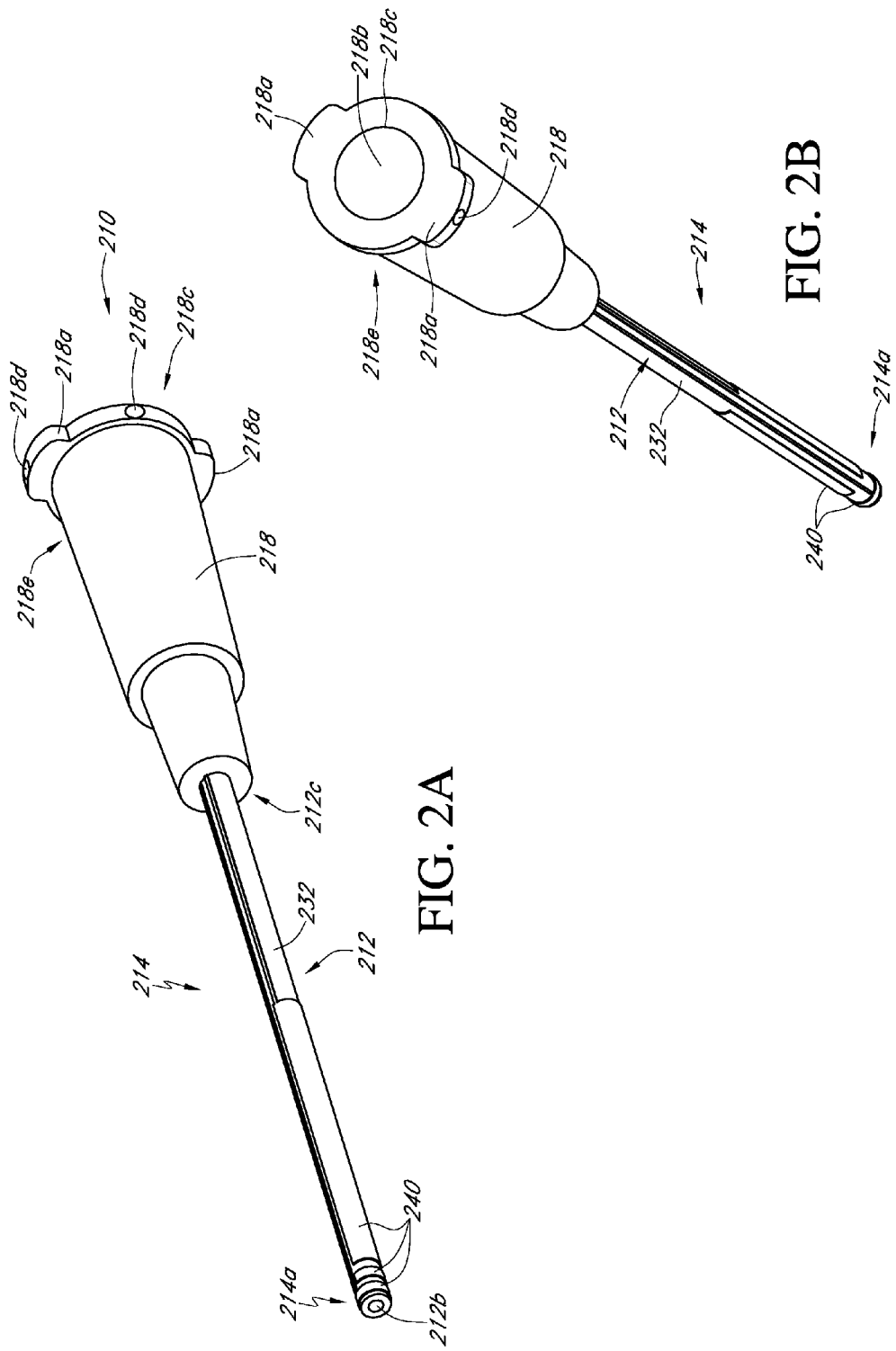

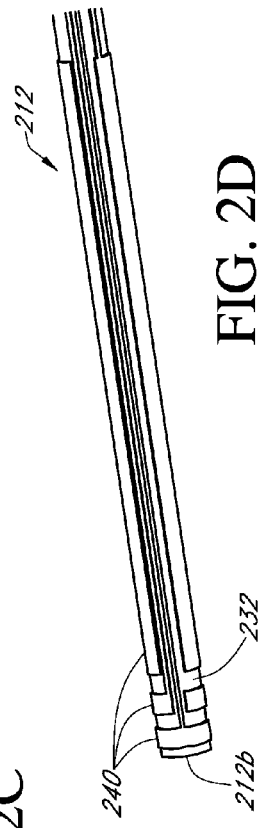
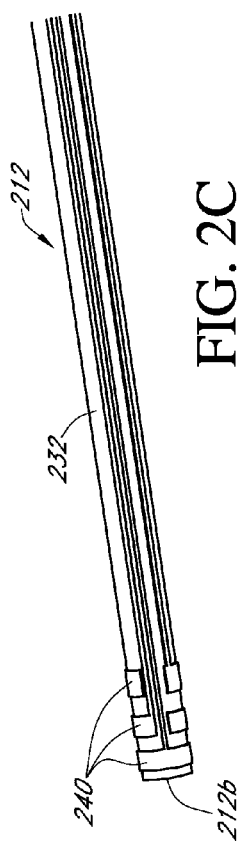
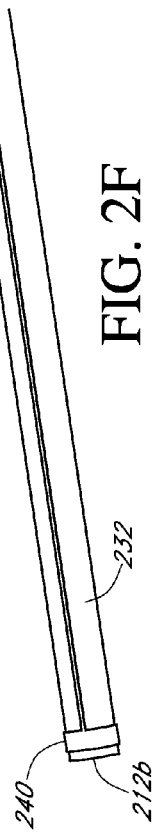
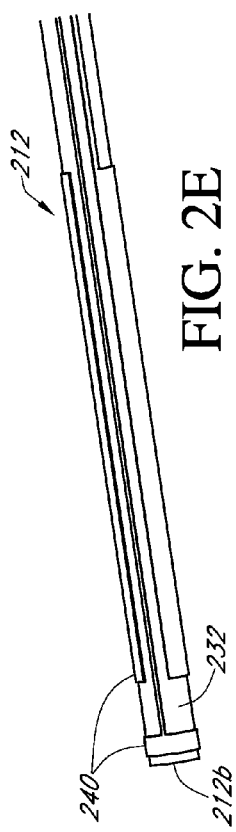

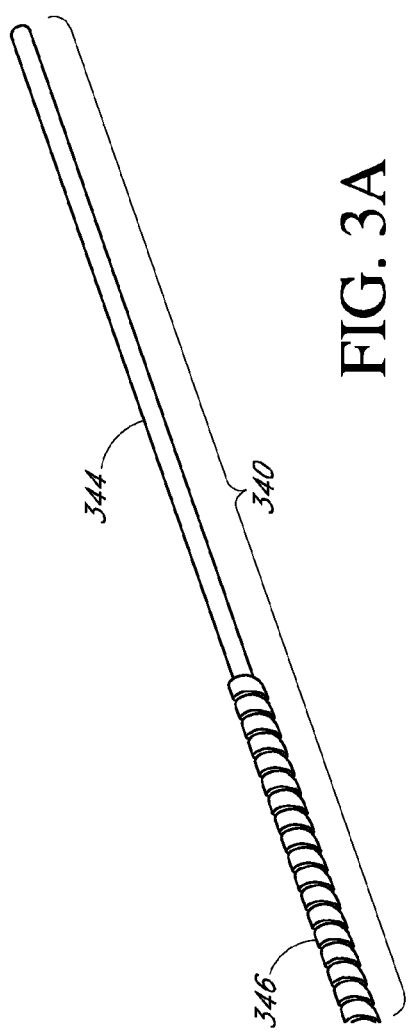
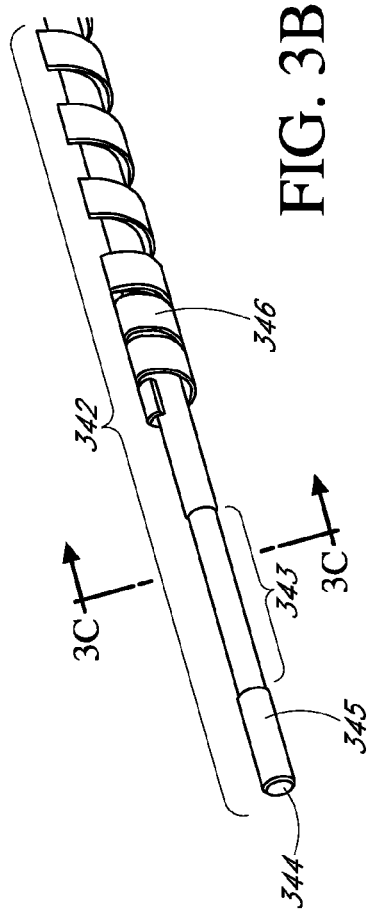
FIG. 3A
FIG. 3B

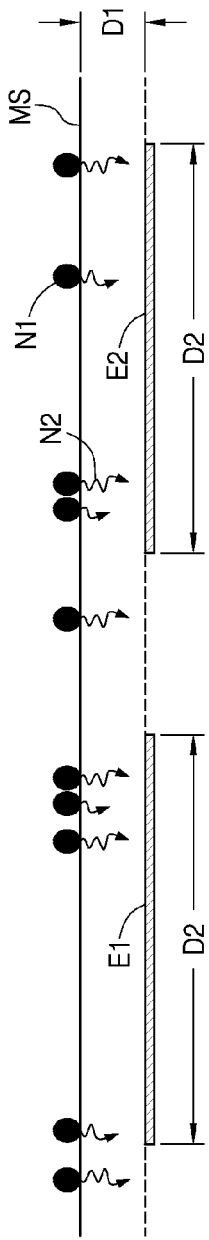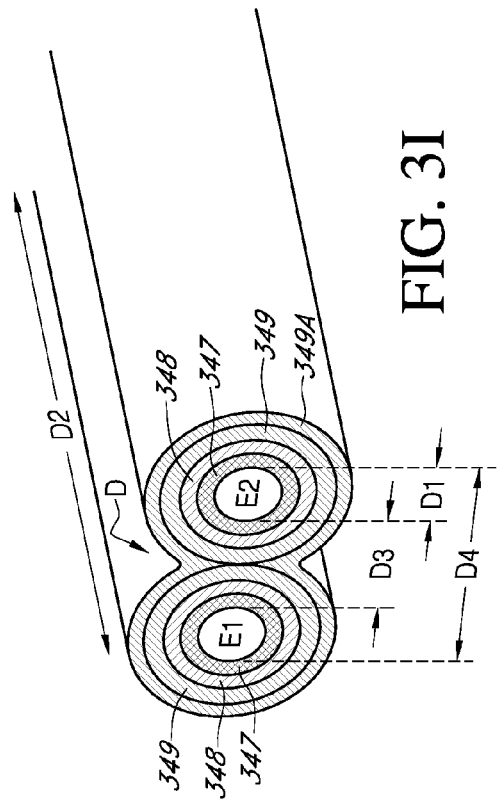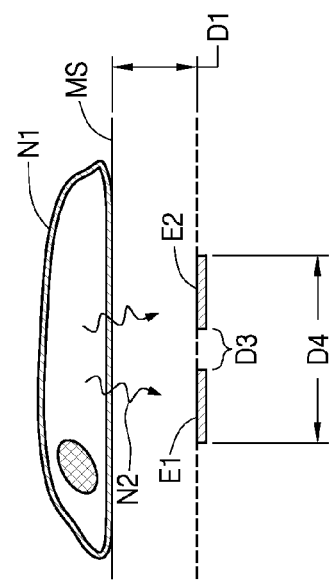
FIG. 3G
FIG. 3I
FIG. 3H

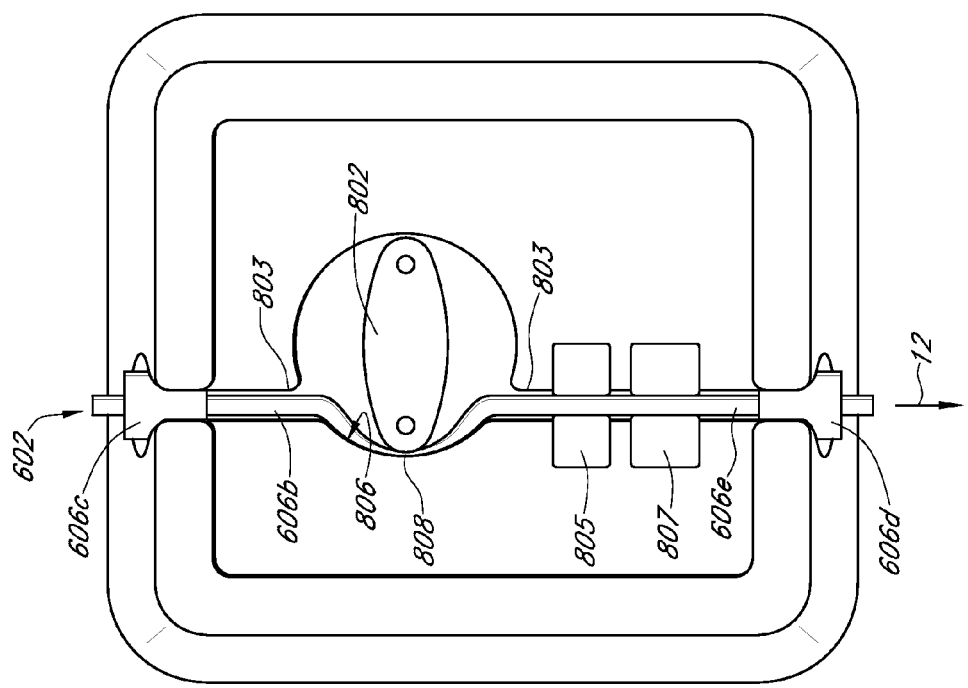

ANALYTE SENSOR

CROSS-REFERENCE TO RELATED APPLICATIONS

This application is a continuation-in-part of U.S. application Ser. No. 12/055,114 filed Mar. 25, 2008; and is a continuation-in-part of U.S. application Ser. No. 12/055,149 filed Mar. 25, 2008; and is a continuation-in-part of U.S. application Ser. No. 12/055,203 filed Mar. 25, 2008; and is a continuation-in-part of U.S. application Ser. No. 12/055,227 filed Mar. 25, 2008. U.S. application Ser. No. 12/055,227 is a continuation-in-part of U.S. application Ser. No. 11/691,466 filed Mar. 26, 2007; and is a continuation-in-part of U.S. application Ser. No. 11/691,424 filed Mar. 26, 2007; and is a continuation-in-part of U.S. application Ser. No. 11/691,432 filed Mar. 26, 2007; and is a continuation-in-part of U.S. application Ser. No. 11/691,426 filed Mar. 26, 2007. U.S. application Ser. No. 12/055,203 is a continuation-in-part of U.S. application Ser. No. 11/691,466 filed Mar. 26, 2007; and is a continuation-in-part of U.S. application Ser. No. 11/691,424 filed Mar. 26, 2007; and is a continuation-in-part of U.S. application Ser. No. 11/691,432 filed Mar. 26, 2007; and is a continuation-in-part of U.S. application Ser. No. 11/691,426 filed Mar. 26, 2007. U.S. application Ser. No. 12/055,149 is a continuation-in-part of U.S. application Ser. No. 11/691,466 filed Mar. 26, 2007; and is a continuation-in-part of U.S. application Ser. No. 11/691,424 filed Mar. 26, 2007; and is a continuation-in-part of U.S. application Ser. No. 11/691,432 filed Mar. 26, 2007; and is a continuation-in-part of U.S. application Ser. No. 11/691,426 filed Mar. 26, 2007. U.S. application Ser. No. 12/055,114 is a continuation-in-part of U.S. application Ser. No. 11/691,466 filed Mar. 26, 2007; and is a continuation-in-part of U.S. application Ser. No. 11/691,424 filed Mar. 26, 2007; and is a continuation-in-part of U.S. application Ser. No. 11/691,432 filed Mar. 26, 2007; and is a continuation-in-part of U.S. application Ser. No. 11/691,426 filed Mar. 26, 2007. U.S. application Ser. No. 11/691,466 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,432 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,426 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. U.S. application Ser. No. 11/691,424 filed Mar. 26, 2007 is a continuation-in-part of U.S. application Ser. No. 11/543,396 filed Oct. 4, 2006; and is a continuation-in-part of U.S. application Ser. No. 11/543,490 filed Oct. 4, 2006; and is a continuation-in-part of U.S. application Ser. No. 11/543,404 filed Oct. 4, 2006. The disclosures of each of the above-mentioned applications is hereby expressly incorporated by reference in its entirety and is hereby expressly made a portion of this application.

FIELD OF THE INVENTION

The preferred embodiments relate generally to systems and methods for measuring an analyte in a host.

BACKGROUND OF THE INVENTION

In today's medical practice, analyte levels in patient biological samples (e.g., fluids, tissues and the like collected from patients) are routinely measured during the process of diagnosing, monitoring and/or prognosticating a patient's medical status. For example, a basic metabolic panel (e.g., BMP or chem.-7) measures sodium, potassium, chloride, bicarbonate, blood urea nitrogen (BUN), creatinine and glucose. Bodily sample analyte tests are routinely conducted in a variety of medical settings (e.g., doctor's office, clinic, hospital, by medical personnel) and in the home by the host and/or a caretaker. For example, some medical conditions require frequent testing of blood analyte levels. For example, diabetes mellitus, a disorder in which the pancreas cannot create sufficient insulin (Type I or insulin dependent) and/or in which insulin is not effective (Type 2 or non-insulin dependent), is one exemplary medical condition, wherein bodily fluid samples (e.g., blood, interstitial fluid) are routinely tested, in order to ascertain the patient's (e.g., host's) glucose status, often by the host or a caretaker. In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person admitted to a hospital for certain conditions (with or without diabetes) is tested for blood sugar level by a single point blood glucose meter, which typically requires uncomfortable finger pricking methods or blood draws and can produce a burden on the hospital staff during a patient's hospital stay. Due to the lack of convenience, blood sugar glucose levels are generally measured as little as once per day or up to once per hour. Unfortunately, such time intervals are so far spread apart that hyperglycemic or hypoglycemic conditions unknowingly occur, incurring dangerous side effects. It is not only unlikely that a single point value will not catch some hyperglycemic or hypoglycemic conditions, it is also likely that the trend (direction) of the blood glucose value is unknown based on conventional methods. This inhibits the ability to make educated insulin therapy decisions.

A variety of sensors are known that use an electrochemical cell to provide output signals by which the presence or absence of an analyte, such as glucose, in a sample can be determined. For example, in an electrochemical cell, an analyte (or a species derived from it) that is electro-active generates a detectable signal at an electrode, and this signal can be used to detect or measure the presence and/or amount within a biological sample. In some conventional sensors, an enzyme is provided that reacts with the analyte to be measured, and the byproduct of the reaction is qualified or quantified at the electrode. An enzyme has the advantage that it can be very specific to an analyte and also, when the analyte itself is not sufficiently electro-active, can be used to interact with the analyte to generate another species which is electro-active and to which the sensor can produce a desired output. In one conventional amperometric glucose oxidase-based glucose sensor, immobilized glucose oxidase catalyses the oxidation of glucose to form hydrogen peroxide, which is then quantified by amperometric measurement (for example, change in electrical current) through a polarized electrode.

SUMMARY OF THE INVENTION

In a first aspect, an integrated sensor system is provided for measuring an analyte in a sample of a host and for fluid infusion into the host, comprising: an analyte sensor configured and arranged for measuring an analyte concentration in a biological sample of a circulatory system of a host; a vascular access device; tubing assembly comprising tubing; and a flow control device configured to regulate exposure of the analyte sensor to a biological sample and to a reference solution according to a flow profile, wherein the flow control device comprises a valve, and wherein the valve is configured and arranged with a gravity flow position and a controlled flow position.

In an embodiment of the first aspect, the system is configured such that the analyte sensor is flushed by the reference solution when the valve is in the gravity flow position.

In an embodiment of the first aspect, the gravity flow position comprises a first flow rate of the solution, wherein the controlled flow position comprises a second flow rate of the solution, and wherein a ratio of the first flow rate to the second flow rate is at least about 10:1.

In an embodiment of the first aspect, the gravity flow position has a flow rate of at least about 600 ml/hr.

In an embodiment of the first aspect, the controlled flow position has a flow rate of from about 0.5 ml/hr to about 4.0 ml/hour.

In an embodiment of the first aspect, the valve is configured and arranged to receive the tubing in a substantially linear configuration.

In an embodiment of the first aspect, the valve and the tubing assembly are configured and arranged such that the tubing is in a stretched state after installation of the tubing in the valve.

In an embodiment of the first aspect, valve is configured and arranged such that the tubing is substantially linear in the gravity flow position and the tubing is substantially non-linear in the controlled flow position.

In an embodiment of the first aspect, the valve is configured and arranged to preclude tubing installation when the valve is in the controlled flow position.

In an embodiment of the first aspect, the valve is configured and arranged to receive the tubing assembly in only one orientation.

In an embodiment of the first aspect, the valve and tubing assembly are configured and arranged to releasably interlock such that a portion of the valve mechanically interlocks with a portion of the tubing assembly.

In an embodiment of the first aspect, the vascular access device and the tubing assembly are configured and arranged to substantially preclude rotational movement between the vascular access device and the tubing assembly when engaged.

In an embodiment of the first aspect, the system further comprises a free-flow mitigation device.

In an embodiment of the first aspect, the free-flow mitigation device comprises a spring clip occluder located on the tubing assembly.

In an embodiment of the first aspect, the system is configured for electronic control of the free-flow mitigation device.

In an embodiment of the first aspect, the system further comprises an electronic solenoid associated with the flow control device, wherein the electronic solenoid provides electronic control of the free-flow mitigation device.

In an embodiment of the first aspect, the system is configured and arranged such that the free-flow mitigation device precludes flow responsive to at least one of power removal, loss to the system, and loss to the flow control device.

In an embodiment of the first aspect, the system is configured and arranged such that the free-flow mitigation device is controlled at least in part by the flow profile.

In an embodiment of the first aspect, the system further comprises an intravenous bag containing a reference solution, wherein the reference solution has a known analyte concentration.

In an embodiment of the first aspect, the analyte sensor is configured to measure at least one analyte selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In a second aspect, a system configured to measure at least one analyte in a host is provided, the system comprising: a vascular access device comprising a first portion configured for insertion into a host and a second portion configured to remain outside the host after insertion of the first portion; at least one analyte sensor located within the second portion of the vascular access device, such that the at least one analyte sensor is exposed to a biological sample when the biological sample is drawn back by a distance of about 40 mm or less into the vascular access device, when the vascular access device is in fluid communication with a circulatory system of the host; and a flow control device configured to regulate exposure of the at least one analyte sensor to a biological sample and to a reference solution according to a flow profile.

In an embodiment of the second aspect, the at least one analyte sensor is exposed to the biological sample when a volume of about 300 µl or less of the biological sample is drawn back.

In an embodiment of the second aspect, the at least one analyte sensor is exposed to the biological sample when a volume of about 200 µl or less of the biological sample is drawn back.

In an embodiment of the second aspect, the vascular access device comprises a catheter.

In an embodiment of the second aspect, the second portion comprises a connecting end of the catheter, wherein the connecting end is configured for connection to tubing.

In an embodiment of the second aspect, the vascular access device is a catheter, and wherein the catheter is 22 gauge or smaller.

In an embodiment of the second aspect, the second portion comprises a fluid coupler, wherein the fluid coupler is configured to releasably mate with the catheter.

In an embodiment of the second aspect, the at least one sensor is incorporated into the second portion.

In an embodiment of the second aspect, the at least one sensor is located on an inner surface of the second portion.

In an embodiment of the second aspect, the at least one sensor is disposed within a lumen of the second portion.

In an embodiment of the second aspect, at least a portion of the at least one sensor is disposed in an orientation substantially parallel to a longitudinal axis of the second portion.

In an embodiment of the second aspect, at least a portion of the at least one sensor is disposed in an orientation substantially perpendicular to a longitudinal axis of the second portion.

In an embodiment of the second aspect, the at least one sensor comprises an exposed electroactive surface area with a dimension substantially equal to a width of a lumen of the second portion.

In an embodiment of the second aspect, the exposed electroactive surface area intersects the lumen of the second portion.

In an embodiment of the second aspect, the second portion is configured to provide identification information associated with the flow profile.

In an embodiment of the second aspect, the system is configured to program the flow profile of the flow control device in response to an automatic receipt of the identification information.

In an embodiment of the second aspect, the identification information is provided by a mechanical structure of the second portion.

In an embodiment of the second aspect, the identification information is provided by electronics of the second portion.

In an embodiment of the second aspect, the vascular access device comprises at least two lumens, and wherein the system is configured and arranged to infuse a fluid into a first lumen of the vascular access device, and wherein the system is configured and arranged to draw back a biological sample into a second lumen of the vascular access device.

In an embodiment of the second aspect, the at least one analyte sensor is configured to measure an analyte selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the second aspect, the system comprises at least three analyte sensors located within the second portion of the vascular access device, wherein the three sensors in combination are configured to measure at least three analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the second aspect, the system comprises at least eight analyte sensors located within the second portion of the vascular access device, wherein the three sensors in combination are configured to measure at least eight analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the second aspect, a lumen of the second portion is wider than a lumen of the first portion.

In a third aspect, a system configured to measure at least one analyte in a host is provided, the system comprising: a catheter comprising a first portion configured for insertion into a host and a second portion configured to remain outside the host after insertion of the first portion; and at least one analyte sensor located within the second portion of the catheter, such that the at least one analyte sensor is exposed to a biological sample when the biological sample is drawn back into the catheter to a distance of about 40 mm or less, when the catheter is in fluid communication with a circulatory system of the host.

In an embodiment of the third aspect, the at least one analyte sensor is exposed to the biological sample when a volume of about 300 μl or less of the biological sample is drawn back.

In an embodiment of the third aspect, the at least one analyte sensor is exposed to the biological sample when a volume of about 200 μl or less of the biological sample is drawn back.

In an embodiment of the third aspect, the catheter is 22 gauge or smaller.

In an embodiment of the third aspect, the second portion comprises a fluid coupler, wherein the fluid coupler is configured to releasably mate with the catheter.

In an embodiment of the third aspect, the at least one sensor is incorporated into the second portion.

In an embodiment of the third aspect, the at least one sensor is located on an inner surface of the second portion.

In an embodiment of the third aspect, the at least one sensor is disposed within a lumen of the second portion.

In an embodiment of the third aspect, at least a portion of the at least one sensor is disposed in an orientation substantially parallel to a longitudinal axis of the second portion.

In an embodiment of the third aspect, at least a portion of the at least one sensor is disposed in an orientation substantially perpendicular to a longitudinal axis of the second portion.

In an embodiment of the third aspect, the at least one sensor comprises an exposed electroactive surface area with a dimension substantially equal to a width of a lumen of the second portion.

In an embodiment of the third aspect, the exposed electroactive surface area intersects the lumen of the second portion.

In an embodiment of the third aspect, the second portion is configured to provide identification information associated with a flow profile.

In an embodiment of the third aspect, the system is configured to program the flow profile of the flow control device in response to an automatic receipt of the identification information.

In an embodiment of the third aspect, the identification information is provided by a mechanical structure of the catheter.

In an embodiment of the third aspect, the identification information is provided by electronics associated with the catheter.

In an embodiment of the third aspect, the catheter comprises at least two lumens, and wherein the system is configured and arranged to infuse a fluid into a first lumen of the catheter, and wherein the system is configured and arranged draw back a biological sample into a second lumen of the catheter.

In an embodiment of the third aspect, the at least one analyte sensor is configured to measure an analyte selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the third aspect, the system comprises at least three analyte sensors located within the second portion of the catheter, wherein the three sensors in combination are configured to measure at least three analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the third aspect, the system comprises at least eight analyte sensors located within the second portion of the catheter, wherein the eight sensors in combination are configured to measure at least eight analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the third aspect, the system further comprises a flow control device configured to regulate exposure of the at least one sensor to a biological sample and to a solution according to a flow profile.

In an embodiment of the third aspect, a lumen of the second portion is wider than a lumen of the first portion.

In a fourth aspect, a system configured to measure at least one analyte in a biological sample of the host is provided, the system comprising: a fluid coupler comprising a first end and a second end, wherein the first end is configured to releasably mate with a connecting end of a catheter, and wherein the second end is configured to releasably mate with a tubing assembly; and at least one analyte sensor located within the fluid coupler such that when the fluid coupler is mated to a catheter inserted into a circulatory system of a host, the at least one analyte sensor is exposed to a biological sample when the biological sample is drawn back into the catheter to a distance of about 40 mm or less.

In an embodiment of the fourth aspect, the at least one analyte sensor is exposed to the biological sample when a volume of about 300 µl or less of the biological sample is drawn back.

In an embodiment of the fourth aspect, the at least one analyte sensor is exposed to the biological sample when a volume of about 200 µl or less of the biological sample is drawn back.

In an embodiment of the fourth aspect, the at least one analyte sensor is incorporated into the fluid coupler.

In an embodiment of the fourth aspect, the at least one analyte sensor is located on an inner surface of the fluid coupler.

In an embodiment of the fourth aspect, the at least one analyte sensor is disposed within a lumen of the fluid coupler.

In an embodiment of the fourth aspect, at least a portion of the at least one sensor is disposed in an orientation substantially parallel to a longitudinal axis of the fluid coupler.

In an embodiment of the fourth aspect, at least a portion of the at least one sensor is disposed in an orientation substantially perpendicular to a longitudinal axis of the fluid coupler.

In an embodiment of the fourth aspect, the at least one sensor comprises an exposed electroactive surface area with a dimension substantially equal to a width of a lumen of the fluid coupler.

In an embodiment of the fourth aspect, the exposed electroactive surface area intersects the lumen of the fluid coupler.

In an embodiment of the fourth aspect, the fluid coupler is configured to provide identification information associated with a flow profile.

In an embodiment of the fourth aspect, the system is configured to program the flow profile of the flow control device in response to an automatic receipt of the identification information.

In an embodiment of the fourth aspect, the identification information is provided by a mechanical structure of the fluid coupler.

In an embodiment of the fourth aspect, the identification information is provided by electronics associated with the fluid coupler.

In an embodiment of the fourth aspect, the fluid coupler comprises at least two lumens, and wherein the system is configured and arranged to infuse a fluid into a first lumen of the fluid coupler, and wherein the system is configured and arranged draw back a biological sample into a second lumen of the fluid coupler.

In an embodiment of the fourth aspect, the at least one analyte sensor is configured to measure an analyte selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the fourth aspect, the system comprises at least three analyte sensors located within the fluid coupler, wherein the three sensors in combination are configured to measure at least three analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the fourth aspect, the system comprises at least eight analyte sensors located within the fluid coupler, wherein the three sensors in combination are configured to measure at least eight analytes selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

In an embodiment of the fourth aspect, the system further comprises a catheter.

In an embodiment of the fourth aspect, the system further comprises a flow control device configured to regulate exposure of the at least one sensor to a biological sample and to a solution according to a flow profile.

In a fifth aspect, a method for evaluating a change in a sensitivity of an analyte sensor over a predetermined time period is provided, the method comprising: receiving sensor data from an analyte sensor, wherein the sensor data comprises one or more sensor analyte values measured in a biological sample of a host; intermittently calculating a sensitivity of the analyte sensor based at least in part on reference analyte data; and evaluating a change in sensitivity by evaluating a plurality of time-spaced sensitivity calculations over a predetermined time period.

In an embodiment of the fifth aspect, the predetermined time period is less than or equal to about 30 minutes.

In an embodiment of the fifth aspect, the predetermined time period is less than or equal to about 20 minutes.

In an embodiment of the fifth aspect, the predetermined time period is less than or equal to about 10 minutes.

In an embodiment of the fifth aspect, the step of evaluating a change in sensitivity comprises evaluating at least two sensitivity measurements during the predetermined time period.

In an embodiment of the fifth aspect, the method further comprises averaging and/or filtering the at least two sensitivity measurements prior to the step of evaluating the at least two sensitivity measurements.

In an embodiment of the fifth aspect, the step of evaluating a change in sensitivity comprises comparing the change in sensitivity with one or more criteria.

In an embodiment of the fifth aspect, the method further comprises using a most recent sensitivity calculation evaluated to calibrate the analyte sensor when the change in sensitivity meets one or more criteria.

In an embodiment of the fifth aspect, the method further comprises not using a most recent sensitivity calculation evaluated to calibrate the analyte sensor when the change in sensitivity does not meet one or more criteria.

In an embodiment of the fifth aspect, the step of intermittently calculating a sensitivity of the analyte sensor comprises intermittently receiving a reference analyte value.

In an embodiment of the fifth aspect, the step of intermittently receiving a reference analyte value comprises periodically receiving a measured analyte concentration from a reference analyte solution.

In an embodiment of the fifth aspect, the step of intermittently receiving a reference analyte value comprises receiving a reference analyte value obtained from an in vitro analyte monitor.

In an embodiment of the fifth aspect, the step of evaluating a sensitivity is iteratively performed on the plurality of time-spaced sensitivity calculations over the predetermined time period.

In an embodiment of the fifth aspect, the predetermined time period is at least about 30 minutes.

In an embodiment of the fifth aspect, the predetermined time period is at least about 60 minutes.

In an embodiment of the fifth aspect, the predetermined time period is at least about 120 minutes.

In an embodiment of the fifth aspect, the step of evaluating a sensitivity is iteratively performed on the plurality of time-spaced sensitivity calculations over the predetermined time period.

In an embodiment of the fifth aspect, the step of evaluating a sensitivity comprises evaluating all sensitivity calculations over a sensor session.

In an embodiment of the fifth aspect, the step of evaluating a sensitivity is based at least in part on a priori sensitivity information.

In an embodiment of the fifth aspect, the a priori sensitivity information is an expected profile.

In an embodiment of the fifth aspect, the a priori sensitivity information defines a range of acceptable change in sensitivity.

In an embodiment of the fifth aspect, the analyte sensor comprises a first working electrode and a second working electrode, wherein the first working electrode is configured to provide a first signal comprising an analyte component and a baseline component and wherein the second working electrode is configured to provide a second signal comprising a baseline component without an analyte component.

In an embodiment of the fifth aspect, the step of intermittently calculating a sensitivity of the analyte sensor is based at least in part on the first signal.

In an embodiment of the fifth aspect, the step of intermittently calculating a sensitivity of the analyte sensor is based at least in part on the second signal.

In an embodiment of the fifth aspect, the method further comprises subtracting the second signal from the first signal to obtain a subtracted signal, wherein the step of intermittently calculating a sensitivity of the analyte sensor is based at least in part on the subtracted signal.

In an embodiment of the fifth aspect, the analyte sensor is intermittently exposed to a biological sample and to a reference solution.

In an embodiment of the fifth aspect, the step of intermittently calculating a sensitivity of the analyte sensor is based at least in part on a signal obtained when the analyte sensor is exposed to a biological sample.

In an embodiment of the fifth aspect, the step of intermittently calculating a sensitivity of the analyte sensor is based at least in part on a signal obtained when the analyte sensor is exposed to a reference solution.

In an embodiment of the fifth aspect, the step of intermittently calculating a sensitivity of the analyte sensor is based at least in part on a signal obtained when the analyte sensor is exposed to a biological sample and a signal obtained when the analyte sensor is exposed to a reference solution.

In a sixth aspect, a system for evaluating a change in a sensitivity of an analyte sensor over a predetermined time period is provided, the system comprising: an analyte sensor; and a computer system, wherein the computer system comprises: an input module configured to receive sensor analyte data and reference analyte data, wherein the sensor data comprises one or more sensor analyte values measured in a biological sample of a host and wherein the reference data comprises one or more reference analyte values; and a processor module configured to intermittently calculate a sensitivity of the analyte sensor based at least in part on the reference analyte data and to evaluate a change in sensitivity by evaluating a plurality of time-spaced sensitivity calculations over a predetermined time period.

In an embodiment of the sixth aspect, the predetermined time period is less than or equal to about 30 minutes.

In an embodiment of the sixth aspect, the predetermined time period is less than or equal to about 20 minutes.

In an embodiment of the sixth aspect, the predetermined time period is less than or equal to about 10 minutes.

In an embodiment of the sixth aspect, the processor module is configured to evaluate the change in sensitivity at least in part by evaluating at least two sensitivity measurements during the predetermined time period.

In an embodiment of the sixth aspect, the processor module is further configured to average and/or filter the at least two sensitivity measurements prior to evaluating the at least two sensitivity measurements.

In an embodiment of the sixth aspect, the processor module is further configured to compare the change in sensitivity with one or more criteria.

In an embodiment of the sixth aspect, the processor module is further configured to use a most recent sensitivity calculation evaluated to calibrate the analyte sensor when the change in sensitivity meets one or more criteria.

In an embodiment of the sixth aspect, the processor module is further configured to not use a most recent sensitivity calculation evaluated to calibrate the analyte sensor when the change in sensitivity does not meet one or more criteria.

In an embodiment of the sixth aspect, the predetermined time period is at least about 30 minutes.

In an embodiment of the sixth aspect, the predetermined time period is at least about 60 minutes.

In an embodiment of the sixth aspect, the predetermined time period is at least about 120 minutes.

In an embodiment of the sixth aspect, the processor module is configured to iteratively evaluate a sensitivity of the plurality of time-spaced sensitivity calculations over the predetermined time period.

In an embodiment of the sixth aspect, the processor module is configured to evaluate all sensitivity calculations over a sensor session.

In an embodiment of the sixth aspect, the processor module is configured to evaluate a sensitivity based at least in part on a priori sensitivity information.

In an embodiment of the sixth aspect, the a priori sensitivity information is an expected profile.

In an embodiment of the sixth aspect, the a priori sensitivity information defines a range of acceptable change in sensitivity.

In an embodiment of the sixth aspect, the analyte sensor data comprises a first signal comprising an analyte component and a baseline component and a second signal comprising a baseline component without an analyte component.

In an embodiment of the sixth aspect, the processor module is configured to calculate a sensitivity of the analyte sensor based at least in part on the first signal.

In an embodiment of the sixth aspect, the processor module is configured to calculate a sensitivity of the analyte sensor based at least in part on the second signal.

In an embodiment of the sixth aspect, the processor module is further configured to calculate a sensitivity of the analyte sensor based at least in part on a subtracted signal, wherein the subtracted signal comprises the second signal subtracted from the first signal.

In an embodiment of the sixth aspect, the system further comprises a flow control device configured to intermittently expose the sensor to the biological sample and to a reference solution.

In an embodiment of the sixth aspect, the processor module is configured to intermittently calculate a sensitivity of the analyte sensor based at least in part on a signal obtained when the analyte sensor is exposed to the biological sample.

In an embodiment of the sixth aspect, the processor module is configured to intermittently calculate a sensitivity of the analyte sensor based at least in part on a signal obtained when the analyte sensor is exposed to the reference solution.

In an embodiment of the sixth aspect, the processor module is configured to intermittently calculate a sensitivity of the analyte sensor based on a signal obtained when the analyte sensor is exposed to the biological sample and a signal obtained when the analyte sensor is exposed to the reference solution.

In a seventh aspect, a method for performing a diagnostic of an analyte sensor system is provided, comprising: providing a sensor system comprising an analyte sensor and a flow control device configured to intermittently expose the analyte sensor to a biological sample and an infusion solution, wherein the analyte sensor comprises: a first working electrode configured to provide a first signal comprising an analyte component and a baseline component; and a second working electrode configured to provide a second signal comprising a baseline component substantially without an analyte component; and evaluating the sensor system based at least in part on the second signal.

In an embodiment of the seventh aspect, the second signal comprises a signal waveform, and wherein the step of evaluating the sensor system comprises evaluating the signal waveform for at least one of an expected shape and a pattern when the analyte sensor is exposed to at least one of the biological sample and the infusion solution.

In an embodiment of the seventh aspect, the step of evaluating the signal waveform comprises evaluating at least one of a similarity and a correlation between the signal waveform and a waveform template.

In an embodiment of the seventh aspect, the waveform template is based at least in part on a priori information.

In an embodiment of the seventh aspect, the waveform template is based at least in part on a signal waveform measured by the sensor system.

In an embodiment of the seventh aspect, the step of evaluating at least one of a similarity and a correlation of the signal waveform to a waveform template comprises performing a correlation waveform analysis.

In an embodiment of the seventh aspect, the method further comprises updating the waveform template when at least one of the similarity and the correlation between the signal waveform and the waveform template meets one or more criteria.

In an embodiment of the seventh aspect, the method further comprises detecting a level of interferent in the biological sample, wherein the waveform template is updated when the level of interferent meets one or more criteria.

In an embodiment of the seventh aspect, the step of evaluating the signal waveform comprises evaluating a monotonicity of the signal waveform.

In an embodiment of the seventh aspect, the step of evaluating a monotonicity of the signal waveform comprises performing a correlation waveform analysis of the signal waveform with the waveform template.

In an embodiment of the seventh aspect, the step of evaluating a monotonicity of the signal waveform comprises performing a time-series analysis.

In an embodiment of the seventh aspect, the step of evaluating the sensor system comprises detecting an interferent by evaluating at least one of an amplitude, a change in amplitude, a signal waveform, and a change in a signal waveform of the second signal when the sensor is exposed to the biological sample.

In an embodiment of the seventh aspect, the step of detecting an interferent is further based at least in part on a calibrated analyte value.

In an embodiment of the seventh aspect, the method further comprises controlling a display of the sensor system based at least in part on a level of interferent detected on the second signal.

In an embodiment of the seventh aspect, the method further comprises processing the first signal and the second signal to obtain a subtracted signal, wherein the step of processing is based at least in part a level of interferent of the sensor system.

In an embodiment of the seventh aspect, the method further comprises determining a level of reliability of the sensor system by comparing at least one of an amplitude, a change in amplitude, a signal waveform, and a change in a signal waveform of the second signal to one or more criteria.

In an embodiment of the seventh aspect, the method further comprises controlling a display of the sensor system based at least in part on the level of reliability of the sensor system.

In an embodiment of the seventh aspect, the step of evaluating comprises determining a success of a biological sample draw-back from a host's circulatory system to the analyte sensor.

In an embodiment of the seventh aspect, the method further comprises displaying an analyte value measured during the biological sample draw-back in response to a determination of a successful biological sample draw-back.

In an embodiment of the seventh aspect, the step of evaluating comprises determining a success of infusing the infusion solution such that the biological sample is washed from the sensor.

In an embodiment of the seventh aspect, the step of determining a success of infusing comprises displaying an analyte value measured in the biological sample after infusing the infusion solution in response to a determination of a successful infusion.

In an eighth aspect, a system for performing a diagnostic of an analyte sensor system is provided, comprising: an analyte sensor system comprising a sensor, wherein the analyte sensor comprises a first working electrode configured to provide a first signal comprising an analyte component and a baseline component and a second working electrode configured to provide a second signal comprising a baseline component substantially without an analyte component; a flow control device configured to intermittently expose the analyte sensor to a biological sample and an infusion solution; and a processor module configured to evaluate the analyte sensor system based at least in part on the second signal.

In an embodiment of the eighth aspect, the second signal comprises a signal waveform, and wherein the processor module is configured to evaluate the signal waveform for at least one of an expected shape and a pattern when the analyte sensor is exposed to at least one of the biological sample and the infusion solution.

In an embodiment of the eighth aspect, the processor module is configured to evaluate the signal waveform by evaluating at least one of a similarity and a correlation between the signal waveform and a waveform template.

In an embodiment of the eighth aspect, the waveform template is based at least in part on a priori information.

In an embodiment of the eighth aspect, the waveform template is based at least in part on a signal waveform measured by the analyte sensor system.

In an embodiment of the eighth aspect, the processor module is configured to evaluate at least one of a similarity and a correlation between the signal waveform and the waveform template by performing a correlation waveform analysis.

In an embodiment of the eighth aspect, the processor module is further configured to update the waveform template when at least one of a similarity and a correlation between the signal waveform and the waveform template meets one or more criteria.

In an embodiment of the eighth aspect, the processor module is configured to detect a level of an interferent in the biological sample, and wherein the processor module is further configured to update the waveform template when the level of the interferent meets one or more criteria.

In an embodiment of the eighth aspect, the processor module is configured to evaluate the signal waveform by evaluating a monotonicity of the signal waveform.

In an embodiment of the eighth aspect, the processor module is configured to evaluate a monotonicity at least in part by performing a correlation waveform analysis of the signal waveform with a waveform template.

In an embodiment of the eighth aspect, the processor module is configured evaluate a monotonicity at least in part by performing a time-series analysis.

In an embodiment of the eighth aspect, the processor module is configured to detect an interferent at least in part by evaluating at least one of an amplitude, a change in amplitude, a signal waveform, and a change in a signal waveform of the second signal when the sensor is exposed to a biological sample.

In an embodiment of the eighth aspect, the processor module is configured to detect an interferent at least in part by evaluating a calibrated analyte value with one or more criteria.

In an embodiment of the eighth aspect, the one or more criteria are based on physiological feasibility.

In an embodiment of the eighth aspect, the processor module is configured to control a display of the analyte sensor system based at least in part on a level of an interferent detected on the second signal.

In an embodiment of the eighth aspect, the processor module is further configured to process the first signal and the second signal to obtain a subtracted signal based at least in part on a level of an interferent of the sensor system.

In an embodiment of the eighth aspect, the processor module is configured evaluate a level of reliability of the sensor system at least in part by comparing at least one of an amplitude, a change in amplitude, a signal waveform, and a change in a signal waveform of the second signal to one or more criteria.

In an embodiment of the eighth aspect, the processor module is configured to control a display of the sensor system based at least in part on a level of reliability of the sensor system.

In an embodiment of the eighth aspect, processor module is further configured determine a success of drawing-back of a biological sample from a host's circulatory system to the analyte sensor, based at least in part on the evaluation of the analyte sensor system.

In an embodiment of the eighth aspect, the processor module is configured to display an analyte value measured during the biological sample draw-back, in response to a determination of a successful draw-back of the biological sample.

In an embodiment of the eighth aspect, the processor module is further configured to determine a success of infusing the infusion solution such that the biological sample is washed from the sensor.

In an embodiment of the eighth aspect, the processor module is configured to display an analyte value measured in the biological sample after infusing the infusion solution, in response to a determination of a successful infusion.

In a ninth aspect, a method for determining a stability of an analyte sensor is provided, the method comprising: exposing an analyte sensor to a biological sample, wherein the analyte sensor comprises a first working electrode that measures an analyte component and a baseline component and a second working electrode that measures a baseline component substantially without an analyte component; receiving sensor data from the analyte sensor, wherein the sensor data comprises first sensor data associated with the first working electrode and second sensor data associated with the second working electrode; and determining a stability of the analyte sensor based at least in part on the second sensor data.

In an embodiment of the ninth aspect, the second sensor data comprises a plurality of time spaced data points, and wherein the step of determining a stability of the analyte sensor comprises evaluating a change in amplitude of two or more of the plurality of time spaced data points.

In an embodiment of the ninth aspect, the step of exposing the analyte sensor to a biological sample comprises intermittently exposing the analyte sensor to a biological sample and to an infusion solution.

In an embodiment of the ninth aspect, the step of evaluating comprises comparing a plurality of time spaced points measured when the analyte sensor is exposed to the biological sample.

In an embodiment of the ninth aspect, the step of evaluating comprises comparing a first point measured when the analyte sensor is exposed to the biological sample to a second point measured when the analyte sensor is exposed to the infusion solution.

In an embodiment of the ninth aspect, the step of evaluating comprises evaluating transient information of the second sensor data during a step change from exposure of the sensor to the infusion solution to exposure of the sensor to the biological sample.

In an embodiment of the ninth aspect, the method further comprises determining a predetermined level of stability when a change in an amplitude of the second sensor data meets one or more criteria.

In an embodiment of the ninth aspect, the method further comprises controlling a display associated with the analyte sensor system in response to the determination of the predetermined level of stability.

In an embodiment of the ninth aspect, the step of controlling a display comprises providing at least one of a numeric estimated analyte value, a directional trend of analyte concentration, and a graphical representation of a plurality of estimated analyte values.

In an embodiment of the ninth aspect, the step of controlling a display comprises requesting reference analyte data.

In an embodiment of the ninth aspect, the step of determining a stability of the analyte sensor is performed during a predetermined time period.

In an embodiment of the ninth aspect, the step of determining a stability of the analyte sensor is performed after a predetermined time period.

In an embodiment of the ninth aspect, the method further comprises repeating the step of determining a stability, wherein the step is conducted after a system re-start.

In an embodiment of the ninth aspect, the analyte sensor is a glucose sensor.

In a tenth aspect, a system for determining a stability of an analyte sensor is provided, the system comprising: an analyte sensor; and a computer system, the computer system comprising: an input module operatively connected to the analyte sensor and configured to receive sensor data from an analyte sensor, wherein the analyte sensor comprises a first working electrode configured to provide first sensor data comprising an analyte component and a baseline component and a second working electrode configured to provide second sensor data comprising a baseline component substantially without an analyte component; and a processor module configured to determine a stability of the analyte sensor based at least in part on the second sensor data.

In an embodiment of the tenth aspect, the processor module is configured to determine a stability of the analyte sensor at least in part by evaluating a change in amplitude of a plurality of time spaced points from the second sensor data.

In an embodiment of the tenth aspect, the system further comprises a flow control device configured and arranged to intermittently expose the analyte sensor to a biological sample and to an infusion solution.

In an embodiment of the tenth aspect, the processor module is configured to evaluate the change in amplitude at least in part by comparing a plurality of time spaced points from the second sensor data measured when the analyte sensor is exposed to the biological sample.

In an embodiment of the tenth aspect, the processor module is configured to evaluate the change in amplitude at least in part by comparing a first point measured when the analyte sensor is exposed to the biological sample to a second point measured when the analyte sensor is exposed to the infusion solution.

In an embodiment of the tenth aspect, the processor module is configured to evaluate the change in amplitude at least in part by evaluating transient information of the second sensor data during a step change from exposure of the sensor to the infusion solution to exposure of the sensor to the biological sample.

In an embodiment of the tenth aspect, the processor module is configured to determine a level of stability when a change in amplitude of a plurality of time spaced points from the second sensor data meets one or more criteria.

In an embodiment of the tenth aspect, the processor module is configured to control a display of calibrated sensor based at least in part on the level of stability.

In an embodiment of the tenth aspect, the calibrated sensor data comprises at least one of a numeric estimated analyte value, a directional trend of analyte concentration, and a graphical representation of a plurality of estimated analyte values.

In an embodiment of the tenth aspect, the processor module is configured to request reference analyte data based at least in part on the level of stability.

In an embodiment of the tenth aspect, the processor module is further configured to determine a stability of the analyte sensor during a predetermined time period.

In an embodiment of the tenth aspect, processor module is further configured to determine a stability of the analyte sensor after a predetermined time period.

In an embodiment of the tenth aspect, the analyte sensor is a glucose sensor.

Figure 1A:
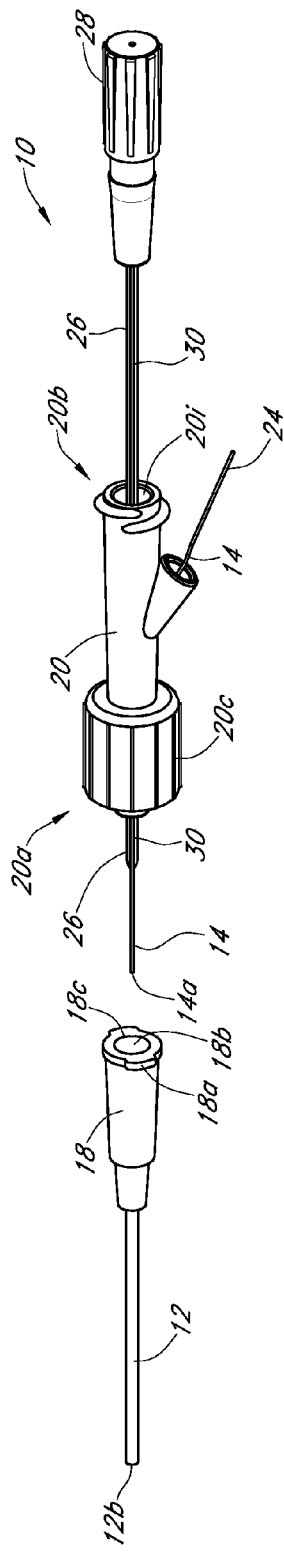
FIG. 1A is a perspective view of one embodiment of an analyte sensor system, including a vascular access device (e.g., a catheter), a sensor, a fluid connector, and a protective sheath.

FIG. $1C_1$ is a close-up cut away view of a portion of the analyte sensor system of FIG. 1A.

FIG. $1C_2$ is a close-up cut away view of a portion of the analyte sensor system of FIG. 1A.

Figure 1B:
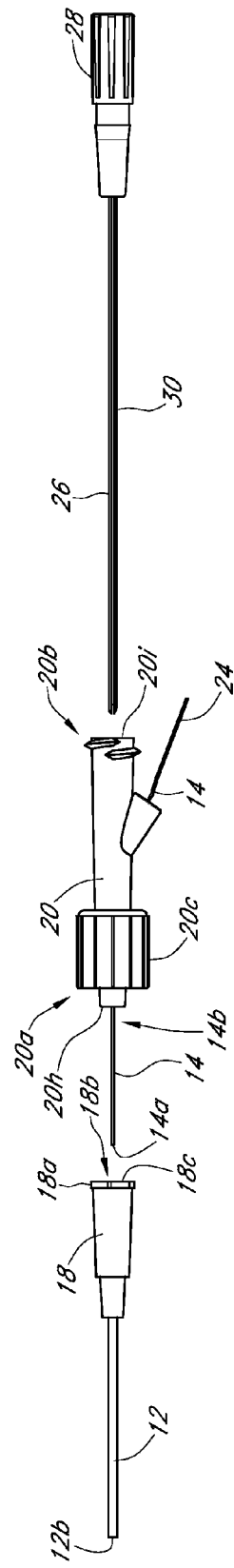
FIG. 1B is a side view of the analyte sensor system of FIG. 1A, showing the protective sheath removed.
Figure 1D:
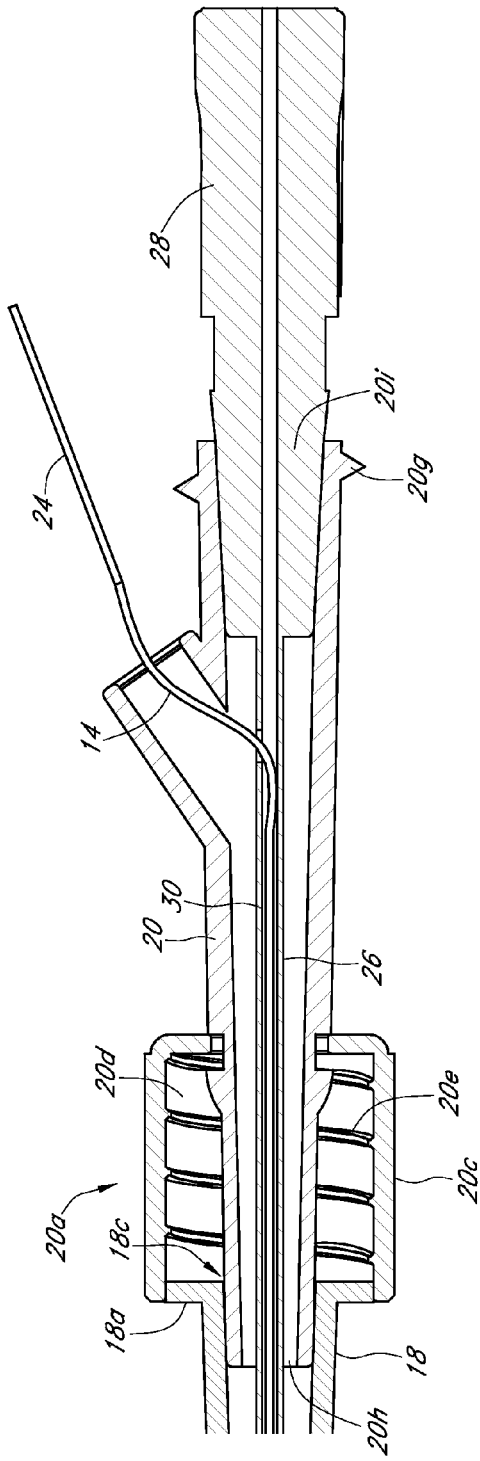

FIG. 1D is a close-up cut away view of a portion of the analyte sensor system of FIG. 1A.

Figure 1E:
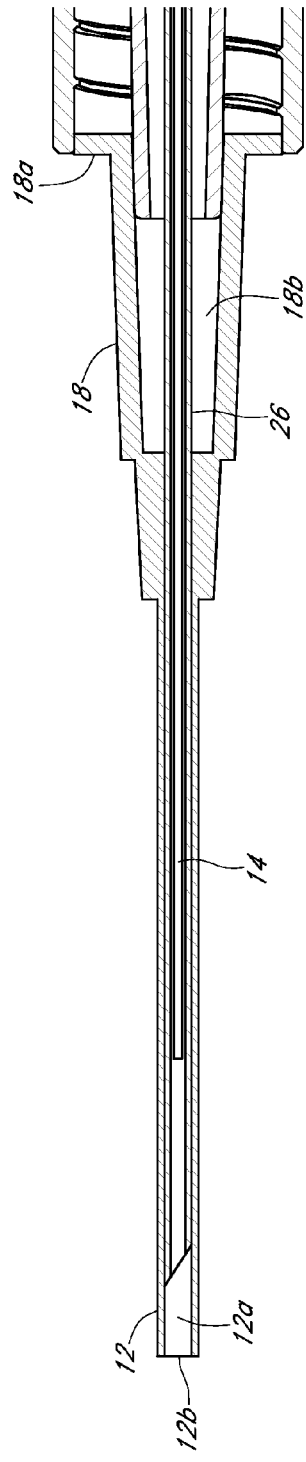

FIG. 1E is a close-up cut away view of a portion of the analyte sensor system of FIG. 1A.

Figure 1F:
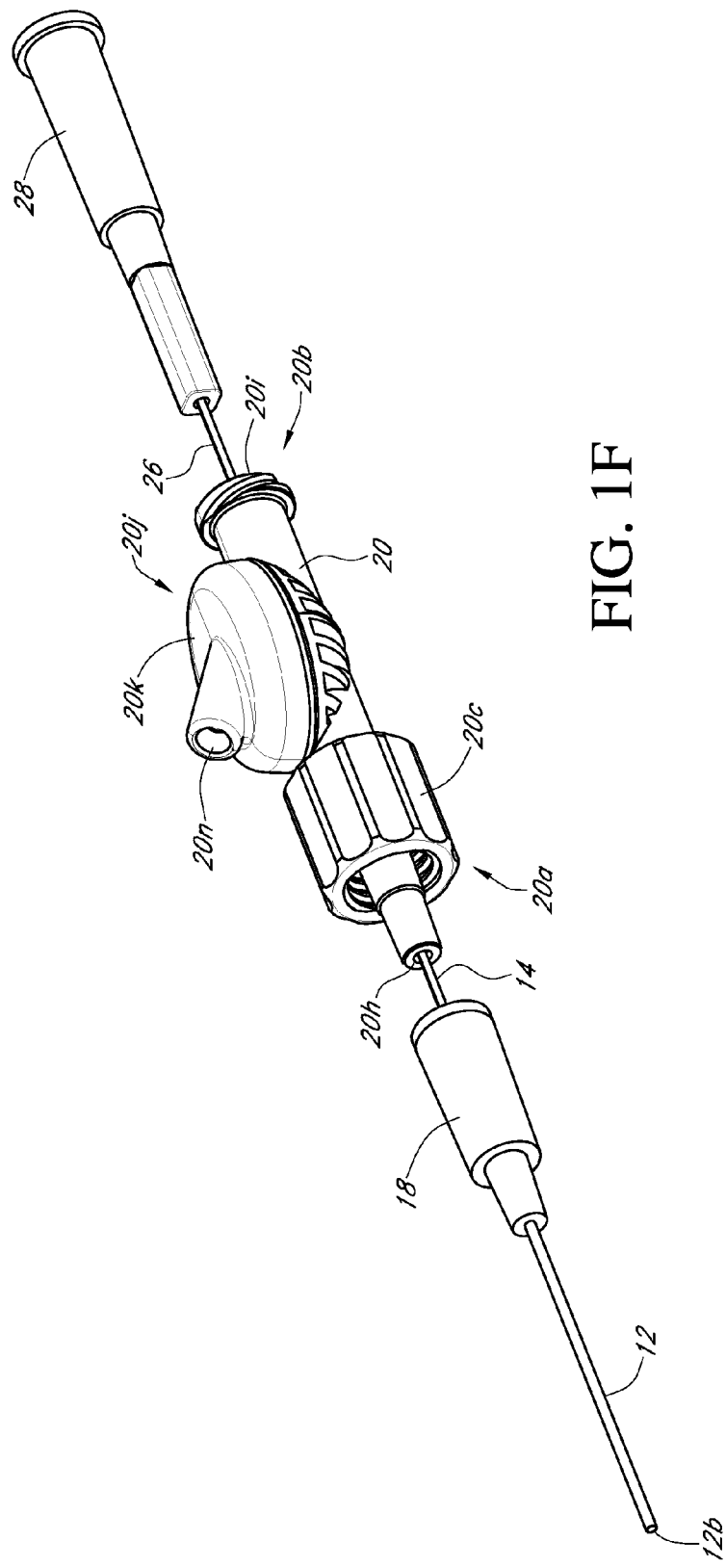

FIG. 1F is a schematic an analyte sensor system in another embodiment, including a vascular access device, a sensor, a fluid connector, and a protective sheath.

Figure 1G:
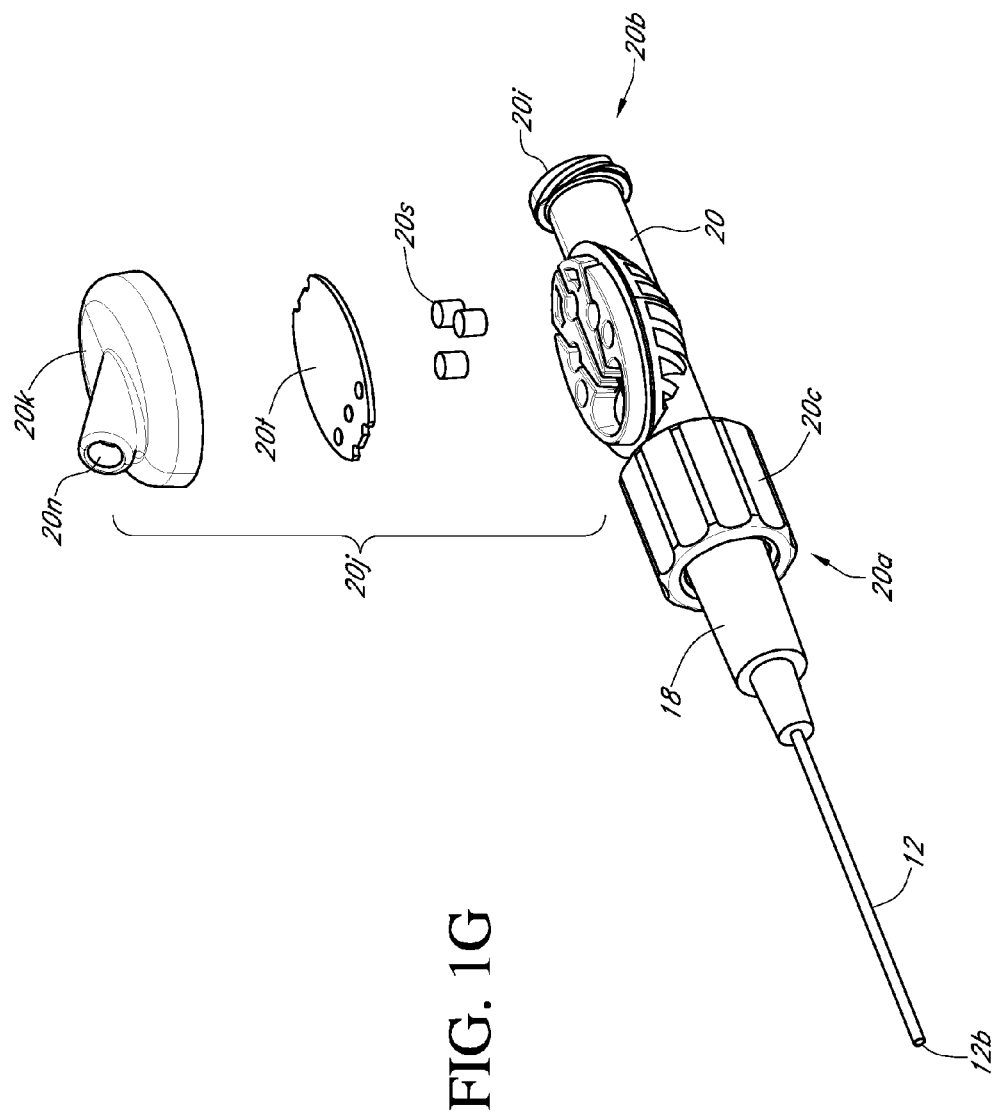

FIG. 1G is an exploded view of the analyte sensor system of FIG. 1F.

Figure 1H:
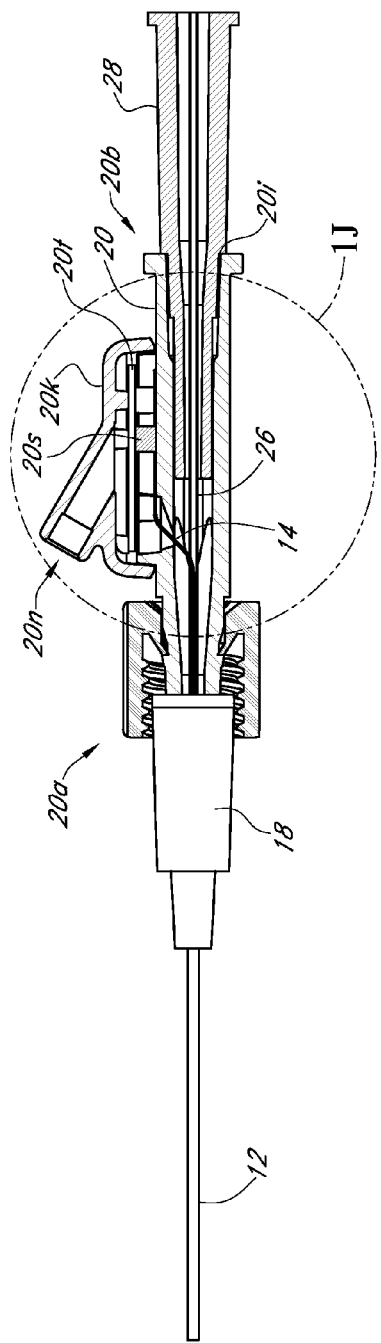

FIG. 1H is a cut-away view of the analyte sensor system of FIG. 1F.

Figure 1J:
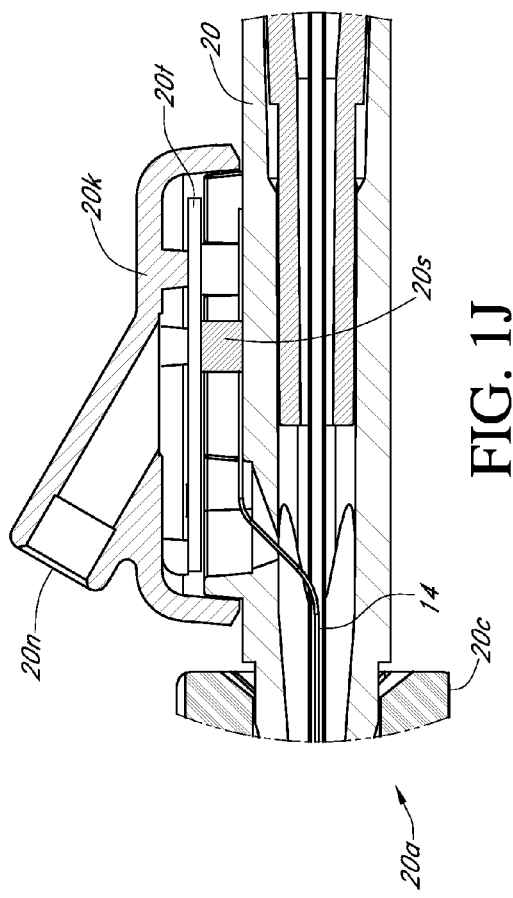

FIG. 1J is a magnified view of the encircled portion of the analyte sensor system of FIG. 1H.

Figure 1K:
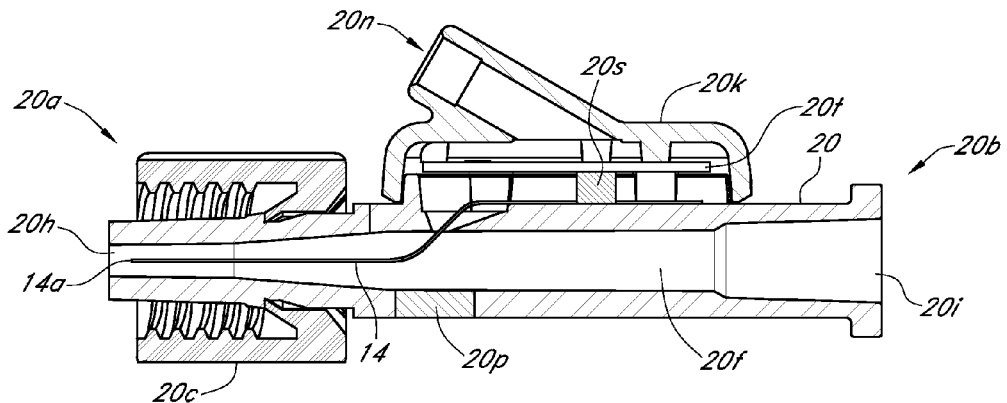

FIG. 1K is a cut-away view of an analyte sensor system in another embodiment.

Figure 1L:
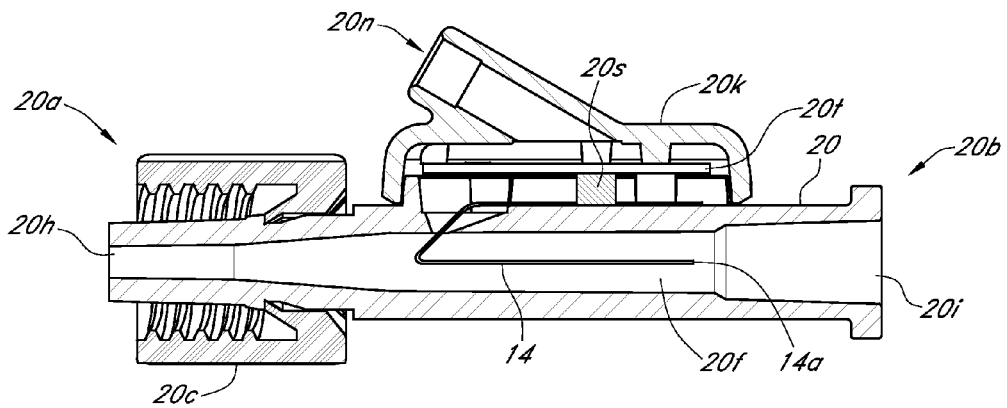

FIG. 1L is a cut-away view of an analyte sensor system in another embodiment.

Figure 1M:
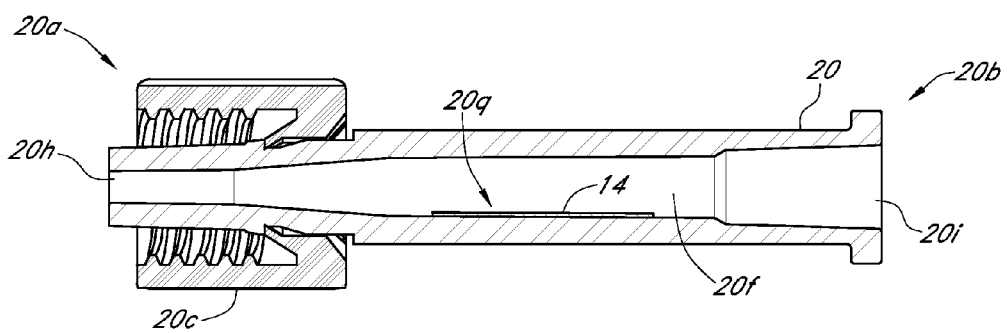

FIG. 1M is a cut-away view of an analyte sensor system in another embodiment.

FIG. 2A is a perspective view of another embodiment of the analyte sensor system, including a catheter with a sensor integrally formed thereon.

FIG. 2B is a perspective view of the analyte sensor system of FIG. 2A.

FIG. 2C is a close-up view of a portion of the analyte sensor system of FIG. 2A in an alternative configuration of an embodiment having three electrodes disposed on the catheter.

FIG. 2D is a close-up view of a portion of the analyte sensor system of FIG. 2A in an alternative configuration of an embodiment having three electrodes disposed on the catheter.

FIG. 2E is a close-up view of a portion of the analyte sensor system of FIG. 2A in an alternative embodiment having two electrodes disposed on the catheter.

FIG. 2F is a close-up view of a portion of the analyte sensor system of FIG. 2A in an alternative embodiment having one electrode disposed on the catheter.

Figure 2G:
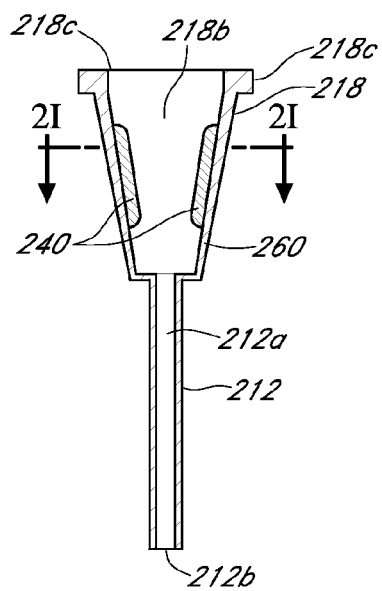

FIG. 2G is a cross-section of analyte sensor system in one embodiment, including a plurality of analyte sensors disposed within the connector of a catheter.

Figure 2H:
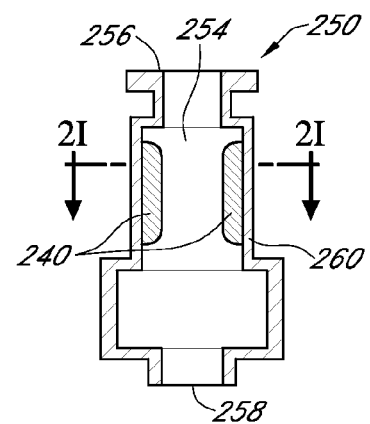

FIG. 2H is a cross-section of analyte sensor system in one embodiment, including a plurality of analyte sensors disposed within a fluid coupler, such as but not limited to a connector, a valve, and a Leur lock.

Figure 2I:
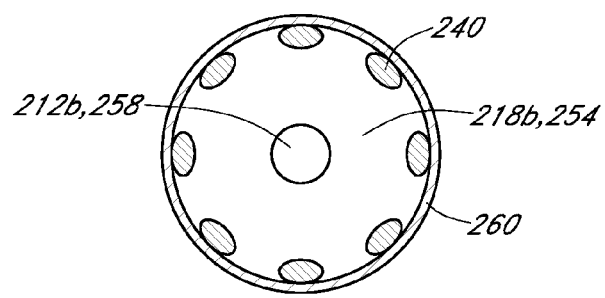

FIG. 2I is a cross-section of analyte sensor system of FIG. 2H, taken along line 2I-2I.

Figure 2J:
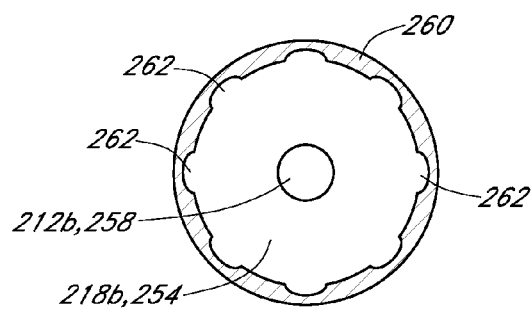

FIG. 2J is a cross-section of analyte sensor system of FIG. 2H, taken along line 2I-2I.

Figure 2K:
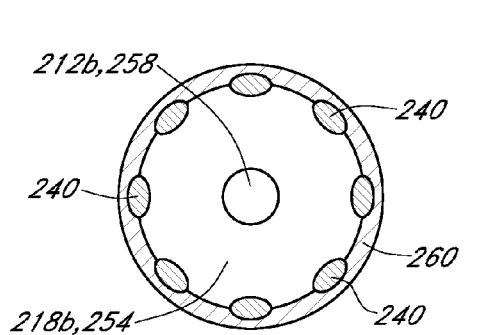

FIG. 2K is a cross-section of analyte sensor system of FIG. 2H, taken along line 2I-2I.

Figure 2L:
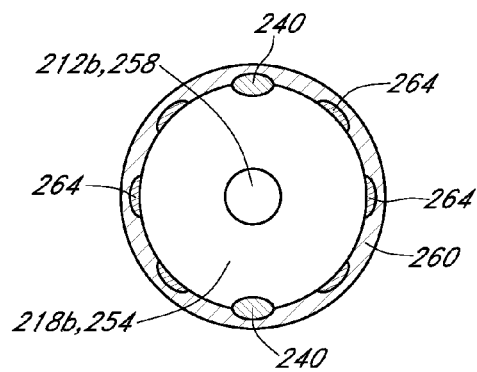

FIG. 2L is a cross-section of analyte sensor system of FIG. 2H, taken along line 2I-2I.

Figure 2M:
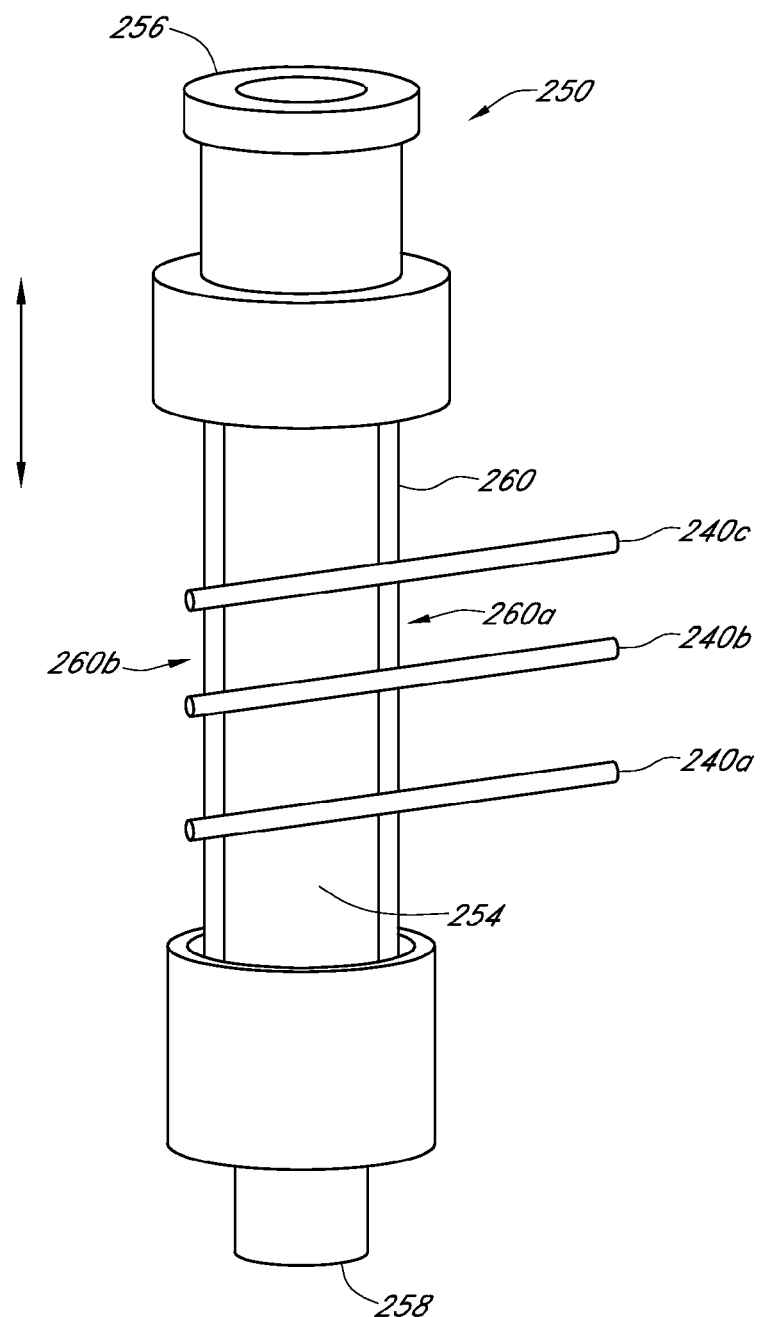

FIG. 2M is a side view schematic of an analyte sensor system in another embodiment, including a plurality of electrodes disposed in a fluid coupler.

Figure 2N:
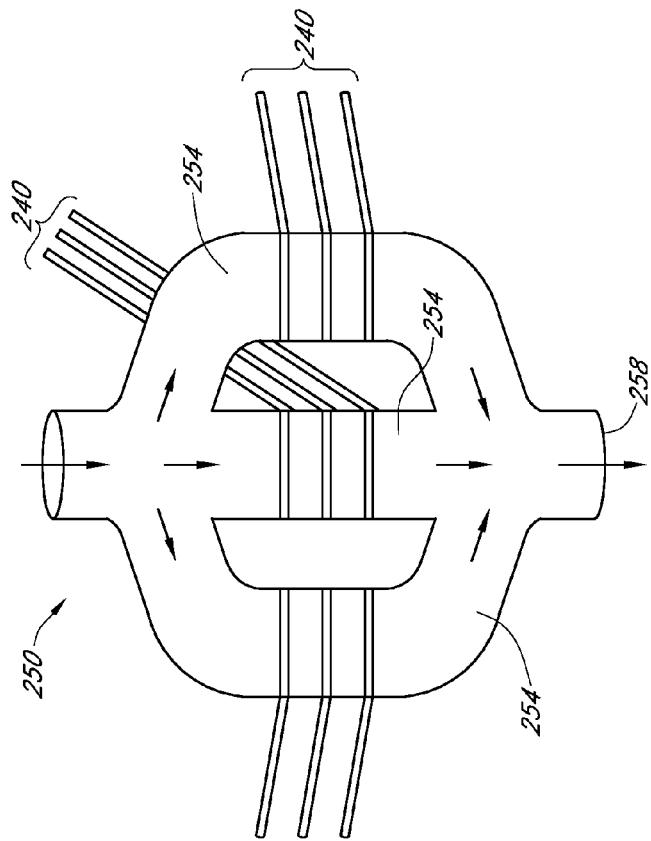
Figure 2N:
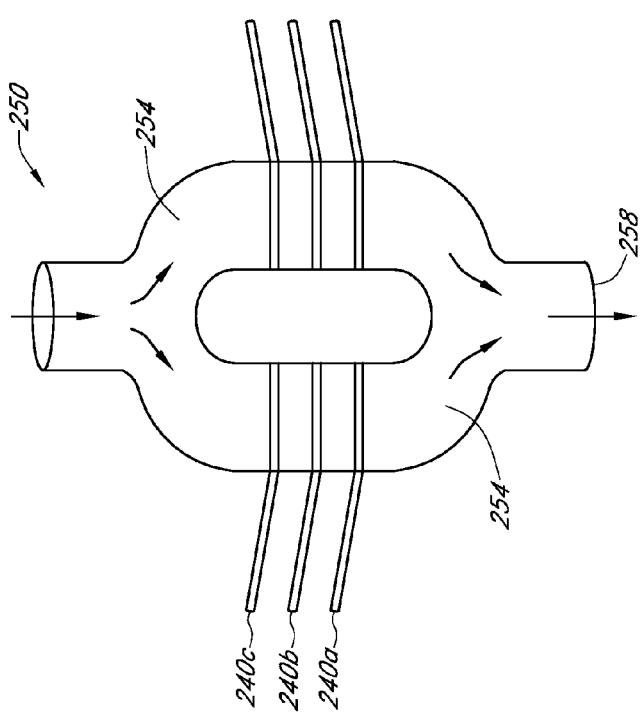

FIG. 2N is a schematic of an analyte sensor system in yet another embodiment, including a fluid coupler having a plurality of lumens, each of which includes an analyte sensor.

Figure 2O:
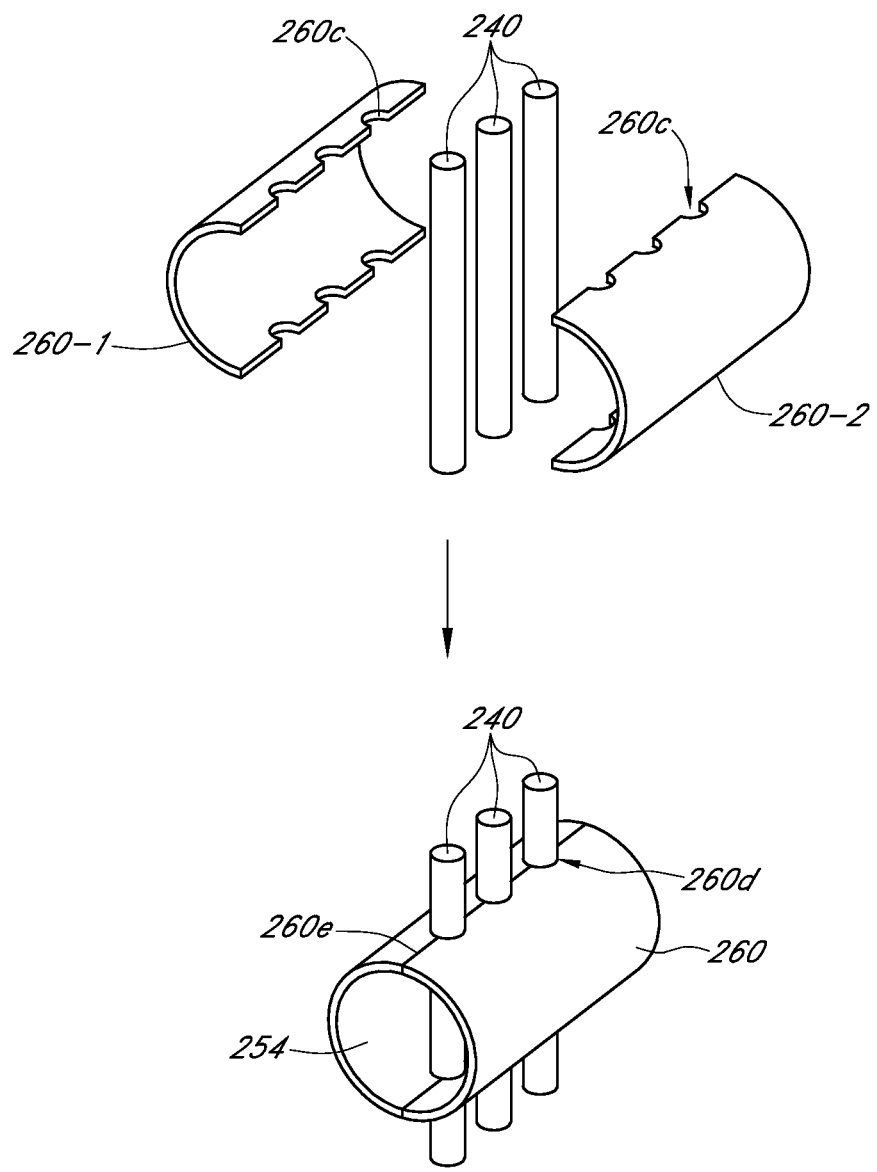

FIG. 2O is a schematic illustrating a method of manufacturing the analyte sensor system of FIG. 2M, in one embodiment.

Figure 2P:
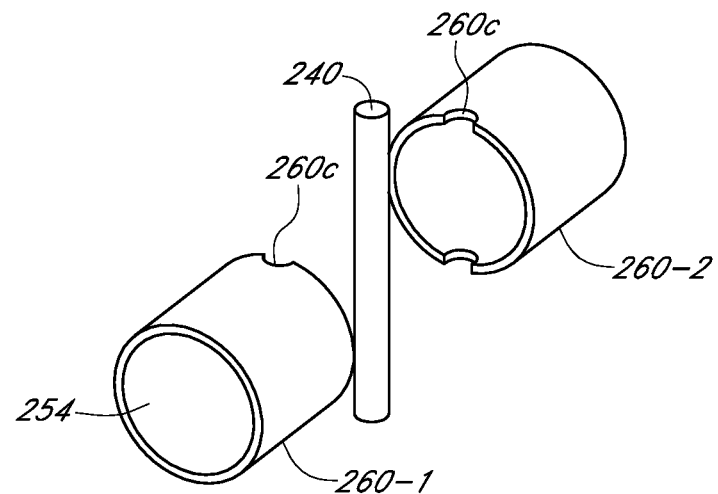
Figure 2P:
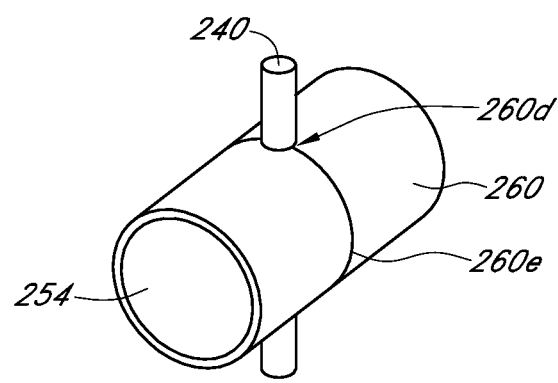

FIG. 2P is a schematic illustrating a method of manufacturing the analyte sensor system of FIG. 2M, in another embodiment.

Figure 2Q:
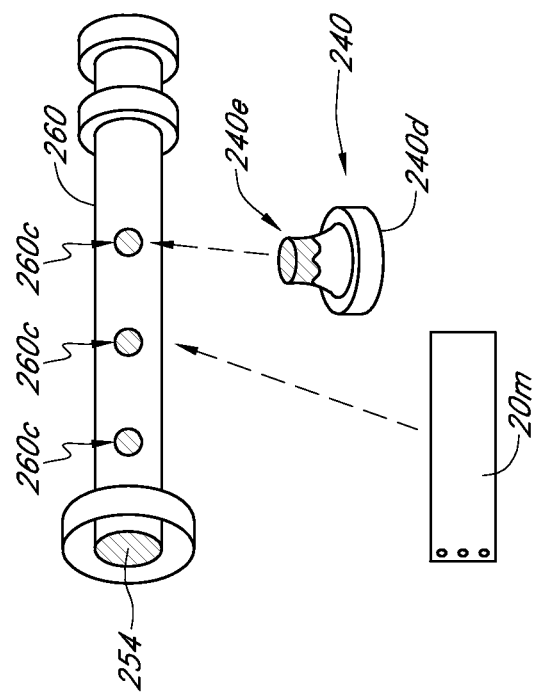

FIG. 2Q is a side view schematic of an analyte sensor system, including a fluid coupler including a plurality of sensor electrodes disposed therein, in one embodiment.

Figure 2R:
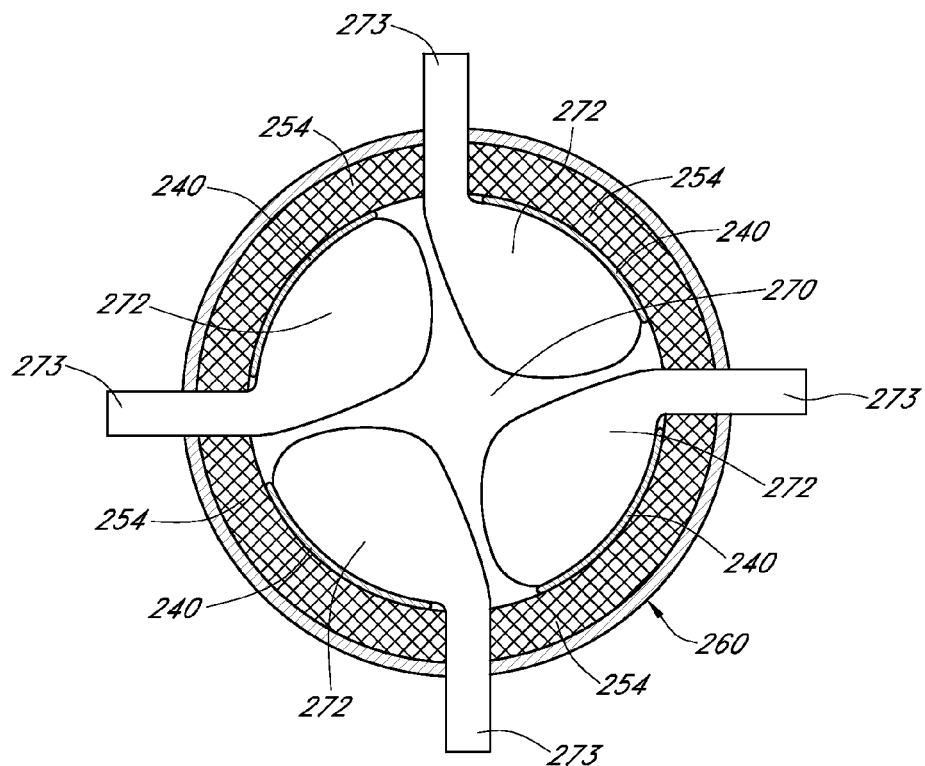

FIG. 2R is a cross-sectional schematic of an analyte sensor system, including a fluid coupler including a plurality of sensor electrodes disposed therein, in another embodiment.

Figure 2S:
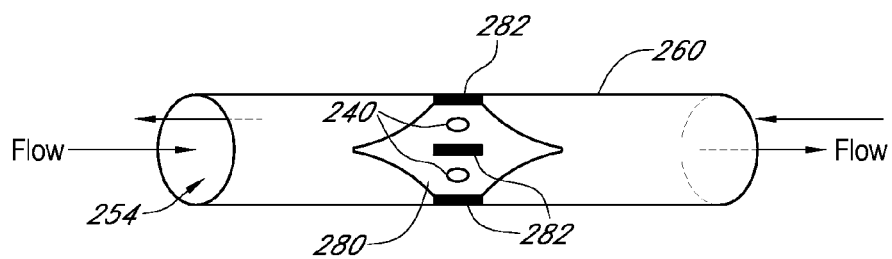

FIG. 2S is a side view schematic of an analyte sensor system, including a fluid coupler including a plurality of sensor electrodes disposed therein, in still another embodiment.

FIG. 3A is a perspective view of a first portion of one embodiment of an analyte sensor.

FIG. 3B is a perspective view of a second portion of the analyte sensor of FIG. 3A.

Figure 3C:
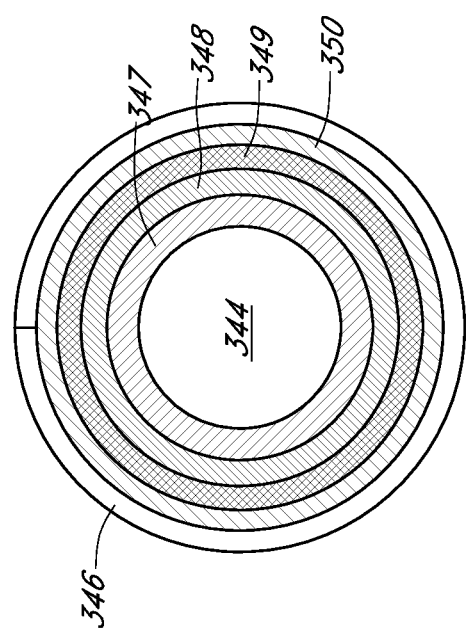

FIG. 3C is a cross section of the analyte sensor of FIG. 3B, taken on line C-C.

Figure 3D:
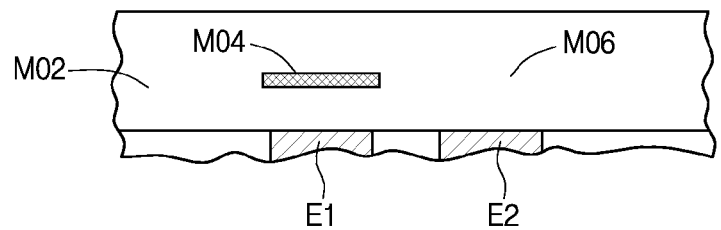

FIG. 3D is a cross-sectional schematic view of a sensing region of a dual-electrode continuous analyte sensor in one embodiment wherein an active enzyme of an enzyme domain is positioned over the first working electrode but not over the second working electrode.

Figure 3E:
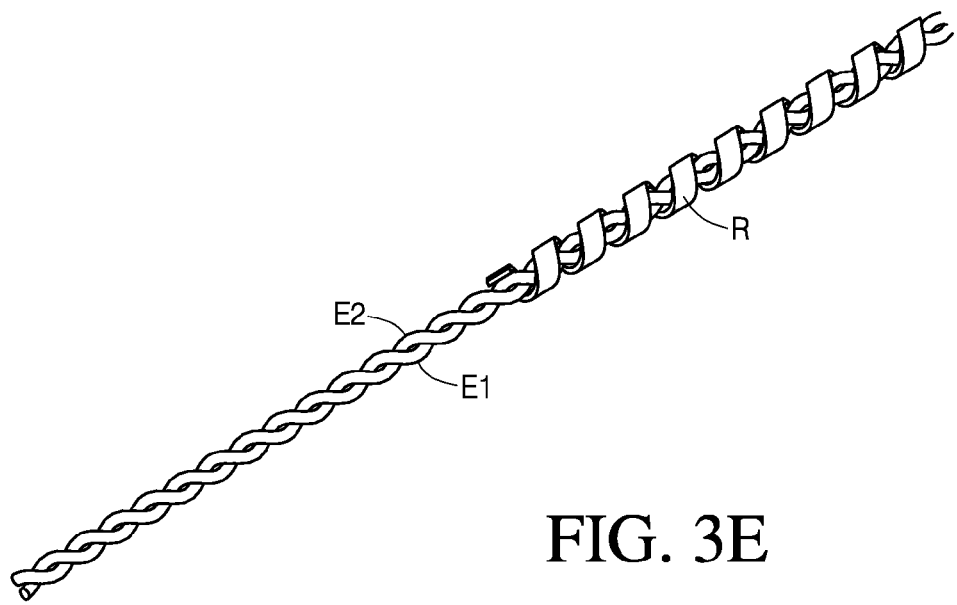

FIG. 3E is a perspective view of a dual-electrode continuous analyte sensor in one embodiment.

Figure 3F:
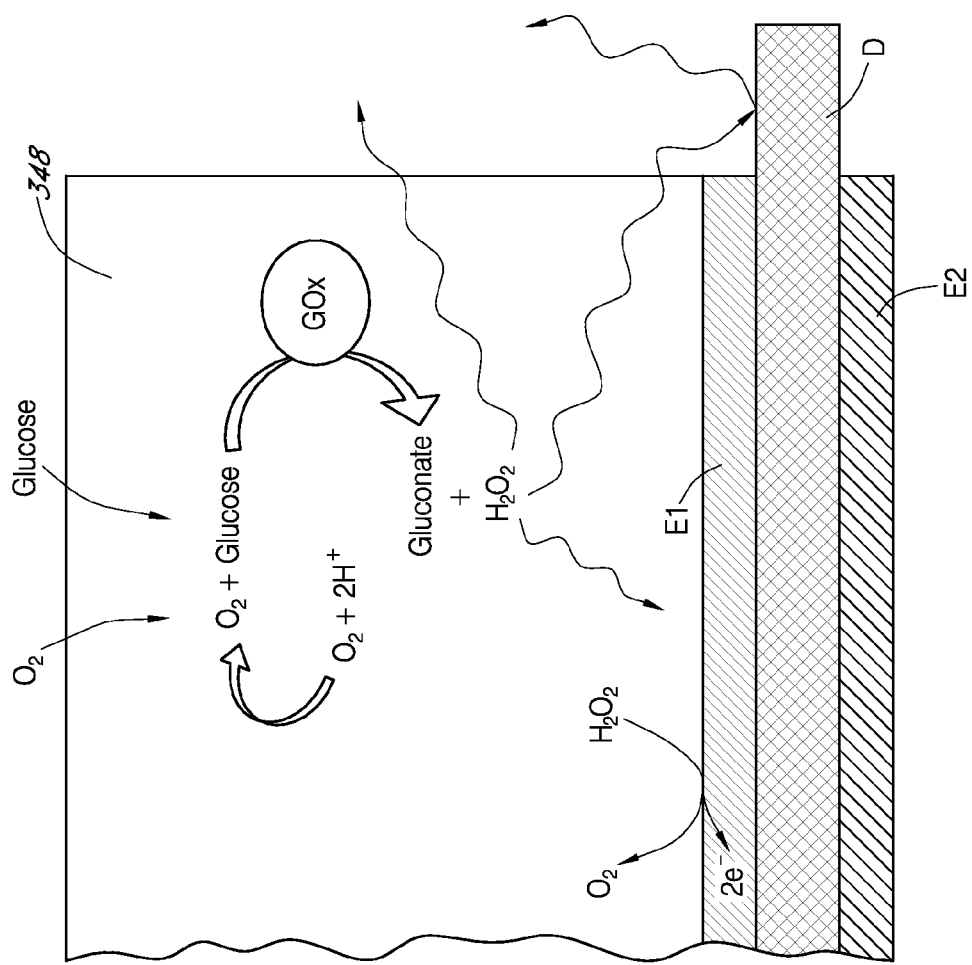

FIG. 3F is a schematic illustrating metabolism of glucose by Glucose Oxidase (GOx) and one embodiment of a diffusion barrier D that substantially prevents the diffusion of $H_2O_2$ produced on a first side of the sensor (e.g., from a first working electrode that has active GOx) to a second side of the sensor (e.g., to the second working electrode that lacks active GOx).

FIG. 3G is a two-dimensional schematic of a dual-electrode sensor in one embodiment, illustrating the sensor's first and second electroactive surfaces (of the first and second working electrodes, respectively) beneath a sensor membrane, wherein noise-causing species produced by a plurality of point sources can impinge upon an electroactive surface.

FIG. 3H is a two-dimensional schematic of a dual-electrode sensor in one embodiment, illustrating the sensor's first and second electroactive surfaces (of the first and second working electrodes, respectively) beneath a sensor membrane, wherein noise from a single point source (e.g., a cell) can impinge upon both electroactive surfaces.

FIG. 3I is a cross-sectional schematic illustrating a dual-electrode sensor, in one embodiment, including a physical diffusion barrier.

Figure 3J:
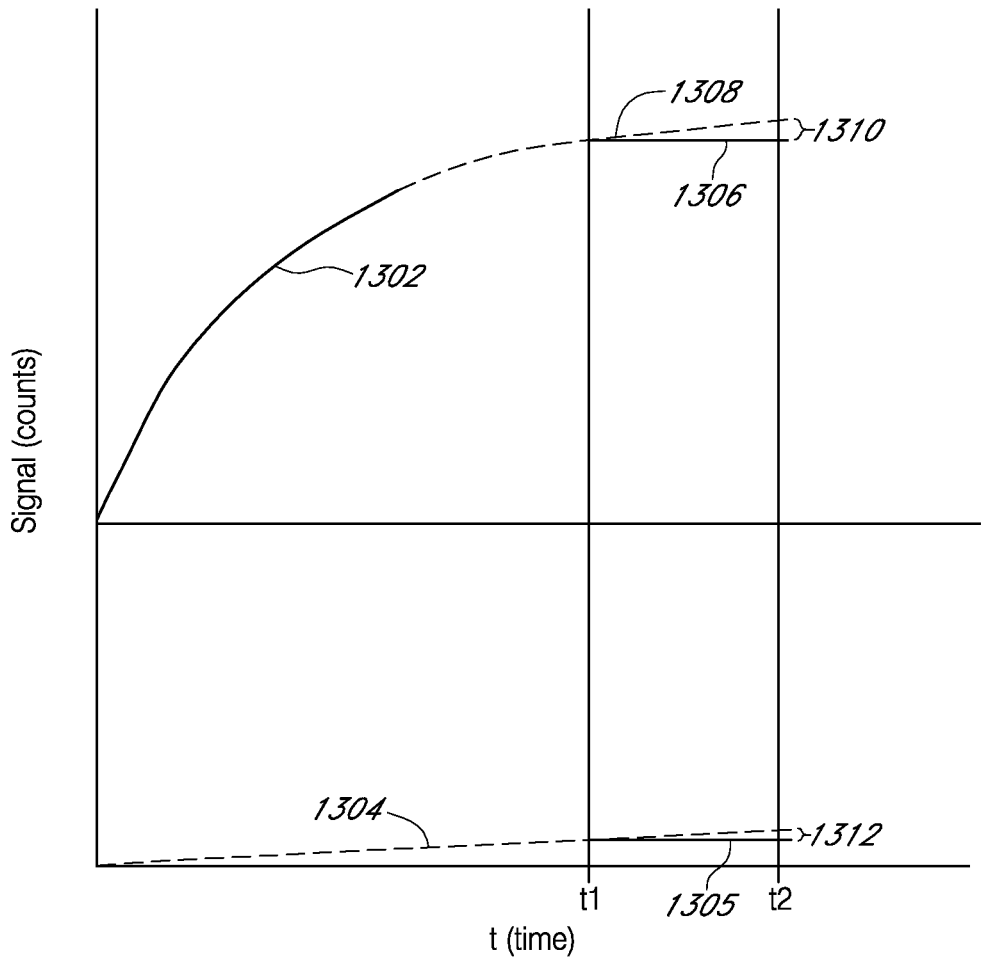

FIG. 3J is a graph illustrating signal response of the electrodes of a dual-electrode sensor, in one embodiment.

Figure 3K:
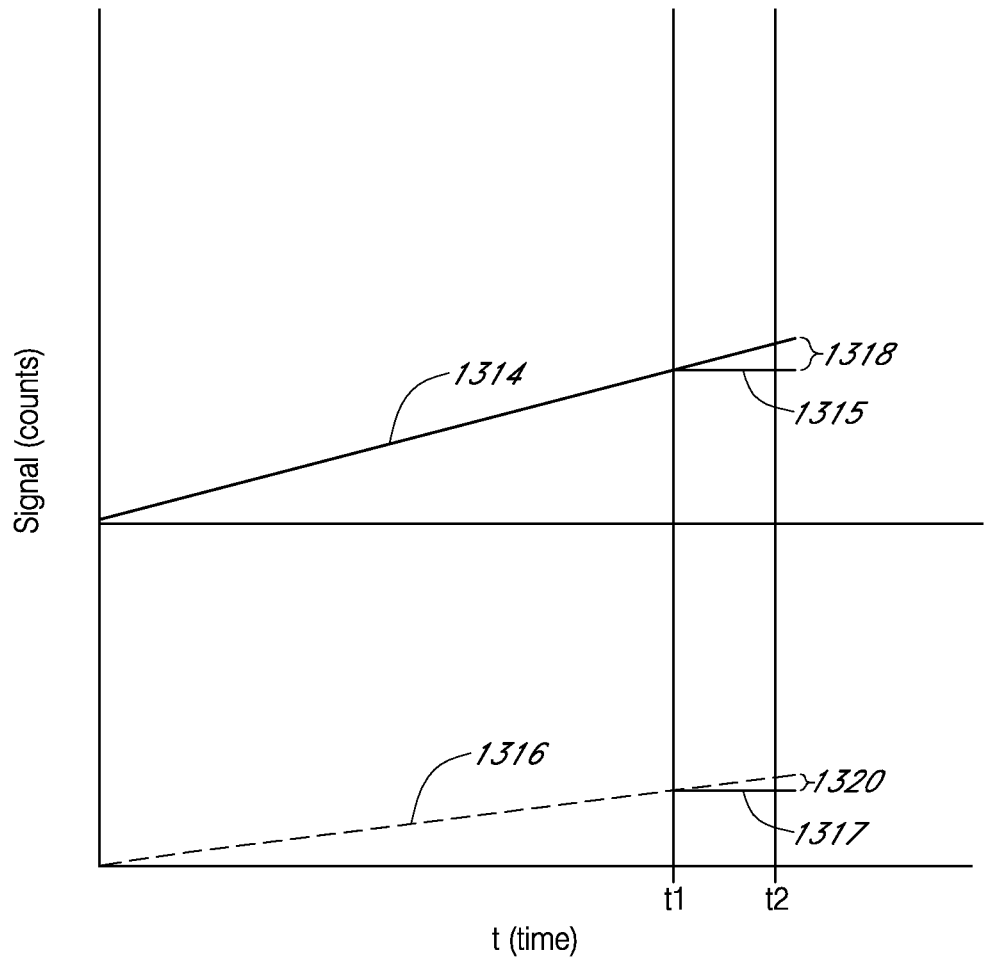

FIG. 3K is a graph illustrating signal response of the electrodes of a dual-electrode sensor, in one embodiment.

Figure 4:
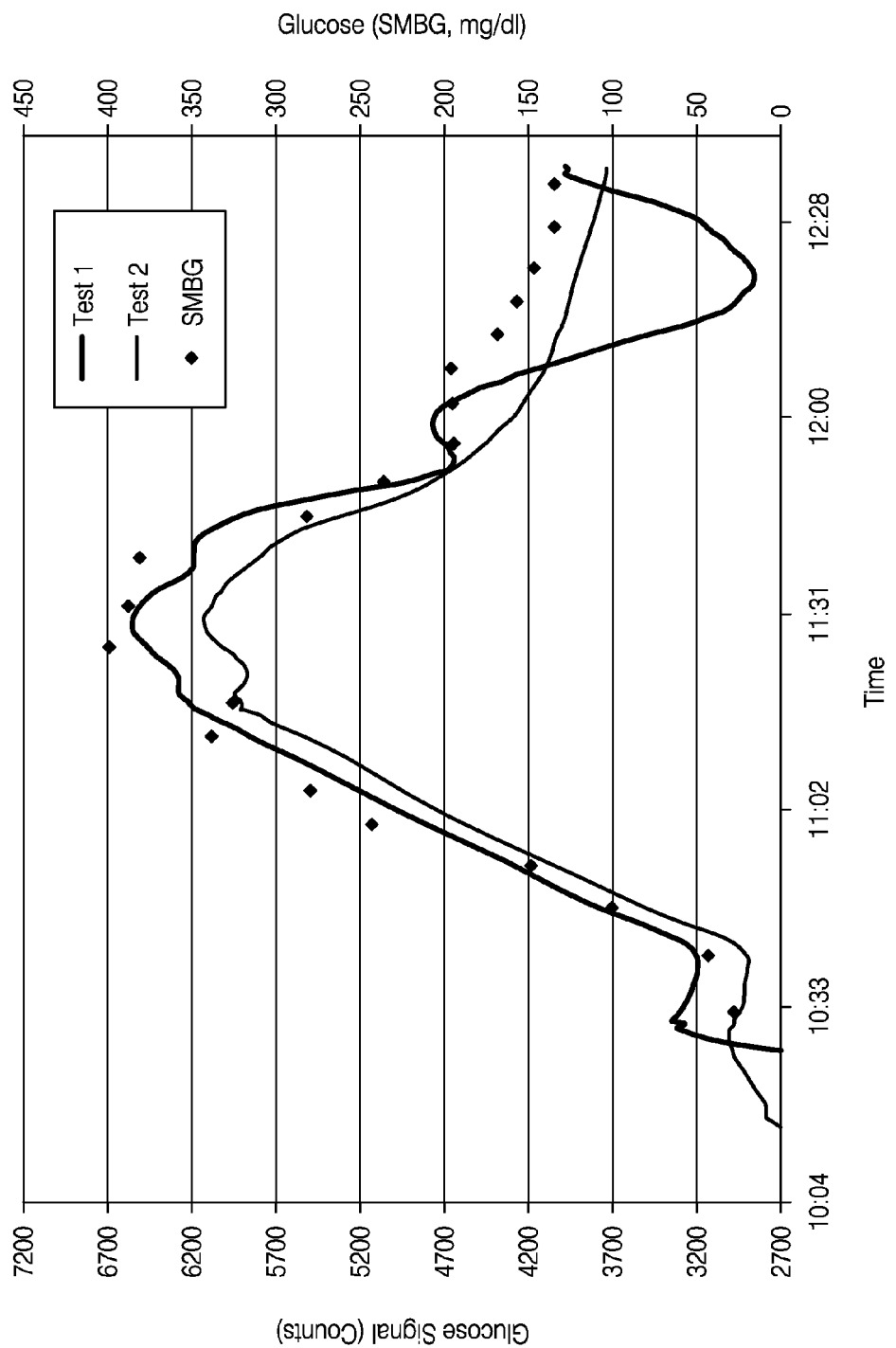

FIG. 4 is a graph illustrating in vivo function of an analyte sensor system of the embodiment shown in FIG. 1A.

Figure 5:
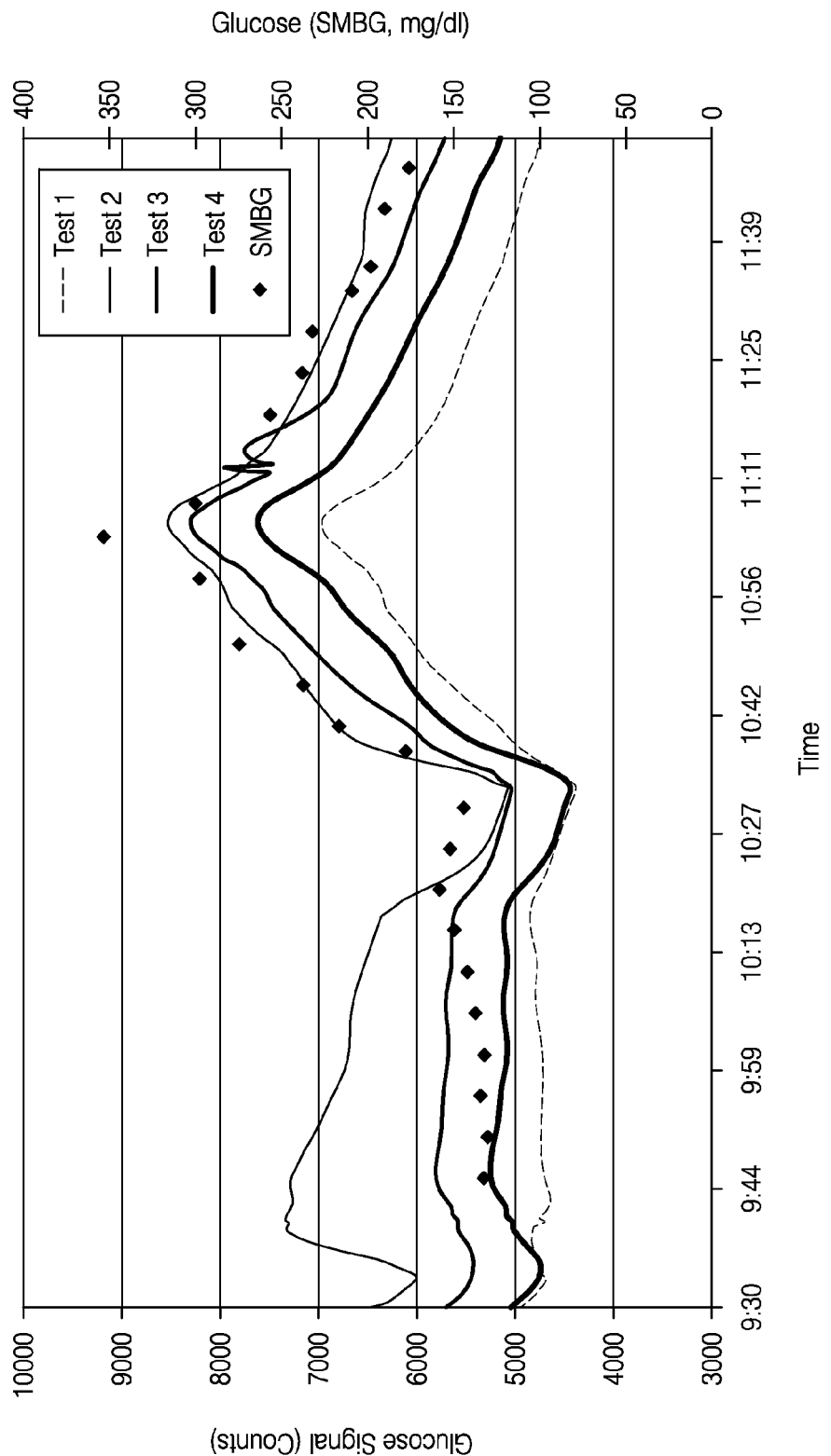

FIG. 5 is a graph illustrating in vivo function of an analyte sensor system of the embodiment shown in FIG. 1A.

Figure 6:
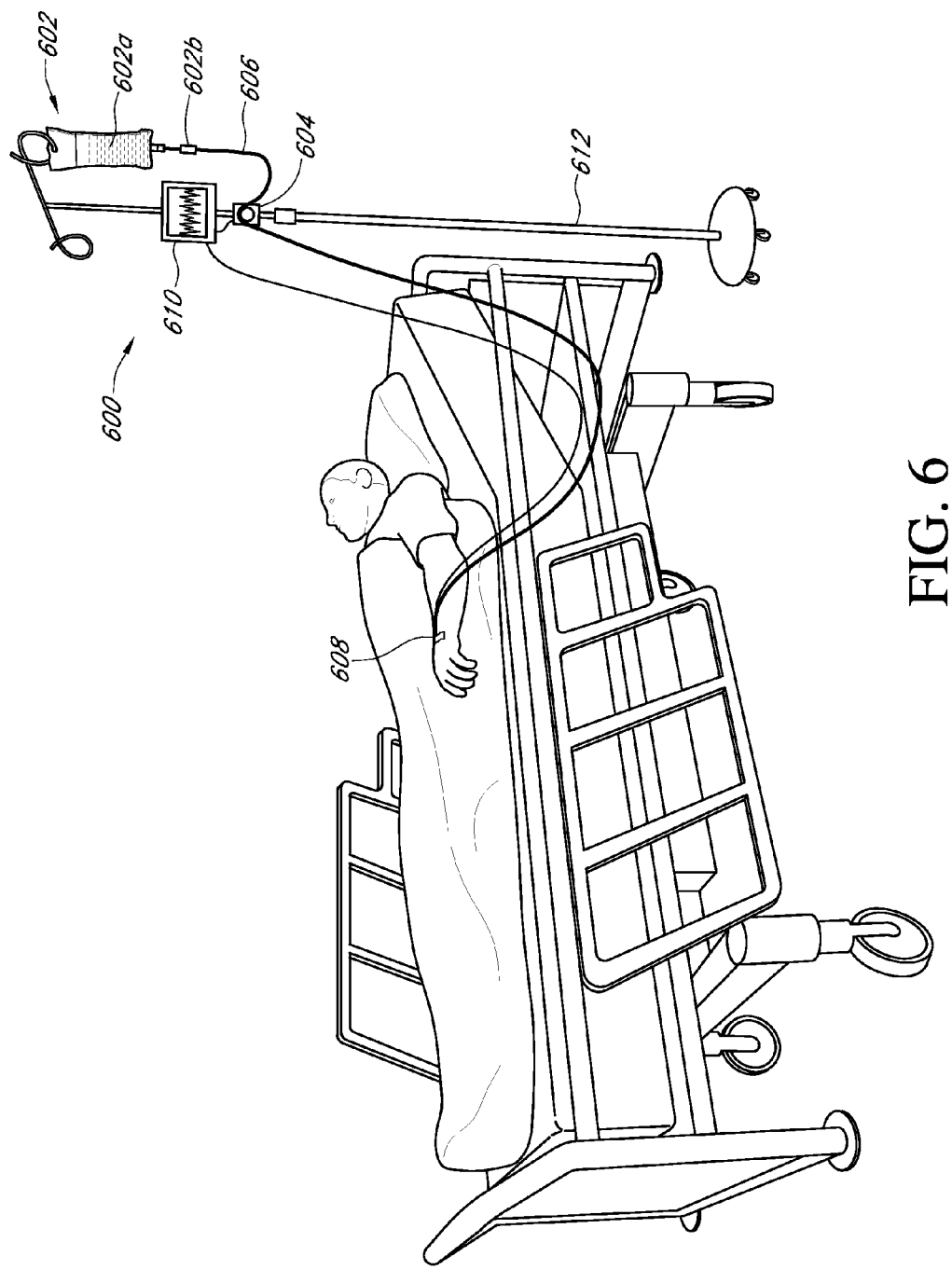

FIG. 6 is a schematic of an integrated sensor system.

Figure 7:
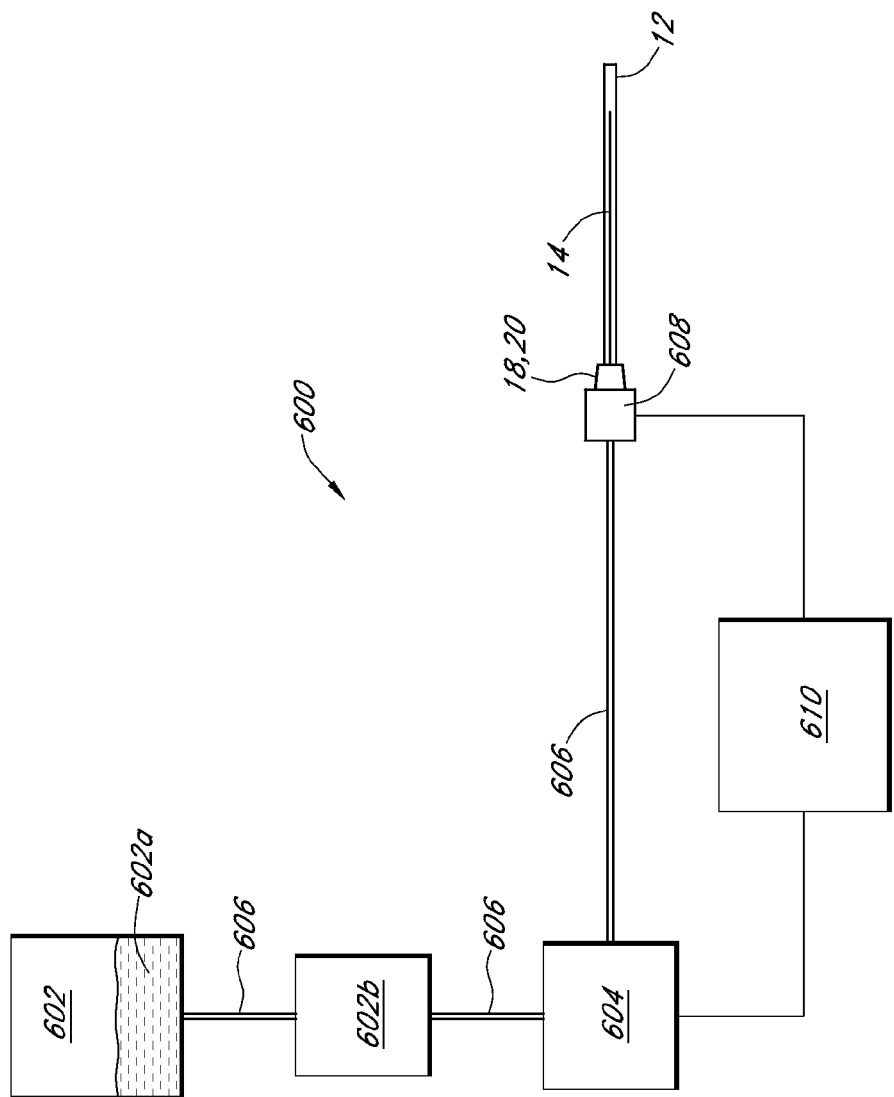

FIG. 7 is a block diagram of an integrated sensor system

Figure 8A:
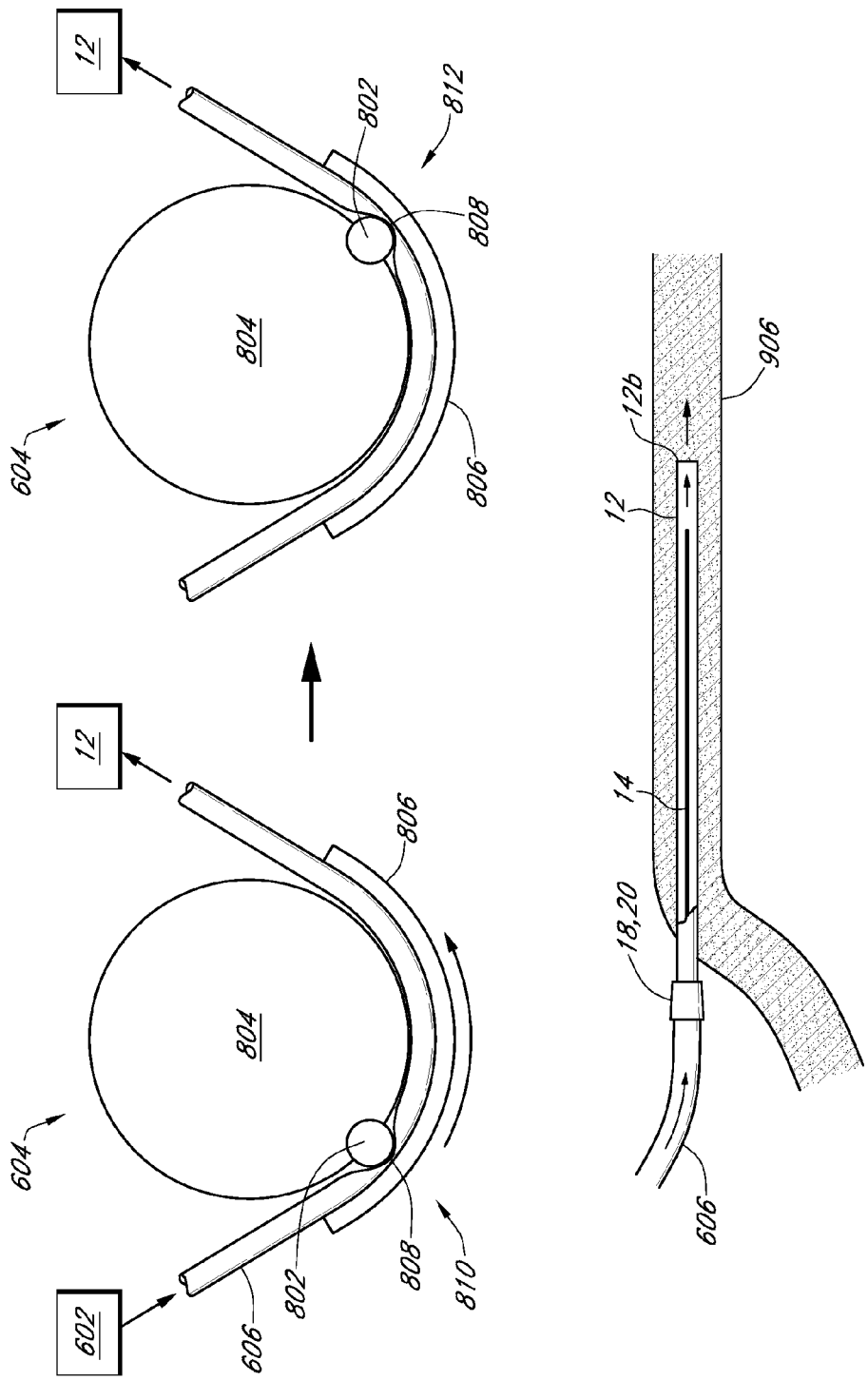
Figure 8B:
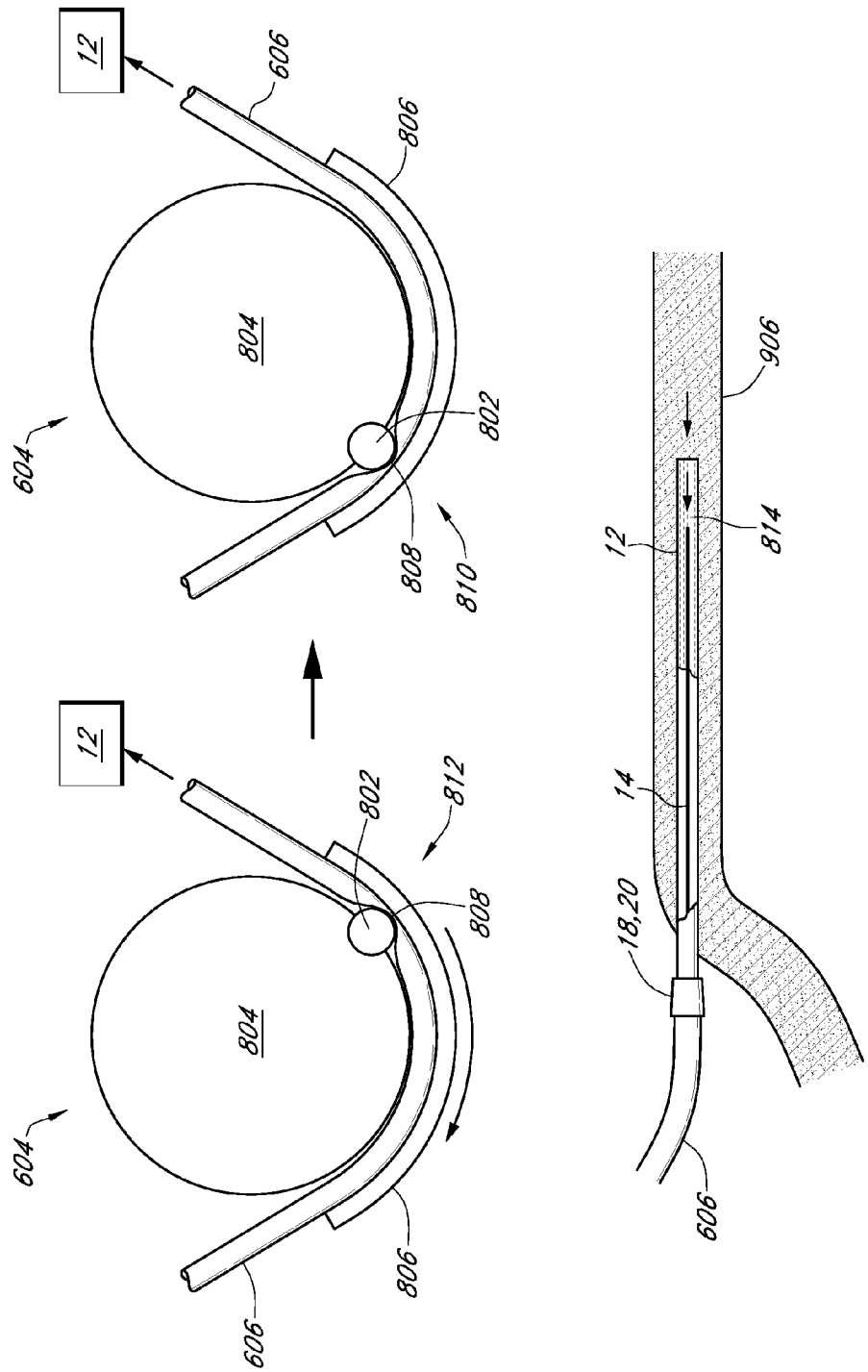
Figure 8C:
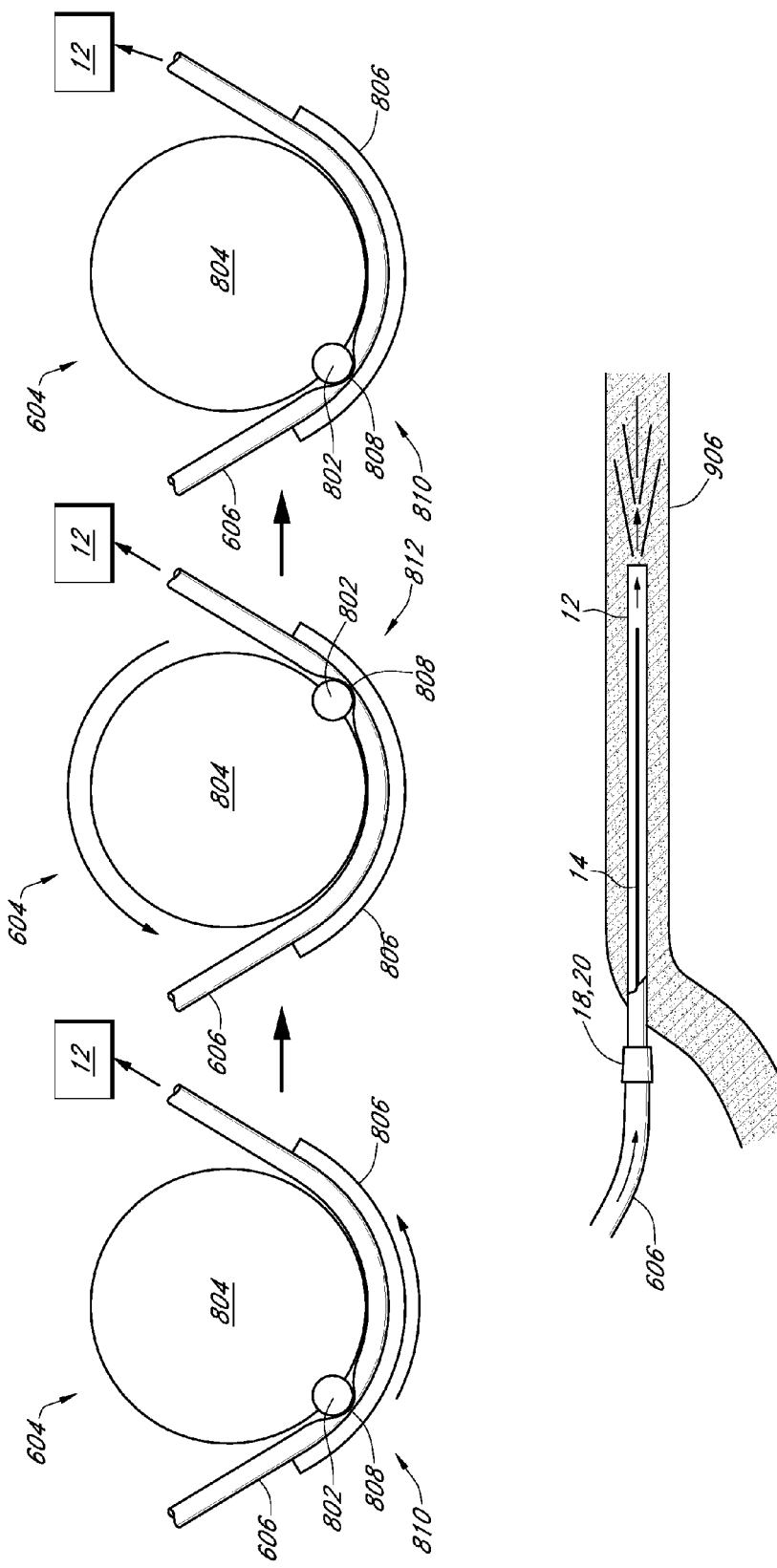

FIGS. 8A through 8C are schematic illustrations of a flow control device in one exemplary embodiment, including is relative movement/positions and the consequential effect on the flow of fluids through the sensor/catheter inserted in a host.

Figure 9:
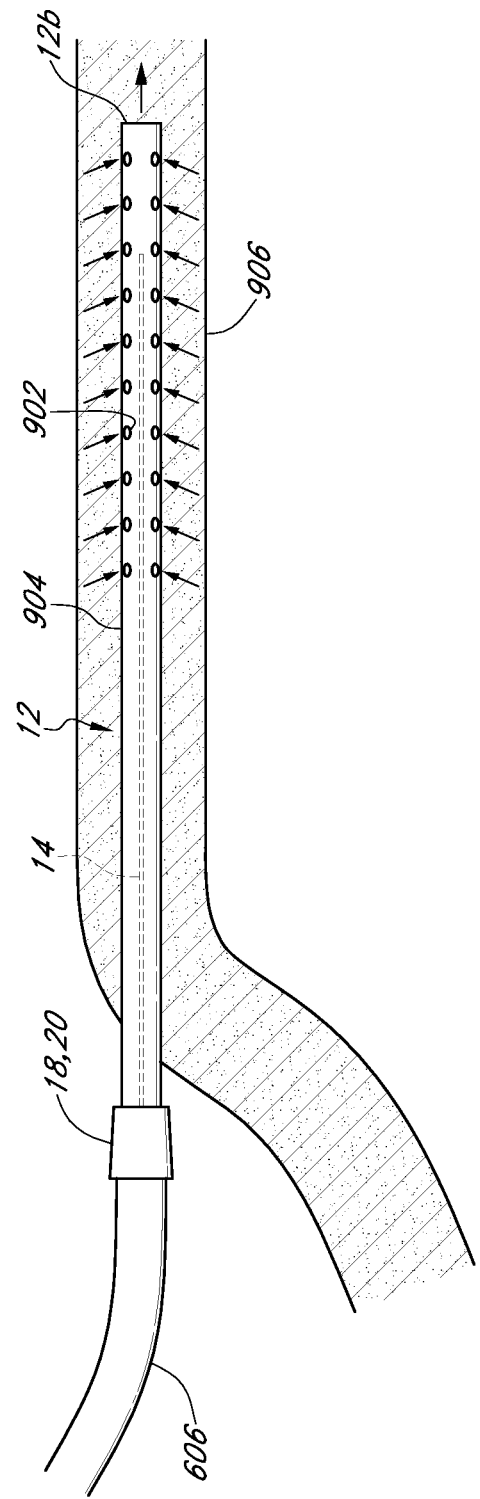

FIG. 9 is a cut-away illustration of one exemplary embodiment of a catheter implanted in a host's vessel.

Figure 10A:
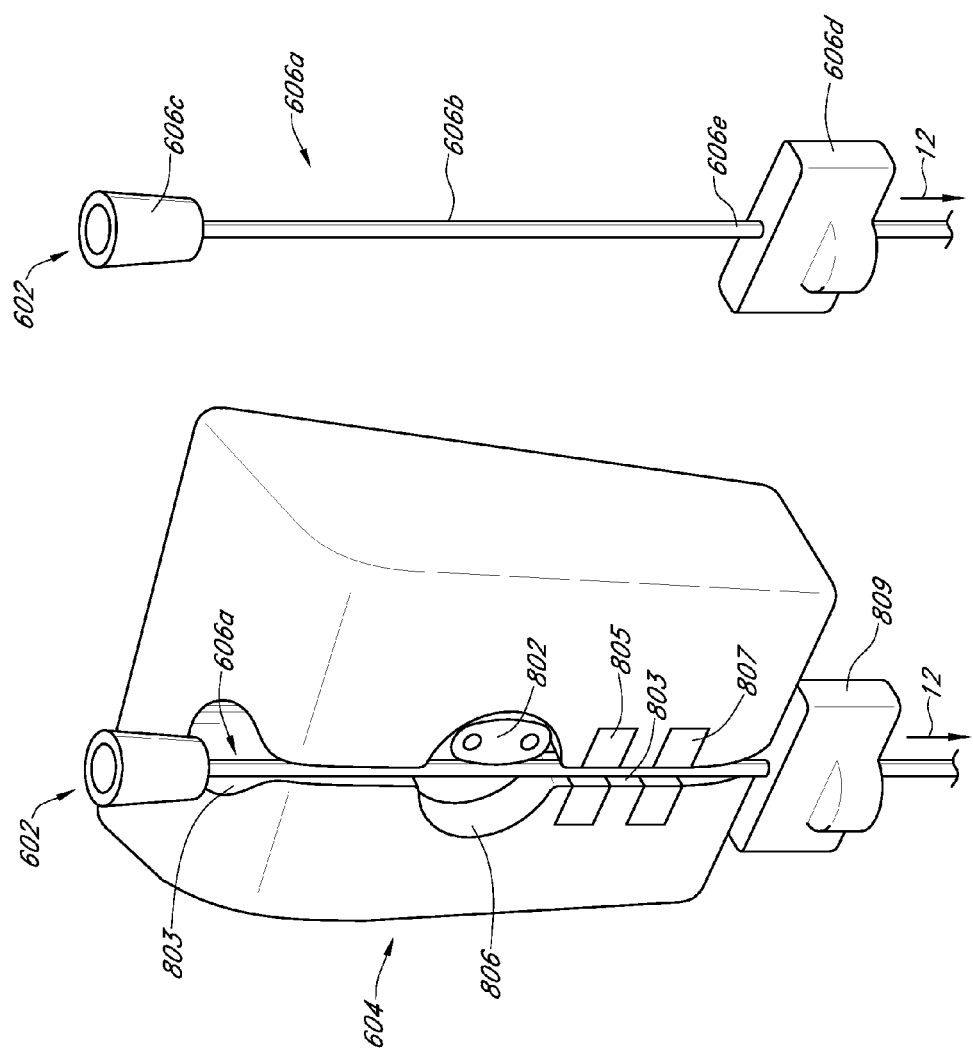

FIG. 10A is a schematic illustrating one exemplary embodiment of a flow control device and tubing assembly.

Figure 10B:
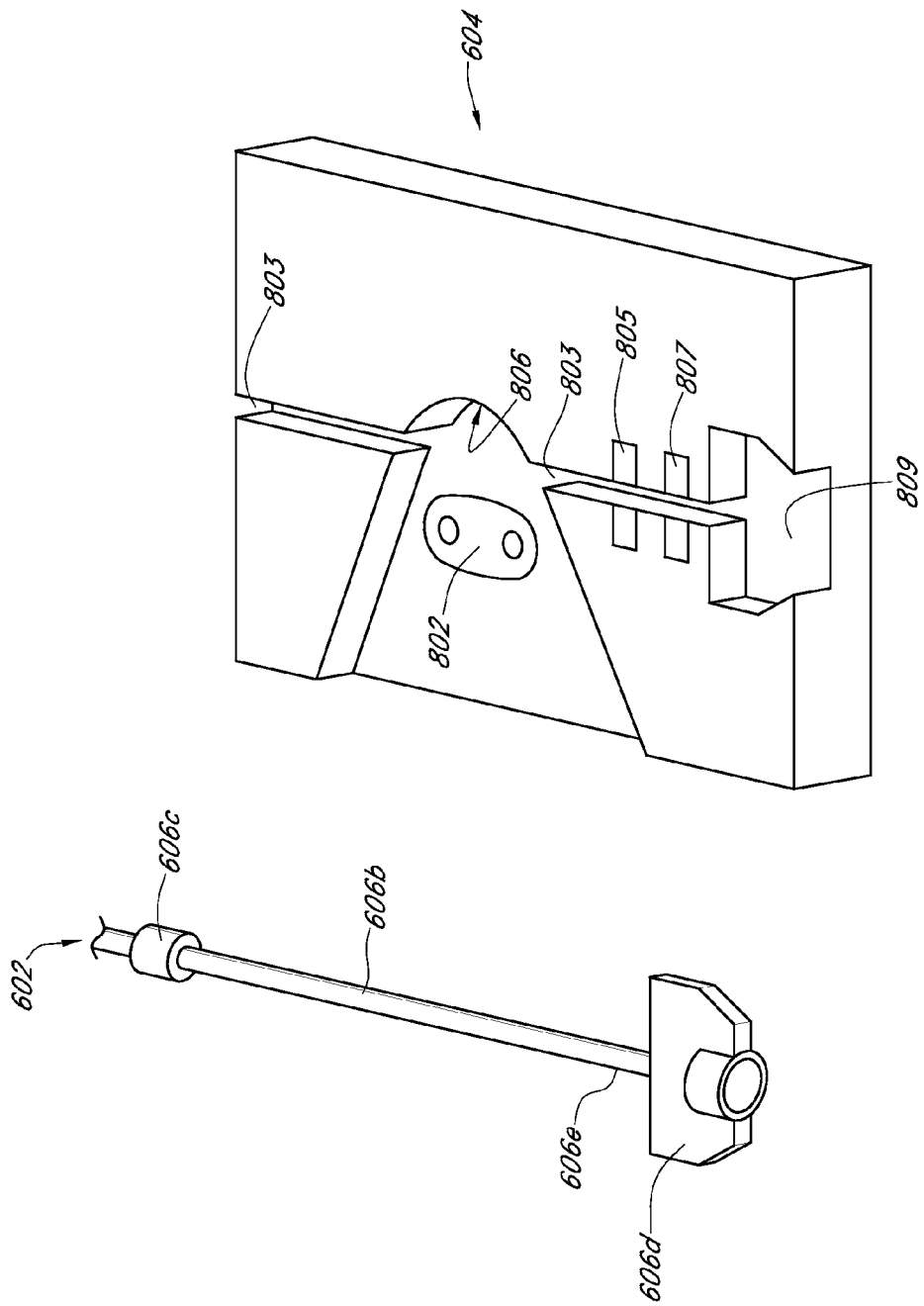

FIG. 10B is a schematic illustrating another exemplary embodiment of a flow control device and tubing assembly.

Figure 10C:
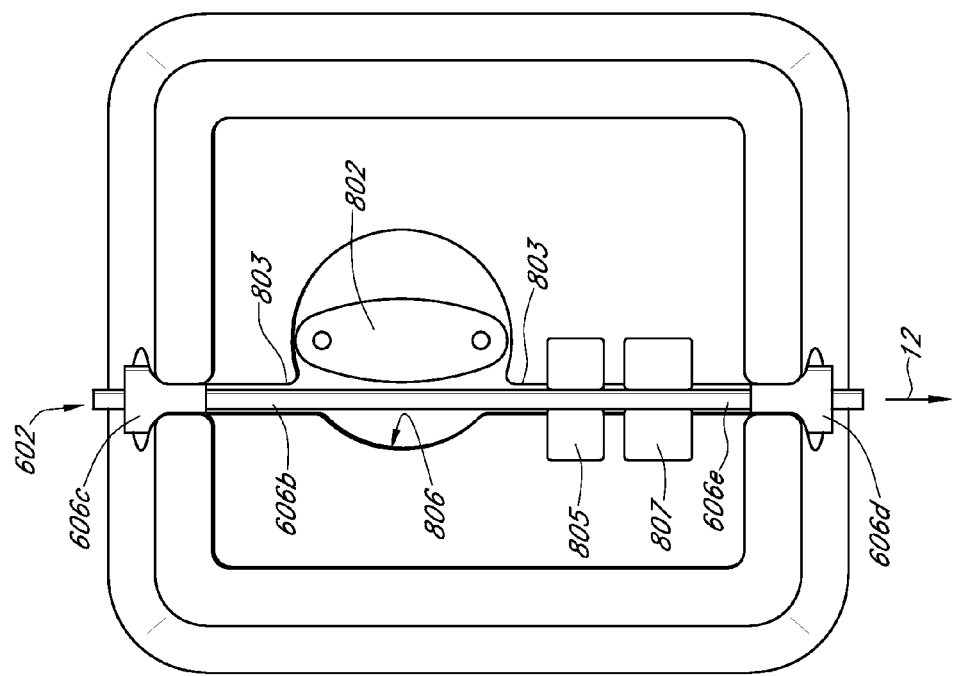

FIG. 10C is a schematic illustrating another exemplary embodiment of a flow control device with installed tubing assembly, wherein the valve is in a gravity flow position.

FIG. 10D is a schematic illustrating another exemplary embodiment of a flow control device with installed tubing assembly, wherein the valve is in a controlled-flow position.

Figure 10E:
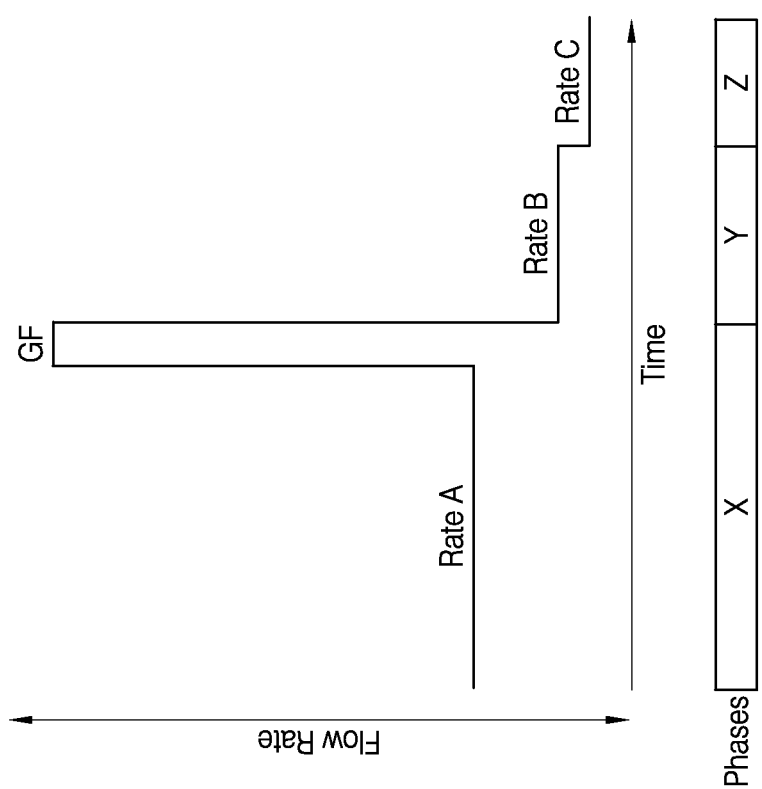

FIG. 10E is a graph illustrating an exemplary flow profile, in one embodiment.

Figure 11:
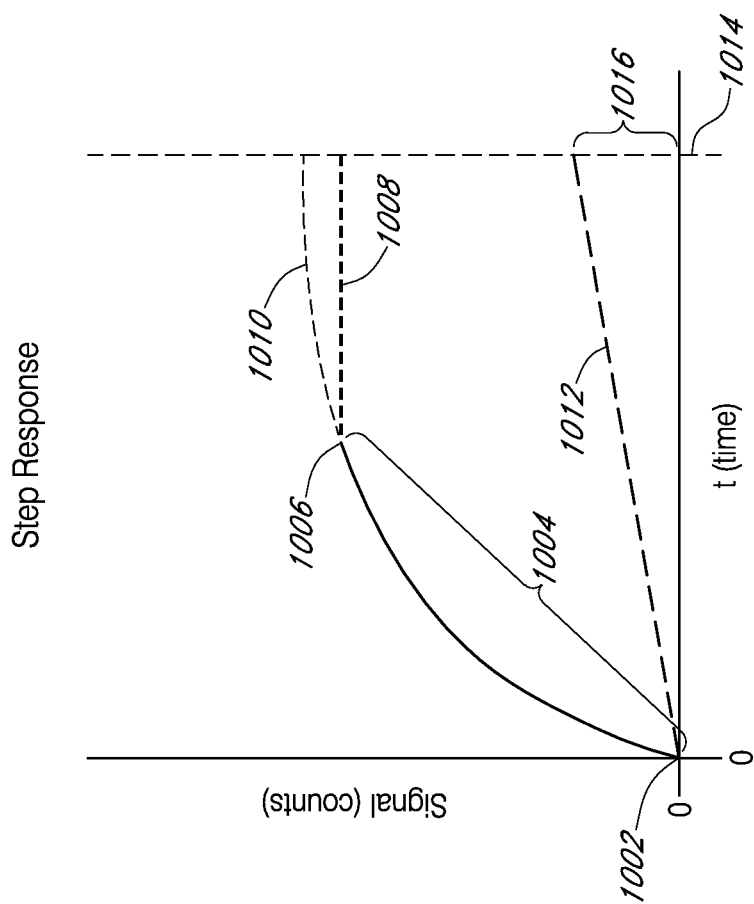

FIG. 11 is a graph that schematically illustrates a signal produced during exposure of the sensor to a step change in analyte concentration, in one exemplary embodiment.

Figure 12:
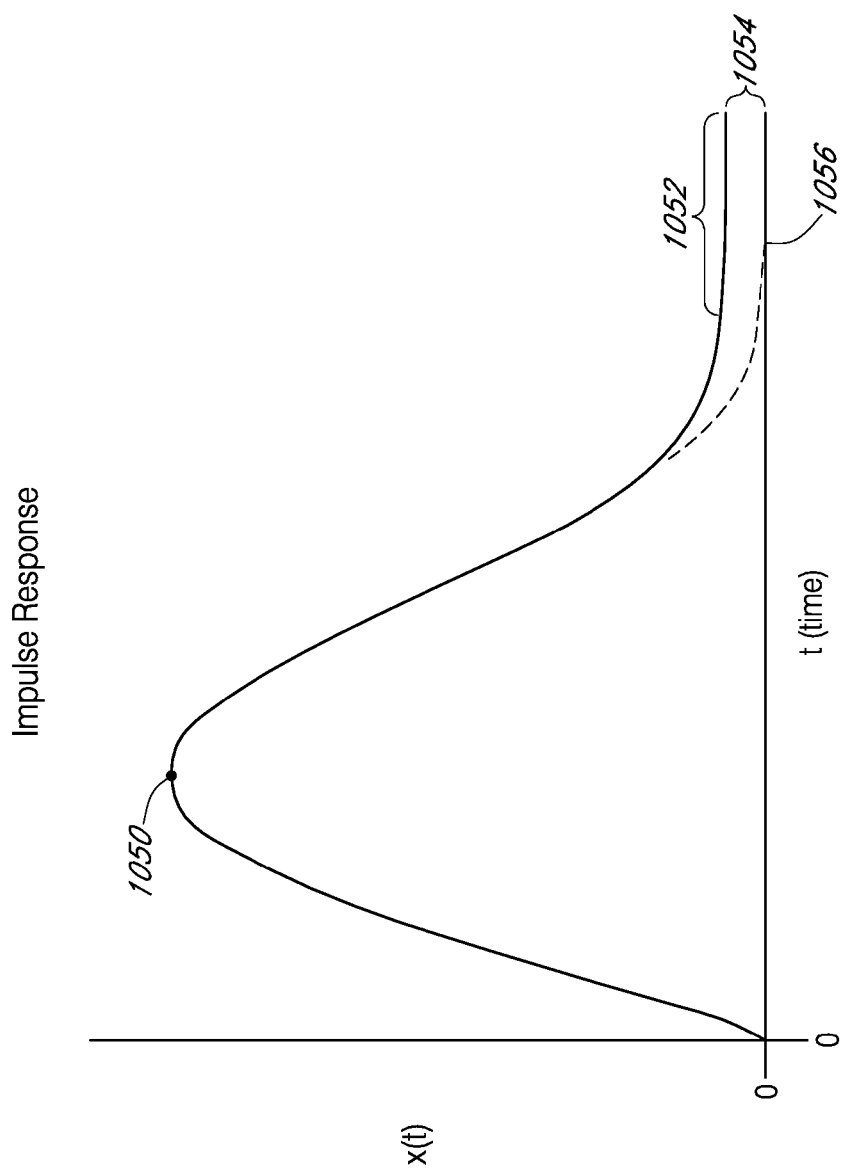

FIG. 12 is a graph that schematically illustrates a derivative of the step response shown in FIG. 9.

Figure 13:
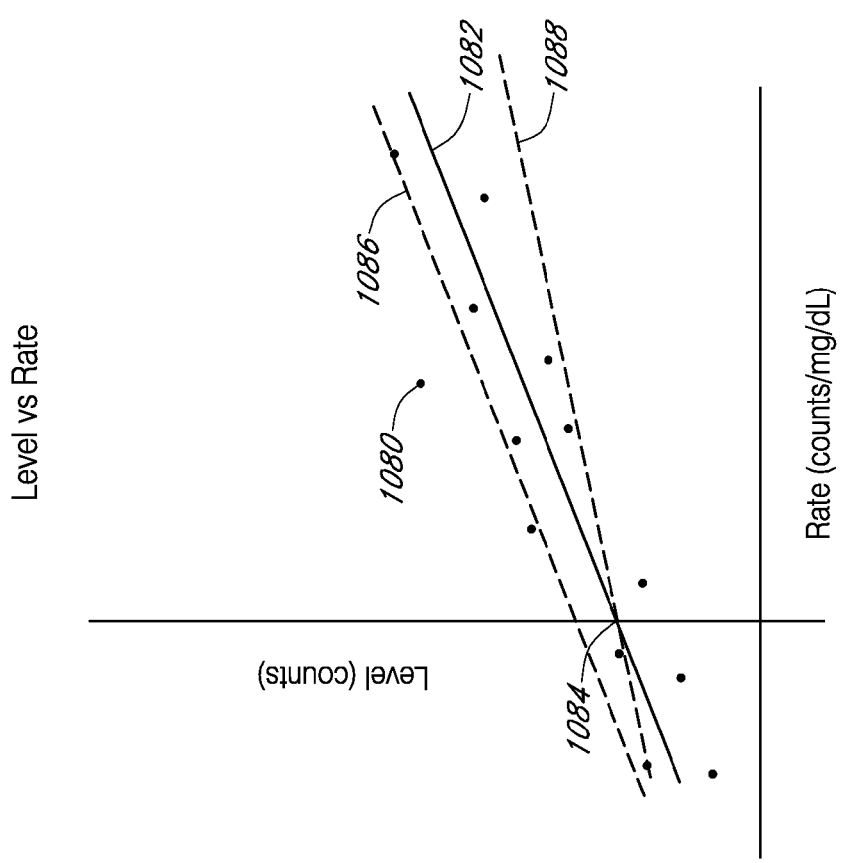

FIG. 13 is a graph that illustrates level vs. rate for a plurality of time-spaced signals associated with exposure of the sensor to biological samples of unknown or uncalibrated analyte concentration.

Figure 14:
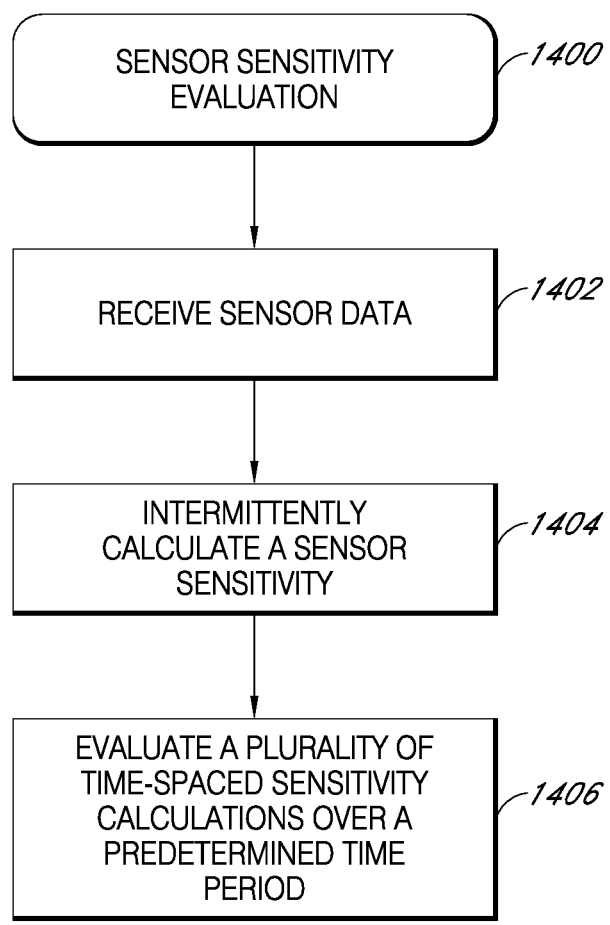

FIG. 14 is a flow chart illustrating sensor sensitivity evaluation, in one embodiment.

Figure 15:
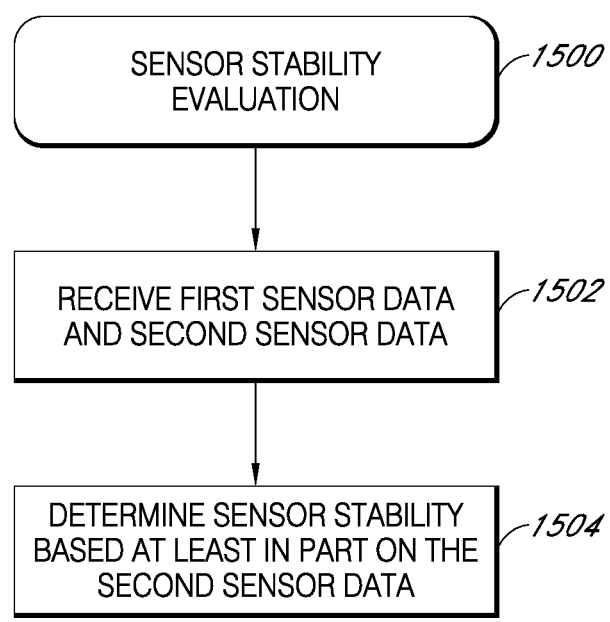

FIG. 15 is a flow chart illustrating sensor stability evaluation, in one embodiment.

Figure 16:
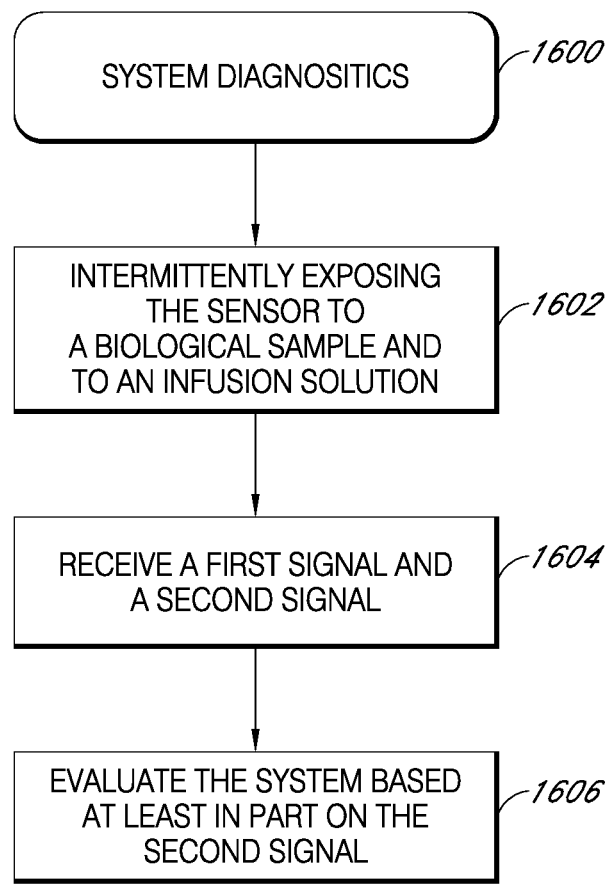

FIG. 16 is a flow chart illustrating system diagnostics, in one embodiment.

Figure 17:
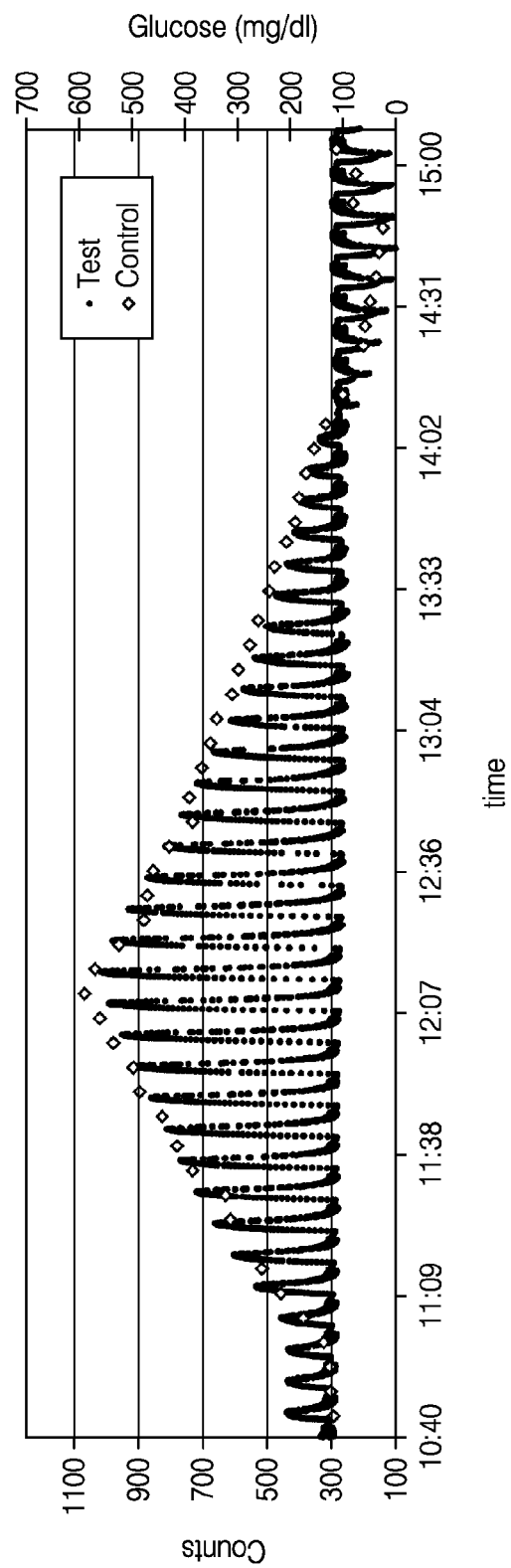

FIG. 17 is a graphical representation showing exemplary glucose sensor data and corresponding blood glucose values over time in a pig.

Figure 18:
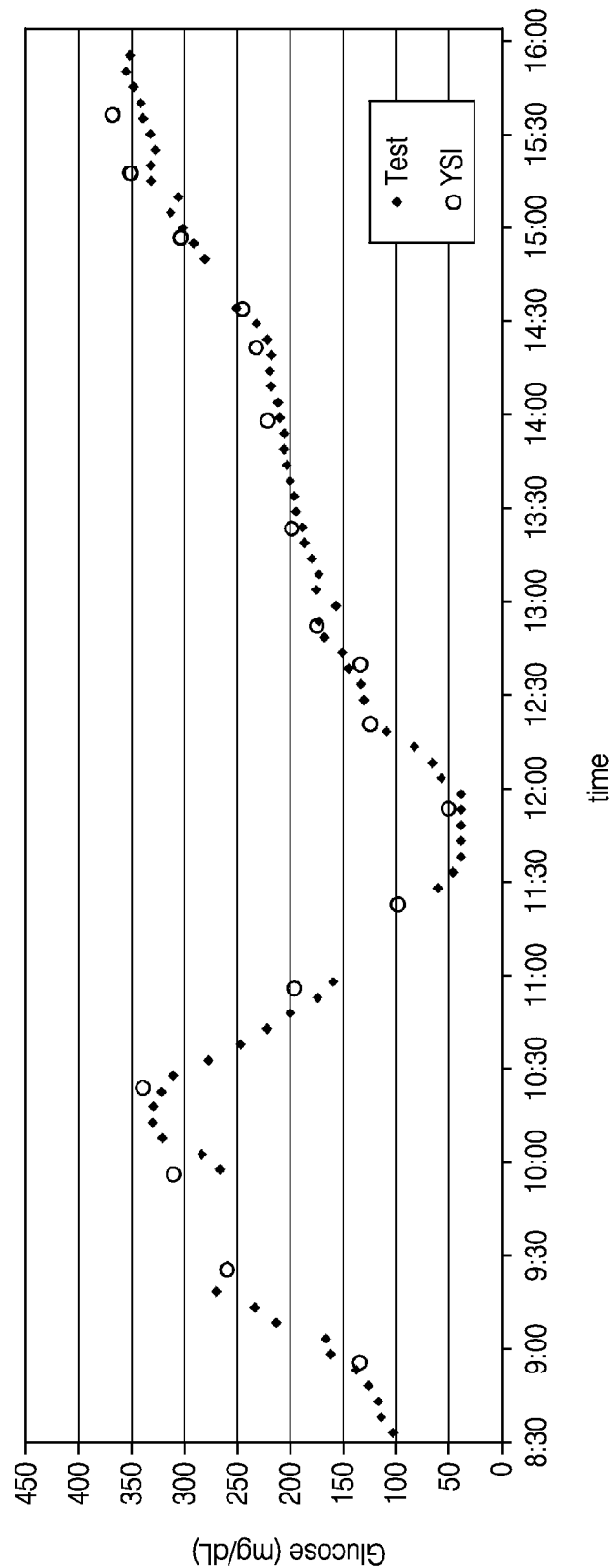

FIG. 18 is a graphical representation showing exemplary calibrated glucose sensor data (test) and corresponding blood glucose values (YSI control) over time in a human.

Figure 19A:
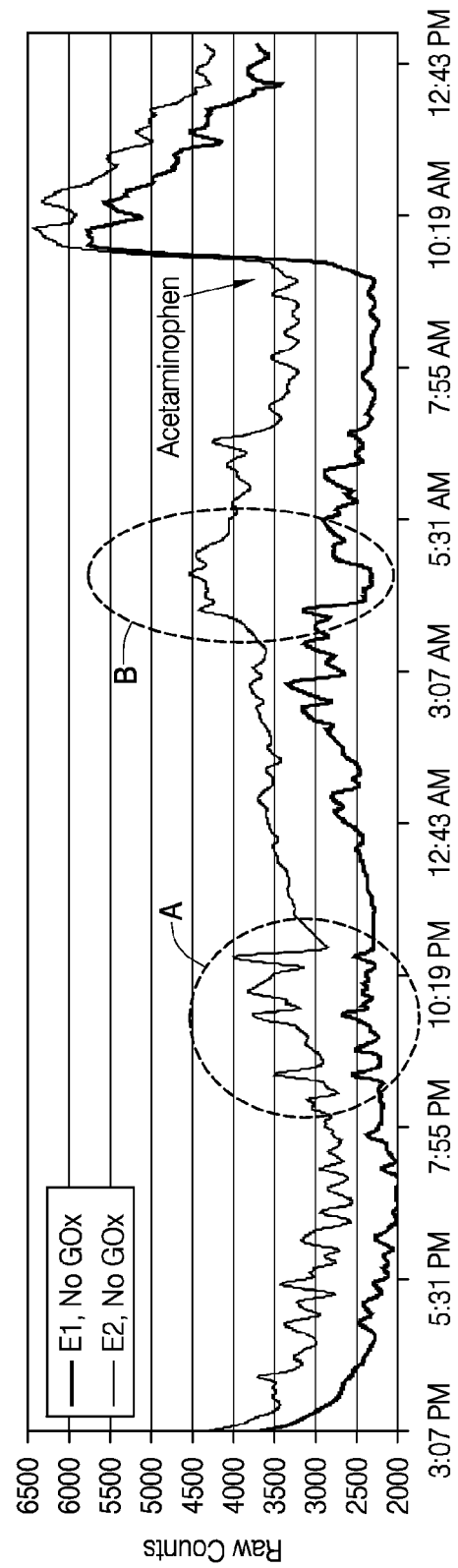

FIG. 19A is a graph that illustrates an in vivo signal (counts) detected from a dual-electrode sensor, in one embodiment, implanted in a non-diabetic human host.

Figure 19B:
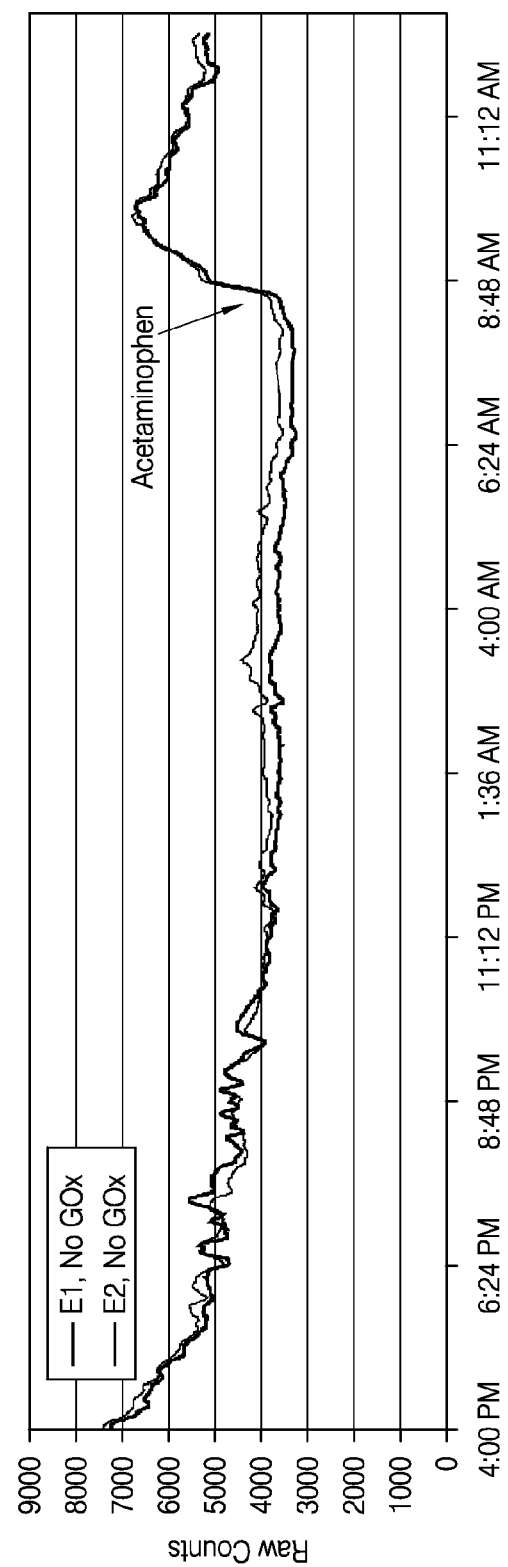

FIG. 19B is a graph that illustrates an in vivo signal (counts) detected from a dual-electrode, in another embodiment, implanted in a non-diabetic human host.

Figure 20A:
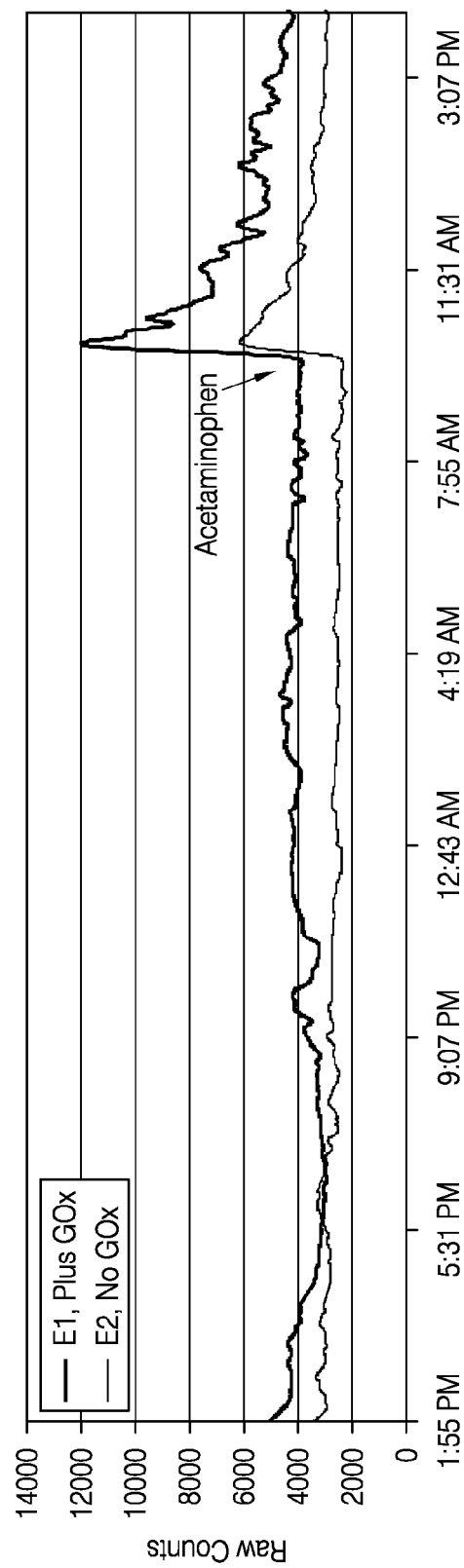

FIG. 20A is a graph that illustrates an in vivo signal (counts) detected from a dual-electrode, in one embodiment, implanted in a non-diabetic human host.

Figure 20B:
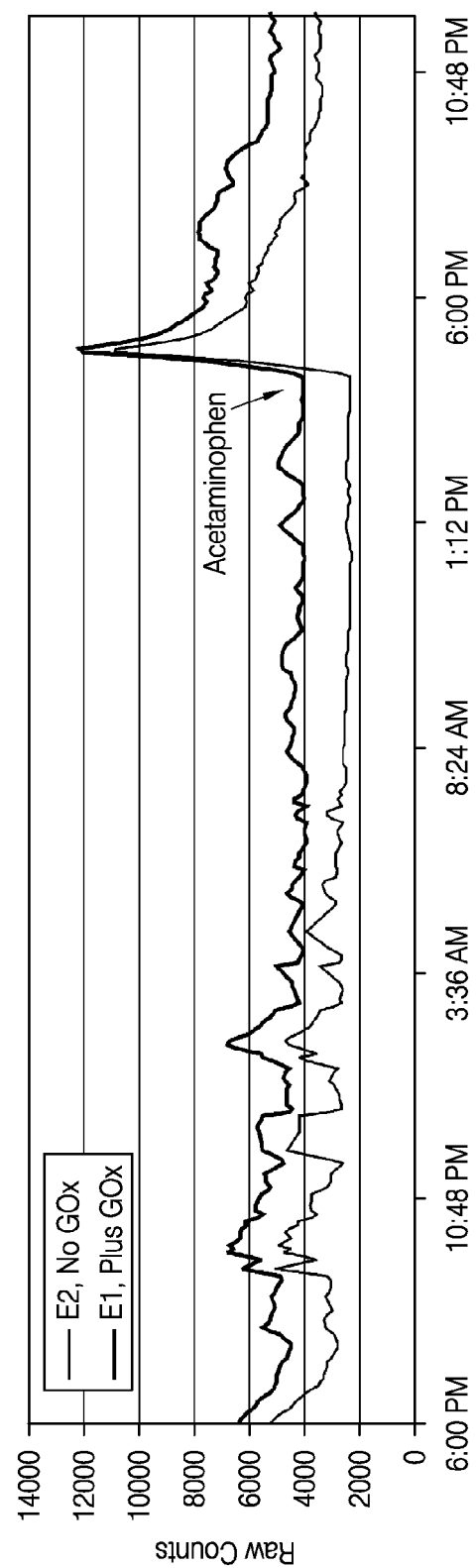

FIG. 20B is a graph that illustrates an in vivo signal (counts) detected from a dual-electrode, in another embodiment, implanted in a non-diabetic human host.

Figure 21A:
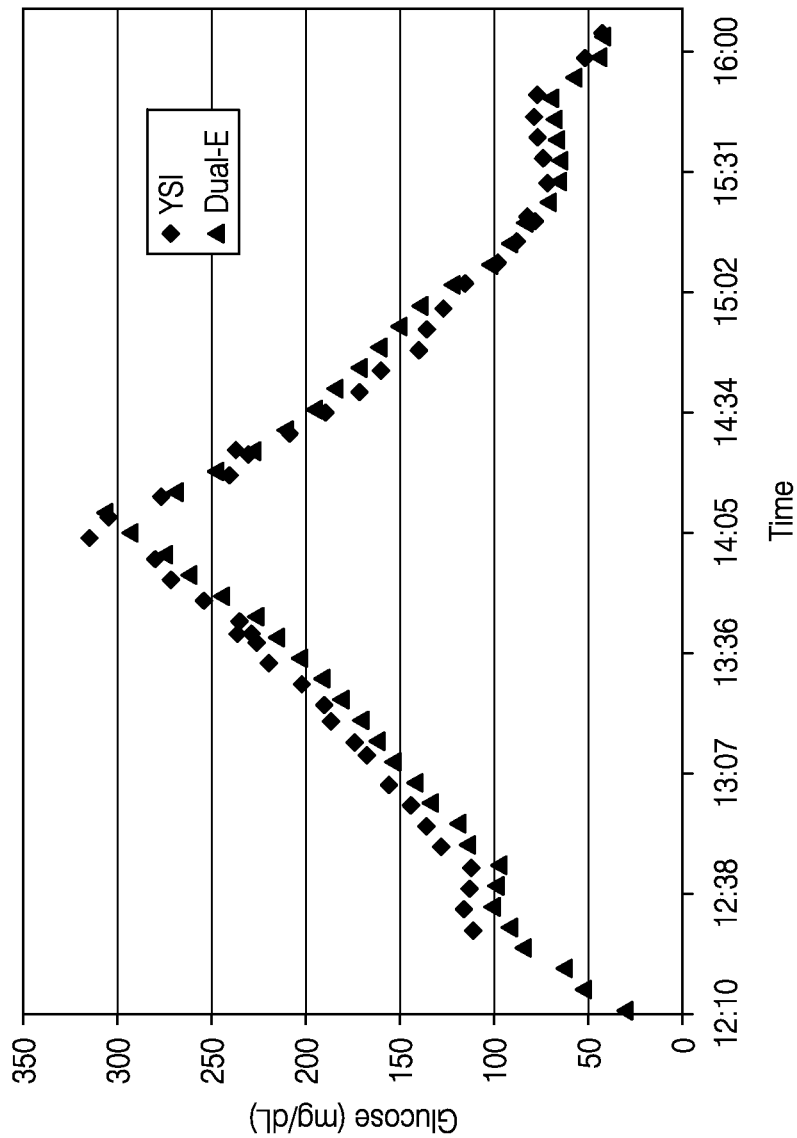

FIG. 21A is a graph that illustrates an in vivo glucose values detected from a dual-electrode, in another embodiment, implanted in a non-diabetic porcine host.

Figure 21B:
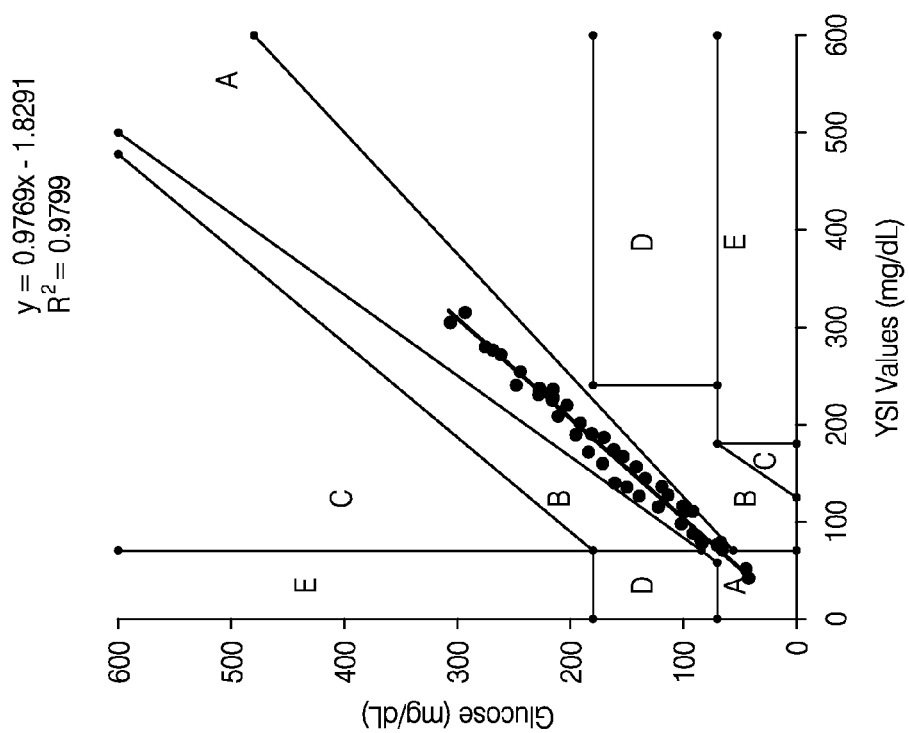

FIG. 21B is a Clark Error Grid graph of the data of FIG. 21A.

Figure 22:
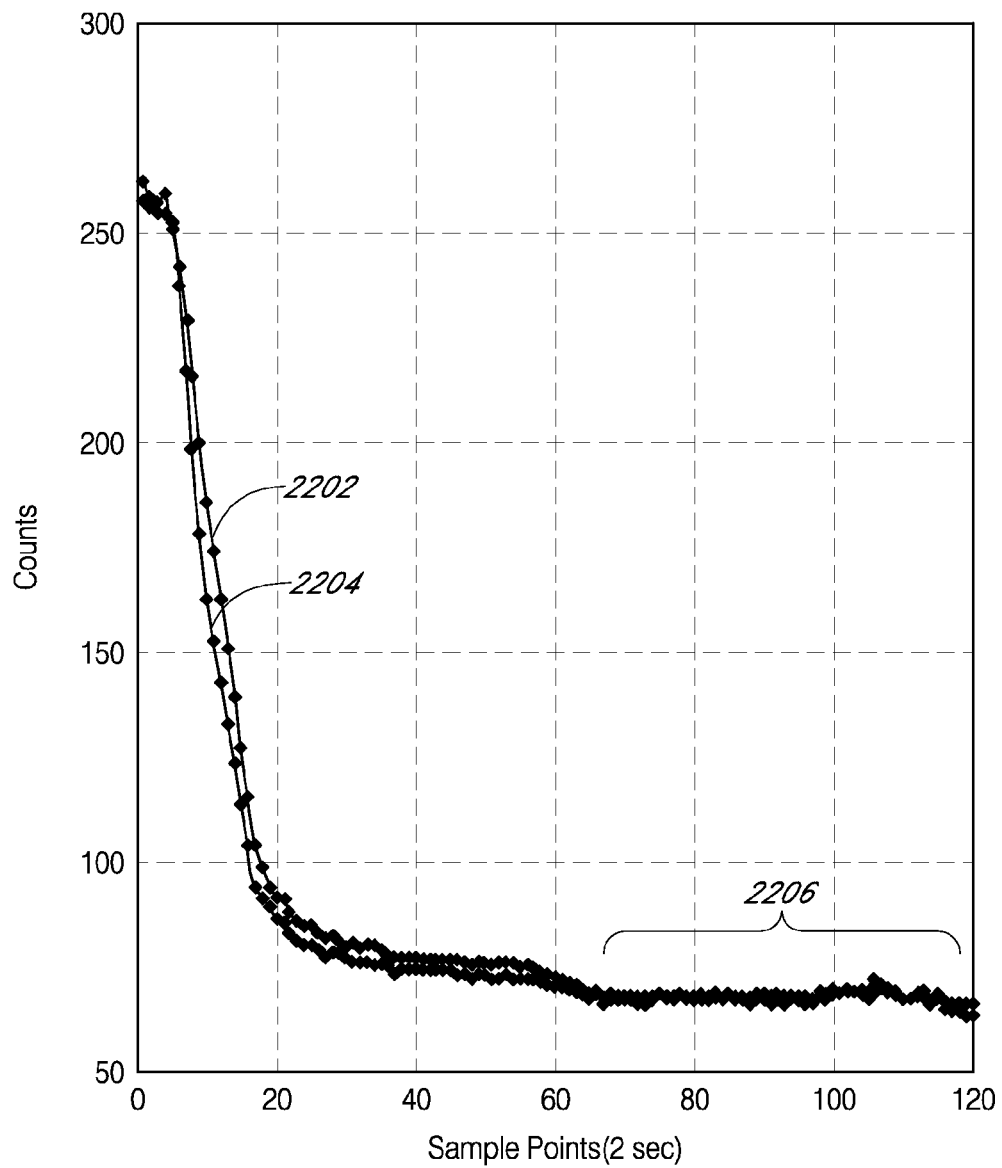

FIG. 22 is a graph of a signal waveform generated during a successful infusion of the reference solution into the host versus the adaptive calibration waveform template.

Figure 23:
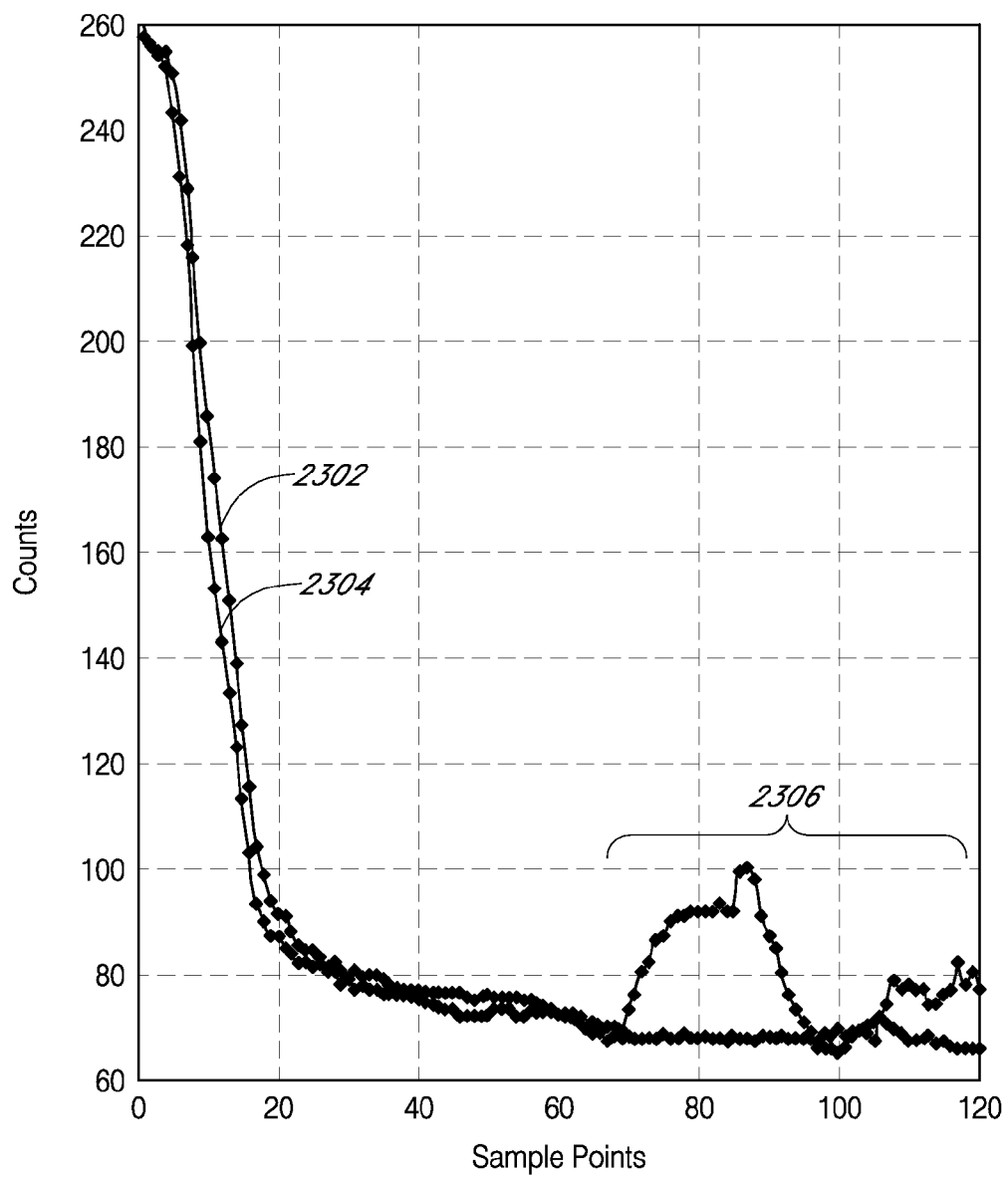

FIG. 23 is a graph of a signal waveform generated during an unsuccessful infusion of the reference solution into the host versus the adaptive calibration waveform template.

Figure 24:
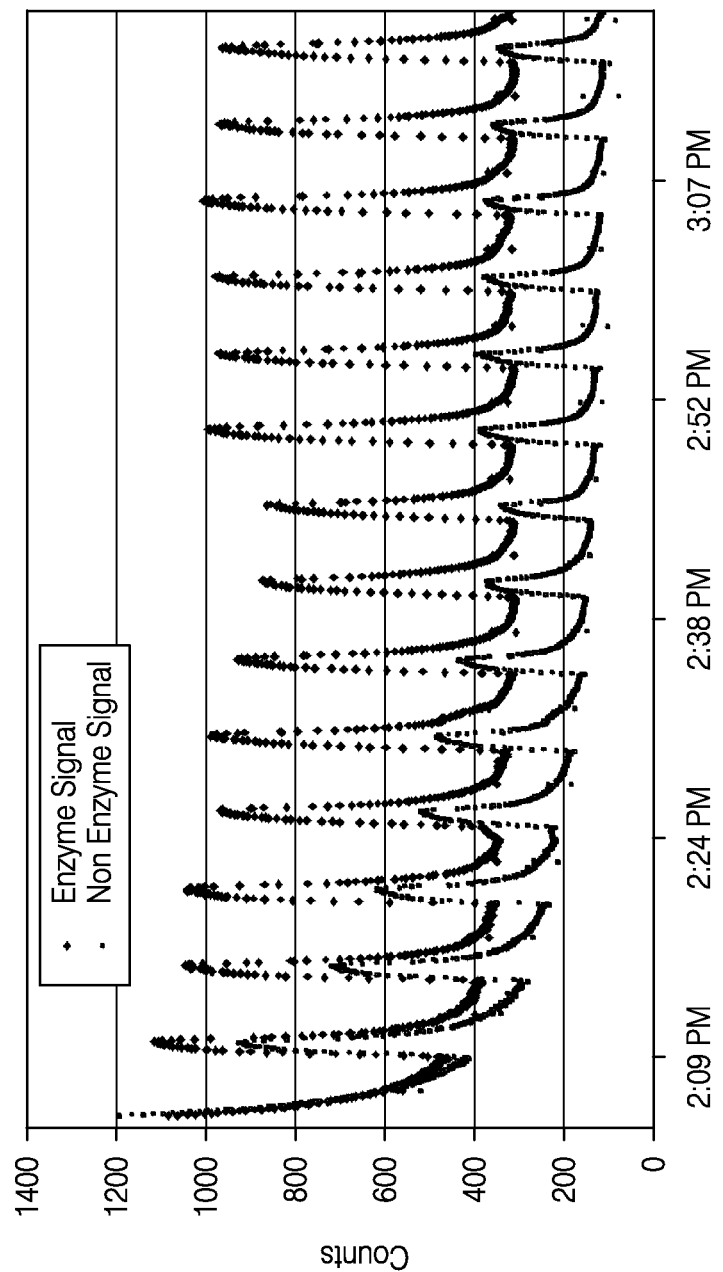

FIG. 24 is a graph of the signals generated from the plus-enzyme working electrode and from the no-enzyme working electrode illustrating sensor stabilization.

Figure 25:
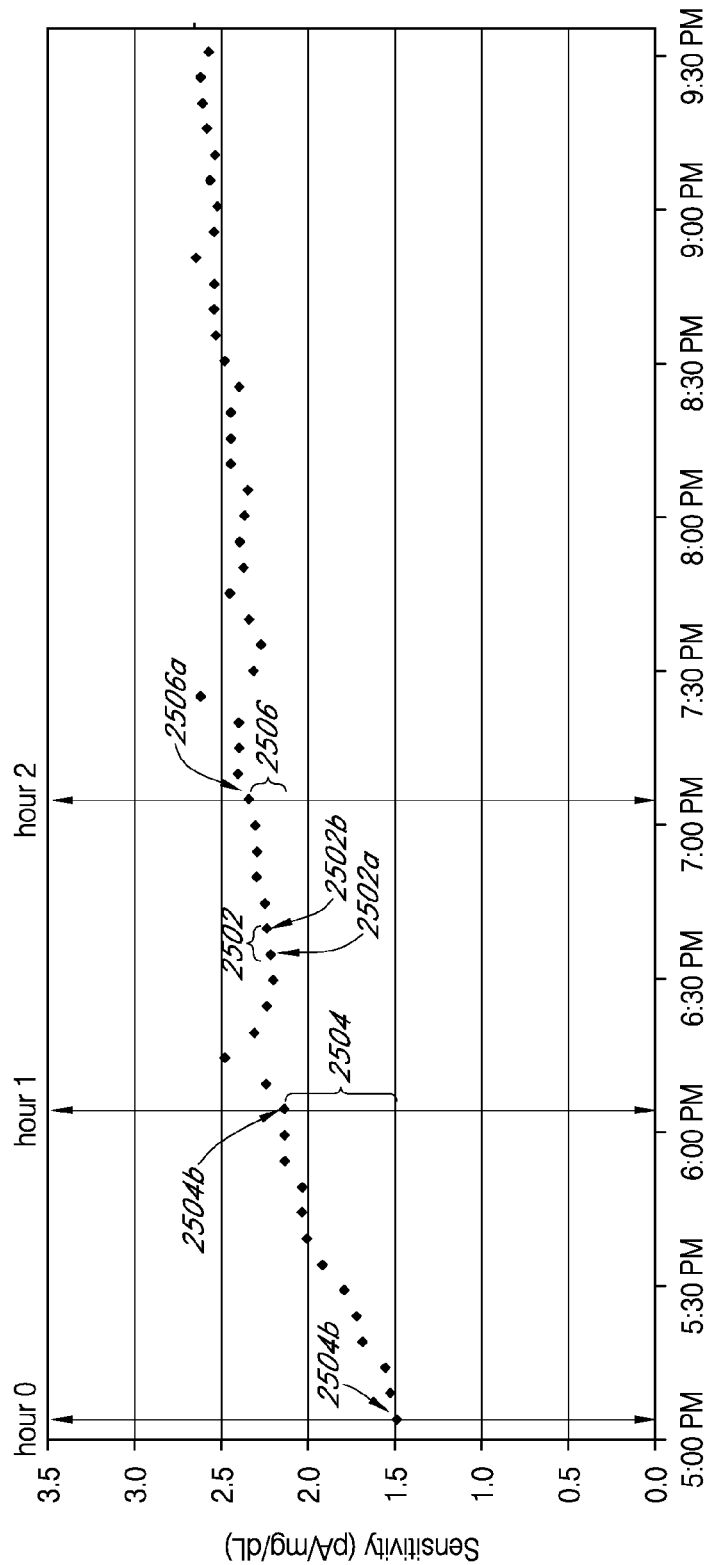

FIG. 25 is a graph illustrating sensor sensitivity over time.

DETAILED DESCRIPTION OF THE PREFERRED EMBODIMENT

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the preferred embodiments.

DEFINITIONS

In order to facilitate an understanding of the preferred embodiments, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological sample (e.g., bodily fluids, including, blood, serum, plasma, interstitial fluid, cerebral spinal fluid, lymph fluid, ocular fluid, saliva, oral fluid, urine, excretions or exudates). Analytes can include naturally occurring substances, artificial substances, metabolites, and/or reaction products. In some embodiments, the analyte for measurement by the sensing regions, devices, and methods is albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, metabolic markers, and drugs. However, other analytes are contemplated as well, including but not limited to acetaminophen, dopamine, ephedrine, terbutaline, ascorbate, uric acid, oxygen, d-amino acid oxidase, plasma amine oxidase, xanthine oxidase, NADPH oxidase, alcohol oxidase, alcohol dehydrogenase, pyruvate dehydrogenase, diols, Ros, NO, bilirubin, cholesterol, triglycerides, gentisic acid, ibuprophen, L-Dopa, methyl dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, *Myoglobin*, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin);

narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The term "antegrade" as used herein is a broad term, and is to be given its ordinary and customary meaning to a person of ordinary skill in the art (and are not to be limited to a special or customized meaning), and refers without limitation to orientation (e.g., of a catheter) with the direction of blood flow.

The term "baseline," "noise" and "background signal" as used herein are broad terms, and are to be given their ordinary and customary meaning to a person of ordinary skill in the art (and is not to be limited to a special or customized meaning), and refers without limitation to a component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation/reduction potential that overlaps with hydrogen peroxide). In some embodiments wherein a calibration is defined by solving for the equation $y=mx+b$, the value of b represents the baseline, or background, of the signal.

The terms "baseline and/or sensitivity shift," "baseline and/or sensitivity drift," "shift," and "drift" as used herein are broad terms, and are to be given their ordinary and customary meaning to a person of ordinary skill in the art (and are not to be limited to a special or customized meaning), and refer without limitation to a change in the baseline and/or sensitivity of the sensor signal over time. While the term "shift" generally refers to a substantially distinct change over a relatively short time period, and the term "drift" generally refers to a substantially gradual change over a relatively longer time period, the terms can be used interchangeably and can also be generally referred to as "change" in baseline and/or sensitivity.

The term "biological sample" as used herein is a broad term, and is to be given its ordinary and customary meaning to a person of ordinary skill in the art (and it is not to be limited to a special or customized meaning), and refers without limitation to a sample of a host body, for example, blood, serum, plasma, interstitial fluid, cerebral spinal fluid, lymph fluid, ocular fluid, saliva, oral fluid, urine, sweat, excretions, exudates, and the like.

The term "blood chemistry analysis device" as used herein is a broad term, and is to be given its ordinary and customary meaning to a person of ordinary skill in the art (and are not to be limited to a special or customized meaning), and refers without limitation to a device that measures a variety of blood components, characteristics or analytes therein. In one embodiment, a blood chemistry analysis device periodically withdraws an aliquot of blood from the host, measures glucose, $O_2$, $CO_2$, $PCO_2$, $PO_2$, potassium, sodium, pH, lactate, urea, bilirubin, creatinine, hematocrit, various minerals, and/or various metabolites, and the like, and returns the blood to the host's circulatory system. A variety of devices exist for testing various blood properties/analytes at the bedside, such as but not limited to the blood gas and chemistry devices manufactured by Via Medical (Austin, Tex., USA).

The term "blood pressure monitor" as used herein is a broad term, and is to be given its ordinary and customary meaning to a person of ordinary skill in the art (and are not to be limited to a special or customized meaning), and refers without limitation to an instrument for monitoring the blood pressure of a human or other animal. For example, a blood pressure monitor can be an invasive blood pressure monitor, which periodically monitors the host's blood pressure via a peripheral artery, using a blood pressure transducer, such as but not limited to a disposable blood pressure transducer. Utah Medical Products Inc. (Midvale, Utah, USA) produces a variety of DELTRAN® Brand disposable blood pressure transducers that are suitable for use with various embodiments disclosed herein.

The term "calibration" as used herein is a broad term, and is to be given its ordinary and customary meaning to a person of ordinary skill in the art (and is not to be limited to a special or customized meaning), and refers without limitation to the relationship and/or process of determining the relationship between the sensor data and the corresponding reference data, which can be used to convert sensor data into values substantially equivalent to the reference data. In some embodiments, namely, in continuous analyte sensors, calibration can be updated or recalibrated over time if changes in the relationship between the sensor data and reference data occur, for example, due to changes in sensitivity, baseline, transport, metabolism, and the like.

The term "casting" as used herein is a broad term, and is to be given its ordinary and customary meaning to a person of ordinary skill in the art (and is not to be limited to a special or customized meaning), and refers without limitation to a process where a fluid material is applied to a surface or surfaces and allowed to cure or dry. The term is broad enough to encompass a variety of coating techniques, for example, using a draw-down machine (i.e., drawing-down), dip coating, spray coating, spin coating, and the like.

The term "catheter" as used herein is a broad term, and is to be given its ordinary and customary meaning to a person of ordinary skill in the art (and are not to be limited to a special or customized meaning), and refers without limitation to a tube that can be inserted into a host's body (e.g., cavity, duct or vessel). In some circumstances, catheters allow drainage or injection of fluids or access by medical instruments or devices. In some embodiments, a catheter is a thin, flexible tube (e.g., a "soft" catheter). In alternative embodiments, the catheter can be a larger, solid tube (e.g., a "hard" catheter). The term "cannula" is interchangeable with the term "catheter" herein.

The term "coaxial" as used herein is a broad term, and is to be given its ordinary and customary meaning to a person of ordinary skill in the art (and it is not to be limited to a special or customized meaning), and refers without limitation to having a common axis, having coincident axes or mounted on concentric shafts.

The term "constant analyte" as used herein is a broad term, and is to be given its ordinary and customary meaning to a person of ordinary skill in the art (and it is not to be limited to a special or customized meaning), and refers without limitation to an analyte that remains relatively constant over a time period, for example over an hour to a day as compared to other variable analytes. For example, in a person with diabetes, oxygen and urea may be relatively constant analytes in particular tissue compartments relative to glucose, which is known to oscillate between about 40 and 400 mg/dL during a 24-hour cycle. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The terms "constant noise" and "constant background" as used herein are broad terms, and are to be given their ordinary and customary meaning to a person of ordinary skill in the art (and it is not to be limited to a special or customized meaning), and refer without limitation to the component of the background signal that remains relatively constant over time. For example, certain electroactive compounds found in the human body are relatively constant factors (e.g., baseline of the host's physiology) and do not significantly adversely affect accuracy of the calibration of the glucose concentration (e.g., they can be relatively constantly eliminated using the equation y=mx+b). In some circumstances, constant background noise can slowly drift over time (e.g., increases or decreases), however this drift need not adversely affect the accuracy of a sensor, for example, because a sensor can be calibrated and re-calibrated and/or the drift measured and compensated for.

The terms "continuous" and "continuously" as used herein are broad terms, and are to be given their ordinary and customary meanings to a person of ordinary skill in the art (and are not to be limited to a special or customized meaning), and refer without limitation to the condition of being marked by substantially uninterrupted extension in space, time or sequence. In one embodiment, an analyte concentration is measured continuously or continually, for example at time intervals ranging from fractions of a second up to, for example, about 1, 2, 5, 10, 15, 20, 30, 40, 50 or 60 minutes, or longer. It should be understood that continuous glucose sensors generally continually measure glucose concentration without required user initiation and/or interaction for each measurement, such as described with reference to U.S. Pat. No. 6,001,067, for example. These terms include situations wherein data gaps can exist (e.g., when a continuous glucose sensor is temporarily not providing data).

The term "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (regularly or irregularly) performed, for example, about every 5 to 10 minutes.

The term "count" as used herein is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode. In some embodiments, the terms can refer to data that has been integrated or averaged over a time period (e.g., 5 minutes).

The terms "coupling" and "operatively coupling" as used herein are broad terms, and are to be given their ordinary and customary meanings to a person of ordinary skill in the art (and are not to be limited to a special or customized meaning), and refer without limitation to a joining or linking together of two or more things, such as two parts of a device or two devices, such that the things can function together. In one example, two containers can be operatively coupled by tubing, such that fluid can flow from one container to another. Coupling does not imply a physical connection. For example, a transmitter and a receiver can be operatively coupled by radio frequency (RF) transmission/communication.

The term "diffusion barrier" as used herein is a broad term, and is to be given its ordinary and customary meaning to a person of ordinary skill in the art (and is not to be limited to a special or customized meaning) and refers without limitation to something that obstructs the random movement of compounds, species, atoms, molecules, or ions from one site in a medium to another. In some embodiments, a diffusion barrier is structural, such as a wall that separates two working electrodes and substantially prevents diffusion of a species from one electrode to the other. In some embodiments, a diffusion barrier is spatial, such as separating working electrodes by a distance sufficiently large enough to substantially prevent a species at a first electrode from affecting a second electrode. In other embodiments, a diffusion barrier can be temporal, such as by turning the first and second working electrodes on and off, such that a reaction at a first electrode will not substantially affect the function of the second electrode.

The term "dip coating" as used herein is a broad term, and is to be given its ordinary and customary meaning to a person of ordinary skill in the art (and is not to be limited to a special or customized meaning), and refers without limitation to coating, which involves dipping an object or material into a liquid coating substance.

The term "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane.

The term "electrochemical break-in" as used herein is a broad term, and is to be given its ordinary and customary meaning to a person of ordinary skill in the art (and is not to be limited to a special or customized meaning), and refers without limitation to the time, after in vitro and/or in vivo settling of the current output from the sensor following the application of the potential to the sensor.

The term "electrochemically reactive surface" as used herein is a broad term, and is to be given its ordinary and customary meaning to a person of ordinary skill in the art (and is not to be limited to a special or customized meaning), and refers without limitation to a surface where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The terms "electronic connection," "electrical connection," "electrical contact" as used herein are broad terms, and are to be given their ordinary and customary meaning to a person of ordinary skill in the art (and is not to be limited to a special or customized meaning), and refer without limitation to any connection between two electrical conductors known to those in the art. In one embodiment, electrodes are in electrical connection with the electronic circuitry of a device.

The terms "electronics" and "sensor electronics" as used herein are broad terms, and are to be given their ordinary and customary meaning to a person of ordinary skill in the art (and are not to be limited to a special or customized meaning), and refer without limitation to electronics operatively coupled to the sensor and configured to measure, process, receive, and/or transmit data associated with a sensor. In some embodiments, the electronics include at least a potentiostat that provides a bias to the electrodes and measures a current to provide the raw data signal. The electronics are configured to calculate at least one analyte sensor data point. For example, the electronics can include a potentiostat, A/D converter, RAM, ROM, and/or transmitter. In some embodiments, the potentiostat converts the raw data (e.g., raw counts) collected from the sensor and converts it to a value familiar to the host and/or medical personnel. For example, the raw counts from a glucose sensor can be converted to milligrams of glucose per deciliter of blood (e.g., mg/dl). In some embodiments, the sensor electronics include a transmitter that transmits the signals from the potentiostat to a receiver (e.g., a remote analyzer, such as but not limited to a remote analyzer unit), where additional data analysis and glucose concentration determination can occur.

The term "ex vivo portion" as used herein is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "fluid communication" as used herein is a broad term, and is to be given its ordinary and customary meaning to a person of ordinary skill in the art (and are not to be limited to a special or customized meaning), and refers without limitation to two or more components (e.g., things such as parts of a body or parts of a device) functionally linked such that fluid can move from one component to another. These terms do not imply directionality.

The term "GOx" as used herein is a broad term, and is to be given their ordinary and customary meaning to a person of ordinary skill in the art (and it is not to be limited to a special or customized meaning), and refers without limitation to the enzyme Glucose Oxidase (e.g., GOx is an abbreviation).

The term "helix" as used herein is a broad term, and is to be given its ordinary and customary meaning to a person of ordinary skill in the art (and it is not to be limited to a special or customized meaning), and refers without limitation to a spiral or coil, or something in the form of a spiral or coil (e.g. a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "host" as used herein is a broad term, and is to be given its ordinary and customary meaning to a person of ordinary skill in the art (and is not to be limited to a special or customized meaning), and refers without limitation to animals or plants, for example humans.

The term "hyperglycemia" as used herein is a broad term, and is to be given its ordinary and customary meaning to a person of ordinary skill in the art (and are not to be limited to a special or customized meaning), and refers without limitation to a condition in which an excessive or high amount of glucose exists in a host. Hyperglycemia is one of the classic symptoms of diabetes mellitus. Non-diabetic hyperglycemia is associated with obesity and certain eating disorders, such as bulimia nervosa. Hyperglycemia is also associated with other diseases (or medications) affecting pancreatic function, such as pancreatic cancer. Hyperglycemia is also associated with poor medical outcomes in a variety of clinical settings, such as intensive or critical care settings.

The term "hypoglycemia" as used herein is a broad term, and is to be given its ordinary and customary meaning to a person of ordinary skill in the art (and are not to be limited to a special or customized meaning), and refers without limitation to a condition in which a limited or low amount of glucose exists in a host. Hypoglycemia can produce a variety of symptoms and effects but the principal problems arise from an inadequate supply of glucose as fuel to the brain, resulting in impairment of function (neuroglycopenia). Derangements of function can range from vaguely "feeling bad" to coma, and (rarely) permanent brain damage or death.

The terms "inactive enzyme" or "inactivated enzyme" as used herein are broad terms, and are to be given their ordinary and customary meaning to a person of ordinary skill in the art (and it is not to be limited to a special or customized meaning), and refer without limitation to an enzyme (e.g., glucose oxidase, GOx) that has been rendered inactive (e.g., "killed" or "dead") and has no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "indwell" as used herein is a broad term, and is to be given its ordinary and customary meaning to a person of ordinary skill in the art (and are not to be limited to a special or customized meaning), and refers without limitation to reside within a host's body. Some medical devices can indwell within a host's body for various lengths of time, depending upon the purpose of the medical device, such as but not limited to a few hours, days, or weeks, to months, years, or even the host's entire lifetime. In one exemplary embodiment, an arterial catheter may indwell within the host's artery for a few hours, days, a week, or longer, such as but not limited to the host's perioperative period (e.g., from the time the host is admitted to the hospital to the time he is discharged).

The terms "insulative properties," "electrical insulator" and "insulator" as used herein are broad terms, and are to be given their ordinary and customary meaning to a person of ordinary skill in the art (and is not to be limited to a special or customized meaning) and refers without limitation to the tendency of materials that lack mobile charges to prevent movement of electrical charges between two points. In one exemplary embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The terms "integral," "integrally," "integrally formed," integrally incorporated," "unitary" and "composite" as used herein are broad terms, and are to be given their ordinary and customary meaning to a person of ordinary skill in the art (and they are not to be limited to a special or customized meaning), and refer without limitation to the condition of being composed of essential parts or elements that together make a whole. The parts are essential for completeness of the whole. In one exemplary embodiment, at least a portion (e.g., the in vivo portion) of the sensor is formed from at least one platinum wire at least partially covered with an insulative coating, which is at least partially helically wound with at least one additional wire, the exposed electroactive portions of which are covered by a membrane system (see description of FIG. 1B or 9B); in this exemplary embodiment, each element of the sensor is formed as an integral part of the sensor (e.g., both functionally and structurally).

The terms "interferants" and "interfering species" as used herein are broad terms, and are to be given their ordinary and customary meaning to a person of ordinary skill in the art (and they are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation/reduction potential that overlaps with the analyte to be measured, producing a false positive signal. In another example of an electrochemical sensor, interfering species are substantially non-constant compounds (e.g., the concentration of an interfering species fluctuates over time). Interfering species include but are not limited to compounds with electroactive acidic, amine or sulfhydryl groups, urea, lactic acid, phosphates, citrates, peroxides, amino acids, amino acid precursors or break-down products, nitric oxide (NO), NO-donors, NO-precursors, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid electroactive species produced during cell metabolism and/or wound healing, electroactive species that arise during body pH changes and the like.

The term "in vivo portion" as used herein is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "medical device" as used herein is a broad term, and is to be given its ordinary and customary meaning to a person of ordinary skill in the art (and are not to be limited to a special or customized meaning), and refers without limitation to an instrument, apparatus, implement, machine, contrivance, implant, in vitro reagent, or other similar or related article, including a component part, or accessory which is intended for use in the diagnosis of disease or other conditions, or in the cure, mitigation, treatment, or prevention of disease, in man or other animals, or intended to affect the structure or any function of the body of man or other animals. Medical devices that can be used in conjunction with various embodiments of the analyte sensor system include any monitoring device requiring placement in a human vessel, duct or body cavity, a dialysis machine, a heart-lung bypass machine, blood collection equipment, a blood pressure monitor, an automated blood chemistry analysis device and the like.

The terms "membrane" and "membrane system" as used herein are broad terms, and are to be given their ordinary and customary meaning to a person of ordinary skill in the art (and are not to be limited to a special or customized meaning), and refer without limitation to a permeable or semi-permeable membrane that can be comprised of one or more domains and is typically constructed of materials of one or more microns in thickness, which is permeable to oxygen and to an analyte, e.g. glucose or another analyte. In one example, the membrane system includes an immobilized glucose oxidase enzyme, which enables a reaction to occur between glucose and oxygen whereby a concentration of glucose can be measured.

The term "membrane break-in" as used herein is a broad term, and is to be given its ordinary and customary meaning to a person of ordinary skill in the art (and is not to be limited to a special or customized meaning), and refers without limitation to equilibration of the membrane to its surrounding environment (e.g., physiological environment in vivo).

The term "needle" as used herein is a broad term, and is to be given its ordinary and customary meaning to a person of ordinary skill in the art (and is not to be limited to a special or customized meaning), and refers without limitation to a slender hollow instrument for introducing material into or removing material from the body.

The term "non-constant noise" or non-constant background" as used herein are broad terms, and are to be given their ordinary and customary meaning to a person of ordinary skill in the art (and it is not to be limited to a special or customized meaning), and refer without limitation to a component of the background signal that is relatively non-constant, for example, transient and/or intermittent. For example, certain electroactive compounds, are relatively non-constant (e.g., intermittent interferents due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The term "non-enzymatic" as used herein is a broad term, and is to be given their ordinary and customary meaning to a person of ordinary skill in the art (and it is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied.

The terms "operatively connected," "operatively linked," "operably connected," and "operably linked" as used herein are broad terms, and are to be given their ordinary and customary meaning to a person of ordinary skill in the art (and are not to be limited to a special or customized meaning), and refer without limitation to one or more components linked to one or more other components. The terms can refer to a mechanical connection, an electrical connection, or any connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry. The terms include wired and wireless connections.

The term "potentiostat" as used herein is a broad term, and is to be given its ordinary and customary meaning to a person of ordinary skill in the art (and is not to be limited to a special or customized meaning), and refers without limitation to an electronic instrument that controls the electrical potential between the working and reference electrodes at one or more preset values. Typically, a potentiostat works to keep the potential constant by noticing changes in the resistance of the system and compensating inversely with a change in the current. As a result, a change to a higher resistance would cause the current to decrease to keep the voltage constant in the system. In some embodiments, a potentiostat forces whatever current is necessary to flow between the working and counter electrodes to keep the desired potential, as long as the needed cell voltage and current do not exceed the compliance limits of the potentiostat.

The term "pressure transducer" as used herein is a broad term, and is to be given its ordinary and customary meaning to a person of ordinary skill in the art (and are not to be limited to a special or customized meaning), and refers without limitation to a component of an intra-arterial blood pressure monitor that measures the host's blood pressure.

The terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, and the like designed to perform arithmetic or logic operations using logic circuitry that responds to and processes the basic instructions that drive a computer.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The term "pump" as used herein is a broad term, and is to be given its ordinary and customary meaning to a person of ordinary skill in the art (and are not to be limited to a special or customized meaning), and refers without limitation to a device used to move liquids, or slurries. In general, a pump moves liquids from lower pressure to higher pressure, and overcomes this difference in pressure by adding energy to the system (such as a water system).

The term "sensor break-in" as used herein is a broad term, and is to be given its ordinary and customary meaning to a person of ordinary skill in the art (and is not to be limited to a special or customized meaning), and refers without limitation to the time (after implantation) during which the sensor's signal is becoming substantially representative of the analyte (e.g., glucose) concentration (e.g., where the current output from the sensor is stable relative to the glucose level). The signal may not be 'flat' when the sensor has broken-in, but in general, variation in the signal level at that point is due to a change in the analyte (e.g., glucose) concentration. In some embodiments, sensor break-in occurs prior to obtaining a meaningful calibration of the sensor output. In some embodiments, sensor break-in generally includes both electrochemical break-in and membrane break-in.

The terms "small diameter sensor," "small structured sensor," and "micro-sensor" as used herein are broad terms, and are to be given their ordinary and customary meaning to a person of ordinary skill in the art (and are not to be limited to a special or customized meaning), and refer without limitation to sensing mechanisms that are less than about 2 mm in at least one dimension, and more preferably less than about 1 mm in at least one dimension. In some embodiments, the sensing mechanism (sensor) is less than about 0.95, 0.9, 0.85, 0.8, 0.75, 0.7, 0.65, 0.6, 0.5, 0.4, 0.3, 0.2, or 0.1 mm. In some embodiments, the sensing mechanism is a needle-type sensor, wherein the diameter is less than about 1 mm (see, for example, U.S. Pat. No. 6,613,379 and U.S. Patent Publication No. US-2006-0020187-A1, each of which is incorporated herein by reference in its entirety). In some alternative embodiments, the sensing mechanism includes electrodes deposited on a planar substrate, wherein the thickness of the implantable portion is less than about 1 mm, see, for example U.S. Pat. No. 6,175,752 and U.S. Pat. No. 5,779,665, both of which are incorporated herein by reference in their entirety.

The terms "raw data," "raw data stream", "raw data signal", "data signal", and "data stream" as used herein are broad terms, and are to be given their ordinary and customary meaning to a person of ordinary skill in the art (and are not to be limited to a special or customized meaning), and refer without limitation to an analog or digital signal from the analyte sensor directly related to the measured analyte. For example, the raw data stream is digital data in "counts" converted by an A/D converter from an analog signal (for example, voltage or amps) representative of an analyte concentration. The terms can include a plurality of time spaced data points from a substantially continuous analyte sensor, each of which includes individual measurements taken at time intervals ranging from fractions of a second up to, for example, 1, 2, or 5 minutes or longer. In some embodiments, the terms can refer to data that has been integrated or averaged over a time period (e.g., 5 minutes).

The term "regulator" or "flow control device," as used herein are broad terms, and are to be given their ordinary and customary meaning to a person of ordinary skill in the art (and are not to be limited to a special or customized meaning), and refer without limitation to a device that regulates the flow of a fluid or gas, for example, a valve or a pump.

The term "retrograde" as used herein is a broad term, and is to be given its ordinary and customary meaning to a person of ordinary skill in the art (and are not to be limited to a special or customized meaning), and refers without limitation to orientation (e.g., of a catheter) against the direction of blood flow.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte.

The terms "sensitivity" and "slope" as used herein are broad terms, and are to be given their ordinary and customary meaning to a person of ordinary skill in the art (and are not to be limited to a special or customized meaning), and refer without limitation to an amount of electrical current produced by a predetermined amount (unit) of the measured analyte. For example, in one preferred embodiment, a glucose sensor has a sensitivity (or slope) of from about 1 to about 25 picoAmps of current for every 1 mg/dL of glucose.

The terms "sensor" and "sensor system" as used herein are broad terms, and are to be given their ordinary and customary meaning to a person of ordinary skill in the art (and are not to be limited to a special or customized meaning), and refer without limitation to a device, component, or region of a device by which an analyte can be quantified.

The term "sheath" as used herein is a broad term, and is to be given its ordinary and customary meaning to a person of ordinary skill in the art (and are not to be limited to a special or customized meaning), and refers without limitation to a covering or supporting structure that fits closely around something, for example, in the way that a sheath covers a blade. In one exemplary embodiment, a sheath is a slender, flexible, polymer tube that covers and supports a wire-type sensor prior to and during insertion of the sensor into a catheter.

The term "single point glucose monitor" as used herein is a broad term, and is to be given its ordinary and customary meaning to a person of ordinary skill in the art (and is not to be limited to a special or customized meaning), and refers without limitation to a device that can be used to measure a glucose concentration within a host at a single point in time, for example, some embodiments utilize a small volume in vitro glucose monitor that includes an enzyme membrane such as described with reference to U.S. Pat. No. 4,994,167 and U.S. Pat. No. 4,757,022. It should be understood that single point glucose monitors can measure multiple samples (for example, blood, or interstitial fluid); however only one sample is measured at a time and typically requires some user initiation and/or interaction.

The term "slot" as used herein is a broad term, and is to be given its ordinary and customary meaning to a person of ordinary skill in the art (and are not to be limited to a special or customized meaning), and refers without limitation to a relatively narrow opening.

The terms "solvent" and "solvent system" as used herein are broad terms, and are to be given their ordinary and customary meaning to a person of ordinary skill in the art (and are not to be limited to a special or customized meaning), and refer without limitation to substances (e.g., liquids) capable of dissolving or dispersing one or more other substances. Solvents and solvent systems can include compounds and/or solutions that include components in addition to the solvent itself.

The term "specific gravity" as used herein is a broad term, and is to be given its ordinary and customary meaning to a person of ordinary skill in the art (and is not to be limited to a special or customized meaning), and refers without limitation to the ratio of density of a material (e.g., a liquid or a solid) to the density of distilled water.

The term "spin coating" as used herein is a broad term, and is to be given its ordinary and customary meaning to a person of ordinary skill in the art (and is not to be limited to a special or customized meaning), and refers without limitation to a coating process in which a thin film is created by dropping a raw material solution onto a substrate while it is rotating.

The term "spray coating" as used herein is a broad term, and is to be given its ordinary and customary meaning to a person of ordinary skill in the art (and is not to be limited to a special or customized meaning), and refers without limitation to coating, which involves spraying a liquid coating substance onto an object or material.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, an amount greater than 50 percent, an amount greater than 60 percent, an amount greater than 70 percent, an amount greater than 80 percent, or an amount greater than 90 percent.

The term "twisted" as used herein is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

The term "valve" as used herein is a broad term, and is to be given its ordinary and customary meaning to a person of ordinary skill in the art (and are not to be limited to a special or customized meaning), and refers without limitation to a device that regulates the flow of substances (either gases, fluidized solids, slurries, or liquids), for example, by opening, closing, or partially obstructing a passageway through which the substance flows. In general, a valve allows no flow, free flow and/or gravity flow and/or metered flow through movement of the valve between one or more discreet positions.

The term "vascular access device" as used herein is a broad term, and is to be given its ordinary and customary meaning to a person of ordinary skill in the art (and are not to be limited to a special or customized meaning), and refers without limitation to any device that is in communication with the vascular system of a host. Vascular access devices include but are not limited to catheters, shunts, blood withdrawal devices, connectors, valves, tubing and the like.

Overview

Intensive care medicine or critical care medicine is concerned with providing greater than ordinary medical care and/or observation to people in a critical or unstable condition. In recent years, an increasingly urgent need has arisen, for more intensive care medicine. People requiring intensive care include those recovering after major surgery, with severe head trauma, life-threatening acute illness, respiratory insufficiency, coma, hemodynamic insufficiency, severe fluid imbalance or with the failure of one or more of the major organ systems (life-critical systems or others). More than five million people are admitted annually to intensive care units (ICUs) and critical care units (CCUs) in the United States.

Intensive care is generally the most expensive, high technology and resource intensive area of medical care. In the United States estimates of the year 2000 expenditure for critical care medicine ranged from $15-55 billion accounting for about 0.5% of GDP and about 13% of national health care expenditure. As the U.S. population ages, these costs will increase substantially. Accordingly, there is an urgent need to reduce costs while at the same time reducing ICU/CCU mortality rates by improving care.

Intensive medical care requires frequent testing and/or monitoring of a variety of analytes, such as but not limited to albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug. Some embodiments disclosed herein are suitable for use in an intensive care or critical care unit of a medical care facility for substantially continuously measuring the concentration of one or more analytes in the host.

For example, diabetes is one medical condition requiring frequent testing of the host's analyte levels (e.g., blood glucose levels), in hospital settings. Hosts having diabetes, for example, are at risk of developing hyperglycemia, a medical condition in which an excessive amount of glucose circulates in a host. Perioperative hyperglycemia is associated with increased rates and severity of myocardial infarction (MI) and stroke, while tight glucose control with intravenous (IV) insulin therapy is linked to a 30% reduction in mortality one year after admission for acute MI. Furthermore, strict in-hospital glucose control is associated with 40% reductions of morbidity, mortality, sepsis, dialysis, blood transfusions, as well as reduced length of stay, reduced costs and the like. On the other hand, diabetic hosts are also susceptible to hypoglycemia (e.g., excessively low circulating blood glucose), which can cause shock and death (immediate problems), which the clinical staff rigorously avoids, often by maintaining the host at elevated blood glucose concentrations (which can degrade the clinical outcome in the long run) and causes the problems of hyperglycemia discussed above. Unfortunately, using generally available technology, tight glucose control requires frequent monitoring of the host by the clinical staff, IV insulin or injections, and on-time feeding. Frequent monitoring typically requires a nurse or other staff member to measure the host's glucose concentration using a lancet (to obtain a blood sample) and a hand held glucose monitor. The nurse can perform this task many times a day (e.g., every hour or more frequently). This task becomes an undue burden that takes the nurse away from his/her other duties, or requires extra staff. In spite of clinically demonstrated improvements associated with tight glucose control, institutions are slow to adopt the therapy due to the increased workload on the staff as well as a pervasive fear of hypoglycemia, which is potentially life ending.

Therefore, there is an urgent need for devices and methods that offer continuous, robust analyte monitoring, to improve patient care and lower medical costs. Some embodiments disclose systems and methods to reduce and/or minimize the interaction required to regularly (e.g., continuously) measure the host's glucose concentration. Additional and/or alternative analytes can also be continuously monitored using the devices and methods of the preferred embodiments. The preferred embodiments describe systems and methods for providing continuous analyte monitoring while providing alarms or alerts that aid in avoiding adverse events.

The in vivo continuous analyte monitoring system of the preferred embodiments can be used in clinical settings, such as in the hospital, the doctor's office, long-term nursing facilities, or even in the home. The present device can be used in any setting in which frequent or continuous analyte monitoring is desirable. For example, in the ICU, hosts are often recovering from serious illness, disease, or surgery, and control of host glucose levels is important for host recovery. For example, use of a continuous glucose sensor as described in the some embodiments allows tight control of host glucose concentration and improved host care, while reducing hypoglycemic episodes and reducing the ICU staff work load. For example, the system can be used for the entire hospital stay or for only a part of the hospital stay.

In another example, the continuous glucose monitor of the preferred embodiments can be used in medical settings wherein the host is unable to communicate with the medical staff, such as an ER setting. For example, in the ER, a host may be unconscious and therefore unable to communicate with the staff. In another example, a very young, non-verbal host may also be unable to communicate with the staff regarding his or her condition. In still another example, a host undergoing surgery is unable to communicate with the anesthesiologist, due to certain drugs being delivered. Routine use of a continuous analyte monitors (e.g., glucose, calcium, sodium, potassium, $CO_2$, chloride, blood urea nitrogen, creatinine, pH, oxygen, albumin, total protein, alkaline phosphatase, alanine amino transferase, aspartate amino transferase, bilirubin, phosphate, electrolytes, hematocrit and/or drugs) can enable medical staff to monitor and respond to analyte concentration changes indicative of the host's condition without host input.

In yet another example, a continuous analyte monitor can be used in the general hospital population to monitor host analyte concentrations, for various lengths of time, such as during the entire hospital stay or for a portion of the hospital stay (e.g., only during surgery). For example, a diabetic host's glucose concentration can be monitored during his or her entire stay. In another example, a cardiac host's glucose can be monitored during surgery and while in the ICU, but not after being moved to the general host population. In another example, a jaundiced newborn infant can have his or her bilirubin concentration continuously monitored by an in-dwelling continuous analyte monitor until the condition has receded.

In addition to use in the circulatory system, the analyte sensor of the preferred embodiments can be used in other body locations. In some embodiments, the sensor is used subcutaneously. In another embodiment, the sensor can be used intracranially. In another embodiment, the sensor can be used within the spinal compartment, such as but not limited to the epidural space. In some embodiments, the sensor of the preferred embodiments can be used with or without a catheter.

Applications/Uses

One aspect of the preferred embodiments provides a system for in vivo continuous analyte monitoring (e.g., albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, a drug, various minerals, various metabolites, and the like) that can be operatively coupled to a catheter to measure analyte concentration within the host's blood stream. In some embodiments, the system includes an analyte sensor that extends a short distance into the blood stream (e.g., out of the catheter) without substantially occluding the catheter or the host's blood stream. The catheter can be fluidly coupled to additional IV and diagnostic devices, such as a saline bag, an automated blood pressure monitor, or a blood chemistry monitor device. In some embodiments, blood samples can be removed from the host via the sensor system, as described elsewhere herein. In one embodiment, the sensor is a glucose sensor, and the medical staff monitors the host's glucose level. In other embodiments, described elsewhere herein, the analyte sensor is disposed within or on the catheter itself, such as the in vivo portion of the catheter. In still other embodiments, the analyte sensor is disposed entirely within and/or on the fluid coupler, which is in turn fluidly coupled to a catheter or other vascular access device, as described elsewhere herein.

FIGS. 1A to 1J illustrate two embodiments of an exemplary analyte sensor system 10 for measuring an analyte, as described elsewhere herein, that includes a catheter 12 configured to be inserted or pre-inserted into a host's blood stream. In clinical settings, catheters are often inserted into hosts to allow direct access to the circulatory system without frequent needle insertion (e.g., venipuncture). Suitable catheters can be sized as is known and appreciated by one skilled in the art, such as but not limited to from about 1 French (0.33 mm) or less to about 30 French (10 mm) or more; and can be, for example, 2, 3, 4, 5, 6, 7, 8, 9, 10, 11, 12, 13, 14, 15, 16, 17, 18, 19, or 20 French (3 French is equivalent to about 1 mm) and/or from about 33 gauge or less to about 16 gauge or more, for example, 33, 32, 31, 30, 29, 28, 27, 26, 25, 24, 23, 22, 21, 20, 19, 18, 17, or 16 gauge. Additionally, the catheter can be shorter or longer, for example 0.75, 1.0, 1.25, 1.5, 1.75, 2.0 inches in length or longer. In some embodiments, the catheter is a venous catheter. In other embodiments, the catheter is configured for insertion into a peripheral or a central artery. In some embodiments, the catheter is configured to extend from a peripheral artery to a central portion of the host's circulatory system, such as but not limited to the heart. In still other embodiments, the catheter is configured for insertion into neonatal or other pediatric hosts (e.g., 22-24 gauge or smaller). The catheter can be manufactured of any medical grade material known in the art, such as but not limited to polymers and glass as described herein. A catheter can include a single lumen or multiple lumens. A catheter can include one or more perforations, to allow the passage of host fluid through the lumen of the catheter.

The terms "inserted" or "pre-inserted" as used herein are broad terms, and are to be given their ordinary and customary meaning to a person of ordinary skill in the art (and are not to be limited to a special or customized meaning), and refer without limitation to insertion of one thing into another thing. For example, a catheter can be inserted into a host's blood stream. In some embodiments, a catheter is "pre-inserted," meaning inserted before another action is taken (e.g., insertion of a catheter into a host's blood stream prior to insertion of a sensor into the catheter). In some exemplary embodiments, a sensor is coupled to a pre-inserted catheter, namely, one that has been previously inserted (or pre-inserted) into the host's circulatory system. Alternatively, the sensor and the catheter can be configured to be inserted together and/or the sensor can be integrally formed with the catheter.

Referring now to FIGS. 1A to 1J, in some embodiments, the catheter 12 is a thin, flexible tube having a lumen 12a, such as is known in the art. In some embodiments, the catheter can be rigid; in other embodiments, the catheter can be custom manufactured to desired specifications (e.g., rigidity, dimensions, etc). The catheter can be a single-lumen catheter or a multi-lumen catheter. In some embodiments, the catheter is a peripheral catheter configured and arranged for insertion into a peripheral vessel (e.g., vein and/or artery) in a host's arm and/or leg. In some embodiments, the catheter is a central catheter, configured and arranged for insertion into a host's central vessel (e.g., internal jugular vein, subclavian vein, femoral vein and/or pulmonary artery). At the catheter's proximal end is a small orifice 12b for fluid connection of the catheter to the blood stream. At the catheter's distal end is a connector 18, such as a Leur connector or other fluid connector known in the art.

The illustrations of FIGS. 1A to 1J show two exemplary embodiments of the connector 18 including a flange 18a and a duct 18b. In the exemplary embodiment, the flange 18a is configured to enable connection of the catheter to other medical equipment (e.g., saline bag, pressure transducer, blood chemistry device, and the like) or capping (e.g., with a bung and the like). Although one exemplary connector is shown, one skilled in the art appreciates a variety of standard or custom made connectors suitable for use with the preferred embodiments. The duct 18b is in fluid communication with the catheter lumen and terminates in a connector orifice 18c.

In some embodiments, the catheter is inserted into the host's blood stream, such as into a vein or artery by any useful method known in the art. Generally, prior to and during insertion, the catheter is supported by a hollow needle or trochar (not shown). For example, the supported catheter can be inserted into a peripheral vein or artery, such as in the host's arm, leg, hand, or foot. Typically, the supporting needle is removed (e.g., pulled out of the connector) and the catheter is connected (e.g., via the connector 18) to IV tubing and a saline drip, for example. However, in one embodiment, the catheter is configured to operatively couple to medical equipment, such as but not limited to a sensor system of the preferred embodiments. Additionally and/or alternatively, the catheter can be configured to operatively couple to another medical device, such as a pressure transducer, for measurement of the host's blood pressure.

In some embodiments, the catheter and the analyte sensor are configured to indwell within the host's blood stream in vivo. An indwelling medical device, such as a catheter or implant, is disposed within a portion of the body for a period of time, from a few minutes or hours to a few days, months, or even years. An indwelling catheter is typically inserted within a host's vein or artery for a period of time, often 2 or more days, a month, or even a few months. In some embodiments, the catheter can indwell in a host's artery or vein for the length of a perioperative period (e.g., the entire hospital stay) or for shorter or longer periods. In some embodiments, the use of an indwelling catheter permits continuous access of an analyte sensor to a blood stream while simultaneously allowing continuous access to the host's blood stream for other purposes, for example, the administration of therapeutics (e.g., fluids, drugs, etc.), measurement of physiologic properties (e.g., blood pressure), fluid removal, and the like.

Referring again to FIGS. 1A to 1J, the system 10 also includes an analyte sensor 14 configured to extend through the catheter lumen 12a (see FIG. 1E), out of the catheter orifice 12b and into the host's blood stream by about 0.010 inches to about 1 inch, or shorter or longer lengths. In some embodiments, however, the sensor may not extend out of the catheter, for example, can reside just inside the catheter tip. The sensor can extend through the catheter in any functional manner. In some embodiments, the sensor is configured to be held (e.g., located, disposed) on an inner surface (e.g., the lumenal surface) or outer surface of the catheter. In some embodiments, the sensor is deposited (e.g., formed) on a surface of the catheter. In some embodiments, a sensor is attached to a surface of the catheter, such as by an adhesive and/or welding. In some other embodiments, the sensor is configured to "free float" within the lumen of the catheter. In some embodiments, the sensor resides within the fluid coupler.

In some embodiments, the sensor 14 is configured to measure the concentration of an analyte (e.g., albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, various drugs, various minerals, various metabolites, and the like) within the host's blood stream. In some preferred embodiments, the sensor includes at least one electrode (see, e.g., FIG. 3B), for example a working electrode; however any combination of working electrode(s), reference electrode(s), and/or counter electrode(s) can be implemented as is appreciated by one skilled in the art. For example, in some preferred embodiments, the sensor includes at least two working electrodes, as is described with reference to FIGS. 3D through 3I. In still other embodiments, two or more analyte sensors are in fluid communication with the vascular access device (e.g., disposed within the vascular access device), such that two or more analytes can be monitored simultaneously, and/or sequentially, continuously and/or intermittently, and the like. Preferably, the sensor 14 includes at least one exposed electroactive area (e.g., working electrode), a membrane system (e.g., including an enzyme), a reference electrode (proximal to or remote from the working electrode), and an insulator material. Various systems and methods for design and manufacture of continuous analyte sensors are described in more detail elsewhere herein. In some embodiments, the sensor is a needle-type continuous analyte sensor, configured as disclosed in U.S. Patent Publication No. US-2006-0020192-A1 and U.S. Patent Publication No. US-2006-0036143-A1, both of which are incorporated herein by reference in their entirety. In some embodiments, the sensor is disposed on a planar substrate, configured as disclosed in U.S. Pat. No. 6,175,752, U.S. Pat. No. 6,512,939 and U.S. Pat. No. 7,402,153, each of which are incorporated herein by reference in their entirety. In some embodiments, the sensor is configured to measure glucose concentration. Exemplary sensor configurations are discussed in more detail, elsewhere herein.

Referring to an embodiment illustrated in FIGS. 1A to 1E, the sensor has a proximal end 14a and a distal end 14b. At its distal end 14b, the sensor 14 is associated with (e.g., connected to, held by, extends through, and the like) a fluid coupler 20 having first and second sides (20a and 20b, respectively). The fluid coupler is configured to mate (via its first side 20a) to the catheter connector 18. In one embodiment, a skirt 20c is located at the fluid coupler's first side and includes an interior surface 20d with threads 20e (see FIGS. 1D and 1E). In this embodiment, the fluid coupler is configured to mate with the connector flange 18a, which is screwed into the fluid coupler via the screw threads. However, in other embodiments, the fluid coupler is configured to mate with the connector using any known mating configuration, for example, a snap-fit, a press-fit, an interference-fit, and the like, and can include a locking mechanism to prevent separation of the connector and fluid coupler. The fluid coupler 20 includes a lumen 20f extending from a first orifice 20h on its first side 20a to a second orifice 20i located on the fluid coupler's second side 20b (FIGS. 1C1 to 1E). When the catheter connector is mated with the fluid coupler, the catheter's lumen 12a is in fluid communication with the fluid coupler's lumen 20f via orifices 18c and 20h.

FIGS. 1A to 1D show one embodiment of a fluid coupler 20, namely, a Y-coupler; however, any known coupler configuration can be used, including but not limited to a straight coupler, a T-coupler, a cross-coupler, a custom configured coupler, and the like. In some embodiments, the fluid coupler includes at least one valve (e.g., a septum, a 3-way valve, a stop-cock valve), which can be used for a variety of purposes (e.g., injection of drugs). As another example, FIGS. 1F-1J illustrate a fluid coupler configured for connection of the sensor to sensor electronics via a female socket 20n configured to releasably mate with a male plug on an electronic cable. The fluid coupler can be made of any convenient material, such as but not limited to plastic, glass, metal or combinations thereof and can be configured to withstand known sterilization techniques.

In the exemplary embodiment, the second side 20b of the fluid coupler 20 is configured to be operably connected to IV equipment, another medical device or to be capped, and can use any known mating configuration, for example, a snap-fit, a press-fit, an interference-fit, and the like. In one exemplary embodiment, the second side 20b is configured to mate with a saline drip, for delivery of saline to the host. For example, the saline flows from an elevated bag of sterile saline via tubing, through the fluid coupler, through the catheter and into the host's blood system (e.g., vein or artery). In another embodiment, a syringe can be mated to the fluid coupler, for example, to withdraw blood from the host, via the catheter. Additional connection devices (e.g., a three-way valve) can be operably connected to the fluid coupler, to support additional functionality and connection of various devices, such as but not limited to a blood pressure transducer.

Referring to the exemplary embodiment of FIGS. 1A and 1E, at least a portion of the sensor 14 passes through the fluid coupler 20 (e.g., the fluid coupler lumen 20f) and is operatively connected to sensor electronics (not shown) via a hardwire 24. In alternative embodiments however, the sensor electronics can be disposed in part or in whole with the fluid coupler (e.g., integrally with or proximal to) or can be disposed in part or in whole remotely from the fluid coupler (e.g., on a stand or at the bed side). Connections between the sensor and sensor electronics (in part or in whole) can be accomplished using known wired or wireless technology. In one exemplary embodiment, the sensor is hardwired to the electronics located substantially wholly remote from the fluid coupler (e.g., disposed on a stand or near the bedside); one advantage of remote electronics includes enabling a smaller sized fluid coupler design. In another exemplary embodiment, a portion of the sensor electronics, such as a potentiostat, is disposed on the fluid coupler and the remaining electronics (e.g., electronics for receiving, data processing, printing, connection to a nurses' station, etc.) are disposed remotely from the fluid coupler (e.g., on a stand or near the bedside). One advantage of this design can include more reliable electrical connection with the sensor in some circumstances. In this embodiment, the potentiostat can be hardwired directly to the remaining electronics or a transmitter can be disposed on or proximal to the fluid coupler, for remotely connecting the potentiostat to the remaining electronics (e.g., by radio frequency (RF)). In another exemplary embodiment, all of the sensor electronics can be disposed on the fluid coupler. In still another embodiment, the sensor electronics disposed on the fluid coupler include a potentiostat.

Referring again to FIGS. 1A to 1E, a protective sheath 26 is configured to cover at least a portion of the sensor 14 during insertion, and includes hub 28 and slot 30. In general, the protective sheath protects and supports the sensor prior to and during insertion into the catheter 12 via the connector 18. The protective sheath can be made of biocompatible polymers known in the art, such as but not limited to polyethylene (PE), polyurethane (PE), polyvinyl chloride (PVC), polycarbonate (PC), nylon, polyamides, polyimide, polytetrafluoroethylene (PTFE), Teflon, nylon and the like. The protective sheath includes a hub 28, for grasping the sheath (e.g., while maintaining sterilization of the sheath). In this embodiment, the hub additionally provides for mating with the second side 20b of the fluid coupler 20, prior to and during sensor insertion into the catheter. In this exemplary embodiment, the slot of the protective sheath is configured to facilitate release of the sensor therefrom. In this embodiment, after the sensor has been inserted into the catheter, the hub is grasped and pulled from the second side of the fluid coupler. This action peels the protective sheath from the sensor (e.g., the sensor slides through the slot as the sheath is removed), leaving the sensor within the catheter. The second side of the fluid coupler can be connected to other medical devices (e.g., a blood pressure monitor) or an IV drip (e.g., a saline drip), or capped. In alternative embodiments, the sheath can fold (e.g., fold back or concertinas) or retract (e.g., telescope) during insertion, to expose the sensor. In other embodiments, the sheath can be configured to tear away from the sensor before, during, or after insertion of the sensor. In still other embodiments, the sheath can include an outlet hole 30a, to allow protrusion of the sensor from the back end of the sheath (e.g., near the hub 28). One skilled in the art will recognize that additional configurations can be used, to separate the sensor 14 from the sheath 26.

In some embodiments, the sensor includes at least two working electrodes 14, which can be twisted and/or bundled, such as in a helical and/or coaxial configuration. In some embodiments, the two working electrodes are twisted into a "twisted pair," which can be configured to be inserted into and to extend within a vascular access device, such as a catheter 12 or cannula implanted in a host's vein or artery, as is described in more detail in the section entitled "Integrated Sensor System." In some embodiments, the twisted pair is configured to reside within the lumen 12a of the catheter 12; while in other embodiments, the twisted pair is configured to protrude from the catheter's proximal orifice 12b. In still other embodiments, the twisted pair is configured to intermittently protrude from the catheter's proximal orifice 12b.

In some embodiments, the sheath 26 can be optional, depending upon the sensor design. For example, the sensor can be inserted into a catheter or other vascular access device with or without the use of a protective sheath). In some embodiments, the sensor can be disposed on the outer surface of a catheter (as described elsewhere herein) or on the inner surface of a catheter; and no sheath is provided. In other embodiments, a multi-lumen catheter can be provided with a sensor already disposed within one of the lumens; wherein the catheter is inserted into the host's vein or artery with the sensor already disposed in one of the lumens. In one exemplary embodiment, the system includes a catheter having multiple lumens, and is configured and arranged to infuse a fluid in a first lumen of the catheter and to draw back a biological sample into a second lumen of the catheter. In a further embodiment, an analyte sensor is located in the second lumen of the catheter. In some embodiments, the system is configured to infuse a fluid into the second lumen, such as to reinfuse a drawn back sample into the host and/or to wash the sensor. In some embodiments, a flow control device is configured and arranged for infusion of at least two solutions, such as via a multi-lumen catheter, and includes at least two valves, such as described with reference to FIGS. 8A through 10D.

In some alternative embodiments, an analyte sensor is integrally formed on a catheter. In various embodiments, the catheter can be placed into a host's vein or artery in the usual way a catheter is inserted, as is known by one skilled in the art, and the host's analyte concentration measured substantially continuously. In some embodiments, the sensor system can be coupled to one or more additional devices, such as a saline bag, an automated blood pressure monitor, a blood chemistry monitor device, and the like. In one exemplary embodiment, the integrally formed analyte sensor is a glucose sensor.

FIGS. 1F through 1J illustrate another embodiment of the sensor system, wherein the fluid coupler 20 includes a housing 20j configured and arranged for electrical connection of the analyte sensor 14 to at least some system electronics, such as an electronic cable (not shown). The housing 20j includes a housing cover 20k and an electrical connector 20n. While a female socket 20n (e.g., configured to releasably mate with a male plug) is shown, any electrical connection known in the art can be used, as is appreciate by one skilled in the art.

FIGS. 1G-1H are exploded and cut-away views, respectively, of the embodiment shown in FIG. 1F. The encircled portion of FIG. 1H is shown in FIG. 1J and illustrates the configuration of the distal portion of the analyte sensor 14 within the housing 20j, in this embodiment. The analyte sensor can be configured and arranged to detect one or more analytes, as described elsewhere herein. The proximal portion (ex vivo portion) of the analyte sensor 14 is configured and arranged for electrical connection with the sensor electronics via one or more elastomeric contacts and/or connectors 20s and a printed circuit board (PCB) 20t disposed within the housing. In this embodiment, the connection is a solderless connection. However, in some embodiments, electrical connection of the electrodes to the electronics can be made by other means, for example, wires, contact pads, pogo pins, domed metallic contacts, cantilevered fingers, metallic springs, soldering and/or conductive adhesive. In the embodiment shown in FIGS. 1G-1J, an elastomeric contact and/or connector 20s, which can be manufactured of an conductive elastomeric material such as a carbon black elastomer, makes an electrical connection between each of the sensor's electrodes (e.g., working (plus or minus enzyme), counter and/or reference electrodes) and the PCB. For example, as shown in FIG. 1J, the electrodes make contact with the elastomeric contacts, and the elastomeric contacts make contact with the PCB. The PCB is configured and arranged to make an electrical connection with at least some of the system electronics, such as but not limited to by socket 20n. Conductive elastomers are advantageously employed because their resilient properties create a natural compression against mutually engaging contacts, forming a secure press fit therewith. In some embodiments, conductive elastomers can be molded in such a way that pressing the elastomer against an adjacent contact performs a wiping action on the surface of the contact, thereby creating a cleaning action during initial connection. Additionally, in some embodiments, the sensor 14 extends through the contacts 20s wherein the sensor is electrically and mechanically secured by the relaxation of elastomer around the sensor.

In an alternative embodiment, a conductive, stiff plastic forms the contacts, which are shaped to comply upon application of pressure (for example, a leaf-spring shape). Contacts of such a configuration can be used instead of a metallic spring, for example, and advantageously avoid the need for crimping or soldering through compliant materials; additionally, a wiping action can be incorporated into the design to remove contaminants from the surfaces during connection. Non-metallic contacts can be advantageous because of their seamless manufacturability, robustness to thermal compression, non-corrosive surfaces, and native resistance to electrostatic discharge (ESD) damage due to their higher-than-metal resistance.

While in this embodiment (e.g., shown in FIGS. 1H and 1J), the proximal portion (e.g., part of the ex vivo portion, also referred to herein as the first portion) of each electrode physically contacts the bottom of (e.g., beneath) an elastomeric connector, the electrodes can make an electrical connection with elastomeric contacts by a variety of other ways. For example, in some embodiments, one or more of the electrodes can contact the top and/or side of the elastomeric contacts (e.g., above and/or beside). In still other embodiments, an electrode can intersect an elastomeric contact (e.g., pass through at least a portion of the elastomeric contact). In yet another embodiment, the proximal portion of an electrode can be wrapped around an elastomeric contact. Additional configurations are considered in the preferred embodiments. For example, the different configurations can be combined, such as for example, with one electrode touching the bottom of a first elastomeric contact, a second electrode touching the top of a second elastomeric contact, and a third electrode passing through yet another elastomer contact.

In some embodiments, the interior of the housing is configured to guide placement of the electrodes for contact with the elastomeric contacts, which can simplify manufacturing and ensure formation of a good electrical contact between each electrode and its corresponding elastomeric contact. For example, in the embodiment shown in FIGS. 1H and 1J, pathways (e.g., recessed) are provided, to guide the placement of the electrode wires within the housing, and wells or cups are provided to receive the elastomeric contacts. For example, in FIG. 1G, the proximal portion of each of the sensor's electrodes are received into one of the three pathways provided, an elastomeric contact 20s is placed in each of the three wells, and then the PCB 20t is placed on top of the elastomeric contacts. Then, the housing cover 20k, which, in some embodiments, includes a connector 20n, is applied to close the housing.

FIG. 1K illustrates another embodiment of the analyte sensor 14 is incorporated into a fluid coupler 20. In this embodiment, the sensor is configured such that it extends at least a portion of the length of the lumen 20f of the fluid coupler, but does not extend out of the fluid coupler itself (e.g., past the fluid coupler's first orifice 20h). When the fluid coupler of this embodiment is fluidly coupled to an implanted catheter, the first side 20a of the fluid coupler releasably mates with the catheter hub 18, such that a portion of the fluid coupler's first orifice 20h is located within a portion of the catheter hub's duct or lumen (e.g., 18b, see FIGS. 1D-1E). Accordingly, in this embodiment, the sensor tip 14a can be located within the catheter hub's duct or lumen. Advantageously, this embodiment simplifies device installation as no insertion of the sensor into a catheter is required. Additionally, sensor performance is maintained because the sensor is protected by the fluid coupler's hard structure during connection of the fluid coupler to the catheter (e.g., the sensor cannot be accidentally touched, bent or flexed during installation).

As described elsewhere herein, function of an enzymatic analyte sensor is dependent upon the kinetics of the enzyme comprised in the sensor. For example, the function of a glucose sensor is dependent upon the kinetics of the glucose oxidase contained in the sensor's membrane. As is understood by one skilled in the art, enzyme kinetics are influenced by the availability of the reactants. When all required reactants are freely available, the enzyme will react at its maximum rate, given the prevailing temperature and pH conditions. If, on the other hand, the concentration of one of the reactants is low (e.g., limiting), the enzyme reaction will proceed at a slower rate, which is associated with the concentration of the limited reactant. Accordingly, to measure the concentration of a particular reactant (e.g., the analyte), that reactant should be present in limiting amounts. In other words, the other reactants (e.g., a co-reactant) should be present in excess (e.g., non-limiting amounts). For example, glucose and oxygen are the reactants of some GOX-containing glucose sensors. Since the analyte is glucose, oxygen (e.g., the co-reactant) should be present in excess (e.g., non-limiting), so that the reaction rate is dependent upon the glucose concentration. In some circumstances, however, the co-reactant is limiting. For example, if ischemia occurs around and/or near the sensor, the amount of available oxygen can be reduced and thus become the limiting reactant. In another example, the analyte can exist in excess (e.g., in the body) relative to the concentration of a reactant, such as oxygen. In some embodiments, the sensor is configured to compensate for a limiting reactant, such as but not limited to oxygen. For example, the membrane can be configured and arranged to restrict the amount of excess reactant that diffuses therethrough (e.g., see the section entitled "Resistance Domain.") In other embodiments, the sensor can be configured to increase the level of limiting reactant (e.g., co-reactant). For example, in some embodiments, the membrane can include a domain configured to increase the concentration of oxygen. In other embodiments, the vascular access device, such as the ex vivo portion of a catheter or a fluid coupler can be configured to increase the amount of oxygen (e.g., co-reactant) available to the enzyme. For example, the fluid coupler 20 of FIG. 1K includes an enrichment body 20p configured and arranged to increase the oxygen concentration at the sensor 14. An enrichment body 20p can be provided in many forms. For example, in the embodiment shown in FIG. 1K, the enrichment body includes an "oxygen port" including a membrane, plug or filter located in a side of the fluid coupler. In this embodiment, the oxygen port intersects the fluid coupler wall, such that oxygen can diffuse from the exterior of the fluid coupler to the lumen 20f. In some embodiments, the oxygen port includes a plug and/or membrane formed of silicone, ePTFE or other polymer known to increase oxygen diffusion. In other embodiments, the enrichment body 20p includes an "oxygen capacitor" configured to absorb oxygen when the oxygen concentration (e.g., around the sensor) is high, and to release the absorbed (e.g., stored) oxygen when the oxygen concentration is low. For example, in some embodiments, the infusion solution is oxygenated, such that as the infusion solution flows through the fluid coupler and/or catheter and contacts the oxygen capacitor, the capacitor absorbs at least some of the oxygen present in the solution. Then, when blood is drawn back and contacts the capacitor, at least some of the oxygen stored in the capacitor diffuses into the blood. For example, in some embodiments, the oxygen capacitor is an oxygen-absorbing and oxygen-releasing polymer applied to the lumenal surface of the fluid coupler and/or catheter. In other embodiments, the oxygen capacitor is a membrane or plug attached to the lumenal surface of the catheter and/or fluid coupler. In yet another embodiment, the enrichment body is inserted into the lumen of the fluid coupler and/or catheter hub.

FIG. 1L illustrated an embodiment similar to that of FIG. 1K, except that at least a portion of the sensor 14 extends toward the fluid coupler's 20 second side 20b. In some embodiments, the sensor tip extends to the fluid coupler's second orifice 20i, but not there past. In other embodiments, the sensor is configured to extend into connected tubing. Accordingly, in this embodiment, the sensor's electroactive surface(s) can be located at any point along the length of the fluid coupler's lumen 20f.

FIG. 1M illustrates yet another embodiment of an analyte sensor incorporated into a fluid coupler 20. In this embodiment, at least one analyte sensor 14 is located on a support 20q that is located on the lumenal surface of the fluid coupler. In some embodiments, the support, including the at least one analyte sensor located thereon, is inserted into the fluid coupler via an orifice (e.g., 20i). In other embodiments, the fluid coupler includes a port (e.g., an orifice, hole or opening, not shown) configured and arranged to receive the support (e.g., the port and the support are configured to mate with each other), such as via insertion through the wall of the fluid coupler. In some embodiments, the at least one analyte sensor comprises two or more analyte sensors, wherein the analyte sensors are configured to detect one or more analytes. In some embodiments, the at least one analyte sensor comprises 3, 4, 5, 6, 7, 8, 9, 10 or more analytes sensors. In some embodiments, the at least one analyte sensor comprises a plurality of micro-fabricated sensors, such as but not limited to a sensor array. The sensor(s) can be applied to and/or deposited on the support using any method known in the art, such as but not limited to thin and/or thin film techniques, printing, plating, and the like. In some embodiments, an analyte sensor is configured to intersect the support, such as described with reference to FIGS. 2M-2Q. In some embodiments, the sensor (e.g., working electrode) is substantially flush with the support, similar to the manner of some glucose test strips that have electrodes printed on a planar support using thin and/or thick film techniques. In some embodiments, the sensor (e.g., working electrode) is at least partially embedded in the support. For example, the working electrode material can be deposited in a groove or well located on the support. In preferred embodiments, the support is manufactured from a polymer. Preferably, the polymer is configured for malleability during manufacture but also provides sufficient strength to function as a side of the fluid coupler. In other embodiments, the support is formed from a metal, a ceramic or glass. The support can have any shape, such as a planar or non-planar shape. In some embodiments, the support has a planar lumenal surface (e.g., the surface of the support that faces the lumen of the fluid coupler). However, in other embodiments, the support's lumenal surface is curved. In some embodiments, the support (e.g., with sensor(s) applied thereto) is received into a port. In some embodiments, the support makes a friction fit into the port. In other embodiments, the support and port are configured for a snap fit of the support into the port. In some embodiments, the support can be secured into the port with an adhesive, hooks, pins, and/or via welding. In other embodiments, the support (including one or more analyte sensors) is inserted into the lumen of the fluid coupler. For example, in one embodiment, the fluid coupler does not include a port; rather the support (e.g., including sensors) is inserted through one of the fluid coupler's orifices, such that the support is located adjacent to and/or on the fluid coupler's lumenal surface. In a further embodiment, the support is configured to conform to the lumenal surface of the fluid coupler. In some embodiments, the support is attached to the lumenal surface of the fluid coupler, such as with adhesive or welding. In some embodiments, a catheter hub includes a port configured for receipt of the support. Advantageously, manufacturing the sensor(s) on a support and then integrating them with the fluid coupler simplify manufacturing and reduce costs by enabling high through put, automated manufacturing methods. Additionally, a wider array of sensors and custom-order sensors can be easily manufactured (e.g., as "panels" of sensors that test a panel of analytes) and subsequently integrated into the fluid couplers and/or catheter hubs. For example, in one embodiment cassettes of sensors are manufactured in an automated reel-to-reel process wherein sensor panels (e.g., 2, 3, 4, 5, 6, 7, 8, 9, 10, 12, 13, 14, 15, 16, 17, 18, 19 or 20 or more sensors) are applied to a continuous roll of polymer material (e.g., the support), wherein the individual sensor cassettes are subsequently cut out of the roll, such as using a die. In a second automated process, the completed sensor cassettes are installed into the ports of separately manufactured fluid couplers. Sensor electronics, such as a PCB and electronic connectors are applied in yet another automated process. In some embodiments, 2, 3, 4, 5, or more different types of sensor cassettes (e.g., each type of sensor cassette includes a different panel of analyte sensors) can be manufactured (e.g., simultaneously on separate manufacturing lines or on a single line at different times) and then subsequently integrated into separately manufactured fluid couplers. In other embodiments, for fluid couplers and/or catheters hubs having different configurations, each configuration includes a port configured to receive a single size and/or shape of sensor cassette, wherein the size and/or shape of the cassette is associated with a fluid coupler or catheter configuration. In some embodiments, each type of sensor cassette (e.g., analyte panel) includes a unique shape, such that it must be received by a port configured to mate with it, similar to an interlocking lock and key, such that certain cassettes are used with certain fluid couplers and/or catheters. In some embodiments, certain interlocking cassette and port configurations are associated with a particular panel of analytes and/or a client. In yet another embodiment, the sensor cassettes are configured to be replaceable prior-to and/or during use. For example, in one embodiment, the fluid coupler is provided with two or more types of cassettes (e.g., different panels), such that the user inserts a selected cassette into the fluid coupler's port prior to use. In an alternative embodiment, the fluid coupler can be provided with two or more cassettes of the same type, such that the cassette can be changed out during use. For example, if a sensor on a first cassette fails, the cassette can be replaced with a second cassette of the same type. Analyte sensors and manufacturing methods suitable for use with these embodiments can be found in U.S. Pat. No. 5,108,819, U.S. Pat. No. 5,178,957, U.S. Pat. No. 5,879,828, U.S. Pat. No. 6,175,752, U.S. Pat. No. 6,284,478, U.S. Pat. No. 6,329,161, U.S. Pat. No. 6,565,509, U.S. Pat. No. 6,990,366, U.S. Pat. No. 6,134,461, U.S. Pat. No. 7,003,336, U.S. Pat. No. 6,784,274, U.S. Pat. No. 6,103,033, and U.S. Pat. No. 5,899,855, each of which is incorporated herein by reference in its entirety.

FIGS. 2A to 2B illustrate one exemplary embodiment of an analyte sensor integrally formed on a catheter. The system 210 is configured to measure an analyte and generally includes a catheter 212 configured for insertion into a host's blood stream (e.g., via a vein or artery) and a sensor at least partially integrally formed on the catheter's exterior surface 232. Preferably, the sensor 214 includes at least one exposed electroactive area 240 (e.g., a working electrode), a membrane system (e.g., including an enzyme), a reference electrode (proximal to or remote from the working electrode), and an insulator.

In this embodiment, the catheter includes a lumen 212a and an orifice 212b at its proximal end, for providing fluid connection from the catheter's lumen to the host's blood stream (see FIG. 2A).

In some embodiments, the catheter is inserted into a vein, as described elsewhere herein. In other embodiments, the catheter is inserted into an artery, as described elsewhere herein. The catheter can be any type of venous or arterial catheter commonly used in the art (e.g., peripheral catheter, central catheter, Swan-Gantz catheter, etc.). The catheter can be made of any useful medical grade material (e.g., polymers and/or glass) and can be of any size, such as but not limited to from about 1 French (0.33 mm) or less to about 30 French (10 mm) or more; for example, 2, 3, 4, 5, 6, 7, 8, 9, 10, 11, 12, 13, 14, 15, 16, 17, 18, 19, or 20 French (3 French is equivalent to about 1 mm). In some embodiments, the catheter is configured and arranged for insertion into neonatal or other pediatric hosts (e.g., 22-24 gauge or smaller). In certain embodiments, the catheter can be a single lumen catheter or a multi-lumen catheter. In some embodiments, the catheter can include one or more perforations, to allow the passage of host fluid through the lumen of the catheter. In one embodiment, the catheter is a dual-lumen catheter wherein a first lumen is configured to receive an analyte sensor and a second lumen is configured for fluid infusion. In preferred embodiments, the catheter is configured such that the orifice of the first lumen is sufficiently proximal to connector (of the catheter) relative to the orifice of the second lumen, that samples drawn back into the first lumen (e.g., to be tested by the analyte sensor) are substantially undiluted by the infused fluid.

At its distal end 212c, the catheter 212 includes (e.g., in fluid communication) a connector 218. The connector can be of any known type, such as a Leur lock, a T-connector, a Y-connector, a cross-connector or a custom configuration, for example. In some embodiments, the connector includes at least one valve. At a second side 218e (e.g., back end), the connector 218 can be operatively connected to a saline system (e.g., saline bag and tubing), other medical devices (e.g., automatic blood chemistry machine, dialysis machine, a blood bag for collecting donated blood, etc.), or capped.

In some embodiments, the system 210 includes sensor electronics (not shown) operatively connected to the analyte sensor, wherein the sensor electronics are generally configured to measure and/or process the sensor data as described in more detail elsewhere herein. In some embodiments, the sensor electronics can be partially or wholly disposed with (e.g., integral with, disposed on, or proximal to) the connector 218 at the distal end of the catheter or partially or wholly remote from the catheter (e.g., on a stand or on the bedside). In one embodiment, the sensor electronics disposed with the connector include a potentiostat. In some embodiments, the sensor electronics are configured to measure the host's analyte concentration substantially continuously. For example, the sensor can measure the analyte concentration continuously or at time intervals ranging from fractions of a second up to, for example, 1, 2, or 5 minutes or longer.

FIGS. 2C to 2F illustrate additional embodiments of the sensor shown in FIGS. 2A to 2B. The catheter 212 is shown with an integral sensor 214 having at least one electrode 240 formed on its exterior surface 232 (e.g., FIG. 2F). In general, the sensor can be designed with 1, 2, 3, 4 or more electrodes and can be connected by traces (or the like) to electrical contacts 218d (or the like) at the second end of the connector 218 (e.g., FIGS. 2A to 2F). In some embodiments, the sensor is hard-wired to the sensor electronics; alternatively, any operable connection can be used. Preferably, the sensor includes at least one working electrode and at least one reference or counter electrode. In some embodiments, the reference electrode is located proximal to the at least one working electrode (e.g., adjacent to or near to the working electrode). In some alternative embodiments, the reference electrode is located remotely from the working electrode (e.g., away from the working electrode, such as but not limited to within the lumen of the catheter 212 (or connector 218), on the exterior of the sensor system, in contact with the patient (e.g., on the skin), or the like). In some embodiments, the reference electrode is located proximal to or within the fluid connector, such as but not limited to, coiled about the catheter adjacent to the fluid connector or coiled within the fluid connector and in contact with fluid flowing through the fluid coupler, such as saline or blood. In some embodiments, the sensor can also include one or more additional working electrodes (e.g., for measuring baseline, for measuring a second analyte, or for measuring a substantially non-analyte related signal, and the like, such as described in more detail in U.S. Patent Publication No. US-2005-0143635-A1 and U.S. Patent Publication No. US-2007-0027385-A1, which are incorporated herein by reference in their entirety. In some embodiments one or more counter electrodes can be provided on a surface of the catheter or within or on the fluid connector.

In some of the preferred embodiments, the catheter is designed to indwell within a host's blood flow (e.g., a peripheral vein or artery) and remain in the blood flow for a period of time (e.g., the catheter is not immediately removed). In some embodiments, the indwelling catheter can be inserted into the blood flow for example, for a few minutes or more, or from about 1 to 24 hours, or from about 1 to 10 days, or even longer. For example, the catheter can indwell in the host's blood stream during an entire perioperative period (e.g., from host admittance, through an operation, and to release from the hospital).

In some embodiments, the catheter is configured as an intravenous catheter (e.g., configured to be inserted into a vein). The catheter can be inserted into any commonly used vein, such as in a peripheral vein (e.g., one of the metacarpal veins of the arm); in some embodiments (e.g., such as described with reference to FIGS. 1A to 1E) the analyte sensor inserted into a catheter. In alternative embodiments, the sensor is integrally formed on a catheter such as described in more detail with reference to FIGS. 2A to 2F, for example. Other veins, such as leg or foot veins, hand veins, or even scalp or umbilical veins, can also be used.

In addition to sensing analyte levels via a sensor system as described herein, the intravenous catheter can be used for delivery of fluids and/or drugs to the host's circulatory system. The catheter can be configured to be coupled to other medical devices or functions, for example, saline, blood products, total parenteral feeding or medications can be given to the host via the indwelling intravenous catheter. In some embodiments, the catheter can be operatively connected to a pump, such as an infusion pump, to facilitate flow of the fluids into the host and a desired rate. For example, an infusion pump can pump saline into the host at a rate of 1 cc per minute, or at higher or lower rates. The rate of infusion can be changed (increased or decreased). For example, an infusion can be temporarily stopped, to permit injection of pain medication into the IV system, followed by increasing the infusion rate (e.g., for 5 minutes) to rapidly deliver the pain medication to the host's circulatory system.

In some embodiments, the catheter is configured as an arterial catheter (e.g., configured to be inserted into an arterial line or as part of an arterial line). Typically, an arterial catheter is inserted in the wrist (radial artery), armpit (axillary artery), groin (femoral artery), or foot (pedal artery). Generally, arterial catheters provide access to the host's blood stream (arterial side) for removal of blood samples and/or application of test devices, such as but not limited to a pressure transducer (for measuring blood pressure automatically), however, arterial catheters can also be used for delivery of fluids or medications. In one embodiment, a catheter is inserted into an arterial line and the sensor inserted into the catheter (e.g., functionally coupled) as described elsewhere herein. Saline filled non-compressible tubing is then coupled to the sensor, followed by a pressure transducer. An automatic flushing system (e.g., saline) is coupled to the tubing as well as a pressure bag to provide the necessary pressure. Electronics are generally operatively coupled to the pressure transducer for calculating and displaying a variety of parameters including blood pressure. Other medical devices can also be connected to the arterial catheter, to measure various blood components, such as but not limited to $O_2$, $CO_2$, $PCO_2$, $PO_2$, potassium, sodium, pH, lactate, urea, bilirubin, creatinine, hematocrit, various minerals, various metabolites, and the like.

In another embodiment, a blood pressure measurement system is inserted into the host and can be used as is known in the art. The analyte sensor (e.g., glucose sensor), such as the embodiment shown in FIGS. 1A-1E, is inserted into the pre-inserted (e.g., already in-dwelling) catheter using the following general methodology. First, the pressure transducer is temporarily disabled by disconnecting from the pre-inserted catheter. A cap (optionally) covers the protective slotted sheath and can be removed so as to enable the sensor to be grasped at the fluid coupler. The sheath, which is generally more rigid than the sensor but less flexible than a needle, is then threaded through the pre-inserted catheter so as to extend beyond the catheter into the blood stream (e.g., by about 0.001 inches to about 1 inches). The sheath is then removed by sliding the sensor through a small outlet hole and/or slot in the sheath. Thus, the sensor remains within the pre-inserted catheter and the fluid coupler, which supports the distal portion of the sensor, is coupled to the catheter itself Saline filled non-compressible tubing is then coupled to the second side (e.g., back end) of the fluid coupler. The sensor electronics (whether adjacent to the fluid coupler or otherwise wired to the fluid coupler) are then operatively connected (e.g., wired or wirelessly) to the sensor to initiate sensor function.

In some embodiments, a portion of the sensor system (e.g., sensor, catheter, or other component) can be configured to allow removal of blood samples from the host's blood stream (e.g., artery or vein). Sample removal can be done using any systems and methods known in the art, for example, as is practiced for removing a blood sample from an arterial catheter (e.g., and arterial line). In one such exemplary embodiment, any tubing or equipment coupled to the second side of the fluid coupler is disconnected. A syringe is then be coupled to the second side and blood removed via the catheter by pulling back on the syringe plunger. In a further embodiment, saline can be flushed through the fluid coupler and catheter. In another embodiment, the fluid coupler can be configured with a side valve, to allow coupling of a syringe, for removal of blood samples or delivery of fluids, such as medications, without disconnecting attached tubing of equipment, and the like. In still another embodiment, a valve or diaphragm, for access to the system by a syringe, can be coupled into the tubing at a short distance from the fluid coupler. In yet another embodiment, the sensor is integrally formed on the arterial catheter, such as the embodiment shown in FIGS. 2A-2B, and tubing can be disconnected from the connector, a syringe operably associated with the connector, and blood removed with the syringe. After blood collection, the syringe is removed and the tubing reconnected to the connector.

In still another embodiment, the analyte sensor can be functionally coupled to an extracorporeal blood flow device. A variety of devices exist for testing various blood properties and/or analytes at the bedside, such as but not limited to the blood gas and chemistry devices manufactured by Via Medical, Austin, Tex., USA. These devices generally withdraw a blood sample from the host, test the blood sample, and then return it to the host. Such a device can be connected in series to the arterial catheter, with the sensor in-between, and using systems and methods known in the art. In one embodiment, a sensor, such as the embodiment shown in FIGS. 1A-1E, is functionally connected to an in-dwelling arterial catheter, as described herein, and the extracorporeal blood flow device is connected to the second side of the fluid coupler. In an alternative embodiment, the sensor is integrally formed on the arterial catheter, such as the embodiment shown in FIGS. 2A-2F, and the extracorporeal blood flow device is functionally connected to the connector 218. Other devices, such as but not limited to dialysis machines, heart-lung bypass machines or blood collection bags, or other vascular access devices, can be functionally coupled to the analyte sensor.

The analyte sensor system of the preferred embodiments can be designed with a variety of alternative configurations. In some embodiments, the sensor is connected to a fluid connection device. The fluid connection device in these embodiments can be any standard fluid connection device known in the art, such as a fluid coupler, or a fluid coupler custom manufactured to preferred specifications. On its first side, the fluid coupler is configured to couple to an existing catheter or cannula (as described with reference to FIGS. 1A-1E). The catheter (or cannula) is typically inserted into a vascular access device and/or into a hospital host during a hospital stay. For example, the catheter can be inserted into an arterial line (e.g., for removing blood samples or for measuring blood pressure using a pressure transducer) or a venous line (e.g., for intravenous delivery of drugs and other fluids). In general practice, the catheter is inserted into the host's blood vessel, for example, and maintained there for a period of time during the host's hospital stay, such as part of the stay or during the entire stay (e.g., perioperatively). In one alternative embodiment, another vascular access device (e.g., other than a catheter) can be used to receive the sensor. In yet another alternative embodiment, the sensor system of the preferred embodiments can be inserted into a vascular access device (e.g., rather than the vascular system directly). Some examples of vascular access devices include but are not limited to, catheters, shunts, automated blood withdrawal devices and the like.

In some embodiments, such as the embodiment illustrated in FIGS. 1A to 1E, the system 10 is configured such that the sensor is inserted into a vascular access device, such as but not limited to a catheter 12 (e.g., a catheter that has been inserted into the host's blood stream prior to sensor insertion). In general, catheters are small, flexible tubes (e.g., soft catheter) but they can also be larger, rigid tubes. Catheters are inserted into a host's body cavity, vessel, or duct to provide access for fluid removal or insertion, or for access to medical equipment. Catheters can also be inserted into extracorporeal devices, such as but not limed to an arterio-venous shunt for the transfer of blood from an artery to a vein. Some catheters are used to direct access to the circulatory system (e.g., venous or arterial catheters, Swan Gantz catheters) to allow removal of blood samples, the infusion of fluids (e.g., saline, medications, blood or total parenteral feeding) or access by medical devices (e.g., stents, extracorporeal blood chemistry analysis devices, invasive blood pressure monitors, etc.).

Preferably, the sensor is designed to include a protective cap, as illustrated in FIGS. 1A-1E. Namely, FIGS. 1A and 1B illustrates the catheter (the catheter cap having been removed prior to insertion), well known to those skilled in the art, which can be inserted into the host's blood vessel using standard methods. The sensor 14 is configured for measurement of an analyte (e.g., glucose) in the host's body, and is in fluid connection within the catheter lumen, which is in fluid connection with the fluid coupler 20 of the sensor. The first side 20a of the fluid coupler 20 of the sensor is designed to couple to the catheter, e.g., by screwing or snapping thereon, and can also couple (on its second side 20b) with other medical devices. One advantage of the fluid coupler is that it provides for a small amount of bleed back, to prevent air bubbles in the host's blood stream.

The exemplary sensor system 10 of FIGS. 1A and 1B further includes a slotted protective sheath 26 that supports and protects the sensor during sensor insertion, for example, the sheath increases the sensor visibility (e.g., the sensor is so thin that it can be difficult for some people to see without the protective sheath) and provides for ease of sliding the sensor into the catheter. The slotted protective sheath is configured to fit within the fluid coupler and houses the sensor during insertion of the sensor into the catheter (e.g., an indwelling catheter within the host's blood flow). Preferably, the protective sheath is substantially more rigid than the sensor and at the same time substantially more flexible that a standard syringe needle, however other designs are possible. To facilitate removal of the protective sheath, a slot 30 is provided with an optional outlet hole 30a, which is described in more detail with reference to FIG. 1C, and a hub 28. By grasping and pulling the hub, the user (e.g., health care professional) can withdraw the protective sheath after coupling the fluid coupler to the catheter. Prior to insertion of the sensor, a cap is provided, to cover the protective sheath, for example, to keep the sheath and sensor sterile, and to prevent damage to the components during shipping and/or handling.

In general, the sensor system is configured with a potentiostat and/or sensor electronics that are operatively coupled to the sensor. In some embodiments, a portion of the sensor electronics, such as the potentiostat, can be disposed directly on the fluid coupler. However, some or all of the sensor electronics (including the potentiostat) can be disposed remotely from the fluid coupler (e.g., on the bedside or on a stand) and can be functionally coupled (e.g., wired or wireless), as is generally known to those skilled in the art.

FIGS. 1C1 and 1C2 are cross-sectional views (not to scale) of the fluid coupler, including a protective sheath 26, a sensor 14, and a cap 32 (cap to be removed prior to insertion) in one embodiment. The protective sheath 26 extends through the fluid coupler and houses the sensor, for sensor insertion into a catheter. The protective sheath includes an optional outlet hole 30a, through which the sensor extends and a slot 30 along a length of the protective sheath that communicates with the outlet hole and enables the protective sheath to be removed after the sensor has been inserted into the host's body. The protective sheath includes a hub 28 for ease of handling.

In some embodiments, the glucose sensor is utilized in combination with another medical device (e.g., a medical device or access port that is already coupled to, applied to, or connected to the host) in a hospital or similar clinical setting. For example, a catheter can be inserted into the host's vein or artery, wherein the catheter can is connected to additional medical equipment. In an alternative example, the catheter is placed in the host to provide quick access to the host's circulatory system (in the event of a need arising) and is simply capped. In another example, a dialysis machine can be connected to the host's circulatory system. In another example, a central line can be connected to the host, for insertion of medical equipment at the heart (e.g., the medical equipment reaches the heart through the vascular system, from a peripheral location such as a leg or arm pit).

In practice of coupling to a catheter, before insertion of the sensor, the access port is opened. In one exemplary embodiment of a pre-inserted catheter that is capped, the cap is removed and the sensor inserted into the catheter. The back end of the sensor system can be capped or attached to additional medical equipment (e.g., saline drip, blood pressure transducer, dialysis machine, blood chemistry analysis device, etc.). In another exemplary embodiment, medical equipment (e.g., saline drip, blood pressure transducer, dialysis machine, blood chemistry analysis device, etc.) is already connected to the catheter. The medical equipment is disconnected from the catheter, the sensor inserted into (and coupled to) the catheter and then the medical equipment reconnected (e.g., coupled to the back end of the sensor system).

In some embodiments, the sensor is inserted directly into the host's circulatory system without a catheter or other medical device. In one such exemplary embodiment, the sheath covering the sensor is relatively rigid and supports the sensor during insertion. After the sensor has been inserted into the host's vein or artery, the supportive sheath is removed, leaving the exposed sensor in the host's vein or artery. In an alternative example, the sensor is inserted into a vascular access device (e.g., with or without a catheter) and the sheath removed, to leave the sensor in the host's vein or artery (e.g., through the vascular access device).

In various embodiments, in practice, prior to insertion, the cap 32 over the protective sheath is removed as the health care professional holds the glucose sensor by the fluid coupler 20. The protective sheath 26, which is generally more rigid than the sensor but more flexible than a needle, is then threaded through the catheter so as to extend beyond the catheter into the blood flow (e.g., by about 0.010 inches to about 1 inches). The protective sheath is then removed by sliding the sensor through the (optional) outlet hole 30a and slotted portion 30 of the sheath (e.g., by withdrawing the protective sheath by pulling the hub 28). Thus the sensor remains within the catheter; and the fluid coupler 20, which holds the sensor 14, is coupled to the catheter itself (via its connector 18). Other medical devices can be coupled to the second side of the fluid coupler as desired. The sensor electronics (e.g., adjacent to the fluid coupler or otherwise coupled to the fluid coupler) are then operatively connected (e.g., wired or wirelessly) to the sensor for proper sensor function as is known in the art.

In another embodiment, the catheter 12 includes a plurality of perforations (e.g., holes) that allow the host's fluid (e.g., blood) to flow through the lumen 12a of the catheter. The fluid flowing through the catheter can make contact with a sensor 14 inserted therein. In a further embodiment, the sensor does not protrude out of the catheter's tip 12b and the host's blood flowing through the perforated catheter's lumen contacts the sensor's electroactive surfaces.

In still another embodiment, the catheter 12 includes at least a first lumen and a second lumen. The sensor 14 is configured for insertion into the catheter's first lumen. The second lumen can be used for infusions into the host's circulatory system or sample removal without disturbing the sensor within the first lumen.

FIGS. 2A-2F are schematic views of a sensor integrally formed (integrally incorporated) onto a surface of a catheter, in some exemplary embodiments. In some embodiments, the sensor can be integrally formed on an exterior surface 232 of the catheter. In other embodiments, the sensor can be integrally formed on an interior surface of the catheter (e.g., on a lumenal surface). In still other embodiments, the sensor can be integrally formed on the sensor's tip (e.g., as indicated by 214a). In yet other embodiments, the sensor can be integrally incorporated with the catheter, for example by bonding a sensor of the type described in FIGS. 3A to 3C into an inner or outer surface of the catheter.

In some embodiments, one or more of the electrodes is deposited on the in vivo portion of the catheter 212, such as via screen-printing and/or electrospinning. In some embodiments, at least one of the electrodes 240, such as but not limited to a counter and/or a reference electrode is deposited within the ex vivo portion of the catheter (e.g., within the connector/hub). In one embodiment, two working electrodes 240 are disposed on the exterior surface 232 of the catheter's in vivo portion. The first working electrode is configured to generate a signal associated with the analyte and with non-analyte-related species that have an oxidation/reduction potential that overlaps with that of the analyte. The second working electrode is configured to generate a signal associated with non-analyte-related species that have an oxidation/reduction potential that overlaps with that of the analyte. As described elsewhere herein, the signals of the first and second working electrodes can be processed to provide a substantially analyte-only signal. Continuous analyte sensors including two working electrodes are described in greater detail elsewhere herein, in U.S. Patent Publication No. US-2007-0027385-A1, U.S. Patent Publication No. US-2007-0213611-A1, U.S. Patent Publication No. US-2007-0027284-A1, U.S. Patent Publication No. US-2007-0032717-A1, U.S. Patent Publication No. US-2007-0093704-A1, and U.S. Patent Publication No. US-2008-0083617-A1, each of which is incorporated herein by reference in its entirety.

In some alternative embodiments, one or more analyte sensors are disposed (e.g., deposited, formed) on the exterior surface of the in vivo portion of the catheter. Each sensor can include one, two or more working electrodes. The electrodes can be configured as described elsewhere therein. In some embodiments, the catheter 12 is configured with two or more analyte sensors, wherein each of the sensors is configured to detect a different analyte and/or a property of the sample, as described elsewhere herein. For example, in some embodiments, the sensors are configured to detect at least two analytes such as but not limited to albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker, various drugs, various minerals, various metabolites, and the like. In some embodiments, at least one of the sensors is configured to detect a property of the host's blood, such as but not limited to pH, oxygen tension, $PCO_2$, $PO_2$, temperature, hematocrit, and the like. In some circumstances, one or more of the plurality of analyte sensor can be configured as a back-up or redundant sensor to a first sensor, such as to confirm the correct functioning of the first sensor. For example, two glucose sensors could be disposed within the connector, such that the second glucose sensor provides a confirmation of the first glucose sensor's measurements.

Generally, the sensor system is provided with a cap 32 that covers the catheter and the in vivo portion of the integral sensor (e.g., see FIG. $1C_2$). A needle or trochar that runs the length of the catheter supports the device during insertion into the host's blood stream. Prior to use, medical caregiver holds the device by the fluid connector 218 and removes the cap to expose the in vivo portion of the device (e.g., the catheter). The caregiver inserts the in vivo portion of the device into one of the host's veins or arteries (depending upon whether the catheter is an intravenous catheter or an arterial catheter). After insertion, the needle is withdrawn from the device. The device is then capped or connected to other medical equipment (e.g., saline bag, pressure transducer, blood collection bag, total parenteral feeding, dialysis equipment, automated blood chemistry equipment, etc.). In some alternative embodiments, the sensor-integrated catheter can be in communication (e.g., fluid communication) with the host's vascular system through a vascular access device.

In some embodiments, an analyte sensor system includes a sensing mechanism substantially similar to that described in U.S. Patent Publication No. US-2006-0020187-A1, which is incorporated herein by reference in its entirety; for example, with platinum working electrode and silver reference electrode coiled there around. Alternatively, the reference electrode can be located remote from the working electrode so as not to be inserted into the host, and can be located, for example, within the fluid coupler 20, thereby allowing a smaller footprint in the portion of the sensor adapted for insertion into the body (e.g., blood stream); for example, without a coiled or otherwise configured reference electrode proximal to the working electrode. Although a platinum working electrode is discussed, a variety of known working electrode materials can be utilized (e.g., Platinum-Iridium or Iridium). When located remotely, the reference electrode can be located away from the working electrode (e.g., the electroactive portion) at any location and with any configuration so as to maintain bodily and/or in fluid communication therewith as is appreciated by one skilled in the art.

In an alternative embodiment, the sensor tip 14a includes an enlarged, atraumatic area, for example a dull or bulbous portion about two times the diameter of the sensor or larger. In one exemplary embodiment, the enlarged portion is created by heating, welding, crushing or bonding a substantially rounded structure onto the tip of the sensor (e.g., polymer or metal). In another exemplary embodiment, the tip of the sensor is heated (e.g., arc welded or flash-butt resistance welded) to cause the tip to enlarge (e.g., by melting). The enlarged portion can be of any atraumatic shape, such as but not limited to oval, round, cone-shaped, cylindrical, teardrop, etc. While not wishing to be bound by theory, it is believed that an atraumatic or enlarged area enables enhanced stability of a small diameter sensor in the blood flow and ensures that the sensor remains within the blood flow (e.g., to avoid piercing a vessel wall and/or becoming inserted subluminally.)

In some embodiments, one or more additional working electrodes can be provided on the sensor for measuring baseline, and thereby subtracting the baseline from the first working electrode to obtain a glucose-only signal and/or to measure additional analytes, as disclosed in copending U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, all of which are herein incorporated by reference in their entirety.

Referring now to FIGS. 2A-2E in more detail, some embodiments of the analyte sensor system include a catheter 212 adapted for inserting into a host in a hospital or clinical setting, wherein the analyte sensor 214 is built integrally with the catheter 212. For example, a glucose sensor can be integrally formed on the catheter itself. FIGS. 2A-2B illustrate one embodiment, wherein the catheter 212 is configured both for insertion into a host, and can be configured to couple to other medical devices on its ex vivo end. However, coupling to other medical devices is not necessary. In some embodiments, the catheter includes a connector 218 configured for connection to tubing or other medical devices, as described herein. The embodiment shown in FIGS. 2A-2B includes two or three electrodes 240 on the outer surface of the in vivo portion of the catheter 212. In some embodiments, the catheter is perforated (as described elsewhere herein) and at least one electrode is disposed within the lumen (not shown) of the perforated catheter. In some embodiments, the catheter includes a single lumen. In other embodiment, the catheter includes two or more lumens.

With reference to FIGS. 2C-2E, in some embodiments, at least one working electrode 240 is disposed on the exterior surface of the in vivo portion of the catheter. Alternatively, the at least one working electrode can be disposed on an interior surface of the catheter, on the tip of the catheter, extend from the catheter, and the like. In general, the preferred embodiments can be designed with any number of electrodes, including one or more counter electrodes, one or more reference electrodes, and/or one or more auxiliary working electrodes. In further embodiments, the electrodes can be of relatively larger or smaller surface area, depending upon their uses. In one example, a sensor includes a working electrode and a reference electrode that has a larger surface area (relative to the surface area of the working electrode) on the surface of the catheter. In another example, a sensor includes a working electrode, a counter electrode, and a reference electrode sized to have an increased surface area as compared to the working and/or counter electrode. In some embodiments, the reference electrode is disposed at a location remote from the working electrode, such as within the connector (e.g., coiled within the connector). In some embodiments, the reference electrode is located on the host's body (e.g., in body contact).

The electrodes 240 can be deposited on the catheter using any suitable techniques known in the art, for example, thick or thin film deposition techniques. The electrodes can be formed of any advantageous electrode materials known in the art (e.g., platinum, platinum-iridium, palladium, graphite, gold, carbon, silver, silver-silver chloride, conductive polymer, alloys, combinations thereof, and the like). In other embodiments, one or more of the electrodes is formed from an electrically conductive material (e.g., wire or foil comprising platinum, platinum-iridium, palladium, graphite, gold, carbon, silver, silver-silver chloride, conductive polymer, alloys, combinations thereof, and the like) applied to the exterior surface of the catheter, such as but not limited twisting, coiling, rolling or adhering.

In some embodiments, the catheter is (wired or wirelessly) connected to sensor electronics (not shown, disposed on the catheter's connector and/or remote from the catheter) so as to electrically connect the electrodes on the catheter with the sensor electronics. The inserted catheter (including the sensor integrally formed thereon) can be utilized by other medical devices for a variety of functions (e.g., blood pressure monitor, drug delivery, etc).

Referring now to FIGS. 2G through 2S, in some preferred embodiments a plurality of analyte sensors 240 are disposed within a widened portion of the catheter, such as but not limited to a flared portion and/or a connector portion 212, or within the interior of a connector 250, such as but not limited to a Leur lock, a Y-connector, a T-connector, an X-connector, and a valve, wherein a first side/end of the connector is configured to be coupled and/or connected to another vascular access device, such as a catheter or cannula, and a second side (e.g., end) of the connector is configured to be coupled/connected to other IV equipment, such as another connector, a valve, IV tubing, and the like.

FIG. 2G is a cross section of a vascular access device including a plurality of analyte sensors 240 in one embodiment. The vascular access device, such as a catheter includes an in vivo portion configured for insertion into a circulatory system of the host, including a lumen 212a, and a connector 218 having a wall 260 defining a duct 218b. In some embodiments, an inner diameter of the connector is greater than an inner diameter of the in vivo portion. For example, in some embodiments, the vascular access device is a 20-gauge or smaller catheter. In some embodiments, the in vivo portion of the catheter is configured and arranged for insertion into a circulatory system of a pediatric host, such as but not limited to a neonatal host. The vascular access device is configured and arranged for receipt of a sample of a bodily fluid of a host (e.g., blood after catheter insertion). At the proximal end, also referred to herein as the in vivo portion, the vascular access device includes a catheter 212 having a lumen 212a and a small orifice 212b. At the distal end, also referred to here as the ex vivo portion, the vascular access device includes a connector 218, also referred to herein as the "hub." The hub includes an orifice 218c, which is configured for connection (e.g., fluid communication) with other IV equipment, such as via one or more flanges 218a. The connector 218 also includes a duct 218b, also referred to a widened portion (as compared to lumen 212a, which may be referred to as the connector's lumen. A plurality of analyte sensors 240 is disposed within the duct 218b. In some embodiments, the device includes an analyte sensor 240, wherein at least a portion of the analyte sensor is located in the lumen or duct, such that the analyte sensor is located within about 60, 55, 50, 45, 40, 35, 30, 25, 20, 15, 10, 5, 4, 3, 2, or 1-mm or less from a source of the biological sample. For example, in some embodiments, the electroactive surfaces are within about 40-mm or less of the blood prior to drawing the blood back into the hub of an implanted catheter or into a fluid coupler connected to an implanted catheter. In some embodiments, the analyte sensor is located within about 30-mm or less from a source of the sample. Configuring the system such that the analyte sensor (s) (e.g., the electroactive surfaces of the electrodes) are located within only 60-mm or less from the sample (e.g., prior to drawing back the sample into the catheter) translates into a requirement for only very small sample volumes. For example, in some embodiments, the device is configured such that the analyte sensor is bathed in the sample when (no more than) about 1000, 900, 800, 700, 600, 500, 400, 300, 200, 100, 50, 25, 15, 10, or 5-µl or less of the bodily fluid (e.g., blood) is drawn back. In some embodiments, one or more of the analyte sensors 240 is deposited and/or formed on a surface of the duct 218b, such as by screen printing or other useful deposition techniques. In some embodiments, one or more of the analyte sensors 240 is applied to the duct's surface, such as by adhering or micro welding a previously formed sensor to the duct's surface. In some embodiments, at least a portion of one or more of the analyte sensors 240 is unattached to the duct's surface. The analyte sensors can be configured to detect one or more analytes using any means known in the art, such as but not limited to electrochemical detection, enzymatic detection, chemical detection, physical detection, immunochemical detection, optical detection, radiometric detection, and combinations thereof. For example, in one embodiment of a device including three sensors 240 within the hub 218, a first sensor 240 is configured to detect glucose electrochemically, a second sensor 240 is configured to detect oxygen optically, and the third sensor 240 is configured to detect bilirubin immunochemically.

In one exemplary embodiment, a system configured to measure one or more analytes in a host is provided, wherein the system includes a vascular access device including a first portion configured for insertion into a host and a second portion configured to remain outside the host after insertion of the first portion; at least one analyte sensor 240 located within the second portion of the vascular access device, such that the at least one analyte sensor is exposed to a biological sample when the biological sample is drawn back about 40-mm or less, when the vascular access device is in fluid communication with a circulatory system of the host; and a flow control device configured to regulate exposure of the at least one sensor to a biological sample and to a reference solution according to a flow profile. In some embodiments, the system is configured such that the at least one analyte sensor is exposed to the biological sample when about 300-µl or less of the biological sample is drawn back. In another embodiment, the system is configured such that the at least one analyte sensor is exposed to the biological sample when about 200-µl or less of the biological sample is drawn back. In some embodiments, the vascular access device includes a catheter. For example, in some embodiments, the catheter is 22-gauge or smaller. In some embodiments, a lumen of the second portion is wider than a lumen of the first portion. For example, the lumen (e.g., duct) of a catheter hub is wider than the lumen of the in vivo portion of the catheter, in exemplary embodiments. In some embodiments, the second portion includes a connecting end on the catheter. For example, the second end of the catheter (e.g., the hub) is configured and arranged for connection to tubing (e.g., IV tubing, the tubing assembly). In other embodiments, the second portion includes a fluid coupler, wherein the fluid coupler is configured to releasably mate with a catheter. In some embodiments, the at least one sensor is incorporated into the second portion (e.g., the ex vivo portion of the catheter), such as on an inner surface of the second portion. In some embodiments, at least a portion of the at least one sensor is disposed in an orientation substantially parallel to a longitudinal axis of the second portion. In some embodiments, at least a portion of the at least one sensor is disposed in an orientation substantially perpendicular to a longitudinal axis of the second portion. In some embodiments, the at least one sensor includes an exposed electroactive surface area with a dimension substantially equal to a width of a lumen of the second portion. In some embodiments, the exposed electroactive surface area intersects the lumen of the second portion. In some embodiments, the at least one analyte sensor includes at least three analyte sensors located within the second portion of the catheter. In a further embodiment, the at least one analyte sensor includes at least eight analyte sensors located within the second portion of the catheter. In some embodiments, the second portion is configured to provide identification information associated with a flow profile, such as described elsewhere herein. In some embodiments, the system is configured to program the flow profile (of a flow control device) in response to automatic receipt of the identification information. In some embodiments, the identification information is provided by a mechanical structure of the second portion (e.g., the catheter). In some embodiments, the identification information is provided by electronics of the second portion (e.g., the catheter).

In another exemplary embodiment, a system configured to measure one or more analytes in a host is provided, wherein the system includes a fluid coupler including a first end and a second end, wherein the first end is configured to releasably mate with a connecting end of a catheter, and wherein the second end is configured to releasably mate with a tubing assembly; and at least one analyte sensor located within the fluid coupler such that when the fluid coupler is mated to a catheter inserted into a circulatory system of a host, the at least one analyte sensor is exposed to a biological sample when the biological sample is drawn back about 40-mm or less. In one embodiment, the at least one sensor is located on an inner surface of the fluid coupler. In some embodiments, the at least one sensor is incorporated into the fluid coupler. In a further embodiment, the at least one sensor is disposed within a lumen of the fluid coupler (e.g., the second portion). In some embodiments, the system is configured such that the at least one analyte sensor is exposed to the biological sample when about 300-µl or less of the biological sample is drawn back. In another embodiment, the system is configured such that the at least one analyte sensor is exposed to the biological sample when about 200-µl or less of the biological sample is drawn back. In some embodiments, the at least one sensor is incorporated into the fluid coupler. In some embodiments, the at least one sensor is located on an inner surface of the fluid coupler. In some embodiments, the at least one sensor is disposed within a lumen of the fluid coupler. The at least one analyte sensor can be disposed in an orientation substantially parallel to a longitudinal axis of the fluid coupler, or in an orientation substantially perpendicular to the longitudinal axis of the fluid coupler. In some embodiments, the at least one sensor includes an exposed electroactive surface area with a dimension substantially equal to a width of a lumen of the fluid coupler, such as described with reference to FIGS. 2M-2P. In some further embodiments, the exposed electroactive surface area intersects the lumen of the fluid coupler. In preferred embodiments, the fluid coupler is configured to provide identification information associated with a flow profile, such as described with reference to FIG. 10E, herein. For example, in one embodiment, the system is configured to program the flow profile of the flow control device in response to automatic receipt of the identification information. In some embodiments, the identification information is provided by a mechanical structure of the fluid coupler. For example, in some embodiments, a portion of the fluid coupler is configured to form a mechanical interlock with a portion of the flow control device and/or the tubing assembly, wherein formation of the mechanical interlock automatically selects a flow profile associated with the fluid coupler (or with a catheter size, with a type of host (e.g., infant host versus child host versus adult host) and the like). In some other embodiments, the fluid coupler includes electronics that provide identification information. In still other embodiments, the fluid coupler includes both a mechanical structure and electronics configured to provide the identification information associated with the flow profile. In some embodiments, the fluid coupler includes multiple lumens, wherein the system is configured and arranged to infuse a fluid a fluid in a first lumen of the fluid coupler, and to draw back a biological sample into a second lumen of the fluid coupler. For examples, in embodiments wherein the at least one analyte sensor is located in the second lumen, a hydration, nutrition and/or medicament solution can be infused via the first lumen without substantially affecting the at least one sensor. In some embodiments, the system is configured to infuse another solution, such as a calibration, wash or hydration solution through the second lumen of the fluid coupler, such as for washing the sensor and/or for making reference measurements. While some embodiments include a single analyte sensor located in the fluid coupler, in other embodiments, the at least one analyte sensor includes at least 2, 3, 4, 5, 6, 7, 8, or 9 or more analyte sensors. In some embodiments, two or more of the analyte sensors are configured to detect the same analyte, such as for a back-up (e.g., in case a first sensor fails the other sensor can be used) and/or as a quality check (e.g., to make sure the sensors are working substantially the same). In other embodiments, the analyte sensors are each configured to measure a different analyte. In still other embodiments, some of the analyte sensors are configured to detect the same analyte, while the remaining analyte sensors are configured to detect different analytes. One skilled in the art appreciates the variety of possible analyte sensor configuration combinations.

In some embodiments, the system is configured and arranged such that the at least one analyte sensor is located within about 35, 30, 25, 20, 15, 10, 5, 4, 3, 2, or 1-mm or less from a source of the biological sample. In some embodiments, the at least one analyte sensor is located (e.g., within the vascular access device), such that the analyte sensor is bathed in the sample when about 1000, 900, 800, 700, 600, 500, 400, 300, 200, 100, 50, 25, 15, 10, or 5-µl or less of the bodily fluid (e.g., blood) is drawn back. In some embodiments, a lumen of the second portion is wider than a lumen of the first portion. For example, the lumen of the fluid coupler is wider than the lumen of the catheter. In some embodiments, the second portion is a fluid coupler, wherein the fluid coupler is configured to releasably mate with the catheter. In some embodiments, the at least one sensor is incorporated into the second portion. For example, in one embodiment, the at least one sensor is located on an inner surface (e.g., the lumenal surface) of the fluid coupler (e.g., the second portion). In a further embodiment, the at least one sensor is disposed within a lumen of the fluid coupler (e.g., the second portion). In some embodiments, at least a portion of the at least one sensor is disposed in an orientation substantially parallel to a longitudinal axis of the fluid coupler (e.g., the second portion). In some embodiments, at least a portion of the at least one sensor is disposed in an orientation substantially perpendicular to a longitudinal axis of the fluid coupler (e.g., the second portion). In some embodiments, the at least one sensor includes an exposed electroactive surface area with a dimension substantially equal to a width of a lumen of the fluid coupler (e.g., the second portion). In some embodiments, the exposed electroactive surface area intersects the lumen of the fluid coupler (e.g., the second portion). In some embodiments, the fluid coupler (e.g., the second portion) is configured to provide identification information associated with the flow profile. In some embodiments, the system is configured to program the flow profile of the flow control device in response to automatic receipt of the identification information (e.g., via a wired or wireless connection and/or triggered by a physical and/or operable connection of the vascular access device (e.g., fluid coupler and/or catheter) with the flow control device and/or system electronics). In some embodiments, the identification information is provided by a mechanical structure of the fluid coupler (e.g., the second portion). In some embodiments, the identification information is provided by electronics of the fluid coupler (e.g., the second portion).

In some embodiments, the at least one analyte sensor is configured to measure an analyte selected from the group consisting of albumin, alkaline phosphatase, alanine transaminase, aspartate aminotransferase, bilirubin, blood urea nitrogen, calcium, $CO_2$, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug. In some embodiments, the at least one analyte sensor includes at least three analyte sensors located within the second portion of the vascular access device and configured to measure at least three analytes. For example, in one embodiment the second portion of the vascular access device is the second portion of a catheter (e.g., the ex vivo portion, the hub), and the at least three analyte sensors are located therein. In some embodiments, the at least one analyte sensor includes at least eight analyte sensors located within the second portion of the vascular access device (e.g., the fluid coupler or the second portion (e.g., hub or ex vivo portion) of a catheter) and configured to measure at least eight analytes.

In one exemplary embodiment, the catheter is a peripheral catheter (e.g., for insertion into a vein located in an arm and/or leg) having the analyte sensor located within the catheter hub. In some embodiments, the volume that the catheter hub can hold has been restricted (e.g., reduced), such as by fabricating the catheter hub with a reduced internal diameter. In this embodiment, the sample is drawn back only about 50, 45, 40 or 35-mm (e.g., into the catheter hub, depending upon the length of the catheter), such that the analyte sensor is bathed in the sample.

In yet another exemplary embodiment, the analyte sensor is located within the lumen of a fluid coupler (e.g., configured for fluid connection with a catheter). In this embodiment, when the fluid coupler is coupled to an implanted peripheral catheter, the sensor's electrodes are bathed in a sample when the sample is drawn back a distance of about 50, 45, 40, 35 or 30-mm, depending upon the length of the catheter, which correlates with a sample volume of about 500, 450, 400, 350, 300 or 250-µl or less.

Alternatively, when the catheter is coupled to a central catheter (e.g., a catheter for insertion into vessels in the body, such as to access the heart), the distance the sample is drawn back (e.g., to sufficiently contact/bathe the electrodes such that analyte measurements can be taken) is much farther (e.g., relative to the distance of draw-back into a peripheral catheter), since central catheters range from about 12 to about 24-inches in length. Thus, in this exemplary embodiment, the distance the sample is drawn back includes the entire length of the central catheter (including the catheter's hub) and a portion of the connector, such as but not limited to about 12, 13, 14 or 15 inches, to about 18, 19, 20, 21, 22, 23, 24 or 25-inches or more, depending upon the length of the catheter, which can correspond with a sample volume of about 1.5-ml, 1.25-ml, 1-ml, 900-µl, 800-µl, 700-µl, 600-µl or 500-µl or less, depending upon the catheter's size and/or configuration, the fluid coupler's configuration, and the like. If the sensor extends from the fluid coupler into the central catheter, the distance the sample is drawn back is reduced to a portion of the central catheter's length, with a corresponding reduction in sample volume.

FIG. 2H is a cross section of a vascular access device including a plurality of analyte sensor 240 in another embodiment. In this embodiment, the vascular access device is a connector 250 (e.g., fluid coupler) and/or valve, such as but not limited to a Leur lock, a Y-connector, a T-connector, and an X-connector. In general, the connector 250 (e.g., fluid coupler) is configured to be coupled/connected to vascular access devices, such that a fluid can pass between two vascular access devices coupled to the connector's two ends. For example, a first end of the connector can be coupled to a catheter or cannula implanted (e.g., pre-implanted) in a host's vein or artery, and a second end of the connector can be coupled to another connector, a valve, IV tubing, and IV bag, a test device, etc. In some embodiments, the connector 240 is a fluid coupler, such as described with reference for FIGS. 1A-1M and 2M-2S. The connector includes a duct 254 (e.g., lumen) and a proximal orifice 258. A plurality of analyte sensors 240 is disposed within the duct 254. As described with reference to the device shown in FIG. 2G, the plurality of analyte sensors can be disposed within the duct 254 using any means known in the art. In some embodiments, one or more of the analyte sensors are deposited (e.g., formed) on a surface of the duct 254 (e.g., on an interior surface). In some embodiments, one or more of the analyte sensors are applied to the surface of the duct 254. In some embodiments, one or more of the analyte sensors is configured to pass through (e.g., intersect) the wall 252 of the connector such that a first portion of the sensor 240 is disposed within the duct 254 and a second portion of the sensor 240 is disposed at the exterior of the connector 250 (described in more detail herein).

FIG. 2I is a cross-section of a vascular access device of either FIG. 2G or FIG. 2H taken along line 2I-2I, looking towards the proximal end of the vascular access device. The device includes a duct/lumen 212b/254 defined by a wall 260. The in vivo orifice (also referred to as the proximal orifice with relation to the host) of the device is represented by circle 212b/258. As shown in this embodiment, a plurality of sensors can be disposed within the duct, such as but not limited at the in the interior surface of the wall. In some embodiments, the device includes two analyte sensors. In some embodiments, the device includes 3, 4, 5, 6, 7 or more analyte sensors. In some embodiments, one or more of the analyte sensors are configured to be disposed entirely within the duct (e.g., to not protrude out of the duct). In some embodiments, one or more analyte sensors can be configured such that a portion thereof protrudes out the duct, such as but not limited to into the lumen of a catheter 212 or through the proximal orifice 212b/258 of the device. In some embodiments, a portion or one or more of the sensors can be configured to protrude through the ex vivo orifice (also referred to as the distal orifice with ration to the host) of the device. The analyte sensors 240 disposed within the device can be of any configuration and can use any detection method, including but not limited to electrochemical, enzymatic, optical, radiometric, chemical, physical, immunochemical and the like, including a combination thereof.

FIG. 2J is a cross-section of a vascular access device of either FIG. 2G or FIG. 2H taken along line 2I-2I, looking towards the proximal end of the vascular access device, prior to installation of any analyte sensors 240. FIG. 2K depicts the FIG. 2J device after sensor installation. In this embodiment, a plurality of sensor sites 262 is located at the surface of the wall 260. While FIGS. 2J and 2K depict the sensor sites 262 as being depressions in the wall 260, the sensor sites 262 can be of any configuration, such as but not limited to a portion of the wall's inner surface that is flush with the remaining portion of the inner surface, a textured portion of the inner surface, a channel, a hole, and the like. In some embodiments, the sensor sites can have a plurality of configurations. For example, in a device including four sensor sited 262, a first site can have a first configuration, the second and third sites a second configuration, and the fourth site yet another configuration.

FIG. 2L is a cross-section of a vascular access device of either FIG. 2G or FIG. 2H taken along line 2I-2I, looking towards the proximal end of the vascular access device, in an alternative embodiment. In this embodiment, the sensor sites 262 can be formed to include a plug 264 and/or a breakaway portion of the wall 260, which can be removed to enable sensor installation. For example, a plug/breakaway portion can be pushed and/or punched out of the sensor site and then the sensor installed in the sensor site. In some embodiments, removal of a plug/breakaway portion creates a channel through the wall, such that a sensor (at least a portion thereof) can be inserted through the channel and into the duct 254. In some embodiments, the portion of an installed sensor remaining on the external side of the wall is configured to functionally connect to sensor electronics, as is appreciated by one skilled in the art. While not wishing to be bound by theory, it is believed that this configuration enables increased accuracy and speed in device assembly because the sensors can be manufactured separately from the device and then installed into the device in a "plug-and-play" fashion.

FIG. 2M illustrates another embodiment of the analyte sensor system configured to measure one or more analytes in a bodily fluid of a host, namely a fluid coupler (e.g., connector) 250 having a wall 260, a lumen 254, a first end 258 configured and arranged for fluid communication with a vascular access device, and a second end 256 configured and arranged for fluid communication with an infusion device, such as via IV tubing and/or a tubing assembly, such as described elsewhere herein. The analyte sensor 240 (e.g., 240a, 240b and/or 240c) is configured and arranged to generate a signal associated with an analyte in a sample of a circulatory system of a host (e.g., a bodily fluid such as but not limited to blood), wherein at least a portion of the analyte sensor is disposed within the lumen 254 of the fluid coupler 250. In preferred embodiments, the device is configured such that, when it is fluidly connected to an implanted catheter, at least a portion of the analyte sensor 240 is located within about 60, 55, 50, 45, 40, 35, 30, 25, 20, 15, 10, 5, 4, 3, 2, or 1-mm or less from the source of the sample, such as from the tip of the inserted catheter. In some embodiments, the analyte sensor is located within about 30-mm or less from a source of the sample. Advantageously, locating the sensor close to the source of sample (e.g., bodily fluid, blood) and configuring the system for use of very small samples, including return of the sample to the host, limits the loss of blood from the host, thereby enabling the use of the device in circumstances, such as neonatal and critical care settings, wherein loss of blood is a critical issue for host health and/or survival. For example, in one embodiment, the device is configured such that analyte sensor is bathed in the sample when about 1000, 900, 800, 700, 600, 500, 400, 300, 200, 100, 50, 25, 15, 10, or 5-µl of the bodily fluid is drawn back.

In some embodiments, the vascular access device (e.g., a catheter or a fluid coupler) includes a longitudinal axis. For example, if the device is a catheter, the longitudinal axis can extend from the tip 212b of the in vivo portion to the hub orifice 218c. In another example, if the device is a fluid coupler, the longitudinal axis can extend from the proximal orifice 258 to the distal orifice 256. The analyte sensor (e.g., the electrodes, electroactive surfaces) can be disposed in the catheter hub or fluid coupler lumen in various orientations with relation to the longitudinal axis. For example, in some embodiments, the analyte sensor is disposed in an orientation parallel to the longitudinal axis. For example, in one embodiment, the analyte sensor intersects the wall 260, such that the electroactive surface(s) are located along an interior (e.g., luminal) surface of the wall. For example, the electrode can intersect the wall at two points that are separated by a longitudinal distance on the wall, such that the electroactive surface(s) are oriented parallel to the longitudinal axis of the device. For example, with reference to the device of FIG. 2M, in an alternative embodiment, one or more of the electrodes (e.g., 240a, 240b and/or 240c) can intersect the wall at two points along one side of the device (e.g., 260a or 260b) such that the length of the electrode runs parallel to the longitudinal axis of the device. For example, if the device includes three electrodes, the electrodes can be spaced about the inner circumference of the lumen, such as but not limited to equidistant from each other, wherein each electrode runs parallel along the luminal wall in an orientation parallel to the longitudinal axis of the device. In another embodiment, one or more sensors (e.g., twisted and/or bundled working and/or reference electrodes, instead of individual electrodes) can be placed in the device such that a length of the electroactive surfaces of the sensor(s) is parallel to the longitudinal axis of the device. For example, the device could include 2, 3, 4, 5 or more analyte sensors. In some embodiments, the reference electrode is disposed remotely from the working and/or counter electrode(s). In some embodiments, one reference electrode is configured to function as the reference electrode for two or more analyte sensors.

In some embodiments, the electrode(s) are disposed within the catheter hub or fluid coupler such that they are oriented perpendicularly to a longitudinal axis of the device. Returning again to the exemplary embodiment illustrated in FIG. 2M, the device can be configured such that the individual electrodes (e.g., 240a, 240b and 240c) intersect wall 260 on opposite sides (e.g., 260a and 260b) of the device, such that each electrode is perpendicular to the longitudinal axis of the fluid coupler. For example, in some embodiments, the first and second points can be connected by a line that is perpendicular to the longitudinal axis of the device. One skilled in the art appreciates that while FIG. 2M illustrates individual electrodes 240a, 240b and 240c, in other embodiments, one complete sensor (e.g., having bundled and/or twisted working, counter and/or reference electrodes) can be used. In some further embodiments, the device is configured such that the electroactive surface of each electrode has a surface area having a first dimension (e.g., length or width) substantially equal to a diameter of the lumen of the connector or hub. For example, in the embodiment shown in FIG. 2M, the length of the electroactive surfaces (e.g. window 343 of FIG. 3B) can be substantially equal to the inner diameter of the fluid coupler. In a further example, each electrode can be formed, including the membrane, as described herein, inserted through the wall(s) of fluid coupler (e.g., through holes or using a needle to pierce the wall(s) formed of elastomeric material as described herein), such that the electroactive surface is disposed within the lumen, excess electrode material removed from one side (e.g., 260b) and then electrical connection with system electronics (e.g., via soldering electrical wires) on the opposite side (e.g., 260a).

While the electrodes of the embodiment illustrated in FIG. 2M are disposed individually, additional configurations are contemplated in the preferred embodiments. For example, in some embodiments, the electrodes are bundled and/or twisted, such that the electrodes intersect the wall together. In other embodiments, the analyte sensor includes an electrode located within the lumen of the in vivo portion of the catheter, such as at the tip 212b of the catheter. In another embodiment, the electrode is located at and/or on the luminal surface of the in vivo portion of the catheter. For example, in some embodiments, the electrodes are deposited on a flexible support, which is inserted into the lumen. In another example, in some embodiments, the electrodes are deposited on the flexible support when the flexible support having a planar configuration, which is then cut to size, rolled into a cylindrical configuration (such that the electrodes are within the interior of the cylinder), and then inserted into the catheter lumen. In a further exemplary embodiment, the flexible support is formed of an appropriate material to form the in vivo portion of a catheter, electrodes are applied to a surface of the material (e.g., when in a planar configuration) using methods known in the art, the material is cut to size, rolled and the cut edges sealed (e.g., by welding or an adhesive), and a catheter hub applied thereto, such that the rolled and sealed flexible support forms the wall of the in vivo portion of the catheter, wherein the electrodes are located on the luminal surface of the electrode wall. Forming the catheter and electrodes in this manner enables easy manufacturing techniques and a variety of electrode configurations, such as but not limited to linear electrodes, circular electrodes, electrodes that spiral along/ around the interior of the catheter, and the like. In additional embodiments, a plurality of analyte sensors (e.g., including two or more electrodes) can be disposed in the catheter lumen, such that two or more analytes can be measured, or such that redundant sensors (e.g., two or more glucose sensors) can measure a single analyte.

FIG. 2N illustrates an embodiment of a fluid coupler configured to include two or more analyte sensors, namely the fluid coupler is divided into two or more channels, each of which includes an analyte sensor. In one illustrated embodiment, the fluid coupler is divided into two flow channels 254 (e.g., two lumens), each with an analyte sensor disposed therein (e.g., electrode 240a, 240b and 240c). For example, the analyte sensor in one flow channel can be configured to detect glucose and the analyte sensor in the other flow channel can be configured to detect a cardiac marker, in one embodiment. In another illustrated embodiment, the fluid coupler is divided into three flow channels (e.g., three lumens), each with an analyte sensor disposed therein. Inclusion of additional lumens enables incorporation of additional analyte sensors such that each analyte sensor receives a sample uncontaminated by reagents and/or products and/or for infusion of a medicament. For example, a glucose sensor using GOX to detect glucose generates $H_2O_2$, which can affect the other sensors of the device. If the sensors are located in separate lumens, the $H_2O_2$ generated by the glucose sensor cannot affect the sensors located in the other lumens. As a further example, sample that is drawn back flows into each of the lumens, such that each of the sensors is bathed in sample uncontaminated by reagents and reaction products from another of the sensors. When the device is flushed (e.g., with saline or calibrant solution), each of the sensors are washed and does not contaminate another sensor with its reagents/ reaction products. Accordingly, in some embodiments, the fluid coupler is divided into additional channels, such as a network of 4, 5, 6, 7, 8, 9, 10 or more channels, such that panels of analytes can be continuously measured at the same time. In some embodiments, the fluid coupler is miniaturized, thereby providing a micro-scale, multi-sensor device, such that about 5, 10, 15, 20, 25, 30, 40, 50, 100 or more analytes can be continuously monitored simultaneously. This configuration provides certain advantages, such as but not limited to, this device is amenable to high-throughput, modular manufacturing on an assembly line; the device can be connected to a wide variety of catheters currently in use; a plurality of sensors can be used simultaneously; and the device is amenable to custom-made analyte panels (e.g., Hospital #1 wants glucose and oxygen sensors, while Hospital #2 wants glucose, creatinine and temperature sensors).

A variety of techniques can be used to manufacture an integrated fluid coupler and analyte sensor device. For example, in some embodiments, the wall 260 is formed of a self-sealing material (not shown), such that the analyte sensor can be inserted through the wall using a needle. For example, a needle containing the sensor in its barrel can be inserted through the wall, followed by withdrawal of the needle over the sensor, such that the sensor remains inserted through the wall. For example, polymer tubing, such as but not limited to silicone tubing, can be used to form the central body of a fluid coupler, and connector ends (e.g., configured for connecting the fluid coupler to a catheter and/or tubing) attached thereto. Additional methods of manufacturing the preferred embodiments are detailed in the section entitled "Multi-Sensor Apparatus."

FIGS. 2O and 2P illustrate another method of manufacturing an integrated fluid coupler and analyte sensor device, such as that shown in FIG. 2M. In one embodiment, the fluid coupler is formed of two or more mateable portions (e.g., 260-1, 260-2), wherein the first and second mateable portions are configured and arranged to form a seal 260e when mated together, such that the lumen is formed 254. For example, the two mateable portions can be formed by injection molding a suitable medical-grade plastic. In the embodiment shown in FIG. 2O, the two mateable portions 260-1, 260-2 are configured to mate together, such as but not limited to in a clam shell configuration. One or both of the two mateable portions 260- 1, 260-2 includes an indentation 260c on the sealing edge(s) (e.g., mating edges) configured to receive an analyte sensor (and/or an electrode). In the illustrated embodiment, the two mateable portions each include three indentations, wherein the indentations are configured to receive the electrodes 240. In some embodiments, the sensor electrodes are inserted separately (e.g., as opposed to in a bundled or twisted configuration). In a further embodiment, the electrodes can be spaced along the length of the lumen to optimize fluid flow and analyte detection. For example, in some embodiments, the electrodes are spaced equally within the lumen (e.g., the distance between electrodes 240a and 240b is substantially equal to the distance between electrodes 240b and 240c). In some embodiments, the device is configured such that the diameter of the lumen is substantially the same as the length of the electroactive surfaces (e.g., which span the lumen). Additional configurations are contemplated, such as non-linear spacing and non-equal spacing of the electrodes.

Referring again to FIGS. 2O and 2P, in some embodiments, a grommet 260d can be included at the point at which the electrode intersects the mated wall. In other embodiments, the wall surrounding the electrode (e.g., at 260d) can be welded, to form a seal between the electrode and the wall. In some embodiments, the seal is fluid-tight. In some embodiments, a portion of the wall material is melted by the welding, such that a portion of the melted wall material can soak into the membrane of the electrode. FIG. 2P illustrates an alternative method of forming the integrated fluid coupler and analyte sensor device, wherein the two mateable portions 260-1, 260-2 comprise cylinders configured to mate together such that the analyte sensor 240 spans the lumen 254.

A connection between the analyte sensor (and/or individual electrodes) and sensor electronics can be made on the exterior surface of the fluid connector. For example, in some embodiments, the analyte sensor electrodes are soldered to wires, which in turn make electrical connection with the sensor electronics. In other embodiments, the electrodes are clipped off substantially flush with the exterior surface of the wall and a PCB 20t (e.g., configured to make suitable electrical connection with each of the electrodes) is attached to the clipped-off ends of the electrodes (e.g., via adhesive or welding), such that the electrical connections are made; the PCB is then used to connect the sensor to sensor electronics. In still other embodiments, elastomeric contacts can be used to make a connection between the electrodes and sensor electronics, in a manner similar to that illustrated in FIGS. 1H and 1J. Additional methods of connecting analyte sensors to sensor electronics are appreciated by those skilled in the art.

FIG. 2Q illustrates an alternative embodiment of an integrated fluid coupler and analyte sensor device, in which the electrodes are formed of conductive elastomeric material (e.g., contacts 240). A portion of the fluid coupler can be configured with one or more holes 260c to receive the elastomeric contacts. For example, the fluid coupler can be injection molded of plastic, including the holes 260c configured to receive the elastomeric contacts 240. The electrode/elastomeric contacts can be formed of any conductive elastomeric materials, such as but not limited to carbon black elastomer. Each elastomeric contact is configured with an interior side 240e and an exterior side 240d. The interior side is configured and arranged as an electrode, such as one or more working electrodes (plus and/or minus enzyme), a counter electrode or a reference electrode, as described elsewhere herein. The exterior side is configured and arranged for electrical connection with the sensor electronics. The electrode/elastomeric contact can have any useful shape, such that the interior side can be inserted through a hole of the fluid coupler, such that the electroactive surface can be bathed by a sample drawn back into the fluid coupler, and such that the exterior side is sufficiently exposed for making the electrical connection with the sensor electronics. The conductive material can be formed into any shape. For example, the electrode/elastomeric contact can be a ball, or wedge or cylinder. In the embodiment shown in FIG. 2Q, the electrode/elastomeric contact includes a cylindrical body with a flat electroactive surface at the interior side 240e, and sloped or flared sides. The interior side 240e is configured and arranged to be substantially flush with the lumenal surface of the fluid conduit wall, such that fluid turbulence, biofouling and/or clotting is/are substantially reduced when the device is in use. The exterior side 240d includes a flat butt end, which is somewhat larger in diameter than cylindrical body, and a shoulder. In some embodiments, the elastomeric material is sufficiently pliable that the elastomeric contact can conform to the structure of the hole, when it is inserted into the hole; such that it makes a substantially water-tight seal with the wall of the fluid coupler. For example, in the illustrated embodiments, the flared sides are configured to conform to the hole (e.g., an interference fit), such that the conformed side and the shoulder make a water-tight seal with the wall of the fluid conduit.

Electrical connection between the electrode/elastomeric contacts 240 and sensor electronics can be made with their exterior surfaces by any method known in the art. For example, in some embodiments, a PCB 20t configured and arranged for electrical contact with the elastomeric contacts is adhered over the elastomeric contacts. A cover, such as one configured with a female connector 20n (e.g., see cover 20k in FIGS. 1H-1J) is adhered over the PCB, or the PCB is hardwired to an electrical cable. In another embodiment, the electrode/elastomeric contacts are simply soldered to the wires of an electrical cable. In still other embodiments, conductive traces (e.g., vias) is applied to the exterior surface of the fluid conduit (e.g., prior to insertion of the electrode/elastomeric contacts) such that when the elastomeric contacts are inserted into the holes, the shoulder of each electrode/elastomeric contact makes an electrical connection with one of the conductive traces. The electrical traces, in turn, make electrical connections with sensor electronics, as is known to one skilled in the art.

Use of electrode/elastomeric contacts 240 enables unique manufacturing methods which are amenable to high throughput, modular manufacturing. In one embodiment, the individual electrode/elastomeric contacts are formed and then processed in batches, such as to deposit the electroactive surfaces and membranes on the interior surfaces. For example, to prepare a batch of working electrode/elastomeric contacts, a batch of unprepared elastomeric contacts (e.g., 100, 1000, etc.) can be placed, head-up, in a holder. Platinum or other conductive electrode material can then be deposited on the heads, sides and/or entire electrode/elastomeric contacts using suitable means such as electroplating, electrospinning, spraying, and the like, to form the electroactive surfaces. A membrane is applied as one or more layers, using known thin-film or thick-film techniques. To form reference electrode/elastomeric contacts, Ag/AgCl particles or other conductive electrode material can be mixed or otherwise formed in or on the material used to form the electrode/elastomeric contacts, or Ag/AgCl can be applied to the interior surfaces of the reference electrode/elastomeric contacts, for example.

In a another embodiment, the electrode/elastomeric contacts are formed by preparing a sheet of the elastomeric conductive material, preparing a surface of the sheet, such as forming an electroactive surface thereon, and then punching the individual electrode/elastomeric contacts from the sheet.

FIG. 2R is a cross-section of another embodiment of a fluid coupler including a continuous analyte sensor 240 disposed within the lumen 254. Namely, a central body 270 is inserted within the lumen. The central body includes conductive bodies 272 disposed within a non-conductive material. Each conductive body 272 includes a conductive member 273, for making electrical contact with sensor electronics. The sensor electrodes 240 are deposited on the conductive bodies 272, such that when the central body 270 is inserted into the lumen of the fluid coupler, the electrodes are bathed in sample when the sample is drawn back. In some embodiments, the conductive members provide stabilization to the central body. In other embodiments, the central body and conductive members are configured and arranged such that the lumen is divided into a plurality of chambers (e.g., smaller lumens), such that a plurality of analyte sensors are deposited on the conductive bodies and such that each analyte sensor contacts a separate sample (e.g., uncontaminated by reagents or reaction products from an analyte sensor in another chamber). In one embodiment, the central body is configured as an elongated core, such as but not limited to a cylindrical core. In some embodiments, the central body 270 is configured as a plurality of conductive bodies 272, which run the length of the central body, bundled in a dielectric material, wherein the conductive members 273 extend out an end of the central body (e.g., rather than out the sides as shown in FIG. 2R). In this embodiment, a plurality of analyte sensors can be deposited on the conductive bodies, wherein the central body is inserted into the lumen of the fluid coupler.

FIG. 2S illustrates yet another embodiment of an analyte sensor disposed in a fluid coupler, including an electrode support 280 having one or more analyte sensors 240 deposited thereon. The electrode support 280 is configured and arranged to optimize fluid flow there around and to substantially reduce biofouling and/or clotting thereon. For example, in some embodiments, the electrode support 280 is cigar or football shaped. The electrodes can be working, counter and/or reference electrodes. In some embodiments, the electrode support 280 is stabilized by stabilizers 282. While the stabilizers 282 shown in FIG. 2S are "fin" shaped, a variety of other shapes, such as projections, extensions, detents, and the like can be used. In preferred embodiments, the stabilizers substantially maintain the electrode support 280 within the fluid stream such that the electrode support 280 is substantially immobile, such that the flow of fluid about the electrode support 280 is substantially even (e.g., the same rate there around).

In some embodiments, the device is formed by injection molding, using techniques known in the art. In one exemplary embodiment, the sensors are placed in a mold, which is configured to hold the sensors in such an orientation that after the injection molding procedure, the sensors will be in the correct location and/or orientation for correct function of the device. After the sensors are placed in the mold, the mold is closed and injected with a material (e.g., molten plastic). During the injection molding process, the wall 260 of the device is thus formed about a portion of each sensor 240, such that a sensing portion of each sensor (e.g., electroactive surface) will be disposed within the duct 212b/258 and another portion of each sensor (e.g., a portion configured for connection to sensor electronics) will be disposed at the exterior of the device. Similar manufacturing techniques are used for the manufacture of syringes and lancets, wherein the plastic portion of the device is formed about a portion of the needle.

In a medical setting, a variety of vascular access devices can be simultaneously made available for use in conjunction with a flow control device, as described elsewhere herein. As is understood by one skilled in the art, each vascular access device can require a unique flow profile, such that the flow control device infuses and draws back the correct amounts of fluid and/or sample, at the correct time and for the correct lengths of time, to enable optimal sensor operation. In some circumstances, a caretaker may select the wrong flow profile for an installed vascular access device; a medical error that might harm the patient. Accordingly, in some embodiments, the vascular access device is configured and arranged to provide identification information to flow control device, wherein the identification information is associated with the flow profile. For example, in some embodiments the identification information is provided by a mechanical structure (e.g., an engageable mechanical interlock wherein the vascular access device includes one of two portions of the mechanical interlock and the flow control device includes the second of the two portions of the mechanical interlock). In some embodiments, the identification information is provided by electronics of the vascular access device (e.g., a bar code (e.g., identified by a bar code scanner incorporated into the flow control device), an RFID chip configured for communication with the electronics of the vascular access device and the like). In some preferred embodiments, a flow profile associated with the vascular access device is initiated by the flow control device, after identification of the vascular access device via the identification module. In preferred embodiments, the system is configured to program the flow profile of the flow control device in response to automatic receipt of the identification information (e.g., transmission of the identification information without required user interaction). In this embodiment, because the user does not enter which flow profile to use with the vascular access device, user error is reduced, which in turn increases patient safety.

While not wishing to be bound by theory, a number of the systems and methods disclosed in the preferred embodiments (e.g., an analyte sensor to be disposed in communication with the host's blood), can be employed in transcutaneous (e.g., transdermal) or wholly implantable analyte sensor devices. For example, the sensor could be integrally formed on the in vivo portion of a subcutaneous device or a wholly implantable device. As another example, an enlarged surface area (e.g., bulbous end) can useful in the design of a transcutaneous analyte sensor.

Exemplary Sensor Configurations

Referring to FIGS. 3A to 3C, in some embodiments, the sensor can be configured similarly to the continuous analyte sensors disclosed in co-pending U.S. Patent Publication No. US-2007-0197889-A1 herein incorporated by reference in its entirety. The sensor includes a distal portion 342, also referred to as the in vivo portion, adapted for insertion into the catheter as described above, and a proximal portion 340, also referred to as an ex vivo portion, adapted to operably connect to the sensor electronics. Preferably, the sensor includes two or more electrodes: a working electrode 344 and at least one additional electrode, which can function as a counter electrode and/or reference electrode, hereinafter referred to as the reference electrode 346. A membrane system is preferably deposited over the electrodes, such as described in more detail with reference to FIGS. 3A to 3C, below.

FIG. 3B is an expanded cutaway view of a distal portion of the sensor in one embodiment, showing working and reference electrodes. In preferred embodiments, the sensor is formed from a working electrode 344 (e.g., a wire) and a reference electrode 346 helically wound around the working electrode 344. An insulator 345 is disposed between the working and reference electrodes to provide electrical insulation therebetween. Certain portions of the electrodes are exposed to enable electrochemical reaction thereon, for example, a window 343 can be formed in the insulator to expose a portion of the working electrode 344 for electrochemical reaction.

In preferred embodiments, each electrode is formed from a fine wire with a diameter of from about 0.001 inches or less to about 0.050 inches or more, for example, and is formed from, e.g. a plated insulator, a plated wire, or bulk electrically conductive material. For example, in some embodiments, the wire used to form a working electrode is about 0.002, 0.003, 0.004, 0.005, 0.006, 0.007, 0.008, 0.009, 0.010, 0.015, 0.020, 0.025, 0.030, 0.035, 0.040 or 0.045 inches in diameter. Although the illustrated electrode configuration and associated text describe one preferred method for forming a sensor, a variety of known sensor configurations can be employed with the analyte sensor system of the preferred embodiments, such as U.S. Pat. No. 5,711,861, U.S. Pat. No. 6,642,015, U.S. Pat. No. 6,654,625, U.S. Pat. No. 6,565,509, U.S. Pat. No. 6,514,718, U.S. Pat. No. 6,465,066, U.S. Pat. No. 6,214,185, U.S. Pat. No. 5,310,469, U.S. Pat. No. 5,683,562, U.S. Pat. No. 6,579,690, U.S. Pat. No. 6,484,046, U.S. Pat. No. 6,512,939, U.S. Pat. No. 6,424,847, and U.S. Pat. No. 6,424,847, for example. Each of the above patents is incorporated in its entirety herein by reference. The above patents are not inclusive of all applicable analyte sensors; in general, it should be understood that the disclosed embodiments are applicable to a variety of analyte sensor configurations. It is noted that much of the description of the preferred embodiments, for example the membrane system described below, can be implemented not only with in vivo sensors, but also with in vitro sensors, such as blood glucose meters (SMBG).

In some embodiments, the working electrode comprises a wire formed from a conductive material, such as platinum, platinum-iridium, palladium, graphite, gold, carbon, conductive polymer, alloys, and the like. Although the electrodes can by formed by a variety of manufacturing techniques (bulk metal processing, deposition of metal onto a substrate, and the like), it can be advantageous to form the electrodes from plated wire (e.g. platinum on steel wire) or bulk metal (e.g. platinum wire). It is believed that electrodes formed from bulk metal wire provide superior performance (e.g. in contrast to deposited electrodes), including increased stability of assay, simplified manufacturability, resistance to contamination (e.g. which can be introduced in deposition processes), and improved surface reaction (e.g. due to purity of material) without peeling or delamination.

In some embodiments, the working electrode is formed of platinum-iridium or iridium wire. In general, platinum-iridium and iridium materials are generally stronger (e.g., more resilient and less likely to fail due to stress or strain fracture or fatigue). It is believed that platinum-iridium and/or iridium materials can facilitate a wire with a smaller diameter to further decrease the maximum diameter (size) of the sensor (e.g., in vivo portion). Advantageously, a smaller sensor diameter both reduces the risk of clot or thrombus formation (or other foreign body response) and allows the use of smaller catheters.

The electroactive window 343 of the working electrode 344 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

In preferred embodiments, the working electrode 344 is covered with an insulating material 345, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). While not wishing to be bound by theory, it is believed that the lubricious (e.g., smooth) coating (e.g., parylene) on the sensors of some embodiments contributes to minimal trauma and extended sensor life. While parylene coatings are generally preferred in some embodiments, any suitable insulating material can be used, for example, fluorinated polymers, polyethyleneterephthalate, polyurethane, polyimide, other nonconducting polymers, and the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

The reference electrode 346, which can function as a reference electrode alone, or as a dual reference and counter electrode, is formed from silver, silver/silver chloride, and the like. In some embodiments, the reference electrode 346 is juxtapositioned and/or twisted with or around the working electrode 344; however other configurations are also possible (e.g. coiled within the fluid connector/hub 18 or within a fluid coupler 20 or an intradermal or on-skin reference electrode). In the illustrated embodiments, the reference electrode 346 is helically wound around the working electrode 344. The assembly of wires is then optionally coated or adhered together with an insulating material, similar to that described above, so as to provide an insulating attachment.

In some embodiments, a silver wire is formed onto the sensor as described above, and subsequently chloridized to form silver/silver chloride reference electrode. Advantageously, chloridizing the silver wire as described herein enables the manufacture of a reference electrode with optimal in vivo performance. Namely, by controlling the quantity and amount of chloridization of the silver to form silver/silver chloride, improved break-in time, stability of the reference electrode and extended life has been shown with some embodiments. Additionally, use of silver chloride as described above allows for relatively inexpensive and simple manufacture of the reference electrode.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), and the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g. a parylene coating, without damaging, e.g. an underlying platinum conductor. One additional advantage of sodium bicarbonate blasting includes its polishing action on the metal as it strips the polymer layer, thereby eliminating a cleaning step that might otherwise be necessary.

In the embodiment illustrated in FIG. 3B, a radial window 343 is formed through the insulating material 345 to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer.

In some applications, cellular attack or migration of cells to the sensor can cause reduced sensitivity and/or function of the device, particularly after the first day of implantation. However, when the exposed electroactive surface is distributed circumferentially about the sensor (e.g. as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.25 mm (about 0.01 inches) to about 0.375 mm (about 0.015 inches). In such embodiments, the exposed surface area of the working electrode is preferably from about 0.000013 in$^2$ (0.0000839 cm$^2$) or less to about 0.0025 in$^2$ (0.016129 cm$^2$) or more (assuming a diameter of from about 0.001 inches to about 0.010 inches and a length of from about 0.004 inches to about 0.078 inches). The preferred exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g. sample rate, current draw, A/D converter bit resolution, etc.), the membrane system (e.g. permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g. an electrode which can be used to generate oxygen, which is configured as a baseline subtracting electrode, or which is configured for measuring additional analytes). U.S. Patent Publication No. US-2005-0161346-A1, U.S. Patent Publication No. US-2005-0143635-A1, and U.S. Patent Publication No. US-2007-0027385-A1 describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal including glucose and baseline (e.g., background noise) and the additional working electrode is configured to measure a baseline signal consisting of baseline only (e.g., configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal.

Although the embodiments of FIGS. 3A to 3C illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator therebetween. Alternatively, the reference electrode comprises a tube with a working electrode disposed or coiled inside, including an insulator therebetween. In another alternative embodiment, a polymer (e.g., insulating) rod is provided, wherein the electrodes are deposited (e.g., electroplated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

Preferably, the electrodes and membrane systems of the preferred embodiments are coaxially formed, namely, the electrodes and/or membrane system all share the same central axle. While not wishing to be bound by theory, it is believed that a coaxial design of the sensor enables a symmetrical design without a preferred bend radius. Namely, in contrast to prior art sensors comprising a substantially planar configuration that can suffer from regular bending about the plane of the sensor, the coaxial design of the preferred embodiments do not have a preferred bend radius and therefore are not subject to regular bending about a particular plane (which can cause fatigue failures and the like). However, non-coaxial sensors can be implemented with the sensor system of the preferred embodiments.

In addition to the above-described advantages, the coaxial sensor design of the preferred embodiments enables the diameter of the connecting end of the sensor (proximal portion) to be substantially the same as that of the sensing end (distal portion) such that the protective slotted sheath is able to insert the sensor into the catheter and subsequently slide back over the sensor and release the sensor from the protective slotted sheath, without complex multi-component designs.

In one such alternative embodiment, the two wires of the sensor are held apart and configured for insertion into the catheter in proximal but separate locations. The separation of the working and reference electrodes in such an embodiment can provide additional electrochemical stability with simplified manufacture and electrical connectivity. One skilled in the art will appreciate that a variety of electrode configurations can be implemented with the preferred embodiments.

In addition to the above-described configurations, the reference electrode can be separated from the working electrode, and coiled within a portion of the fluid connector, in some embodiments. In another embodiment, the reference electrode is coiled within the fluid connector and adjacent to its first side. In an alternative embodiment, the reference electrode is coiled within the fluid connector and adjacent to its second side. In such embodiments, the reference electrode is in contact with fluid, such as saline from a saline drip that is flowing into the host, or such as blood that is being withdrawn from the host. While not wishing to be bound by theory, this configuration is believed to be advantageous because the sensor is thinner, allowing the use of smaller catheters and/or a reduced likelihood to thrombus production.

In another embodiment, the reference electrode 346 can be disposed farther away from the electroactive portion of the working electrode 343 (e.g., closer to the fluid connector). In some embodiments, the reference electrode is located proximal to or within the fluid coupler, such as but not limited to, coiled about the catheter adjacent to the fluid coupler or coiled within the fluid coupler and in contact with fluid flowing through the fluid coupler, such as saline. These configurations can also minimize at least a portion of the sensor diameter and thereby allow the use of smaller catheters and reduce the risk of clots.

In addition to the embodiments described above, the sensor can be configured with additional working electrodes as described in U.S. Patent Publication No. US-2005-0143635-A1, U.S. Pat. No. 7,081,195, and U.S. Patent Publication No. US-2007-0027385-A1, herein incorporated by reference in their entirety. For example, in one embodiment have an auxiliary working electrode, wherein the auxiliary working electrode comprises a wire formed from a conductive material, such as described with reference to the glucose-measuring working electrode above. Preferably, the reference electrode, which can function as a reference electrode alone, or as a dual reference and counter electrode, is formed from silver, Silver/Silver chloride, and the like.

In some embodiments, the electrodes are juxtapositioned and/or twisted with or around each other; however other configurations are also possible. In one example, the auxiliary working electrode and reference electrode can be helically wound around the glucose-measuring working electrode. Alternatively, the auxiliary working electrode and reference electrode can be formed as a double helix around a length of the glucose-measuring working electrode. The assembly of wires can then be optionally coated together with an insulating material, similar to that described above, in order to provide an insulating attachment. Some portion of the coated assembly structure is then stripped, for example using an excimer laser, chemical etching, and the like, to expose the necessary electroactive surfaces. In some alternative embodiments, additional electrodes can be included within the assembly, for example, a three-electrode system (including separate reference and counter electrodes) as is appreciated by one skilled in the art.

In some alternative embodiments, the sensor is configured as a dual-electrode system (e.g., FIGS. 2M-2O, 2Q-2S, and 3D-3I) configured and arranged to detect two analyte and/or configured as plus-enzyme and minus-enzyme electrodes, as described herein. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (without active enzyme, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the inserted sensor in this alternative embodiment can be made less dependent on the values/range of the paired measurements, less sensitive to error in manual blood glucose measurements, and can facilitate the sensor's use as a primary source of glucose information for the user. U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1 each describe systems and methods for subtracting the baseline from a sensor signal, each of which is incorporated herein by reference in its entirety.

In some alternative dual-electrode system embodiments, the analyte sensor is configured to transmit signals obtained from each electrode separately (e.g. without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g. without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some embodiments, the reference electrode can be disposed remotely from the working electrode. In one embodiment, the reference electrode remains within the fluid flow, but is disposed within the fluid coupler. For example, the reference electrode can be coiled within the fluid coupler such that it is contact with saline flowing into the host, but it is not in physical contact with the host's blood (except when blood is withdrawn from the catheter). In another embodiment, the reference electrode is removed from fluid flow, but still maintains bodily fluid contact. For example, the reference electrode can be wired to an adhesive patch that is adhered to the host, such that the reference electrode is in contact with the host's skin. In yet another embodiment, the reference electrode can be external from the system, such as but not limited to in contact with the exterior of the ex vivo portion of the system, in fluid or electrical contact with a connected saline drip or other medical device, or in bodily contact, such as is generally done with EKG electrical contacts. While not wishing to be bound by theory, it is believed to locating the reference electrode remotely from the working electrode permits manufacture of a smaller sensor footprint (e.g., diameter) that will have relatively less affect on the host's blood flow, such as less thrombosis, than a sensor having a relatively larger footprint (e.g., wherein both the working electrode and the reference electrode are adjacent to each other and within the blood path).

In some embodiments of the sensor system, in vivo portion of the sensor (e.g., the tip 14a) has an enlarged area (e.g., a bulbous, nail head-shaped, football-shaped, cone-shaped, cylindrical, etc. portion) as compared a substantial portion of the sensor (e.g., diameter of the in vivo portion of the sensor). The sensor tip can be made bulbous by any convenient systems and methods known in the art, such as but not limited to arc welding, crimping, smashing, welding, molding, heating, and plasma arc welding. While not wishing to be bound by theory, it is believed that an enlarged sensor tip (e.g., bulbous) will prevent vessel piercing as the sensor is pushed forward into the vessel.

The sensor of the preferred embodiments is designed with a minimally invasive architecture so as to minimize reactions or effects on the blood flow (or on the sensor in the blood flow). Accordingly, the sensor designs described herein, consider minimization of dimensions and arrangement of the electrodes and other components of the sensor system, particularly the in vivo portion of the sensor (or any portion of the sensor in fluid contact with the blood flow).

Accordingly, in some embodiments, a substantial portion of the in vivo portion of the sensor is designed with at least one dimension less than about 0.020, 0.015, 0.012, 0.010, 0.008, 0.006, 0.005, 0.004 inches. In some embodiments, a substantial portion of the sensor that is in fluid contact with the blood flow is designed with at least one dimension less than about 0.015, 0.012, 0.010, 0.008, 0.006, 0.005, 0.004, 0.003, 0.002, 0.001 inches. As one exemplary embodiment, a sensor such as described in more detail with reference to FIGS. 1A to 1C is formed from a 0.004 inch conductive wire (e.g., platinum) for a diameter of about 0.004 inches along a substantial portion of the sensor (e.g., in vivo portion or fluid contact portion). As another exemplary embodiment, a sensor such as described in more detail with reference to FIGS. 1A to 1C is formed from a 0.004 inch conductive wire and vapor deposited with an insulator material for a diameter of about 0.005 inches along a substantial portion of the sensor (e.g., in vivo portion or fluid contact portion), after which a desired electroactive surface area can be exposed. In the above two exemplary embodiments, the reference electrode can be located remote from the working electrode (e.g., formed from the conductive wire). While the devices and methods described herein are directed to use within the host's blood stream, one skilled in the art will recognize that the systems, configurations, methods and principles of operation described herein can be incorporated into other analyte sensing devices, such as but not limited to subcutaneous devices or wholly implantable devices such as described in U.S. Patent Publication No. US-2006-0016700-A1, which is incorporated herein by reference in its entirety.

FIG. 3C is a cross section of the sensor shown in FIG. 3B, taken at line C-C. Preferably, a membrane system (see FIG. 3C) is deposited over the electroactive surfaces of the sensor and includes a plurality of domains or layers, such as described in more detail below, with reference to FIGS. 3B and 3C. The membrane system can be deposited on the exposed electroactive surfaces using known thin film techniques (for example, spraying, electro-depositing, dipping, and the like). In one exemplary embodiment, each domain is deposited by dipping the sensor into a solution and drawing out the sensor at a speed that provides the appropriate domain thickness. In general, the membrane system can be disposed over (deposited on) the electroactive surfaces using methods appreciated by one skilled in the art.

In general, the membrane system includes a plurality of domains, for example, an electrode domain 347, an interference domain 348, an enzyme domain 349 (for example, including glucose oxidase), and a resistance domain 350, as shown in FIG. 3C, and can include a high oxygen solubility domain, and/or a bioprotective domain (not shown), such as is described in more detail in U.S. Patent Publication No. US-2005-0245799-A1, and such as is described in more detail below. The membrane system can be deposited on the exposed electroactive surfaces using known thin film techniques (for example, vapor deposition, spraying, electro-depositing, dipping, and the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

In some embodiments, one or more domains of the membrane systems are formed from materials such as described above in connection with the porous layer, such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Patent Publication No. US-2005-0245799-A1 describes biointerface and membrane system configurations and materials that may be applied to the preferred embodiments.

Electrode Domain

In selected embodiments, the membrane system comprises an electrode domain. The electrode domain 347 is provided to ensure that an electrochemical reaction occurs between the electroactive surfaces of the working electrode and the reference electrode, and thus the electrode domain 347 is preferably situated more proximal to the electroactive surfaces than the interference and/or enzyme domain. Preferably, the electrode domain includes a coating that maintains a layer of water at the electrochemically reactive surfaces of the sensor. In other words, the electrode domain is present to provide an environment between the surfaces of the working electrode and the reference electrode, which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain 347 includes a flexible, water-swellable, hydrogel film having a "dry film" thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 3, 2.5, 2, or 1 microns, or less, to about 3.5, 4, 4.5, or 5 microns or more. "Dry film" thickness refers to the thickness of a cured film cast from a coating formulation by standard coating techniques.

In certain embodiments, the electrode domain 347 is formed of a curable mixture of a urethane polymer and a hydrophilic polymer. Particularly preferred coatings are formed of a polyurethane polymer having carboxylate or hydroxyl functional groups and non-ionic hydrophilic polyether segments, wherein the polyurethane polymer is crosslinked with a water-soluble carbodiimide (e.g. 1-ethyl- 3-(3-dimethylaminopropyl)carbodiimide (EDC)) in the presence of polyvinylpyrrolidone and cured at a moderate temperature of about 50° C.

In some preferred embodiments, the electrode domain 347 is formed from a hydrophilic polymer (e.g., a polyamide, a polylactone, a polyimide, a polylactam, a functionalized polyamide, a functionalized polylactone, a functionalized polyimide, a functionalized polylactam or a combination thereof) that renders the electrode domain substantially more hydrophilic than an overlaying domain, (e.g., interference domain, enzyme domain). In some embodiments, the electrode domain is formed substantially entirely and/or primarily from a hydrophilic polymer. In some embodiments, the electrode domain is formed substantially entirely from PVP. In some embodiments, the electrode domain is formed entirely from a hydrophilic polymer. Useful hydrophilic polymers include but are not limited to poly-N-vinylpyrrolidone (PVP), poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers is preferred in some embodiments. In some preferred embodiments, the hydrophilic polymer(s) is not crosslinked. In alternative embodiments, crosslinking is preferred, such as by adding a crosslinking agent, such as but not limited to EDC, or by irradiation at a wavelength sufficient to promote crosslinking between the hydrophilic polymer molecules, which is believed to create a more tortuous diffusion path through the domain.

An electrode domain formed from a hydrophilic polymer (e.g. PVP) has been shown to substantially reduce break-in time of analyte sensors; for example, a glucose sensor utilizing a cellulosic-based interference domain such as described in more detail elsewhere herein. In some embodiments, a uni-component electrode domain formed from a single hydrophilic polymer (e.g. PVP) has been shown to substantially reduce break-in time of a glucose sensor to less than about 2 hours, less than about 1 hour, less than about 20 minutes and/or substantially immediately, such as exemplified in Examples 9 through 11 and 13. Generally, sensor break-in is the amount of time required (after implantation) for the sensor signal to become substantially representative of the analyte concentration. Sensor break-in includes both membrane break-in and electrochemical break-in, which are described in more detail elsewhere herein. In some embodiments, break-in time is less than about 2 hours. In other embodiments, break-in time is less than about 1 hour. In still other embodiments, break-in time is less than about 30 minutes, less than about 20 minutes, less than about 15 minutes, less than about 10 minutes, or less. In a preferred embodiment, sensor break-in occurs substantially immediately. Advantageously, in embodiments wherein the break-in time is about 0 minutes (substantially immediately), the sensor can be inserted and begin providing substantially accurate analyte (e.g. glucose) concentrations almost immediately post-insertion, for example, wherein membrane break-in does not limit start-up time.

While not wishing to be bound by theory, it is believed that providing an electrode domain that is substantially more hydrophilic than the next more distal membrane layer or domain (e.g. the overlaying domain; the layer more distal to the electroactive surface than the electrode domain, such as an interference domain or an enzyme domain) reduces the break-in time of an implanted sensor, by increasing the rate at which the membrane system is hydrated by the surrounding host tissue. While not wishing to be bound by theory, it is believed that, in general, increasing the amount of hydrophilicity of the electrode domain relative to the overlaying layer (e.g. the distal layer in contact with electrode domain, such as the interference domain, enzyme domain, etc.), increases the rate of water absorption, resulting in reduced sensor break-in time. The hydrophilicity of the electrode domain can be substantially increased by the proper selection of hydrophilic polymers, based on their hydrophilicity relative to each other and relative to the overlaying layer (e.g. cellulosic-based interference domain), with preferred polymers being substantially more hydrophilic than the overlaying layer. In one exemplary embodiment, PVP forms the electrode domain, the interference domain is formed from a blend of cellulosic derivatives, such as but not limited to cellulose acetate butyrate and cellulose acetate; it is believed that since PVP is substantially more hydrophilic than the cellulosic-based interference domain, the PVP rapidly draws water into the membrane to the electrode domain, and enables the sensor to function with a desired sensitivity and accuracy and starting within a substantially reduced time period after implantation. Reductions in sensor break-in time reduce the amount of time a host must wait to obtain sensor readings, which is particularly advantageous not only in ambulatory applications, but particularly in hospital settings where time is critical.

While not wishing to be bound by theory, it is believed that when the water absorption of the overlaying domain (e.g. the domain overlying the electrode domain) is less than the water absorption of the electrode domain (e.g. during membrane equilibration), then the difference in water absorption between the two domains will drive membrane equilibration and thus membrane break-in. Namely, increasing the difference in hydrophilicity (e.g. between the two domains) results in an increase in the rate of water absorption, which, in turn, results in a decrease in membrane break-in time and/or sensor break-in time. As discussed elsewhere herein, the relative hydrophilicity of the electrode domain as compared to the overlaying domain can be modulated by a selection of more hydrophilic materials for formation of the electrode domain (and/or more hydrophobic materials for the overlaying domain(s)). For example, an electrode domain with hydrophilic polymer capable of absorbing larger amounts of water can be selected instead of a second hydrophilic polymer that is capable of absorbing less water than the first hydrophilic polymer. In some embodiments, the water content difference between the electrode domain and the overlaying domain (e.g. during or after membrane equilibration) is from about 1% or less to about 90% or more. In other embodiments, the water content difference between the electrode domain and the overlaying domain is from about 10% or less to about 80% or more. In still other embodiments, the water content difference between the electrode domain and the overlaying domain is from about 30% or less to about 60% or more. In preferred embodiments, the electrode domain absorbs 5 wt. % or less to 95 wt. % or more water, preferably 5, 10, 15, 20, 25, 30, 35, 40, 45, or 50 wt. % to about 55, 60, 65, 70, 75, 80, 85, 90 or 95 wt. % water than the adjacent (overlaying) domain (e.g. the domain that is more distal to the electroactive surface than the electrode domain).

In another example, the rate of water absorption by a polymer can be affected by other factors, such as but not limited to the polymer's molecular weight. For example, the rate of water absorption by PVP is dependent upon its molecular weight, which is typically from about 40 kDa or less to about 360 kDa or more; with a lower molecular weight PVP (e.g. 40 kDa) absorbing water faster than a higher molecular weight PVP. Accordingly, modulating factors, such as molecular weight, that affect the rate of water absorption by a polymer, can promote the proper selection of materials for electrode domain fabrication. In one embodiment, a lower molecular weight PVP is selected, to reduce break-in time.

Preferably, the electrode domain is deposited by known thin film deposition techniques (e.g. spray coating or dip-coating the electroactive surfaces of the sensor). In some embodiments, the electrode domain is formed by dip-coating the electroactive surfaces in an electrode domain solution (e.g., 5, 10, 15, 20, 25 or 30% or more PVP in deionized water) and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 to about 3 inches per minute into the electrode domain solution, with a preferred dwell time of from about 0.5 to about 2 minutes in the electrode domain solution, and a preferred withdrawal rate of from about 0.25 to about 2 inches per minute from the electrode domain solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes. In another embodiment, the electroactive surfaces of the electrode system is dip-coated and cured at 50° C. under vacuum for 20 minutes a first time, followed by dip coating and curing at 50° C. under vacuum for 20 minutes a second time (two layers). In still other embodiments, the electroactive surfaces can be dip-coated three or more times (three or more layers). In other embodiments, the 1, 2, 3 or more layers of PVP are applied to the electroactive surfaces by spray coating or vapor deposition. In some embodiments, a crosslinking agent (e.g. EDC) can be added to the electrode domain casting solution to promote crosslinking within the domain (e.g. between electrode domain polymer components, latex, etc.). In some alternative embodiments however, no crosslinking agent is used and the electrode domain is not substantially crosslinked.

In some embodiments, the deposited PVP electrode domain 347 has a "dry film" thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns.

Although an independent electrode domain 347 is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

Interferents are molecules or other species that are reduced or oxidized at the electrochemically reactive surfaces of the sensor, either directly or via an electron transfer agent, to produce a false positive analyte signal (e.g., a non-analyte-related signal). This false positive signal causes the host's analyte concentration (e.g., glucose concentration) to appear higher than the true analyte concentration. False-positive signal is a clinically significant problem in some conventional sensors. For example in a case of a dangerously hypoglycemic situation, wherein the host has ingested an interferent (e.g., acetaminophen), the artificially high glucose signal can lead the host to believe that he is euglycemic (or, in some cases, hyperglycemic). As a result, the host can make inappropriate treatment decisions, such as taking no action, when the proper course of action is to begin eating. In another example, in the case of a euglycemic or hyperglycemic situation, wherein a host has consumed acetaminophen, an artificially high glucose signal caused by the acetaminophen can lead the host to believe that his or her glucose concentration is much higher than it truly is. Again, as a result of the artificially high glucose signal, the host can make inappropriate treatment decisions, such as giving himself too much insulin, which in turn can lead to a dangerous hypoglycemic episode.

In preferred embodiments, an interference domain 348 is provided that substantially restricts or blocks the flow of one or more interfering species therethrough; thereby substantially preventing artificial signal increases. Some known interfering species for a glucose sensor, as described in more detail herein, include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain of the preferred embodiments is less permeable to one or more of the interfering species than to the measured species, e.g. the product of an enzymatic reaction that is measured at the electroactive surface(s), such as but not limited to $H_2O_2$.

In one embodiment, the interference domain 348 is formed from one or more cellulosic derivatives. Cellulosic derivatives can include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose. While cellulosic derivatives are generally preferred, other polymeric polysaccharides having similar properties to cellulosic derivatives can also be employed in the preferred embodiments.

In one preferred embodiment, the interference domain 348 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. In some embodiments, a blend of two or more cellulose acetate butyrates having different molecular weights is preferred. While a "blend" as defined herein (a composition of two or more substances that are not substantially chemically combined with each other and are capable of being separated) is generally preferred, in certain embodiments a single polymer incorporating different constituents (e.g. separate constituents as monomeric units and/or substituents on a single polymer chain) can be employed instead. Additionally, a casting solution or dispersion of cellulose acetate butyrate at a wt. % of from about 5% to about 25%, preferably from about 5%, 6%, 7%, 8%, 9%, 10%, 11%, 12%, 13%, 14% or 15% to about 16%, 17%, 18%, 19%, 20%, 21%, 22%, 23%, 24% or 25%, and more preferably from about 5% to about 15% is preferred. Preferably, the casting solution includes a solvent or solvent system, for example an acetone:ethanol solvent system. Higher or lower concentrations can be preferred in certain embodiments. In alternative embodiments, a single solvent (e.g. acetone) is used to form a symmetrical membrane domain. A single solvent is used in casting solutions for forming symmetric membrane layer(s). A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g. functional groups). It can also be desirable to include additional substances in the casting solutions or dispersions, e.g. functionalizing agents, crosslinking agents, other polymeric substances, substances capable of modifying the hydrophilicity/hydrophobicity of the resulting layer, and the like.

In one alternative embodiment, the interference domain 348 is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. In some embodiments, a blend of two or more cellulose acetates having different molecular weights is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g. functional groups). It can also be desirable to include additional substances in the casting solutions or dispersions such as described in more detail above.

In addition to forming an interference domain from only cellulose acetate(s) or only cellulose acetate butyrate(s), the interference domain 348 can be formed from combinations or blends of cellulosic derivatives, such as but not limited to cellulose acetate and cellulose acetate butyrate, or combinations of layer(s) of cellulose acetate and layer(s) of cellulose acetate butyrate. In some embodiments, a blend of cellulosic derivatives (for formation of an interference domain) includes up to about 10 wt. % or more of cellulose acetate. For example, about 1, 2, 3, 4, 5, 6, 7, 8, 9 wt. % or more cellulose acetate is preferred, in some embodiments. In some embodiments, the cellulosic derivatives blend includes from about 90 wt. % or less to about 100 wt. % cellulose acetate butyrate. For example, in some embodiments, the blend includes about 91, 92, 93, 94, 95, 96, 97, 98 or 99 wt. % cellulose acetate butyrate. In some embodiments, the cellulosic derivative blend includes from about 1.5, 2.0, 2.5, 3.0 or 3.5 wt. % cellulose acetate to about 98.5, 98.0, 97.5, 97.0 or 96.5 wt. % cellulose acetate butyrate. In other embodiments, the blend includes from about 4, 4.5, 5, 5.5, 6, 6.5, 7, 7.5 or 8 wt. % cellulose acetate to about 96, 95.5, 95, 94.5, 94, 93.3, 93, 92.5 or 92 wt. % cellulose acetate butyrate. In still other embodiments, the blend includes from about 8.5, 9.0, 9.5, 10.0, 10.5 or 11.0 wt. % cellulose acetate to about 91.5, 91.0, 90.5, 90, 89.5 or 89 wt. % cellulose acetate butyrate.

In some embodiments, preferred blends of cellulose acetate and cellulose acetate butyrate contain from about 1.5 parts or less to about 60 parts or more cellulose acetate butyrate to one part of cellulose acetate. In some embodiments, a blend contains from about 2 parts to about 40 parts cellulose acetate butyrate to one part cellulose acetate. In other embodiments, about 4, 6, 8, 10, 12, 14, 16, 18 or 20 parts cellulose acetate butyrate to one part cellulose acetate is preferred for formation of the interference domain 348. In still other embodiments, a blend having from 22, 24, 26, 28, 30, 32, 34, 36 or 38 parts cellulose acetate butyrate to one part cellulose acetate is preferred. As is discussed elsewhere herein, cellulose acetate butyrate is relatively more hydrophobic than cellulose acetate. Accordingly, the cellulose acetate/cellulose acetate butyrate blend contains substantially more hydrophobic than hydrophilic components.

Cellulose acetate butyrate is a cellulosic polymer having both acetyl and butyl groups, in addition to hydroxyl groups. Acetyl groups are more hydrophilic than butyl groups, and hydroxyl groups are more hydrophilic than both acetyl and butyl groups. Accordingly, the relative amounts of acetyl, butyl and hydroxyl groups can be used to modulate the hydrophilicity/hydrophobicity of the cellulose acetate butyrate of the cellulose acetate/cellulose acetate butyrate blend. A cellulose acetate butyrate can be selected based on the compound's relative amounts of acetate, butyrate and hydroxyl groups; and a cellulose acetate can be selected based on the compounds relative amounts of acetate and hydroxyl groups. For example, in some embodiments, a cellulose acetate butyrate having about 35% or less acetyl groups, about 10% to about 25% butyl groups, and hydroxyl groups making up the remainder is preferred for formation of the interference domain 348. In other embodiments a cellulose acetate butyrate having from about 25% to about 34% acetyl groups and from about 15 to about 20% butyl groups is preferred. In still other embodiments, the preferred cellulose acetate butyrate contains from about 28% to about 30% acetyl groups and from about 16 to about 18% butyl groups. In yet another embodiment, the cellulose acetate butyrate can have no acetate groups and from about 20% to about 60% butyrate groups. In yet another embodiment, the cellulose acetate butyrate has about 55% butyrate groups and no acetate groups.

While an asymmetric interference domain can be used in some alternative embodiments, a symmetrical interference domain 348 (e.g., of cellulosic-derivative blends, such as but not limited to blends of cellulose acetate components and cellulose acetate butyrate components) is preferred in some embodiments. Symmetrical membranes are uniform throughout their entire structure, without gradients of pore densities or sizes, or a skin on one side but not the other, for example. In various embodiments, a symmetrical interference domain 348 can be formed by the appropriate selection of a solvent (e.g. no anti-solvent is used), for making the casting solution. Appropriate solvents include solvents belonging to the ketone family that are able to solvate the cellulose acetate and cellulose acetate butyrate. The solvents include but are not limited to acetone, methyl ethyl ketone, methyl n-propyl ketone, cyclohexanone, and diacetone alcohol. Other solvents, such as furans (e.g. tetra-hydro-furan and 1,4-dioxane), may be preferred in some embodiments. In one exemplary embodiment, from about 7 wt. % to about 9 wt. % solids (e.g. a blend of cellulosic derivatives, such as cellulose acetate and cellulose acetate butyrate) are blended with a single solvent (e.g. acetone), to form the casting solution for a symmetrical interference domain. In another embodiment, from about 10 to about 15% solids are blended with acetone to form the casting solution. In yet another embodiment, from about 16 to about 18% solids are blended with acetone to form the casting solution. A relatively lower or greater weight percent of solids is preferred to form the casting solution, in some embodiments.

The casting solution can be applied either directly to the electroactive surface(s) of the sensor or on top of an electrode domain layer (if included in the membrane system). The casting solution can be applied using any known thin film technique, as discussed elsewhere herein. Additionally, in various embodiments, a symmetrical interference domain 348 includes at least one layer; and in some embodiments, two, three or more layers are formed by the sequential application and curing of the casting solution.

The concentration of solids in the casting solution can be adjusted to deposit a sufficient amount of solids on the electrode in one layer (e.g. in one dip or spray) to form a membrane layer with sufficient blocking ability, such that the equivalent glucose signal of an interferent (e.g. compounds with an oxidation or reduction potential that overlaps with that of the measured species (e.g. $H_2O_2$)), measured by the sensor, is about 60 mg/dL or less. For example, in some embodiments, the casting solution's percentage of solids is adjusted such that only a single layer (e.g. dip one time) is required to deposit a sufficient amount of the cellulose acetate/cellulose acetate butyrate blend to form a functional symmetric interference domain that substantially blocks passage therethrough of at least one interferent, such as but not limited to acetaminophen, ascorbic acid, dopamine, ibuprofen, salicylic acid, tolbutamide, tetracycline, creatinine, uric acid, ephedrine, L-dopa, methyl dopa and tolazamide. In some embodiments, the amount of interference domain material deposited by as single dip is sufficient to reduce the equivalent glucose signal of the interferant (e.g. measured by the sensor) to about 60 mg/dl or less. In preferred embodiments, the interferent's equivalent glucose signal response (measured by the sensor) is 50 mg/dl or less. In more preferred embodiments, the interferent produces an equivalent glucose signal response of 40 mg/dl or less. In still more preferred embodiments, the interferent produces an equivalent glucose signal response of less than about 30, 20 or 10 mg/dl. In one exemplary embodiment, the interference domain is configured to substantially block acetaminophen passage therethrough, wherein the equivalent glucose signal response of the acetaminophen is less than about 30 mg/dl.

In alternative embodiments, the interference domain 348 is configured to substantially block a therapeutic dose of acetaminophen. The term "therapeutic dose" as used herein is a broad term, and is to be given its ordinary and customary meaning to a person of ordinary skill in the art (and is not to be limited to a special or customized meaning), and refers without limitation to the quantity of any substance required to effect the cure of a disease, to relieve pain, or that will correct the manifestations of a deficiency of a particular factor in the diet, such as the effective dose used with therapeutically applied compounds, such as drugs. For example, a therapeutic dose of acetaminophen can be an amount of acetaminophen required to relieve headache pain or reduce a fever. As a further example, 1,000 mg of acetaminophen taken orally, such as by swallowing two 500 mg tablets of acetaminophen, is the therapeutic dose frequently taken for headaches. In some embodiments, the interference membrane is configured to block a therapeutic dose of acetaminophen, wherein the equivalent glucose signal response of the acetaminophen is less than about 60 mg/dl. In a preferred embodiment, the interference membrane is configured to block a therapeutic dose of acetaminophen, wherein the equivalent glucose signal response of the acetaminophen is less than about 40 mg/dl. In a more preferred embodiment, the interference membrane is configured to block a therapeutic dose of acetaminophen, wherein the equivalent glucose signal response of the acetaminophen is less than about 30 mg/dl.

While not wishing to be bound by theory, it is believed that, with respect to symmetrical cellulosic-based membranes, there is an inversely proportional balance between interferent blocking and analyte sensitivity. Namely, changes to the interference domain configuration that increase interferent blocking can result in a corresponding decrease in sensor sensitivity. Sensor sensitivity is discussed in more detail elsewhere herein. It is believed that the balance between interferent blocking and sensor sensitivity is dependent upon the relative proportions of hydrophobic and hydrophilic components of the membrane layer (e.g. the interference domain), with sensors having more hydrophobic interference domains having increased interferent blocking but reduces sensitivity; and sensors having more hydrophilic interference domains having reduced interferent blocking but increased sensitivity. It is believed that the hydrophobic and hydrophilic components of the interference domain can be balanced, to promote a desired level of interferent blocking while at the same time maintaining a desired level of analyte sensitivity. The interference domain hydrophobe-hydrophile balance can be manipulated and/or maintained by the proper selection and blending of the hydrophilic and hydrophobic interference domain components (e.g. cellulosic derivatives having acetyl, butyryl, propionyl, methoxy, ethoxy, propoxy, hydroxyl, carboxymethyl, and/or carboxyethyl groups). For example, cellulose acetate is relatively more hydrophilic than cellulose acetate butyrate. In some embodiments, increasing the percentage of cellulose acetate (or reducing the percentage of cellulose acetate butyrate) can increase the hydrophilicity of the cellulose acetate/cellulose acetate butyrate blend, which promotes increased permeability to hydrophilic species, such as but not limited to glucose, $H_2O_2$ and some interferents (e.g. acetaminophen). In another embodiment, the percentage of cellulose acetate butyrate is increased to increase blocking of interferants, but less permeability to some desired molecules, such as $H_2O_2$ and glucose, is also reduced.

One method, of manipulating the hydrophobe-hydrophile balance of the interference domain, is to select the appropriate percentages of acetyl groups (relatively more hydrophilic than butyl groups), butyl groups (relatively more hydrophobic than acetyl groups) and hydroxyl groups of the cellulose acetate butyrate used to form the interference domain 348. For example, increasing the percentage of acetate groups on the cellulose acetate butyrate will make the cellulose acetate butyrate more hydrophilic. In another example, increasing the percentage of butyl groups on the cellulose acetate butyrate will make the cellulose acetate butyrate more hydrophobic. In yet another example, increasing the percentage of hydroxyl groups will increase the hydrophilicity of the cellulose acetate butyrate. Accordingly, the selection of a cellulose acetate butyrate that is more or less hydrophilic (or more or less hydrophobic) can modulate the over-all hydrophilicity of the cellulose acetate/cellulose acetate butyrate blend. In one exemplary embodiment, an interference domain can be configured to be relatively more hydrophobic (and therefore block interferants more strongly) by reducing the percentage of acetyl or hydroxyl groups or by increasing the percentage of butyl groups on the cellulose acetate butyrate used in the casting solution (while maintaining the relative ratio of cellulose acetate to cellulose acetate butyrate).

In some alternative embodiments, the interference domain 348 is formed of a blend of cellulosic derivatives, wherein the hydrophilic and hydrophobic components of the interference domain are balanced, such that the glucose sensitivity is from about 1 pA/mg/dL to about 100 pA/mg/dL, and at least one interferent is sufficiently blocked from passage through the interference domain such that the equivalent glucose signal response of the at least one interferent is less than about 60 mg/dL. In a preferred embodiment, the glucose sensitivity is from about 5 pA/mg/dL to about 25 pA/mg/dL. In a more preferred embodiments, the glucose sensitivity is from about 5 pA/mg/dL to about 25 pA/mg/dL and the equivalent glucose signal response of the at least one interferent is less than about 40 mg/dL. In a still more preferred embodiments, the glucose sensitivity is from about 5 pA/mg/dL to about 25 pA/mg/dL and the equivalent glucose signal response of the at least one interferent is less than about 30 mg/dL. In some embodiments, the balance between hydrophilic and hydrophobic components of the interference domain can be achieved by adjusting the amounts of hydrophilic and hydrophobic components, relative to each other, as well as adjusting the hydrophilic and hydrophobic groups (e.g. acetyl, butyryl, propionyl, methoxy, ethoxy, propoxy, hydroxyl, carboxymethyl, and/or carboxyethyl groups) of the components themselves (e.g. cellulosic derivatives, such as but not limited to cellulose acetate and cellulose acetate butyrate).

In some alternative embodiments, additional polymers, such as NAFION®, can be used in combination with cellulosic derivatives to provide equivalent and/or enhanced function of the interference domain 348. As one example, a layer of a 5 wt. % NAFION® casting solution was applied over a previously applied (e.g., and cured) layer of 8 wt. % cellulose acetate, e.g., by dip coating at least one layer of cellulose acetate and subsequently dip coating at least one layer NAFION® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference domain 348 of the preferred embodiments. In general, the formation of the interference domain on a surface utilizes a solvent or solvent system, in order to solvate the cellulosic derivative(s) (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method for deposition, its desired thickness, and the like. However, a percent solute of from about 1 wt. % to about 25 wt. % is preferably used to form the interference domain solution so as to yield an interference domain having the desired properties. The cellulosic derivative (or other polymer) used, its molecular weight, method for deposition, and desired thickness can be adjusted, depending upon one or more other of the parameters, and can be varied accordingly as is appreciated by one skilled in the art.

In some alternative embodiments, other polymer types that can be utilized as a base material for the interference domain 348 including polyurethanes, polymers having pendant ionic groups, and polymers having controlled pore size, for example. In one such alternative embodiment, the interference domain includes a thin, hydrophobic membrane that is non-swellable and restricts diffusion of high molecular weight species. The interference domain 48 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074,307, U.S. Patent Publication No. US-2005-0176136-A1, U.S. Pat. No. 7,081,195, and U.S. Patent Publication No. US-2005-0143635-A1. In some alternative embodiments, a distinct interference domain is not included.

In some embodiments, the interference domain 348 is deposited either directly onto the electroactive surfaces of the sensor or onto the distal surface of the electrode domain, for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes In general, the membrane systems of the preferred embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. Preferably, the interference domain 348 is deposited by spray or dip coating. In one exemplary embodiment of a needle-type (transcutaneous) sensor such as described herein, the interference domain is formed by dip coating the sensor into an interference domain solution using an insertion rate of from about 0.5 inch/min to about 60 inches/min, preferably 1 inch/min, a dwell time of from about 0 minute to about 2 minutes, preferably about 1 minute, and a withdrawal rate of from about 0.5 inch/minute to about 60 inches/minute, preferably about 1 inch/minute, and curing (drying) the domain from about 1 minute to about 30 minutes, preferably from about 3 minutes to about 15 minutes (and can be accomplished at room temperature or under vacuum (e.g., 20 to 30 mmHg)). In one exemplary embodiment including cellulose acetate butyrate interference domain, a 3-minute cure (i.e., dry) time is preferred between each layer applied. In another exemplary embodiment employing a cellulose acetate interference domain, a 15 minute cure (i.e., dry) time is preferred between each layer applied.

In some embodiments, the dip process can be repeated at least one time and up to 10 times or more. In other embodiments, only one dip is preferred. The preferred number of repeated dip processes depends upon the cellulosic derivative(s) used, their concentration, conditions during deposition (e.g., dipping) and the desired thickness (e.g., sufficient thickness to provide functional blocking of certain interferents), and the like. In some embodiments, 1 to 3 microns may be preferred for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain 348. In some embodiments, the interference domain 348 of the preferred embodiments can be useful as a bioprotective or biocompatible domain, namely, a domain that interfaces with host tissue when implanted in an animal (e.g., a human) due to its stability and biocompatibility.

Enzyme Domain

In preferred embodiments, the membrane system further includes an enzyme domain 349 disposed more distally from the electroactive surfaces than the interference domain 348; however other configurations can be desirable. In the preferred embodiments, the enzyme domain provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See, e.g., U.S. Patent Publication No. US-2005-0054909-A1.

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment of needle-type (transcutaneous) sensor such as described herein, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g. 20 to 30 mmHg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 350 disposed more distal from the electroactive surfaces than the enzyme domain. Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Publication No. US-2005-0090607-A1.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In some embodiments, the resistance domain is formed from a silicone polymer modified to allow analyte (e.g., glucose) transport.

In some embodiments, the resistance domain is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, triblock, alternating, random, comb, star, dendritic, and graft copolymers (block copolymers are discussed in U.S. Pat. No. 4,803,243 and U.S. Pat. No. 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®. U.S. Patent Publication No. US-2007-0244379-A1 which is incorporated herein by reference in its entirety, describes systems and methods suitable for the resistance and/or other domains of the membrane system of the preferred embodiments.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In another preferred embodiment, physical vapor deposition (e.g., ultrasonic vapor deposition) is used for coating one or more of the membrane domain(s) onto the electrodes, wherein the vapor deposition apparatus and process include an ultrasonic nozzle that produces a mist of micro-droplets in a vacuum chamber. In these embodiments, the micro-droplets move turbulently within the vacuum chamber, isotropically impacting and adhering to the surface of the substrate. Advantageously, vapor deposition as described above can be implemented to provide high production throughput of membrane deposition processes (e.g., at least about 20 to about 200 or more electrodes per chamber), greater consistency of the membrane on each sensor, and increased uniformity of sensor performance, for example, as described below.

In some embodiments, depositing the resistance domain (for example, as described in the preferred embodiments above) includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed that is characterized in that ascorbate does not substantially permeate therethrough.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can typically provide adequate coverage by the resistance domain. Spraying the resistance domain material and rotating the sensor at least two times by 120° provides even greater coverage (one layer of 360° coverage), thereby ensuring resistivity to glucose, such as is described in more detail above.

In preferred embodiments, the resistance domain is spray coated and subsequently cured for a time of from about 15 minutes to about 90 minutes at a temperature of from about 40° C. to about 60° C. (and can be accomplished under vacuum (e.g. from 20 to 30 mmHg)). A cure time of up to about 90 minutes or more can be advantageous to ensure complete drying of the resistance domain.

In one embodiment, the resistance domain is formed by spray coating at least six layers (namely, rotating the sensor seventeen times by 120° for at least six layers of 360° coverage) and curing at 50° C. under vacuum for 60 minutes. However, the resistance domain can be formed by dip coating or spray coating any layer or plurality of layers, depending upon the concentration of the solution, insertion rate, dwell time, withdrawal rate, and/or the desired thickness of the resulting film. Additionally, curing in a convention oven can also be employed.

In certain embodiments, a variable frequency microwave oven can be used to cure the membrane domains/layers. In general, microwave ovens directly excite the rotational mode of solvents. Consequently, microwave ovens cure coatings from the inside out rather than from the outside in as with conventional convection ovens. This direct rotational mode excitation is responsible for the typically observed "fast" curing within a microwave oven. In contrast to conventional microwave ovens, which rely upon a fixed frequency of emission that can cause arcing of dielectric (metallic) substrates if placed within a conventional microwave oven, Variable Frequency Microwave (VFM) ovens emit thousands of frequencies within 100 milliseconds, which substantially eliminates arcing of dielectric substrates. Consequently, the membrane domains/layers can be cured even after deposition on metallic electrodes as described herein. While not wishing to be bound by theory, it is believe that VFM curing can increase the rate and completeness of solvent evaporation from a liquid membrane solution applied to a sensor, as compared to the rate and completeness of solvent evaporation observed for curing in conventional convection ovens.

In certain embodiments, VFM is can be used together with convection oven curing to further accelerate cure time. In some sensor applications wherein the membrane is cured prior to application on the electrode (see, for example, U.S. Patent Publication No. US-2005-0245799-A1, which is incorporated herein by reference in its entirety), conventional microwave ovens (e.g., fixed frequency microwave ovens) can be used to cure the membrane layer.

Treatment of Interference Domain/Membrane System

Although the above-described methods generally include a curing step in formation of the membrane system, including the interference domain, the preferred embodiments further include an additional treatment step, which can be performed directly after the formation of the interference domain and/or some time after the formation of the entire membrane system (or anytime in between). In some embodiments, the additional treatment step is performed during (or in combination with) sterilization of the sensor.

In some embodiments, the membrane system (or interference domain) is treated by exposure to ionizing radiation, for example, electron beam radiation, UV radiation, X-ray radiation, gamma radiation, and the like. Alternatively, the membrane can be exposed to visible light when suitable photoinitiators are incorporated into the interference domain. While not wishing to be bound by theory, it is believed that exposing the interference domain to ionizing radiation substantially crosslinks the interference domain and thereby creates a tighter, less permeable network than an interference domain that has not been exposed to ionizing radiation.

In some embodiments, the membrane system (or interference domain) is crosslinked by forming free radicals, which may include the use of ionizing radiation, thermal initiators, chemical initiators, photoinitiators (e.g., UV and visible light), and the like. Any suitable initiator or any suitable initiator system can be employed, for example, α-hydroxyketone, α-aminoketone, ammonium persulfate (APS), redox systems such as APS/bisulfite, or potassium permanganate. Suitable thermal initiators include but are not limited to potassium persulfate, ammonium persulfate, sodium persulfate, and mixtures thereof.

In embodiments wherein electron beam radiation is used to treat the membrane system (or interference domain), a preferred exposure time is from about 6 k or 12 kGy to about 25 or 50 kGy, more preferably about 25 kGy. However, one skilled in the art appreciates that choice of molecular weight, composition of cellulosic derivative (or other polymer), and/or the thickness of the layer can affect the preferred exposure time of membrane to radiation. Preferably, the exposure is sufficient for substantially crosslinking the interference domain to form free radicals, but does not destroy or significantly break down the membrane or does not significantly damage the underlying electroactive surfaces.

In embodiments wherein UV radiation is employed to treat the membrane, UV rays from about 200 nm to about 400 nm are preferred; however values outside of this range can be employed in certain embodiments, dependent upon the cellulosic derivative and/or other polymer used.

In some embodiments, for example, wherein photoinitiators are employed to crosslink the interference domain, one or more additional domains can be provided adjacent to the interference domain for preventing delamination that may be caused by the crosslinking treatment. These additional domains can be "tie layers" (i.e., film layers that enhance adhesion of the interference domain to other domains of the membrane system). In one exemplary embodiment, a membrane system is formed that includes the following domains: resistance domain, enzyme domain, electrode domain, and cellulosic-based interference domain, wherein the electrode domain is configured to ensure adhesion between the enzyme domain and the interference domain. In embodiments wherein photoinitiators are employed to crosslink the interference domain, UV radiation of greater than about 290 nm is preferred. Additionally, from about 0.01 to about 1 wt % photoinitiator is preferred weight-to-weight with a preselected cellulosic polymer (e.g., cellulose acetate); however values outside of this range can be desirable dependent upon the cellulosic polymer selected.

In general, sterilization of the transcutaneous sensor can be completed after final assembly, utilizing methods such as electron beam radiation, gamma radiation, glutaraldehyde treatment, and the like. The sensor can be sterilized prior to or after packaging. In an alternative embodiment, one or more sensors can be sterilized using variable frequency microwave chamber(s), which can increase the speed and reduce the cost of the sterilization process. In another alternative embodiment, one or more sensors can be sterilized using ethylene oxide (EtO) gas sterilization, for example, by treating with 100% ethylene oxide, which can be used when the sensor electronics are not detachably connected to the sensor and/or when the sensor electronics must undergo a sterilization process. In one embodiment, one or more packaged sets of transcutaneous sensors (e.g., 1, 2, 3, 4, or 5 sensors or more) are sterilized simultaneously.

Therapeutic Agents

A variety of therapeutic (bioactive) agents can be used with the analyte sensor system of the preferred embodiments, such as the analyte sensor system of the embodiments shown in FIGS. 1A-3C. In some embodiments, the therapeutic agent is an anticoagulant. The term "anticoagulant" as used herein is a broad term, and is to be given its ordinary and customary meaning to a person of ordinary skill in the art (and is not to be limited to a special or customized meaning), and refers without limitation to a substance the prevents coagulation (e.g., minimizes, reduces, or stops clotting of blood). In some embodiments, an anticoagulant is included in the analyte sensor system to prevent coagulation within or on the sensor (e.g., within or on the catheter or within or on the sensor).

Suitable anticoagulants for incorporation into the sensor system include, but are not limited to, vitamin K antagonists (e.g., Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g., Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g., Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban) and the like.

In one embodiment, heparin is incorporated into the analyte sensor system. In a further embodiment, heparin is coated on the catheter (inner and/or outer diameter) and/or sensor, for example, by dipping or spraying. While not wishing to be bound by theory, it is believed that heparin coated on the catheter and/or sensor prevents aggregation and clotting of blood on the analyte sensor system, thereby preventing thromboembolization (e.g., prevention of blood flow by the thrombus or clot) and/or subsequent complications. In another embodiment, an antimicrobial is coated on the catheter (inner and/or outer diameter) and/or sensor.

In some embodiments, the therapeutic agent is an antimicrobial. The term "antimicrobial agent" as used in the preferred embodiments means antibiotics, antiseptics, disinfectants and synthetic moieties, and combinations thereof, that are soluble in organic solvents such as alcohols, ketones, ethers, aldehydes, acetonitrile, acetic acid, methylene chloride and chloroform.

Classes of antibiotics that can be used include tetracyclines (i.e. minocycline), rifamycins (i.e. rifampin), macrolides (i.e. erythromycin), penicillins (i.e. nafeillin), cephalosporins (i.e. cefazolin), other beta-lactam antibiotics (i.e. imipenem, aztreonam), aminoglycosides (i.e. gentamicin), chloramphenicol, sulfonamides (i.e. sulfamethoxazole), glycopeptides (i.e. vancomycin), quinolones (i.e. ciprofloxacin), fusidic acid, trimethoprim, metronidazole, clindamycin, mupirocin, polyenes (i.e. amphotericin B), azoles (i.e. fluconazole) and beta-lactam inhibitors (i.e. sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

Examples of antiseptics and disinfectants are hexachlorophene, cationic bisiguanides (i.e. chlorhexidine, cyclohexidine) iodine and iodophores (i.e. povidoneiodine), parachloro-meta-xylenol, triclosan, furan medical preparations (i.e. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

These antimicrobial agents can be used alone or in combination of two or more of them. The antimicrobial agents can be dispersed throughout the material of the sensor and/or catheter. The amount of each antimicrobial agent used to impregnate the medical device varies to some extent, but is at least of an effective concentration to inhibit the growth of bacterial and fungal organisms, such as staphylococci, gram-positive bacteria, gram-negative bacilli and *Candida*.

In some embodiments, the membrane system of the preferred embodiments preferably include a bioactive agent, which is incorporated into at least a portion of the membrane system, or which is incorporated into the device and adapted to diffuse through the membrane.

There are a variety of systems and methods by which the bioactive agent is incorporated into the membrane of the preferred embodiments. In some embodiments, the bioactive agent is incorporated at the time of manufacture of the membrane system. For example, the bioactive agent can be blended prior to curing the membrane system, or subsequent to membrane system manufacture, for example, by coating, imbibing, solvent-casting, or sorption of the bioactive agent into the membrane system. Although the bioactive agent is preferably incorporated into the membrane system, in some embodiments the bioactive agent can be administered concurrently with, prior to, or after insertion of the device intravascularly, for example, by oral administration, or locally, for example, by subcutaneous injection near the implantation site. A combination of bioactive agent incorporated in the membrane system and bioactive agent administration locally and/or systemically can be preferred in certain embodiments.

In general, a bioactive agent can be incorporated into the membrane system, and/or incorporated into the device and adapted to diffuse therefrom, in order to modify the tissue response of the host to the membrane. In some embodiments, the bioactive agent is incorporated only into a portion of the membrane system adjacent to the sensing region of the device, over the entire surface of the device except over the sensing region, or any combination thereof, which can be helpful in controlling different mechanisms and/or stages of thrombus formation. In some alternative embodiments however, the bioactive agent is incorporated into the device proximal to the membrane system, such that the bioactive agent diffuses through the membrane system to the host circulatory system.

The bioactive agent can include a carrier matrix, wherein the matrix includes one or more of collagen, a particulate matrix, a resorbable or non-resorbable matrix, a controlled-release matrix, and/or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the membrane system, while in others the bioactive agent is sorbed into the membrane system, for example, by adsorption, absorption, or imbibing. The bioactive agent can be deposited in or on the membrane system, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the membrane system. The bioactive agent can be incorporated into a polymer using techniques such as described above, and the polymer can be used to form the membrane system, coatings on the membrane system, portions of the membrane system, and/or any portion of the sensor system.

The membrane system can be manufactured using techniques known in the art. The bioactive agent can be sorbed into the membrane system, for example, by soaking the membrane system for a length of time (for example, from about an hour or less to about a week or more, preferably from about 4, 8, 12, 16, or 20 hours to about 1, 2, 3, 4, 5, or 7 days).

The bioactive agent can be blended into uncured polymer prior to forming the membrane system. The membrane system is then cured and the bioactive agent thereby cross-linked and/or encapsulated within the polymer that forms the membrane system.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015, which is incorporated herein by reference in its entirety, discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the membrane system. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the membrane system by solvent casting, wherein a solution including dissolved bioactive agent is disposed on the surface of the membrane system, after which the solvent is removed to form a coating on the membrane surface.

The bioactive agent can be compounded into a plug of material, which is placed within the device, such as is described in U.S. Pat. No. 4,506,680 and U.S. Pat. No. 5,282,844, which are incorporated herein by reference in their entirety. In some embodiments, it is preferred to dispose the plug beneath a membrane system; in this way, the bioactive agent is controlled by diffusion through the membrane, which provides a mechanism for sustained-release of the bioactive agent in the host.

Release of Bioactive Agents

Numerous variables can affect the pharmacokinetics of bioactive agent release. The bioactive agents of the preferred embodiments can be optimized for short- and/or long-term release. In some embodiments, the bioactive agents of the preferred embodiments are designed to aid or overcome factors associated with short-term effects (e.g., acute inflammation and/or thrombosis) of sensor insertion. In some embodiments, the bioactive agents of the preferred embodiments are designed to aid or overcome factors associated with long-term effects, for example, chronic inflammation or build-up of fibrotic tissue and/or plaque material. In some embodiments, the bioactive agents of the preferred embodiments combine short- and long-term release to exploit the benefits of both.

As used herein, "controlled," "sustained," or "extended" release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the preferred embodiments generally refers to release over a period of from about a few minutes or hours to about 2, 3, 4, 5, 6, or 7 days or more.

Loading of Bioactive Agents

The amount of loading of the bioactive agent into the membrane system can depend upon several factors. For example, the bioactive agent dosage and duration can vary with the intended use of the membrane system, for example, the intended length of use of the device and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, wherein the bioactive agent is incorporated into the membrane system without a carrier matrix, the preferred level of loading of the bioactive agent into the membrane system can vary depending upon the nature of the bioactive agent. The level of loading of the bioactive agent is preferably sufficiently high such that a biological effect (e.g., thrombosis prevention) is observed. Above this threshold, bioactive agent can be loaded into the membrane system so as to imbibe up to 100% of the solid portions, cover all accessible surfaces of the membrane, and/or fill up to 100% of the accessible cavity space. Typically, the level of loading (based on the weight of bioactive agent(s), membrane system, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the membrane system with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulate bioactive agents, the release of the agents from these polymeric systems generally occurs by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the encapsulating polymer. With time, the polymer erodes and generates increased porosity and microstructure within the device. This creates additional pathways for release of the bioactive agent.

In some embodiments, the sensor is designed to be bioinert, e.g., by the use of bioinert materials. Bioinert materials do not substantially cause any response from the host. As a result, cells can live adjacent to the material but do not form a bond with it. Bioinert materials include but are not limited to alumina, zirconia, titanium oxide or other bioinert materials generally used in the "catheter/catheterization" art. While not wishing to be bound by theory, it is believed that inclusion of a bioinert material in or on the sensor can reduce attachment of blood cells or proteins to the sensor, thrombosis or other host reactions to the sensor.

Dual-Electrode Analyte Sensors

In general, electrochemical analyte sensors provide at least one working electrode and at least one reference electrode, which are configured to generate a signal associated with a concentration of the analyte in the host, such as described herein, and as appreciated by one skilled in the art. The output signal is typically a raw data stream that is used to provide a useful value of the measured analyte concentration in a host to the patient or doctor, for example. However, the analyte sensors of the preferred embodiments may further measure at least one additional signal. For example, in some embodiments, the additional signal is associated with the baseline and/or sensitivity of the analyte sensor, thereby enabling monitoring of baseline and/or sensitivity changes that may occur in a continuous analyte sensor over time.

In preferred embodiments, the analyte sensor comprises a first working electrode E1 and a second working electrode E2, in addition to a reference electrode, which is referred to as a dual-electrode system herein. The first and second working electrodes may be in any useful conformation, as described in U.S. Patent Publication No. US-2007-0027385-A1, U.S. Patent Publication No. US-2007-0213611-A1, U.S. Patent Publication No. US-2007-0027284-A1, U.S. Patent Publication No. US-2007-0032717-A1, U.S. Patent Publication No. US-2007-0093704-A1, and U.S. Patent Publication No. US-2008-0083617-A1, each of which is incorporated herein by reference in its entirety. In some preferred embodiments, the first and second working electrodes are twisted and/or bundled. For example, two wire working electrodes can be twisted together, such as in a helix conformation. The reference electrode can then be wrapped around the twisted pair of working electrodes. In some preferred embodiments, the first and second working electrodes include a coaxial configuration. A variety of dual-electrode system configurations are described with reference to FIGS. 7A1 through 11 of the references incorporated above. In some embodiments, the sensor is configured as a dual electrode sensor, such as described in U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, each of which is incorporated herein by reference in its entirety. However, a dual-electrode system can be provided in any planar or non-planar configuration, such as can be appreciated by one skilled in the art, and can be found in U.S. Pat. No. 6,175,752, U.S. Pat. No. 6,579,690, U.S. Pat. No. 6,484,046, U.S. Pat. No. 6,512,939, U.S. Pat. No. 6,477,395, U.S. Pat. No. 6,424,847, U.S. Pat. No. 6,212,416, U.S. Pat. No. 6,119,028, U.S. Pat. No. 6,400,974, U.S. Pat. No. 6,595,919, U.S. Pat. No. 6,141,573, U.S. Pat. No. 6,122,536; European Patent Publication No. EP 1153571, U.S. Pat. No. 6,512,939, U.S. Pat. No. 5,605,152, U.S. Pat. No. 4,431,004, U.S. Pat. No. 4,703,756, U.S. Pat. No. 6,514,718, U.S. Pat. No. 5,985,129, PCT Patent Publication No. WO04/021877, U.S. Pat. No. 5,494,562, U.S. Pat. No. 6,120,676, and U.S. Pat. No. 6,542,765, each of which are incorporated in there entirety herein by reference in their entirety. In general, it is understood that the disclosed embodiments are applicable to a variety of continuous analyte measuring device configurations FIG. 3D illustrates a dual-electrode system in preferred embodiments. The dual-electrode sensor system includes a first working electrode E1 and the second working electrode E2, both of which are disposed beneath a sensor membrane M02, such as but not limited to a membrane system similar to that described with reference to FIG. 3C and/or FIGS. 3F through 3I. The first working electrode E1 is disposed beneath an active enzymatic portion M04 of the sensor membrane M02, which includes an enzyme configured to detect the analyte or an analyte-related compound. Accordingly, the first working electrode E1 is configured to generate a first signal composed of both signal related to the analyte and signal related to non-analyte electroactive compounds (e.g., physiological baseline, interferents, and non-constant noise) that have an oxidation/reduction potential that overlaps with the oxidation/reduction potential of the analyte. This oxidation/reduction potential may be referred to as a "first oxidation/reduction potential" herein. The second working electrode E2 is disposed beneath an inactive-enzymatic or non-enzymatic portion M06 of the sensor membrane M02. The non-enzymatic portion M06 of the membrane includes either an inactivated form of the enzyme contained in the enzymatic portion M04 of the membrane or no enzyme. In some embodiments, the non-enzymatic portion M06 can include a non-specific protein, such as BSA, ovalbumin, milk protein, certain polypeptides, and the like. The non-enzymatic portion M06 generates a second signal associated with noise of the analyte sensor. The noise of the sensor comprises signal contribution due to non-analyte electroactive species (e.g., interferents) that have an oxidation/reduction potential that substantially overlaps the first oxidation/reduction potential (e.g., that overlap with the oxidation/reduction potential of the analyte). In some embodiments of a dual-electrode analyte sensor configured for fluid communication with a host's circulatory system, the non-analyte related electroactive species comprises at least one species selected from the group consisting of interfering species, non-reaction-related hydrogen peroxide, and other electroactive species.

In one exemplary embodiment, the dual-electrode analyte sensor is a glucose sensor having a first working electrode E1 configured to generate a first signal associated with both glucose and non-glucose related electroactive compounds that have a first oxidation/reduction potential. Non-glucose related electroactive compounds can be any compound, in the sensor's local environment that has an oxidation/reduction potential substantially overlapping with the oxidation/reduction potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the blood surrounding the sensor. These unknown compounds can be constant or non-constant (e.g., intermittent or transient) in concentration and/or effect. In some circumstances, it is believed that some of these unknown compounds are related to the host's disease state. For example, it is known that blood chemistry changes dramatically during/after a heart attack (e.g., pH changes, changes in the concentration of various blood components/protein, and the like). Additionally, a variety of medicaments or infusion fluid components (e.g., acetaminophen, ascorbic acid, dopamine, ibuprofen, salicylic acid, tolbutamide, tetracycline, creatinine, uric acid, ephedrine, L-dopa, methyl dopa and tolazamide) that may be given to the host may have oxidation/reduction potentials that overlap with that of $H_2O_2$.

In this exemplary embodiment, the dual-electrode analyte sensor includes a second working electrode E2 that is configured to generate a second signal associated with the non-glucose related electroactive compounds that have the same oxidation/reduction potential as the above-described first working electrode (e.g., para supra). In some embodiments, the non-glucose related electroactive species includes at least one of interfering species, non-reaction-related $H_2O_2$, and other electroactive species. For example, interfering species includes any compound that is not directly related to the electrochemical signal generated by the glucose-GOx reaction, such as but not limited to electroactive species in the local environment produces by other bodily processes (e.g., cellular metabolism, a disease process, and the like). Other electroactive species includes any compound that has an oxidation/reduction potential similar to or overlapping that of $H_2O_2$.

The non-analyte (e.g., non-glucose) signal produced by compounds other than the analyte (e.g., glucose) obscured the signal related to the analyte, contributes to sensor inaccuracy, and is considered background noise. As described in greater detail in the section entitled "Noise Reduction," background noise includes both constant and non-constant components and must be removed to accurately calculate the analyte concentration. While not wishing to be bound by theory, it is believed that the sensor of the preferred embodiments are designed (e.g., with symmetry, coaxial design and/or integral formation, and interference domain of the membrane described elsewhere herein) such that the first and second electrodes are influenced by substantially the same external/environmental factors, which enables substantially equivalent measurement of both the constant and non-constant species/noise. This advantageously allows the substantial elimination of noise on the sensor signal (using electronics described elsewhere herein) to substantially reduce or eliminate signal effects due to noise, including non-constant noise (e.g., unpredictable biological, biochemical species, medicaments, pH fluctuations, $O_2$ fluctuations, or the like) known to effect the accuracy of conventional continuous sensor signals. Preferably, the sensor includes electronics operably connected to the first and second working electrodes. The electronics are configured to provide the first and second signals that are used to generate glucose concentration data substantially without signal contribution due to non-glucose-related noise. Preferably, the electronics include at least a potentiostat that provides a bias to the electrodes. In some embodiments, sensor electronics are configured to measure the current (or voltage) to provide the first and second signals. The first and second signals are used to determine the glucose concentration substantially without signal contribution due to non-glucose-related noise such as by but not limited to subtraction of the second signal from the first signal or alternative data analysis techniques. In some embodiments, the sensor electronics include a transmitter that transmits the first and second signals to a receiver, where additional data analysis and/or calibration of glucose concentration can be processed. U.S. Patent Publication No. US-2005-0027463-A1, U.S. Patent Publication No. US-2005-0203360-A1 and U.S. Patent Publication No. US-2006-0036142-A1 describe systems and methods for processing sensor analyte data and are incorporated herein by reference in their entirety.

In preferred embodiments, the dual-electrode sensor is configured such that the first and second working electrodes E1, E2 are equivalently influenced by in vivo environmental factors. For example, in one embodiment, the dual-electrode sensor is configured for fluid communication with the circulatory system of the host, such as by implantation in the host's vein or artery via a vascular access device (also referred to as a fluid communication device herein) such as a catheter and/or cannula. When the sensor is contacted with a sample of the host's circulatory system (e.g., blood), the first and second working electrodes E1, E2 are configured such that they are equivalently influenced by a variety of environmental factors impinging upon the sensor, such as but not limited to non-analyte related electroactive species (e.g., interfering species, non-reaction-related $H_2O_2$, an other electroactive species). Because the first and second working electrodes are equivalently influenced by in vivo environmental factors, the signal component associated with the in vivo environmental factors (e.g., non-analyte related species with an oxidation/reduction potential that overlaps with that of the analyte) can be removed from the signal detected by the first working electrode (e.g., the first signal). This can give a substantially analyte-only signal. The effects of in vivo environmental factors upon the dual-electrode system are discussed in greater detail elsewhere herein with reference to FIGS. 3G-3I.

In preferred embodiments, the dual-electrode sensor includes electronics (e.g., a processor module, processing memory) that are operably connected to the first and second working electrodes and are configured to provide the first and second signals to generate analyte concentration data substantially without signal contribution due to non-analyte-related noise. For example, the sensor electronics process and/or analyze the signals from the first and second working electrodes and calculate the portion of the first electrode signal that is due to analyte concentration only. The portion of the first electrode signal that is not due to the analyte concentration can be considered to be background, such as but not limited to noise. Accordingly, in one embodiment of a dual-electrode sensor system configured for fluid communication with a host's circulatory system (e.g., via a vascular access device) the system comprising electronics operably connected to the first and second working electrodes; the electronics are configured to process the first and second signals to generate analyte concentration data substantially without signal contribution due to noise.

As a non-limiting example, FIG. 3E illustrates one preferred embodiment, the dual-electrode analyte sensor. In this embodiment, the sensor comprises a first working electrode E1 configured to detect the analyte and a second working electrode E2, wherein the first and second working electrodes are formed of two wire working electrodes twisted together to form a "twisted pair." The first working electrode E1 is disposed beneath an enzymatic portion of the membrane (not shown) containing an analyte-detecting enzyme. For example, in a glucose-detecting dual-electrode analyte sensor, a glucose-detecting enzyme, such as GOX, is included in the enzymatic portion of the membrane. Accordingly, the first working electrode E1 detects signal due to both the analyte and non-analyte-related species that have an oxidation/reduction potential that substantially overlaps with the oxidation/reduction potential of the analyte. The second working electrode E2 is disposed beneath a portion of the membrane comprising either inactivated enzyme (e.g., inactivated by heat, chemical or UV treatment) or no enzyme. Accordingly, the second working electrode E2 detects a signal associated with only the non-analyte electroactive species that have an oxidation/reduction potential that substantially overlaps with that of analyte. For example, in the glucose-detecting dual-electrode analyte sensor described above, the non-analyte (e.g., non-glucose) electroactive species have an oxidation/reduction potential that overlaps substantially with that of H₂O₂. A reference electrode R, such as a silver/silver chloride wire electrode, is wrapped around the twisted pair. The three electrodes E1, E2 and R are connected to sensor electronics (not shown), such as described elsewhere herein. In preferred embodiments, the dual-electrode sensor is configured to provide an analyte-only signal (e.g., glucose-only signal) substantially without a signal component due to the non-analyte electroactive species (e.g., noise). For example, the dual-electrode sensor is operably connected to sensor electronics that process the first and second signals, such that a substantially analyte-only signal is provided (e.g., output to a user). In other exemplary embodiments, the dual-electrode sensor can be configured for detection of a variety of analytes other than glucose, such as but not limited to urea, creatinine, succinate, glutamine, oxygen, electrolytes, cholesterol, lipids, triglycerides, hormones, liver enzymes, and the like.

With reference to the analyte sensor embodiments disclosed herein, the surface area of the electroactive portion of the reference (and/or counter) electrode is at least six times the surface area of the working electrodes. In other embodiments, the reference (and/or counter) electrode surface is 1, 2, 3, 4, 5, 7, 8, 9 or 10 times the surface area of the working electrodes. In other embodiments, the reference (and/or counter) electrode surface area is 11, 12, 13, 14, 15, 16, 17, 18, 19 or 20 times the surface area of the working electrodes. For example, in a needle-type glucose sensor, similar to the embodiment shown in FIG. 3E, the surface area of the reference electrode (e.g., R) includes the exposed surface of the reference electrode, such as but not limited to the electrode surface facing away from the working electrodes E1, E2.

In various embodiments, the electrodes can be stacked or grouped similar to that of a leaf spring configuration, wherein layers of electrode and insulator (or individual insulated electrodes) are stacked in offset layers. The offset layers can be held together with bindings of non-conductive material, foil, or wire. As is appreciated by one skilled in the art, the strength, flexibility, and/or other material property of the leaf spring-configured or stacked sensor can be either modified (e.g., increased or decreased), by varying the amount of offset, the amount of binding, thickness of the layers, and/or materials selected and their thicknesses, for example. Alternative dual-electrode configurations include those illustrated in FIGS. 2G-2S, as described herein.

In preferred embodiments, the analyte sensor substantially continuously measures the host's analyte concentration. In some embodiments, for example, the sensor can measure the analyte concentration every fraction of a second, about every fraction of a minute or every minute. In other exemplary embodiments, the sensor measures the analyte concentration about every 2, 3, 4, 5, 6, 7, 8, 9, or 10 minutes. In still other embodiments, the sensor measures the analyte concentration every fraction of an hour, such as but not limited to every 15, 30 or 45 minutes. Yet in other embodiments, the sensor measures the analyte concentration about every hour or longer. In some exemplary embodiments, the sensor measures the analyte concentration intermittently or periodically. In one preferred embodiment, the analyte sensor is a glucose sensor and measures the host's glucose concentration about every 4-6 minutes. In a further embodiment, the sensor measures the host's glucose concentration every 5 minutes.

As a non-limiting example, dual-electrode glucose sensor can be manufactured as follows. In one embodiment, the working electrodes are first coated with a layer of insulating material (e.g., non-conductive material or dielectric) to prevent direct contact between the working electrodes E1, E2 and the reference electrode R. At this point, or at any point hereafter, the two working electrodes can be twisted and/or bundled to form a twisted pair. A portion of the insulator on an exterior surface of each working electrode is etched away, to expose the electrode's electroactive surface. In some embodiments, an enzyme solution (e.g., containing active GOx) is applied to the electroactive surfaces of both working electrodes, and dried. Thereafter, the enzyme applied to one of the electroactive surfaces is inactivated. As is known in the art, enzymes can be inactivated by a variety of means, such as by heat, treatment with inactivating (e.g., denaturing) solvents, proteolysis, laser irradiation or UV irradiation (e.g., at 254-320 nm). For example, the enzyme coating one of the electroactive surfaces can be inactivated by masking one of the electroactive surfaces (e.g., electrodes, E1, temporarily covered with a UV-blocking material); irradiating the sensor with UV light (e.g., 254-320 nm; a wavelength that inactivates the enzyme, such as by cross-linking amino acid residues) and removing the mask. Accordingly, the GOx on E2 is inactivated by the UV treatment, but the E1 GOx is still active due to the protective mask. In other embodiments, an enzyme solution containing active enzyme is applied to a first electroactive surface (e.g., E1) and an enzyme solution containing either inactivated enzyme or no enzyme is applied to the second electroactive surface (e.g., E2). Thus, the enzyme-coated first electroactive surface (e.g., E1) detects analyte-related signal and non-analyte-related signal; while the second electroactive surface (e.g., E2), which lacks active enzyme, detects non-analyte-related signal. As described herein, the sensor electronics can use the data collected from the two working electrodes to calculate the analyte-only signal.

In some circumstances, cross talk can interfere with analyte/noise detection. In general, cross talk occurs when signal (e.g., in the form of energy and/or a detectable species such as but not limited to $H_2O_2$) is transferred from one electrode (e.g., the first working electrode) to another (e.g., the second working electrode), and detected as a signal by the other electrode. To prevent cross talk, in preferred embodiments, the first and second working electrodes E1, E2 are separated by diffusion barrier, such as an insulator, a non-conductive material, a reference electrode and/or the like.

FIG. 3F illustrates the use of a diffusion barrier to prevent cross talk in a dual-electrode glucose sensor, in one embodiment. The first and second working electrodes E1, E2 are disposed beneath a membrane 348 and separated by a diffusion barrier D. Within the membrane, glucose is metabolized by the GOx enzyme, which produces $H_2O_2$. The $H_2O_2$ produced by the enzymatic reaction can diffuse in any direction through the membrane 348. A portion of the $H_2O_2$ diffuses to the surface of the first working electrode and is detected due to the transfer of two electrons to the electrode. Another portion of the $H_2O_2$ can diffuse out of the membrane. Since the diffusion barrier D is disposed between the working electrodes, the diffusion barrier substantially blocks diffusion of $H_2O_2$ to the second working electrode E2. If no diffusion barrier were present, the $H_2O_2$ would be able to diffuse to the second working electrode E2 and cause a signal also referred to as cross talk. A variety of diffusion barriers can be employed to prevent cross talk. In some embodiments, the diffusion barrier D is a physical diffusion barrier, such as a structure between the working electrodes that blocks glucose and $H_2O_2$ from diffusing from the first working electrode E1 to the second working electrode E2. In other embodiments, the diffusion barrier D is a spatial diffusion barrier, such as a distance between the working electrodes that blocks glucose and $H_2O_2$ from diffusing from the first working electrode E1 to the second working electrode E2. In still other embodiments, the diffusion barrier D is a temporal diffusion barrier, such as a period of time between the activity of the working electrodes such that if glucose or $H_2O_2$ diffuses from the first working electrode E1 to the second working electrode E2, the second working electrode E2 will not substantially be influenced by the $H_2O_2$ from the first working electrode E1.

Accordingly, in some preferred embodiments, the dual-electrode sensor comprises an insulator, such as an electrical insulator, located between the first and second working electrodes, wherein the insulator comprises a physical diffusion barrier. The physical diffusion barrier is configured to structurally block a substantial amount of diffusion of at least one of an analyte (e.g., glucose) and a co-analyte (e.g., $H_2O_2$) between the first and second working electrodes. In some embodiments, the diffusion barrier comprises a structure that protrudes from a plane that intersects both the first and second working electrodes. In a further embodiment, the structure that protrudes comprises an electrical insulator and/or an electrode.

In some preferred embodiments, the dual-electrode sensor comprises an insulator located between the first and second working electrodes, wherein the insulator comprises a diffusion barrier configured to substantially block diffusion of at least one of an analyte and a co-analyte between the first and second working electrodes. In preferred embodiments, the diffusion barrier comprises a temporal diffusion barrier configured to block or avoid a substantial amount of diffusion or reaction of at least one of the analyte and the co-analyte between the first and second working electrodes.

In still other preferred embodiments, the dual-electrode sensor comprises a sensor membrane configured to substantially block diffusion of at least one of an analyte and a co-analyte between the first and second working electrodes by a discontinuity of the sensor membrane between the first and second working electrodes. A discontinuity of the sensor membrane is a type of physical diffusion barrier formed by a portion of the membrane between the two working electrodes, in some embodiments, wherein a discontinuity in the membrane structure blocks diffusion of $H_2O_2$ between the electrodes. Discontinuities of sensor membranes are discussed in greater detail with reference to FIG. 3I, in the section entitled "Sensor Configurations for Equivalent Measurement of Noise."

In some embodiments, the dual-electrode sensor system is configured for fluid communication with a host's circulatory system, such as via a vascular access device. A variety of vascular access devices suitable for use with a dual-electrode analyte sensor are described elsewhere herein. In some embodiments, the vascular access device comprises a lumen and at least a portion of the sensor is disposed within the lumen; and in some embodiments, at least a portion of the sensor can extend into the vascular system. In some embodiments, the vascular access device comprises a hub and the continuous analyte sensor is disposed substantially within the hub. In some embodiments, the system includes a fluid coupler configured and arranged to mate with the vascular access device on a first end; wherein the sensor is disposed within a portion of the fluid coupler and/or at a surface of the fluid coupler. In some embodiments, the sensor is configured to reside substantially above a plane defined by the host's skin. In some embodiments, the sensor is disposed on a surface of the vascular access device. In some embodiments, the vascular access device is configured for insertion into at least one of an artery, a vein, a fistula, and an extracorporeal circulatory device configured to circulate at least a portion of the host's blood outside of the host's body. In some embodiments, the system includes a flow control device in fluid communication with the vascular access device. The flow control device is configured to meter a flow of a fluid (e.g., blood, saline, a reference solution) through the vascular access device. In some embodiments, the flow control device is further configured to control fluid contact with the continuous analyte sensor, as is described in the section entitled "Integrated Sensor System."

In preferred embodiments, the sensor electronics (e.g., electronic components) are operably connected to the first and second working electrodes. The electronics are configured to calculate at least one analyte sensor data point. For example, the electronics can include a potentiostat, A/D converter, RAM, ROM, transmitter, and the like. In some embodiments, the potentiostat converts the raw data (e.g., raw counts) collected from the sensor to a value familiar to the host and/or medical personnel. For example, the raw counts from a glucose sensor can be converted to milligrams of glucose per deciliter of glucose (e.g., mg/dl). In some embodiments, the electronics are operably connected to the first and second working electrodes and are configured to process the first and second signals to generate a glucose concentration substantially without signal contribution due to non-glucose noise artifacts. The sensor electronics determine the signals from glucose and non-glucose related signal with an overlapping measuring potential (e.g., from a first working electrode) and then non-glucose related signal with an overlapping measuring potential (e.g., from a second electrode). The sensor electronics then use these data to determine a substantially glucose-only concentration, such as but not limited to subtracting the second electrode's signal from the first electrode's signal, to give a signal (e.g., data) representative of substantially glucose-only concentration, for example. In general, the sensor electronics may perform additional operations, such as but not limited to data smoothing and noise analysis.

In preferred embodiments, the dual-electrode sensor includes electronics (e.g., a processor module, processing memory) that are operably connected to the first and second working electrodes and are configured to provide the first and second signals to generate an analyte concentration data substantially without signal contribution due to non-analyte-related noise. For example, the sensor electronics process and/or analyze the signals from the first and second working electrodes and calculate the portion of the first electrode signal that is due to analyte concentration only. The portion of the first electrode signal that is not due to the analyte concentration can be considered to be background, such as but not limited to noise. Accordingly, in one embodiment of a dual-electrode sensor system configured for fluid communication with a host's circulatory system (e.g., via a vascular access device) the system comprising electronics operably connected to the first and second working electrodes; the electronics are configured to process the first and second signals to generate analyte concentration data substantially without signal contribution due to noise.

In some embodiments, the dual-electrode analyte sensor includes a reference sensor/system, as described elsewhere therein, whereby reference data can be provided for calibration (e.g., internal to the system), without the use of an external (e.g., separate from the system) analyte-measuring device. In an exemplary embodiment, the dual-electrode sensor is a glucose sensor and external glucose data points (e.g., from a hand-held glucose meter or a YSI device) are not required for calibration of a dual-electrode glucose sensor system that includes a reference sensor. In some embodiments, the reference sensor is configured to be disposed within the same local environment as the dual-electrode analyte sensor, such that the reference sensor and the dual-electrode analyte sensor can be simultaneously exposed to a sample. In some embodiments, the reference sensor/system can be disposed remotely from the dual-electrode sensor. In these embodiments, the electronics module is configured to process the reference data with the first and second signals to generate analyte concentration data substantially without signal contribution due to noise. In some embodiments, the electronics module is configured to calibrate the dual-electrode analyte sensor data using the reference sensor data, as described elsewhere herein.

In some embodiments, the electronics module is configured to determine a scaling factor (k) as described in the section entitled "Calibration Systems and Methods." Briefly, a scaling factor defines a relationship between the enzymatic portion of the membrane and the non-enzymatic portion of the membrane. Accordingly, in some embodiments, the electronics module, also referred to as the processor module herein, is configured to and/or comprises programming to calibrate the analyte sensor data using the scaling factor, such that the calibrated sensor data does not include inaccuracies that can arise due to small differences between the plus- and minus-enzyme portions of the membrane at the first and second working electrodes, respectively.

In some embodiments, the system is configured to calibrate the continuous dual-electrode analyte sensor using a reference fluid (e.g., 602a), as described in the section entitled "integrated sensor system." In some embodiments, the system is configured to calibrate the sensor using single-point calibration, in other embodiments, the system is configured to calibrate the sensor without a reference data point provided by an external analyte monitor (e.g., SMBG, YSI), as described elsewhere herein. In some embodiments, the system includes a reference sensor configured to generate a signal associated with a reference analyte in the sample (e.g., internal to the system), wherein the continuous analyte sensor is further configured to generate a third signal associated with the reference analyte, and wherein the system is configured to calibrate the continuous analyte sensor using the reference signal and the third signal. In some embodiments, the reference sensor comprises an optical sensing apparatus, such as but not limited to an optical $O_2$ sensor. In preferred embodiments, the continuous analyte sensor is a glucose sensor. In other embodiments, a substantial portion of the continuous analyte sensor has a diameter of less than about 0.008 inches, as is described elsewhere herein.

In some further embodiments, the continuous analyte sensor further comprises a bioinert material or a bioactive agent incorporated therein or thereon. Applicable bioactive agent include but are not limited to vitamin K antagonists, heparin group anticoagulants, platelet aggregation inhibitors, enzymes, direct thrombin inhibitors, Dabigatran, Defibrotide, Dermatan sulfate, Fondaparinux, and Rivaroxaban.

As a non-limiting example, in some preferred embodiments, a method for continuously detecting an analyte in the host in vivo using a dual-electrode analyte sensor is provided. In some embodiments, a vascular access device (e.g., a catheter) is inserted into the host's circulatory system, such as into a vein or artery. The sensor is contacted with a sample of the circulatory system, such as a sample of blood withdrawn into the catheter. A first signal is generated by the sensor, wherein the first signal is associated with associated with the analyte and non-analyte related electroactive compounds having a first oxidation/reduction potential in a sample of the circulatory system of the host. In preferred embodiments, the analyte sensor is configured to detect glucose. A second signal is also generated, wherein the second signal is associated with noise of the analyte sensor, wherein the noise comprises signal contribution due to non-analyte related electroactive species with an oxidation/reduction potential that substantially overlaps with the first oxidation/reduction potential in the sample. The first and second signals are processed to provide a processed signal substantially without a signal component associated with noise. In some embodiments, the first and second signals are processed to provide a scaling factor, which can then be used to calibrate the first signal. In some embodiments, a reference sensor is also contacted with the sample, and a third signal associated with a reference analyte generated. In some embodiments, the reference sensor is an optical detection apparatus, such as but not limited to an optical $O_2$ sensor. In this embodiment, the first and second signals can be calibrated using the third and/or reference signal. In some preferred embodiments, the processing step comprises evaluating steady-state information and transient information, wherein the first and second signals each comprise steady-state and transient information. In some further embodiments, the evaluating step includes evaluating at least one of sensitivity information and baseline information, wherein the steady-state information comprises the sensitivity and baseline information.

Optical Detection

In some embodiments, the continuous analyte sensor is configured to detect the analyte by optical means. In some embodiments, various types of Raman and/or fluorescent spectroscopic detection are used. For example, glucose can be detected via fiber optic visible fluorescence, using glucose dehydrogenase (GDH) and a modified flavin adenine dinucleotide (FAD) coenzyme system, Concanavalin A, or hexokinase. In some embodiments, a fluorescent molecule (e.g., a fluorophore) is attached to the co-enzyme or to a hydrogen peroxide end-product reactant, as in a calorimetric detection system. In an alternative embodiment, ferrocene is modified and used as a mediator in the reaction of GOX (or GHD) with glucose, wherein a pH-sensitive fluorophore is used to detect the reaction. In some embodiments, fiber optic probes are constructed by applying membrane systems configured for optical/fluorescent detection to an optical fiber. In some embodiments, multiple fiber optic probes are bundled, which enables a variety of integrative and/or subtractive signal correlations/corrections and to enhance error detection. Examples of optical detection can be found in U.S. Pat. No. 7,289,836 and U.S. Pat. No. 7,149,562, each of which is incorporated by reference herein in its entirety.

Sensor Signal Generation

In some embodiments, a continuous analyte detection system is provided, including a sensor configured and arranged for fluid contact with a host's circulatory system and a processor module. The sensor comprises both a continuous analyte sensor (e.g., either non-dual-electrode or dual-electrode) and a reference sensor. For example, in some embodiments the system includes a continuous analyte sensor including a working electrode and a reference electrode, and a reference sensor. In other embodiments, the system includes a dual-electrode analyte sensor, including first and second working electrodes and a reference electrode, and a reference sensor. The continuous analyte sensor is configured and arranged to generate a first signal associated with a test analyte and a second signal associated with a reference analyte. For example, in one embodiment, the test analyte is glucose and the reference analyte is oxygen; thus, the first signal is associated with glucose and the reference signal is associated with oxygen. The reference sensor is configured to generate a reference signal that is also associated with the reference analyte. In general, a "reference analyte" can be any analyte that can be measured by both the analyte sensor and the reference sensor, such those analytes listed under the definition of "analyte" in the section entitled "Definitions." In preferred embodiments, the reference analyte is one that is relatively stable within the host's body, such as but not limited to $O_2$, succinate, glutamine, and the like. In this embodiment, the processor module is configured to and/or comprises programming to process the second signal (e.g., related to the reference analyte) and the reference signal to calibrate the first signal (e.g., related to the analyte). In some embodiments, the processor module calibrates the second signal (e.g., the reference analyte signal detected by the analyte sensor) using the reference signal provided by the reference sensor, and then to calibrate the first signal (e.g., the analyte signal) using the second signal.

As a non-limiting example, in some embodiments, the system's continuous analyte sensor is a dual-electrode sensor that comprises both first and second working electrodes E1, E2. Accordingly, the first working electrode is disposed beneath an active enzymatic portion of a sensor membrane and generates a signal (e.g., the first signal) associated with both the analyte (e.g., glucose) and non-analyte related electroactive compounds (e.g., non-glucose compounds that have an oxidation/reduction potential that substantially overlaps with the oxidation/reduction potential of glucose). Additionally, the second working is disposed beneath an inactive-enzymatic or a non-enzymatic portion of the sensor membrane and generates a non-analyte-related signal associated with the non-analyte electroactive species. In this embodiment, the processor module configured to and/or comprises programming to process signals from the first and second working electrodes, and to thereby generate a first signal substantially without a non-analyte signal component.

The second signal (e.g., related to the reference analyte) can be generated by various means. For example, in some embodiments, the first working electrode of the dual-electrode analyte sensor is configured to generate both the first signal and the second signal. For example, in some embodiments, pulsed amperometric detection, including switching, cycling or pulsing the voltage of the electrode in an electrochemical system (e.g., between a positive voltage (e.g., +0.6 for detecting glucose) and a negative voltage (e.g., −0.6 for detecting oxygen)) can be employed to determine an oxygen measurement. For example, the first working electrode is configured to generate a signal associated with the analyte when a potential of +0.6 mV is applied thereto. If the potential is switch to −0.6 mV, then the first working electrode becomes an $O_2$ sensor and measures a signal associate with the amount of $O_2$ passing through the sensor's membrane system. U.S. Pat. No. 4,680,268, which is incorporated by reference herein, described pulsed amperometric detection in greater detail. Additional oxygen sensors are described in U.S. Pat. No. 6,512,939, which is incorporated herein by reference.

As a non-limiting example, in one embodiment the dual-electrode analyte sensor is a glucose sensor configured for fluid communication with a host's circulatory system, wherein the sensor is configured to generate a first signal associated with glucose (at the first working electrode E1) at an applied potential of 0.6 mV, and then to generate a second signal associated with $O_2$ (also at the first working electrode E1) at an applied potential of −0.6 mV. Thus, in some embodiments, the potential applied to the first working electrode can be switched from +0.6 mV to −0.6 mV, such that the first working electrode switches from measuring the analyte-related signal (e.g., glucose) to measuring the second signal (e.g., associated with $O_2$).

In some alternative embodiments, the second working electrode E2 (e.g., instead of the first working electrode E1) is configured to generate the second signal. As a non-limiting example, in another embodiment the dual-electrode analyte sensor is a glucose sensor configured for fluid communication with a host's circulatory system, wherein the sensor is configured to generate a first signal associated with glucose (at the first working electrode E1) at an applied potential of 0.6 mV, to generate a non-analyte-related signal (at the second working electrode E2) at an applied potential of 0.6 mV, and then to generate a second signal associated with $O_2$ (also at the second working electrode E2) at an applied potential of −0.6 mV. Thus, in some embodiments, the potential applied to the second working electrode can be switched from 0.6 mV to −0.6 mV, such that the second working electrode switches from measuring the non-analyte-related signal to measuring the second signal (e.g., associated with $O_2$).

In still other embodiments, the second signal can be generated by a third working electrode disposed beneath the sensor's membrane. As a non-limiting example, in another embodiment the dual-electrode analyte sensor is a glucose sensor configured for fluid communication with a host's circulatory system, wherein the sensor is configured to generate a first signal associated with glucose (at the first working electrode E1) at an applied potential of 0.6 mV, to generate a non-analyte-related signal (at the second working electrode E2) at an applied potential of 0.6 mV, and then to generate the second signal associated with $O_2$ (at the third working electrode, e.g., E3, not shown) at an applied potential of −0.6 mV. Thus, in some embodiments, switching the applied potential from 0.6 mV to −0.6 mV is not required.

As described above, the system includes a reference sensor. In some embodiments, the reference sensor is an optical sensing apparatus, as described above. In other embodiments, the reference sensor is configured to detect the reference analyte by any means known in the art, such as but not limited to electrochemical, chemical, physical, immunochemical, calorimetric and/or radiometric means. Preferably, the reference sensor is disposed in the same local environment as the continuous analyte sensor, but not under the membrane system of the continuous analyte sensor. For example, the reference sensor can be disposed adjacent to the continuous analyte sensor, such that when the continuous analyte sensor is contacted with a sample the reference sensor is simultaneously contacted by the sample. As a non-limiting example, in some embodiments, a dual-electrode continuous analyte sensor and a reference sensor are disposed adjacently, such that they can be simultaneously exposed to a sample of the host's circulatory system.

As a non-limiting example, in some embodiments, a dual-electrode sensor includes a first working electrode configured to detect the analyte (including non-analyte-related noise) and a second working electrode is configured to detect the signal associated with non-analyte-related noise. In some embodiments, the first and second working electrodes are bundled and/or twisted, and the reference sensor is disposed adjacent to the first and second working electrodes. In some embodiments, either the first or the second working electrodes of the dual-electrode sensor is configured to detect a signal associated with the reference analyte (e.g., a second signal); while in other embodiments, the dual-electrode sensor includes a third working electrode configured to detect the reference analyte (e.g., the second signal).

As a non-limiting example, in one embodiment of a system comprising both a dual-electrode sensor and an optical reference sensor, the dual-electrode sensor is both a glucose sensor and an $O_2$ sensor, and the reference sensor is an optical $O_2$ sensor. Accordingly, as described elsewhere herein, the first working electrode of the dual-electrode sensor is configured to detect a signal associated with both glucose and non-glucose-related electroactive species (in a sample of the host's circulatory system), and the second working electrode is configured to detect the non-glucose related electroactive species. Either the first working electrode or the second working electrode is configured to detect $O_2$, such as via switching the applied potential from 0.6 mV to −0.6 MV, as described elsewhere herein. The reference sensor, which can be bundled with the dual-electrode sensor, is configured to optically detect a reference signal associated with the $O_2$ concentration of the sample. In some embodiments, instead of using the first or second working electrodes to detect $O_2$, the dual-electrode sensor includes a third electrode configured to detect $O_2$.

In preferred embodiments, the signal related to a reference analyte (e.g., $O_2$) can be used to calibrate the signals from a continuous analyte sensor, such as in the event of a drift in sensor sensitivity and/or baseline. Accordingly, the signals related to the reference analyte, from the continuous analyte and reference sensors, can be processed to determine a calibration factor. The calibration factor can then be used to calibrate the continuous analyte sensor data. As used herein, the term "calibration factor" as used herein is a broad term, and is to be given its ordinary and customary meaning to a person of ordinary skill in the art (and is not to be limited to a special or customized meaning), and refers without limitation to a mathematical function generated by processing the reference analyte-related signal of the continuous analyte sensor and the reference analyte-related signal of the reference sensor, which can be used to calibrate the continuous analyte sensor data initially and/or responsive to an occurrence of a drift in sensor sensitivity and/or baseline.

In some embodiments, a method for measuring an analyte in a host is provided. First, a continuous analyte detection system, which includes a continuous analyte sensor and a reference sensor, is provided. In preferred embodiments, the continuous analyte sensor is configured and arranged to generate a first signal associated with a test analyte (e.g., glucose) and a second signal associated with a reference analyte (e.g., $O_2$), and the reference sensor configured to generate a reference signal associated with the reference analyte (e.g., $O_2$).

Next, the detection system is exposed to a sample of a host's circulatory system in vivo. For example, the detection system can be fluidly coupled to a vascular access device implanted in a host's circulatory system, such that a sample of the host's blood can be drawn back an contacted with the detection system. Preferably, the continuous analyte sensor and the reference sensor are exposed to the sample simultaneously. Accordingly, measurements of the reference analyte can be made at the same time by the continuous analyte and reference sensors. In some embodiments, a fluid flow device configured for fluid communication with the circulatory system of the host and to meter a flow of a fluid therethrough is provided. In these embodiments, the fluid flow device comprises a vascular access device configured for insertion into either an artery or a vein of the host. Such fluid flow devices are described in detail in the sensor entitled "Integrated Sensor System." In preferred embodiments, the fluid flow device is coupled with the continuous analyte detection system, and a sample of the circulatory system of the host is withdrawn. In some preferred embodiments, the fluid flow device is further configured to meter the flow of a non-bodily fluid through the vascular access device. Non-bodily fluids include a variety of sterile infusion fluids, such as but are not limited to saline, reference solutions such as a glucose solution of defined concentration, nutritional supplements, IV medicaments, and the like.

When the sample contacts the system, signals are received from the continuous analyte sensor and the reference sensor. The signals received include a first signal (e.g., related to the test analyte, such as but not limited to glucose), a second signal (e.g., related to the reference analyte, such as but not limited to $O_2$) and a reference signal (e.g., related to the reference analyte). In some embodiments, the first signal is received from a first working electrode disposed under an enzymatic portion of a membrane system. For example, in the case of a glucose detection system, the first working electrode is disposed beneath a portion of the membrane system including active GOX and detects a first signal associated with the concentration of glucose in the sample. In some embodiments, the first working electrode also received the second signal, as described elsewhere herein. In other embodiments, the second signal is received from a second working electrode that is also disposed under the membrane system. In some embodiments, the second working electrode configured to also receive a non-analyte-related signal. For example, the second working electrode is disposed under a non-enzymatic portion of the membrane system, in some embodiments. In some other embodiments, the non-analyte-related signal is received from a third working electrode disposed under a non-enzymatic portion of the membrane system. In some embodiments, the reference sensor is configured to detect the reference analyte optically. For example, in some embodiments, the reference analyte is oxygen. Accordingly, the second signal and the reference signal received are associated with the concentration of oxygen in the sample.

After the signals have been received, a calibration factor is calculated, wherein the calibration factor is associated with a sensitivity and/or baseline of the continuous analyte sensor. For example, in some embodiments, the continuous analyte detection system is exposed to a bodily fluid (e.g., blood) and the calculating step includes comparing steady-state information of the first signal and steady-state information of the second signal. In some embodiments, the calibration factor can be calculated by examining the transient information of the first and second signals.

In some other embodiments, the continuous analyte detection system is configured to be exposed to a non-bodily fluid, such as saline or a reference fluid, such as to wash the previous blood sample off of the device. During the washing procedure, the non-bodily fluid can be held substantially stagnant (e.g., no flow or very little flow of the fluid past the sensor) for a period of time. During this period of time, the working electrodes of the continuous analyte sensor detect signals associated with non-analyte-related compounds diffusion to the first and second working electrodes. For example, in some embodiments, a saline solution containing a defined amount of glucose is used to wash the sensor. When the glucose-containing saline is held stagnant (e.g., after washing the previous sample off of the sensor), the GOX at the first working electrode metabolizes glucose diffusing through the membrane. As the glucose is metabolized, the reactant (e.g., $H_2O_2$) begins to accumulate and produce signals at both the first and second working electrodes. As a result, the signal increase on each of the first and second working electrodes (e.g., during the time period) can be compared to calculate the calibration factor. This method for calculating the calibration factor is discussed in greater detail elsewhere herein, with reference to FIGS. 3J and 3K.

After the calibration factor has been calculated, the signal(s) from the continuous analyte sensor are calibrated using the calibration factor. The process of calculating the calibration factor and then using the newly calculated calibration factor to calibrate the signals can be continuous, continual and/or intermittent; such that at time passes the calibration factor and calibration are updated. Thus, the system is configured to evaluate changes in membrane sensitivity and/or baseline, to adjust the calculation of analyte concentrations accordingly, whereby the host is provided with more accurate data for use in therapy decision-making.

Multi-Sensor Apparatus

In some preferred embodiments, a multi-sensor apparatus configured for the detection of a plurality of analytes in a circulatory system of a host in vivo is provided. FIGS. 2G through 2S illustrate some exemplary embodiments of such a device. In preferred embodiments, the multi-sensor apparatus is a vascular access device (e.g., a catheter) or a connector configured for fluid communication with the circulatory system of the host. Preferably, the multi-sensor apparatus includes a lumen (e.g., a duct) sufficiently large to house the plurality of sensors, as described elsewhere herein. In an exemplary embodiment, the multi-sensor apparatus comprises a plurality of analyte sensors, wherein the plurality of analyte sensor are configured to detect at least one analyte and to contact a sample of the host's circulatory system. In one exemplary embodiment, the multi-sensor apparatus comprises a lumen, an external surface, and two orifices, wherein a first orifice is proximal relative to the host and the second orifice is distal. In some embodiments, such as in a catheter, the proximal orifice is referred to herein as the in vivo orifice and the distal orifice is referred to as the ex vivo orifice. Preferably, at least the distal orifice is configured to couple with a fluid flow device (or a component thereof), such as but not limited to a connector or coupler, a valve, IV tubing, a pump, and the like. For example, in an embodiment wherein the multi-sensor apparatus is a catheter, the distal orifice (e.g., the ex vivo orifice) is configured to couple to IV tubing, various types of IV connectors, and the like. In some embodiments, both the proximal and distal orifices are configured to couple with IV equipment. For example, in an embodiment wherein the multi-sensor apparatus is configured as a connector (e.g., a Leur lock) the proximal orifice is configured to couple with a vascular access device (e.g., a catheter/cannula), IV tubing, and/or other connectors, and the distal end is configured to couple with a fluid flow device (e.g., IV tubing, a pump, etc.). Preferably; a plurality of analyte sensors are disposed within the lumen of the multi-sensor apparatus. For example, 2, 3, 4, 5, 6, 7, or more sensors can be disposed within the lumen of the multi-sensor apparatus. In some embodiments, each of the plurality of analyte sensor is configured to detect a different analyte. In some embodiments, two or more of the plurality of analyte sensors are configured to detect the same analyte, thereby providing redundancy and/or fail-safes in analyte detection and/or sensor function.

FIG. 2G provides an exemplary embodiment of a multi-sensor apparatus, namely a catheter, including an in vivo portion configured for insertion into the host and an ex vivo portion 218 (e.g., a connector or hub) configured to remain outside the host's body after implantation/insertion of the in vivo portion into a host. The in vivo portion may also be referred to as the proximal portion/end of the catheter (e.g., with respect to the host) includes an in vivo orifice at or near the catheter's tip, for fluid communication with the host's circulatory system upon implantation into the host's vein or artery, or in an extracorporeal circulatory device. The ex vivo portion of the catheter may also be referred to as the proximal portion (e.g., with respect to the host). A plurality of analyte sensors 240 are disposed within the catheter's connector/hub, such as within the lumen/duct 254 and/or within a widened portion of the catheter's in vivo portion.

FIG. 2H provides another exemplary embodiment of a multi-sensor apparatus, namely a connector, such as a Leur lock, a Y-connector, a T-connector, an X-connector, or a valve configured for connecting IV equipment. The multi-sensor apparatus includes a proximal orifice (e.g., with respect to the host) configured to couple with a vascular access device (e.g., a catheter/cannula) or with various IV equipment, such as IV tubing or another connector, and a distal orifice (e.g., with respect to the host) configured to fluidly couple to other IV equipment, as described herein and is known to one skilled in the art. The analyte sensors 240 are disposed within the multi-sensor apparatus's lumen or duct 254.

In various embodiments, the analyte sensors (of the multi-sensor apparatus) can be configured to detect an analyte using any means known in the art, such as but not limited to by enzymatic, chemical, physical, electrochemical, spectrophotometric, polarimetric, calorimetric, radiometric, or immunochemical techniques, or by a combination of these techniques. Further more, each sensor can use a different detection technique. For example, a first analyte sensor can detect a first analyte using a first technique, a second analyte sensor can detect a second analyte using a second technique, a third analyte sensor can detect a third analyte using a third technique, and so on. Additionally, in some embodiments, a detection technique can be used by more than one of the analyte sensors, wherein the technique is modified to detect a particular analyte of interest by each of the sensors. For example, a first sensor can be configured to detect glucose enzymatically, and a second sensor can be configured to detect cholesterol enzymatically. In some embodiments, one of the plurality of sensors is configured to detect an analyte optically, as described elsewhere herein. Additionally, in some embodiments, two or more of the sensors are configured to detect the same analyte, either by the same or different detection techniques.

FIGS. 2I through 2L are cross-sections of the multi-sensor apparatus of FIGS. 2G and 2H taken along line 2I-2I, looking towards the proximal ends (e.g., 212b/258) of the devices. A plurality of analyte sensors 240 is located at the luminal surface of wall 260 (e.g., the interior surface of the hub/connector). In some embodiments, one or more of the plurality of sensors is integrally formed with the multi-sensor apparatus. In some embodiments, the multi-sensor apparatus includes a plurality of sensor sites 262, wherein each sensor site 262 is configured to receive a sensor. In some embodiments, at least one of the plurality of sensor sites 262 comprises a breakaway portion (or a plug) configured for insertion therethrough of a sensor, such that at least a portion of the sensor is disposed within the lumen. One or more of the breakaway portions can be removed, such a by punching them out, to form a channel through the wall 260. In some embodiments, the multi-sensor apparatus is manufactured such that one or more of the sensor sites includes a channel (e.g., through the wall), such that a sensor can be inserted there through. The sensor(s) can be installed by insertion through the channel(s). An adhesive, press-fit, clip or other attachment means can be use to secure the sensor(s) in place. In some embodiments, a portion of a sensor 240 (e.g., the sensing portion) inserted through the wall 260 is disposed at the surface of the duct/lumen. In some embodiments, the portion of the sensor protrudes into the duct/lumen 254. In some further embodiments, at least another portion of the sensor is disposed at the external surface of the connector/hub. In some embodiments, one or more sensors can be disposed (e.g., installed) within the duct/lumen by adhering the sensor at the surface of the duct/lumen. In some embodiments, one or more of the sensors is deposited at the surface of the duct/lumen using known analyte sensor deposition techniques. In some embodiments, conductive traces, leads or wires can be applied/installed, such that the sensor(s) can be connected to device electronics, as is understood by one skilled in the art. For example, the device shown in FIGS. 1A and 1B include a conductive lead 24, for connecting the analyte sensor to electronics.

Referring again to FIG. 2G, in some embodiments, the multi-sensor apparatus is a vascular access device comprising an in vivo portion and an ex vivo portion. In some preferred embodiments, the plurality of analyte sensors are disposed only within the ex vivo portion of the device, and thus do not extend into the in vivo portion (e.g., catheter 212). In this embodiment, the plurality of sensors does not extend beyond a plain defined by the host's skin. In some embodiments, the in vivo portion of the multi-sensor apparatus includes a widened portion, such as a portion adjacent to and/or near to the hub, and one or more of the plurality of sensors are disposed within the widened portion. In some embodiments, one or more of the analyte sensor can be configured to extend into the in vivo portion, and in some embodiments to extend into the host's circulatory system.

Referring again to FIG. 2H, in some embodiments, the multi-sensor apparatus is a connector configured to be disposed outside the host's body. Accordingly, the multi-sensor apparatus does not include an in vivo portion. In this embodiment, the multi-sensor apparatus is configured to fluidly couple to a vascular access device at its proximal end and to a flow control device at its distal end, such that the flow control device can meter the flow of a non-bodily fluid (e.g., saline, a glucose solution, etc.) through the device and into the host, as well as withdrawal of blood samples from the host (e.g., such that the sample(s) contact the analyte sensor(s)) and (optionally) reinfusion of the blood samples to the host. The multi-sensor apparatus of this embodiment includes a lumen and/or duct, in which the plurality of analyte sensors is disposed. In some embodiments, at least one of the plurality of analyte sensors is configured to extend into the lumen of a fluidly coupled catheter; and in some further embodiments to extend through the catheter and into the host's circulatory system.

In preferred embodiments, at least one of the plurality of sensors (of the multi-sensor apparatus) is configured to generate a signal associated with a concentration of an analyte in a sample of the host's circulatory system. More preferably, each of the analyte sensors generates a signal associated with a concentration of each sensor's respective analyte in the blood sample withdrawn from the host. In some embodiments, the sensors can be configured to generate signals associated with 1, 2, 3, 4, 5, 6, 7, 8, 9, 10 or more analytes and/or properties of the sample of the host's circulatory system. In some embodiments, two or more of the sensors are configured to detect the same analyte, such as to provide system redundancy and/or fail-safes. The analyte sensors can be configured to detect a wide variety of analytes, such as but not limited to glucose, oxygen, $CO_2$ (carbon dioxide, bicarbonate), pH, creatinine, urea (nitrogen), bilirubin, electrolytes (e.g., sodium, potassium, chloride, phosphorous, magnesium), albumin, total protein, liver enzymes (e.g., alkaline phosphatase, alanine amino transferase, aspartate amino transferase), antibodies against infective agents, fibrinogen, fibronectin, lipids, triglycerides, cholesterol-protein complexes and ratios thereof (e.g., LDL, HDL, chylomycrons), hormones (e.g., T3, T4, TSH, hGH, interleukins, etc.), medicaments, metabolites, and the like. A more extensive list of analytes can be found in the "Definitions" section. In some embodiments, at least one of the plurality of sensors is configured to generate a signal associated with a property of a sample of the host's circulatory system. Blood properties include but are not limited to pH, temperature, oxygen tension, hematocrit, viscosity, clotting, pressure, and the like.

The multi-sensor apparatus of the preferred embodiments can be manufactured using a variety of techniques known in the art. For example, in some embodiments, the analyte sensors are integrally formed with the multi-sensor apparatus. In some embodiments, at least one of the pluralities of sensors is deposited within the lumen of the multi-sensor apparatus, such as in the lumen/duct of the connector of the hub of the device illustrated in FIG. 2G, or in the lumen/duct of the device of FIG. 2H. In some embodiments, one or more of the analyte sensors is configured to extend out of the connector/hub. For example, in the exemplary embodiment illustrated in FIG. 2G one or more analyte sensors 240 can be configured to extend into and/or through the lumen 212a of the catheter 212. In another example, in the exemplary embodiment illustrated in FIG. 2H one or more analyte sensors 240 can be configured to extend out of the proximal end of the multi-sensor apparatus, such that the sensor(s) can be inserted into and/or through a vascular access device.

In some embodiments, the non-sensor portion of a multi-sensor apparatus is formed, and then the plurality of sensors are applied/installed. In some embodiments, at least one of the pluralities of sensors is deposited within the lumen, such as by screen printing. In some embodiments, at least one of the pluralities of sensors is applied to the interior surface of the lumen, such as via an adhesive.

Alternatively, the multi-sensor apparatus may be formed about the plurality of analyte sensors, such as by using injection molding. For example, a mold is prepared, including sites for the analyte sensors (e.g., these will be "sensor sites," as described elsewhere herein, when the manufacture process is complete). Prior to injection molding, the sensors (e.g., previously manufactured) are placed in the sites. The mold is closed and a material, such as but not limited to, e.g., molten plastic, is injected into the mold. The material fills all of the spaces within the mold, including flowing around portions of the analyte sensors, such that when the mold is cooled, the analyte sensors will be held in place by the wall of the multi-sensor apparatus. For example, one or more of the sensors pass through the wall of the multi-sensor apparatus. In another example, the sensor can be oriented such that when the injection molding process is completed, the analyte sensor is disposed on the surface of the lumen. In some embodiments, one or more of the analyte sensors can be installed in the multi-sensor apparatus during injection molding, followed by application of one or more additional sensors to the lumen of the device. Alternatively, the body of the multi-sensor apparatus, such as a fluid coupler, can be formed as mating injection-molded portions/pieces that mate together about sensors placed in sensor receiving sites (e.g., see FIGS. 2O-2P). A detailed description of this manufacturing process can be found in the section entitled "Exemplary Sensor Configurations." In still other embodiments, the multi-sensor apparatuses can be formed as shown in FIGS. 2Q-2S, as described elsewhere herein, by inserting whole sensors in place of individual electrodes, for example.

As a non-limiting example, a method for making a multi-sensor apparatus for the detection of a plurality of analytes in a circulatory system of a host in vivo is provided, in some embodiments. In some embodiments, a plurality of sensors is first provided. The sensors can be configured to detect one or more analytes using a variety of detection means known to one skilled in the art. Next, a multi-sensor apparatus is formed about the plurality of sensors. The multi-sensor apparatus formed includes a lumen, an external surface, and at least one orifice configured for coupling with a fluid flow device, as described herein.

As another non-limiting example, in some embodiments, a method for making a multi-sensor apparatus for the detection of a plurality of analytes in a circulatory of a host in vivo includes providing a multi-sensor apparatus comprising a lumen, an external surface, and at least one orifice configured for coupling with a fluid flow device a plurality of sensors; followed by forming a plurality of sensor within and/or on the multi-sensor apparatus.

As yet another non-limiting example, a method for detecting of a plurality of analytes in a circulatory of a host in vivo using a multi-sensor apparatus of the preferred embodiments, is provided. Accordingly, a multi-sensor apparatus of the preferred embodiments is applied to the circulatory system of a host. As described elsewhere herein, the multi-sensor apparatus includes a lumen and a plurality of sensors, wherein the at least two sensor are disposed above a plane defined by the skin of the host when the multi-sensor apparatus is applied to the host's circulatory system. For example, in some embodiments, the multi-sensor apparatus is a catheter with sensors in the hub/connector, which is inserted/implanted into a host's artery/vein. After the catheter has been inserted/implanted into the host, at least two of the sensors remain disposed outside the host's body, as defined by the host's skin. As another example, in some embodiments, the multi-sensor apparatus is a connector with sensors within its lumen. In this embodiment, the multi-sensor apparatus must be fluidly coupled to a vascular access device, so that blood can be withdrawn from the host's artery/vein and then contact the sensors within the connector. Thus, at least two of the sensors within this embodiment of the multi-sensor apparatus remain disposed outside the host's body, as defined by the host's skin.

Next, a sample (e.g., blood) is withdrawn from the host's circulatory system. When the sample is withdrawn, it is then contacted with the plurality of sensors. Each of the sensors then generates a signal. As described elsewhere herein, each sensor is configured to detect an analyte. Accordingly, the signal generated by each sensor is associated with the analyte that sensor was configured to detect. The sensors can be configured to generate the signal using any method know in the art, such as but not limited to electrochemically generating the signal, optically generating the signal, radiochemically generating the signal, physically generating the signal, chemically generating the signal, immunochemically generating the signal, and/or enzymatically generating a signal, or combinations thereof.

In some embodiments, a withdrawn sample is reinfused into the host. For example, a flow control device can meter the flow of an infusion fluid into the host, and the infusion fluid pushes the withdrawn sample back into the host. In some embodiments, the device is configured to dispose of the withdrawn sample, such as by directing the sample to a waste container.

As described herein, in some embodiments, an infusion fluid is metered through the multi-sensor apparatus, and infused into the host. In some embodiments, the plurality of sensors is washed with the infusion fluid. For example, infusion of about 0.5, 1, 5, 10, 15 ml or more of infusion fluid into the host can effectively wash a previous blood sample off of the plurality of analyte sensor in some embodiments. A variety of infusion fluids can be used, including but not limited to saline, reference fluids, medicaments, parenteral nutrition fluids, hydration fluid and the like.

In preferred embodiments, the signal of at least one of the plurality of sensors can be calibrated. A variety of calibration methods can be used. In some embodiments, one or more of the analyte sensors can be calibrated using one or more reference data points provided by a device separate from the multi-sensor apparatus/system. For example, a hand-held glucose meter can be used to provide one or more data points for calibrating a glucose sensor disposed in the multi-sensor apparatus. In some embodiments, a substantially stable and/or constant analyte found in the host's blood can be used to calibrate one or more of the plurality of analyte sensors. In some embodiments, data from a recently disconnected multi-sensor apparatus can be used to calibrate one or more of the sensors of a newly installed/applied multi-sensor apparatus. In some embodiments, one of the pluralities of analyte sensors can be used to calibrate one or more of the other sensors. In some embodiments, one or more of the sensors can be calibrated by the manufacturer. Additional methods of calibration that can be used with the multi-sensor apparatus of the preferred embodiments are described elsewhere herein.

Noise

Generally, implantable sensors measure a signal (e.g., counts) related to an analyte of interest in a host. For example, an electrochemical sensor can measure glucose, creatinine, or urea in a host, such as an animal, especially a human. Generally, the signal is converted mathematically to a numeric value indicative of analyte status, such as analyte concentration. However, it is not unusual for a sensor to experience a certain level of noise. The term "noise" generally refers to a signal detected by the sensor that is substantially non-analyte related (e.g., non-glucose related). In other words, things other than the analyte concentration substantially cause noise. Noise is clinically important because it can reduce sensor performance, such as by making the analyte concentration appear higher or lower than the actual concentration. For example, if a host is hyperglycemic (e.g., blood sugar too high, greater than ~120 mg/dl) or euglycemic (e.g., ~80-120 mg/dl), noise can cause the host's blood sugar to appear higher than it truly is, which can lead to improper treatment decisions, such as to give the host an excessive insulin dose. An excessive insulin dose, in some circumstances, can lead to a dangerous hypoglycemic state (e.g., blood sugar too low, less than ~80 mg/dl). In the case of a hypoglycemic host, noise can cause the hosts blood sugar to appear euglycemic or even hyperglycemic, which can also lead to improper treatment decisions, such as not eating when necessary or taking insulin, for example. Accordingly, since noise can cause error and reduce sensor performance, noise reduction is desirable.

Noise is comprised of two components, constant noise and non-constant noise, and can be caused by a variety of factors, ranging from mechanical factors to biological factors. For example, it is known that macro- or micro-motion, ischemia, pH changes, temperature changes, pressure, stress, or even unknown mechanical, electrical, and/or biochemical sources can cause noise. In general, "constant noise" (sometimes referred to as constant background or baseline) is caused by factors that are relatively stable over time, including but not limited to electroactive species that arise from generally constant (e.g., daily) metabolic processes. In contrast, "non-constant noise" (sometimes referred to as non-constant background) is caused by transient events, such as during wound healing or in response to an illness, or due to ingestion (e.g., some drugs). In particular, noise can be caused by a variety of interfering species (constant or non-constant). Interfering species can be compounds, such as drugs that have been administered to the host, or products of various host metabolic processes. Exemplary interferents include but are not limited to a variety of drugs (e.g., acetaminophen), $H_2O_2$ from exterior sources, reactive metabolic species (e.g., reactive oxygen and nitrogen species, some hormones, etc.). In some circumstances, constant noise-causing factors can have an affect on the sensor signal similar to non-constant noise-causing factors, such as when the concentration of a constant noise-causing factor temporarily increases, such as due to temporary lack of lymph flow (see discussion of intermittent sedentary noise).

Noise can be difficult to remove from the sensor signal by calibration using standard calibration equations (e.g., because the background of the signal does not remain constant). Noise can significantly adversely affect the accuracy of the calibration of the analyte signal. Additionally noise, as described herein, can occur in the signal of conventional sensors with electrode configurations that are not particularly designed to measure noise substantially equally at both active and in-active electrodes (e.g., wherein the electrodes are spaced and/or non symmetrical, noise may not be equally measured and therefore not easily removed using conventional dual-electrode designs).

Noise can be recognized and/or analyzed in a variety of ways. In preferred embodiments, the sensor data stream is monitored, signal artifacts are detected and data processing is based at least in part on whether or not a signal artifact has been detected, such as described in U.S. Patent Publication No. US-2005-0043598-A1. Additional description can also be found in U.S. Patent Publication No. US-2007-0032706-A1, both herein incorporated by reference in their entirety.

Reduction of Noise

Noise can be recognized and substantially reduced and/or eliminated by a variety of sensor configurations and/or methods, such as by using 1) sensor configurations that block and/or remove the interferent, or that specifically detect the noise and 2) mathematical algorithms that recognize and/or remove the signal noise component. The preferred embodiments provide devices and methods for reducing and/or eliminating noise, such as by blocking interferent passage to the sensor's electroactive surfaces, diluting and/or removing interferents around the sensor and mathematically determining and eliminating the noise signal component. Those knowledgeable in the art will recognize that the various sensor structures (e.g., multiple working electrodes, membrane interference domains, etc.), bioactive agents, algorithms and the like disclosed herein can be employed in a plurality of combinations, depending upon the desired effect and the noise reduction strategy selected. In preferred embodiments, the sensor comprises at least two working electrodes (one with and one without enzyme over its electroactive surface) and an interference domain configured to substantially block interferent passage therethrough, such that at least some interferent no longer has a substantial affect on sensor measurements (e.g., at either working electrode). The term "interference domain," as used herein is a broad term, and is to be given its ordinary and customary meaning to a person of ordinary skill in the art (and it is not to be limited to a special or customized meaning), and refers without limitation to any mechanism of the membrane system configured to reduce any kind of noise or interferants, such as constant and/or non-constant noise. "Noise-reducing mechanisms" as used herein is a broad term, and is to be given its ordinary and customary meaning to a person of ordinary skill in the art (and it is not to be limited to a special or customized meaning), and refers without limitation to any sensor system component configuration that reduces and/or eliminates noise on the sensor signal. Such structural configurations include but are not limited to electrode configurations (e.g., two or more working electrodes), membrane configurations (e.g., interference domain), algorithmic configurations (e.g., signal processing to remove an identified noise component of the signal), and the like. In some embodiments, the interference domain is a component of the membrane system, such as shown in FIG. 3C. However, the interference domain can be disposed at any level (e.g., layer or domain) of the membrane system (e.g., more proximal or more distal to the electroactive surfaces than as shown in FIG. 3C). In some other embodiments, the interference domain is combined with an additional membrane domain, such as the resistance domain or the enzyme domain.

In another aspect, the sensor is configured to reduce noise, including non-constant non-analyte related noise with an overlapping measuring potential with the analyte. A variety of noise can occur when a sensor has been implanted in a host. Generally, implantable sensors measure a signal (e.g., counts) that generally comprises at least two components, the background signal (e.g., background noise) and the analyte signal. The background signal is composed substantially of signal contribution due to factors other than glucose (e.g., interfering species, non-reaction-related hydrogen peroxide, or other electroactive species with an oxidation/reduction potential that overlaps with the analyte or co-analyte). The analyte signal (e.g., glucose) is composed substantially of signal contribution due to the analyte. Consequently, because the signal includes these two components, a calibration is performed in order to determine the analyte (e.g., glucose) concentration by solving for the equation $y=mx+b$, where the value of b represents the background of the signal.

In some circumstances, the background is comprised of both constant (e.g., baseline) and non-constant (e.g., noise) factors. Generally, it is desirable to remove the background signal, to provide a more accurate analyte concentration to the host or health care professional.

The term "baseline" as used herein is a broad term, and is to be given its ordinary and customary meaning to a person of ordinary skill in the art (and is not to be limited to a special or customized meaning), and refers without limitation to a substantially constant signal derived from certain electroactive compounds found in the human body that are relatively constant (e.g., baseline of the host's physiology, non-analyte related). Therefore, baseline does not significantly adversely affect the accuracy of the calibration of the analyte concentration (e.g., baseline can be relatively constantly eliminated using the equation $y=mx+b$).

In contrast, "noise" as used herein is a broad term, and is to be given its ordinary and customary meaning to a person of ordinary skill in the art (and is not to be limited to a special or customized meaning), and refers without limitation to a substantially intermittent signal caused by relatively non-constant factors (e.g., the presence of intermittent noise-causing compounds that have an oxidation/reduction potential that substantially overlaps the oxidation/reduction potential of the analyte or co-analyte and arise due to the host's ingestion, metabolism, wound healing, and other mechanical, chemical and/or biochemical factors, also non-analyte related). Noise can be difficult to remove from the sensor signal by calibration using standard calibration equations (e.g., because the background of the signal does not remain constant). Noise can significantly adversely affect the accuracy of the calibration of the analyte signal. Additionally noise, as described herein, can occur in the signal of conventional sensors with electrode configurations that are not particularly designed to measure noise substantially equally at both active and in-active electrodes (e.g., wherein the electrodes are spaced and/or non symmetrical, noise may not be equally measured and therefore not easily removed using conventional dual-electrode designs).

There are a variety of ways noise can be recognized and/or analyzed. In preferred embodiments, the sensor data stream is monitored, signal artifacts are detected, and data processing is based at least in part on whether or not a signal artifact has been detected, such as described in U.S. Patent Publication No. US-2005-0043598-A1 and U.S. Patent Publication No. US-2007-0027370-A1, herein incorporated by reference in their entirety.

Accordingly, if a sensor is designed such that the signal contribution due to baseline and noise can be removed, then more accurate analyte concentration data can be provided to the host or a healthcare professional.

One embodiment provides an analyte sensor (e.g., glucose sensor) configured for insertion into a host for measuring an analyte (e.g., glucose) in the host. The sensor includes a first working electrode disposed beneath an active enzymatic portion of a membrane on the sensor; a second working electrode disposed beneath an inactive- or non-enzymatic portion of the membrane on the sensor; and electronics operably connected to the first and second working electrode and configured to process the first and second signals to generate an analyte (e.g., glucose) concentration substantially without signal contribution due to non-glucose related noise artifacts.

In one embodiment, the sensor is configured to substantially eliminate (e.g., subtract out) noise due to mechanical factors. Mechanical factors include macro-motion of the sensor, micro-motion of the sensor, pressure on the sensor, local tissue stress, and the like. Since both working electrodes are constructed substantially symmetrically and identically, and due to the sensor's small size, the working electrodes are substantially equally affected by mechanical factors impinging upon the sensor. For example, if a build-up of noise-causing compounds occurs (e.g., due to the host pressing upon and manipulating (e.g., fiddling with) the sensor, for example) both working electrodes will measure the resulting noise to substantially the same extend, while only one working electrode (the first working electrode, for example) will also measure signal due to the analyte concentration in the host's body. The sensor then calculates the analyte signal (e.g., glucose-only signal) by removing the noise that was measured by the second working electrode from the total signal that was measured by the first working electrode.

Non-analyte related noise can also be caused by biochemical and/or chemical factors (e.g., compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing). As with noise due to mechanical factors, noise due to biochemical/chemical factors will impinge upon the two working electrodes of the preferred embodiments (e.g., with and without active GOx) about the same extent, because of the sensor's small size and symmetrical configuration. Accordingly, the sensor electronics can use these data to calculate the glucose-only signal, as described elsewhere herein.

In one exemplary embodiment, the analyte sensor is a glucose sensor that measures a first signal associated with both glucose and non-glucose related electroactive compounds having a first oxidation/reduction potential. For example, the oxidation/reduction potential of the non-glucose related electroactive compounds substantially overlaps with the oxidation/reduction potential of $H_2O_2$, which is produced according to the reaction of glucose with GOx and subsequently transfers electrons to the first working electrode (e.g., E1; FIG. 3F). The glucose sensor also measures a second signal, which is associated with background noise of the glucose sensor. The background noise is composed of signal contribution due to noise-causing compounds (e.g., interferents), non-reaction-related hydrogen peroxide, or other electroactive species with an oxidation/reduction potential that substantially overlaps with the oxidation/reduction potential of $H_2O_2$ (the co-analyte). The first and second working electrodes integrally form at least a portion of the sensor, such as but not limited to the in vivo portion of the sensor, as discussed elsewhere herein. Furthermore, the sensor has a diffusion barrier that substantially blocks (e.g., attenuates) diffusion of glucose or $H_2O_2$ between the first and second working electrodes. In various embodiments, the sensor includes a diffusion barrier configured to be physical, spatial, and/or temporal.

FIG. 3F is a schematic illustrating one embodiment of a sensor (e.g., a portion of the in vivo portion of the sensor, such as but not limited to the sensor electroactive surfaces) having one or more components that act as a diffusion barrier (e.g., prevent diffusion of electroactive species from one electrode to another). The first working electrode E1 is coated with an enzyme layer 348 comprising active enzyme. For example, in a glucose sensor, the first working electrode E1 is coated with glucose oxidase enzyme (GOx). A second working electrode E2 is separated from the first working electrode E1 by a diffusion barrier D, such as but not limited to a physical diffusion barrier (e.g., either a reference electrode or a layer of non-conductive material/insulator). The diffusion barrier can also be spatial or temporal, as discussed elsewhere herein.

Glucose and oxygen diffuse into the enzyme layer 348, where they react with GOx, to produce gluconate and $H_2O_2$. At least a portion of the $H_2O_2$ diffuses to the first working electrode E1, where it is electrochemically oxidized to oxygen and transfers two electrons (e.g., $2e^-$) to the first working electrode E1, which results in a glucose signal that is recorded by the sensor electronics (not shown). The remaining $H_2O_2$ can diffuse to other locations in the enzyme layer or out of the enzyme layer (illustrated by the wavy arrows). Without a diffusion barrier D, a portion of the $H_2O_2$ can diffuse to the second working electrode E2, which results in an aberrant signal that can be recorded by the sensor electronics as a non-glucose related signal (e.g., background).

Preferred embodiments provide for a substantial diffusion barrier D between the first and second working electrodes (E1, E2) such that the $H_2O_2$ cannot substantially diffuse from the first working electrode E1 to the second working electrode E2. Accordingly, the possibility of an aberrant signal produced by $H_2O_2$ from the first working electrode E1 (at the second working electrode E2) is reduced or avoided.

In some alternative embodiments, the sensor is provided with a spatial diffusion barrier between electrodes (e.g., the working electrodes). For example, a spatial diffusion barrier can be created by separating the first and second working electrodes by a distance that is too great for the $H_2O_2$ to substantially diffuse between the working electrodes. In some embodiments, the spatial diffusion barrier is about 0.01, 0.02, 0.03, 0.04, 0.05, 0.06, 0.07, or 0.08 inches to about 0.09, 0.10, 0.11, or 0.120 inches. In other embodiments, the spatial diffusion barrier is about 0.020 inches to about 0.050 inches. Still in other embodiments, the spatial diffusion barrier is about 0.055 inches to about 0.095 inches. A reference electrode R (e.g., a silver or silver/silver chloride electrode) or a non-conductive material (e.g., a polymer structure or coating such as Parylene) can be configured to act as a spatial diffusion barrier.

In some preferred embodiment, the sensor is an indwelling sensor, such as configured for insertion into the host's circulatory system via a vein or an artery. In some exemplary embodiments, an indwelling sensor includes at least two working electrodes that are inserted into the host's blood stream through a catheter. The sensor includes at least a reference electrode that can be disposed either with the working electrodes or remotely from the working electrodes. The sensor includes a spatial, a physical, or a temporal diffusion barrier. A spatial diffusion barrier can be configured as described in U.S. Patent Publication No. US-2008-0083617-A1 which is incorporated by reference herein in its entirety.

In one exemplary embodiment of an indwelling analyte sensor, such as but not limited to an intravascular glucose sensor to be used from a few hours to ten days or longer. Namely, the sensor includes two working electrodes. A first working electrode detects the glucose-related signal (due to active GOx applied to the electroactive surface) as well as non-glucose related signal. The second working electrode detects only the non-glucose related signal (because no active GOx is applied to its electroactive surface). $H_2O_2$ is produced on the first working electrode (with active GOx). If the $H_2O_2$ diffuses to the second working electrode (the no GOx electrode) an aberrant signal will be detected at this electrode, resulting in reduced sensor activity. Accordingly, it is desirable to separate the electroactive surfaces with a diffusion barrier, such as but not limited to a spatial diffusion barrier. Indwelling sensors are described in more detail in copending U.S. Patent Publication No. US-2008-0119703-A1, herein incorporated in its entirety by reference.

To configure a spatial diffusion barrier between the working electrodes, the location of the active enzyme (e.g., GOx) is dependent upon the orientation of the sensor after insertion into the host's artery or vein. For example, in an embodiment configured for insertion in the host's blood flow (e.g., in an artery or vein), active GOx and the inactive GOX (or no GOx) would be applied to two working electrodes such that the active GOX would be downstream from the inactive GOX (e.g., relative to the direction of blood flow). Due to this configuration, $H_2O_2$ produced at plus-GOX electroactive surface would be carrier down stream (e.g., away from minus-GOX electroactive surface) and thus not affect the non-enzymatic working electrode.

In some embodiments, a physical diffusion barrier is provided by a physical structure, such as an electrode, insulator, and/or membrane. For example, in some embodiments, an insulator or reference electrode disposed between the working electrodes acts as a diffusion barrier. As another example, the diffusion barrier can be a bioprotective membrane (e.g., a membrane that substantially resists, attenuates or blocks the transport of a species (e.g., hydrogen peroxide), such as a polyurethane. As yet another example, the diffusion barrier can be a resistance domain, as described in more detail elsewhere herein; namely, a semipermeable membrane that controls the flux of oxygen and an analyte (e.g., glucose) to the underlying enzyme domain. Numerous other structures and membranes can function as a physical diffusion barrier as is appreciated by one skilled in the art.

In other embodiments, a temporal diffusion barrier is provided (e.g., between the working electrodes). By temporal diffusion barrier is meant a period of time that substantially prevents an electroactive species (e.g., $H_2O_2$) from diffusing from a first working electrode to a second working electrode. For example, in some embodiments, the differential measurement can be obtained by switching the bias potential of each electrode between the measurement potential and a non-measurement potential. The bias potentials can be held at each respective setting (e.g., high and low bias settings) for as short as milliseconds to as long as minutes or hours. Pulsed amperometric detection (PED) is one method for quickly switching voltages, such as described in Bisenberger, M.; Brauchle, C.; Hampp, N. A triple-step potential waveform at enzyme multisensors with thick-film gold electrodes for detection of glucose and sucrose. *Sensors and Actuators* 1995, B. 181-189, which is incorporated herein by reference in its entirety. In some embodiments, bias potential settings are held long enough to allow equilibration.

One preferred embodiment provides a glucose sensor configured for insertion into a host for measuring glucose in the host. The sensor includes first and second working electrodes and an insulator located between the first and second working electrodes. The first working electrode is disposed beneath an active enzymatic portion of a membrane on the sensor and the second working electrode is disposed beneath an inactive- or non-enzymatic portion of the membrane on the sensor. The sensor also includes a diffusion barrier configured to substantially block (e.g., attenuate, restrict, suppress) diffusion of glucose or hydrogen peroxide between the first and second working electrodes.

In a further embodiment, the glucose sensor includes a reference electrode configured integrally with the first and second working electrodes. In some embodiments, the reference electrode can be located remotely from the sensor, as described elsewhere herein. In some embodiments, the surface area of the reference electrode is at least six times the surface area of the working electrodes. In some embodiments, the sensor includes a counter electrode that is integral to the sensor or is located remote from the sensor, as described elsewhere herein.

In a further embodiment, the glucose sensor detects a first signal associated with glucose and non-glucose related electroactive compounds having a first oxidation/reduction potential (e.g., the oxidation/reduction potential of $H_2O_2$). In some embodiments, the glucose sensor also detects a second signal is associated with background noise of the glucose sensor comprising signal contribution due to interfering species, non-reaction-related hydrogen peroxide, or other electroactive species with an oxidation/reduction potential that substantially overlaps with the oxidation/reduction potential of hydrogen peroxide; the first and second working electrodes integrally form at least a portion of the sensor; and each of the first working electrode, the second working electrode and the non-conductive material/insulator are configured provide at least two functions such as but not limited to electrical conductance, insulation, structural support, and a diffusion barrier In further embodiments, the glucose sensor includes electronics operably connected to the first and second working electrodes. The electronics are configured to calculate at least one analyte sensor data point using the first and second signals described above. In still another further embodiment, the electronics are operably connected to the first and second working electrode and are configured to process the first and second signals to generate a glucose concentration substantially without signal contribution due to non-glucose noise artifacts.

Sensor Configurations for Equivalent Measurement of Noise Signals at the Two Working Electrodes In dual-electrode biosensors (e.g., an analyte sensor having two working electrodes E1, E2), noise can be caused by a variety of sources, for example, located outside (e.g., by noise-causing species produced metabolically and/or consumed by the host) or within (e.g., crosstalk) the sensor. In some circumstances, biological and/or metabolic processes occurring in the host's body, such as in the locale of the implanted sensor, can cause noise. These metabolic processes, such as but not limited to wound healing, the body's response to illness and even daily cellular metabolic processes, can generate noise-causing metabolic species (e.g., compounds, substances) that impinge upon the sensor and cause noise on the signal. For example, some noise-causing species, the levels of which are relatively stable due to production during daily cellular metabolism, generally cause constant noise. In another example, some noise-causing species, the levels of which fluctuate due to production by intermittent metabolic process (e.g., wound healing or response to infection), generally cause non-constant noise. Noise-causing metabolic species include but are not limited to externally generated $H_2O_2$ (e.g., produced outside the sensor), compounds having electroactive acidic, amine or sulfhydryl groups, urea, lactic acid, phosphates, citrates, peroxides, amino acids (e.g. L-arginine), amino acid precursors or break-down products, nitric oxide (NO), NO-donors, NO-precursors, reactive oxygen species or other electroactive species or metabolites produced during cell metabolism and/or wound healing, for example. Noise-causing species, such as drugs, vitamins and the like, can also be consumed by the host. These noise causing species include but are not limited to acetaminophen, ascorbic acid, dopamine, ephedrine, ibuprofen, L-dopa, methyldopa, salicylate, tetracycline, tolazamide, tolbutamide and triglycerides. Further discussion of noise and its sources can be found in U.S. Patent Publication No. US-2007-0027370-A1 and U.S. Patent Publication No. US-2007-0235331-A1, both of which are incorporated herein by reference in their entirety.

In dual-electrode sensors, noise can also be generated within the sensor, namely due to diffusion of a measured species (e.g., $H_2O_2$) from a first working electrode (e.g., the $H_2O_2$ is generated in an active enzymatic portion of the sensor membrane associated with the first working electrode) to a second working electrode and detection thereby (e.g., which is associated with a non-enzymatic portion of the sensor membrane). This type of noise is commonly referred to as "crosstalk." Crosstalk is undesirable as it causes sensor error, which can result in inaccurate reporting of sensor data. In conventional sensors, a common solution to the problem of crosstalk is to space the two working electrodes far enough apart that a measured species diffusing from one working electrode cannot reach the other working electrode; unfortunately, such spacing does not enable substantially equivalent measurement of noise-cause species, as discussed in more detail elsewhere herein. Unlike conventional sensors, the sensors of the preferred embodiments ensure accurate subtraction of noise signal by ensuring substantially equivalent measurement of the noise (e.g., noise component, constant and/or non-constant noise components) detected by the two working electrodes.

Depending upon the scale (e.g., point) of reference, noise has a dual nature. On a larger scale, with respect to the in vivo portion of the sensor and the surrounding tissue, noise occurs randomly (e.g., is scattered, intermittent, dispersed, unevenly distributed) in the local of an implanted sensor. Yet, on a smaller scale, such as that of a few cells (e.g., 100-300 microns), noise is a localized phenomenon because it creates hot spots of noise-causing species generation whose effects extend about a thousandths of an inch (e.g., localized nature, character). A "hot spot" of noise generation is referred to herein as a "point source." A point source (e.g., a localized hot spot for noise generation) can be a cell or a group of cells adjacent to the sensor membrane, or a noise-causing species (e.g., compound, substance, molecule) that diffused to the location of sensor implantation, such as by diffusion between cells (e.g., to the sensor). For example, in the circumstance of a single point source in contact with the sensor membrane's surface, noise is a local phenomenon, because the noise-causing species' ability to affect adjacent structures is limited by the maximum distance it can diffuse (e.g., through the membrane), which is generally very short (e.g., a few microns, such as between about 1-µm to about 500-µm). Due to the random yet localized nature of noise, the configuration of the electroactive surfaces (of the working electrodes) can substantially affect noise measurement. With respect to the configuration and arrangement (e.g., surface area) of the dual-electrode sensor's electroactive surfaces, the random yet localized nature of noise is discussed in greater detail below.

FIG. 3G is a two-dimensional schematic illustrating, on the scale of a sensor and the surrounding tissue (e.g., a generally larger scale), the random nature of noise relative to a dual-electrode sensor, in one exemplary embodiment. This figure is for illustrative purposes only, and should not be considered as a to-scale representation of a particular sensor configuration or of the events discussed herein. In the embodiment shown in FIG. 3G, the dual-electrode analyte sensor includes two electroactive surfaces E1, E2 disposed beneath the sensor's membrane. While FIG. 3G illustrates only one dimension of the electroactive surfaces, in some embodiments, the electroactive surfaces (e.g., the surface area of each electroactive surface) can include both a length and a width. In some embodiments, the area can include additional dimensions, such as a circumference and/or a height. In some embodiments, the sensor can have a planar configuration. In some embodiments, the sensor can have a cylindrical, pyramidal, polygonal configuration. It should also be understood that the electroactive surfaces E1, E2 are shown as boxes as a matter of illustrative convenience; however, electroactive surfaces can be thinner or thicker than illustrated in FIG. 3G or elsewhere herein. The membrane has a thickness D1 and a surface MS. Depending upon the membrane configuration, fabrication methods and/or materials, D1 can vary in size, from less than about 0.001, 0.002, 0.003, 0.004, 0.005, 0.006, 0.007, 0.008, 0.009, or 0.010 inches to more than about 0.011, 0.012, 0.013, 0.014, 0.015, 0.015, 0.016, 0.017, 0.018, 0.019, 0.020, 0.025, 0.03, 0.035, or 0.050 inches. In some embodiments, a preferred membrane thickness is between about 0.001, 0.0012, 0.0014, 0.0016, or 0.0018 inches to about 0.002, 0.0022, 0.0024, 0.0026, 0.0028, or 0.003 inches. Noise-causing species (represented by squiggly arrows N2) can be generated by and/or at point sources N1 (e.g., noise hot spots) unevenly distributed relative the in vivo portion of the sensor. For example, some of the point sources N1 (shown in FIG. 3G) are concentrated at one end of electroactive surface E1, while some are distributed more evenly across electroactive surface E2. In some circumstances, the point source may be one or more cells (e.g., in contact with the membrane surface MS) that release the noise-causing species during wound healing or another metabolic process, such as when a sensor is implanted in vivo. In some circumstances, the implanted sensor can be located within the diffusion distance of one or more noise-causing species produced during a nearby metabolic process. In some circumstances, the noise-causing species (e.g., a compound consumed by the host) can be carried to the local of the sensor via the circulatory and/or lymph system and diffuse to the sensor (e.g., between cells).

Random and/or unequally distributed noise can be generated in a variety of circumstances. For example, a peroxide-generating immune cell could be located adjacent to one electroactive surface but not the other. In general, a noise-causing species must be generated and/or occur close enough to the sensor membrane such that it can diffuse to (and through) the membrane, to the electroactive surfaces, and affect the sensor signal. If the noise-causing species is generated farther away from the membrane than the diffusion distance of the noise-causing species, then the noise-causing species may be unable to reach the electroactive surfaces, and therefore may have little effect on sensor signal. For example, $H_2O_2$ (produced by metabolic process when the sensor is implanted in a host) must be generated sufficiently close to the membrane for it to diffuse to the membrane and affect sensor function. The maximum distance that the noise-causing species can diffuse (e.g., from the cell to the membrane, from one working electrode to another working electrode) and still substantially affect sensor function is referred to herein as a "diffusion distance."

The sensor electronics are configured to mathematically correct for noise on the sensor signal (e.g., such as by subtraction of the noise signal, applying a filter, averaging, or other calculations), such that a substantially analyte-only signal can be presented to the user. The inventors have discovered that successful mathematical correction of noise on the sensor signal can be substantially affected by the equivalence (e.g., similarity) of the noise signals detected by the two working electrodes. If the detected noise signals are substantially equivalent (e.g., similar amounts, amplitudes, levels, relatively equal), then the calculations will produce a more accurate resultant analyte signal. If, on the other hand, the detected noise signals are not substantially equal (e.g., have very different amplitudes and/or wave forms), then the calculations will have a greater degree of error. While not wishing to be bound by theory, it is believed that presentation of more accurate sensor data (e.g., to the host) will improve the host's management of his or her diabetes, which will prevent the immediate risks of hypoglycemia (e.g., loss of consciousness and death) and postpone and/or prevent long term diabetes complications (blindness, loss of limb, kidney dysfunction, and the like). Additionally, the increased accuracy afforded by the sensors of the preferred embodiment increases the feasibility of insulin dosing and/or an artificial pancreas system based on a continuous glucose sensor.

In order to compensate for the unevenly distributed nature of noise (e.g., the point sources are randomly and/or non-equally and/or non-equivalently distributed relative to the in vivo portion of the sensor) and thereby render the noise components equivalent, a continuous dual-electrode glucose sensor having sufficiently large electroactive surfaces, such that the noise components can be substantially equalized (e.g., made and/or become equivalent) by integration there across, is provided in one embodiment. The first working electrode includes a first electroactive surface (E1, FIG. 3G) disposed beneath an active enzymatic portion (e.g., plus-GOx) of the sensor's membrane, as described elsewhere herein. The first electroactive surface includes a first area (e.g., first electroactive surface area) configured to detect a first signal (e.g., including an analyte-related component and a noise component) having a first noise component related to a noise-causing species. The sensor also includes a second working electrode having a second electroactive surface (E2, FIG. 3G) disposed beneath an inactive-enzymatic or a non-enzymatic portion of the sensor membrane, as described elsewhere herein. For example, an inactive-enzymatic portion of the membrane can include inactivated GOx or no GOx. The second electroactive surface includes a second area (e.g., second electroactive surface area) configured to generate a second signal having a second noise component related to the noise-causing species. In preferred embodiments, the first and second areas are dimensioned (e.g., sized) to be sufficiently large such that the first and second noise components integrated there across, such that the first and second integrated noise signals (e.g., from the first and second electroactive surfaces, respectively) are substantially equivalent. In some embodiments, the first and second integrated noise signals (e.g., noise components) are within 20% of each other (e.g., plus or minus 10%). In some embodiments, the first and second electroactive surfaces are dimensioned to integrate noise caused by a plurality of local point sources that produce noise-causing species in vivo.

FIG. 3H is a two-dimensional schematic illustrating the localized character of noise species (represented by squiggly arrows N2) generated by a point source N1, when examined from a cellular scale, as discussed elsewhere herein. FIG. 3H depicts a cross-section of a sensor, in one embodiment, wherein the sensor includes two working electrodes having electroactive surfaces E1 and E2, and a membrane having surface MS and thickness D1. Distance D3 separates the electroactive surfaces; the distance between their outer edges is denoted by D4. Note that dimension D2, described above, is not shown in this figure. The sensor of this exemplary embodiment can have a variety of configurations, such as but not limited to planar, cylindrical or polygonal. Accordingly, the dimensions of an electroactive surface's surface area (referred to as "area" herein) can include but are not limited to length, width, height, and/or circumference. For example, in some embodiments, the area of each electroactive surface is defined by a length and a width. In some embodiments, the area includes a length or width and a circumference. In some embodiments, the area includes length, width and height. Additionally, it is known to one skilled in the art that, in some circumstances, differences in signal amplitude and/or sensitivity (e.g., from the two working electrodes), due to differences in electrode sizes (or some differences in compositions of membranes) can be corrected (adjusted, compensated for, calibrated out) mathematically. For example, if a first electroactive surface is two times as large as the second electroactive surface, then the signal from the second electroactive surface can be multiplied by two, such that the sensitivities are substantially similar.

Referring now to FIG. 3H, in this exemplary circumstance the point source (e.g., noise hot spot) is an individual cell N1 disposed adjacent to the membrane surface MS and generally above and/or over the sensor's electroactive surfaces E1, E2. The cell can produce noise-causing substances (e.g., N2) that can diffuse to and affect its local environment. In general, the ability of a noise-causing substance to affect the local environment is limited by the maximum distance the substance can diffuse (e.g., the substance's diffusion distance). In some circumstances, some of the noise-causing substances can diffuse through the sensor membrane and affect the sensor's electroactive surfaces. While not wishing to be bound by theory, the inventors have found that in order for the two electroactive surfaces to be substantially equivalently affected by the noise N2 from a point source, such as a cell, the electroactive surfaces must be affected by substantially the same microenvironment. In various circumstances, the electroactive surfaces will be affected by substantially the same microenvironment, if the electroactive surfaces are configured and arranged such that the electroactive surfaces are sufficiently close together and/or their external edges are sufficiently close together.

FIG. 3H shows that the sensor's electroactive surfaces E1, E2 are separated by a distance D3 and their outer edges are spaced a distance D4 (e.g., in at least one dimension), in one exemplary embodiment. In this example, a point source N1 (e.g., a cell) of noise-causing species 1006 is adjacent to the membrane's surface MS. If the electroactive surfaces are configured and arranged such that D3 is sufficiently small, then the noise-causing species diffusing from the point source can impinge equivalently on both of the electroactive surfaces. Additionally or alternatively, if D4 is sufficiently small (e.g., the electroactive surfaces are sufficiently narrow in at least one dimension), then the noise-causing species diffusing from the point source can impinge equivalently on both of the electroactive surfaces. Accordingly, in preferred embodiments, the electroactive surfaces are spaced a distance (e.g., relative to each other, D3) such that the electroactive surfaces (e.g., at least a portion of each electroactive surface) detect substantially equivalent noise from a point source. In some embodiments, the electroactive surfaces are sufficiently close together (e.g., such that the noise components measured are substantially equal) when the distance between the electroactive surfaces (D3) is between about 0.5-times to about 10-times (or more) the membrane thickness (D1). In some preferred embodiments, the electroactive surfaces are sufficiently close together when D3 is about 2-, 3-, 4-, 5-, 6-, 7-, 8-, or 9-times the membrane thickness. In some embodiments, D3 is between about 5, 10, 15, 20, 25, 30, 35, 40, 45, or 50 microns or less to about 55, 60, 65, 70, 75, 80, 85, 90, 95, or 100 microns or more. In preferred embodiments, D3 is between about 20 to about 40 microns. In some embodiments, D4 is between about 25 microns or less to about 500 microns or more.

Depending upon the sensor's configuration, in some embodiments, D4 can be the distance between the outer edges of the electroactive surfaces, or D4 can be a distance equivalent to the maximum diameter of the bundles and/or twisted pair of working electrodes. For example, FIG. 3H illustrates a cross-section of a sensor (e.g., width and height), but doesn't illustrate any additional dimensions (e.g., length). The cross-section could be that of a planar sensor configuration, wherein the sensor also includes an additional dimension that has not been shown, such as but not limited to D2. In some circumstances, the sensor can have a non-planar configuration. For example, in the embodiment shown in FIG. 3I, the working electrodes E1, E2 are fabricated from two wires. Since the wires are cylindrical, the electroactive surfaces do not include outer edges. In this exemplary circumstance, D4 is the total diameter of the bundled and/or twisted pair of working electrodes. In both types of sensor configurations (e.g., planar and non-planar), if D4 is sufficiently small, then the two working electrodes can be equivalently affected by noise-causing species N2 derived from a point source N1.

As described above, dual-electrode sensors can be affected by internally generated noise (e.g., generated by the sensor). The inventors have found that, in general, when D3 is sized to be sufficiently small such that the electroactive surfaces are equivalently affect by noise from an adjacent point source, the electroactive surfaces are also close enough together that crosstalk (an internally generated noise) can occur. In general, crosstalk is detection of an analyte signal generated at the plus-GOx working electrode (wherein the electrode includes the membrane portion thereon) by the minus-GOx working electrode (including the No GOx membrane portion thereon). For example, when the measured species is $H_2O_2$, crosstalk occurs when the $H_2O_2$ diffuses from the plus-GOx enzyme domain to the No GOx working electrode and is detected (e.g., a signal is generated on the No GOx electrode). In general, crosstalk is undesirable as it causes sensor error. However, in order for the two working electrodes to measure equivalent noise signals from a point source N1, the electroactive surfaces must be spaced very close together. Accordingly, in preferred embodiments, this distance (D3) is less than a crosstalk diffusion distance of the measured species. In other words, D3 is shorter than the diffusion distance of $H_2O_2$ (e.g., the maximum distance $H_2O_2$ can diffuse from a first electrode to a second and still cause a signal on the second electrode).

In conventional dual-electrode sensors, spacing the electroactive surfaces within the crosstalk diffusion distance of the measured species is generally undesirable due to increased sensor error. However, in preferred embodiments, the sensor includes a physical diffusion barrier configured to attenuate crosstalk by physically blocking (e.g., suppressing, blocking, restricting) some of the crosstalk from the active enzymatic portion of the sensor membrane to the second electroactive surface. More preferably, the physical diffusion barrier is configured and arranged to attenuate and/or physically block a substantial amount of the measurable species (e.g., $H_2O_2$) diffusing from the active enzymatic portion of the membrane to the second electroactive surface, such that there is substantially no signal associated with crosstalk measured at the second working electrode.

FIG. 3I is a schematic illustrating a perspective view of a cross-section of a dual-electrode sensor that includes a physical diffusion barrier D, in one exemplary embodiment. In this embodiment, wires form the working electrodes E1, E2. The working electrodes each include a membrane, including an electrode domain 347, an enzyme domain 248 and a resistance domain 249. For example, E1 includes a first electrode domain, a first enzyme domain (Plus GOx) and a first resistance domain, and E2 includes a second electrode domain, a second enzyme domain (No GOx) and a second resistance domain. In this particular exemplary embodiment, the electrodes are placed together and coated with an additional resistance domain 249A (e.g., a third resistance domain). Depending upon the circumstances, the electrodes can be placed and/or held together using a variety of methods, such as bundling, twisting, wrapping, and the like, either alone or in combination. The distances shown are as follows; a thickness of the membrane D1, at least one dimension of the electroactive surface D2, a distance between the electroactive surfaces D3, and a distance between the outer edges of the electroactive surfaces D4. In the illustrated exemplary embodiment, the first and second electroactive surfaces extend about the circumferences of E1 and E2 (or portions thereof), respectively.

In preferred embodiments, the physical diffusion barrier D is disposed between the electroactive surfaces of working electrodes E1 and E2. In some embodiments, the physical diffusion barrier is formed of one or more membrane materials, such as those used in formation of an interference domain and/or a resistance domain. Such materials include but are not limited to silicones, polyurethanes, cellulose derivatives (cellulose butyrates and cellulose acetates, and the like) and combinations thereof, as described elsewhere herein. In some embodiments, the physical diffusion barrier includes one or more membrane domains. For example, in the exemplary embodiment of FIG. 3I, the physical diffusion barrier is a discontinuous portion of the membrane (e.g., separate, distinct or discontinuous membrane structures) disposed between the first and second electroactive surfaces, and can include one or more membrane portion(s) within distance D3 (e.g., interference and/or resistance domains). For example, in some embodiments, $H_2O_2$ diffusing from the Plus GOX working electrode to the No GOx working electrode must pass through two "sensor membranes" such as the first and second resistance domains disposed on E1 and E2 respectively, and optionally electrode, interference and/or enzyme domains disposed on E2. In some embodiments, the physical diffusion barrier includes first and second barrier layers formed independently on the first and second electrodes. In some embodiments the barrier layer is the resistance domain 349. In still other embodiments, the physical diffusion barrier can be a continuous membrane (and/or membrane domain(s)) disposed between the electroactive surfaces. In some embodiments, the physical diffusion barrier attenuates (e.g., suppresses, blocks, prevents) diffusion of the $H_2O_2$ (e.g., crosstalk) by at least 2-fold. In preferred embodiments, crosstalk is attenuated at least 5-fold. In a more preferred embodiment, crosstalk is attenuated at least 10-fold. In some embodiments, the physical diffusion barrier attenuates crosstalk at least about 50%. In a further embodiment, the physical diffusion barrier is configured and arranged to physically block an amount of the measured species diffusing from the active enzymatic portion of the membrane to the second electroactive surface, such that there is substantially no signal associated with crosstalk measured at the second working electrode.

In some embodiments, a dual-electrode sensor having a physical barrier layer can be fabricated by initially preparing (e.g., fabricating, building) the first and second working electrodes E1, E2 independently (e.g., separately from each other), followed by joining and/or grouping and/or bundling the working electrodes and optionally applying one or more additional membrane domains fabrication. In this exemplary embodiment, to the first working electrode E1, an optional electrode domain 347, an enzyme domain 348 (e.g., plus-GOx), and at least one layer of the resistance domain material 349 (e.g., first resistance domain) are sequentially applied. Similarly, to the second working electrode E2, an optional electrode domain 347, an enzyme domain 348 (e.g., no-GOx), and at least one layer of the resistance domain material 349 (e.g., second resistance domain) are sequentially applied. The working electrodes are then held together, such as but not limited to by bundling and/or twisting them together, wrapping a material around them, or by any other method known in the art. In this embodiment, the physical diffusion barrier D includes a discontinuous portion of a membrane (e.g., the initial layers of the resistance domain material applied independently to the two working electrodes) disposed between the first and second electroactive surfaces.

In an alternative exemplary sensor embodiment, the sensor includes working electrodes (including electroactive surfaces) disposed on a planar substrate and/or surface. The electroactive surfaces can be spaced a distance D3 that is sufficiently close together that the electroactive surfaces are equivalently affected by an adjacent noise hot spot (e.g., point source). In this configuration, D3 is also sufficiently small that crosstalk can occur between the Plus GOx working electrode (wherein the term "electrode" includes the membrane disposed thereon, for the purposes of this example) and the No GOx working electrode. However, in preferred embodiments, crosstalk is substantially attenuated by a physical diffusion barrier disposed between the working electrodes. Namely, the electrode domains (if present) and enzyme domains can be separately applied to the working electrodes and/or electroactive surfaces; followed by application of a continuous resistance domain applied thereon, such that a portion the resistance domain is deposited between the working electrodes. For example, a portion of resistance domain deposited on a planar substrate and between working electrodes can attenuate diffusion of the measured species (e.g., $H_2O_2$) from E1 to E2, such that the noise measured on E1 and E2 is equivalent.

In the context of glucose sensors, one skilled in the art recognizes that equivalent noise signals can have different amplitudes, but equivalent signal patterns (e.g., rises, falls, trends and the like) such that a noise component can be subtracted out (as described elsewhere herein) while compensating for any difference in signal amplitude (e.g., sensitivity of the first and second working electrodes), as described elsewhere herein. In some circumstances, the membrane portions associated with the working electrodes (e.g., of a dual-electrode sensor) can possess different sensitivities (e.g., signal sensitivities), such that the amplitudes of the noise components measured by the working electrodes are not equivalent. In some circumstances, the areas of the electroactive surfaces may be different sizes, which can also result in non-equivalent signal amplitudes, differences in measured baselines and/or sensitivities between the first and second working electrodes. While such differences in signal baseline and/or sensitivity can be corrected mathematically (e.g., by mathematical filters), mathematical correction of noise, in general, is improved when the signal sensitivities of the first and second working electrodes are closer. Accordingly, in a preferred embodiment, an additional resistance domain 349A (e.g., applied continuously over the discontinuous resistance domains 349 described elsewhere herein) is provided, such that the signal sensitivities are equivalent. In the exemplary embodiment shown in FIG. 3I, the signal sensitivities are substantially equalized on a sensor including the combination of discontinuous resistance domains (e.g., resistance domains 349, applied independently to E1 and E2) and a continuous resistance domain 349A (e.g., applied over and/or adjacent to the discontinuous resistance domains). In other words, the noise signals detected on both E1 and E2 will have substantially the same amplitude (e.g., intensity, amount), as described with reference to Example 7, below. In a preferred embodiment, the sensitivities (of the working electrodes) are within 40% of each other (e.g., plus or minus 20%). In a preferred embodiment, the sensitivities (of the working electrodes) are within 20% of each other (e.g., plus or minus 10%). In a more preferred embodiment, the sensitivities (of the working electrodes) are within 10% of each other (e.g., plus or minus 5%).

In an alternative embodiment, the sensor electrodes can be disposed on a planar, cylindrical, pyramidal or otherwise shaped support. For example, the sensor's first and second working electrodes can be conductive traces deposited, such as by screen printing, sputtering or other thin film techniques known in the art, on a planar substrate. In this alternative embodiment, a physical diffusion barrier can be formed by layers of resistance domain material deposited separately (e.g., discontinuously) on each working electrode and/or between the electrodes, for example.

In the exemplary embodiments described above, diffusion of the $H_2O_2$ from the first working electrode E1 to the electroactive surface of the second working electrode E2 is first attenuated by the resistance domain 349 disposed over the first working electrode E1 (an independently formed first barrier layer), and then again by the resistance domain 349 disposed over the second working electrode E2 (an independently formed second barrier layer), such that only insubstantial amounts of $H_2O_2$ can reach the electroactive surface of the second working electrode. In preferred embodiments, the first and second resistance domains are configured and arranged to reduce diffusion of the measurable species (e.g., $H_2O_2$) from the first electroactive surface to the second electroactive surface by at least 2-fold. In more preferred embodiments, the physical diffusion barrier is configured and arranged to reduce diffusion of the measurable species by at least 10-fold. In some embodiments, the physical diffusion barrier is configured and arranged to reduce diffusion of the measurable species by at least 3-, 4-, 5-, 6-, 7-, 8-, or 9-fold. In some embodiments, the physical diffusion barrier is configured and arranged to reduce diffusion of the measurable species by at least 20-, 30-, 40- or 50-fold, or more. In some embodiments, the sensor's working electrodes E1, E2 are by an insulator, which insulates the working electrodes from each other. In some embodiments, the insulator is at least a portion of the sensor membrane.

In some embodiments, a continuous glucose sensor configured for insertion into a host and detecting glucose in the host is provided. In general, the sensor includes first and second working electrodes, wherein each working electrode includes an electroactive surface (each including an area) disposed beneath a sensor membrane. The first electroactive surface (e.g., of the first working electrode) is disposed beneath an active enzymatic portion (plus-GOx) of the membrane while the second electroactive surface (of the second working electrode) is disposed beneath a non-enzymatic (no-GOx) portion of the membrane. The non-enzymatic portion of the membrane can include inactivated enzyme and/or no enzyme. Additionally, each working electrode is configured to generate a signal having a noise component related to a noise-causing species. In some circumstances, the noise-causing species is non-constant and related to a biological process. Preferably, the first and second areas are sufficiently large such that the noise components (e.g., first and second noise components detected by the first and second working electrodes) are substantially equivalent. In some embodiments, the first and second areas are each greater than the sum of the diameters of about 10 average human cells, in at least one dimension. In some embodiments, the first and second areas are each greater than about 500 µm, in at least one dimension. Preferably, the first and second areas (e.g., of the electroactive surfaces) are configured and arranged such that the signals caused by a plurality of local point sources (that produce noise-causing species when implanted in a host) can be integrated along each area (e.g., each area independently from the other). In some further embodiments, the first and second areas are configured and arranged to integrate signals detected about a circumference of the sensor. Preferably, the first and second electroactive surfaces are spaced a distance that is less than a crosstalk diffusion distance of a measured species, such as $H_2O_2$ produced in the active enzymatic portion of the membrane. In some embodiments, the sensor includes a physical diffusion barrier configured and arranged to physically block some crosstalk from the active enzymatic portion of the membrane to the second electroactive surface. In some further embodiments, the physical diffusion barrier is configured and arranged to physically block a substantial amount of the measurable species diffusing from the active enzymatic portion of the membrane to the second electroactive surface (e.g., crosstalk), such that there is substantially no signal associated with crosstalk measured at the second working electrode. In some embodiments, the physical diffusion barrier is a discontinuous portion of the membrane disposed between the first and second electroactive surfaces. In some further embodiments, the physical diffusion barrier includes a first barrier layer formed on the first working electrode and a second barrier layer formed on the second working electrode, wherein the first and second barrier layers are independently formed (e.g., formed separately on the two electroactive surfaces). In some further embodiments, the physical diffusion barrier includes a first resistance domain formed on the first working electrode and a second resistance domain formed on the second working electrode, and wherein the first and second resistance domains are configured and arranged to reduce diffusion of the measurable species (e.g., crosstalk) from the active enzymatic portion of the sensor to the second electroactive surface by at least 2-fold. In a preferred embodiment, the physical diffusion barrier can reduce the diffusion of the measurable species (e.g., crosstalk) by at least 10-fold.

In some embodiments, the continuous glucose sensor includes first and second working electrodes, each working electrode including an electroactive surface (each including an area) disposed beneath a sensor membrane. As described elsewhere herein, the first electroactive surface is disposed beneath an active enzymatic portion of the membrane and the second electroactive surface is disposed beneath a non-enzymatic portion of the membrane. Preferably, the sensor includes a physical diffusion barrier, and the first and second electroactive surfaces are disposed sufficiently close together that the first and second noise components (detected by the first and second working electrodes) are substantially equivalent. In some embodiments, the distance between the first and second electroactive surfaces is less than about twice the thickness of the membrane. In some embodiments, the first and second electroactive surfaces are spaced a distance that is less than or equal to about a crosstalk diffusion distance of a measurable species, such as the $H_2O_2$ produced in the active enzymatic portion of the sensor membrane. In some embodiments, the physical diffusion barrier is configured and arranged to physically block some diffusion of the measurable species from the active enzymatic portion of the membrane to the second electroactive surface (e.g., crosstalk). In preferred embodiments, the physical diffusion barrier blocks a substantial amount of the measurable species, such that there is substantially no signal associated with crosstalk measured at the second working electrode. In some embodiments, the physical diffusion barrier is a discontinuous portion of the membrane disposed between the first and second electroactive surfaces. In some embodiments, the physical diffusion barrier is a first barrier layer formed on the first electrode and a second barrier layer formed on the second electrode, wherein the first and second barrier layers are independently formed. In some embodiments, the physical diffusion barrier includes a first resistance domain formed on the first electrode and a second resistance domain formed on the second electrode. Preferably, the first and second resistance domains reduce diffusion of the measurable species (e.g., crosstalk) by at least 2-fold. In more preferred embodiments, the diffusion of the measurable species is reduced by at least 10-fold. In some embodiments, the membrane is an insulator that insulates the first working electrode from the second working electrodes. In some further embodiments, the first and second areas are sufficiently large that the first and second noise components are substantially equivalent.

Sensor Electronics

The analyte sensor system has electronics, also referred to as a "computer system" that can include hardware, firmware, and/or software that enable measurement and processing of data associated with analyte levels in the host. In one exemplary embodiment, the electronics include a potentiostat, a power source for providing power to the sensor, and other components useful for signal processing. In another exemplary embodiment, the electronics include an RF module for transmitting data from sensor electronics to a receiver remote from the sensor. In another exemplary embodiment, the sensor electronics are wired to a receiver, which records the data and optionally transmits the data to a remote location, such as but not limited to a nurse's station, for tracking the host's progress and to alarm the staff is a hypoglycemic episode occurs. In another exemplary embodiment, the sensor electronics include a processor module configured to and/or comprises programming for processing sensor data, as described elsewhere herein. In some exemplary embodiments, the sensor electronics include a receiving module for receiving sensor signals, such as but not limited to from the working electrode(s), and/or externally provided reference data points. In some embodiments, the processor module can include the receiving module. The processor module and the receiving module can be located together and/or in any combination of sensor electronics local to and/or remote from the sensor.

Various components of the electronics of the sensor system can be disposed on or proximal to the analyte sensor, such as but not limited to disposed on the fluid coupler 20 of the system, such as the embodiment shown in FIG. 1A. In another embodiment, wherein the sensor is integrally formed on the catheter (e.g., see FIG. 2A) and the electronics are disposed on or proximal to the connector 218. In some embodiments, only a portion of the electronics (e.g., the potentiostat) is disposed on the device (e.g., proximal to the sensor), while the remaining electronics are disposed remotely from the device, such as on a stand or by the bedside. In a further embodiment, a portion of the electronics can be disposed in a central location, such as a nurse's station.

In additional embodiments, some or all of the electronics can be in wired or wireless communication with the sensor and/or other portions of the electronics. For example, a potentiostat disposed on the device can be wired to the remaining electronics (e.g., a processor, a recorder, a transmitter, a receiver, etc.), which reside on the bedside. In another example, some portion of the electronics is wirelessly connected to another portion of the electronics, such as by infrared (IR) or RF. In one embodiment, a potentiostat resides on the fluid coupler and is connected to a receiver by RF; accordingly, a battery, RF transmitter, and/or other minimally necessary electronics are provided with the fluid coupler and the receiver includes an RF receiver.

Preferably, the potentiostat is operably connected to the electrode(s) (such as described above), which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device.

In some embodiments, the electronics include an A/D converter that digitizes the analog signal into a digital signal, also referred to as "counts" for processing. Accordingly, the resulting raw data stream in counts, also referred to as raw sensor data, is directly related to the current measured by the potentiostat.

Typically, the electronics include a processor module that includes the central control unit that controls the processing of the sensor system. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Patent Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like.

In some embodiments, the processor module comprises a digital filter (e.g., programming), for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

In some embodiments, the processor module is configured to and/or comprises programming to build the data packet for transmission to an outside source, for example, an RF transmission to a receiver. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module further comprises a transmitter portion that determines the transmission interval of the sensor data to a receiver, and the like. In some embodiments, the transmitter portion, which determines the interval of transmission, is configured to be programmable. In one such embodiment, a coefficient can be chosen (e.g. a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g. reduced battery consumption, timeliness of reporting sensor values, etc.)

In some embodiments, the processor is further configured to and/or further comprises programming to perform the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. In such cases, the processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing. Alternatively, some portion of the data processing (such as described with reference to the processor elsewhere herein) can be accomplished at another (e.g., remote) processor and can be configured to be in wired or wireless connection therewith.

In some embodiments, an output module, which is integral with and/or operatively connected with the processor, includes programming for generating output based on the data stream received from the sensor system and it's processing incurred in the processor. In some embodiments, output is generated via a user interface.

In some embodiments, a user interface is provided integral with (e.g., on the patient inserted medical device), proximal to (e.g., a receiver near the medical device including bedside or on a stand), or remote from the sensor electronics (e.g., at a central station such as a nurse's station), wherein the user interface comprises a keyboard, speaker, vibrator, backlight, liquid crystal display (LCD) screen, and one or more buttons. The components that comprise the user interface include controls to allow interaction of the user with the sensor system. The keyboard can allow, for example, input of user information, such as mealtime, exercise, insulin administration, customized therapy recommendations, and reference analyte values. The speaker can produce, for example, audible signals or alerts for conditions such as present and/or estimated hyperglycemic or hypoglycemic conditions. The vibrator can provide, for example, tactile signals or alerts for reasons such as described with reference to the speaker, above. The backlight can be provided, for example, to aid a user in reading the LCD in low light conditions. The LCD can be provided, for example, to provide the user with visual data output, such as is described in U.S. Patent Publication No. US-2005-0203360-A1. In some embodiments, the LCD is a touch-activated screen, enabling each selection by a user, for example, from a menu on the screen. The buttons can provide for toggle, menu selection, option selection, mode selection, and reset, for example. In some alternative embodiments, a microphone can be provided to allow for voice-activated control.

In some embodiments, prompts or messages can be displayed on the user interface to convey information to the user, such as reference outlier values, requests for reference analyte values, therapy recommendations, deviation of the measured analyte values from the estimated analyte values, and the like. Additionally, prompts can be displayed to guide the user through calibration or trouble-shooting of the calibration.

Additionally, data output from the output module can provide wired or wireless, one- or two-way communication between the user interface and an external device. The external device can be any device that wherein interfaces or communicates with the user interface. In some embodiments, the external device is a computer, and the system is able to download historical data for retrospective analysis by the patient or physician, for example. In some embodiments, the external device is a modem or other telecommunications station, and the system is able to send alerts, warnings, emergency messages, and the like, via telecommunication lines to another party, such as a doctor or family member. In some embodiments, the external device is an insulin pen, and the system is able to communicate therapy recommendations, such as insulin amount and time to the insulin pen. In some embodiments, the external device is an insulin pump, and the system is able to communicate therapy recommendations, such as insulin amount and time to the insulin pump. The external device can include other technology or medical devices, for example pacemakers, implanted analyte sensor patches, other infusion devices, telemetry devices, and the like.

The user interface, including keyboard, buttons, a microphone (not shown), and optionally the external device, can be configured to allow input of data. Data input can be helpful in obtaining information about the patient (for example, meal time, insulin administration, and the like), receiving instructions from a physician (for example, customized therapy recommendations, targets, and the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, and the like) can be used to provide input helpful in data processing. In one embodiment, the user interface can prompt the patient to select an activity most closely related to their present activity, such as medication taken, surgical procedures, and the like, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input, which can be helpful in data processing.

Algorithms

In some embodiments, calibration of an analyte sensor can be required, which includes data processing that converts sensor data signal into an estimated analyte measurement that is meaningful to a user. In general, the sensor system has a computer system (e.g., within the electronics) that receives sensor data (e.g., a data stream), including one or more time-spaced sensor data points, measured by the sensor. The sensor data point(s) can be smoothed (filtered) in certain embodiments using a filter, for example, a finite impulse response (FIR) or infinite impulse response (IIR) filter. During the initialization of the sensor, prior to initial calibration, the system can receive and store uncalibrated sensor data, however it can be configured to not display any data to the user until initial calibration and, optionally, stabilization of the sensor has been established. In some embodiments, the data stream can be evaluated to determine sensor break-in (equilibration of the sensor in vitro or in vivo).

In some embodiments, the system is configured to receive reference data from a reference analyte monitor, including one or more reference data points, also referred to as calibration information in some embodiments. The monitor can be of any suitable configuration. For example, in one embodiment, the reference analyte points can comprise results from a self-monitored blood analyte test (e.g., from a finger stick test, YSI, Beckman Glucose Analyzer, and the like), such as those described in U.S. Pat. No. 6,045,567, U.S. Pat. No. 6,156,051, U.S. Pat. No. 6,197,040, U.S. Pat. No. 6,284,125, U.S. Pat. No. 6,413,410, and U.S. Pat. No. 6,733,655. In one such embodiment, the user can administer a self-monitored blood analyte test to obtain an analyte value (e.g., point) using any suitable analyte sensor, and then enter the numeric analyte value into the computer system. In another such embodiment, a self-monitored blood analyte test comprises a wired or wireless connection to the computer system so that the user simply initiates a connection between the two devices, and the reference analyte data is passed or downloaded between the self-monitored blood analyte test and the system. In yet another such embodiment, the self-monitored analyte test is integral with the receiver so that the user simply provides a blood sample to the receiver, and the receiver runs the analyte test to determine a reference analyte value.

In some alternative embodiments, the reference data is based on sensor data from another substantially continuous analyte sensor such as described herein, or another type of suitable continuous analyte sensor. In an embodiment employing a series of two or more continuous sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

In some embodiments, the sensor system is coupled to a blood analysis device that periodically or intermittently collects a sample of the host's blood (e.g., through the sensor system) and measures the host's glucose concentration. In some embodiments, the blood analysis device collects a blood sample from the host about every 30 minutes, every hour, or every few hours (e.g., 2, 3, 4, 5, 6, 8, 9 or 10 hours or longer). In other embodiments, the blood analysis device can be activated manually (e.g., by a healthcare worker) to collect and analyze a blood sample from the host. The glucose concentration data generated by the blood analysis device can be used by the sensor system for calibration data. In some embodiments, the sensor system can electronically receive (either wired or wirelessly) these calibration data (from the blood analysis device). In other embodiments, these calibration data can be entered into the sensor system (e.g., sensor system electronics) by hand (e.g., manually entered by a healthcare worker).

In some embodiments, the sensor system is provided with one or more calibration solutions (e.g., glucose solutions). In some embodiments, the sensor is shipped in a calibration solution (e.g., soaked). The sensor is activated to calibrate itself (using the calibration solution in which it was shipped) before insertion into the host. In some embodiments, the sensor is shipped (e.g., soaked or dry) with one or more vials of calibration solution. The sensor can be soaked (e.g., sequentially) in the vial(s) of calibration solution; calibration data points collected and the sensor calibrated using those calibration points, before inserting the sensor into the host.

In one exemplary embodiment, the sensor is a glucose sensor, and it is shipped soaking in a sterile 50 mg/dl glucose solution with two accompanying calibration solutions (e.g., 100 mg/dl and 200 mg/dl sterile glucose solutions). Prior to insertion into the host, calibration data points are collected with the sensor in the 50 mg/dl, 100 mg/dl and 200 mg/dl glucose solutions respectively. The sensor system can be calibrated using the collected calibration data points (e.g., using regression as described in more detail elsewhere herein). In an alternative exemplary embodiment, the sensor is shipped dry (e.g., not soaking in a solution or buffer) with at least one calibration solution, for calibrating the sensor prior to insertion into the host. In some embodiments, a hand held glucose monitor (e.g., SMBG device described herein) can test the calibration solutions to generate calibration data points, which are transferred electronically or manually to the sensor system for calibration.

In some embodiments, a data matching module, also referred to as the processor module, is configured to and/or comprises programming to matches reference data (e.g. one or more reference analyte data points) with substantially time corresponding sensor data (e.g., one or more sensor data points) to provide one or more matched data pairs. One reference data point can be matched to one time corresponding sensor data point to form a matched data pair. Alternatively, a plurality of reference data points can be averaged (e.g., equally or non-equally weighted average, mean-value, median, and the like) and matched to one time corresponding sensor data point to form a matched data pair, one reference data point can be matched to a plurality of time corresponding sensor data points averaged to form a matched data pair, or a plurality of reference data points can be averaged and matched to a plurality of time corresponding sensor data points averaged to form a matched data pair.

In some embodiments, a calibration set module, also referred to as the calibration module or processor module, is configured to and/or comprises programming to form an initial calibration set from a set of one or more matched data pairs, which are used to determine the relationship between the reference analyte data and the sensor analyte data. The matched data pairs, which make up the initial calibration set, can be selected according to predetermined criteria. The criteria for the initial calibration set can be the same as, or different from, the criteria for the updated calibration sets. In certain embodiments, the number (n) of data pair(s) selected for the initial calibration set is one. In other embodiments, n data pairs are selected for the initial calibration set wherein n is a function of the frequency of the received reference data points. In various embodiments, two data pairs make up the initial calibration set or six data pairs make up the initial calibration set. In an embodiment wherein a substantially continuous analyte sensor provides reference data, numerous data points are used to provide reference data from more than 6 data pairs (e.g., dozens or even hundreds of data pairs). In one exemplary embodiment, a substantially continuous analyte sensor provides 288 reference data points per day (every five minutes for twenty-four hours), thereby providing an opportunity for a matched data pair 288 times per day, for example. While specific numbers of matched data pairs are referred to in the preferred embodiments, any suitable number of matched data pairs per a given time period can be employed.

In some embodiments, a conversion function module, also referred to as the conversion module or processor module, is configured to and/or comprises programming to use the calibration set to create a conversion function. The conversion function substantially defines the relationship between the reference analyte data and the analyte sensor data.

A variety of known methods can be used with the preferred embodiments to create the conversion function from the calibration set. In one embodiment, wherein a plurality of matched data points form the calibration set, a linear least squares regression is used to calculate the conversion function; for example, this regression calculates a slope and an offset using the equation $y=mx+b$. A variety of regression or other conversion schemes can be implemented herein.

In some alternative embodiments, the sensor is a dual-electrode system. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (with the enzyme domain removed, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the implanted sensor in this alternative embodiment can be made less dependent on the values/range of the paired measurements, less sensitive to error in manual blood glucose measurements, and can facilitate the sensor's use as a primary source of glucose information for the user. U.S. Patent Publication No. US-2005-0143635-A1 describes systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g., without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some alternative embodiments, the processor module is configured to and/or comprises programming to use a regression equation y=mx+b to calculate the conversion function; however, prior information can be provided for m and/or b, thereby enabling calibration to occur with fewer paired measurements. In one calibration technique, prior information (e.g. obtained from in vivo or in vitro tests) determines a sensitivity of the sensor and/or the baseline signal of the sensor by analyzing sensor data from measurements taken by the sensor (e.g. prior to inserting the sensor). For example, if there exists a predictive relationship between in vitro sensor parameters and in vivo parameters, then this information can be used by the calibration procedure. For example, if a predictive relationship exists between in vitro sensitivity and in vivo sensitivity, $m \approx f(m_{in\ vitro})$ then the predicted m can be used, along with a single matched pair, to solve for b (b=y−mx). If, in addition, b can be assumed=0, for example with a dual-electrode configuration that enables subtraction of the baseline from the signal such as described above, then both m and b are known a priori, matched pairs are not needed for calibration, and the sensor can be completely calibrated e.g. without the need for reference analyte values (e.g. values obtained after implantation in vivo.)

In another alternative embodiment, prior information can be provided to guide or validate the baseline (b) and/or sensitivity (m) determined from the regression analysis. In this embodiment, boundaries can be set for the regression line that defines the conversion function such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g. by a retrospective analysis of sensor sensitivities and/or baselines collected from a set of sensors/patients, assuming that the set is representative of future data).

In some alternative embodiments, the sensor system does not require initial and/or update calibration by the host; in these alternative embodiments, also referred to as "zero-point calibration" embodiments, use of the sensor system without requiring a reference analyte measurement for initial and/or update calibration is enabled. In general, the systems and methods of the preferred embodiments provide for stable and repeatable sensor manufacture, particularly when tightly controlled manufacturing processes are utilized. Namely, a batch of sensors of the preferred embodiments can be designed with substantially the same baseline (b) and/or sensitivity (m) (+/−10%) when tested in vitro. Additionally, the sensor of the preferred embodiments can be designed for repeatable m and b in vivo. Thus, an initial calibration factor (conversion function) can be programmed into the sensor (sensor electronics and/or receiver electronics) that enables conversion of raw sensor data into calibrated sensor data solely using information obtained prior to implantation (namely, initial calibration does not require a reference analyte value). Additionally, to obviate the need for recalibration (update calibration) during the life of the sensor, the sensor is designed to minimize drift of the sensitivity and/or baseline over time in vivo. Accordingly, the preferred embodiments can be manufactured for zero point calibration.

In some embodiments, a sensor data transformation module, also referred to as the calibration module, conversion module, or processor module, is configured to and/or comprises programming to use the conversion function to transform sensor data into substantially real-time analyte value estimates, also referred to as calibrated data, or converted sensor data, as sensor data is continuously (or intermittently) received from the sensor. For example, the sensor data, which can be provided to the receiver in "counts," is translated in to estimate analyte value(s) in mg/dL. In other words, the offset value at any given point in time can be subtracted from the raw value (e.g., in counts) and divided by the slope to obtain the estimate analyte value:

$$mg/dL = \frac{(rawvalue - \text{offset})}{\text{slope}}$$

In some embodiments, an output module is configured to and/or comprises programming to provide output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

In some embodiments, annotations are provided on the graph; for example, bitmap images are displayed thereon, which represent events experienced by the host. For example, information about meals, medications, insulin, exercise, sensor insertion, sleep, and the like, can be obtained by the receiver (by user input or receipt of a transmission from another device) and displayed on the graphical representation of the host's glucose over time. It is believed that illustrating a host's life events matched with a host's glucose concentration over time can be helpful in educating the host to his or her metabolic response to the various events.

In yet another alternative embodiment, the sensor utilizes one or more additional electrodes to measure an additional analyte. Such measurements can provide a baseline or sensitivity value for use in calibrating the sensor. Furthermore, baseline and/or sensitivity values can be used to trigger events such as digital filtering of data or suspending display of data, all of which are described in more detail in U.S. Patent Publication No. US-2005-0143635-A1.

In one exemplary embodiment, the sensor can be calibrated by a calibration solution. For example, after the sensor system has been inserted into the host, a calibration solution can be injected so as to pass across the electroactive surface of the analyte-measuring electrode and the sensor calibrated thereby. For example, the saline drip can be changed to a known IV glucose or dextrose solution (e.g., D50—a 50% dextrose solution, or D5W—a 5% dextrose solution). In one embodiment, a known volume of D5W is infused into the host at a known rate over a predetermined period of time (e.g., 5, 10, 15 or 20 minutes, or for shorter or longer periods). During and/or after the period of infusion, the sensor measures the signal at the analyte-measuring working electrode. The system, knowing the specifications of the infused calibration solution (also referred to as a calibration information in some embodiments), can calibrate the signal to obtain host's glucose concentration as is appreciated by one skilled in the art. In a further embodiment, two or more glucose or dextrose solutions can be infused, with a corresponding signal being measured during each infusion, to provide additional data for sensor calibration. Calibration can be performed after the sensor has first been inserted into the host, after a break-in time, at two or more different levels (high/low), regularly, intermittently, in response to sensor drift/shift, automatically or any other time when calibration is required. In some alternative embodiments, calibration can be determined during sensor break-in, such as described in more detail elsewhere herein.

In some circumstances, catheters are flushed with saline. For example, the analyte sensor system of the preferred embodiments can be flushed with saline prior to application of control solutions, after which a predetermined amount of glucose solution is flushed by the sensor, as described above, and the sensor is calibrated there from.

In still another embodiment, a blood sample can be withdrawn from an artery or vein, and used to calibrate the sensor, for example, by using a hand-held glucose meter, by an automatic extracorporeal glucose sensor such as but not limited to in conjunction with an automated bedside clinical chemistry device, or by sending the blood sample to the clinical laboratory for glucose analysis, after which the data is input (e.g., into the electronics associated with the sensor system).

In some embodiments, the sensor can be calibrated (and/or re-calibrated) during use (after initial calibration), for example, by withdrawing one or more blood samples (also referred to as calibration information in some embodiments), through the catheter (see FIGS. 1 and 2) and used for calibration of the sensor, such as by measuring the glucose concentration of the blood sample with an additional system, such as but not limited to a hand-held glucose meter, optical methods or additional electrochemical methods. Blood samples can be withdrawn manually or automatically; additionally or alternatively, blood samples are withdrawn at regular intervals or at selected times, for example, using an extracorporeal blood analysis device as described herein.

In another embodiment of sensor calibration (and/or re-calibration) during use, a calibration solution (e.g., 40 mg/dL equivalent glucose, D540 or D5W) can be flushed through or by the sensor to enable calibration of the sensor (e.g., at one time, intermittently, or continuously), such as described in more detail above. In these embodiments, calibration solution can be flushed manually or automatically through the system; additionally or alternatively, calibration solution can be flushed at regular intervals or at selected times. In one exemplary embodiment, the system can be provided with a dual lumen, one for saline and another for the control solution. Additionally, the system is configured to automatically switch from the saline to control solution and perform the real-time system calibration, and then switch back to the saline solution.

Calibration Systems and Methods for Dual-Electrode Sensors

As described herein, continuous analyte sensors define a relationship between a sensor-generated signal and a reference measurement that is meaningful to a user (for example, blood glucose in mg/dL). This defined relationship must be monitored to ensure that the continuous analyte sensor maintains a substantially accurate calibration and thereby continually provides meaningful values to a user. Unfortunately, both sensitivity m and baseline b changes can occur during in vivo sensor use, which requires calibration updates (e.g., recalibration). Generally, any physical properties of the sensor or the fluid surrounding the sensor can influence diffusion or transport of molecules through the membrane, and thereby produce fluctuations in sensitivity and/or baseline, which in turn affect the sensor's calibration. These physical properties include, but are not limited to, blockage of sensor surface area due to cells and/or blood clotting at the membrane, biofouling, blood flow/sheer rate, blood pH, temperature, hematocrit, interfering drugs in the host's system, certain metabolic processes, disrupted host electrolyte balance due to disease and/or trauma, thickness and/or components of the sensor's membrane system, and the like.

In one aspect of the preferred embodiments, systems and methods are provided for measuring changes in sensitivity m, also referred to as changes in solute transport or membrane changes, of an analyte sensor implanted in a host over a time period. Preferably, the sensitivity value is a signal obtained by measuring a constant analyte other than the analyte being measured by the analyte sensor. For example, in a glucose sensor, a non-glucose constant analyte is measured, wherein the signal is measured beneath the membrane system on the glucose sensor. While not wishing to be bound by theory, it is believed that by monitoring the sensitivity m over a time period, a change associated with solute transport through the membrane system (e.g., diffusion there through) can be measured and used as an indication of a sensitivity change in the analyte measurement. In other words, a membrane monitor is provided, which is capable of monitoring changes in the membrane surrounding an implantable device, thereby enabling the measurement of sensitivity changes of an analyte sensor over time.

In some embodiments, the analyte sensor is provided with an auxiliary electrode (e.g., a second working electrode) configured as a transport-measuring electrode disposed beneath the membrane system. The transport-measuring electrode can be configured to measure any of a number of substantially constant analytes or factors, such that a change measured by the transport-measuring electrode can be used to indicate a change in solute (for example, glucose) transport through the membrane system. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time.

In some embodiments, the transport-measuring electrode measures analytes similar to the analyte being measured by the analyte sensor. For example, in some embodiments of a glucose sensor, water soluble analytes are believed to better represent the changes in sensitivity to glucose over time than non-water soluble analytes (due to the water-solubility of glucose), however relevant information may be ascertained from a variety of molecules. Although some specific examples are described herein, one skilled in the art appreciates a variety of implementations of sensitivity values that can be used as to qualify or quantify solute transport through the membrane of the analyte sensor.

In one embodiment of a glucose sensor, the transport-measuring electrode is configured to measure urea, which is a water-soluble constant analyte that is known to react directly or indirectly at a hydrogen peroxide sensing electrode (similar to the working electrode of the glucose sensor example described in more detail above). In one exemplary implementation wherein urea is directly measured by the transport-measuring electrode, the glucose sensor comprises a membrane system as described in more detail above, however, does not include an active interference domain or active enzyme directly above the transport-measuring electrode, thereby allowing the urea to pass through the membrane system to the electroactive surface for measurement thereon. In one alternative exemplary implementation wherein urea is indirectly measured by the transport-measuring electrode, the glucose sensor comprises a membrane system as described in more detail above, and further includes an active uricase oxidase domain located directly above the transport-measuring electrode, thereby allowing the urea to react at the enzyme and produce hydrogen peroxide, which can be measured at the electroactive surface thereon.

In some embodiments, the change in sensitivity m is measured by measuring a change in oxygen concentration and to indicate when recalibration of the system may be advantageous. In one alternative embodiment, oxygen is measured using pulsed amperometric detection on the glucose-measuring working electrode (eliminating the need for a separate auxiliary electrode), such as by switching the applied potential from +0.6 mV to −0.6 mV. In another embodiment, the auxiliary electrode is configured as an oxygen-measuring electrode. In some embodiments, a third electrode can be configured as an oxygen-measuring electrode. In another embodiment, an oxygen sensor (not shown) is added to the glucose sensor, as is appreciated by one skilled in the art, eliminating the need for an auxiliary electrode.

In some embodiments, sensitivity changes in an intravascular dual-electrode continuous analyte sensor can be provided via a reference sensor, such as an oxygen sensor, as described in the section entitled "Optical Detection." In some embodiments, auto-calibration (e.g., without a manual, external (to the system) reference value) is enabled by exposing the dual-electrode sensor and the reference sensor simultaneously to a reference/calibration solution, whereby reference data is provided for calibration of the sensor data. Advantageously, a dual-electrode continuous analyte sensor is configured to measure baseline b, and changes in sensitivity m are measured by exposure of the dual-electrode sensor to the reference/calibration solution. In some embodiments, the system is configured for "on demand" auto-calibration, such as via configuring the system such that a user can initiate (e.g., command) auto-calibration via a user interface (e.g., via selection from a menu, pressing a pre-programmed button and the like).

In some alternative embodiments, sensitivity changes can be used to update calibration. For example, the measured change in transport can be used to update the sensitivity m in the calibration equation. While not wishing to be bound by theory, it is believed that in some embodiments, the sensitivity m of the calibration of the glucose sensor is substantially proportional to the change in solute transport measured by the transport-measuring electrode.

It should be appreciated by one skilled in the art that in some embodiments, the implementation of sensitivity values of the preferred embodiments typically necessitate an addition to, or modification of, the existing electronics (for example, potentiostat configuration or settings) of the glucose sensor and/or receiver.

In some embodiments, the signal from the oxygen measuring electrode may be digitally low-pass filtered (for example, with a passband of $0\text{-}10^{-5}$ Hz, dc-24 hour cycle lengths) to remove transient fluctuations in oxygen, due to local ischemia, postural effects, periods of apnea, or the like. Since oxygen delivery to tissues is held in tight homeostatic control, this filtered oxygen signal should oscillate about a relatively constant. In the interstitial fluid, it is thought that the levels are about equivalent with venous blood (40 mmHg). Once implanted, changes in the mean of the oxygen signal (for example, >5%) may be indicative of change in transport through the membrane (change in sensor sensitivity and/or baseline due to changes in solute transport) and the need for system recalibration.

The oxygen signal may also be used in its unfiltered or a minimally filtered form to detect or predict oxygen deprivation-induced artifact in the glucose signal, and to control display of data to the user, or the method for smoothing, digital filtering, or otherwise replacement of glucose signal artifact. In some embodiments, the oxygen sensor may be implemented in conjunction with any signal artifact detection or prediction that may be performed on the counter electrode or working electrode voltage signals of the electrode system. U.S. Patent Publication No. US-2005-0043598-A1, which is incorporated by reference in its entirety herein, describes some methods of signal artifact detection and replacement that may be useful such as described herein.

Preferably, the transport-measuring electrode is located within the same local environment as the electrode system associated with the measurement of glucose, such that the transport properties at the transport-measuring electrode are substantially similar to the transport properties at the glucose-measuring electrode.

In a second aspect the preferred embodiments, systems and methods are provided for measuring baseline, namely non-glucose related electroactive compounds in the host. Preferably the auxiliary working electrode (e.g., second working electrode, non-enzymatic working electrode) is configured to measure the baseline of the analyte sensor over time. In some embodiments, the glucose-measuring working electrode (e.g., first working electrode) is a hydrogen peroxide sensor coupled to a membrane system containing an active enzyme located above the electrode. In some embodiments, the auxiliary working electrode (e.g., second working electrode) is another hydrogen peroxide sensor that is configured similar to the glucose-measuring working electrode however a portion of the membrane system above the base-measuring electrode does not have active enzyme therein, such as described in more detail with reference to FIG. 3D. The auxiliary working electrode provides a signal substantially comprising the baseline signal, b, which can be (for example, electronically or digitally) subtracted from the glucose signal obtained from the glucose-measuring working electrode to obtain the signal contribution due to glucose only according to the following equation:

$$Signal_{glucose\ only} = Signal_{glucose\text{-}measuring\ working\ electrode} - Signal_{baseline\text{-}measuring\ working\ electrode}$$

In some embodiments, electronic subtraction of the baseline signal from the glucose signal can be performed in the hardware of the sensor, for example using a differential amplifier. In some alternative embodiments, digital subtraction of the baseline signal from the glucose signal can be performed in the software or hardware of the sensor or an associated receiver, for example in the microprocessor.

One aspect the preferred embodiments provides for a simplified calibration technique, wherein the variability of the baseline has been eliminated (namely, subtracted). Namely, calibration of the resultant differential signal ($Signal_{glucose\ only}$) can be performed with a single matched data pair by solving the following equation:

$$y=mx$$

While not wishing to be bound by theory, it is believed that by calibrating using this simplified technique, the sensor is made less dependent on the range of values of the matched data pairs, which can be sensitive to human error in manual blood glucose measurements, for example. Additionally, by subtracting the baseline at the sensor (rather than solving for the baseline b as in conventional calibration schemes), accuracy of the sensor may increase by altering control of this variable (baseline b) from the user to the sensor. It is additionally believed that variability introduced by sensor calibration may be reduced.

In some embodiments, the glucose-measuring working electrode (e.g., first working electrode) is a hydrogen peroxide sensor coupled to a membrane system containing an active enzyme located above the electrode, such as described in more detail above; however the baseline signal is not subtracted from the glucose signal for calibration of the sensor. Rather, multiple matched data pairs are obtained in order to calibrate the sensor (for example using y=mx+b) in a conventional manner, and the auxiliary/second working electrode is used as an indicator of baseline shifts in the sensor signal. Namely, the auxiliary/second working electrode is monitored for changes above a certain threshold. When a significant change is detected, the system can trigger a request (for example, from the patient or caregiver) for a new reference glucose value (for example, SMBG), which can be used to recalibrate the sensor. By using the auxiliary/second working electrode signal as an indicator of baseline shifts, recalibration requiring user interaction (namely, new reference glucose values) can be minimized due to timeliness and appropriateness of the requests. In some embodiments, the sensor is re-calibrated responsive to a baseline shifts exceeding a preselected threshold value. In some embodiments, the sensor is calibrated repeatedly at a frequency responsive to the rate-of-change of the baseline.

In yet another alternative embodiment, the electrode system of the preferred embodiments is employed as described above, including determining the differential signal of glucose less baseline current in order to calibrate using the simplified equation (y=mx), and the auxiliary/second working electrode is further utilized as an indicator of baseline shifts in the sensor signal. While not wishing to be bound by theory, it is believed that shifts in baseline may also correlate and/or be related to changes in the sensitivity m of the glucose signal. Consequently, a shift in baseline may be indicative of a change in sensitivity m. Therefore, the auxiliary working electrode is monitored for changes above a certain threshold. When a significant change is detected, the system can trigger a request (for example, from the patient or caregiver) for a new reference glucose value (for example, SMBG), which can be used to recalibrate the sensor. By using the auxiliary (second) signal as an indicator of possible sensitivity changes, recalibration requiring user interaction (new reference glucose values) can be minimized due to timeliness and appropriateness of the requests.

In yet another alternative embodiment, wherein a dual-electrode analyte system is use, the baseline signal is (electronically or digitally) subtracted from the glucose+baseline signal to obtain a glucose signal substantially without baseline. Accordingly, calibration of the resultant difference signal can be performed by solving the equation y=mx using a sensitivity value (m), which can be obtained from 1) the measured reference (calibrant) solution, b) by pairing a reference analyte signal with a reference analyte value (internal reference sensor example) and/or 3) with a sensitivity value obtained a priori (e.g., during sensor manufacture, such as but not limited to by testing in an isotonic solution). Accordingly, calibration of the implanted sensor in this embodiment can be less sensitive or insensitive to user error associated with providing external reference measurements, and can facilitate the sensor's use as a primary source of glucose information for the user. However, a single external reference value (e.g., from an external test device such as SMBG and/or YSI testing of a host blood sample) can be used to calibrate the sensor in some embodiments. U.S. Patent Publication No. US-2005-0143635-A1 describes systems and methods for subtracting the baseline from a sensor signal.

It is noted that, in some embodiments, infrequent new matching data pairs (e.g., auto-calibration, on demand calibration) may be useful over time to recalibrate the sensor because the sensitivity m of the sensor may change over time (for example, due to maturation of the membrane that may increase or decrease the glucose and/or oxygen availability to the sensor). However, the baseline shifts that have conventionally required numerous and/or regular blood glucose reference measurements for updating calibration (for example, due to interfering species, metabolism changes, or the like) can be consistently and accurately eliminated using the systems and methods of the preferred embodiments, allowing reduced interaction from the patient (for example, requesting less frequent reference glucose values such as daily or even as infrequently as monthly).

An additional advantage of the sensor of the preferred embodiments includes providing a method for eliminating signal effects of interfering species, which have conventionally been problematic in electrochemical glucose sensors. Namely, electrochemical sensors are subject to electrochemical reaction not only with the hydrogen peroxide (or other analyte to be measured), but additionally may react with other electroactive species that are not intentionally being measured (for example, interfering species), which cause a change in signal strength due to this interference. In other words, interfering species are compounds with an oxidation or reduction potential that overlap with the analyte being measured. Interfering species such as acetaminophen, ascorbate, and urate, are notorious in the art of glucose sensors for producing inaccurate signal strength when they are not properly controlled. Some glucose sensors utilize a membrane system that blocks at least some interfering species, such as ascorbate and urate. Unfortunately, it is difficult to find membranes that are satisfactory or reliable in use, especially in vivo, which effectively block all interferants and/or interfering species (for example, see U.S. Pat. No. 4,776,944, U.S. Pat. No. 5,356,786, U.S. Pat. No. 5,593,852, U.S. Pat. No. 5,776,324, and U.S. Pat. No. 6,356,776).

The preferred embodiments are particularly advantageous in their inherent ability to eliminate the erroneous transient and non-transient signal effects normally caused by interfering species. For example, if an interferant such as acetaminophen is ingested by a host implanted with a conventional implantable electrochemical glucose sensor (namely, one without means for eliminating acetaminophen), a transient non-glucose related increase in signal output would occur. However, by utilizing the electrode system of the preferred embodiments, both working electrodes respond with substantially equivalent increased current generation due to oxidation of the acetaminophen, which would be eliminated by subtraction of the auxiliary electrode signal from the glucose-measuring electrode signal.

In summary, the system and methods of the preferred embodiments simplify the computation processes of calibration, decreases the susceptibility introduced by user error in calibration, and eliminates the effects of interfering species. Accordingly, the sensor requires less interaction by the patient (for example, less frequent calibration), increases patient convenience (for example, few reference glucose values), and improves accuracy (via simple and reliable calibration).

In another aspect of the preferred embodiments, the analyte sensor is configured to measure any combination of changes in baseline and/or in sensitivity, simultaneously and/or iteratively, using any of the above-described systems and methods. While not wishing to be bound by theory, the preferred embodiments provide for improved calibration of the sensor, increased patient convenience through less frequent patient interaction with the sensor, less dependence on the values/range of the paired measurements, less sensitivity to error normally found in manual reference glucose measurements, adaptation to the maturation of the membrane over time, elimination of erroneous signal due to non-constant analyte-related signal so interfering species, and/or self-diagnosis of the calibration for more intelligent recalibration of the sensor.

Preferably, a dual-electrode sensor's working electrodes E1, E2 should function identically, with identical sensitivity and/or baseline measurements. However, in some circumstances, small differences in the portions of the membrane at the first and second working electrodes can result in slight differences in membrane sensitivities (m) and/or the baselines (b) signal associated with the working electrodes. While not wishing to be bound by theory, it is believed that such small differences can arise during manufacture, for example, when E1 and E2 have one or more separate manufacturing steps. Additionally, the compositions of the enzyme domains can be slightly different. For example, an E1 enzyme domain can be somewhat more hydrophilic than an E2 enzyme domain manufactured without any added enzyme. In some circumstances, certain characteristics of the blood samples (e.g., pH, certain medicaments in the host's circulatory system, temperature, $pO_2$) to which the sensor is exposed can, amplify the effects of these differences. In some circumstances, these small differences (between E1 and E2) can contribute to sensor inaccuracies. In preferred embodiments, such sensor inaccuracies can be avoided by use of a scaling factor (k) that is calculated by evaluating the signal response at each of the working electrodes. In some embodiments, the scaling factor is measured in vitro, prior to sensor implantation.

In one preferred embodiment, a scaling factor (k) is calculated by evaluating the signal response after at point at which substantially all of the analyte present in a blood sample should have been used up. FIG. 3J is a graph that illustrates exemplary data collected upon exposure of a dual-electrode continuous analyte sensor to a blood sample. The Y-axis represents the signal generated and the X-axis represents time. The top graph is data generated by the plus-enzyme working electrode (e.g., first working electrode, E1). The bottom graph is time-corresponding data generated by the minus-enzyme working electrode (e.g., non-enzymatic, second working electrode, E2). In general, when the sensor is exposed to a blood sample, the E1 signal will increase 1302 until substantially all of the available analyte is used up (e.g., at t1) by the enzyme at the plus-enzyme working electrode. In general, as with most enzymes, when all of the substrate (e.g., analyte) is used up, the signal should plateau (e.g., line 1306). However, in spite of the lack of substrate (e.g., analyte) for the enzyme, the signal actually continues to increase a small amount, as is shown by line 1308. While not wishing to be bound by theory, it is believed that the signal increase 1310 is due to signals caused by non-analyte-related electroactive species, which diffuse through the membrane more slowly than the analyte. This signal increase (line 1304) is also observed on the non-enzymatic working electrode (e.g., E2). Accordingly, the signal response for E2, during the time period of t1 to t2, is the difference between lines 1305 and 1304. The scaling factor (k, also referred to as the "buildup ratio") can be determined by evaluating the signal response at the two working electrodes (e.g., between $t_1$ and $t_2$) using the formula:

$$k^{Sensor} = \frac{\text{Signal\_response}_{Enzyme}}{\text{Signal\_response}_{NoEnzyme}}$$

Accordingly, for the exemplary data shown in FIG. 3J, the scaling factor (k) is equal to the ratio of the plus-enzyme signal response 1310 to the minus-enzyme signal response 1312. In a related embodiment, a scaling factor can be calculated by evaluating data generated at the early portion of the curve, soon after the switch from a wash/reference solution (e.g., saline, glucose, etc.) to blood, such as between about 2 second and about 2 minutes after the switch from blood to non-bodily fluid. The scaling factor can then be used to adjust the data (e.g., calibrate) for differences in membrane sensitivities, thereby providing increased sensor accuracy. In some embodiments, the dual-electrode sensor is a glucose sensor. However, dual-electrode sensors can be configured to detect other analytes as described elsewhere herein.

In some embodiments, the scaling factor can be determined by evaluating the signal responses of the first and second working electrodes E1, E2 during exposure of the sensor to a non-bodily fluid (e.g., saline, reference/calibration solution, hydration fluid, wash fluid, nutritional fluid, medicament, etc.). As described elsewhere herein, an intravascularly implanted dual-electrode analyte sensor can be washed and/or or calibrated between exposures to blood samples. To measure the signal response at the working electrodes, the non-bodily fluid can be held stagnant (e.g., substantially not moving) for a period of time (e.g., from t1 to t2). Signal responses at the working electrodes, during the time period, can then be evaluated.

FIG. 3K is a graph that illustrates exemplary data received upon exposure of a dual-electrode sensor to a non-bodily fluid. The Y-axis represents signal generated at the working electrodes and the X-axis represents time. The top graph is data generated by the plus-enzyme working electrode (e.g., first working electrode, E1). The bottom graph is time-corresponding data generated by the minus-enzyme working electrode (e.g., non-enzymatic, second working electrode, E2). Starting at t=0, the flow of fluid over the dual-electrode continuous analyte sensor is stopped, such that the fluid is substantially stagnant (e.g., not moving). At the first working electrode E1 (with enzyme), an increasing signal is generated, as is represented by line 1314. An increasing signal is also generated at the second working electrode E2 (no enzyme), as is illustrated by line 1316. The E1 signal response (1318) is the difference between lines 1315 and 1314 at t2. Similarly, the E2 signal response (1320) is the difference between lines 1317 and 1316 at t2. While not wishing to be bound by theory, it is believed that the observed signal response is due to diffusion of non-analyte-related electroactive species through the plus and minus enzyme membrane portions, which are then detected at the working electrodes. The sensor scaling factor can be calculated using the equation described above.

In some embodiments, to improve sensor accuracy, a scaling factor can be calculated by comparing the signal response of a test sensor ($k^{TestSensor}$) to the signal response of a "perfect sensor" ($k^{PerfectSensor}$), using the following formula:

$$ScalingFactor = \frac{k^{TestSensor}}{k^{PerfectSensor}}$$

The signal response ($k^{PerfectSensor}$) for a perfect dual-electrode sensor (can be determined empirically by testing a plurality of sensors in the laboratory, such as by using methods known in the art.

As described in more detail elsewhere herein, useful information (e.g., sensitivity and/or scaling factor) can be extrapolated from periods in which the signal is transient, for example, during sensor break-in and/or during a period of signal artifact (e.g., noise). In some embodiments, the scaling factor is determined during electrochemical break-in of the sensor. Additionally or alternatively, the scaling factor is determined during a period of signal artifact, for example, wherein the flow of fluid across the sensor manipulated (e.g., disrupted) intentionally and/or accidentally (and detected). In one exemplary embodiment, the flow control device of the preferred embodiment is configured to jitter, reciprocate and/or dither in such a way so as to more effectively wash the sensor; in this exemplary embodiment, signal artifact is induced on the signal by the induced flow turbulence, which can be used to obtain useful information by transient analysis of the signal.

Due to the kinetics of the signal during these transient events, a noise amplitude can be determined for each of the first and second working electrodes of a dual electrode system, and the noise amplitude compared to obtain a scaling factor. In one embodiment, the scaling factor is determined by using a residual analysis, wherein filtered (e.g., smoothed) data is compared to raw data (e.g., in local and/or remote electronics) to obtain a signal residual. In one such embodiment, a signal residual is calculated as the difference between the filtered data and the raw data. For example, at one time point (or one time period that is represented by a single raw value and single filtered value), the filtered data can be measured at 50,000 counts and the raw data can be measured at 55,500 counts, which would result in a signal residual of 5,500 counts. In some embodiments, the residuals provide the noise amplitude information, which can be compared to obtain a scaling factor. However, in some embodiments, a stream of residuals (e.g., individual time points during a kinetic period of the signal) for each of the first and second working electrodes are averaged (e.g., using a moving average, or the like), and compared, to provide noise amplitude information for each of the first and second working electrodes, which can be used to define a scaling factor.

In some embodiments, the manufacturer determines a baseline (e.g., $b_{offset}$) and/or a scaling factor prior to sensor use in a host, such as but not limited to testing in one or more reference solutions, such as but not limited to an isotonic solution. The prospectively determined baseline (e.g., $b_{offset}$) and/or scaling factor can be included with the sensor provided to the user, such as by providing a calibration code that can be entered (e.g., manually) into the system electronics, that can be automatically detected by the system electronics upon sensor coupling thereto (e.g., via a detectable memory), and the like, similar to the manufacturer-provided calibration codes for glucose test strips.

As a non-limiting example, in preferred embodiments, a system for measuring an analyte, wherein differences in first and second working electrodes is accounted for, is provided. In this embodiment, the system includes a continuous analyte sensor, a vascular access device, a receiving module, and a processing module. The continuous analyte sensor is configured for exposure to a host's circulatory system in vivo, such as via fluidly coupling with a vascular access device in fluid contact with the host's circulatory system. The continuous analyte sensor includes first and second working electrodes E1, E2. The first working electrode E1 is disposed beneath an enzymatic portion of a membrane system, wherein the enzymatic portion includes an enzyme for detecting the analyte. For example, if the analyte is glucose, the enzymatic portion includes GOX. If the analyte is cholesterol, the enzyme is a cholesterol-metabolizing enzyme. The second working electrode E2 is disposed beneath a non-enzymatic portion of the membrane system, which includes either no enzyme or an inactive form of the enzyme. For example, the enzyme can be inactivated by a variety of methods, such as denaturing by heating, UV exposure, treatment with a protease or a denaturing chemical, and the like. In some embodiments, the enzyme layer of the membrane system over E2 (e.g., the electroactive surface) includes another protein, such as BSA or ovalbumin, which is not involved in the metabolism of the analyte.

The system includes a receiving module configured to receive the signals from the working electrodes (e.g., a first signal from E1 and a second signal from E2). As described elsewhere herein, the first signal is associated with both the analyte and non-analyte related electroactive compounds; the second signal is associated with non-analyte related electroactive compounds. The non-analyte related compounds have an oxidation/reduction potential that substantially overlaps with the analyte's oxidation/reduction potential. Accordingly, if the dual-electrode sensor is configured to detect glucose, E1 detects a signal having components associated with glucose and non-glucose species that have oxidation/reduction potentials that substantially overlap with the oxidation and/or reduction potential of glucose (sometimes referred to herein as a first oxidation/reduction potential), and E2 detects a signal related to the non-glucose species that have oxidation/reduction potentials that substantially overlap with the oxidation and/or reduction potential of glucose.

The system includes a processor module configured to and/or comprising programming that processes the first and second signals and to estimate a scaling factor. As described herein, the scaling factor defines a relationship between the first and second working electrodes (e.g., associated with the measured baseline of each first and second working electrodes). Preferably, the processor module processes the first and second signals using the scaling factor, to thereby obtain a signal (e.g., a glucose value) substantially without contribution due to non-analyte related electroactive compounds. For example, wherein the equation $b=kz$ defines the relationship (scaling factor (k)) between the baseline (b) of the first (enzymatic) working electrode and the baseline z of the second (non-enzymatic) working electrode. A calibration equation ($y=mx+b$) can be modified to include the scaling factor to calibrate the sensor ($y-kz=mx$).

In some preferred embodiments, the system includes a flow control device is configured to meter a flow of a fluid through the vascular access device. In some embodiments, the fluid is a bodily fluid and the flow control device is configured to withdraw a sample of bodily fluid (e.g., blood) from the host such that the sensor is contacted with the bodily fluid. In a further embodiment, the processor module is configured to and/or comprises programming that compares steady-state information of the first signal and steady-state information of the second signal. In some embodiments, the fluid is a non-bodily fluid and the flow control device is configured to hold the non-bodily fluid substantially stagnant during a time period, as described herein. In preferred embodiments, the processor module is configured to and/or comprises programming that compares a signal increase on each of the first and second working electrodes during the time period during which the non-bodily fluid is held stagnant, as described herein.

In preferred embodiments, a method for processing sensor data from a dual-electrode continuous analyte sensor, including estimating a scaling factor (k), is provided. The dual-electrode sensor, as described herein, is configured for in vivo exposure to a host's circulatory system. The dual-electrode continuous analyte sensor is applied to the host, such as via fluidly coupling the sensor to a fluid flow device. In some embodiments, the sensor is configured for insertion into a catheter or is a part of the catheter, as described above. In some embodiments, the sensor is part of a connecting device, such as a Leur lock, which is fluidly coupled to a catheter at a first end and to the rest of the fluid flow device (e.g., via IV tubing), such that blood samples can be withdrawn and contacted with the sensor. After the sensor has been applied to the host, signals from the working electrodes can be received, as described elsewhere herein. A scaling factor, which defines a relationship between a the first and second working electrodes, can be estimated from the received signals, and then the scaling factor can be used to process the signals and thereby to obtain a signal substantially without contribution due to non-analyte related electroactive compounds. In some embodiments, the scaling factor is determined while contacting the sensor with a bodily fluid (see above), such as by comparing steady-state information of the first signal and steady-state information of the second signal. In some embodiments, the scaling factor is determined while contacting the sensor with a substantially stagnant non-bodily fluid, such as by comparing a signal increase on each of the working electrodes during exposure to the substantially stagnant non-bodily fluid.

While not wishing to be bound by theory, it is believed that determination of a scaling factor as described herein provides a number of advantages. First, sample collection/testing is alternated with calibration and/or washing, sensor calibration is continuous and biofouling is substantially reduced. Since there is little biofouling, the sensor functions more rapidly (e.g., $T_{90}$ is reached more rapidly). Since the sensor is continuously calibrated during use (e.g., such that background is removed) the user receives more accurate glucose information/values to be used in making therapeutic decisions. Thus, it is substantially easier and safer for the host to maintain tight control over his or her glucose levels, which can result in a better quality of life and reduced long-term diabetic complications.

In many circumstances, glucose sensors can be calibrated using data provided either by an analyte testing device separate from the continuous analyte sensor system. For example, points for a continuous glucose sensor, one or more reference data may be provided by testing a blood sample with a handheld glucose meter or with an YSI glucose test device. However, in some preferred embodiments, a system, including a continuous analyte sensor (single working electrode or dual working electrode), is configured to provide one or more data points, with which the continuous analyte sensor can be calibrated, without the use of a separate (e.g., external to the system) device and/or testing of reference fluids.

Accordingly, in preferred embodiments, the continuous analyte detection system includes a continuous analyte sensor (e.g., described elsewhere herein) and a reference analyte sensor. The continuous analyte sensor is configured to detect a first signal associated with a test analyte and a second signal is associated with a reference analyte. The reference sensor is configured to generate a reference signal associated with the reference analyte. The test analyte can be any analyte that the sensor is configured to continuously monitor in the host. For example, in some preferred embodiments, the test analyte is glucose. The reference analyte is an analyte other than the test analyte, which is substantially stable within the host. For example, in general, the concentration of the reference analyte (e.g., in the host's circulatory system) does not fluctuate rapidly. In some preferred embodiments, the reference analyte is oxygen ($O_2$); however, a variety of other analytes can be used. The reference analyte selected is an analyte that can be measured by both the continuous analyte sensor and the reference sensor.

The continuous analyte sensor can be any type of continuous analyte sensor, including a continuous analyte sensor having a single working electrode or dual-working electrodes. In some embodiments, the continuous analyte sensor is a single working electrode continuous analyte sensor configured to detect glucose, and the first signal is associated with glucose. In this embodiment, the working electrode is configured to detect the second signal (associated with the reference analyte). For example, in some embodiments, the sensor is configured to generate a signal associated with glucose when a +0.6 mV potential is applied to the sensor. In some circumstances, the sensor can detect another analyte, if a different potential is applied thereto. For example, if a −0.6 mV potential is applied, the sensor can detect $O_2$. Accordingly, in some embodiment, the system is configured to detect both glucose and $O_2$ (e.g., first and second signals) at the working electrode of the continuous analyte sensor, by switching the potential applied to the sensor. In some embodiments, the continuous analyte sensor includes an auxiliary electrode, which can be configured to detect the reference analyte (second signal), as described herein with reference to "transport-measuring" electrodes.

In other embodiments, the continuous analyte sensor is a dual-working electrode continuous analyte sensor configured to detect glucose, and the first signal (detected by the working electrode disposed beneath an enzymatic portion of the membrane) is associated with glucose. In some embodiments, the system is configured to detect the second signal (associated with the reference analyte) using the dual-electrode sensor's first working electrode (E1, with enzyme) as described above. In other embodiments, the system is configured to detect the second signal (reference analyte) using the dual-electrode sensors second working electrode (E2, no enzyme), such as by applying a −0.6 mV potential thereto. In this embodiment, the second signal associated with the reference analyte should not be confused with the signal detected by the second working electrode that is associated with non-analyte-related electroactive species that have an oxidation/reduction potential that substantially overlaps with the analyte's oxidation/reduction potential. For example, in some embodiments, the dual-electrode sensor is configured such that when a +0.6 mV potential is applied to the second working electrode (E2, disposed beneath a non-enzymatic portion of the membrane) the signal generated is associated with the non-analyte-related electroactive species that have an oxidation/reduction potential that substantially overlaps with the analyte's oxidation/reduction potential; then, when a −0.6 mV potential is applied to the second working electrode, the second working electrode detects the second signal (associated with the reference analyte).

In some embodiments, the continuous analyte sensor includes more than two working electrodes disposed beneath the membrane. In one exemplary embodiment, the sensor includes a first working electrode E1 configured to generate a signal associated with the analyte (the first signal), a second working electrode E2 configured to generate a second signal associated with the reference analyte, and a third working electrode E3 configured to generate a signal associated with the non-analyte-related electroactive species that have an oxidation/reduction potential that substantially overlaps with the analyte's oxidation/reduction potential. In some embodiments, the sensor can include an additional working electrode (e.g., E4, $E_n$) configured to detect another reference analyte and/or to generate signals associated with non-analyte-related species that have oxidation/reduction potentials that overlap with that of another analyte, the reference analyte, another reference analyte, and the like.

In preferred embodiments, the reference sensor is not disposed beneath the analyte sensor's membrane and is configured to detect the reference analyte using any means known in the art, such as but not limited to electrochemical, enzymatic, chemical, physical, immunochemical, radiometric, and the like. In some preferred embodiments, the reference sensor is an optical sensing apparatus configured to detect the reference analyte. For example, the reference sensor can be an optical $O_2$ sensing apparatus configured to use one of a variety of optical detection methods known in the art and a described herein in the section entitled "Optical Detection."

In preferred embodiments, the system is configured such that the continuous analyte sensor and the reference sensor are disposed in the same local environment and are therefore simultaneously exposed to (e.g., contacted by/with) the sample (e.g., blood). For example, in some embodiments, the system can be configured such that the continuous analyte sensor is a wire sensor configured to extend into a catheter, and the reference sensor comprises an optical fiber that is configured both to detect the reference analyte and to extend into a catheter such that the detecting portion of the reference sensor is adjacent to the sensing portion of the continuous analyte sensor. In another exemplary embodiment, the continuous analyte sensor and the reference sensor are disposed within a connector; such as described in the section entitled "Multi-sensor apparatus." In still another exemplary embodiment, the continuous analyte sensor and the reference sensor are integrally formed on a vascular access device, such as on the in vivo portion of a catheter. For example, an optical fiber can be incorporated into the in vivo portion of the catheter during manufacture (e.g., such as via injection molding techniques known in the art) or by attaching the optical fiber with an adhesive, and subsequent the deposition of the continuous analyte sensor electrodes to the exterior surface of the in vivo portion of the catheter, as described herein.

In preferred embodiments, the system includes a processor module configured to and/or comprises programming that processes the second signal (associated with the reference analyte) and the reference signal to calibrate the first signal (associated with the analyte). For example, in some embodiments, the processor module uses the reference signal, which is generated by a sensor outside the membrane, to calibrate the second signal (generated under the membrane). Accordingly, shifts in baseline and/or sensitivity, which can arise over time during use of the sensor, are accounted for prior to calibration of the first signal (generated under the membrane). The processor configured to then calibrate the first signal (analyte signal) using the calibrated second signal, which generates a first signal substantially without a non-analyte signal component (and substantially unaffected by shifts in sensitivity (m) and/or baseline (b)).

As a non-limiting example, in one embodiment, the system includes a continuous glucose sensor configured to detect a first signal associated with glucose and a second signal associated with $O_2$. The system also includes an optical sensing apparatus configured to detect $O_2$. The system is configured such that the glucose sensor and the optical $O_2$ sensing apparatus can be exposed simultaneously to a sample. This method for calibration requires measurement of a second analyte that is already being monitored. For example, optical sensors are almost always used to measure $O_2$ in the host. In some embodiments, the glucose sensor's first working electrode generates both the analyte signal and the $O_2$ signal. In some embodiments, an electrode other than the first working electrode (e.g., a second or third working electrode) is configured to generate the $O_2$ signal. Then the optical $O_2$ sensor can be used to calibrate the $O_2$ electrode (of glucose sensor system). Assuming there is a known relationship between the sensitivities of an electrode configured to generate a glucose signal and an electrode configured to generate an $O_2$ signal, then the sensor's glucose electrode can be calibrated by the $O_2$ electrode.

While not wishing to be bound by theory, it is believed that an analyte detection system configured to calibrate the analyte signal using a second/reference analyte provides a plurality of advantages. Primarily, calibration of a system of the preferred embodiments does not require input (manually or automatically) of reference data points from a secondary detection system (e.g., separate from the analyte detection system), such as a hand-held glucose meter. Similarly, no special IV bag, mechanical components or dedicated IV lines are required. A wide variety of analytes can be detected by both electrochemical means and a secondary means, such as optical detection methods. All of these advantages conflate to provide highly accurate, "plug-and-play" style continuous analyte detection system that is usable in a wide variety of settings.

Integrated Sensor System

System Overview

In the hospital environment, such as in Intensive Care Units, patients commonly have multiple access points to their circulatory systems, for drug and fluid infusion, and for each blood sample collection. In such settings, a variety of analytes in the host's blood are regularly monitored, by collection of a blood sample and sending the sample to an on-site laboratory for analysis. This system had serious drawbacks, such as giving slow, non-continuous analyte monitoring results and requiring a lot of hospital staff attention. For example, tight control of glucose levels is critical to patient outcome in a critical care medical setting, especially for diabetic hosts. Maintaining tight glucose control with current technology poses an undue burden to medical personnel, due to time constraints and the extensive patient contact required. Reducing medical staff workload is a key component of improving patient care in this setting. The preferred embodiments disclose systems and methods to automatically and continuously test host analytes at the bedside while reducing and/or minimizing staff-patient interactions. Additionally, the preferred embodiments decrease testing intervals and improve sensor accuracy and reliability.

FIGS. 6 and 7 illustrate one preferred embodiment of the integrated sensor system 600 (e.g., for use at the bedside), which couples to the analyte sensor 14 (e.g., a glucose sensor) and vascular access device 12 (e.g., a catheter placed in a peripheral vein or artery) described above (see FIGS. 1A-1E), and which includes at least one fluid reservoir 602 (e.g., a bag of calibration or IV hydration solution), a flow control device 604 (e.g., to control delivery of an infusion fluid 602a from the reservoir to the host via the catheter), a local analyzer 608 and a remote analyzer 610. In some embodiments, the analyte sensor is configured to reside within the catheter lumen 12a (see FIGS. 1A-1E). In some embodiments, the sensor is disposed within the catheter such the sensor does not protrude from the catheter orifice 12b. In other embodiments, the sensor is disposed within the catheter such that at least a portion of the sensor protrudes from the catheter orifice. In still other embodiments, the sensor is configured to move between protruding and non-protruding configurations. The analyte sensor and vascular access device used in the integrated sensor system 600 can be any types known in the art, such as but not limited to analyte sensors and vascular access devices described above, in the sections entitled "Applications/Uses" and "Exemplary Sensor Configurations." For convenience, the vascular access device 12 will be referred to as a catheter herein. However, one skilled in the art appreciates that other vascular access devices can be used in place of a catheter.

In some embodiments, at least one electronics module (not shown) is included in the local and/or remote analyzers 608, 610 respectively, for controlling execution of various system functions, such as but not limited to system initiation, sensor calibration, movement of the flow control device 604 from one position to another, collecting and/or analyzing data, and the like. In preferred embodiments, the components and functions of the electronics module can be divided into two or more parts, such as between the local analyzer and remote analyzer, as is discussed in greater detail in the sections entitled "Local Analyzer" and "Remote Analyzer."

In some embodiments, the flow control device 604 includes one or more valves and is configured to control fluid delivery to the host and sample take-up (e.g., drawing blood back into the catheter until at least the sensor's electroactive surfaces are contacted by the blood). In some embodiments, the sensor 14 dwells within the lumen 12a of the catheter 12, as described elsewhere herein. In some embodiments, wherein an internal calibration is performed, an infusion fluid (e.g., calibration solution 602a) flows over the indwelling sensor 14 and is infused into the host. Generally, analyte in the solution 602a can be measured when the sensor electroactive surfaces are in contact with the solution 602a. In some embodiments, the measurements of the solution 602a can be used to calibrate the sensor 14. After calibration, the system is configured such that a sample (e.g., blood or other bodily fluid) contacts the sensor's electroactive surfaces (e.g., by drawing blood back into the catheter). When the sample contacts the electroactive surfaces, the sample's analyte concentration can be detected by the sensor 14. When a sample is drawn back, the sample can then be returned to the host. In some embodiments, the integrated sensor system 600 cycles between calibration (e.g., measurement of a reference calibration solution) and measurement (e.g., of a sample, such as blood, glucose concentration). In some embodiments, the system 600 continues operation in this cyclical manner, until the system 600 is either disconnected from the host or turned off for a period of time (e.g., during movement of the host from one location to another). For example, in one embodiment, the system 600 cycles between the calibration and measurement steps from about every 30 seconds or less to about every 2 hours or more. In another embodiment, the system 600 cycles between the calibration and measurement steps of from about every 2 minutes to about every 45 minutes. In still another embodiment, the system 600 cycles between the calibration and measurement steps from about every 1 minute to about every 10 minutes. In some embodiments, the user can adjust the time between steps. In some embodiments, the user can adjust the time between each step. In some embodiments, the system 600 can perform additional steps, such as but not limited to a flushing step, a keep vein open step (KVO), an extended infusion step, and the like. In some embodiments, the time is dependent upon sensors that detect a reference solution (e.g., calibration solution) and/or sample (e.g., blood) at the electroactive surfaces.

The integrated sensor system 600 of the preferred embodiments provides several advantages over prior art technology. Namely, in preferred embodiments, continuous analyte monitoring is enabled. When the analyte is glucose, continuous glucose monitoring enables tight glucose control, which can lead to reduced morbidity and mortality among diabetic hosts. Additionally, the medial staff is not unduly burdened by additional patient interaction requirements. Advantageously, there is no net sample (e.g., blood) loss for the host, which is a critical feature in some clinical settings. For example, in a neonatal intensive care unit, the host is extremely small and loss of even a few milliliters of blood can be life threatening. Furthermore, returning the body fluid sample to the host, instead of delivering to a waste container greatly reduces the accumulation of biohazardous waste that requires special disposal procedures. The integrated sensor system components, as well as their use in conjunction with an indwelling analyte sensor, are discussed in greater detail below.

Fluids

Referring to FIGS. 6 and 7, in preferred embodiments, the integrated sensor system 600 includes at least one reservoir 602 that contains an infusion fluid 602a, such as but not limited to reference (e.g., calibration), hydration and/or flushing solutions. For simplicity, the infusion fluid 602a will be referred to herein as a solution 602a. However, one skilled in the art recognizes that a wide variety of infusible fluids can be used in the embodiments discussed herein.

In some embodiments, the reservoir 602 includes a container such as but not limited to an IV bag. In other embodiments, the reservoir 602 can include two or more IV bags, or any other sterile infusion fluid container. In some embodiments, the reservoir 602 is a multi-compartment container, such as but not limited to a multi-compartment IV bag. If two or more solutions 602a (e.g., calibration solutions, flush solutions, medication delivery solutions, etc.) are used, the solutions 602a can be contained in two or more IV bags or in a multi-compartment IV bag, for example. In some embodiments, it is preferred to use a single solution 602a. Use of a single solution 602a for calibration, catheter flushing and the like simplifies the system 600 by reducing the complexity and/or number of system 600 components required for system 600 function. In some embodiments, two or more solutions 602a are preferred, and can be provided by a multi-compartment IV bag or two or more separate reservoirs 602 (e.g., two or more bags, each containing a different solution 602a). Advantageously, use of multiple solutions 602a can increase system functionality 600 and can improve sensor accuracy.

Any infusion fluid (e.g., solution 602a) known in the art can be used in conjunction with the present system 600. In some embodiments, the solution 602a is an analyte-containing solution that can be used as a reference or standard for sensor 14 calibration (generally referred to as a reference and/or calibration solution in the art). In some embodiments, a solution 602a can be used as a flushing solution, to wash a sample off the sensor 14 and out of the catheter 12. In some embodiments, two or more solutions 602a (e.g., having different analyte concentrations) can used to provide two or more calibration measurements. In one exemplary embodiment, the analyte sensor 14 is a glucose sensor, and the solution 602a contains dextrose or glucose at a concentration of from about 0 mg/dl to about 400 mg/dl. In preferred embodiments, the solution 602a contains from about 75 mg/dl to about 200 mg/dl glucose. In more preferred embodiments, the solution 602a contains from about 100 mg/dl to about 150 mg/dl glucose. In some embodiments, the solution 602a is an isotonic saline solution. In some embodiments, the solution 602a contains a sufficient concentration of an anticoagulant to substantially prevent blood clotting in and/or near the catheter 14. In some embodiments, the solution 602a contains a sufficient concentration of or antimicrobial to substantially prevent infection in and/or near the catheter. In one exemplary embodiment, the reservoir 602 is a 500 ml bag containing a sterile solution 602a including 0.9% sodium chloride in water (e.g., normal saline), 2 IU/ml heparin and 100 mg/dl dextrose. In another exemplary embodiment, the reservoir 602 is a 500 ml bag containing heparinized saline.

In some embodiments, one, two or more solutions 602a can be used in conjunction with the integrated sensor system 600. For example, in some embodiments, two or more calibration solutions 602a (e.g., solutions with different analyte concentrations) can be used. In one preferred embodiment, the analyte sensor 14 is a glucose sensor and the calibration solution 602a includes a glucose concentration of from 0 mg/dl to about 300 mg/dl or more. In one exemplary embodiment, a single calibration solution 602a (e.g., having a 100 mg/dl glucose concentration) can be used. In another exemplary embodiment, two calibration solutions 602a (e.g., having 100 mg/dl and 0 mg/dl glucose concentrations) can be used. In other exemplary embodiments, three calibration (e.g., 0 mg/dl glucose, 75 mg/dl glucose and 300 mg/dl glucose) solutions 602a can be used. In still other embodiments, more than three calibration solutions 602a can be used. In addition to calibration solutions 602a, non-calibration solutions 602a can be used in conjunction with the integrated sensor system 600, such as but not limited to intravenously administered drugs, insulin, enzymes, nutritional fluids, and the like.

In some circumstances, it is preferred to infuse two or more different solutions (e.g., provided in separate IV bags) to the host through the same IV tubing, while not mixing the solutions in the tubing. In some embodiments, the system is configured to infuse two or more separate solutions without mixing by inserting (e.g., injecting) a small oxygen bubble between the two different solutions as they are released from the IV bags (e.g., when switching from one solution to the other). In some embodiments, alternative gases or a small amount of glycerin is substituted for oxygen. The size of the bubble necessary to separate the two fluids depends in part on the inner diameter of the tubing. For example, a smaller bubble is required when smaller internal diameter tubing is used than when larger internal diameter tubing is used. In some embodiments, the bubble has a volume of from about 1, 3, 5-μl to about 6, 8, 10, 15, 20, 25 or 30-μl or greater. In some embodiments, the bubble is injected at the flow control device. In some embodiments, the system includes a bubble injector.

The solution 602a can be provided to the user in a variety of ways, depending upon local hospital protocol and/or physician preference. In some embodiments, the solution 602a is supplied pre-mixed (e.g., an IV bag containing sodium chloride, dextrose and heparin), such that fluid reservoir 602 can be connected to an infusion set and infused into the host with minimal effort. In other embodiments, one or more of the solution components 602a can be provided separately, such that the final solution 602a is prepared at the host's bedside, at the nurse's station or in the hospital pharmacy, for example. In one exemplary embodiment, the solution 602a can be provided to the medical staff as a kit including a bag of sterile solution (e.g., water) and injectable sodium chloride, dextrose and heparin aliquots of sufficient quantity to prepare the final solution 602a. The solution 602a can be mixed at the bedside or at a location remote from the host, and then applied to the host and to the integrated sensor system 600. In some embodiments, the reservoir 602 is a 500 ml or 1000 ml bag containing a sterile solution of heparinized saline and 100 mg/dl, 150 mg/dl or 200 mg/dl glucose.

In various preferred embodiments, the solutions 602a are administered with standard IV administration lines, such as those commonly used today, such as a sterile, single-use IV set, referred to herein as tubing 606. In some embodiments, the tubing 606 can be provided with the solution(s) 602a. While in other embodiments, the tubing 606 can be provided separately from the solution(s) 602a or other system components. Additional system 600 components that can be provided with the solution(s) 602a include but are not limited to a sensor 14, a catheter 12, tubing 606, a local analyzer 608, wires and/or cables for hard-wire connections between system components, and the like.

In some embodiments, multiple solutions 602a can be infused through a multi-lumen catheter 12, such as but not limited to a two-lumen or three-lumen catheter. In some embodiments, the sensor 14 is disposed in one of the catheter's lumens 12a, through which one or more calibration solutions 602a can be passed, while other fluids (e.g., hydration fluids, drugs, nutritional fluids) to be delivered to the patient are infused through the other catheter 12 lumens 12a (e.g., second, third or more lumens).

In some embodiments, the reservoir 602 is held by a support 612. The support 612 can take many forms, such as an elevated support. In some embodiments, the support 612 is an IV pole, such those commonly used in medical care facilities. In some embodiments, the reservoir 602 is suspended on the support 612, and the height of the reservoir 602 can be adjusted (e.g., raised or lowered) to modulate solution 602a discharge from the reservoir 602.

In some embodiments, the reservoir 602 and solution 602a can be provided with one or more system 600 components, such as in a kit. In one exemplary embodiment, a kit including the components to mix the solution 602a can include an analyte sensor 14 and a standard infusion set (e.g., catheter 12, cannula, IV tubing 606, etc.). In other embodiments, a kit can include a premixed solution 602a, with an analyte sensor 14. In various embodiments, a kit can contain instructions for use, such as for mixing the solution 602a and applying it to the integrated sensor system 600. Advantageously, providing either a pre-mixed solution 602a or solution components with one or more system 600 components (e.g., sensor 14, catheter 12, tubing 606, local analyzer 608) can increase efficiency of medical care and provide ease of use to the nursing staff.

Flow Regulators

Still referring to FIGS. 6 and 7, in some embodiments, a flow regulator 602b controls the solution 602a flow rate from the reservoir 602 to the flow control device 604, which is described below. A variety of flow regulators can be used with the preferred embodiments, including but not limited to pinch valves, such as rotating pinch valves and linear pinch valves, cams and the like. In one exemplary embodiment, the flow regulator 602b is a pinch valve, supplied with the IV set and located on the tubing 606 adjacent to and below the drip chamber. In some embodiments, a flow regulator 602b controls the flow rate from the reservoir 602 to a flow control device 604, which is described in the section entitled "Flow Control Device." In some embodiments, a flow regulator is optional; and a flow control device 604 controls the flow rate (e.g., from the reservoir 602 to the catheter 14, described elsewhere herein).

Flow Control Device

In preferred embodiments, the integrated sensor system 600 includes a flow control device 604. In some embodiments, the flow control device 604 is configured to regulate the exposure of the sensor 14 to the solution 602a and to host sample (e.g., blood or other bodily fluid). In some embodiments, the flow control device 604 can include a variety of flow regulating devices, such as but not limited to valves, cams, pumps, and the like. In one exemplary embodiment, the flow control device 604 includes a simple linear pinch valve. In another exemplary embodiment, the flow control device 604 includes two or more linear pinch valves. In another exemplary embodiment, the flow control device 604 includes one or more non-linear pinch valves. In another exemplary embodiment, the flow control device 604 includes a global valve. In still another exemplary embodiment, the flow control device 604 includes a gate valve, such as but not limited to a rising stem or non-rising-stem valve. In another exemplary embodiment, the flow control device 604 includes a butterfly valve or a ball valve. In still another exemplary embodiment, the flow control device 604 includes a pump, such as but not limited to volumetric infusion pumps, peristaltic pumps, piston pumps and syringe pumps. In still other exemplary embodiments, the flow control device 604 can be configured to vary the pressure at the reservoir 602, such as but not limited to a pressure cuff around an IV bag and/or raising/lowering the reservoir adjust head pressure. In some embodiments, the flow control device 604 includes a gravity-fed valve. In still other embodiments, the flow control device 604 is configured to use flow dynamics at the catheter 12, to regulate exposure to the sensor to solution or sample, as described elsewhere herein. Although some exemplary glucose sensors are described in detail herein, the system 600 can be configured to utilize a variety of analyte sensors including a variety of measurement technologies, such as enzymatic, chemical, physical, electrochemical, spectrophotometric, polarimetric, calorimetric, radiometric, and the like.

Referring now to a preferred embodiment wherein the sensor is an enzyme-based sensor, it is known to those skilled in the art that the rate of an enzymatic reaction is temperature dependent. Depending upon the enzyme, temperature reductions generally slow enzymatic reaction rates; temperature increases generally increase reaction rates. Since the analyte sensors 14 described in the preferred embodiment herein depend upon an enzyme (e.g., GOX) to detect the analyte (e.g., glucose) temperature changes during sensor calibration can result in artifacts on the sensor signal. For example, if the solution 602a temperature is reduced (relative to body temperature), the enzymatic reaction will proceed at a reduced rate (relative to the rate at body temperature), causing the solution's analyte concentration to appear artificially low, which can result in improper sensor calibration. In some circumstances, changes in the relative temperatures of the area of the host's body surrounding the sensor (e.g., the blood contacting the sensor and the flesh surrounding the implanted sensor) and of the solution 602a can be caused by the host moving the implant site, covering (or uncovering) an implant site with a blanket, application of a heating pad or ice to the implant site, and the like. In some circumstances, a high flow rate can cause large temperature fluctuations when the sensor is alternately exposed to blood and solution 602a. For example, if the flow rate is sufficiently slow, the infusion fluid 602a can be sufficiently warmed by the body before it contacts the sensor; thus the calibration measurements taken will be made at a temperature substantially similar to the temperature with the test measurements are taken in blood. If the flow rate is too fast, the infusion fluid 602a will not warm up sufficiently, and the temperature will be too cold when the calibration measurements are taken, which can lead to improper sensor calibration. An improperly calibrated sensor can aberrantly measure the analyte concentration in the sample (e.g., blood from the host). Aberrant readings of sample analyte concentration can lead to improper treatment decisions by the medical staff and/or the host. The effects of temperature on enzymatic reaction rates can be mathematically described using a temperature coefficient. Signal artifacts caused by temperature-related reductions in enzyme reaction rate are referred to herein as temperature coefficient artifacts.

Generally, the host tissue in which the catheter 12 has been implanted surrounds an in vivo portion of the catheter 12. In preferred embodiments, the flow control device 604 is configured to pass the solution 602a through the catheter 12 at a rate such that the solution's temperature substantially equilibrates with the temperature of the surrounding host tissue. In one exemplary embodiment, the flow control device 604 maintains a flow rate of from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more. In one exemplary embodiment, the flow rate is from about 0.5 μl/min or less to about 1.5 ml/min or more. In one preferred embodiment, the flow rate is from about 1 μl/min to about 1.0 ml/min. In one exemplary preferred embodiment, the flow rate is from about 0.01 ml/min to about 0.2 ml/min. In another exemplary preferred embodiment, the flow rate is from about 0.05 ml/min to about 0.1 ml/min. Advantageously, since the flow control device 604 infuses the solution 602a at a rate sufficient to allow substantial temperature equilibration with the surrounding tissue, sensor 14 accuracy is improved and the integrated sensor system 600 has substantially no temperature coefficient artifacts.

In some alternative embodiments, a faster flow rate that does not allow for temperature equilibration is preferred. In such circumstances, measurement inaccuracies due to temperature coefficient can be generally eliminated mathematically using $b_{offset}$ and the calibration methods described in the section entitled "Systems and Methods for Processing Sensor Data."

In some embodiments, sample is taken up into the same catheter lumen 12a through which the solution 602a is infused into the host (described elsewhere herein). Thus, it is preferred that mixing of the sample and the solution 602a is prevented. Similarly, it can be advantageous to detect when the sensor 14 is in contact with undiluted sample and/or undiluted solution. In some preferred embodiments of the integrated sensor system 600, the flow control device 604 is configured to substantially prevent mixing of two or more fluids, such as but not limited to the solution 602a and a host sample (e.g., blood). In preferred embodiments, mixing can be substantially prevented by a combination of factors, including specific gravity and flow rate. It is known that two solutions with different specific gravities tend not to mix, provided that the fluids are moved at a sufficiently slow rate (e.g., flow rate). Human whole blood has a specific gravity of about 1.05-1.06, while an infusion solution of 5% dextrose and 0.225% NaCl has a specific gravity of about 1.0189. Due to the difference in specific gravities, a blood sample and the solution 602a tend to resist mixing within the tubing 606 when the flow rate is sufficiently slow. In preferred embodiments, the sample and the solution 602a are moved within the catheter lumen 12a at a rate such that substantially no mixing occurs therebetween. In some embodiments, the flow rate is from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more. In some embodiments, the flow rate is from about 0.01 ml/min to about 1.0 ml/min. In one exemplary embodiment, the flow rate is from about 0.02 ml/min to about 0.35 ml/min. In another exemplary embodiment, the flow rate is from about 0.02 ml/min to about 0.2 ml/min. In yet another exemplary embodiment, the flow rate is from about 0.085 ml/min to about 0.2 ml/min.

In preferred embodiments, the flow control device 604 can include a variety of fluid flow-regulating devices known in the art. In some embodiments, the flow control device 604 includes one or more valves, such as but not limited to linear and non-linear roller valves, linear and non-linear pinch valves, bi-directional valves (either linear or non-linear), peristaltic rollers, cams, combinations thereof, and the like. In some other embodiments, the flow control device 604 is configured to generate sufficient "head pressure" to overcome the host's blood pressure such that the solution 602a is infused into the host at a controlled rate; this can include elevating the fluid reservoir 602 (e.g., gravity fed) and using a valve to control the fluid flow rate out of the reservoir 602 and into the host. In one exemplary embodiment, the fluid flows at a maximum rate (e.g., about 6.25 ml/hr, 0.1 ml/min) such that a maximum fluid volume of about 150 ml/day can be infused into the host, however ranges much higher and/or lower can be implemented with the preferred embodiments.

In one exemplary embodiment, the flow control device 604 is a rotating pinch valve that has first and second positions. The valve can move between the two positions, for example, backward and forward, and thereby move fluids in and out of the catheter, as described in the section entitled "Flow Control Device Function." Namely, solution 602a can be moved from the reservoir 602, over the electroactive surfaces of the sensor 14 and into the host; and sample can be drawn up from the host, to cover the electroactive surfaces of the sensor 14, and then pushed back into the host, by movement of the valve between the first and second positions.

In one exemplary embodiment, the flow control device includes a rotating pinch valve as described with reference to FIGS. 8A through 8C. Although FIGS. 8A to 8C describe one implementation of a rotating pinch valve that can be implemented with the sensor system, some alternatives include rotating pinch valves with multiple pinch surfaces, for example around the circumference of the rotatable axle (FIGS. 8A-8C, 804), which enables the use of one valve for multiple infusion fluids (e.g., using multiple IV lines).

In some embodiments, the flow control device 604 includes one or more cams that regulate the flow rate. In one embodiment, the flow control device 604 includes a plurality of fixed orifices, which are opened and closed by the cams. As the cams are rotated, the flow increases and/or decreases in response. In one exemplary embodiment, the flow control device 604 includes three openings and three cams that mate with the openings (one cam per opening); fluid can flow through each opening at a given rate, X ml/min. Accordingly, when the cams close all three openings, flow is stopped. When one of the openings is opened, the fluid flows at X ml/min. If two openings are opened, fluid flows at 2X ml/min. Similarly, when the three openings are opened (e.g., by turning the cams such that they no longer close the openings), the fluid flows at 3X ml/min.

In another example, the flow control device 604 includes a plurality of cams and an equal plurality to tubes 606 passing through the cams, such that each cam can pinch closed the tube 606 that passes through it. In an exemplary embodiment, the cams are arranged such that they pinch and roll the tubing 606, such that fluid is pushed into the host and sample taken up at pre-determined rates and times. For example, the flow control device 604 can include two cams, each having a tube 606 threaded therethrough. The cams are arranged such that each cam pinches and rolls the tubing 606 passing therethrough to push fluid into the host at one or more rates and to take up a blood sample.

In yet another example, the flow control device includes a rotating ball valve controlled by a motor, wherein the direction of the ball valve can be utilized to control a variety of functions, such as flow direction of the fluid.

As described in related herein, the sensor can be calibrated using more than one reference/calibration solution. For example, in some embodiments, the system is configured to calibrate using two reference solutions. In some embodiments, two solutions are used by metering the flow of one solution with the flow control device and intermittently stopping and intermittently manually injecting the second solution such that the solution contacts the sensor a sufficient period of time for calibration measurements to be taken. However, in preferred embodiments, the flow control device is configured to automate such "intermittent" calibrations (e.g., instead of manually injecting the calibration solution into the tubing) by actuating a secondary valve in a time-dependent manner, wherein the secondary valve in configured to meter the second calibration solution. The secondary valve can take on a variety of configurations, such as but not limited to a pinch valve, a ratchet valve, a cam, locking bearings or a ball valve (within the tubing).

As a non-limiting example, the secondary valve is a pinch valve that includes a ratcheting disk attached to the front of the flow control valve (e.g., via an axle), first and second arms, and includes a pin that can engage the tip of the second arm. In some preferred embodiments, the first and second arms are connected to each other by a joint, which includes a biasing means, such as a torsional spring, that pushes the second arm toward the ratcheting disk. The joint includes a stop pin, which limits the distance the second arm can move away from the ratcheting disk. The first arm includes a detent (e.g., a finger) that is pressed into the tubing (threaded through the flow control device) by another biasing means configured to push the first arm toward the ratcheting disk. Accordingly, in some embodiments, when the flow control device rotates in the first direction the ratcheting disk is not engaged, and the first arm pinches the tube closed. In other embodiments, when the flow control device rotates in the first direction, the disk rotates with the flow control device such that the tip of the second arm rides up and over the pin of the secondary valve. When the flow control device rotates in the second direction, it is configured to engage the ratcheting disk and has two positions. As the flow control device rotates to the first position, blood is taken up into the catheter. At this point, the flow control device is configured to reverse and rotate in the first direction. However, a portion of the time, the flow control device rotates to the second position. As the flow control device rotates to the second position, the ratcheting disk remains engaged and the disk rotates far enough that the pin (on the disk) engages the tip of the second arm. Accordingly, the second arm is pushed away from the flow control device. The continued movement of the second arm is prevented by the stop pin. Since the second arm must continue to move away from the flow control device/ratcheting disk, the first arm is engaged by the second arm, and the entire structure is pushed away from the flow control device. Accordingly, the pinch on the tubing (e.g., by the detent) is relieved and the fluid in the tubing can flow. After a desired amount of fluid has flowed through the tubing, the pinch of the tubing (by the detent) is reapplied, by moving the flow control device/ratcheting disk in the first direction.

As another non-limiting example, in some embodiments the flow control device includes a cam configured to control the pinching and un-pinching of the tubing. For example, a cam (e.g., weighted) is attached to the flow control device or another structure (e.g., a ratcheting disk) attached to the flow control device. The tubing is compressed (pinched) by a detent on an arm. The arm has a joint and is biased towards the flow control device via a biasing means. At desired time points, the flow control device is configured to move the cam to a second position (e.g., 180°), such that the arm is pushed upward (e.g., by the cam) and the pinch of the tubing is relieved. When the pinch of the tubing is relieved, the solution can flow through the tubing. The flow control device then returns the cam to its first position, so that the tubing is recompressed (pinched) and fluid flow is stopped.

In some embodiments, an electronics module (not shown) is incorporated into the flow control device 604, to provide local control over flow control device function; in these embodiments, the flow control device function can be transmitted to the local and/or remote analyzer for processing. In other embodiments, a remote analyzer 610 and/or electronics module, such as but not limited to a computer system, controls the flow control device 604. System 600 components that regulate the flow control device 604 are discussed in greater detail elsewhere herein.

In a further embodiment, the flow control device 604 is a computer controlled rolling pinch valve that acts on the exterior of sterile tubing 606 in order to control the flow rate of a solution 602a from an elevated fluid reservoir 602 into the host. In preferred embodiments, the flow control device 604 is configured to pinch and roll a small volume of tubing 606 such that a sample of host blood is drawn up into the catheter 12 (e.g., with a sensor 14 disposed therein) for analyte measurement, and to then push the sample back into the host with a solution (e.g., the calibration solution 602a). In general, the flow control device 604 is configured to oscillate between drawing up a blood sample and allowing flow of the calibration solution 602a at a predetermined rate. In some embodiments, the flow control device 604 includes at least one "hard stop" that ensures that the flow control device 604 does not move to a position that could endanger and/or injure the host, such as by draining the IV bag 602 of fluid 602a or inappropriately (e.g., excessively) withdrawing blood, for example.

Tubing and Catheter

Referring again to FIGS. 6 and 7, in preferred embodiments, the integrated sensor system 600 includes tubing 606 (e.g., sterile tubing configured for use in intravascular fluid infusion) and a catheter 12, to deliver the solution 602a from the reservoir 602 to the host. Generally, the tubing 606 and catheter 12 are sterile, single use devices generally used in medical fluid infusion, and may be referred to as an "infusion set." An infusion set may include additional components, such as but not limited to a cannula or needle for implanting the catheter, sterilization fluid (e.g., on a gauze pad) for cleaning and/or sterilizing the insertion site (e.g., the host's skin), tape, gauze, and the like. IV tubing is available in a variety of sizes and configurations, which find use in the preferred embodiments. For example, the tubing can be any size internal diameter, such as from about 0.5 mm to about 5 mm internal diameter. In various embodiments, the tubing can include a drip chamber and/or one or more access devices, such as but not limited to stopcocks, diaphragms and the like.

Catheters 12 are available in a variety of sizes and configurations. Catheters 12 for use in conjunction with an analyte sensor 14 are described in detail, elsewhere herein. Briefly, the catheter 12 can be any single- or multi-lumen catheter having a straight or divided tubing connector (e.g., straight-through, single shut off, double shut off, non-spill couplings, valves, T-connectors, Y-connectors, X-connectors, pinch clamps, Leur locks, back-flow valves, and the like). In some embodiment, the catheter is configured for insertion into the venous side of the host's circulatory system. In other embodiments, the catheter is configured for insertion into the arterial side of the host's circulatory system, into either a peripheral or a central artery. In some embodiments, the catheter 12 is configured with an integrally formed sensor 14. In alternative embodiments, a non-integral sensor 14 is configured for insertion into the catheter 12 after catheter insertion. In some embodiments, the catheter 12 is a single lumen catheter that is configured for infusion of a fluid.

In another embodiment, the catheter includes at least two lumens (e.g., a dual-lumen catheter), wherein each lumen includes an orifice configured and arranged for fluid communication with the bodily fluid of the host. In some embodiments, the first lumen is configured for fluid infusion and the second lumen is configured for insertion of an analyte sensor. In preferred embodiments, the orifice of the second lumen is located more proximal to the second end of the catheter (e.g., the catheter hub) than the first lumen orifice, such that a bodily fluid drawn back into the second lumen is substantially undiluted by a fluid infused through the first lumen. Accordingly, a sample substantially undiluted by fluid being infused into the host can be drawn back for testing by the analyte sensor located in the second lumen. In this embodiment, the catheter is no longer a "dedicated line" that is dedicated to the analyte sensor. In some embodiments, the catheter includes three or more lumens. During insertion, a cannula or needle can be inserted into one of the catheter's lumens, such that the catheter is substantially supported during the insertion process. For example, in some embodiments, the sensor and dual-lumen catheter can be provided to the user with a cannula pre-inserted into the first lumen and the sensor pre-inserted into the second lumen. After insertion, the cannula is removed (the sensor remains in the second lumen) and IV tubing is connected to the catheter hub. In some embodiments, the catheter, such as but not limited to a dual lumen catheter, is formed from an extruded polymer containing an amount of Ag and/or AgCl such that the catheter itself functions as a reference electrode.

In some preferred embodiments, an indwelling sensor 14 is disposed within the catheter's lumen 12*a*. In some embodiments, the catheter 12 and sensor 14 are provided to a user together. In other embodiments, the catheter 12 and sensor 14 are supplied separately. In an alternative embodiment, the catheter 12 is a multi-lumen catheter configured for infusion of two or more solutions. In preferred embodiments, a sensor 14 is disposed within one of the catheter's multiple lumens 12*a*. For example, a calibration solution 602*a* (e.g., 100 mg/dl glucose in saline) can be infused through the lumen 12*a* in which the sensor 14 is disposed, while a hydration fluid (e.g., including a medication) can be infused through a second lumen. Advantageously, a dual lumen catheter 12 allows non-interrupted system use while other fluids are concurrently provided to the host.

In some embodiments, only the working electrode(s) of the sensor 14 are disposed within the catheter lumen 12*a* and the reference electrode is disposed remotely from the working electrode(s). In other embodiments, the sensor 14 is configured to intermittently protrude from the catheter lumen 12*a*.

Referring now to FIGS. 10A-10D, in some embodiments, the flow control device and the IV tubing (e.g., the tubing set) are configured and arranged to releasably mate in a specific orientation. In some embodiments, the flow control device (e.g., the valve 604) and the tubing (referred to herein as a "tubing assembly" 606*a* or a tubing set) are configured and arranged for uni-directional tubing installation (e.g., the tubing can be installed in only one direction). For example, the tubing assembly shown in FIGS. 10A-10D includes first and second connector ends 606*c*, 606*d* joined by a central portion of tubing 606*b*. The central portion of tubing is sufficiently elastic that the tubing assembly can be stretched during installation into the valve. For example, the tubing assembly is held by the first and second ends 606*c*, 606*d* during insertion into grove 803 of the valve. After the tubing is installed in the groove, the first and second ends are released, allowing the central portion to relax into a less-stretched configuration. In some embodiments, the valve and/or tubing (e.g., the central portion) are configured and arranged such that the tubing is in a stretched state (e.g., elongated configuration) after installation. For example, the tubing can be slightly shorter than the distance from one end of the valve to the other (e.g., the longitudinal length of the groove). In some embodiments, the tension created by the remaining stretch in the central portion helps to hold the tubing assembly in place during valve operation. Advantageously, uni-directional tubing installation can enable alignment of tubing components with specific valve components, such that the aligned tubing and valve components can function together, such as described in the section entitled "Free Flow Mitigation."

In further embodiments, the valve and tubing (e.g., tubing assembly 606*a*) are configured and arranged to form a mechanical interlock when mated. Advantageously, the mechanical interlock can reinforce and/or enable uni-directional tubing installation and/or help to maintain the installation of the tubing within the valve during valve operation. The mechanical interlock includes releasably engageable first and second portions; namely, the valve comprises the first portion 809 (described elsewhere herein) of the mechanical interlock and the tubing assembly comprises the second portion (e.g., the second end 606*d* of the tubing assembly 606*a*) of the mechanical interlock. For example, in FIGS. 10A and 10B, the bottom portion 606*d* of the tubing assembly 606*a* is configured as a male connector (e.g., including wings, fins, detents, fingers, etc.) configured to releasably mate with a female interconnection 809 on the valve. For example, in the embodiment illustrated in FIG. 10A, the bottom portion 606*d* of the tubing assembly includes a male interconnection (e.g., a key) having a rectangular body and an optional female portion of a Leur connector (e.g., for releasably mating with the male Leur connector of IV tubing); the valve's interlocking female interconnection (e.g., a lock) includes a rectangular receptacle sized to receive the male interconnection, including a cylindrical indentation (e.g., a concave groove or well) sized and/or shaped to receive the optional Leur connector of the bottom portion. As another example, in the embodiment illustrated in FIG. 10B, the bottom portion 606*d* of the tubing assembly includes fins having curved edges. Advantageously, the mechanical interlock, of the tubing assembly and the valve, prevents twisting (e.g., rotational movement) of the tubing assembly within the valve.

In some embodiments, the configuration of an interconnection (e.g., the male interconnection of the tubing assembly and/or the female interconnection of the valve) is associated with a specific flow profile. For example, a first interconnection configuration is associated with a first flow profile; a second interconnection configuration is associated with a second flow profile; and so on. In a further embodiment, the interconnection and/or flow profile is associated with a specific system configuration, such as for use in a specific circumstance. For example, the system can be configured for uses in pediatric and/or adult hosts. Each type of host has a set of requirements associated with the system configuration. For example, a pediatric host is much smaller than an adult host, and thus may require a smaller catheter/fluid coupler and analyte sensor and slower infusion relative to an adult host. In some embodiments, the system is configured to recognize an interconnection (e.g., the configuration) and to use (e.g., program, select) the flow profile associated with the recognized interconnection. In some embodiments, the interconnection is mechanical. In other embodiments, the interconnection includes an electronic component, such as but not limited to an RFID chip located in the tubing assembly (e.g., in the male interconnection of the mechanical interlock) that is detected by the flow control device.

As is described elsewhere herein, the valve is configured and arranged for at least two fluid flow positions, namely a gravity flow (also referred to as free flow) position and a controlled flow position. For example, in some embodiments, the valve is configured and arranged such that the tubing is substantially straight in the gravity flow position and the tubing is substantially non-linear in the controlled flow position. In general, the position of the valve, including its direction and rate of movement, is associated with (e.g., corresponds to) the flow position, which in turn is associated with (e.g., corresponds to) a flow rate. FIG. 10C illustrates the gravity flow valve position, which corresponds to a valve position in which the valve is substantially open (e.g., the tubing 606*b* of the tubing assembly is not substantially pinched), such that the infusion fluid can flow freely through the valve. In some embodiments, the gravity flow position comprises a flow rate of at least about 600 ml/hr (e.g., 10-ml/min). In contrast, the controlled flow position (e.g., FIG. 10D) includes a pinch 808 in the tubing 606b and movement of the pinch in the tubing (e.g., by the valve), such that the rate of fluid flow (e.g., including flow direction) is controlled by the valve. In some embodiments, the controlled flow position provides a flow rate of from about 0.001, 0.002, 0.003, 0.003, 0.004, 0.005, 0.006, 0.007, 0.008 or 0.009-ml/min or less to about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1-ml/min or more. In some embodiments, the controlled flow position provides a flow rate from about 0.006, 0.007, 0.008, 0.009, 0.01, or 0.02-ml/min to about 0.03, 0.04, 0.05, 0.06, 0.07, 0.08, 0.09 or 0.1-ml/min. In some embodiments, the controlled flow position provides a flow rate from about 0.5-ml/hr to 4-ml/hr. Accordingly, in preferred embodiments, the valve is configured and arranged to preclude tubing installation when the valve is in a controlled flow position. Preferably, the tubing is installed when the valve is in a gravity flow position (e.g., FIG. 10C), wherein the valve is positioned such that the tubing can be installed in a substantially straight (e.g., linear, un-pinched) configuration.

In preferred embodiments, the vascular access device (e.g., the catheter and/or fluid coupler) and the tubing 606 (e.g., tubing assembly 606a) are configured and arranged to substantially preclude twisting (e.g., rotational movement) between the vascular access device and the tubing when engaged (e.g., fluidly connected, in fluid communication with each other). Accordingly, in some embodiments, the interconnecting portions of the vascular access device and the tubing include a mechanical structure configured to prevent rotational movement of the connection past a predetermined point. For example, the interconnection of the vascular access device and the tubing includes a Leur lock, wherein the vascular access device includes the female portion of the Leur connection and the tubing includes the male portion of the Leur connection. In one embodiment, the female portion of the Leur connector includes a groove configured to mate with a detent on the male portion of the Leur connector, such that the male portion can be rotated within the female portion only until the detent enters the groove. In one embodiment, additional mechanisms for prevent twisting between the vascular access device and the tubing are contemplated in the preferred embodiments.

Free Flow Mitigation

As described herein, the valve includes a gravity flow valve position, which allows fluid to flow freely through the valve and into the host. In preferred embodiments, the system is configured to regulate the amount of fluid allowed to flow into the host, since unregulated flow (e.g., free flow) of IV solution into the host could be deleterious to the host's health. For example, if the IV solution contained a drug, such as insulin or heparin, infusion of too much IV solution could cause an unsafe drop in blood sugar or an unsafe decrease in the host's ability to form blood clots, respectively. However, in certain circumstances, such as a power failure, the system can be inadvertently stopped in the gravity flow valve position. Accordingly, to prevent unregulated flow (e.g., free flow) of fluid into the host, such as in the event of a power failure and/or related circumstances, in preferred embodiments, the system includes a free flow mitigation device biased in an occluded position. In some embodiments, the system is configured and arranged such that the free-flow mitigation device precludes flow through the tubing responsive to power removal and/or loss of power to the system and/or flow control device. In some embodiments, the free flow mitigation device 606e is incorporated into the tubing assembly 606a, such that flow through the tubing is blocked until the valve activates (e.g., opens) the free flow mitigation device. In one exemplary embodiment, the free flow mitigation device 606e is a spring-clip occluder that closes (e.g., blocks, pinches, occludes) the tubing until it is activated. For example, in some embodiments, the valve includes an electronic solenoid 807 that is configured and arranged to activate the spring-clip occluder (e.g., causes the spring-clip occluder to open, such that fluid can flow through the tubing, biases the free flow mitigation device in an un-occluded position), when the tubing is installed in the valve. In preferred embodiments, the free flow mitigation device 606e is located within the tubing 606a such that the free flow mitigation device is aligned with the portion of the valve that activates it. For example with reference to FIG. 10A, the valve includes an electronic solenoid 807 located along grove 803, such that (when the tubing assembly is installed) the spring-clip occluder 606e is aligned with the electronic solenoid. In preferred embodiments, the electronic solenoid is configured and arranged such that free flow mitigation device returns to the occluded position (e.g., blocks free flow) responsive to power removal, such as during a power failure, during installation of the tubing into the valve (e.g., at the beginning of a sensor session), turning the system off (e.g., at the end of use and/or of a sensor session), and the like. Preferably, the system is configured and arranged for electronic control of the free flow mitigation device. For example, in preferred embodiments, the valve controls the flow of fluid into the host and drawback of samples for testing, according to a flow profile (described elsewhere herein). In preferred embodiments, the system is configured to electronically control the opening and closing of the free flow mitigation device (e.g., by energizing and de-energizing the solenoid) in response to the flow profile. For example, when the flow profile specifies infusion into the host or sample drawback, the system electronically activates the solenoid, which in turn biases the free flow mitigation device in the open position, so that the fluid can be infused, samples can be drawn back to the analyte sensor, samples can be returned to the host, the analyte sensor can be washed with infusion solution, drugs can be infused, and the like. Some free flow mitigation devices suitable for use with the present system can be found in U.S. Pat. No. 5,810,323, U.S. Pat. No. 6,142,979, and U.S. Pat. No. 6,749,591, all of which are incorporated by reference herein in their entirety.

Sample-Contacting Sensor

In preferred embodiments, the integrated sensor system 600 is configured such that at least the sensor's electroactive surfaces can be exposed to a sample and the sample's analyte concentration can be detected. Contacting the sensor 14 with the sample can be accomplished in a variety of ways, depending upon sensor and/or catheter configuration. A wide variety of catheter 12 and/or sensor 14 configurations can be implemented in the preferred embodiments, to expose the sensor's electroactive surfaces to a biological sample. In one exemplary embodiment, the catheter 12 is disposed in the host's peripheral vascular system, such as in a peripheral vein or artery, and a blood sample is taken up into the catheter 12 such that the blood contacts the sensor's electroactive surfaces. In another exemplary embodiment, the catheter 12 can be disposed in the host's central vascular system or in an extracorporeal blood flow device, such as but not limited to an arterial-venous shunt, an extravascular blood-testing apparatus, a dialysis machine and the like, wherein blood samples can be taken up into the catheter 12 such that at least the sensor's electroactive surfaces are contacted by the drawn up blood sample.

In one exemplary embodiment, the sensor 14 is configured to reside within the catheter lumen 12a (e.g., not protrude from the catheter tip); and the integrated sensor system 600 is configured to draw back a sample into the catheter lumen 12a such that at least the sensor's electroactive surfaces are contacted by the sample. In some embodiments, the sensor 14 is a small-structured sensor having a width of less than about 1 mm. In one preferred embodiment, the sensor has a width of less than about 0.4 mm. In a more preferred embodiment, the sensor has a width of less than about 0.2 mm. In some embodiments, the catheter 12 has an internal diameter of from about 0.2 mm or less to about 2.0 mm or more, preferably from about 0.5 mm to about 1.0 mm. In some embodiments, the sensor 14 is configured such that its electroactive surfaces are at or adjacent to its tip, and the flow control device 604 is configured to take up sample into the catheter lumen 12a until the sample covers at least the electroactive surfaces. In some embodiments, the electroactive surfaces are distal from the sensor's tip and sample is drawn farther back into the catheter lumen 12a until the sample covers the electroactive surfaces. In some embodiments, the tip of the sensor is disposed about 3 cm, 2 cm, or 1 cm or less from a tip of the catheter.

In some embodiments, the sample taken up into the catheter's lumen 12a covers only a portion of the sensor's in vivo portion. In other embodiments, the sample taken up into the catheter's lumen 12a covers the entire in vivo portion of the sensor 14. In some embodiments, a sample volume of from about 1 µl or less to about 2 ml or more is taken up into the catheter 12 and is sufficient to cover at least the electroactive surfaces of the sensor 14. In some preferred embodiments, the sample volume is from about 10 µl to about 1 ml. In some preferred embodiments, the sample volume is from about 20 µl to about 500 µl. In other preferred embodiments, the sample volume is from about 25 µl to about 150 µl. In more preferred embodiments, the sample volume is from about 2 µl to about 15 µl.

In preferred embodiments, the sample taken up into the catheter's lumen 12a remains within the in vivo portion of the catheter 12. For example, in some embodiments, the sample is not drawn so far back into the catheter 12 that it enters the ex vivo portion of the catheter 12, the tubing 606 or the reservoir 602. In some embodiments, however, the sample can be drawn back as far as the catheter but not into the IV tubing. In some embodiments wherein the catheter 12 is implanted in a host, the blood sample never leaves the host's body (e.g., a plane defined by the host's skin). In some embodiments wherein the catheter 12 is implanted in an extracorporeal device, the sample does not substantially exit the extracorporeal device. In preferred embodiments, wherein blood is taken up into the catheter 12, the blood is returned to the host (or extracorporeal device), which is described elsewhere herein. In preferred embodiments, the sample is blood taken up from the host's circulatory system and into the catheter 12 disposed within the circulatory system.

In another exemplary embodiment of the integrated sensor system, the sensor is configured to protrude from the catheter's orifice 12b, at least intermittently. In preferred embodiments, the sensor is configured to protrude sufficiently far out of the catheter's lumen 12a (e.g., into the circulatory system proper) that the sensor's electroactive surfaces are contacted by sample (e.g., blood). In a further embodiment, the sensor is configured to intermittently protrude from the catheter orifice 12b, such as by moving back and forth, such that the electroactive surfaces are alternately disposed within the catheter 12 and outside of the catheter 12. In one exemplary embodiment of a catheter is implanted in a host's vein, calibration solution 602a is provided within the catheter 12 such that the sensor 14 is disposed within the catheter 12, the sensor 14 is contacted by the calibration solution 602a and calibration measurements can be obtained periodically, when the sensor 14 (e.g., electroactive surfaces) is moved outside of the catheter 12, the sensor 14 is contacted by blood and blood analyte measurements can be obtained.

In some embodiments of the integrated sensor system 600, the catheter 12 and sensor 14 are configured to take advantage of flow dynamics within the host's vascular system. By taking advantage of flow dynamics, the system can be simplified, such that the flow control device functions mainly to allow or block the flow of calibration solution.

FIG. 9 is a cut-away illustration of one exemplary embodiment, in which a catheter 12 is implanted in a host's vessel 906, such as but not limited to an artery or vein. The catheter 12 includes a sidewall 904 that can be configured to include one or more holes 902 (e.g., orifices or openings configured for fluid passage, such as from the exterior sidewall surface into the catheter lumen 12a). The catheter 12 can be inserted into the host's vein (or artery, or an extracorporeal circulatory device) such that the catheter points either in the direction of blood flow (antegrade) or against the direction of blood flow (retrograde). The catheter is configured such that in an antegrade position, blood flows into the catheter lumen 12a via the holes 902 and then out of the catheter orifice 12b. In a retrograde position, blood enters the catheter lumen 12a via the catheter orifice 12b and flows out of the lumen through the holes 902. In some embodiments, the sensor 14 can be disposed within the catheter lumen 12a such that blood flowing between the holes 902 and the orifice 12b contacts at least the sensor's electroactive surfaces. In some embodiments, the sensor 14 is configured to be substantially immobile within the lumen 12a, while in other embodiments the sensor 14 is configured to be substantially moveable within the lumen 12a, as described in more detail elsewhere herein.

Generally, the holes 902 can be placed in any location on the catheter's sidewall 904. In some embodiments, the holes 902 can be located near or adjacent to the catheter orifice 12a. In other embodiments, the holes 902 can be placed remotely from the catheter orifice 12a. The size, shape and number of holes 902 can be selected to optimize the sample volume and flow rate through the catheter lumen 12a. For example, in some embodiments, the holes 902 are round, ellipsoid, rectangular, triangular, star-shaped, X-shaped, slits, combinations thereof, variations there of, and the like. Similarly, in some embodiments, the catheter 12 can have from 1 to about 50 or more holes 902. In other embodiments, the catheter can have from 2 to about 10 or more holes 902.

In some alternative embodiments, the catheter includes at least one size wall orifice in place of an end tip orifice, which allows selective exposure of the sensor to the host's biological sample there through. A variety of alternative catheter configurations are contemplated in conjunction with the preferred embodiments.

In one exemplary embodiment of the integrated sensor system 600, the flow control device 604 is configured to intermittently block the infusion of solution 602a through the catheter 12, which is configured with side holes 902 as described above. Additionally, the analyte sensor is disposed within the catheter lumen 12a such that sample passing between the side holes 902 and the catheter orifice 12b bathes the sensor's electroactive surfaces, during which time an analyte measurement can be obtained. When the flow control device 604 does not block infusion, the solution 602a contacts the sensor's electroactive surfaces; and calibration measurements can be taken.

In some embodiments, a solution 602a can be infused into the catheter 12 at a rate such that the flow of sample between the holes 902 and the orifice 12b is substantially blocked and at least the electroactive surfaces are bathed in the solution 602a (e.g., undiluted solution). In preferred embodiments, the sensor 14 can be calibrated while it is bathed in the undiluted solution 602a.

In preferred embodiments, the sensor 14 is a small-structured sensor with at least one electrode, such as a working electrode, as described elsewhere herein. In some embodiments, the sensor 14 has two or more electrodes, such as but not limited to working, reference and counter electrodes. In some embodiments, the sensor 14 includes a reference electrode disposed remotely from the working electrode, as discussed elsewhere herein. In some embodiments, the sensor 14 includes two or more electrodes that are separated by an insulator, such as described in U.S. Patent Publication No. US-2007-0027385-A1, herein incorporated by reference in its entirety. In preferred embodiments, the electrode is a fine wire, such as but not limited to a wire formed from platinum, iridium, platinum-iridium, palladium, gold, silver, silver chloride, carbon, graphite, gold, conductive polymers, alloys and the like. In some exemplary embodiments, the sensor 14 includes one or more electrodes formed from a fine wire with a diameter of from about 0.001 or less to about 0.010 inches or more. Although the electrodes can by formed by a variety of manufacturing techniques (bulk metal processing, deposition of metal onto a substrate, and the like), it can be advantageous to form the electrodes from plated wire (e.g., platinum on steel wire) or bulk metal (e.g., platinum wire). It is believed that electrodes formed from bulk metal wire provide superior performance (e.g. in contrast to deposited electrodes), including increased stability of assay, simplified manufacturability, resistance to contamination (e.g. which can be introduced in deposition processes), and improved surface reaction (e.g. due to purity of material) without peeling or delamination.

In some embodiments, one or more electrodes are disposed on a support, such as but not limited to a planar support of glass, polyimide, polyester and the like. In some exemplary embodiments, the electrodes include conductive inks and/or pastes including gold, platinum, palladium, chromium, copper, aluminum, pyrolitic carbon, composite material (e.g., metal-polymer blend), nickel, zinc, titanium, or an alloy, such as cobalt-nickel-chromium, or titanium-aluminum-vanadium, and are applied to the support using known techniques, such as but not limited to screen-printing and plating. Additional description can be found in U.S. Pat. No. 7,153,265, U.S. Patent Publication No. US-2006-0293576-A1, U.S. Patent Publication No. US-2006-0253085-A1, U.S. Pat. No. 7,003,340, and U.S. Pat. No. 6,261,440, each of which is incorporated in its entirety by reference herein.

In some embodiments, an optional redundant sensor can be disposed within the catheter lumen, in addition to the sensor 14 described elsewhere herein. In one exemplary embodiment, a sensor 14 and a redundant sensor are disposed within the lumen of a sensor implanted in a host's peripheral vein, such that the electroactive surfaces of the sensor 14 are more proximal to the catheter orifice 12b than the electroactive surfaces of the redundant sensor; wherein blood is taken up into the lumen 12a such that the electroactive surfaces of both the sensor 14 and the redundant sensor are contact by the blood; such that analyte can be detected by both the sensor 14 and the redundant sensor and the redundant sensor measurements are used by the system 600 to confirm the sensor's 14 measurements. In a further embodiment, both the sensor 14 and the redundant sensor are intermittently concurrently contacted by the solution 602a such that both the sensor 14 and the redundant sensor can take calibration measurements of the solution 602a, wherein the calibration measurements of the redundant sensor are at least used to confirm the calibration measurements of the sensor 14. In another embodiment, the calibration measurements from both the sensor 14 and the redundant sensor are used to calibrate the sensor 14.

Local Analyzer

Referring to FIGS. 6 and 7, in some embodiments, the integrated sensor system 600 includes a local analyzer 608 configured to operably connect to a remote analyzer 610. In some embodiments, the local analyzer 608 is proximal to an analyte sensor 14 and the remote analyzer 610 is configured to operably connect to the local analyzer. However, alternative configurations are possible, such as the analyte sensor 14 can be operably connected to both the local and remote analyzers 608, 610 respectively. The remote analyzer 610 of the preferred embodiments is discussed below. In various embodiments, one or more functions of the local analyzer 608 can be transferred to the remote analyzer, as is appreciated by one skilled in the art. Likewise, in some embodiments, one or more functions of the remote analyzer 610 can be incorporated into the local analyzer 608. In further embodiments, functions of the local and/or remote analyzers 608, 610 can be disposed in one, two, three or more physical bodies (e.g., separate housings), depending upon the integrated sensor system 600 configuration and/or component combinations. For example, in one embodiment, the local analyzer 608 includes a potentiostat, a power source (e.g., battery or connection to an electrical source), and data storage; and the local analyzer 608 is configured such that the potentiostat is disposed on the sensor's fluid coupler 20 and the remaining local analyzer 608 components are disposed elsewhere between the local analyzer 608 and the remote analyzer 610 (e.g., connected by wiring).

Operable connections between the local and remote analyzers 608, 610 and the analyte sensor 14 can be accomplished by a hard wire (e.g., USB, serial), RF communication, IR communication, and the like. In some embodiments, operable connections include a connector known in the art, such as but not limited to mating plug and socket units, screw connectors, clips and the like. In some embodiments, the connectors are separable. In other embodiments, the connectors are inseparable. In some embodiments, the connectors include a lock, to prevent inadvertent disconnection. In some embodiments, the local analyzer can be isolated from the remote analyzer by an isolation transformer.

In some embodiments, the local analyzer 608 is operably connected to the sensor 14 (e.g., the sensor electrode(s)), such as by a wire connection. A detailed description of electronic components and configurations is described elsewhere herein, for example, in the section entitled "Sensor Electronics." In some embodiments, the local analyzer 608 is disposed on or adjacent to the sensor, such as on the sensor fluid coupler 20. In one exemplary embodiment, the sensor's fluid coupler 20 includes a local analyzer housing that includes at least a potentiostat. In some embodiments, the housing can include a battery and electronics, such that the sensor 14 can be powered, and data can be collected and/or transmitted to additional system electronics (e.g., electronics units disposed remotely from the sensor, such as on the host's arm, on the host's bed and in the remote analyzer, and the like). In some embodiments, the local analyzer 608 includes a small housing that is connected to the sensor 14 via a short wire (e.g., from about 1 cm or less to about 10 cm or more) and is taped to the host's skin, such as adjacent to the catheter's insertion site on the host's arm or hand. In a further embodiment, the local analyzer 608 includes a connector, such as but not limited to a "plug" configured to mate with a "socket" wired to the sensor 14, such that an electrical connection can be made between the local analyzer 608 and the sensor 14. In another embodiment, the sensor 14 includes a cable having a plug configured to connection to the local analyzer 608 via a socket. In still another embodiment, both the sensor 14 and the local analyzer 608 include cables configured to mate with each other via a plug and socket mechanism. Advantageously, a detachable configuration allows catheter/sensor insertion without a cumbersome connection to the local analyzer 608 as well as re-use of the local analyzer 608. In an alternative exemplary embodiment, the local analyzer 608 is permanently connected to the sensor 14 and cannot be disconnected therefrom; a single use, permanently connected configuration can simplify application to the host, can reduce the possibility of cross-contamination between hosts, does not require cleaning and/or sterilization between hosts, and can reduce operator error during application to the host.

In preferred embodiments, the local analyzer 608 includes at least the minimal electronic components and/or programming required to energize the sensor 14 and collect data therefrom, such as but not limited to a potentiostat. However, in some embodiments, the local analyzer 608 includes additional electronic components that can be programmed to analyze one or more components of the collected raw signal, or to store data, calibration information, a patient ID and the like. In one exemplary embodiment, the local analyzer 608 includes a potentiostat and a battery back up. The battery back up can maintain a potential on the sensor and store data (calibration and/or collected host data) for brief periods of time when the electronics can be disconnected, such as when the host is moved from one location to another. In one exemplary embodiment, the local analyzer 608 is disposed on or adjacent to the sensor 14 and is configured such that the host can be connected to a first remote analyzer 610 at one station, and then disconnected from the first remote analyzer 610, moved to a new location and connected to a second remote analyzer 610 at the new location, and the local analyzer 608 retains sufficient data that the system 600 functions substantially without initialization or substantial delay upon connection to the new (second) remote analyzer 610. In another example, the host can be disconnected from the first remote analyzer 610, taken to another location for a procedure (e.g., for surgery, imaging, and the like) and then reconnected to the first remote analyzer 610 upon return to the original location without substantial loss of system 600 function upon reconnection.

In some embodiments, the local analyzer 608 includes two or more parts, such that only the potentiostat is disposed on or adjacent to the sensor 14 (e.g., sensor fluid coupler 20) or the catheter (e.g., catheter connector 18); other portions of the local analyzer 608 can be disposed remotely from the host, such as in a separate housing wired to the sensor and to the remote analyzer. In one exemplary embodiment, the two parts of the local analyzer 608 can be separated (e.g., unplugged) such that the host can be moved and the local analyzer 608 portion that is attached to the host goes with the host while the remaining portion stays with the remote analyzer 610.

In still other embodiments, all sensor electronics components are disposed remotely from the host, such as in the remote analyzer 610. For example, the sensor 14 can include an appropriate connector, plug and/or wiring to connect the sensor 14 to the remote analyzer 610, which powers the sensor 14, collects raw data from the sensor 14, calibrates the sensor 14, analyzes and presents the data, and the like. In one example, the sensor 14 includes a cable of sufficient length to permit plugging the sensor 14 into a remote analyzer 610 disposed at the host's bedside.

In still other embodiments, the local analyzer 608 can be incorporated into the remote analyzer 610, such as housed in the same body as the remote analyzer 610, for example. In one exemplary embodiment, both the local and remote analyzers 608, 610 are disposed in a housing attached to a support 612 (e.g., connected to an IV pole, placed on a bedside table, connected to the wall, clamped to the head of the host's bed) and connected to the analyte sensor via a wire or cable. In some embodiments, the cables/wires (e.g., for connecting the sensor to the local analyzer and/or the remote analyzer, and/or connecting the local analyzer to the remote analyzer) can be provided in the IV tubing set.

Remote Analyzer

As discussed in the section entitled "Local Analyzer," the integrated sensor system 600 includes a remote analyzer 610. In preferred embodiment, the remote analyzer 610 is configured to at least communicate with the local analyzer 608 and can be configured to control the flow control device 604 described in the sections entitled "Flow Control Device," and "Flow Control Device Function." Generally, the remote analyzer 610 is powered from a standard 120 VAC wall circuit or other suitable power source, for example. In some embodiments, the remote analyzer 610 is disposed at the host's bedside and can be configured to be disposed on a support 612, such as but not limited to, mounted a mobile IV drip pole, attached to the wall, clamped to the host's bed, or sitting on a table or other nearby structure.

In preferred embodiments, the remote analyzer 610 includes a display, such as but not limited to a printout, an LED display, a monitor, a touch-screen monitor and the like. In some embodiments, the remote analyzer 610 includes both a hard copy display, such as a printer configured to print collected data, and a monitor. In some embodiments, the remote analyzer 610 is a programmable touch-screen panel PC configured to have different "screens" and "buttons" for control of system components (e.g., the sensor 14, the flow control device 604, etc.) and to display data, such as but not limited to host identification and condition, host food intake, medication schedules and dosage information, sensor identification, raw data, processed data, calibration information, and the like, such as in tables and/or graphs. In further preferred embodiments, the remote analyzer 610 is configured to be programmed, such that the operator can initiate system functions such as IV fluid line priming, starting and/or stopping the flow control device 604, select among two or more solutions (e.g., between glucose concentrations), select the mode of data delivery (e.g., printer or on-screen), send data to a central location (e.g., the nurse's station or medical records), set alarms (e.g., for low and high glucose), and the like.

In some embodiments, the system 600 is configured to integrate with (e.g., be used in conjunction with) third party medical devices, such as but not limited to a pulse-oxygen meter, a blood pressure meter, a blood chemistry machine, and the like. In such embodiments, the local and/or remote analyzers 608, 610 can be configured to communicate with the third party medical devices, such as but not limited to a patient monitor.

Flow Control Device Function

In some embodiments, the remote analyzer 610 controls the function of the flow control device 604. In some embodiments, the flow control device includes electronics configured to control the flow control device. The flow control device 604 can be configured to perform a number of steps of operation, which are discussed below. Depending upon the system configuration and physician preferences, in some embodiments, one or more of the steps can be performed. In some embodiments, all of the steps are performed. In some embodiments, the steps of operation can be performed in the order in which they are presented herein. In other embodiments, the order of steps of operation can be varied (e.g., repeated, omitted, rearranged), depending upon various parameters, such as but not limited to the calibration solution 602a selected, the particular infusion set selected, catheter 12 size, host condition, analyte of interest, type of sample and location of sample collection, integration with third party devices, additional infusion of fluids and the like.

FIGS. 8A through 8C are schematic illustrations of a flow control device in one exemplary embodiment, including its relative movement/positions and the consequential effect on the flow of fluids through the sensor/catheter inserted in a host. In general, steps performed by the flow control device 604, include the steps of: contacting the sensor 14 with calibration solution 602a (including sensor calibration) and contacting the sensor with a biological sample to be measured. In some embodiments, additional steps can be taken, such as but not limited to keep a vein open (KVO) step and a wash step. In the exemplary embodiment presented in FIGS. 8A though 8C, the flow control device 604 is a roller valve configured to move between at least two positions, 810 and 812, respectively. Movement of the flow control device 604 between positions 810 and 812 effectively concurrently moves the pinch point 808 (e.g., the point at which tubing 606 is pinched) between positions 810 and 812. Additional flow control device positions are discussed below.

The top of FIGS. 8A through 8C are schematic drawings illustrating positions of the flow control device 604. The bottom of FIGS. 8A through 8C, are a cut-away views of an implanted catheter 12, including an indwelling sensor 14, illustrating the corresponding activity at the implantation site, in response to movements of the flow control device 604. For simplicity, for purposes of discussion only, it is assumed that the catheter 12 is implanted in a host's vein, that the sensor 12 does not protrude from the catheter's orifice 12b and that the catheter 14 does not include side holes 902. However, one skilled in the art appreciates that the catheter 14 could be implanted into any vessel of the host or into a variety of extracorporeal devices discussed elsewhere herein.

Step One: Contacting Sensor with Calibration Solution

In general, the system is configured to allow a calibration solution to contact the sensor using a flow control device such as a pump, valve or the like. In some embodiments, such as shown in FIGS. 8A through 8C, the flow control device 604 is a valve configured with a first structure 802 and a second structure 806. For convenience, the first structure 802 is depicted as a roller connected to a rotatable axle 804, however any flow control device such as described in the section entitled "Flow Control Device," can be configured to utilize the concepts and/or functions described herein. In general, when the flow control device is a valve, the valve is configured to allow no flow, gravity flow and/or metered flow through movement of the valve between one or more discreet positions.

In the embodiment shown in FIGS. 8A through 8C, the flow control device 604 is configured such that a tube 606 threaded between the first and second structures 802, 806 (e.g., between the roller and the surface against which the roller presses) is compressed substantially closed. For convenience, the compressed location on the tubing is referred to herein as the "pinch point" 808. In some embodiments, the flow control device 604 is configured such that the pinch point is moved along the tubing, either closer to or farther from the host. As the pinch point 808 is moved closer to the host, the tube 606 is progressively compressed, causing fluid (e.g., solution 602) to be pushed into the host's vascular system (see the corresponding illustration of the sensor within the host's vessel at the bottom of FIG. 8A), at the catheter 12 implantation site. Conversely, as the pinch point 808 is moved away from the host, the portion of tubing 606 on the host side of the pinch point 808 progressively expands, causing sample (e.g., blood) to be drawn up into the catheter lumen 12a. In an alternative embodiment, the flow control device 604 is configured such that the pinch point is substantially stationary and the first and second structures selectively compress the tubing at the pinch point (e.g., the tube 606 is either pinched fully closed or is fully open), which either stops or allows the flow of solution 602a.

In the exemplary embodiment shown in FIG. 8A (bottom), the catheter 12 is implanted in the host's vein 906 (or artery), as described elsewhere herein. A sensor 14 is disposed with the catheter 12. The catheter 12 is fluidly connected to a first end of tubing 606 that delivers the solution 602a to the catheter 12. The solution 602a can move out of the catheter 12 and a sample of blood 814 can move in and out of the catheter 12, via the catheter's orifice 12b. In some alternative embodiments, the catheter 12 includes optional sidewall holes 902 (see FIG. 9, described elsewhere herein) and the solution 602a and blood can move in and out of the catheter 12 via the sidewall holes 902 and the catheter orifice 12b. In some alternative embodiments, the sensor is configured to move in and out of the catheter. In some embodiments, the catheter orifice 12b is disposed in the sidewall 904 (e.g., near the catheter's tip) instead of at the tip. Tubing 606 is fluidly connected to the reservoir 602 on a second end (see FIGS. 6 and 7).

Referring now to a calibration phase to be performed by the exemplary valve of FIG. 8A, in preferred embodiments, the flow control device 604 is configured to perform a step of contacting the sensor 14 with solution 602a, wherein the flow control device 604 moves from position 810 to position 812 (e.g., forward, toward the host/catheter). When the flow control device 604 moves from position 810 to position 812, the pinch point 808 is moved from position 810 to position 812. As the pinch point 808 is moved from position 810 to position 812, a first volume of the calibration solution 602a is pushed through the tubing 606, toward the catheter 12.

Referring again to the bottom of FIG. 8A, a second volume of the solution 602a, which is substantially equal to the first volume, is pushed into the host's vein 906, in response to the first volume of solution 602a moving toward the host. As the second volume of solution 602a is pushed through the catheter 12 and into the host's vein the second volume contacts (e.g., bathes) the analyte sensor 14, including the analyte sensor's electroactive surfaces. In some embodiments, the volume (e.g., the first and second volumes of fluid) moved is from about 3 µl or less to about 1 ml or more. In some preferred embodiments, the volume is from about 10 µl to about 500 µl, or more preferably from about 15 µl to about 50 µl. In general, the volume of fluid pushed through the catheter in a particular phase (e.g., calibration phase) is dependent upon the timing of the phase. For example, if a long phase, such as a 20 minute calibration phase (e.g., as compared to a shorter 5 minute phase) were selected, the volume of fluid pushed during the long phase would be 4× greater than the volume of fluid pushed during the shorter phase. Accordingly, one skilled in the art appreciates that the above described ranges of fluids infusion can be increased and/or decreased simply be increasing or decreasing the measurement phase and/or intervals (i.e., timing). In preferred embodiments, the fluid is moved at a flow rate that is sufficiently slow that the calibration solution's temperature substantially equilibrates with the temperature of the tissue surrounding the in vivo portion of the catheter and/or temperature of bodily fluid (e.g., blood), such that the temperature of the calibration solution and the temperature of the blood are substantially the same. In preferred embodiments, the flow rate is from about 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, 0.001 µl/min or less to about 1, 1.5, 2, 2.5, 3, 3.5, 4, 4.5, 5, 5.5, 6, 6.5, 7, 7.5, 8, 8.5, 9, 9.5, 10.0 ml/min or more. In one exemplary embodiment, the flow control device 604 maintains a flow rate from about 0.9, 0.8, 0.7, 0.6, 0.5, 0.4, 0.3, 0.2, 0.1 or 0.05 µl/min or less to about 1.0, 1.1, 1.2, 1.3, 1.4, 1.5, 1.6, 1.7, 1.8, 1.9 or 2.0 ml/min or more. In one exemplary embodiment, the flow rate is from about 1 µl/min to about 1.0 ml/min. In one exemplary embodiment, the flow rate is from about 0.01 ml/min to about 0.2 ml/min. In another exemplary embodiment, the flow rate is from about 0.05 ml/min to about 0.1 ml/min. In some embodiments, the flow rate is 0.0 ml/min.

In some embodiments, the system is configured such that the speed of the movement between the first and second discreet positions is regulated or metered to control the flow rate of the fluid through the catheter. In some embodiments, the system is configured such that the time of movement between the first and second discreet positions is from about 0.001, 0.005, 0.01, 0.02, 0.03, 0.04, 0.05, 0.06, 0.07, 0.08, 0.09, 0.1, 0.15, 0.2, 0.25, 0.3, 0.4, 0.5, 0.6, 0.7, 0.8, 0.9 or 1.0 seconds or less to about 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29 or 30 seconds or more, preferably from about 0.5 to 10 seconds. In some embodiments, the system is configured such that an amount of pinch of the tubing regulates the flow rate of the fluid through the catheter. In some embodiments, the fluid flow is regulated through a combination of metering and/or pinching techniques, for example. Depending on the type of flow control device (e.g., valve), a variety of methods of metering and/or regulating the flow rate can be implemented as is appreciated by one skilled in the art.

Preferably, the sensor is configured to measure a signal associated with the solution (e.g., analyte concentration) during the movement of the flow control device from position 810 to position 812 and/or during contact of the sensor 14 with the solution 602a. Electronics, such as an electronic module included in either the local or remote analyzer 608, 610 controls signal measurement and processing, such as described in more detail elsewhere herein.

In general, a calibration measurement can be taken at any time during the flow control device 604 movement from position 810 to position 812, and including a stationary (stagnant) time there after. In some embodiments, one or more calibration measurements are taken at the beginning of the flow control device 604 movement from position 810 to position 812. In other embodiments, one or more calibration measurements are taken at some time in the middle of the flow control device 604 movement from position 810 to position 812. In some embodiments, one or more calibration measurements are taken near the completion of the flow control device 604 movement from position 810 to position 812. In some embodiments, one or more calibration measurements are taken after completion of the flow control device 604 movement from position 810 to position 812. In still other embodiments, the flow control device is positioned such that fluid can flow followed by positioning the flow control device such that there is no fluid flow (e.g., 0 ml/min) during the calibration measurement. In preferred embodiments, one or more calibration measurements are taken when the temperature of the solution 602a has substantially equilibrated with the temperature of the tissue surrounding the in vivo portion of the implanted catheter 12. Processing of calibration measurements and sensor calibration are described elsewhere herein.

As a non-limiting example, in some embodiments, the sensor can be calibrated using one or more reference solutions. For example, if the analyte is glucose, a suitable reference (e.g., calibration solution) is saline containing 0, 25, 50, 75, 100, 125, 150, 175, 200, 225, 250, 275, 300 mg/dl glucose or more. In some embodiments, two or more such reference solutions can be used to calibrate the sensor. In some embodiments, a baseline value of the sensor can be obtained by generating a signal when the sensor is exposed to a 0 mg/dl reference solution (e.g., 0 mg/dl analyte). In some embodiments, updated baseline values are continuously obtained by repeatedly exposing the sensor to the 0 mg/dl reference solution, such as every 1, 2, 3, 4, 5, 10, 20, 30, 40, 50, or 60 or more minutes. In some embodiments, updated baseline values are continuously obtained by exposing the sensor to the 0 mg/dl reference solution for periods of time and continuously collecting baseline values. For example, the sensor can be exposed to the 0 mg/dl reference solution for 5, 10, 15, 20, 25, 30, 40, 50, or 60 minutes, or longer, while baseline signals are continuously generated. In this embodiment, sensitivity m calibration values can be obtained intermittently by exposing the sensor to an analyte-containing reference solution intermittently, such as but not limited to every 5, 10, 15, 20, 25, 30, 40, 50, or 60 minutes, or longer, such as at the conclusion of the exposure to the 0 mg/dl solution. In other embodiments, such calibrations measurements (e.g., to obtain a baseline value) are performed "intermittently," such as once every 24 hours.

In some embodiments, sensitivity m calibration values are obtained substantially continuously/continually, such as by exposure of the sensor to one or more analyte-containing reference solutions every 1, 2, 3, 4, 5, 10, 20, 30, 40, 60 or more minutes. In some embodiments, sensitivity m calibration values are obtained substantially continuously/continually by exposure of the sensor to one or more analyte-containing reference solutions for a period of time, such as but not limited to for 5, 10, 15, 20, 25, 30, 40, 50, or 60 minutes, or longer, while sensitivity signals are continuously generated. In one exemplary embodiment, continuous calibration measurements are performed by passing a 100-mg/dl glucose calibration solution across the sensor (e.g., to detect shifts in sensitivity m), and the intermittent calibration measurements are performed to determine baseline b, by passing a 0-mg/dl calibration solution across the sensor. While not wishing to be bound by theory, it is believed that in some circumstances, baseline drift is greater than sensitivity drift. Accordingly, in some embodiments, the system is configured to perform baseline calibration measurements (with 0-mg/dl glucose) automatically (e.g., every 5-minutes) and a sensitivity calibration measurement (with 100-mg/dl) intermittently (e.g., every hour).

Step Two: Sample Collection and Measurement

In general, the system is configured to allow a sample (e.g., blood) to contact the sensor using the flow control device. Referring now to the top of FIG. 8B, the flow control device 604 is configured to draw back (or take-in) a sample (e.g., blood) from the host. For example, to collect a sample, the flow control device 604 reverses and moves backward (e.g., away from the host/catheter), from position 812 to position 810, thereby causing the pinch point 808 to move away from the host. As the pinch point is moved from position 812 to position 810, the tube 606 (on the host side of the pinch point 808) expands (e.g., the tube volume increases).

Referring now to the bottom of FIG. 8B, as the tube volume increases, a small, temporary vacuum is created, causing sample 814 (e.g., blood) to be taken up into the catheter lumen 12a. In some embodiments, the flow control device 604 is configured to take up a sufficient volume of sample 814 such that at least the sensor's electroactive surfaces are contacted by the sample 814. In some embodiments, a sample volume of from about 95, 90, 85, 80, 75, 70, 65, 60, 55, 50, 45, 40, 35, 30, 25, 20, 15, 10, 9.0, 8.0, 7.0, 6.0, 5.0, 4.0, 3.0, 2.0, 1.0, 0.9, 0.8, 0.7, 0.6, 0.5, 0.4, 0.3, 0.2, or 0.1 μl or less to about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, or 2 ml or more is taken up into the catheter 12 and is sufficient to cover at least the electroactive surfaces of the sensor 14. In some embodiments, the sample volume is from about 10 μl to about 1 ml. In some embodiments, the sample volume is from about 20 μl to about 500 μl. In other embodiments, the sample volume is from about 25 μl to about 150 μl. In other embodiments, the sample volume is from about 2 μl to about 15 μl.

In some embodiments, the sample taken up into the catheter is taken up substantially no farther than the skin (or a plane defined by the skin of the patient). In some embodiments, the sample is taken up into the catheter substantially no farther than the catheter's inner lumen (e.g., substantially not into the IV tubing.)

In some embodiments, the rate of sample take-up is sufficiently slow that the temperature of the sample substantially equilibrates with the temperature of the surrounding tissue. Additionally, in some embodiments, the rate of sample take-up is sufficiently slow such that substantially no mixing of the sample 814 and solution 602a occurs. In some embodiments, the flow rate is from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more. In one exemplary embodiment, the flow rate is from about 0.001 ml/min or less to about 2.0 ml/min or more. In preferred embodiments, the flow rate is from about 0.01 ml/min to about 1.0 ml/min. In one exemplary preferred embodiment, the flow rate is from about 0.02 ml/min to about 0.35 ml/min. In another exemplary preferred embodiment, the flow rate is from about 0.0.02 ml/min to about 0.2 ml/min. In yet another exemplary preferred embodiment, the flow rate is from about 0.085 ml/min to about 0.2 ml/min.

As described above, in some embodiments, the system is configured such that the speed of the movement between the first and second discreet positions is regulated or metered to control the flow rate of the fluid through the catheter. In some embodiments, the system is configured such that the time of movement between the first and second discreet positions is from about 0.001, 0.005, 0.01, 0.02, 0.03, 0.04, 0.05, 0.06, 0.07, 0.08, 0.09, 0.1, 0.15, 0.2, 0.25, 0.3, 0.4, 0.5, 0.6, 0.7, 0.8, 0.9 or 1.0 seconds to about 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29 or 30 seconds, preferably from about 0.5 to 10 seconds. In some embodiments, the system is configured such that an amount of pinch of the tubing regulates the flow rate of the fluid through the catheter. In some embodiments, regulate the fluid flow through a combination of metering and/or pinching techniques, for example. Depending on the type of flow control device (e.g., valve), a variety of methods of metering and/or regulating the flow rate can be implemented as is appreciated by one skilled in the art.

Measurements of sample analyte concentration can be taken while the electroactive surfaces are in contact with the sample 814. An electronics module included in the local and/or remote analyzer 608, 610 controls sample analyte measurement, as described elsewhere herein. In some embodiments, one sample measurement is taken. In some embodiments, a plurality of sample measurements are taken, such as from about 2, 3, 4, 5, 6, 7, 8, 9, or 10 measurements to about 20, 25, 30, 35, 40, 45 or 50 or more measurements and/or at a sample rate of from about 1 measurement per second to about 1 measurement per minute. In some embodiments, the rate is from about 1 measurement per 2 seconds to about 1 measurement per 30 seconds. In preferred embodiments, sample measurements are taken substantially continuously, such as but not limited to substantially intermittently, as described elsewhere herein.

Optional Step: Flush

In some exemplary embodiments, the flow control device 604 is configured to perform one or more steps, in addition to steps one and two, described above. A flush step, during which the sensor 14 and/or catheter 12 are substantially washed and/or cleaned of host sample, is one such optional step.

Referring now to the top of FIG. 8C, the exemplary flow control device 604 performs a flush step by moving forward from position 810 (e.g., toward the host/catheter), past position 812 (e.g., around and over the top of structure 804) and back to position 810. For convenience, the movement illustrated by an arrow in the top of FIG. 8C is referred to herein as the "flush movement."

Referring now to the bottom of FIG. 8C, the flush movement pushes forward a volume of solution 602a (e.g., a third volume) that pushes the collected blood sample 814 into the host. In some embodiments, the third volume of solution 602a is substantially equal to the first and second volumes described above. In some embodiments, the flush movement is repeated at least one time. In some embodiments, the flush movement is repeated two, three or more times. With the exception of the first flush movement, which pushes the sample 814 back into the host, each repeat of the flush movement pushes a volume of solution 602a into the host, for example. In some embodiments, the flush movement pushes the third volume of solution 602a into the host at a rate of from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, or 10.0 ml/min or more. In some embodiments the flush movement pushes the third volume of solution into the host at a rate of from about 1.0 μl/min to about 1.0 ml/min. In alternative embodiments, the flow control device 604 is moved to a fully opened position (e.g., no pinch) and the flow regulator 602b is set at a setting that allows more solution (e.g., an increased volume and/or at a faster rate) to infuse into the host than during the calibration phase (e.g., step one, above). In preferred embodiments, the flush movement washes enough blood off of the analyte sensor's electroactive surfaces that the sensor 14 can measure the solution 602a substantially without any interference by any remaining blood. In some embodiments, the flush step is incorporated into step one, above.

Generally, the solution 602a is flushed through the catheter 12, to ensure that a sufficient amount of the sample has been removed from the sensor 14 and the catheter lumen 12a, such that a calibration measurement can be taken. However, in some embodiments, sample is collected, measured and flushed out, followed by collection of the next sample, substantially without sensor calibration; the flush step can be executed between samples to ensure that the sample being analyzed is substantially uncontaminated by the previous sample. In some embodiments, a relatively extended flush is used, while in other embodiments the flush is just long enough to ensure no blood remains.

In some embodiments, the effectiveness of the flushing movement is dependent upon the solution 602a composition (e.g., concentrations of sodium chloride, glucose/dextrose, anticoagulant, etc.). Accordingly, the amount of solution 602a required to ensure that substantially no sample remains in the catheter 12 and/or on the sensor 14 can depend on the solution 602a composition. For example, relatively more flush movements may be required to completely remove all of the sample when a non-heparinized solution is selected than when a heparinized solution is selected. In some embodiments, the effectiveness of the flushing movement is also dependent upon the flush flow rate. For example, a relatively faster flow rate can be more effective in removing sample from the sensor than a slower flow rate, while a slower flow rate can more effectively move a larger volume of fluid. Accordingly, in some embodiments, the number of flush movements selected is dependent upon the calibration solution and flow rate selected. In some embodiments, the flush step flow rate is from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, or 10.0 ml/min or more, and last for from about 55, 50, 45, 40, 35, 30, 25, 20, 15, 10, 9, 8, 7, 6, 5, 4, 3, 2, or 1 seconds or less to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 minutes or more. In one exemplary embodiment, about 0.33 ml of solution 602a is flushed at a rate of about 1.0 ml/min, which takes about 20 seconds.

In some embodiments, the flush step returns the sample 814 (e.g., blood) to the host, such that the host experiences substantially no net sample loss. Further more, the flush movement washes the sensor 14 and catheter lumen 12a of a sufficient amount of sample, such that an accurate calibration measurement (e.g., of undiluted solution 602a) can be taken during the next step of integrated sensor system 600 operations. In some embodiments, the number of sequential flush movements is sufficient to only wash substantially the sample from the sensor 14 and catheter lumen 12a. In other embodiments, the number of sequential flush movements can be extended past the number of flush movements required to remove the sample from the sensor and catheter lumen, such as to provide additional fluid to the host, for example.

At the completion of the flush step, the flow control device 604 returns to step one, illustrated in FIG. 8A. In some embodiments, the steps illustrated in FIGS. 8A through 8C are repeated, until the system 600 is disconnected from the catheter/sensor, either temporarily (e.g., to move a host to an alternate location for a procedure) or permanently (e.g., at patient discharge or expiration of sensor life time). In some embodiments, additional optional steps can be performed.

Optional Step: Keep Vein Open (KVO)

Thrombosis and catheter occlusion are known problems encountered during use of an IV system, such as when the fluid flow is stopped for a period of time or flows at a too slow rate. For example, thrombi in, on and/or around the catheter 12, such as at the catheter's orifice 12b can cause an occlusion. Occlusion of the catheter can require insertion of a new catheter in another location. It is known that a slow flow of IV solution (e.g., saline or calibration fluid; with or without heparin) can prevent catheter occlusion due to thrombosis. This procedure is know as keep vein open (KVO).

In general, to infuse a fluid into a host, the infusion device must overcome the host's venous and/or arterial pressure. For example, during infusion of a hydration fluid, the IV bag is raised to a height such that the head pressure (from the IV bag) overcomes the venous pressure and the fluid flows into the host. If the head pressure is too low, some blood can flow out of the body and in to the tubing and/or bag. This sometimes occurs when the host stands up or raises his or her arm, which increases the venous pressure relative to the head pressure. This problem can be encountered with any fluid infusion device and can be overcome with a KVO procedure. KVO can maintain sufficient pressure to overcome the host's venous pressure and prevent "back flow" of blood into the tubing and/or reservoir.

In some embodiments, the flow control device 604 can be configured to perform a KVO step, wherein the fluid flow rate is reduced (but not completely stopped) relative to the calibration and/or wash flow rates. In preferred embodiments, the KVO flow rate is sufficient to prevent the catheter 12 from clotting off and is relatively lower than the flow rate used in step one (above). In preferred embodiments, the KVO flow rate is sufficient to overcome the host vessel pressure (e.g., venous pressure, arterial pressure) and is relatively lower than the flow rate used in step one (above). In some embodiments, the KVO flow rate is from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more. In some preferred embodiments, the KVO flow rate is from about 0.02 to about 0.2 ml/min. In some more preferred embodiments, the KVO flow rate is from about 0.05 ml/min to about 0.1 ml/min). In some embodiments, the KVO flow rate is less than about 60%, 50%, 40%, 30%, 20%, or 10% of the calibration and/or flush flow rate(s). In some embodiments, the KVO step is performed for from about 0.25 minutes or less to about 20 minutes or more. In preferred embodiments, the solution 602a flows at a rate such that the temperature of the solution 602a substantially equilibrates with the temperature of the tissue surrounding the in vivo portion of the catheter 12. Advantageously, equilibrating the solution 602a temperature with that of the surrounding tissue reduces the effect of temperature on sensor 14 calibration and/or sample measurement, thereby improving sensor accuracy and consistency. In some embodiments, the KVO step can be incorporated into one or more of the flow control device steps of operation described elsewhere herein, including steps one and two, and the flush step, above.

The KVO step can be executed in one or more ways. In some embodiments, the flow control device 604 can be configured to move to at least one addition position, wherein the tube 606 is partially pinched. For example, the flow control device 604 is configured to move to a position such that the pinch point 808 is partially closed/open. For example, in the embodiment shown in FIGS. 8A through 8C, the flow control device 604 can be moved forward somewhat past position 812, such that the roller 802 causes the tube 606 to be partially pinched. In another example, the flow control device 604 can be moved backwards somewhat behind position 810, such that the roller 802 again causes the tube 606 to be partially pinched. In preferred embodiment, the amount of pinch can be adjusted such that the desired KVO flow rate can be achieved. In some alternative embodiments, KVO is performed by moving the flow control device between positions

810 and 812 (e.g., see FIG. 8A) at a reduced speed, such that the flow rate is from about 0.1 μl/min or less to about 0.5 ml/min or more. In some embodiments, the system is configured such that the time of movement between the first and second discreet positions is from about 0.25 to 30 seconds, preferably from about 5 to 15 seconds. In some preferred embodiments, the tubing is pinched fully closed (e.g., between structures 802 and 806) during the movement from position 810 and 812 (e.g., see FIG. 8A). In some preferred embodiments, after the flow control device reaches position 812, the flow control device flips over the top and back to position 810 (e.g., see FIG. 8C) at a substantially rapid speed that the flow rate remains substantially unchanged. In an even further embodiment, during the KVO step the flow control device alternates between the slow and fast movements at least two times, such that the KVO step lasts a period of time.

In some circumstances, signal artifacts can occur due to the location a catheter is implanted and if the host has moved his or her arm (where the catheter is implanted/inserted) to certain positions (e.g., holding his or her arm up, vertically and/or hanging down). While not wishing to be bound by theory, it is believed that these signal artifacts can arise because femoral veins are relatively small (e.g., 1-2 mm diameter), and in some circumstances an inserted catheter can block the flow of at least some incoming blood, such that the incoming blood is "diverted" around the implantation site by flowing through adjacent alternative veins and/or capillaries. As a result, the blood in the vein containing the catheter can be diluted for a period of time (e.g., after flushing), which can lead to diluted analyte values, which appear as signal artifacts. As time passes, the dilution of the sample by the saline flush dissipates and undiluted blood samples are collected, which leads to termination of the signal artifact(s). The way the host holds his or her arm can affect the length of time required for the signal artifact to dissipate. For example, in some embodiments, if the host holds his or her arm at chest level, the vein is filled by blood at a first rate, and the sample dilution is dissipated within a first time period. If the host holds his or her arm down low, the blood flows through the vein at a second rate that is faster than the first rate, and the dilution is relieved sooner (e.g., within a second time period that is shorter than the first time period). Conversely, if the host raises his or her arm over his or her head, the blood flows into the vein at a third rate that is slower than the first rate; which results in the dilution dissipating within a third period of time that is longer than the first period of time.

In some embodiments, the signal artifacts resulting from blocking of the vein at the site of catheter implantation and subsequent sample dilution can be substantially eliminated (or reduced/shortened) by reducing the volume of 0 mg/dl solution used to wash away the 100-mg/dl calibration solution, depending upon the volume of the 100 mg/dl calibration solution used to calibrate the sensor. For example, in some embodiments a 0.5×, 1×, 2×, 3×, 4×, 5×, 6×, 7×, 8×, 9×, 10× (or greater) volume of the 0-mg/dl solution can be used to sufficiently wash out the volume 100 mg/dl calibration solution. In some embodiments, wherein a sufficiently small volume of 100 mg/dl solution is used during calibration, the flushing can be done at the KVO rate. In some embodiments, signal artifacts are prevented by using smaller volumes of calibration/wash fluids but switching more frequently between the fluids.

Maintaining Patency During a Sensor Session

In some embodiments, the analyte sensor is implanted in the host (e.g., via a vascular access device) for an extended period of time. For example, in some embodiments, a sensor session can last 3, 5, 7, 10, 21, 30 or more days. As used herein, the term "sensor session" is a broad term and refers without limitation to the period of time of sensor is applied to (e.g., implanted in) the host and is being used to obtain sensor values. For example, in some embodiments, a sensor session extends from the time of sensor (e.g., including implanting the vascular access device) implantation to when the sensor is removed. During this period of time, the vein's condition can deteriorate, such that vein and/or vascular access device is no longer patent (e.g., freely open, not occluded), and the system can no longer function optimally. While not wishing to be bound by theory, it is believed that patency can be substantially maintained during a sensor session by metering a reference/calibration solution through the vascular access device a sufficient amount of time (e.g., a percentage of the duration of the sensor session). As used herein, the phrase "a sufficient amount" is a broad term and refers without limitation to an amount that provides a desired function. For example, a sufficient amount can be a sufficient amount of time, a sufficient amount of fluid volume, and the like. In some embodiments, a sufficient amount can be expressed numerically, such as a percent (%), a volume, a weight, a period of time (e.g., minutes, hours, days, months), and the like. For example, in some embodiments, the flow control device is configured to meter a sufficient amount of a reference solution (e.g., through the vascular access device) such that the analyte sensor contacts the reference solution at least about 50%, 55%, 60%, 65%, 70%, 75%, 80%, 85%, 90% or 95% of the time during a sensor session. It is generally preferred that the analyte sensor contacts the reference solution from about 50% to about 80%, 85%, 90% or 95% of the time during a sensor session In some embodiments, the sensor is located in or on the vascular access device and the flow control device meters the reference solution through the vascular access device for a sufficient amount of time (e.g., a portion of the sensor session), with a sufficient flow rate (e.g., from about 0.05 ml/min to about 0.5 ml/min, preferably about 0.1 ml/min) that the vascular access device remains patent during a sensor session. Advantageously, the flow rate is sufficient to maintain a patent vessel without infusing excess fluid. In a preferred embodiment, the vascular access device remains patent during a sensor session of at least about 1, 3, 5, 7, 10, 15, 20, 25, or 30 days, or longer. In one exemplary embodiment, the flow control device is configured to meter the reference solution through the vascular access device for at least about 50% of a sensor session, at a flow rate from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more, such that the vascular access device remains patent during a sensor session of at least about 5 days. In another exemplary embodiment, the flow control device is configured to meter the reference solution through the vascular access device for at least about 65% of a sensor session, at a flow rate from about 0.001 ml/min to about 2.0 ml/min, such that the vascular access device remains patent during a sensor session of between about 5 days and about 30 days. In still another exemplary embodiment, the flow control device is configured to meter the reference solution through the vascular access device for between about 50% and about 80% of a sensor session, at a flow rate from about 0.001 ml/min to about 2.0 ml/min, such that the vascular access device remains patent during a sensor session of at least about 30 days.

Preventing Sensor Biofouling During a Sensor Session

As discussed above, sensor sessions can last from about 3 days to 30 or more days. During this period of time, the sensor is repeatedly exposed to (contacted with) a bodily fluid (e.g., blood). In some circumstances, during sensor exposure to blood, some blood components/material, such as but not limited to proteins, lipids, carbohydrates and cells, can "stick" to the sensor, such that a layer of this material coats at least part of the sensor and the sensor can no longer function accurately. This process of blood components sticking to the sensor and disrupting the sensor's function is generally referred to as "biofouling." While not wishing to be bound by theory, it is believed that biofouling can be substantially reduced and/or eliminated by limiting the length of time the sensor is exposed to blood and/or by maintaining the sensor in a reference solution (or saline) a substantial portion of the sensor session, whereby sensor accuracy is maintained throughout the sensor session. Washing the sensor is described in detail in the section entitled "Maintaining Patency During A Sensor Session."

As a non-limiting example, in some embodiments, the flow control device is configured to meter the reference solution, such that the reference solution contacts the sensor a substantial amount of time such that biofouling does not occur for at least about 3 days of sensor use. For example, the sensor can be contacted with the reference solution about 50%, 60%, 70%, 80%, 90%, or 95% of the sensor session duration. In preferred embodiments, the system is configured such that biofouling does not occur for at least about 7, 10, 21, 30 or more days of sensor use.

In one exemplary embodiment, wherein the sensor is located in or on a vascular access device, the system includes a flow control device configured to meter a reference solution through the vascular access device for a sufficient amount of time and with a sufficient flow rate that substantially no biofouling of the sensor occurs during a sensor session of at least about 3 days. For example, in some embodiments, the flow control device meters the reference solution through the vascular access device for at least about 50% of a sensor session, at a flow rate from about 0.001 ml/min to about 2.0 ml/min, such that substantially no biofouling of the sensor occurs during a sensor session of at least about 5 days. In another exemplary embodiment, the flow control device meters the reference solution through the vascular access device for at least about 65% of a sensor session, at a flow rate from about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 ml/min or less to about 1.0, 1.1, 1.2, 1.3, 1.4, 1.5, 1.6, 1.7, 1.8, 1.9 or 2.0 ml/min or more, such that substantially no biofouling of the sensor occurs during a sensor session of between about 5 days and about 30 days. In still another exemplary embodiment, the flow control device meters the reference solution through the vascular access device for between about 50% and about 80% of a sensor session, at a flow rate from about 0.001 ml/min to about 2.0 ml/min, such that substantially no biofouling of the sensor occurs during a sensor session of at least about 30 days.

Alternative Flow Control Device Configurations

As disclosed above, the flow control device 604 can be configured a variety of ways, which can require modifications to one or more of the steps of operation described above. For example, in some embodiments, the flow control device 604 can be configured to include a simple pinch valve, wherein the valve can be configured to open, close or partially open. In some embodiments, the flow control device 604 can be configured to include a non-linear rolling pinch valve, wherein the roller can move back and forth between opened, closed and partially opened positions, for example.

In some embodiments, the flow control device 604 can include one roller 802 (e.g., first structure) attached to an axle 804 and configured to press against a curved surface 806 (e.g., second structure), such that when the roller 802 is pressing against the curved surface 806 at or between positions 810 and 812, the tubing 606 is pinched completely closed and the flow control device 604 moves the roller 802 forward (e.g., toward the host). In one exemplary embodiment, the flow control device 604 can be configured to perform step one (above, contacting the sensor 14 with solution 602a) by moving the roller 802 forward (e.g., rotating from position 810 to 812, see FIG. 8A), thereby causing solution 602a to flow over the sensor 14. In some embodiments, the flow control device 604 is configured to perform step two (contacting the sensor 14 with sample) by moving the roller 802 backwards (e.g., rotating from position 812 to 810, see FIG. 8B), thereby causing blood 814 to enter the catheter 12 and contact the sensor 14. Additionally, the flow control device 604 can be configured to perform a wash or KVO step by moving the roller 802 forward (from position 810) past position 812 and around the axle 804 until position 810 is again reached a plurality of times sequentially (e.g., see FIG. 8C). In a further example, the flow control device 604 includes two, three or more rollers 802 arranged about axle 804, such as by attachment to an oblong body attached to the axle. In some embodiments, the flow control device includes a plurality of rollers arranged about the axle, wherein the flow control device performs KVO by rotating the rollers about the axle a plurality of times, to substantially continuously push (e.g., for a period of time) the solution forward into the host.

In one alternative embodiment, back flow is substantially stopped, blocked and/or prevented by incorporation of a one-way, pressure-controlled valve into the system, such as at or adjacent to the catheter or sensor connector, whereby fluid can flow into the host only when fluid pressure (e.g., head pressure) is applied to the reservoir-side of the valve. In other words, fluid can only flow in the direction of the host (e.g., toward the host), not backwards towards the reservoir. In some embodiments, the valve is a two-way valve configured such that the pressure required to open the valve is greater than the venous pressure, such that back flow is substantially prevented.

The preferred embodiments provide several advantages over prior art devices. Advantageously, the movement of the solution 602a and sample occur at a metered rate and are unaffected by changes in head pressure, such as but not limited to when the host elevates his or her arm or gets up to move around. Also, sample loss to the host is minimized, first by returning all collected samples to the host; and second by substantially preventing back-flow from the host (e.g., into the tubing or reservoir) with a "hard stop" (e.g., a point beyond which the flow control device cannot move fluid into or out of the host). For example, in one preferred embodiment, the flow control device can be configured to deliver no more than 25-ml of solution to the host per hour. In another exemplary embodiment, the flow control device can be configured to draw back no more than 100 µl of blood at any time. Advantageously, the flow rate of solution 602a and sample 814 is carefully controlled, such that both the sample 814 and the solution 602a remain substantially undiluted. Additionally, the solution 602a warms to the host's local body temperature, such that the integrated sensor system 600 is substantially unaffected by temperature coefficient and sensor 14 accuracy is increased.

FIGS. 10A through 10D illustrate one exemplary embodiment of a flow control device 604 configured and arranged for use with a vascular access device (e.g., catheter and/or fluid coupler) and analyte sensor, such as those described elsewhere herein. The flow control device includes a groove 803 configured to receive the tubing assembly therein 606a. In some embodiments, the groove 803 is configured and arranged to receive the tubing (of the tubing assembly) in a substantially straight configuration. The groove 803 intersects with a valve roller mechanism, which includes an oblong body comprising two rollers 802 (e.g., corresponding to the first structure 802, which is attached to axle 804 of the embodiment shown in FIGS. 8A-8C) and a compression surface 806 (e.g., corresponds to the second structure 806 of the embodiment shown in FIGS. 8A-8C). The valve includes at least two valve positions, a gravity flow valve position and a controlled-flow valve position. FIG. 10C illustrates one embodiment of the gravity flow valve position, in which the rollers 802 are positioned such that they do not compress, pinch and/or occlude the tubing, such that fluid flowing from the IV bag can flow freely through the tubing 606b in the valve. At gravity flow, the rate of fluid flow through tubing 606b is from about 600-ml/hr (e.g., about 10 ml/min) to about 700-ml/hr (e.g., about 1.2 ml/min), depending upon the height of the IV bag 602.

FIG. 10D illustrates one embodiment of the controlled-flow valve position, in which a roller 802 is positioned such that the tubing 606b (of the tubing assembly) is pinched between the roller 802 and compression surface 806 (e.g., pinch point 808 exists), such that movement of fluid through the valve is controlled by the rotation of the oblong body (e.g., to which the roller is attached) on its axle. In the controlled flow position, the valve is configured and arranged to move fluid forward and/or backward at various rates, depending upon the speed and direction of oblong body rotation on the axle. Flow rates can be positive (e.g., infusing fluid) or negative (e.g., drawing back fluid/blood) and can range from about −10.0, −9.0, −8.0, −7.0, −6.0, −5.0, −4.0, −3.0, −2.0, 1.0, −0.9, −0.8, −0.7, −0.6, −0.5, −0.4, −0.3, −0.2, −0.1, −0.05, −0.01, 0.0, 0.01, 0.05, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0 ml/hr to about 20.0, 30.0, 40.0, 50.0, 60.0, 70.0, 80.0, 90.0, 100.0, 110.0, 130.0, 150.0, 175.0, 200.0, 225.0, 250.0, 275.0, 300.0, 350.0, 400.0, or 450.0 ml/hr or more. Useful flow rates and valve movement between the gravity flow and controlled-flow valve positions are described in greater detail elsewhere herein with reference to FIG. 10E.

The valve is configured to receive the tubing 606b (e.g., of the tubing assembly 606a), such as via groove 803 (e.g., tubing path or channel). One skilled in the art understands that while FIGS. 10A-10D illustrate groove 803 running from the top of the valve to the bottom (e.g., on the face or front of the device), additional configurations are possible. Namely, the groove can be located in any direction or orientation along any surface of the device (e.g., top, bottom, sides), or the groove can be enclosed within the device, such as within a housing configured cover, supports and/or limit access to the valve, a portion of the tubing, and/or accessory devices. For example, in some embodiments, the valve is located within a housing, such that the valve and the tubing assembly are accessed via a door. The housing can include one or more orifices, such that the tubing can intersect (e.g., pass through) a wall of the housing and be installed into the valve within the housing. In some embodiments, the door includes a locking mechanism, such as but not limited to a mechanical key or electronics code key (e.g., electronically, such as such as to prevent tampering with the device).

The valve is configured for uni-directional, releasable installation of the tubing assembly 606a (also referred to herein as "tubing set"), such that the tubing assembly's elastic central portion 606b (e.g., tubing) is received by the groove and the tubing's fluid connectors 606c, 606d are disposed at opposite ends of the groove, in some embodiments. In some embodiments, the groove is sized to be somewhat longer than the central portion of the tubing assembly, such that the tubing (of the tubing assembly) must be stretched (e.g., by grasping the connectors and pulling in opposite directions) prior to and/or during installation into the channel/groove. After installation, the connector ends are released, such that the tubing relaxes. However, the tubing remains stretched (e.g., relative to its un-stretched state prior to installation) after installation. Maintaining the tubing in a stretched state can help maintain the tubing assembly within the valve without the tubing moving, twisting, kinking or falling out of the valve. The tubing assembly is configured for fluid communication with an IV bag (e.g., fluid reservoir 602), such as via the first connector 606c, and with the circulatory system of the host, such as via fluid connection of the second connector 606d to a catheter implanted in the host.

In some embodiments, the valve is configured and arranged to receive the tubing assembly in only one orientation. For example, in some embodiments, the valve and the tubing assembly are configured and arranged to releasably interlock such that a portion of the valve mechanically interlocks with a portion of the tubing assembly. For example, in some embodiments, the valve includes the first portion of a mechanical interlock and the tubing assembly includes the second portion of the mechanical interlock. For example, in FIG. 10A, the valve includes a female interconnection 809 sized and shaped to releasably receive and engage the tubing assembly's second connector 606d (which in this embodiment includes rectangular wings that project from a female Leur connector). As is appreciated by one skilled in the art, the system can be configured such that the mechanical interlock is located at either end of the groove 803 (e.g., such that connector 602 forms a portion of the mechanical interlock, instead of connector 606d) or at some point in between. Advantageously, the mechanical interlock reinforces uni-directional installation of the tubing assembly, as well as helping to maintain the tubing within the valve in the correct configuration.

In some embodiments, the mechanical interlock is configured to engage a particular vascular access device (e.g., a specific type of catheter), wherein the mechanical interlock and/or the vascular access device are configured and arranged to provide additional structural and/or electronic identification information, to ensure and/or to promote the use of the correct vascular access device (e.g., catheter, fluid coupler) and/or to enable the correct selection of a flow profile associated with the vascular access device. For example, in one embodiment, the mechanical interlock is configured and arranged to identify (to the flow control device) the type of vascular access device and/or sensor being used (such as for identification of the flow profile that corresponds with the selected catheter). In some embodiments, the mechanical interlock provides identification information to the flow control device, wherein the identification information is associated with the vascular access device and a corresponding flow profile. In preferred embodiments, the identification information is provided automatically, such as by a mechanical structure of the vascular access device. In some embodiments, the identification information is provided by electronics associated with the vascular access device. For example, in one embodiment, the catheter includes the electronics that provide the identification information. In another embodiment, the fluid coupler includes the electronics that provide the identification information. In one exemplary embodiment, the system is configured to select a flow profile associated with a mechanical interlock (e.g., the identification information), when the mechanical interlock is engaged (e.g., the vascular access device is connected to the tubing assembly and/or the flow control device). Additional a mechanical interlock between the second end of the tubing assembly and the vascular access device is configured and arranged to prevent twisting of the connection between the tubing assembly and the vascular access device.

In some embodiments, uni-directional tubing installation is important for aligning functional portions of the valve with functional portions of the tubing assembly. For example the tubing assembly includes an elastic tubing portion configured to be manipulated by the valve (e.g., pinched, etc.). In another example, the valve can include one or more functional elements, such as but not limited to a bubble detector 805 (located along groove 803 and configured and arranged to detect bubbles in the tubing 606*b*) and an electronic solenoid 807 (e.g., configured to align with the free flow mitigation device 606*e* of the tubing and to open the free flow mitigation device, see "Free Flow Mitigation").

Referring now to FIGS. 10C-10D, in some embodiments, the flow control device includes a flow profile comprising two valve positions, a gravity flow position and a controlled flow position. Flow profiles are described in detail with respect to FIG. 10E. In preferred embodiments, the valve is configured and arranged to move between the gravity flow and controlled flow valve positions, such that when the valve is in the gravity flow position, tubing received therein is in a substantially straight (e.g., linear) configuration and when the valve is in the controlled flow positions the tubing received therein is in a substantially non-linear configuration. As a non-limiting example, FIG. 10C illustrates a gravity flow position, in which the valve roller (e.g. the first structure 802, a roller attached to an oblong rotating member or body configured to engage curved surface 806) is oriented (e.g., positioned) such that there is no pinch point in the tubing (e.g., the tubing is not compressed between the first and second structures). In this embodiment, the tubing is in a substantially straight (e.g., un-bent, unpinched, and/or not occluded) configuration when the valve is in the gravity flow position. In the gravity flow position, IV fluid can flow freely through the vascular access device and into the host, simultaneously flushing and/or washing the analyte sensor. FIG. 10D illustrates the valve in a controlled flow position. In the controlled flow position, the rotating member 802 is rotated on its axle to an orientation such that the tubing 606*b* is non-linear (e.g., curved, bent) and a pinch point 808 (e.g., between the rotating member 802 and the compression surface 806) prevents fluid flow. The valve is configured to rotate the roller valve on an axle, such that the pinch point can be moved along the compression surface. Thus, the flow control device moves through a plurality of controlled flow positions. Movement of the valve is similar to the valve movements described with reference to FIGS. 8A-8C. Accordingly, when the tubing is in a bent configuration, the pinch point 808 is pushed forward (e.g., along surface 806) as the rotating member moves forward, and such that an amount of fluid is pushed forward (e.g., infusion fluid, calibrant, sample) through the tubing, as described with reference to FIG. 8A. Similarly, when the tubing is in a bent configuration, the pinch point 808 is pushed backwards (e.g., along surface 806) as the rotating member moves in reverse, such that an amount of fluid is drawn back (e.g., infusion fluid, calibrant, sample) through the tubing, such that a sample is drawn back into the vascular access device and the analyte sensor is bathed in the sample.

FIG. 10E is a graph illustrating an exemplary flow profile, in one embodiment. In preferred embodiments, the flow control device (e.g., the valve) includes a flow profile that is configured and arranged to direct the movements of the flow control device (e.g., between the free flow and controlled flow valve positions, see FIGS. 10C-10D), such that the analyte sensor is alternately bathed in samples and washed by the infusate (e.g., IV fluid, calibrant solution, a medicament solution, and the like). Referring to the exemplary flow profile depicted in FIG. 10E, time is shown on the X-axis and flow rate (e.g., the rate of fluid being moved through the valve) is shown on the Y-axis. Because this is a generic flow profile, for discussion purposes only, the Y-axis is relative and thus has no 0-ml/hr flow rate depicted. A specific flow profile can include a 0-ml/hr flow rate, as well as positive (e.g., valve moving forward) and negative (e.g., valve moving backwards) flow rates. The flow profile includes one or more phases (e.g., phases X, Y and Z); wherein each phase is configured to infuse an amount of fluid, to draw back an amount of sample and/or to hold an amount of fluid (e.g., infusion fluid and/or drawn-back sample) stagnant (e.g., substantially still). In general, a phase is associated with a function, such as but not limited to drawing back a sample (e.g., blood) such that the analyte sensor is bathed in the sample, returning the used sample to the host, washing the analyte sensor (e.g., with solution), calibrating the sensor, maintaining vessel patency, KVO, infusing a hydration fluid, infusing an amount of medicament (e.g., responsive to analyte sensor data and/or to a criterion and/or protocol), and the like. In general, a phase of the flow profile can include one or more flow rates, each of which can last various periods of time. A rate can be selected depending upon the function of the phase of the flow profile, the content of the infusion fluid, the size of the vascular access device (e.g., catheter size, sample size, etc.), a medication protocols, and the like.

As a non-limiting example, the flow profile depicted in FIG. 10E includes three phases (e.g., X, Y, and Z). Phase X includes two flow rates, Rate A and gravity flow (GF). Phase Y includes a second rate (Rate B), which is lower (e.g., slower) than Rate A. Phase Z contains a third rate (Rate C), which is lower than both Rates A and B. At Rates A, B and C, the valve is in a controlled flow valve position. When the valve is in a controlled flow position, it can be stationary (e.g., 0-ml/hr flow rate) or it can move through a plurality of positions in which the tubing is pinched between the roller 802 and the compression surface 806. While not wishing to be bound by theory, one can consider an infinite number of controlled flow positions to exist, wherein the valve creates pinch point 808 by compressing the tubing between the roller 802 and compression surface 806. Similarly, an infinite number of pinch points can exist along the compression surface, provided that the valve is in a controlled flow position. The valve is configured to move at a plurality of speeds, such that the valve can move the pinch point at a plurality of speeds (faster/slower), such that the desired (e.g., programmed and/or re-programmed) flow rates are achieved. For example, fluid can be infused at rates from about 0.0, 0.001, 0.01, 0.1, 0.25, 0.5, 0.75, 1.0, 1.5, 2.0, 2.5, 3.0, 3.5, 4.0, 5.0, 6.0, 7.0, 8.0, 9.0, 10.0 ml/hr to about 20.0, 30.0, 40.0, 50.0, 60.0, 70.0, 80.0, 90.0, 100.0, 110.0, 130.0, 150.0, 175.0, 200.0, 225.0, 250.0, 275.0, 300.0, 350.0, 400.0, or 450.0 ml/hr or more. In another example, sample can be drawn back at rates from about −10.0, −9.0, −8.0, −7.0, −6.0, −5.0, −4.0, −3.0 ml/hr to about −2.0, −1.0, −0.9, −0.8, −0.7, −0.6, −0.5, −0.4, −0.3, −0.2, −0.1, −0.05, −0.01 or −0.001 ml/hr or less. In some embodiments, when the valve is in the controlled flow position, the flow rate is from about 0.5-ml/hour to about 4.0-ml/hr. In some embodiments, a phase of the flow profile can include two, three, four or more rates. In some embodiments, a phase can include a period of gravity flow (e.g., GF), during which the valve is moved to the gravity flow position, which is discussed in greater detail below. In some embodiments, the one or more rates are optimized to achieve the function of the phase relative to a medical protocol. For example, during a wash phase, a slower flow rate can be used if the infusion solution contains heparin, as compared to the flow rate necessary to sufficiently clean the sensor of blood cells when a non-heparinized infusion solution is used. As another example, if the infusion solution contains a medicament, the flow rate of a wash phase can be selected to optimize sensor cleaning while still infusing the desired amount of medicament into the host. In still another example, a slower flow rate can be chosen to flush the sensor and return the sample to a neonatal host, due to the small lumen size of the catheters used in such tiny hosts, such that, for example, excessive amounts of fluid are not infused into the host. In yet another example, during a calibration phase, the calibrant can be slowly infused (e.g. prior to and/or during measurement of the calibration solution), such that the temperature of the calibration fluid equilibrates with the host's body temperature, as described elsewhere herein. In still another example, during a measurement phase, a sample can be drawn back at a rate selected to maintain the temperature of the sample, to prevent rupture of blood cells within the sample, and/or to optimize sensor function.

The flow profile can include periods of gravity flow (GF), during which the valve is in the gravity flow valve position and fluid 602a can flow freely through the valve (e.g., through the tubing received by the valve). The rate of gravity flow is dependent upon the affect of gravity on the infusion fluid, and thus depends in part on the height of the bag 602. For example, the bag can be located relatively higher or lower, with respect to the valve, the floor and/or the host. If the bag is higher, the flow rate will be relatively faster. If the bag is lower, the flow rate will be relatively slower. In some embodiments, gravity flow rates range from about 600, 630 or 650-ml/hour to about 670 or 700-ml/hour or more. In some embodiments, when the valve is in the gravity flow valve position, the flow rate is at least about 600-ml/hr. In some embodiments, the system is configured such that the analyte sensor is flushed (e.g., washed, cleaned, cleaned) by the solution when the valve is in the gravity flow valve position. For example, in some embodiments, gravity flow removes blood cells or other blood components from the sensor and/or the lumen of the vascular access device more efficiently that other (e.g., lower) flow rates.

In some embodiments, washing of the sensor is optimized by setting a ratio of gravity flow rate to controlled flow rate, such as via programming the flow profile to provide the flow rates. For example, in some embodiments, the ratio of gravity flow (e.g., a first flow rate) to controlled flow (e.g., a second flow rate) is at least about 10:1, wherein, the rate of gravity flow lasts 10-times greater than the controlled flow rate. In some embodiments, the ratio of the gravity flow rate to the controlled flow rate is at least about 2:1, 3:1, 4:1, 5:1, 6:1, 7:1, 8:1 or 9:1. In some embodiments, the ratio of the gravity flow rate to the controlled flow rate is from at least about 12:1, 15:1, 20:1, 30:1, 40:1, 50:1, 60:1, 70:1, 80:1, 90:1 or 100:1 to at least about 125:1, 150:1, 175:1, 200:1, 250:1, 300:1, 350:1, 400:1, 450:1, or 500:1 or greater. In some embodiments, the ratio of the gravity flow rate to the controlled flow rate is optimized for sensor washing. For example, the ratio is optimized such that the washed sensor's measurement of the current sample is substantially unaffected by the presence of components of the previous blood sample. For example, in some embodiment, the optimal ratio of the gravity flow rate to the controlled flow rate, for sensor washing, is 10:1. In some embodiments, the optimal ratio (of gravity flow to controlled flow) for sensor washing is at least about 2:1, 3:1, 4:1, 5:1, 6:1, 7:1, 8:1 or 9:1. In some embodiments, the ratio of the gravity flow rate to the controlled flow rate is from at least about 12:1, 15:1, 20:1, 30:1, 40:1, 50:1, 60:1, 70:1, 80:1, 90:1 or 100:1 to at least about 125:1, 150:1, 175:1, 200:1, 250:1, 300:1, 350:1, 400:1, 450:1, or 500:1 or greater. In some embodiments, a period of gravity flow is included in a phase of the flow profile, such as a wash or flush phase, or in a phase configured to infuse a programmed amount of infusion solution (e.g., for hydration, for nutrition and/or to deliver an amount of medicament). In some embodiments, the flow profile is configured to cycle between two or more flow rate ratios. In some embodiments, the ratio of flow rates is associated with the configuration of the system. For example, a system configuration for use in an adult host will have different flow profile requirements than a system configured for use in a pediatric host. In another example, a system configured access of the circulatory system via an artery will have different flow profile requirements than a system configured for access via a vein. In yet another example, a system having the sensor extend into a catheter's lumen may be have different flow profile requirements than a system having a sensor located in a fluid coupler.

Returning to FIG. 10E, the flow profile can be configured differently, depending upon the system configuration, the type of host, and the like. For example, the flow profile can include more or fewer phases. In another example, Phase X can include one or more additional flow rates, or it could consist of only Rate A or only GF. In another example, Rate B can be slower or faster than depicted, including even slower than Rate C or greater than Rate A. In another example, Phase Y can include additional periods of faster and/or slower rates and/or one or more periods of GF. Rate C can be even slower, or it could be faster. If Rate C is a negative rate, then sample is being drawn back and can be drawn back at slower (less negative) or faster (more negative) speeds. In another example, a phase can include two or more flow rates that are alternated intermittently and/or periodically throughout the phase. In yet another example, a phase can include a flow rate of about 0.0 ml/min, wherein the fluid and/or sample is held substantially stagnant for a period of time.

In some embodiments, at least a portion of a flow profile can be repeated. For example, two or more phases can be repeated for a period of time, such as but not limited to a period of time lasting from about 1, 2, 3, 4, 5, 6, 7, 8, 9, 10, 11 or 12 hours to about 0.75, 1, 2, 3, 4 or more days. In some embodiments, the two or more phases of the flow profile are repeated until a criterion is met and/or exceeded (e.g., until a certain period of time has passed, until an amount of medicament is infused, until the host's blood analyte level falls within a preprogrammed range of concentrations, until a caretaker responds to an alarm by pressing a button on the user interface, and the like). In some embodiments, all of the phases of the flow profile are repeated, such as in a cyclical manner, such as until the end of the sensor session (e.g., when the sensor is removed from the host and/or the system is turned off). In some embodiments, the flow profile is configured to be paused and/or interrupted, such as during transfer of the host from his hospital room to another location for a procedure, for example.

In some embodiments, the flow profile is configured to be responsive to the analyte level measured/generated by the sensor. For example, the flow profile can be configured to use one or more optional phases, which can include one or more alternative flow rates, when the analyte measured meets/exceeds a criterion. For example, in some embodiments, the infusion solution includes a medicament. In some embodiments, the flow profile is configured to meter the flow of the medicament solution based at least in part on a measured analyte concentration. In one exemplary embodiment, the sensor includes a glucose sensor, the IV solution contains insulin, and the flow profile is configured to infuse an amount of the insulin solution in response to the host's glucose level. For example, the flow profile can be configured to infuse a low amount of insulin continuously (e.g., a basal amount) and when the host's blood glucose exceeds a programmed range, the flow profile can increase the rate of infusion for a period of time, such as until the host's glucose returns to the range (e.g., a bolus amount). In some embodiments, the amount of medicament (e.g., the insulin solution) to be infused is calculated by the processor module, responsive to the sensor data. In some embodiments, the processor module includes at least a portion of the flow profile. In some embodiments, the flow profile includes an optional phase, such as but not limited to an infusion phase, configured to infuse an amount of medicament. For example, in some embodiments, the processor module includes a medicament infusion phase configured to infuse an amount of insulin sufficient to return the host's blood glucose to a programmed range (e.g., between 80-120 mg/dl glucose). In some exemplary embodiments, the flow profile can be programmed (e.g., re-programmed), such as by the processor module (e.g., responsive to at least one criterion), such that a medicament infusion phase is added to the flow profile for one or more cycles. In some embodiments, the flow profile includes selectable sub-profiles, which can be automatically selected by the flow profile responsive to one or more criteria and/or selectable and/or programmable by a caretaker. In some embodiments, the flow profile includes a menu of selectable flow profiles (e.g., two or more), from which a user can select one to use when applying the system to a host (e.g., installation, set up). For example, in some embodiments, a user can select the flow profile to use from the menu, depending upon host physical properties, a drug to be infused, certain medical protocols, and the like.

As described in the section entitled "Fluids," in some embodiments the infusion solution is a saline solution formulated for infusion into the host. In some embodiments, the infusion solution can contain an amount of the calibrant. For example, if the sensor is a glucose sensor, the infusion solution can contain an amount of glucose (e.g., 50, 75, 100, 125, 150, 175, or 200 mg/dl glucose or more) suitable for calibrating the glucose sensor. This type of solution may be referred to as a "calibration solution." In some embodiments, the medicament solution can include a calibrant. For example, if the sensor is a glucose sensor and the medicament is insulin, the insulin solution can also contain glucose. Alternatively or additionally, the calibration solution and the medicament solutions can be provided separately, such at in separate IV bags. Accordingly, in some embodiments, the system is configured to switch some one IV bag to the other (e.g., from the calibration solution (e.g., glucose) to the medicament solution (e.g., insulin) and vice versa) accordingly to the flow profile. In other embodiments, the system includes as mixing valve configured and arranged to mix the medicament solution and the calibrant solution, wherein a ratio of medicament solution to calibrant solution is based at least in part on a measured analyte concentration. For example, if the host's blood glucose exceeds the programmed range, then the flow profile can respond by directing mixing an amount of the insulin solution into the calibration solution being infused, wherein the amount of insulin is sufficient to return the host's glucose to the programmed range. In some embodiments, the flow control device is further configured and arranged for a piggyback connection with a medicament delivery device, such as a bedside or ambulatory infusion pump. In preferred embodiments, the piggyback connection includes at least one check valve. Check valves can be configured to provide a variety of functions. For example, in some embodiments, the check valve is configured to prevent backflow into the piggybacked medicament delivery device, such as flow of calibration solution into the medicament delivery device's medicament reservoir. In other embodiments, the check valve is configured to prevent inadvertent draining of the medicament reservoir into the host, such as when the system is shut off. Descriptions of some medicament infusion devices suitable to piggyback with the present system can be found in U.S. Patent No. U.S. Pat. No. 4,685,903, U.S. Pat. No. 4,898,578, U.S. Pat. No. 4,925,444, U.S. Pat. No. 5,158,437, U.S. Pat. No. 5,219,279, U.S. Pat. No. 5,207,642, U.S. Pat. No. 5,248, 300, U.S. Pat. No. 5,321,392, U.S. Pat. No. 5,496,273, U.S. Pat. No. 5,522,798, U.S. Pat. No. 5,482,446, U.S. Pat. No. 5,547,470, U.S. Pat. No. 5,551,850, U.S. Pat. No. 5,630,710, U.S. Pat. No. 5,681,285, U.S. Pat. No. 5,685,844, U.S. Pat. No. 5,745,378, U.S. Pat. No. 6,231,320, U.S. Pat. No. 6,231, 560, U.S. Pat. No. 6,269,340, U.S. Pat. No. 6,544,229, U.S. Pat. No. 6,648,821, U.S. Pat. No. 6,817,990, U.S. Pat. No. 6,692,457, U.S. Pat. No. 6,985,870, U.S. Pat. No. 7,018,361, U.S. Pat. No. 7,109,878, U.S. Pat. No. 7,204,823, U.S. Pat. No. 7,402,153, U.S. Pat. No. 7,417,729, U.S. Patent Publication No. US-2007-0060871-A1, U.S. Patent Publication No. US-2007-0112298-A1, U.S. Patent Publication No. US-2007-0213657-A1, U.S. Patent Publication No. US-2007-0299389-A1, U.S. Patent Publication No. US-2008-0033357-A1, U.S. Patent Publication No. US-2008-0097326-A1, U.S. Patent Publication No. US-2008-0103447-A1, U.S. Patent Publication No. US-2008-0154177-A1, U.S. Patent Publication No. US-2008-0147050-A1, U.S. Patent Publication No. US-2008-0161753-A1, and U.S. Patent Publication No. US-2008-0200897-A1, each of which is incorporated herein by reference in its entirety.

As described herein, in some embodiments, the flow control device includes an electronic solenoid 805 configured to operate a free flow mitigation device 606e (e.g., a spring-clip occluder included in the tubing assembly 606a). A free flow mitigation device is configured and arranged to prevent inadvertent free flow of IV solution into the host, such as during tubing installation and removal, or during power interruption to the system. The flow control device and tubing assembly are configured and arranged such that they are functionally engaged after the tubing is installed in the vascular access device. For example, in FIG. 10A, the free flow mitigation device 606e and the electronic solenoid 805 are aligned such that the solenoid can bias (e.g., activate) the spring clip occluder in a non-occluded (e.g., un-pinched, opened) position, when the system is in operation. The spring clip occluder is configured and arranged to be engaged by an electronic solenoid 805 located in the flow control device. In preferred embodiments, the electronic solenoid 807 is configured and arranged such that free flow mitigation device returns to an occluded position when power is removed, such as when the system is turned off on in the event of a power outage. In preferred embodiments, the system configured and arranged to control the free flow mitigation device electronically, such as but not limited to by the flow profile. For example, in one embodiment, after system installation and/or initiation, the flow profile electronically controls the electronic solenoid to maintain the spring clip occluder in an opened position. In another embodiment, the flow profile directs the solenoid to activate (e.g., open, biased in the non-occluded position) the free flow mitigation device during solution infusion and/or sample drawback, and to deactivate (e.g., closed, bias in the occluded position) the free flow mitigation device if the system is paused and/or the system is switched off. In still another embodiment, the flow profile includes a phase with a 0-ml/hr (or 0-ml/min) flow rate, and the flow profile electronically directs the solenoid to deactivate the free flow mitigation device during this phase, and activation (e.g., reactivation) of the free flow mitigation device during the other phases of the flow profile. In some embodiments, the flow profile is configured to deactivate the free flow mitigation device (e.g., via the electronic solenoid) in response to a fail-safe, such as but not limited to in response to a fail-safe programmed to handle a fluidics problem or a sensor failure. Fail-safes are described in detail elsewhere herein.

In some embodiments, the system is configured to infuse an amount of medicament, responsive to the analyte sensor data. In one exemplary embodiment, the system includes a continuous glucose sensor and processor module including a flow profile (e.g., programming) configured for infusion of an amount of an insulin solution (e.g., such that a calculated amount of insulin is infused) in response to the host's glucose concentration. For example, processor module is configured to and/or includes programming that processes the continuous glucose sensor data, whereby the host's glucose level is determined in real time. In preferred embodiments, the processor module is configured to calculate the volume of insulin solution to be infused, such as if the host's blood glucose exceeds a predetermined threshold (e.g., the host is hyperglycemic; e.g., glucose above 120 mg/dl, 130 mg/dl, 140 mg/dl, 150 mg/dl, 160 mg/dl, 170 mg/dl or more), the processor calculates an amount of insulin to be delivered to the host (e.g., an amount of insulin solution sufficient to lower the host's glucose to or near the predetermined range). In preferred embodiments, the processor module re-programs the flow profile to deliver the amount of infusion solution required to deliver the calculated amount of insulin (e.g., a bolus amount), and the flow control device infuses the amount of solution responsive to the re-programming of the flow profile. For example, in some embodiments, the processor module is configured to insert (e.g., add) a medicament infusion phase into the flow profile. As the host's blood glucose level approaches and/or reaches the predetermined range, the processor module is configured to re-program the flow profile to reduce the amount of insulin-containing solution infused. For example, in some embodiments, the processor module is configured to re-program the flow profile to infuse a basal level of insulin, such as during washing of the sensor.

Pumpless Sample Withdrawal

In some circumstances, it is preferred to meter the flow of a fluid through a vascular access device (including withdrawal of at blood sample) without the use of a pump and/or a flow control device (e.g., described above). Accordingly, some embodiments provide a system for continuously measuring an analyte in an artery of a host in vivo, which does not require the use of the flow control device of the preferred embodiments or of a pump. Accordingly, in some preferred embodiments, the system includes an arterial infusion system and continuous analyte sensor coupled thereto. The arterial infusion system is configured and arranged to meter the flow of a fluid into and/or out of an artery of a host, and includes an arterial catheter, a pressure transducer, an infusion fluid, and a pressure system. The pressure system is configured to increase and/or reduce an amount of pressure applied to the infusion fluid, such that when the infusion system is applied to the host (e.g., the catheter is implanted in the host's artery), the pressure system can infuse the infusion fluid, withdraw a blood sample, and reinfuse a withdrawn sample into the host. In general, arteries are pressurized. Accordingly, blood will expelled from a puncture in the artery (e.g., an inserted/implanted catheter, a cut or breakage) unless pressure greater than the arterial pressure is applied thereto, such as via compression, a pressure cuff, a pressurized infusion system, and the like. An arterial pressure system can be configured to infuse fluid into the host by increasing the pressure applied to the infusion fluid, such as (but not limited to) by increasing the pressure applied with a blood pressure cuff, such that the applied pressure overcomes the arterial pressure. In preferred embodiments, the system is configured to withdraw a sample (e.g., contact the sensor with the blood sample) by reducing the applied pressure (in a controlled manner) until a sample of blood is pushed into the catheter (by the arterial pressure) and contacts the sensor. In some embodiments, the withdrawn sample is reinfused into the host, such as by increasing the applied pressure such that the arterial pressure is again overcome and infusion fluid flows into the host. In some embodiments, the withdrawn sample is diverted to waste disposal, such as via a valve. In some embodiments, the system is configured such that the sensing portion of the sensor are disposed within the host's body (e.g., within the artery) as described herein. However, in other embodiments, the sensor is disposed extracorporeally (e.g., above a plane defined by the host's skin) and the sample is withdrawn out of the host's body. In preferred embodiments, the system includes electronics configured to regulate the pressure system, such that infusion and sample withdrawal are controlled.

The analyte sensor can be configured to detect a variety of analytes, as described elsewhere herein. In some embodiments, the analyte sensor includes a single working electrode, which generates a first signal associated with the concentration of the analyte in the sample. In other embodiments, the analyte sensor is a dual-electrode continuous analyte sensor, as described elsewhere herein, and includes a first working electrode configured to generate the first signal (including an analyte-related signal component and a non-analyte-related signal component) and a second working electrode is configured to generate a second signal (including the non-analyte related signal component).

In some embodiments, a method for continuously measuring an analyte in an artery of a host in vivo is provided. In this embodiment, the method includes the steps of coupling a continuous analyte sensor with an arterial catheter system applied to a host, wherein the sensor is configured to generate an analyte-related signal associated with an analyte in a sample, and wherein the arterial catheter system includes an arterial catheter, a pressure transducer, an infusion fluid, and a pressure system configured to increase and/or reduce an amount of pressure applied to the infusion fluid; reducing the amount of pressure, such that a sample of arterial blood contacts the sensor; and generating the analyte-related signal with the sensor. In some embodiments, the coupling step includes coupling the sensor to the arterial catheter, such as by inserting the sensor into a lumen of the arterial catheter. In some embodiments, the method includes a step of reinfusing the sample into the host, such as by increasing the amount of pressure. In some embodiments, the arterial blood pressure of the host is monitored, using the pressure transducer. Arterial pressure monitors are known in the art. In preferred embodiments, the analyte-related signal is processed to provide an analyte value. In some embodiments, the signal is also calibrated.

In some embodiments, the generating step further includes generating a second signal with the sensor, wherein sensor includes a first working electrode configured to generate a first signal including an analyte-related signal component and a non-analyte-related signal component and the second working electrode is configured to generate the second signal including the non-analyte-related signal component. The first and second signals can be processed, to provide a processed signal substantially without a signal component due to the non-analyte-related signal component, and/or to provide a scaling factor. In some embodiments, the generating step further includes generating a reference signal associated with a reference analyte in the sample, wherein the sensor further includes a reference sensor configured to generate the reference signal.

Systems and Methods for Processing Sensor Data

In general, systems and methods for processing sensor data associated with the preferred embodiments and related sensor technologies include at least three steps: initialization, calibration, and measurement. Although some exemplary analyte sensors, such as glucose sensors, are described in detail herein, the systems and methods for processing sensor data can be implemented with a variety of analyte sensors utilizing a variety of measurement technologies including enzymatic, chemical, physical, electrochemical, spectrophotometric, polarimetric, calorimetric, radiometric, and the like. Namely, analyte sensors using any known method, including invasive, minimally invasive, and non-invasive sensing techniques, configured to produce a data signal indicative of an analyte concentration in a host during exposure of the sensor to a biological sample, can be substituted for the exemplary analyte sensor described herein.

In some embodiments, the sensor system is initialized, wherein initialization includes application of the sensor and/or sensor system in or on the host. In some embodiments, the sensor system includes a computer system including programming configured for performing one or more of the following functions: turning the system on, requesting and/or receiving initial data (e.g., time, location, codes, etc), requesting and/or receiving patient data (e.g., age, conditions, medications, insulin dosing, etc), requesting and/or receiving calibration information (e.g., manufacturer calibration lot data, reference information such as solution(s) provided for calibration, etc.), requesting information related to the flow control device, and the like.

In some embodiments, the sensor system is configured with a predetermined initial break-in time. In other embodiments, the sensor system is configured to determine when break-in is complete (e.g., the sensor signal is substantially stabilized). In some embodiments, the sensor's sensitivity (e.g., sensor signal strength with respect to analyte concentration) and/or baseline is used to determine the stability of the sensor; for example, amplitude and/or variability of sensor sensitivity and/or baseline may be evaluated to determine the stability of the sensor signal. In alternative embodiments, detection of pH levels, oxygen, hypochlorite, interfering species (e.g., ascorbate, urea, and acetaminophen), correlation between sensor and reference values (e.g., R-value), and the like may be used to determine the stability of the sensor. In some embodiments, sensor stability is evaluated by determining if and/or when sensor break-in is complete. In some embodiments, the sensor is configured to calibrate during sensor break-in, thereby enabling measurement of the biological sample prior to completion of sensor break-in.

In one embodiment, systems and methods are configured to process calibrated sensor data during sensor break-in. In general, signals associated with a calibration and/or measurement phase of the sensor system can be measured during initial sensor break-in. Using a rate method for measuring an analyte (e.g., measuring the rate of change of a step change), a sensor signal can be calibrated with a correction factor to account for the rate of change of the break-in curve. In one exemplary embodiment, the bottom of sequential step responses (e.g., of calibration phases during sensor break-in) is fit to a line or curve (e.g., using linear or non-linear regression, such as least squares regression), to extrapolate the rate of change of the curve of the sensor break-in. Accordingly, the rate of change measured in a measurement phase is corrected to account for the rate of change of the sensor break-in curve, and the sensor signal calibrated. By calibrating during sensor break-in, sensor data can more quickly be provided (e.g., to the user interface) after sensor insertion.

In some embodiments, systems and methods are configured to determine an initial baseline value of the sensor. In general, baseline refers to a component of an analyte sensor signal that is not substantially related to the analyte concentration. In one example of a glucose sensor, the baseline is composed substantially of signal contribution due to factors other than glucose (for example, interfering species, non-reaction-related hydrogen peroxide, or other electroactive species with an oxidation/reduction potential that overlaps with hydrogen peroxide).

In preferred embodiments, the sensor system includes a computer system including programming configured to determine calibration information and calibrate a signal associated with a biological sample there from. In general, calibration of the signal includes initial calibration, update calibration and/or re-calibration of the sensor signal. Although some systems and methods for calibrating a sensor are described in more detail elsewhere herein, for example in the section entitled, "Sensor Electronics," additional and alternative methods for providing calibration information and calibrating the sensor's signal are provided in the following description and can be used in combination with and/or alternative to the methods described elsewhere herein.

The term "calibration information" generally refers to any information, such as data from an internal or external source, which provides at least a portion of the information necessary to calibrate a sensor. In some embodiments, calibration information includes steady state information, such as baseline information and/or sensitivity information obtained by processing reference data from an internal and/or external reference source, which is described in more detail elsewhere herein. In some embodiments, calibration information includes transient information, such as rate of change information and/or impulse response information obtained by processing a signal produced during exposure of the sensor to a step change (e.g., sudden or nearly sudden change) in analyte concentration, which is described in more detail elsewhere herein.

In some embodiments, steady state information includes reference data from an external source, such as an analyte sensor other than the sensor of the sensor system configured to continuously measure the biological sample, also referred to as external reference data or external reference value(s). In some embodiments, calibration information includes one, two, or more external reference values (e.g., from self-monitoring blood glucose meters (finger stick meters), YSI Glucose Analyzer, Beckman Glucose Analyzer, other continuous glucose sensors, and the like). In some embodiments, one or more external reference values are requested and/or required upon initial calibration. In some embodiments, external reference value(s) are requested and/or required for update calibration and/or re-calibration. In some embodiments, external reference values are utilized as calibration information for calibrating the sensor; additional or alternatively, external reference values can be used to confirm the accuracy of the sensor system and/or to detect drifts or shifts in the baseline and/or sensitivity of the sensor.

In one exemplary embodiment, at least one external reference value in combination with at least one internal reference value together provide calibration information useful for calibrating the sensor; for example, sensitivity of a sensor can be determined from an external reference value and baseline can be at least partially determined from an internal reference value (e.g., a data signal indicative of an analyte concentration in a reference solution during exposure of the sensor to the reference solution, which is described in more detail elsewhere herein).

In another exemplary embodiment, calibration information includes two or more external reference values that provide calibration information useful for calibrating the sensor; for example, at least two SMBG meter values can be used to draw a calibration line using linear regression, which is described in more detail elsewhere herein.

In yet another exemplary embodiment an external reference value is utilized to confirm calibration information otherwise determined (e.g., using internal reference values).

In some embodiments, steady state information includes reference data obtained from the analyte sensor to be calibrated, also referred to as internal reference data or internal reference values. In one exemplary embodiment, internal reference data includes a signal associated with exposure of the sensor to one or more reference solutions (e.g., calibration solutions), which is described in more detail elsewhere herein.

In some embodiments, the sensor system includes one or more reference solutions (e.g., calibration solutions in some embodiments), wherein the system is configured to expose the sensor to the one or more reference solution(s) to provide calibration information (e.g., an internal reference value), such as baseline and/or sensitivity information for the sensor. In one exemplary embodiment, a reference solution including a known analyte concentration is provided, wherein the system is configured to expose the sensor to the reference solution, and wherein the system is configured to produce a data signal indicative of an analyte concentration in the reference solution during exposure of the sensor to the reference solution, as described in more detail elsewhere herein. In some embodiments, two reference solutions with two different analyte concentrations are provided. For example, in order to generate reference values for detecting sensitivity drift of a glucose sensor, two saline solutions containing 100 and 200 mg/dl glucose respectively can be provided.

In general the system can be configured to obtain internal reference values at one or more time points, intermittently, and/or continuously. For example, in some embodiments, calibration for drift in baseline and/or sensitivity can be done at set time intervals, depending upon the severity of the drift. In some circumstances, it is preferred to calibrate very frequently (e.g., between about every 1 minute or less and about every 2, 3, 4, 5, 10, 15, 20 or 30 minutes or longer). In other circumstances, it is preferred to calibrate less frequently (e.g., about every 1, 2, 3, 5, 10, 15 or 24 hours or longer). For example, in some circumstances, baseline drift has a substantial effect on sensor accuracy, while sensitivity drift has little effect. Accordingly, a baseline calibration solution (e.g., 0-mg/dl glucose) can be used to calibrate the baseline about every 5 minutes. Thus, to calibrate for sensitivity drift, an analyte-containing calibration solution (e.g., 100-mg/dl glucose in saline) can be used to calibrate the sensor less frequently, such as about once every 1, 2, 3, 5, 10, 12, 24, 48 or more hours. In some embodiments, one or more external reference values, such as reference values obtained by testing a blood sample with SMBG or a YSI device, can be used to calibrate the system, in addition to the internally provided reference values (e.g., provided via the calibration solutions).

Although much of the description focuses on the use of a reference calibration solution to provide an internal reference value, other sensor technologies, such as optical sensing methods, are known to provide one or more internal reference standards (e.g., of known absorbance, reflectance, fluorescence, etc) to determine baseline and/or sensitivity information, as is appreciated by one skilled in the art; accordingly, the systems and methods described herein can be implemented with other types of internal reference values. Examples of analyte sensors configured for optical detection of the analyte and/or a reference analyte are described in detail in the section entitled "Optical Detection," above. In some embodiments, a "plateau" is reached when the sensor has been exposed to the sample of bodily fluid (e.g., blood) or a reference solution a sufficiently long period of time that the sensor's enzyme has used up (e.g., reacted with, detected) substantially all of the available analyte.

In some embodiments, the sensor system is configured to use a steady state measurement method, from which steady state information can be obtained. Steady state information can be obtained during exposure of the sensor to an analyte concentration when the signal has reached a "plateau" wherein the signal is representative of the analyte concentration; the term plateau does not limit the signal to a flat signal, rather the plateau represents a time point or time period during which the signal is substantially stable and a data point that represents the analyte concentration can be reliably obtained.

FIG. 11 is a graph that schematically illustrates a signal produced during exposure of the sensor to a step change in analyte concentration, in one exemplary embodiment. The x-axis represents time; the y-axis represents sensor signal (e.g., in counts). In general, a step change occurs when a sensor is sequentially exposed to first and second different analyte concentrations, wherein the signal (after the change from exposure of the sensor to the first analyte concentration to exposure of the sensor to the second analyte concentration) includes a measurable rate of change (transient information) that subsequently "plateaus" or substantially "plateaus" to a signal that substantially represents the analyte concentration to which the sensor is exposed (steady state information). As one example, a step change occurs when a sensor is exposed to a reference solution of a first analyte concentration and then subsequently exposed to a reference solution of a second, different, analyte concentration. As another example, a step change occurs when a sensor is exposed to a reference solution of a known analyte concentration and then subsequently exposed to a biological sample of unknown or uncalibrated analyte concentration.

Referring to FIG. 11, at a first time point 1002, a sensor is exposed to a step change in analyte concentration, for example, from a zero concentration reference analyte solution to a biological sample of unknown or uncalibrated analyte concentration. During the initial signal response to the step change, a rate of change 1004 of the signal can be measured for a time period. In some embodiments, for example when the step change is between two known reference solutions, the rate of change information can provide transient information useful for calibrating the sensor, which is described in more detail elsewhere herein. However, if either of the first and/or second analyte concentrations of the step response is not known, the rate of change information, alone, cannot provide sufficient calibration information necessary to calibrate the sensor.

Point 1006 represents a point in time that the signal response shifts from transient information (e.g., rate of change) to steady state information (e.g., plateau), in some embodiments. Namely, the signal, beginning at point 1006, substantially accurately represents the analyte concentration and can be used in steady state equations to determine an analyte concentration, in some embodiments. In one exemplary embodiment of steady state equations useful for calibrating the sensor system, the calibration information is obtained by solving for the equation $y=mx+b$, wherein: "y" represents the sensor data value (e.g., digitized in "counts") determined at a single point (or averaged value over a window of data where signal is indicative of analyte concentration, for example); "b" represents baseline (e.g., unrelated to the analyte); "m" represents sensitivity (e.g., for a glucose sensor, counts/mg/dL); and "x" is the concentration of the reference solution (e.g., known analyte concentration in a reference calibration solution (e.g., glucose in mg/dL)). In this exemplary embodiment, steady state information includes sensitivity and baseline.

In some embodiments, the sensor data value (y) can be obtained from a moving window that intelligently selects a plateau during exposure of the sensor to an analyte concentration. In some embodiments, the sensor system is configured to be exposed to two or more known reference calibration solutions from which steady state information (sensitivity and baseline) can be processed to calibrate the sensor system; namely, by providing two known analyte concentrations, the steady state equation described above can be utilized to solve for baseline and sensitivity of the sensor, which can be utilized to define a conversion function or calibration factor, such as described in more detail elsewhere herein.

Referring again to FIG. 11, point 1006 is a point that can be used as "y" in the steady state equation described above. In some embodiments, the point 1006 is easily determinable as it is the beginning of a signal plateau 1008 (represented by a dashed line); accordingly, the system includes programming to process the data signal to determine the signal plateau and/or a time point therein. In general, a step change produces a signal plateau in the signal response, which is indicative of a steady state response to the analyte concentration measurement. In some embodiments, the system includes programming configured determine the time period (window) during which the signal has reached a plateau and choose a single point or average point from that window.

In some situations, however, the point 1006 and/or plateau 1008 may not be easily determinable. For example, in some sensor systems, the diffusion of certain non-analyte species (e.g., baseline, background and/or interfering species), which may diffuse more slowly than the analyte (e.g., through a membrane system that covers the analyte sensor), do not reach a steady state during the same time period that the analyte reaches a steady state. In these situations, the signal may not "plateau" in a measurable manner because of the reaction of the lagging species through the membrane system, which generate additional signal over the actual analyte plateau 1008. In other words, while the analyte concentration may have reached a plateau, the baseline has not. Dashed line 1010 represents the signal response to a step change in such a situation, for example, wherein the signal does not substantially "plateau" due to the lagging diffusion of certain non-analyte species, resulting in a non-measurable analyte plateau. In these situations, additional information is required in order to provide calibrated analyte sensor data. Systems and methods for providing additional information and/or to provide sufficient calibration information to calibrate an analyte sensor in such situations are described in more detail below, with reference to conjunctive measurements, for example.

In some embodiments, the sensor system is exposed to a reference solution with a known analyte concentration of about zero, and wherein the steady state information comprises baseline information about the sensor in the reference solution. For example, a glucose sensor system can be exposed to a 0 mg/dl glucose solution (e.g., an isotonic solution without any glucose concentration) and the signal associated with the zero glucose concentration in the reference solution provides calibration information (steady state) indicative of at least a portion of the baseline of the sensor.

It has been observed that, in some circumstances, the signal associated with the zero glucose concentration in a reference solution (such as saline) is not equivalent to the baseline signal when the sensor is exposed to a biological sample (e.g., blood) from which the sensor is configured to obtain its analyte concentration measurement; rather the baseline includes an additional amount of signal associated with the differences between the composition of the reference solution and the host's blood. This additional signal is referred to as "offset" (e.g., $b_{offset}$, see FIG. 11, 1016 and associated text). Offset is an indication of the level of noise present in the system, the presence of an interferent in the solution and/or in the blood, and/or the like. In some circumstances, additional information may be required in order to determine and/or confirm baseline of a biological sample (e.g., blood). In some embodiments, 1, 2, 3 or more external reference analyte values are obtained (e.g., via finger stick, a clinical analysis device (e.g., YSI) and the like) and entered into the system, such as for use in determining $b_{offset}$. For example, in some embodiments, the equitation $y=mx+(b+b_{offset})$ is used to calibrate the sensor, wherein m is determined when the sensor is exposed to calibration solution, b is determined from the dual-electrode and $b_{offset}$ is an external reference value, such as but not limited to a finger-stick reference value (in counts). In some embodiments, error is substantially mitigated by evaluating two or more external reference analyte values for deviation therebetween, such as by averaging them, detecting outliers, and the like. In one embodiment, the external reference analyte value is compared to an estimated or calculated analyte value, such as to confirm the accuracy of a calculated $b_{offset}$. For example, in some embodiments, the difference between a finger-stick glucose value (e.g., in counts) and a calculated blood glucose value (e.g., in counts) is used as the $b_{offset}$ in future calculations. In some embodiments, an offset threshold is set, based on a priori information (e.g., determined from numerous in vitro and/or in vivo experiments and/or the literature). For example, in some embodiments, the threshold is based on, at least in part, the maximum and/or minimum possible offsets for a given sensor configuration, a give type of host, and/or the like. In some embodiments, the calibration solution includes additional components provided to overcome baseline in blood, for example. In some embodiments, a factor is determined (e.g., from historical data) to determine an adjustment factor for a difference between baseline in the biological sample (e.g., blood) and baseline in the reference solution. In other embodiments, two calibration solutions are used to evaluate $b_{offset}$. In some embodiments, baselines of the working electrodes is determined prospectively, such as by testing in the reference solution by the manufacturer. In some embodiments, the difference in baseline of a biological sample (e.g., blood) and the baseline of the reference solution, also referred to as $b_{offset}$ herein, is determined using other techniques, such as described in more detail below.

In general, the calibration information described above, including a known baseline and sensitivity, can be used to determine a conversion function or calibration factor applied to convert sensor data ("y") into blood glucose data ("x"), as described in more detail elsewhere herein.

In some embodiments, systems and methods are configured to obtain transient measurement information associated with exposure of the sensor to a reference solution of known analyte concentration and/or a biological fluid of unknown or uncalibrated analyte concentration. In some embodiments, the system is configured obtain transient information by exposing the sensor to a step change in analyte concentration and process the rate of change of the associated signal. In some embodiments, the system is configured to obtain transient information by exposing the sensor to a step change in analyte concentration and processing the impulse response of the associated signal.

In one exemplary embodiment, the sensor is exposed to a first reference solution of a known analyte concentration and then to a second reference solution of a known analyte concentration to determine the rate of change of the signal response. In these embodiments, the equation ($\Delta y/\Delta t = r \cdot \Delta x$) can be used to obtain the transient information, wherein "$\Delta x$" is the difference between the two known solutions that are being measured (e.g., 0 mg/dL to 100 mg/dL in an exemplary glucose sensor), "$\Delta y$" is the measured difference between the sensor data (e.g., in counts) corresponding to the analyte concentration difference in known reference solutions ($\Delta x$), "$\Delta t$" is the time between the two "y" sensor measurements referenced with $\Delta y$, and "r" represents the rate of change calibration factor, or rate of change conversion function, that can be applied for that particular sensor to obtain calibrated blood glucose measurements from sensor rate of change data.

In some embodiments, transient information can be obtained from the rate of change of a signal produced during exposure of the sensor to a biological sample of unknown or uncalibrated analyte concentration. In some embodiments, transient information can be obtained from the step and/or impulse response of a signal produced during exposure of the sensor to a step change in analyte concentration.

In some embodiments, neither steady state information, nor transient calibration measurements are used in isolation in calibrating the sensor system, but rather steady state and transient information are combined to provide calibration information sufficient to calibrate sensor data such as described in more detail, below. For example, in some embodiments, wherein baseline is not completely known (e.g., $b_{offset}$ must be determined), wherein a rate of change calibration factor is not easily determinable (e.g., when multiple known reference solutions cannot be pushed substantially immediately adjacent to each other to provide a rate of change indicative of the step or impulse response), wherein the a steady state measurement cannot be obtained (e.g., due to lagging species affecting the analyte signal plateau), and the like. In some embodiments, both steady state information and transient information are processed by the system to provide sensor calibration, confirmation, and/or diagnostics. In some embodiments, transient sensor information from unknown or uncalibrated blood glucose measurements can be processed to provide calibration information for the sensor system, such as described in more detail below.

In some embodiments, once at least a portion of the calibration information is determined, the sensor system is configured to expose the sensor to a biological sample and measure a signal response thereto. In some embodiments, the sensor can be continuously exposed to the biological sample, wherein at least some external reference values are used as calibration information for calibrating the sensor system. In some embodiments, the sensor can be intermittently exposed to the biological sample, wherein at least some internal reference values are used as calibration information for calibrating the sensor system, also referred to as auto-calibration in some exemplary embodiments.

In some embodiments, the sensor system is calibrated solely using steady state information, such as described in more detail elsewhere herein. In one such embodiment, the sensor system is configured to be exposed to a biological sample and a value (y) determined from the signal plateau, which is used in combination with a conversion function (calibration factor) that uses steady state information (e.g., sensitivity and baseline) to obtain a calibrated analyte concentration (e.g., glucose concentration in mg/dL or mmol/L) equivalent to the measured sensor data value y.

In general, the sensor system of the preferred embodiments can be configured to utilize any combination the steady state information (e.g., from external and/or internal sources) described in more detail elsewhere herein. In some embodiments, the sensor system includes systems and methods configured to calibrate the sensor based on one, two, or more external reference values. In some embodiments, the sensor system includes systems and methods configured to calibrate the sensor based on one or more external reference values, which calibration can be confirmed using an internal reference value (e.g., zero analyte concentration reference solution). In some embodiments, the sensor system includes systems and methods configured to calibrate the sensor based on one external reference value in combination with one internal reference value to determine baseline and sensitivity information. In some embodiments, the sensor system includes systems and methods configured to calibrate the sensor based on internal reference values, also referred to as auto-calibration. In general, auto-calibration includes the use of one or more reference solution to calibrate the sensor system. In some embodiments, the sensor system includes systems and methods configured to calibrate the sensor based on prior information, which is described in more detail elsewhere herein. In some embodiments, the sensor system includes systems and methods configured to calibrate the sensor based on dual working electrodes, by substantially eliminating the baseline component of the steady state calibration equation (e.g., (y=mx)).

In some embodiments, the sensor system includes systems and methods configured to calibrate the sensor based solely on transient information (e.g., rate of change, decay, impulse response, etc) described in more detail elsewhere herein. In one exemplary embodiment, analyte concentration can be determined from the change in sensor data responsive to a step change ($\Delta x$), the time ($\Delta t$) elapsed between the sensor data measurements $\Delta y$, and the rate of change calibration factor/rate of change conversion function, such as described in more detail above.

In some embodiments, the sensor system includes systems and methods configured to calibrate the sensor based on conjunctive information, wherein the calibration information used to calibrate the sensor system includes both steady state information and transient information.

In one exemplary embodiment, the sensor system includes systems and methods configured to calibrate the sensor based on a rate of change (transient information) associated with a signal produced during exposure of the sensor to a step change between a reference solution of known analyte concentration (e.g., 0 mg/dl glucose) and a biological sample; in this exemplary embodiment, a reference value (steady state information) from an external analyte sensor (e.g., blood glucose meter) can be obtained for the analyte concentration in the biological sample, thereby providing sufficient information to solve for calibration using rate of change of the signal response to the step change there between. One advantage of using rate of change calibration methods includes its insensitivity to baseline and interfering species.

In one preferred embodiment, a system is provided for monitoring analyte concentration in a biological sample of a host, the system including: a substantially continuous analyte sensor configured to produce a data signal indicative of an analyte concentration in a host during exposure of the sensor to a biological sample; a reference solution including a known analyte concentration, wherein the system is configured to expose the sensor to the reference solution, and wherein the sensor is configured to produce a data signal indicative of an analyte concentration in the reference solution during exposure of the sensor to the reference solution; and a computer system including programming configured to determine calibration information and calibrate a signal associated with a biological sample there from, wherein the calibration information includes steady state information and transient information. In some embodiments, the calibration information is determined from a signal associated with exposure of the sensor to the reference solution and a signal associated with exposure of the sensor to a biological sample.

One situation wherein steady state information and transient information are useful together for calibrating a sensor system includes a situation where a baseline measurement obtained from an internal reference ($b_{reference}$) provides only a portion of the baseline information necessary for calibrating the sensor system. As one example, the baseline of blood is different from the baseline of saline (e.g., reference) and compounds or molecules that make up the baseline in blood can create artifacts (e.g., $b_{offset}$), which can make calibration using internally derived steady state information alone, difficult. Namely, plateau 1008 (FIG. 11) in the signal responsive to the step change in analyte concentration does not occur in blood, in some embodiments, due to slow diffusion of baseline-causing compounds/molecules to the sensor electroactive surface; instead, an artifact 1010 (FIG. 11) is observed in the signal. Accordingly, in some embodiments, baseline information useful for calibration of a sensor system includes both $b_{reference}$ and $b_{offset}$. A variety of systems and methods of determining $b_{offset}$, which can be useful in providing calibration information and/or diagnostics and fail-safes, has been discovered, as described in more detail elsewhere herein.

In some embodiments, $b_{offset}$ can be determined from transient information derived from a signal associated with exposure of the sensor to a biological sample, wherein the biological sample is of unknown or uncalibrated analyte concentration.

In one preferred embodiment, a system for monitoring analyte concentration in a biological sample of a host is provided, the system including: a substantially continuous analyte sensor configured to produce a data signal indicative of an analyte concentration in a host during exposure of the sensor to a biological sample; a reference solution including a known analyte concentration, wherein the system is configured to expose the sensor to the reference solution, and wherein the system is configured to produce a data signal indicative of an analyte concentration in the reference solution during exposure of the sensor to the reference solution; and a computer system including programming configured to determine calibration information and calibrate a signal associated with a biological sample there from, wherein the calibration information is determined from a signal associated with exposure of the sensor to the reference solution and a signal associated with exposure of the sensor to a biological sample, wherein the biological sample is of unknown or uncalibrated analyte concentration.

In some embodiments, systems and methods are configured to process an impulse response of a signal associated with exposure of the sensor to a biological sample, wherein the biological sample is of unknown or uncalibrated analyte concentration, in order to determine an offset between a baseline measurement associated with a reference solution and a baseline measurement associated with a biological sample (e.g., $b_{offset}$).

FIG. 12 is a graph that schematically illustrates a derivative of the step response shown in FIG. 11. FIG. 12 can also be described, as the impulse response of the signal associated when a sensor is exposed to a step change to a biological sample of unknown or uncalibrated analyte concentration, in one exemplary embodiment. In this embodiment, the impulse response can be defined by a sum of two exponentials functions (e.g., $(ae^{-k1*t} - ae^{-k2*t})$, where k1 and k2 are time constants characteristic of the sensor), wherein the impulse response starts at 0 at t=0 and is expected to decay to 0 as t becomes large (as time passes). The impulse response reaches a peak, shown as point 1050 in FIG. 12, which represents the maximum rate of change of the associated signal (see FIG. 11, for example). Additionally, although it is expected that the signal will decay to 0 as t becomes large, FIG. 12 illustrates a plateau 1052 above the y-axis; namely, wherein the plateau 1052 does not hit 0.

It has been discovered that the positive value 1054 of the plateau substantially represents the slope of the $b_{offset}$ artifact 1010 (FIG. 11). Accordingly, when the slope is drawn from t=0 of the step response (see line 1012 of FIG. 11), the "y" value 1016 of that slope line at the end of the step response 1014, represents $b_{offset}$. Accordingly, $b_{offset}$ can then be added to the equation y=mx+b (where b=$b_{reference}$+$b_{offset}$) and a conversion function (calibration factor) can be determined to calibrate the sensor system (i.e., using both steady state information and transient information and including using the signal associated with exposure of the sensor to a biological sample of unknown or uncalibrated analyte concentration.)

In some alternative embodiments, systems and methods are configured to process an impulse response (such as shown in FIG. 12) associated with a step change (such as shown in FIG. 11) to determine a time point of a steady state measurement during which an analyte concentration can be obtained. As described above, in some circumstances, it can be difficult to determine a steady state time point (e.g., 1006 in FIG. 11) at which time point the signal accurately represents the analyte concentration. Accordingly, systems and methods configured to determine the time point (e.g., 1006 in FIG. 11) in the step response associated with exposure of the sensor to a biological sample of unknown or uncalibrated analyte concentration have been discovered, which time point accurately represents the analyte concentration in the biological sample. Because the impulse response can by defined by exponentials (discussed above), systems and methods can be configured to process the exponential equation (s) with variable parameters to determine a best-fit to the impulse response curve determined from exposure of the sensor to the biological sample. It has been discovered that this best fit of the impulse response provides sufficient information to determine the time point 1056 (FIG. 10) at which the decay curve should have decayed to the y-intercept; namely, the time point 1056 where the decay curve should have hit y=0 indicates the (steady state) time point in the step response (e.g., 1006 in FIG. 11) that accurately represents the analyte concentration without the $b_{offset}$ artifact 1010. Accordingly, (y=mx+b) can then be used to calibrate the sensor system, including the signal value "y"

at the time indicated by the extrapolated impulse response curve (e.g., and using sensitivity and baseline information determined from one or more reference calibration solutions, such as described in more detail elsewhere herein.

In some other alternative embodiments, systems and methods are configured to compare steady state information and transient information for a plurality of time-spaced signals associated with biological samples of unknown or uncalibrated analyte concentration to determine an offset between a baseline measurement associated with a reference solution and a baseline measurement associated with the biological samples.

In some exemplary embodiments, $b_{offset}$ is determined by plotting level (i.e., the point at which the step response plateaus or ends) vs. rate (i.e., maximum rate of change of the step response determined from the peak of the impulse response curve) for a plurality of step responses (e.g., time-spaced signals) and drawing a regression line of the plotted points, such as described in more detail with reference to FIG. 13.

FIG. 13 is a graph that illustrates level vs. rate for a plurality of time-spaced signals associated with exposure of the sensor to biological samples of unknown or uncalibrated analyte concentration. The y-axis represents maximum rate of change for each step response; the x-axis represents level (signal level (e.g., in counts) obtained at the plateau of the signal and/or the end of the step response.) Each point 1080 on the plot represents level vs. rate for each of the plurality of time-spaced signals. A regression line 1082 is drawn using known regression methods, as is appreciated by one skilled in the art. The point 1084 at which the line 1082 crosses the y-axis represents the signal associated with a reference (e.g., 100 mg/dL calibration solution) plus $b_{offset}$. Accordingly, $b_{offset}$ can be determined by subtracting the signal associated with the reference from the point 1084 at which the line 1082 crosses the y-axis. Thus, $b_{offset}$ determined from the plot as described above, can be included in the equation y=mx+b (where b=$b_{reference}$+$b_{offset}$) and a conversion function (calibration factor) can be determined to calibrate the sensor system (i.e., using both steady state information and transient information and including using the signal associated with exposure of the sensor to a biological sample of unknown or uncalibrated analyte concentration.)

In some embodiments, $b_{offset}$ is an adjustable parameter, wherein the sensor system includes systems and methods configured to determine $b_{offset}$ with each measurement cycle (each time the sensor is exposed to the biological sample) and to adjust the calibration factor (conversion function), including $b_{offset}$ with each measurement cycle, responsive to a change in $b_{offset}$ above a predetermined threshold, and/or responsive to external information, for example.

In some embodiments, systems and methods are provided to detect a shift in the baseline and/or sensitivity of the signal based on a comparison of steady state information and transient information, such as described in more detail with reference to FIG. 13. In some embodiments, systems and methods are provided to correct for a shift in the baseline and/or sensitivity of the signal based on a comparison of steady state information and transient information. In some embodiments, systems and methods are provided to initiate a calibration responsive to detection of a shift in the baseline and/or sensitivity of the signal based on a comparison of steady state information and transient information.

Referring again to FIG. 13, regression line 1082 is shown for a selected plurality of time spaced signals. In some embodiments, multiple regression lines can be drawn for a plurality of different windows of time spaced signals (e.g., time-shifted windows). In these embodiments, a comparison of a regression line from a first window of time spaced signals as compared to a regression line drawn from a second window of time spaced signals can be used to diagnose a shift and/or drift in sensor sensitivity and/or baseline. For example, in FIG. 13, line 1082 represents a regression line drawn for a first window of data over a first period of time; dashed line 1086 represents a regression line drawn for a second window of data over a second period of time; and dashed line 1088 represents a regression line drawn for a third window of data over a third period of time. In this example, dashed line 1086 is shifted along the y-axis from the first line 1082, indicating a drift or shift in the sensor's baseline from the first time period to the second time period; dashed line 1088 is shifted along the x-axis from the first line 1082, indicating a drift or shift in the sensor's sensitivity from the first time period to the third time period. Accordingly, a shift in the regression line can be used to diagnose a shift or drift in the sensor's signal and can be used to trigger a corrective action, such as update calibration and/or re-calibration using any of the methods described herein. Additionally or alternatively, the shift in the line can be used to correct a shift or drift in the sensor's signal; for example, the amount of shift in the line can be used to update calibration accordingly (e.g., the change in y-value between two regression lines can be representative of a corresponding change in baseline between two time periods, and the calibration information updated accordingly). One skilled in the art appreciates that some combination of shift or drift of the baseline and sensitivity can occur in some situations, which can be similarly detected and/or corrected for.

Sensor Sensitivity Evaluation

In some circumstances, noise on the sensor signal can be mistaken as a drift in sensor sensitivity. It has been empirically determined, through evaluation of large in vivo and/or in vitro data sets, that sensor sensitivity generally follows an expected pattern of drift, over the period of sensor use. For example, in one exemplary sensor configuration, during the first hour or so, of sensor use (e.g., after start-up and/or re-start-up after a period of disuse), sensitivity tends to change rapidly; after this period, the sensitivity increase tends to level off and/or plateau. However other sensitivity profiles are possible based on sensor design. While each individual sensor's sensitivity profile can vary from that of other such sensors, depending upon factors such as sensor design, membrane chemistry, implantation site, and the like, it has been found that sensor profiles tend to follow an empirically determined pattern of drift within a range of about ±5%, ±10%, ±15%, ±20% or ±25%. Deviations from the expected pattern can be indicative of noise on the sensor, sensor failure, and/or the like, which can be dealt with as described elsewhere herein, such as the section entitled "Diagnostics and Fail-Safes."

FIG. 14 is a flow chart illustrating sensor sensitivity evaluation, in some embodiments. In preferred embodiments, systems and methods are configured to process a plurality of sensitivity calculations, to determine if an apparent sensitivity drift falls within the expected profile.

At block 1400, a method for evaluating a change in sensitivity of an analyte sensor over a predetermined time period is provided. In some embodiments, the predetermined time period is relatively short, such as but not limited to less than or equal to about 30 minutes, also referred to as short-term sensitivity evaluation. In some embodiments, relatively shorter periods of time, such as 25, 20, 15, 10, 5 minutes are preferred. For example, in one embodiment, the evaluated sensitivities are calculated about every 5 minutes. In other embodiments, the predetermined time period is longer. For example, in one embodiment, the time period is at least about 30 minutes, also referred to as long-term sensitivity evaluation. In other embodiments, the predetermined time period is at least about 60 minutes. For example, in some embodiments, the predetermined time period is about 70, 80, 90, 100, 110, 120, 130, 140, 150, 160, 170, 180, 190 or 200 minutes, or longer.

At block 1402, sensor data is received from an analyte sensor. For example, in some embodiments, the system includes an input module, also referred to as the processor module, configured to receive the sensor analyte data. The sensor data can include one or more sensor analyte values measured in a bodily fluid of a host (e.g., blood). In some embodiments, an individual measurement is used. In some embodiments, an average of a plurality of time-spaced points is used. In some embodiments, reference analyte values are also received by the input module. For example, in vivo reference analyte values can be generated when the sensor is contacted with a reference solution. In some embodiments, reference analyte values are intermittently received. For example, in some embodiments, the in vivo reference analyte values are generated when the sensor is intermittently in contact with the reference solution (e.g., calibrant), such as according to the flow profile (e.g., see FIG. 10E). For example, if the sensor is included in an integrated system, such as depicted in FIG. 6 and as described with reference to FIGS. 10A-10E, wherein the flow control device moves between the controlled flow and gravity flow valve positions, such as at flow rates and times specified by the flow profile, and the sensor generates sensor data when the sensor is contacted with blood and reference values when the sensor is in contact with the reference solution. Additionally or alternatively, in some embodiments, the reference analyte value(s) are obtained from an in vitro analyte monitor (e.g., external reference analyte values). For example, a self monitored blood glucose monitor can be used to obtain external reference glucose values (e.g., from a finger-stick blood sample), which can be entered into the system, as described elsewhere herein.

At block 1404, analyte sensor sensitivity is calculated intermittently (e.g., periodically or non-periodically), based at least in part on the reference analyte data, such as described elsewhere herein. For example, in some embodiments, the processor module is configured to and/or includes programming that calculates sensor sensitivity using the formula y=mx+b, wherein m is the sensitivity value (e.g., estimated and/or measured). For example, in some embodiments, the intermittently received reference analyte values are used to intermittently calculate the sensitivity of the analyte sensor, such as but not limited to from about once every 0.25, 0.5, 1, 2, 3, 4, 5, 6, 7, 8, 9, 10, 11, 12, 13, 14, 15, 16, 17, 18, 19, 20, 25 or 30-minutes to about once every 1, 1.5, 2, 2.5 or 3-hours or longer. In some embodiments, a plurality of sensitivities is calculated over a predetermined time period. For example, in some embodiments, the processor is configured to and/or includes programming that calculates 2, 3, 4, 5, 6, 7, 8, 9, 10 or more sensitivities over a pre-programmed time period of 10, 15, 20, 30, 40, 50, 60, 70, 80, 90 or 120-minutes or longer. In some embodiments, the sensitivities are calculated iteratively. For example, as the integrated system cycles through phases of blood and reference solution measurement according to the system's (e.g., the processor module's) flow profile (e.g., programming). In some embodiments, the sensitivity values are filtered, such that each calculated sensitivity value is a filtered value. For example, in some embodiments, the data (e.g., reference analyte values) are filtered prior to use in calculation of the sensor sensitivity m (e.g., via an IIR or FIR filter). In another example, in some embodiments, the data (within a window of data) are averaged (e.g., equally or non-equally weighted average, mean-value, median, or the like) prior to use in calculation of sensor sensitivity. In yet another example, in some embodiments, two or more calculated sensitivities are filtered, averaged, smoothed, and/or the like.

At block 1406, a plurality of time-spaced sensitivity calculations are evaluated over a predetermined time period. For example, in some embodiments, the plurality of time-spaced sensor calculations are evaluated to determine whether or not the sensor's sensitivity did change (e.g., drift), and if so, did the change in calculated sensitivities follow the empirically determined pattern, was the observed change due to noise, and the like, as described below. In some embodiments, the processor is configured to calculate a change (e.g., drift) in sensor sensitivity using the formula $$\text{Drift} = \frac{m_{t1} - m_{t2}}{m_{t1}}$$

and/or the formula $$\text{Drift} = \frac{m_{t1} - m_{t2}}{(m_{t1} + m_{t2})/2},$$

wherein $m_{t1}$ is the calculated sensitivity at time 1, and $m_{t2}$ is the calculated sensitivity at time 2, for example. In preferred embodiments, this evaluation is performed iteratively on the plurality of time-spaced sensitivity calculations over the predetermined time period. In some embodiments, at least two sensitivity values are evaluated during the predetermined time period. For example, in some embodiments, the difference between two sensitivity calculations (e.g., the amount of change) is evaluated. In some embodiments, the at least two sensitivity values are averaged and/or filtered (e.g., smoothed to remove noise) before they are evaluated. Filtering the sensitivity calculations can provide a smoother trajectory (e.g., curve) for evaluation of sensitivity drift by eliminating outliers and/or random noise (e.g., non-specific noise). The sensitivity calculations can be filtered using a variety of methods (e.g., FIR, IIR, averaging) as described elsewhere herein. In other embodiments, all of the sensitivity calculations over the time period are evaluated. In further embodiments, all sensitivity calculations are evaluated at a plurality of time points during sensor use. For example, a sensor session can last from the time when the sensor is implanted and/or the flow control device is turned on to the time when the system is turned off and/or the sensor is removed. In another example, a sensor can be implanted for an extended period of time, such as three or more days, with intermittent periods of use (e.g., when the power is on and the system is functioning). For example, the system may be intermittently powered down, such as during certain medical procedures. The period of sensor use before the powering down is considered to be a sensor session, in some embodiments. Similarly, the period of sensor use after the restart (e.g., power-up, re-power-up) is considered to be a sensor session, in some embodiments.

In some embodiments, a change in sensitivity is evaluated by comparing it (the change in sensitivity) with one or more criteria. For example, in some embodiments, a priori sensitivity information is used (at least in part) to evaluate the change in sensitivity. In general, a priori information includes information, data and/or observations generated during many previous in vitro and/or in vivo experiments, as well as information, data, and/or observations gleaned from the scientific literature. In some embodiments, the a priori sensitivity information includes and/or provides an expected profile (e.g., an expected pattern and/or amount of sensitivity change/drift over time). For example, it has been observed that in some sensor designs, the sensor sensitivity tends to increase over time, wherein the increase tends to occur within an expected range. For example, it has been observed that sensor sensitivity tends to increase over time (e.g., no substantial decrease over time), wherein the increase tends to occur within an expected range, wherein the magnitude of the change is related to the length of time the sensor has been used and/or implanted and/or energized (e.g., turned on). Deviation from the expected profile can be indicative of a failure of a portion of the integrated system, a detrimental change in the host's condition, and/or the like, in some embodiments. In some embodiments, the system is configured to evaluate and/or consider a deviation from the expected profile in combination with additional information (e.g., interferents, noise, completion of break-in, etc.) to determine if a system failure has occurred.

In some embodiments, the a priori sensitivity information defines a range (e.g., within boundaries and/or guard bands) of acceptable change (increase and/or decrease) in sensitivity. For example, in some circumstances, sensitivity can change (e.g., drift) up to about ±5%, ±10%, ±15%, ±20%, ±25%, ±30%, ±40%, ±50%, ±60%, ±70%, ±80%, ±90%, ±100%, ±200% or more over a given time period (e.g., over a time period of about 5, 10, 15, 20, 30, 40, 50, 60, 70, 80, 90, 100, 110 or 120 minutes or longer). In some embodiments, an acceptable change in sensitivity is related to how long the sensor has been in use, implanted and/or energized.

In some embodiments, a change in sensitivity is evaluated using a "cone" of feasible sensitivity values of the sensor, such that aberrant sensitivity changes (e.g., artifacts) are detected whenever the sensitivity value (e.g., amount of sensitivity change, a calculated change in sensitivity over a time period) falls (e.g., occurs) outside of the cone of possibility. In one embodiment, the cone of possible sensitivity values is defined in terms of a range of allowable (or feasible) sensitivity change for a time point during a sensor session. The range of allowable sensitivity change can change over time during a sensor session, for example, by allowing a greater sensitivity change during an earlier time period of a sensor session than a later time period of a sensor session. In general, sensitivity information depends upon sensor design and can be obtained from analysis of data sets (e.g., a priori information). A known feasible range can be represented (e.g., drawn) on a graph as a "cone of possible sensitivity values" (e.g., a range of possible calculated sensitivity values, for the next time period, based at least in part on one or more previously calculated sensitivity value(s) and a priori information). In some embodiments, one or more criteria used to determine the cone of possible sensitivity values are defined by an expected profile. For example, the cone of possibility initiates at the calculated sensitivity value of a first time period (e.g., the point of the cone) and projects forward in time (e.g., becomes broader), such that the broadest portion of the cone (e.g., the "base" of the cone) is located at and/or is projected toward or past the second time period. At the second calculated sensitivity value graphed, another "cone of possibility" can be drawn for the next time period (e.g., a third time period), wherein this new cone of possibility is based on the expected profile, and so on.

Accordingly, in embodiments wherein sensitivity is evaluated in the short-term (e.g., over periods of 30-minutes or less), when the change in sensitivity meets the one or more criteria (e.g., falls within the boundaries of the expected profile, is within a cone of feasible change, and/or the like), the system is configured to use the most recent sensitivity calculation evaluated (e.g., for sensor calibration and the like). Similarly, the system is configured to not use a most recent sensitivity calculation evaluated to calibrate the analyte sensor when the change in sensitivity does not meet one or more criteria. In some circumstances, the change in sensitivity not meeting the one or more criteria can trigger a sensor failure, an alert, an alarm, a fail-safe, and the like, as described elsewhere herein.

In some embodiments, evaluation of sensor sensitivity is conducted using a dual-electrode continuous analyte sensor. As described elsewhere herein, a dual-electrode analyte sensor includes two working electrodes, which are configured to provide two signals. The first signal includes an analyte component and a baseline component. The second signal includes a baseline component without an analyte component. As described elsewhere herein, in some embodiments, sensitivity of a dual-electrode analyte sensor is calculated using the signal from either (or both) of the working electrodes. Accordingly, in some embodiments, the intermittent sensor sensitivity calculations are based at least in part on the first signal or based at least in part on the second signal. In a further embodiment, the second signal is subtracted from the first signal to obtain a subtracted signal, wherein the step of intermittently calculating a sensitivity of the analyte sensor is based at least in part on a subtracted signal, combined with signals measured by the sensor when exposed to reference solution and/or blood. In some embodiments, a difference in sensitivities of the plus-enzyme and no-enzyme working electrodes is evaluated. For example, with respect to a dual-electrode glucose sensor exposed to a calibration solution (e.g., a glucose-containing infusion solution) the sensitivity measured by the no-enzyme electrode can be used as the sensitivity value for the enzyme electrode and/or subtracted signal as described in more detail elsewhere herein.

In some embodiments, sensor sensitivity can be calculated using an external reference value generated from a blood sample (e.g., a split sample, finger-stick), wherein the external reference value is measured using another test device, at the bedside or in a clinical laboratory. For example, in the case of glucose sensors, external reference values can be generated by a finger-stick or testing a blood sample using an YSI device. Use of external reference values (e.g., baseline value obtained via finger-stick and/or YSI) in calculation of sensor sensitivity is preferred in some embodiments, such as but not limited to non-dual-electrode continuous analyte sensors.

In an exemplary embodiment, a method for evaluating a change in sensitivity of an analyte sensor over a predetermined time period is provided, wherein sensor data is received from an analyte sensor, wherein the sensor data includes one or more sensor analyte values measured in a biological sample of a host, a sensitivity of the analyte sensor is intermittently calculated based at least in part on reference analyte data, and a change in sensitivity is evaluated by evaluating a plurality of time-spaced sensitivity calculations over a predetermined time period. For example, the processor module is configured to and/or includes programming that evaluates the change in sensitivity of the analyte sensor over the predetermined time period. In some embodiments, the predetermined time period is less than or equal to about 30, 25, 20, 15, 10, or 5 minutes. In other embodiments, the predetermined time period is at least about 30, 40, 50, 60, 70, 80, 90, 100, 110 or 120 minutes.

In another exemplary embodiment, a system for evaluating a change in sensitivity of an analyte sensor over a predetermined time period is provided. In this embodiment, the system includes a computer system including an input module configured to receive sensor analyte data and reference analyte data, wherein the sensor data includes one or more sensor analyte values measured in a biological sample of a host and wherein the reference data includes one or more reference analyte values, and a processor module configured to (1) intermittently calculate a sensitivity of the analyte sensor based at least in part on the reference analyte data and to (2) evaluate a change in sensitivity by evaluating a plurality of time-spaced sensitivity calculations over a predetermined time period. In some embodiments, the predetermined time period is less than or equal to about 30, 25, 20, 15, 10, or 5 minutes. In other embodiments, the predetermined time period is at least about 30, 40, 50, 60, 70, 80, 90, 100, 110 or 120 minutes.

In some embodiments, wherein the predetermined time period is less than or equal to about 30 minutes, also referred to as short term sensitivity evaluation, evaluating a change in sensitivity includes evaluating at least two sensitivity measurements during the predetermined time period. For example, the processor module is configured to and/or includes programming that evaluates at least two sensitivity measurements during the predetermined time period, to evaluate the change in sensitivity. For example, in one embodiment, the at least two sensitivity measurements are separated by 30 minutes. In other embodiments, the at least two sensitivity measurements are separated by 25, 20, 15, 10, or 5 minutes. In some further embodiments, the processor module is configured to and/or includes programming that averages and/or filters the at least two sensitivity measurements prior to evaluating the at least two sensitivity measurements. In some circumstances, averaging and/or filtering the at least two sensitivity measurements can reduce the affect of outlier data points on the evaluation.

In some embodiments, wherein the predetermined time period is less than or equal to about 30 minutes, the processor module is configured to and/or includes programming that compares the change in sensitivity with one or more criteria. For example, the one or more criteria include but are not limited to an expected profile of sensitivity change for the time period and/or a cone of possibility (e.g., a range of allowable sensitivity change), such as described above. In some embodiments, the processor module is configured to and/or includes programming that uses a most recent sensitivity calculation evaluated to calibrate the analyte sensor when the change in sensitivity meets one or more criteria. In other embodiments, the processor module is configured to and/or includes programming that does not use a most recent sensitivity calculation evaluated to calibrate the analyte sensor when the change in sensitivity does not meet one or more criteria.

In some embodiments, wherein the predetermined time period is less than or equal to about 30 minutes, the step of intermittently calculating a sensitivity of the analyte sensor includes intermittently receiving a reference analyte value. For example, in some embodiments, the processor module (also referred to as a receiving module) is configured to and/or includes programming that intermittently receives the reference analyte value(s). In some circumstances, reference analyte values can be measured by the system. In some embodiments, the system is configured to periodically receive a measured analyte concentration from a reference analyte solution. For example, in some embodiments, the sensor is exposed to the reference analyte solution, such that the sensor measures the analyte concentration of the reference analyte solution. In other embodiments, the reference analyte values are measured outside of the system. For example, in some embodiments, a reference analyte value obtained from an in vitro analyte monitor is received by the system.

In some embodiments, wherein the predetermined time period is less than or equal to about 30 minutes, the step of evaluating a sensitivity is iteratively performed on the plurality of time-spaced sensitivity calculations over the predetermined time period. For example, in some embodiments, the processor module is configured to and/or includes programming that evaluates a sensitivity calculation every 5, 10, 15, 20, 25 or 30 minutes.

In some embodiments, wherein the predetermined time period is at least about 30 minutes, also referred to as long term sensitivity evaluation, the processor module is configured to and/or includes programming that iteratively performs the sensitivity evaluation on the plurality of time-spaced sensitivity calculations over the predetermined time period (e.g., at least about 30 minutes). In some embodiments, the step of evaluating a sensitivity includes evaluating all of the sensitivity calculations over a sensor session. For example, if the sensor session is 3-days, then all of the sensitivity calculations from the sensor session up to the time of sensitivity evaluation are evaluated. Similarly, if the sensor session lasts 4, 5, 6, or 7 days, then all of the sensitivity calculations over that period of days are evaluated. In some embodiments, the processor module is configured to evaluate a sensitivity based at least in part on a priori sensitivity information. For example, a priori sensitivity information can be obtained from previous sensor uses, such as numerous in vitro and/or in vivo experiments. In some embodiments, the a priori sensitivity information includes an expected profile. For example, during the first hour of sensor use, the expected profile may be a line having a slope and/or curvature within a first range; while during the second hour of use the expected profile may be a line having a slope and/or curvature within a second range. In some embodiments, the a priori sensitivity information defines a range of acceptable change in sensitivity, such as described with reference to a cone of possible acceptable and/or feasible sensitivity changes. For example, a range of acceptable change in sensitivity can include changes in sensitivity observed 80%, 85%, 90% or 95% of the time, in numerous previously conducted in vitro and/or in vivo experiments (e.g., uses), for a given time period of sensor use and/or implantation.

In some embodiments of evaluating a change in sensitivity of an analyte sensor over a predetermined time period, the analyte sensor includes two working electrodes configured to provide a first signal (e.g., from the plus-enzyme working electrode) including an analyte component and a baseline component and a second signal e.g., from the no-enzyme (e.g., non-enzymatic) working electrode) including a baseline component without an analyte component. In some further embodiments, the processor module is configured to and/or includes programming that intermittently calculates a sensitivity of the analyte sensor based at least in part on the first signal. In some further embodiments, the step of intermittently calculating a sensitivity of the analyte sensor is based at least in part on the second signal. In some further embodiments, the processor module is configured to and/or includes programming that subtracts the second signal from the first signal to obtain a subtracted signal, wherein the step of intermittently calculating a sensitivity of the analyte sensor is based at least in part on the subtracted signal.

In some embodiments of evaluating a change in sensitivity of an analyte sensor over a predetermined time period, the analyte sensor is intermittently exposed to a biological sample (e.g., blood) and to a reference solution (e.g., an infusion solution containing a defined amount of analyte), such as described elsewhere herein. In some further embodiments, the processor module is configured to and/or includes programming that intermittently calculates a sensitivity of the analyte sensor based at least in part on a signal obtained when the analyte sensor is exposed to a biological sample (e.g., when blood is drawn back by the flow control device, according to the flow profile). In some further embodiments, the processor module is configured to and/or includes programming that intermittently calculates a sensitivity of the analyte sensor based at least in part on a signal obtained when the analyte sensor is exposed to a reference solution (e.g., when the flow control device infuses the reference solution, according to the flow profile). In some further embodiments, the processor module is configured to and/or includes programming that intermittently calculates a sensitivity of the analyte sensor based at least in part on a signal obtained when the analyte sensor is exposed a biological sample and a signal obtained when the analyte sensor is exposed a reference solution. For example, in some embodiments, a subtracted signal, which is derived from the signals obtained when the analyte sensor is exposed to the biological sample and the reference solution, is used for calculation of sensor sensitivity.

Sensor Stability Evaluation

It is known that many continuous analyte sensors, such as but not limited to intravascular sensors, have an initial period of sensor use after which the sensor signal becomes more stable and substantially representative of the analyte concentration (e.g. where the current output from the sensor is stable relative to the analyte level). This period of time is referred to as "break-in" or "run in." Sensor break-in is a two-part process, including electrochemical break-in of the electrodes (e.g., electroactive surfaces) and membrane break-in (e.g., equilibration with the local environment post implantation). In general, break-in is associated with an exponential signal decay related to break-in of the electroactive surfaces. It has been observed that in some sensor system configurations, in addition to the exponential signal decay, the non-enzyme working electrode signal response to blood exposure is unstable for at least the first few cycles of system operation (e.g., 1, 2, 3, 4, 5, 6, 7, 8, 9, 10 or more cycles), depending upon the flow profile and/or sensor configuration. In these circumstances, to effectively remove baseline, in a dual-electrode sensor, it is preferred that the error of the plus-enzyme and no-enzyme working electrodes be within about ±10% of each other. However, the additional instability observed on the no-enzyme working electrode, in these circumstances, tends to increase the difference between the errors (of the two working electrodes), which causes inaccuracies (e.g., errors) in signal processing (e.g., subtraction of the no-enzyme signal from the plus-enzyme signal). While not wishing to be bound by theory, it is believed that the non-enzyme electrode instability is caused, at least in part, by the affects of biological noise and/or interferents on some membrane systems. After break-in is complete, these problems with the no-enzyme signal response are generally no longer observed.

It has been observed that break-in is not a permanent phenomenon. For example, it has been observed that when an implanted (e.g., in use) sensor is turned off (e.g., de-energized), after a time, the signal tends to begin destabilizing. In some circumstances, sensor sensitivity (m) begins to deteriorate. For example, calculated sensitivity values (m) may no longer meet the criteria requirements of a sensitivity evaluation (e.g., fall within the cone of possibility). Further, the longer the sensor remains turned off, the less representative of the analyte concentration the signal can become. However, the sensor can break-in again, if it is re-energized (e.g., turned on again). The length of this next break-in period depends, at least in part, on how long the sensor was turned off. For example, if the sensor was turned off for only 10 to 20 minutes, the break-in period could be about 5-10 minutes. In another example, if the sensor was turned off for three hours, a full hour or longer may be necessary for the break-in process to be completed. Since it is preferred to use a stable analyte sensor when measuring a host's analyte levels, systems and methods for determining when the sensor (e.g., the signal) is stable are provided in some embodiments.

Accordingly, in preferred embodiments, the system is configured and arranged to evaluate sensor stability (e.g., determine when and/or if sensor break-in is complete). Advantageously, evaluation of sensor stability enables improved selection of sensitivity evaluation parameters, and thus improved sensor calibration. For example, in some embodiments, when the sensor is still breaking in, a wider set of sensitivity (e.g., drift) parameters are selected (e.g., to allow greater amounts of drift, such as ±30%, ±40%, ±50%, ±60%, ±70%, ±80%, ±90%, ±100%, ±200% or more sensitivity drift over a given time period (e.g., 30-min, 1-hr, 2-hrs)). Then, when the sensor signal has stabilized, a more narrow set of sensitivity parameters are selected (e.g., ±5%, ±10%, ±15%, ±20% sensitivity drift over about 5, 10 or 15 minutes). In yet another embodiment, when the sensor is still breaking in (e.g., unstable), the baseline can be determined by means other than subtraction of the no-enzyme signal from the plus-enzyme signal, such as but not limited to use of a priori information (e.g., in vitro and/or in vivo) and/or external reference analyte values, as described elsewhere herein. In a further embodiment, the system is configured to prompt the user to enter an external reference value (e.g., a finger-stick) about, near, at and/or after completion of break-in. In some embodiments, the system is configured to intermittently (e.g., 1, 2, 3, 4, 5, 6, 7, or more times every 10, 20, 30, 40, 50 or 60-minute or more) evaluate sensor stability, and to request an external reference value if the sensor has not yet sufficiently stabilized (e.g., if break-in is not yet complete). An average break-in time can be empirically determined (e.g., a priori information). In some embodiments, the system is configured to wait a period of time associated with a predetermined break-in time, and to begin evaluating sensor stability after that time period has passed.

FIG. 15 is a flow chart illustrating sensor stability evaluation, in one embodiment. At block 1500, a method for determining a stability of an analyte sensor is provided, in one embodiment.

At block 1502, sensor data is received from an analyte sensor, such as by a data receiving module (also referred to as the processor module) operably connected to the analyte sensor system and configured to receive the sensor data from the sensor. In preferred embodiments, the sensor is a dual-electrode sensor as described elsewhere herein. For example, the analyte sensor includes (1) a first working electrode (plus-enzyme electrode) configured to provide first sensor data (e.g., a first signal), which includes an analyte component and a baseline component, and (2) a second working electrode (no-enzyme electrode) configured to provide second sensor data (e.g., a second signal), which includes a baseline component without an analyte component. In some embodiments, the processor module is configured to and/or includes programming that uses first sensor data and/or second sensor data, when the dual-electrode sensor is exposed to a blood sample, to evaluate sensor stability. In some embodiments, the processor module is configured to and/or includes programming that uses the first sensor data and/or the second sensor data, when the dual-electrode sensor is exposed to an infusion solution, to evaluate sensor stability. In some embodiments, the processor module is configured to and/or includes programming that uses subtracted signals to evaluate sensor stability. In some embodiments, the processor module is configured to and/or includes programming that uses only the second sensor data, received when the sensor is exposed to blood and/or reference solution, in order to determine when membrane break-in (e.g., membrane stabilization between two working electrodes) is complete.

At block 1504, a stability of the analyte sensor is determined, based at least in part on the second sensor data (e.g., data from the non-enzyme working electrode), such as via the processor module. In some embodiments, the processor module is configured to and/or includes programming that determines sensor stability by evaluating a change in an amplitude of a plurality of time spaced points (e.g., 2, 3, 4, 5, 10, 15, 20, 30, 40, 50 or 100 or more points) from the second sensor data, such as when the sensor is exposed to a sample and/or an infusion solution. The time space points are spaced by about 1, 3, 5, 10, 15, 20 or 30 minutes to about 1, 1.5 or 2-hours or more, in some embodiments. For example, in one embodiment, the processor module is configured to compare the peak amplitudes from a plurality of measurement phases, such as when the sensor is exposed to blood. In one exemplary embodiment, the processor is configured to and/or includes programming that compares the amplitude (e.g., peak) of a first measurement (e.g., blood) phase to the amplitude of a second measurement phase (e.g., the next measurement cycle). In another exemplary embodiment, the processor is configured to and/or includes programming that compares the amplitude of a first calibration (e.g., exposed to calibration or reference infusion solution) phase to the amplitude of a second calibration phase. In another exemplary embodiment, the processor is configured to compare a difference between the amplitudes of the calibration and measurements phases of a first cycle (e.g., of a flow profile) to a difference between the amplitudes of the calibration and measurement phases of a second cycle. In yet another exemplary embodiment, the processor is configured to use the subtracted amplitudes (e.g., the plus-enzyme signal minus the no-enzyme signal). In other embodiments, the processor module is configured to and/or includes programming that compares a first point to a second point, wherein the first point is measured when the analyte sensor is exposed to the biological sample and the second point is measured when the analyte sensor is exposed to the infusion solution (e.g., a calibration, wash and/or infusion phase). In other embodiments, the processor module is configured to and/or includes programming that utilizes transient information, such as described with reference to a step-change and FIG. 11, to evaluate the sensor's stability.

In some embodiments, the processor module is configured to and/or includes programming that evaluates sensor stability using rate of change (ROC) information, such as but not limited to a difference in ROCs between two measurement and/or calibration phases of the second (no-enzyme) signal. In some embodiments, the two measurement phases are consecutive (e.g., obtained during consecutive cycles of the flow profile). However, in other embodiments, the measurement phases are separated by one or more measurement and/or calibration phases (e.g., cycles of the flow profile) and/or spaced in time. For example, in some embodiments, the cycles (e.g., during which the two measurement phases or two calibration phases occur) are separated by 1, 2, 3, 4, 5, 6, 7 or more (intervening) cycles; or the cycles (or phases) are separated by 5, 10, 15, 20, 30, 40, 50, 60, 70, 80, 90, 100, 110 or 120 minutes or longer. In some embodiments, the processor module is configured to wait a period of time, such as but not limited to a predetermined break-in time period (e.g., a period of time approximately the length of an average break-in time for a particular sensor configuration), prior to evaluating sensor stability. In a preferred embodiment, the processor module is configured to evaluate a plurality of ROCs, such as but not limited to a series of 2, 3, 4, 5, 6, 7, 8, 9 or 10 or more ROCs. For example, in one embodiment, the processor module is configured evaluate a first ROC (e.g., calculated for first and second measurement phases) and a second ROC (e.g., calculate between second and third measurement phases), relative to a threshold, and so on. In some embodiments, the processor module is configured to evaluate a plurality of ROCs within a window (e.g., moving or non-moving) of calibration or measurement phases, relative to a threshold.

In one exemplary embodiment, the processor module is configured to and/or includes programming that evaluates sensor stability (e.g., membrane break-in) using a moving predetermined time period (e.g., a moving window) of ROCs calculated from the second signal (e.g., from the no-enzyme electrode). In some embodiments, the moving window encompasses 2, 3, 4, 5 or more calculated ROCs. In some embodiments, the processor module is configured to compare each calculated ROC and/or a difference between two ROCs to a threshold, and to assign the ROC a flag (e.g., +1, −1 or 0; categorized as pass/fail, etc.), based on the comparison. For example, during the first hour of sensor use, the expected ROC is about from ±30%, ±40% or ±50% per every 5, 10, 15 or 20 minutes to about ±60%, ±70%, ±80%, ±90%, ±100%, ±200% or more per every 5, 10, 15 or 20 minutes; whereas, during the second hour of sensor use, the expected ROC is from about ±5% or less every 5, 10, 15 or 20 minutes to about ±10%, ±15%, ±20% or ±25% more every 5, 10, 15 or 20 minutes. Accordingly, if the ROC exceeds the threshold, it is flagged as +1. If the ROC falls below the threshold, then it is flagged as −1. If, on the other hand, the ROC is within the threshold, then it is flagged as zero (0). In some embodiments, the processor module is configured to determine that the sensor is substantially stable (e.g., break-in is complete) when the sum of the flags is zero. For example, if the pre-determined time period (e.g., a window) encompasses five (5) ROCs, the sum of the 5 flags within the window should equal zero, for the sensor to be considered stable. Preferably, the window is a moving window. For example, in some embodiments, the processor is configured to slide the window forward one ROC with each new cycle. In alternative embodiments, the processor module is configured such that the sum of the flags within the moving window must equal zero at least two times before the sensor is determined to be substantially stable. In still other embodiments, the processor is configured to evaluate the flags, wherein the value of a plurality of sequential flags (e.g., 2, 3, 4, 5, 6, 7, 8, 9, 10 or more flags) must equal zero before the sensor is declared to be substantially stable. In some embodiments, the threshold is associated with the expected profile. In some other embodiments, the processor module is configured to evaluate the first signal (e.g., the plus-enzyme signal) when a sensor (dual-electrode or non-dual electrode) is exposed to calibration solution, when determining sensor stability. However, in other embodiments, the system is configured to evaluate sensor stability using data received when the sensor is exposed to blood. For example, in some embodiments of a dual-electrode sensor, the processor module is configured to calculate the second signal ROCs for two or more measurement cycles when the sensor is exposed to blood.

In some embodiments, the sensor is considered to be stable when it reaches a predetermined level (e.g., threshold) of stability (e.g., the signal is stable and/or substantially representative of the analyte concentration). Preferably, the processor module is configured to and/or includes programming that determines a predetermined (e.g., programmed) level of stability has been reached, when an amplitude change of the second sensor data meets one or more criteria. For example, in some embodiments, the one or more criteria are designed (e.g., selected) to detect a predetermined threshold (e.g., range) of plateau of the second sensor data (see FIG. 11 for examples of plateaus (e.g., 1008 and/or 1010)). In some embodiments, the expected range of plateaus is based at least in part on a priori information. Accordingly, in some embodiments, the processor module is configured to determine that the sensor is stable when a plateau of measured second sensor data (e.g., the test data or waveform) is within the expected range, such as but not limited to within about ±5%, ±10%, ±15% or ±20% of the expected range. In addition to a moving window, sensor stability can be evaluated using other statistical techniques, such as but not limited to point-to-point comparisons, evaluating a measured profile relative to an expected profile using covariance, standard deviation, or r-value, and the like.

In preferred embodiments, the system is configured to and/or includes programming that provides an output, such as via an output module, also referred to as a processor module, in response to the determination of the sensor's level of stability relative to a predetermined threshold. For example, in some embodiments, the processor module is configured to and/or includes programming that displays (e.g., via the user interface) an analyte value, information associated with sensor stability and/or other information on a local and/or remote display of the user interface in response to a determination of a sensor's stability meeting a threshold (e.g., does the sensor stability meet the threshold or not). In one exemplary embodiment, the processor module is configured to and/or includes programming that displays a first message when the sensor meets the threshold of stability, and a second message when the sensor does not meet the threshold. In another exemplary embodiment, the processor module is configured to and/or includes programming that selects from a menu of messages, symbols, or other indications, responsive to the level of sensor stability determination. For example, in some embodiments, the output includes an indication of at least one of a numeric estimated analyte value, a directional trend of analyte concentration, and a graphical representation of a plurality of estimated analyte values. For example, the output can indicate a request for reference analyte data. For example, if the sensor is a glucose sensor, the system can request a fingerstick or YSI reference analyte value. In another example, the system can request an injection (e.g., into the tubing) of a defined amount of analyte, such that the system can take a reference measurement as the injected analyte contacts the sensor. In some circumstances, other instructions are provided to the caretaker, in response to the determination of the predetermined level of stability. For example, an alert and/or alarm is sounded, such as by visual and/or auditory components of the user interface.

As described above, the break-in process can occur at various times during sensor use, such as during and/or after start-up and after periods of disuse. Accordingly, in preferred embodiments, the processor module is configured to and/or includes programming that determines stability of the analyte sensor at system start-up and/or after exposure of the sensor to blood and/or a calibration, reference, or infusion solution. In some embodiments, the processor module is configured to and/or includes programming that determines (e.g., evaluates) stability of the analyte sensor after a predetermined time period. For example, it is known that, depending upon the sensor's configuration, break-in can take from about 10, 20, 30 or 40 minutes to about 60, 90, 120 or 180 minutes or longer. For a given type of sensor, the average break-in time (e.g., time period, length of time) can be determined mathematically using a priori information. Accordingly, in some embodiments, the system is configured to begin determining the sensor stability after a predetermined time period (e.g., about half, two-thirds, three-quarters or the entire average break-in period, for that sensor configuration, has passed). In one exemplary embodiment, an exemplary intravascular dual-electrode glucose sensor can take about 1-hour to break-in. In this embodiment, the system is configured to begin determining (e.g., evaluating) sensor stability at about 30, 40, 50 or 60-minutes or longer. In a similar embodiment, analyte sensor stability is determined after a system re-start, such as but not limited to in circumstances when the sensor has been turned off for a period of time. For example, the sensor may be turned off when moving the patient, and then re-started; thus, the sensor's stability is determined when the sensor system is re-started.

In one exemplary embodiment, the analyte sensor is a glucose sensor, such as but not limited to a substantially continuous glucose sensor described herein (see FIGS. 1A-1J, 2G-3I for exemplary sensor configurations). For example, in some embodiments, the sensor is a component of the integrated system depicted in FIG. 6, in some embodiments. Preferably, the system (e.g., the processor module is) configured to and/or includes programming that determines the glucose sensor's stability. For example, the system is configured to begin determining the glucose sensor's stability after about 30, 40, 50, 60 or 70 minutes of implantation. In some embodiments, the glucose sensor is a dual-electrode continuous glucose sensor, such as a sensor configured for implantation into a peripheral vein of the host, wherein the sensor's stability is determined using a plurality of time-spaced sensor data points received from the enzymatic working electrode and/or the non-enzymatic working electrode, such as but not limited to when the sensor is exposed to blood samples (e.g., during a measurement phase of the flow profile) and/or a calibration phase. Determining the glucose sensor's stability can include evaluating the sensor's stability relative to one or more predetermined criteria, such as but not limited to a profile range (e.g., within about ±5%, ±10%, ±15% or ±20% of an average profile) generally observed for that particular type of glucose sensor. In preferred embodiments, the glucose sensor system is configured to determine the sensor's stability iteratively and/or periodically. In a further embodiment, the glucose sensor system is configured to determine the sensor's stability after re-start, such as after a period of disuse, as described herein.

Diagnostics and Fail-Safes

In some embodiments, the system includes programming configured to diagnose a condition of at least one of the sensor and the host responsive to calibration information. In some embodiments, the system intermittently or continuously determines at least some calibration information (e.g., sensitivity information, $b_{offset}$, and the like), each time the sensor is exposed to a reference solution and/or a biological sample.

In one embodiment, systems and methods are configured to find a plateau and/or stable window of data in response to exposure of the sensor to at least one of a reference solution and a biological sample. In some embodiments, if the system cannot find the plateau and/or stable window of data, the system is configured to "fail-safe;" for example, in some circumstances, a lack of plateau and/or stable window of data may be indicative of dilution and/or mixture of the reference solution (e.g., calibration solution) with the biological sample (e.g., blood), and/or interruption/disruption of expected/desired fluid flow. Additionally, in some circumstances, a lack of plateau and/or stable window of data may be indicative of interfering species in the signal.

In general, the term "fail-safe" includes modifying the system (e.g., the processor module) processing and/or display of data in some manner responsive to a detected error, or unexpected condition, and thereby avoids reporting and/or processing of potentially inaccurate or clinically irrelevant analyte values.

In another embodiment, systems and methods are configured to process a signal responsive to exposure of the signal to a reference and/or biological sample to determine whether the signal is within a predetermined range; if the signal falls outside the range, the system is configured to fail-safe.

In some embodiments, systems and methods are configured to determine calibration information including sensitivity information, wherein the system includes programming configured to diagnose an error responsive to a change in sensitivity above a predetermined amount. For example, in a sensor system as described in more detail with reference to the exemplary embodiment of FIGS. 8A to 8C, the system can be configured to determine a sensitivity value during each calibration phase; and wherein the system can be configured to fail-safe when the sensitivity of a calibration phase differs from the previously stored sensitivity by more than a predetermined threshold. In this exemplary embodiment, fail-safe can include not using the sensitivity information to update calibration, for example. While not wishing to be bound by theory, the predetermined threshold described above allows for drift in the sensitivity of the sensor, but prevents large fluctuations in the sensitivity values, which may be caused by noise and/or other errors in the system.

In some embodiments, systems (including programming) and methods are configured to diagnose error in the sensor system by ensuring the sensor signal (e.g., raw signal of the reference solution(s)) is within a predetermined range. In some embodiments, the sensor signal must be within a predetermined range of raw values (e.g., counts, current, etc). In some embodiments, one or more boundary lines can be set for a regression line drawn from the calibration phase. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g., by a retrospective analysis of sensor sensitivities and/or baselines collected from a set of sensors/patients, assuming that the set is representative of future data). U.S. Patent Publication No. US-2007-0197889-A1, which is incorporated herein by reference in its entirety, describes systems and methods for drawing boundaries lines. In some embodiments, different boundaries can be set for different reference solutions.

In some embodiments, systems and methods are configured for performing diagnostics of the sensor system (e.g., continuously or intermittently) during exposure of the sensor to a biological sample, also referred to as the measurement phase, for example, such as described in more detail above with reference to FIGS. 8A to 8C. In some embodiments, diagnostics includes determination and/or analysis of $b_{offset}$. In some embodiments, systems and methods are provided for comparing sequential $b_{offset}$ values for sequential measurement phases. In some embodiments, the system includes programming configured to diagnose an error and fail-safe responsive to a change in the $b_{offset}$ above a predetermined amount. In some embodiments, the system includes programming configured to re-calibrate the sensor responsive to changes in the $b_{offset}$ above a predetermined amount. In some embodiments, the system includes programming configured to detect an interfering species responsive to a change in the $b_{offset}$ above a predetermined amount.

In some embodiments, the system includes programming configured to diagnose a condition of the host's metabolic processes responsive to a change in $b_{offset}$ above a predetermined amount. In some embodiments, the system includes programming configured to display or transmit a message associated with the host's condition responsive to diagnosing the condition. While not wishing to be bound by theory, it is believed that changes in $b_{offset}$ can be the result of an increase (or decrease) in metabolic by-products (electroactive species), which may be a result of wounding, inflammation, or even more serious complications in the host; accordingly, changes in $b_{offset}$ can be useful in diagnosing changes in the host's health condition.

In some embodiments, the system includes programming configured to detect sensor error, noise on the sensor signal, failure of the sensor, changes in baseline, and the like, responsive to a change in $b_{offset}$ above a predetermined amount.

In some embodiments, the system includes programming configured to determine a time constant of the sensor. One method for calculating a time constant for a sensor includes determining an impulse response to a step change, wherein time at the peak of the impulse response represents a time constant for the sensor. While not wishing to be bound by theory, it is believed that the time constant determined from the peak of the impulse response should remain substantially the same throughout the life of the sensor. However, if a shift in the time constant (between step changes and their associated impulse response curves) above a predetermined range is detected, it can be indicative of an unexpected sensor condition or error, for example. Accordingly, by comparing time constants from a plurality of impulse response curves (derived from a plurality of step responses), programming can be configured to diagnose a sensor condition or error and initiate programming (e.g., fail-safe), accordingly.

Accordingly, the system can "fail-safe," including performing one or more of the following fail-safe responses: temporarily or permanently suspending (e.g., discontinuing) display of analyte data, updating calibration or re-calibrating the sensor, requesting external reference values, using external reference value(s) as confirmation of a detected condition, using external reference value(s) to update calibration or re-calibrate the sensor, shutting the system down, processing the sensor data to compensate for the change in $b_{offset}$, transmitting one or more messages to the user interface or other external source regarding the sensor condition, and the like.

In preferred embodiments, the sensor electronics include a fail-safe module that is configured to detect a system malfunction. The fail-safe module can be configured to detect a variety of system malfunctions. For example, the fail-safe module can be configured to detect electrical malfunctions, malfunctions of the system fluidics, malfunctions of the sensor, and/or the like. For example, the system electronics can be configured to test and/or track the functions of different system components, and to intelligently recognize aberrant changed in such functions as possible malfunctions.

In some embodiments, the fail-safe module is configured to detect electrical malfunctions, such as but not limited to short circuit and electrical malfunction associated with start-up and/or sensor break-in. For example, it is known that an I/R drop across an electrochemical sensor's working electrode(s)

generally occurs during use. The I/R drop can be monitored for changes, which can be indicative of an electrical malfunction. Similarly, during use of an analyte sensor in an intravascular system, wherein the sensor is periodically/alternately exposed to at least one reference solution and a blood sample, the generated signal is expected to rise and fall in a regular fashion, for example a recognizable wave-form pattern including peaks and valleys. For example, when the enzyme sensor is exposed to blood, the rate of the step-response indicates the change in glucose from calibration solution to blood. The plateau of the response also indicates the glucose concentration (although the plateau generally indicates the absolute glucose concentration, not the change in glucose concentration). Accordingly, the fail-safe module can be configured to monitor the pattern of step-responses (e.g., over time) for substantial changes/deviations, which can be indicative of electrical malfunctions. For example, in some circumstances, the signal can "rail" or "zero," wherein the signal rapidly changes to a non-physiological analyte value and remains relatively stable at that non-physiological value for a period of time. In some circumstances, the rapid change in value occurs at a rate that is also not physiologically possible. In some circumstances, a comparison of the rate-response (e.g., transient/kinetic information) versus plateau response (e.g., steady state information) of each blood measurement can be used as an indicator of sensitivity drift. Similarly, in some embodiments, comparison of rate-response versus plateau response on a non-enzymatic electrode/sensor when expose to blood can provide information related to the sensor's response to non-glucose species in the sample, which can be used to determine if and/or when to fail-safe.

In some embodiments, the fail-safe module is configured to detect fluidics malfunctions, which can include a malfunction of any part of the system configured to contact and/or move a fluid. For example, the vascular access device (catheter) can become occluded, such as due to blood clotting or pressing the in vivo orifice (e.g., catheter tip) against a vessel wall such that fluid cannot move in an out of the vascular access device. In some circumstances, the tubing can become kinked, the host can move his or her arm such that the catheter becomes bent, bubbles may get into the system, and/or the flow control system can malfunction (e.g., not metering fluid flow into the host or not withdrawing blood samples as it was programmed to do), such that washing, calibration, sample collection and the like are not performed as programmed. For example, the sample can become diluted with calibration solution, there may be clotting on a portion of the sensor, and the like. In one exemplary embodiment, the fail-safe module is configured detect fluidics malfunctions by monitoring the pattern of signal increases/decreases generated on the working electrode(s), to detect periods of time during which the signal does not follow an expected waveform (e.g., using known waveform analysis methods and/or pattern recognition algorithms), such as when the signal hits upper and/or lower limits. For example, if the signal zeros for a period of time, the fluidics system may be unable to withdraw a blood sample due to kinking of the tubing or occlusion of the catheter. In another example, the signal on the working electrode(s) may stop going back down when the tested blood sample should be re-infused into the host and the sensor should be contacted with wash/reference solution, which is indicative of a malfunction of expelling the used sample, washing the sensor, and the like. For example, if the catheter becomes occluded by a blood clot, the flow control system will be unable to meter fluid through the catheter.

In some embodiments, the fail-safe module is also configured to detect malfunctions of the analyte sensor. For example, a sensor malfunction includes but is not limited to noise on the signal, drift of sensor sensitivity and/or baseline, a broken component of the sensor, blood clotting on a portion of the sensor, and cross-talk, as described in more detail elsewhere herein.

In preferred embodiments, the fail-safe module is further to evaluate a detected malfunction against a criterion. One or more criteria can be preprogrammed (including reprogrammed) into the system, such as be a host, a caretaker of the host, and/or the manufacturer. For example, in some embodiments, one or more criteria could be selected from a menu/list of criteria, or manually programmed into the system. Available criteria can be responsive to the different types of malfunctions can occur and/or a user-perceived level of severity and/or urgency.

After a system malfunction has been detected, the fail-safe module is configured to provide an alert, an alarm and/or an instruction, such as to the host and/or a caretaker of the host. For example, the system can be configured to provide an auditory alarm (e.g., beeps, busses, siren, pre-recorded voice message, etc.), a visual alert (e.g., blinking or flashing lights or display screen), a tactile alert (e.g., vibrating), transmitting alerts/instructions to a remote location, such as a nurse's station or a doctor's phone/PDA, and the like.

As a non-limiting example, a method is provided for detecting system malfunctions via the processing of the data of a continuous analyte sensor implanted in a host's circulatory system. As described elsewhere herein, the continuous analyte sensor is configured to generate a signal associated with an in vivo analyte concentration when the sensor is implanted in the host. Additionally, the sensor electronics includes a fail-safe module configured to detect a system malfunction. Accordingly, the method includes exposing the sensor to a sample from the host's circulatory system and detecting a malfunction of the system, such as but not limited to an electrical malfunction, a fluidics malfunction, and/or a sensor malfunction. In some embodiments, an equilibrium analysis and/or a kinetic analysis of received data/signal is performed. As described elsewhere herein, the data include steady state (e.g., sensitivity and/or baseline information) and/or transient state information, which can be evaluated/analyzed to provide alerts, alarms and/or instructions.

As described herein, the system (e.g., the processor module and/or fail-safe module) can be configured to analyze steady state and or transient state information generated during the step-up response of the sensor, such as during the switch from blood to reference solution and vice versa, also referred to as waveform analysis (for example, using pattern recognition algorithms, and the like). For example, by analyzing the step-up waveform of a dual-electrode sensors non-enzymatic working electrode, the quality of blood sample aspiration can be evaluated (e.g., fluidics). Similarly, by analyzing the step-down waveform of the sensor's non-enzymatic working electrode, the quality of washing can be evaluated (e.g., fluidics). As another example, analysis of direction of the step-up response of the plus-enzyme working electrode upon exposure to blood can used to evaluate calibration accuracy.

System Diagnostics

During operation of the integrated system, wherein the system includes a continuous analyte sensor implanted in the host's circulatory system and a flow control device (e.g., FIG. 6-7), system artifacts, such as but not limited to distortion of calibration and analyte measurement waveforms can occur unexpectedly, for a variety of reasons. For example, anything that affects IV tubing can cause a fluidics malfunction, such as the host leaning on the IV tubing, or a blood clot fouling the sensor or occluding the catheter and/or vessel. To some extent, sensor calibration and analyte concentration determination are dependent upon the quality of the calibration and measurement waveforms, respectively. For example, a good quality waveform can be an indicator that the sensor can be accurately calibrated with the data comprised in that waveform and/or in a substantially time-corresponding waveform. However, it has been observed that in some circumstances, a signal waveform will be of poor quality (e.g., not representative of the system's function), and the data contained in that waveform is likely to be unsuitable for subsequent calculations, processes, and the like. For example, a poor quality the waveform can be an indicator that analyte measurements may not be accurate. Such a circumstance could be detrimental to the host's health. In such circumstances, not using (e.g., "throwing out" or disregarding) the poor quality signal waveform and its associated data, for calculating an analyte concentration, maintains sensor accuracy and saves time. Accordingly, preferred embodiments provide systems and methods for performing system diagnostics on the analyte sensor system, for example, such that the quality of a waveform is evaluated prior to use of data comprised in the waveform for sensor calibration and/or determination of analyte calibration.

FIG. 16 is a flow chart illustrating system diagnostics, in one embodiment. At block 1600, a method for performing a diagnostic of an analyte sensor system is provided, wherein the method includes providing a sensor system, which includes an analyte sensor and a flow control device configured to intermittently expose the analyte sensor to a biological sample and to an infusion solution, wherein the analyte sensor includes (1) a first working electrode configured to provide a first signal (e.g., plus-enzyme working electrode) including an analyte component and a baseline component and (2) a second working electrode configured to provide a second signal (e.g., second sensor data) including a baseline component substantially without an analyte component (e.g., no-enzyme working electrode), and evaluating the sensor system based at least in part on the second signal. Suitable dual-electrode continuous analyte sensor systems, such as those including twisted or bundled working electrodes or with working electrodes located within the fluid coupler, are described in detail elsewhere herein, such as but not limited to the sections entitled "Dual-Electrode Analyte Sensors," "Multi-Sensor Apparatus," and "Sensor Configurations for Equivalent Measurement of Noise Signals at the Two Working Electrodes." However, other dual electrode analyte sensors can be used, such as but not limited to those described in U.S. Pat. No. 6,175,752 and U.S. Patent Publication No. US-2008-0119703-A1, U.S. Patent Publication No. US-2008-0108942-A1, and U.S. Patent Publication No. US-2008-0200789-A1, each of which is incorporated herein by reference in its entirety.

In preferred embodiments, the processor module is configured to and/or includes programming that evaluates the second signal (e.g., the no-enzyme signal) for an expected shape and/or pattern when the sensor is exposed to a biological sample and/or to an infusion solution. For example, in some circumstances, this is done to determine if the system fluidics (e.g., draw-back and infusion) are functioning properly. In some embodiments, the system is configured such that the flow profile includes a measurement phase and an infusion phase. During the measurement phases, the flow control device is configured to draw-back a sample, such that the sample contacts the sensor. It has been observed that during a measurement phase, the second signal (e.g., no-enzyme working electrode) waveform tends to rise in a monotonic manner, if the draw-back was successful. It has also been observed (e.g., over numerous in vitro and in vivo experiments) that during infusion (e.g., re-infusion of the drawn-back sample, infusion of calibration, a calibration period/phase), the second signal waveform tends to fall (e.g., decline) in a monotonic manner, if the infusion was successful. Deviation from these observed patterns may indicate that the draw-back or infusion was not successful, and, therefore, data comprised in the waveform may be unsuitable for use in some calculations.

In one exemplary embodiment, the processor module is configured to and/or includes programming that evaluates the second signal to determine a success of drawing back a biological sample from a host's circulatory system to the sensor (e.g., to contact the sensor). For example, in some embodiments, the system is configured to use data contained in the measurement waveform to calculate the analyte concentration, if it (the system, processor module) determines that the draw-back was successful. On the other hand, the system is configured to disregard/not use data comprised in the measured waveform for subsequent calculations (e.g., analyte concentration, sensor calibration, etc.), if it is determined that the draw-back was unsuccessful. In a further embodiment, the system is configured to display an analyte value measured during the biological sample draw-back in response to determining that the draw-back of sample was successful. In another exemplary embodiment, the system is configured to evaluate the signal to determine if an infusion was successful. In some embodiments, a successful infusion includes at least one of re-infusing the biological sample into the host, washing the sensor (e.g., removing a sufficient amount of sample such that substantially accurate data can be obtained during the next sample draw-back without interference from components from the current sample draw-back) and infusing an amount of infusion solution. For example, in some embodiments, determining a successful infusion includes displaying an analyte value measured in a biological sample after the infusing the infusion solution in response to a determination of a successful infusion.

At block 1602, the analyte sensor is intermittently exposed to a biological sample and to an infusion solution. For example, the flow profile can include analyte measurement and calibration phases, such that the flow control device intermittently draws back blood samples that contact the sensor and infuses at least one reference solution, as described elsewhere herein.

At block 1604, the system receives a first signal (e.g., the signal from the first working (e.g., plus-enzyme, enzymatic) electrode) including analyte and baseline (e.g., non-analyte-related) components and a second signal (e.g., the signal from the second working electrode (e.g., the non-enzymatic, no-enzyme electrode) including a baseline component without an analyte component. As is understood in the art, the signal includes a waveform, which is referred to as the "signal waveform" and/or the "test waveform." For example, when the signal (e.g., in counts) is plotted against time, the graph looks like a wave. The waveform is associated with the intermittent (e.g., alternating, cyclical) exposure of the sensor to blood and infusion solution. The iterative (e.g., cyclical, periodic) intermittent exposure of the sensor to blood and infusion solution can generate a plurality of waveforms. If the signal waveform is generated during a calibration phase of the flow profile (e.g., during exposure of the sensor to a calibration solution), also referred to herein as a "calibration signal waveform," then at least a portion of the data generated can be used for calibrating the sensor. If the signal waveform is generated during a measurement phase (e.g., during exposure of the sensor to a sample of the host's blood), also referred to herein as a "measurement signal waveform," then at least a portion of the data generated can be used for determining the host's blood analyte concentration.

At block 1606, the processor module is configured to and/or includes programming that evaluates the system, based at least in part on the second signal (e.g., the no-enzyme signal of the non-enzymatic (e.g., second) working electrode). Since the signal generated by the no-enzyme working electrode includes baseline but substantially no analyte signal component, the shape (e.g., pattern) of the signal waveform generated is associated with (e.g., diagnostic of) the quality of the system's function (e.g., how well the system is functioning). For example, fluidics and sensor function problems are reflected in the waveform as a deviation from an expected pattern, such as but not limited to an average waveform generally observed when a system is in use.

The signal waveform can be evaluated using a variety of methods. In some embodiments, the processor module is configured to and/or includes programming that evaluates the signal waveform (e.g., of the second signal) by evaluating the signal waveform for an expected shape and/or pattern when the sensor is exposed to a biological sample and/or to the infusion solution (e.g., a hydration, reference, and/or calibration solution). For example, it has been observed, through numerous in vitro and in vivo experiments, that the second signal waveform tends, in a characteristic way, to rise (e.g., increase) when the sensor is exposed to sample (e.g., blood) and to fall (e.g., decrease) when the sensor is exposed to an infusion solution. In some embodiments, the processor module evaluates the signal waveform by evaluating a similarity and/or correlation between the signal waveform and a waveform template. In a further embodiment, a second signal waveform is compared to this expected shape (e.g., pattern), such as by visual inspection or similar means. For example, the second signal waveform and the expected waveform pattern can be graphed together, and then observed and/or evaluated to determine if they have a similar shape, if they are close together, if they substantially overlap (e.g., overlap by about 80%, 85%, 90%, or 95%), and the like. In one exemplary embodiment, the system is configured to use at least some of the data from the second signal waveform in subsequent mathematical processes and/or calculations (e.g., sensor calibration, analyte concentration calculation) if the second signal waveform is substantially similar to the expected shape (e.g., pattern; the signal waveform is of sufficiently and/or substantially high quality). In a further embodiment, the system is configured to use at least some of the first signal waveform data (e.g., plus-enzyme electrode) for determining the analyte concentration, calculating sensor sensitivity, calibrating the sensor, and/or the like, when the second signal waveform is substantially similar to an expected shape (e.g., pattern) and/or meets one or more criteria (e.g., falls within a threshold). If the second signal waveform is not sufficiently and/or substantially similar to the expected shape (e.g., pattern) and/or does not meet the one or more criteria (e.g., it is of lower quality), then the system is configured to disregard (e.g., not use, throw out) the second signal waveform data for other purposes, such as subsequent calculations. In a further embodiment, the system is configured to disregard the first signal waveform data (e.g., plus-enzyme electrode) when the second signal waveform is not substantially similar to the expected shape (e.g., pattern) and/or exceeds the threshold.

In preferred embodiments, the processor module is configured to and/or includes programming that uses mathematical methods to evaluate a signal waveform. In some embodiments, one or more waveforms are evaluated using correlation waveform analysis (e.g., cross-correlation). Preferably, correlation waveform analysis quantifies a correlation and/or similarity of corresponding points (e.g., of a measured waveform vs. a waveform template) for a variance, which provides an indication or measurement associated with directional correlation of the points. Additionally or alternatively, waveform analysis can include systems and methods for quantifying overlap of the corresponding points, namely, an amplitude or amount of difference between the measured waveform vs. a waveform template. In some preferred embodiments, waveform analysis ensures normalization of data such that maximum and minimum amplitudes are equivalent for comparison purposes. In general, any of the waveform analysis described herein can be performed on actual waveforms (signal) or transforms of the waveform, as is appreciated by one skilled in the art.

In some embodiments, a level of quality of the signal waveform is evaluated (e.g., a level of reliability). In some further embodiments, the system is configured to perform one or more tasks, such as calibrating the sensor, displaying information, or the like, responsive to the level of quality of the signal waveform, such as described herein. In some embodiments, the level of reliability is classified as pass or fail, good versus bad, acceptable versus not acceptable. In some further embodiments, the system is configured to perform a task when the waveform is classified as pass, acceptable or the like, such as described herein. In some further embodiments, the system is configured to perform another task or do nothing when the waveform is not classified as pass, acceptable, or the like (e.g., the waveform is classified as failed, not acceptable, etc.).

In some embodiments, when the second signal waveform is compared to an expected shape (e.g., pattern), a similarity and/or correlation of the second signal waveform to a waveform template (e.g., seed template) is evaluated. In some embodiments, the waveform template is based at least in part on a priori information. For example, a waveform template (for a measurement or a calibration phase) is generated (e.g., created, calculated, provided, determined, and/or formed) by integrating a plurality of previously generated second signal waveforms. Preferably, a waveform template is generated from a plurality of second signal waveforms obtained during previous in vitro and/or in vivo experiments (e.g., system uses). While in some embodiments, about 2, 5, 10, 20, 30, 40 or 50 second signal waveforms to about 60, 70, 80, 90 or 100 second signal waveforms are integrated to generate (e.g., produce, form) the waveform template, in other embodiments, hundreds or thousands of second signal waveforms are integrated to generate a waveform template (e.g., seed template). In some embodiments, a waveform template is generated from previous sensor sessions from an individual host, such as to provide an adaptive waveform template.

In some embodiments, the waveform template contains information specific to the sensor system in use, in addition to a priori information. For example, in some embodiments, the waveform template is based at least in part on a second signal waveform measured by the system (e.g., the system in use). Preferably, the processor module is configured to and/or includes programming that updates the template waveform (e.g., with the second signal waveform) when a similarity and/or correlation between the (second) signal waveform and the waveform template meets one or more criteria (and/or fall within a threshold). For example, if the second signal waveform substantially correlates with (e.g., at least about 80%, 85%, 90% or 95%) the (current) waveform template, the signal waveform is used to update the waveform template, to generate an updated waveform template (e.g., newest, latest version of, most recently updated), also referred to herein as an "adaptive template." Conversely, if the second signal waveform does not meet the one or more criteria, the system is configured to not integrate the second signal waveform with the waveform template (e.g., the system can "throw out" the poor quality or bad waveform). In some embodiments, a similarity of the second signal waveform to the template is evaluated by plotting the second signal waveform (e.g., the waveform just measured) with the waveform template, wherein the processor module is configured to and/or includes programming that determines a correlation (or deviation) of the two waveforms in shape and/or amplitude. In other embodiments, the second signal waveform is mathematically correlated with the template waveform, to determine how they correlate (or deviate). While not wishing to be bound by theory, it is believed that an adaptive waveform template provides system diagnostics adapted for each host and use of the system. It should be noted herein that an initial waveform template is used when the sensor system is started up, with subsequent use of the adaptive template thereafter. Accordingly, in some embodiments, an adaptive template is substituted for a waveform template as soon as the adaptive template is generated.

In some embodiments, the processor module is configured to and/or includes programming that detects a level of interferent in the biological sample (e.g., such as described elsewhere herein). In some embodiments, the waveform template is updated when the level of interferent meets one or more criteria. For example, in some embodiments, the processor module is configured to update the waveform template when substantially no interferent (e.g., less than about 20%, 10%, 5%, 4%, 3%, 2% or 1% of the signal) is detected. In this embodiment, if interference is detected on the signal (e.g., above 1, 2, 3, 4, or 5% of the signal), then the signal waveform is not used to update the template. If, however, interference is not detected on the signal (or is less than or equal to about 5%, 4%, 3%, 2% or 1% of the signal), then the processor module updates the waveform template (or the adaptive template) with signal waveform. In some embodiments, a lower level of interferent on the signal, such as 15%, 10%, 5%, 4%, 3%, 2% or 1% or less of the signal is acceptable. Accordingly, if the level of interferent detected is less than or equal to the criteria (e.g., within the threshold) then the waveform template (or the adaptive template) is updated with the signal waveform. If the level of interferent does not meet the criteria (e.g., exceeds the threshold) then the waveform template (or adaptive template) is not updated.

In some embodiments, evaluating the sensor system includes detecting an interferent by evaluating an amplitude, a change in amplitude, the signal waveform and/or a change in the signal waveform (e.g., of the second signal) when the sensor is exposed to the biological sample. In some embodiments, interferent detection is further based at least in part on a calibrated analyte value. In one exemplary embodiment, the system is configured to look for a change in analyte concentration (e.g., amplitude) above a threshold (e.g., exceeding a criterion) in combination with evaluating a second signal waveform.

In preferred embodiments, the processor module is configured to and/or includes programming that controls a display of the sensor system based at least in part on a level of interferent detected. For example, in some embodiments, the processor module is configured to not display an analyte value measured in a biological sample in response to an amount (e.g., level) of interferent detected on the second signal based on one or more criteria. For example, when the detected interferent on the no-enzyme working electrode exceeds a predetermined threshold (e.g., an amount of the signal, such as but not limited to 5, 10, 15, 20, or 25% or more of the signal), the analyte value is not displayed. In an exemplary embodiment, what is displayed is responsive to the level of interferent detected. For example, if the level does not meet the criteria, then a first indication (e.g., message or value) is displayed; if the level meets the criteria, then a second indication is displayed; if the level exceeds the criteria, then a third indication is displayed. In another example, if the level of interferent detected meets a first criteria, then an indication or message associated with the first criteria is displayed; if the level of interferent detected meets a second criteria, then an indication or message associated with the second criteria is displayed; and the like.

In some embodiments, processor module is further configured to process the first signal and the second signal to obtain a subtracted signal, wherein the step of processing is based at least in part on the level of interferent on the sensor system. For example, in some circumstances, the signal is processed to remove offset of the baseline and/or compensate for a measured interferent (e.g., one or more interfering species) on the signal, and/or the like, such as described elsewhere herein.

In a further embodiment, the processor module is configured to fail-safe when the no-enzyme signal and the analyte concentration (or change in analyte concentration) do not meet one or more criteria.

As described above, the waveform of the non-enzyme working electrode (e.g., the second signal) has a characteristic pattern. In some embodiments, a characteristic pattern includes monotonicity or substantial monotonicity. The term "monotonicity" as used herein is a broad term, and is to be given its ordinary and customary meaning to a person of ordinary skill in the art (and are not to be limited to a special or customized meaning), and refers without limitation to a quality of a sequence or function, wherein it is either substantially increasing or substantially decreasing in value, such as but not limited to about 80%, 85%, 90%, 95% or more of the time. Thus, a measurement signal waveform generally smoothly rises, while a calibration signal waveform generally falls smoothly. Accordingly, in some embodiments, the step of evaluating the sensor system includes evaluating a monotonicity of the signal waveform (e.g., is the signal waveform monotonic or does is contain bump, jumps, blips, etc.). In some embodiments, the system is configured to evaluate the monotonicity of the signal waveform by performing cross-correlation of the signal waveform with a waveform template. If the signal waveform is not monotonic, is will not correlate well with the waveform template. In other embodiments, the monotonicity of the signal waveform is evaluated by performing a time-series analysis, or the like.

In some embodiments, the processor module is configured to and/or includes programming that evaluates a reliability of the system. For example, in some embodiments, the signal waveforms generated over a period of time (e.g., a window), such as 5, 10, 15, 20 or 30 minutes or longer, are evaluated, such as to ensure that the waveforms are substantially consistent over that period of time. In some embodiments, the window of waveforms to be evaluated is a moving window, encompassing the 1, 2, 3, 4, 5, 6, 7, 8, 9, 10, 20 or 30 (or more) most recently generated second signal waveforms.

In some embodiments, evaluating the reliability of the system includes determining a level of reliability of the sensor system, such as by comparing an amplitude, a change in amplitude, a signal waveform and/or a change in a signal waveform of the second signal to one or more criteria. In some embodiments, the one or more criteria include an expected waveform shape and/or pattern. For example, if the second signal waveforms within a window are substantially monotonic, within a predetermined range of correlation, then the system is configured determine a level of reliability (e.g., reliable or "pass"). Conversely, if the second signal waveforms within a window are outside the predetermined range of monotonicity and/or correlation, the system is configured determine a reduced level of reliability (e.g., not reliable or "fail"). A level of 100% reliability of the sensor system can be defined using known methods, including time-series analysis, standard deviation, variance, covariance, and/or the like. Accordingly, in some embodiments, the level of reliability of the sensor system is 60%, 65%, 70%, 75%, 80%, 85%, 90% or 95% or more as compared to a 100% level as defined by the methods described above, for example. Depending upon the system configuration, various levels of reliability may be acceptable. For example, a low level of reliability may be acceptable for a first system configuration while only a high level of reliability may be acceptable for a second system configuration. Furthermore, in some embodiments, the system is configured to perform one or more functions or tasks, such as but not limited to calculating a value, displaying information, updating a template, and the like, depending upon the level of reliability, wherein the acceptability of the reliability is associated with the system configuration.

In other embodiments, evaluating the reliability of the system includes classifying a signal waveform, such as by comparing an amplitude, a change in amplitude, a signal waveform and/or a change in a signal waveform of the second signal to one or more criteria. For example, a signal waveform can be classified as "pass" or "fail," if it meets the one or more criteria. For example, in some embodiments, the system is configured to pass the signal waveform when it correlates with the template waveform by at least 50, 55, 56, 70, 75, 80, 85, 90 or 95%. The system can be configured to classify a signal waveform as "pass" or "fail" using other mathematical methods, described elsewhere herein. In some embodiments, the system is configured to use at least some of the data in the signal waveform (e.g., second signal) and/or data in a time-corresponding signal waveform (e.g., first signal) for subsequent mathematical processes, such as calibrating the sensor, calculating the analyte value and the like, when the signal waveform is classified (e.g., declared) as "pass," such as described herein. Conversely, in some embodiments, the system is configured to not use the data when the signal waveform is classified as "fail."

In some embodiments, the system is further configured to control a display of the sensor system based at least in part on the level of reliability of the sensor system (e.g., pass or fail). For example, if the system is determined to be reliable, then an analyte value is displayed to the user. If, on the other hand, the level of reliability does not meet one or more criteria, then the system is configured to respond in another way, such as not displaying an analyte value, sounding an alert or alarm, requesting input of information by the user, and the like. In a further embodiment, the system is configured to modify a subtraction of the second signal from the first signal (e.g., processing associated with the subtraction) based at least in part on the reliability of the sensor system.

In some embodiments, the system is configured to evaluate a portion of a second signal waveform, rather than the entire waveform. For example, it have been observed that, in some circumstances, an initial portion of a second signal waveform (e.g., the first eighth, fifth, third, quarter, half, two thirds, three quarters, etc.) may be somewhat unstable, while the portion of the second signal waveform from which data is used in subsequent calculations is substantially stabilized. While not wishing to be bound by theory, it is believed that the initial instability of the second signal waveform observed is caused by minute variations in the function of fluidics system (e.g., mechanical movement of the flow control device), membrane effects caused by switching from an infusion solution to blood (and/or back again, e.g., a step-change), fluid dynamics (e.g., turbulence) and the like that may not affect the reliability of the data. Accordingly, in some embodiments, the system is configured to disregard at least some of the initial portion of the second signal waveform, when performing system diagnostics, such as but not limited to evaluating the system (e.g., system fluidics, system reliability and/or the like).

In some embodiments, the processor module is configured to and/or includes programming that evaluates the sensor system based at least in part on the second signal by determining a success of a biological sample draw-back from a host's circulatory system to the sensor. A success can be determined and/or quantified by a level of reliability. For example, in some embodiments, the system is configured to determine that a drawback or infusion was successful if the reliability is at least 50%. Some embodiments may require a higher level of reliability to determine that the drawback or infusion was successful. For example, in some embodiments, the system is configured to determine that the drawback or infusion was successful when the reliability is at least 55, 60, 65, 70, 75, 80, 85, 90, or 95% or greater.

In some further embodiments, the system is configured to display an analyte value measured during the biological sample draw-back in response to a determination of a successful biological sample draw-back. For example, success of a draw-back (e.g., the level of reliability meets one or more criteria, or the draw-back is classified as pass) is an indication that the analyte sensor is sufficiently contacted by the sample such that an accurate measurement can be made. Thus, the displayed analyte value is not substantially affected by fluidics problems and can therefore be considered reliable. In some embodiments, the system is configured to not display the analyte value measured during the biological sample draw-back, when the draw-back is determined to be unsuccessful, such as when the reliability does not meet the one or more criteria and/or is classified as fail.

In some embodiments, the processor module is configured to and/or includes programming that evaluates the sensor system based at least in part on the second signal by determining a success of infusing the infusion solution such that a biological sample is washed from the sensor. As discussed elsewhere herein, the accuracy of sensor measurement can be affected by the presence of blood components, from the previously drawn back sample, on the sensor. For example, in some circumstances, red blood cells from a previous drawback might affect the current measurement and cause an inaccurate measurement to be made. In some embodiments, this problem can be prevented and/or avoided by sufficiently washing the sensor, such as by reinfusing a drawn-back blood sample and infusing one or more amounts of infusion solution at one or more rates, such as according to a flow profile. Thus, in some embodiments, the system is configured such that the sensor is washed of the biological sample when the success of the infusion meets one or more criteria. For example, in some embodiments, the level of success of infusion is determined and/or quantified by a level of reliability, such as described above. In other embodiments, the infusion is classified as successful (e.g., pass) or not successful (e.g., fail). In some embodiments, the system is configured to display an analyte value measured in a biological sample after the infusing the infusion solution in response to a determination of a successful infusion. Accordingly, if the infusion was successful, the system displays the analyte value; but if the infusion was not successful, the system does not display the analyte value.

As a non-limiting example, wherein the system is configured to use a 100 mg/dl glucose reference solution and the plus-enzyme working electrode is exposed to blood having a glucose concentration greater than 100 mg/dL, the signal response should step up. When the plus-GOX working electrode is exposed to blood having a glucose concentration less than 100 mg/dL, the signal response should step down. If the system calculated a glucose value less than 100 mg/dL (e.g. 70 mg/dL) when the plus-GOX working electrode stepped up, a calibration error is detected and the system can fail-safe. Similarly, if the system calculated a glucose value greater than 100 mg/dL (140 mg/dL) when the plus-GOX working electrode stepped down, an error is detected and the system can fail-safe.

Signal Amplitude and/or Noise Amplitude Analysis and Fail-Safes

In some embodiments, the system is configured to fail-safe when analysis of signal amplitude and/or noise amplitude (residual) of the sensor's working electrode(s) indicates that the integrity of the system's electrical connections are compromised, such as at the sensor or at one or more components of the system's electronics. For example, in the case of a dual-electrode sensor, an accuracy and/or reliability of the relationship of the plus-enzyme signal to the non-enzymatic signal is evaluated by comparing signal amplitudes in calibration solution (or in blood). For example, the non-enzymatic signal being greater than the plus-enzyme signal is indicative of a sensor malfunction, and the system can fail-safe.

In some embodiments, sensor diagnostics evaluates whether the calculated sensitivity falls within a predetermined limit and/or range, for example, 1-10 pA/mg/dL, as described in more detail elsewhere herein. In some embodiments, the sensor diagnostics evaluates a difference in signal (raw, filtered and/or calibrated) between the non-enzymatic working electrode and the enzymatic working electrode (e.g., in reference/calibration solution) to determine whether they fall within predetermined limits and/or ranges. As one example, a sensor/calibration diagnostic evaluates the baseline of the enzymatic and non-enzymatic electrodes to determine whether they fall within a predetermined limit/range.

In some embodiments, the system is configured to use a priori information to set tolerances for sensitivity and/or baseline drift. Preferably, the system is configured to discriminate between measured changes in sensitivity and/or baseline from signal artifacts, such as by using tolerance limits based on historical/empirical data. For example, in some embodiments, if the sensitivity and/or baseline drifts outside predetermined limits and the drift is not a transient artifact (e.g., it persists for a predetermined time period), an error can be detected in sensor function and/or calibration.

In yet another alternative embodiment of signal artifacts detection that utilizes examination or evaluation of the signal information content, filtered (e.g., smoothed) data is compared to raw data (e.g., in sensor electronics or in receiver electronics). In one such embodiment, a signal residual is calculated as the difference between the filtered data and the raw data. For example, at one time point (or one time period that is represented by a single raw value and single filtered value), the filtered data can be measured at 50,000 counts and the raw data can be measured at 55,500 counts, which would result in a signal residual of 5,500 counts. In some embodiments, a threshold can be set (e.g., 5000 counts) that represents a first level of noise (e.g., signal artifact) in the data signal, when the residual exceeds that level. Similarly, a second threshold can be set (e.g., 8,000 counts) that represents a second level of noise in the data signal. Additional thresholds and/or noise classifications can be defined as is appreciated by one skilled in the art. Consequently, signal filtering, processing, and/or displaying decisions can be executed based on these conditions (e.g., the predetermined levels of noise).

Although the above-described example illustrates one method for determining a level of noise, or signal artifact(s), based on a comparison of raw vs. filtered data for a time point (or single values representative of a time period), a variety of alternative methods are contemplated. In an alternative exemplary embodiment for determining noise, signal artifacts are evaluated for noise episodes lasting a certain period of time. For example, the processor (in the sensor or receiver) can be configured to look for a certain number of signal residuals above a predetermined threshold (representing noise time points or noisy time periods) for a predetermined period of time (e.g., a few minutes to a few hours or more).

In one exemplary embodiment, a processor is configured to determine a signal residual by subtracting the filtered signal from the raw signal for a predetermined time period. It is noted that the filtered signal can be filtered by any known smoothing algorithm such as described herein, for example a 3-point moving average-type filter. It is further noted that the raw signal can include an average value, e.g., wherein the value is integrated over a predetermined time period (such as 5-minutes). Furthermore, it is noted that the predetermined time period can be a time point or representative data for a time period (e.g., 5 minutes). In some embodiments, wherein a noise episode for a predetermined time period is being evaluated, a differential can be obtained by comparing a signal residual with a previous signal residual (e.g., a residual at time (t)=0 as compared to a residual at (t)−5 minutes.) Similar to the thresholds described above with regard to the signal residual, one or more thresholds can be set for the differentials, whereby one or more differentials above one of the predetermined differential thresholds defines a particular noise level. It has been shown in certain circumstances that a differential measurement as compared to a residual measurement as described herein, amplifies noise and therefore may be more sensitive to noise episodes, without increasing false positives due to fast, but physiological, rates of change. Accordingly, a noise episode, or noise episode level, can be defined by one or more points (e.g., residuals or differentials) above a predetermined threshold, and in some embodiments, for a predetermined period of time. Similarly, a noise level determination can be reduced or altered when a different (e.g., reduced) number of points above the predetermined threshold are calculated in a predetermined period of time.

In some embodiments, the amplitude of total signal, which can also be described as power of the total signal, analyte signal (with or without baseline (e.g., non-constant noise)), and/or non-constant noise, is periodically or continuously obtained using methods such as are described in more detail elsewhere herein (e.g., RMS method), wherein the amplitude is a measure of the strength of the signal component. In some embodiments, signal artifact events are detected by analysis of amplitudes of various signal components, such as the amplitude of the non-constant noise component as compared to the amplitude of the analyte signal (with or without baseline).

In some embodiments, a start of a signal artifact event is determined when the amplitude (power) of a signal artifact meets a first predetermined condition. In one embodiment, the first predetermined condition includes a residual amplitude of at least about 2, 3, 4, 5, 6, 7, 8, 9, 10, 12, 14, 16, 18, 20 or 25% of the total signal or analyte signal amplitude (with or without baseline). In another embodiment, the first predetermined condition includes a differential amplitude (amplitude of a differential) of at least about 2, 3, 4, 5, 6, 7, 8, 9, 10, 12, 14, 16, 18, 20 or 25% of the total signal or analyte signal amplitude (with or without baseline). In some embodiments, the first predetermined condition includes a plurality of points (e.g., non-constant noise signal, residual, or differential) within a predetermined period (e.g., 5, 10, 30, or 60 minutes) above a predetermined threshold (e.g., an amplitude or a percentage amplitude), wherein the plurality of points includes 2, 3, 4, 5, 6, 7, 8 or more values.

In some embodiments, an end of a signal artifact event is determined when then the amplitude (power) of a signal artifact meets a second predetermined condition. In one embodiment, the second predetermined condition includes a residual amplitude of no more than about 2, 3, 4, 5, 6, 7, 8, 9, 10, 12, 14, 16, 18, 20 or 25% of the total signal or analyte signal amplitude (with or without baseline). In another embodiment, the second predetermined condition includes a differential amplitude of no more than about 2, 3, 4, 5, 6, 7, 8, 9, 10, 12, 14, 16, 18, 20 or 25% of the total signal or analyte signal amplitude (with or without baseline). In some embodiments, the second predetermined condition includes a plurality of points (e.g., non-constant noise signal, residual, or differential) within a predetermined period (e.g., 5, 10, 30, or 60 minutes) below a predetermined threshold (e.g., an amplitude or a percentage amplitude), wherein the plurality of points includes 2, 3, 4, 5, 6, 7, 8 or more values. Additional description can be found in US Patent Publication Nos. US-2005-0043598-A1, US-2007-0032706-A1, US-2007-0016381-A1, and US-2007-0033254-A1, each of which is incorporated by reference herein in its entirety.

Auto-Calibration

Some preferred embodiments are configured for auto-calibration of the sensor system, wherein "auto-calibration" includes the use of one or more internal references to calibrate the sensor system. In some embodiments, auto-calibration includes systems and methods configured to calibrate the sensor based solely on internal reference values. For example, the system can be configured to obtain internal reference values by exposing the sensor to one, two or more calibration/reference solution, as described elsewhere herein. As another example, the sensor can be configured with a reference sensor disposed adjacent to the continuous analyte sensor, wherein both the continuous analyte and reference sensors obtain internal reference values for a substantially constant reference analyte (e.g., $O_2$), which are then used to calibrate the continuous analyte sensor (see the sections entitled "Optical Detection" and "Calibration Systems and Methods of Calibrating Dual-Electrode Sensors" above). However, in some alternative embodiments of auto-calibration, one or more external reference values can be used to complement and/or confirm calibration of the sensor system.

In some preferred embodiments, the system is configured to intermittently expose the sensor to a biological sample; however configurations of the sensor system that allow continuous exposure of the sensor to the biological sample are contemplated. In some embodiments, the system is configured to intermittently or periodically expose the sensor to a reference, however configurations of the sensor system that allow one or more independent or non-regular reference measurements initiated by the sensor system and/or a user are contemplated. In the exemplary embodiment of a sensor system such as described with reference to FIGS. 8A to 8C, the system is configured to cycle between a measurement phase and calibration phase (with optional other phases interlaced therein (e.g., flush and KVO)).

In general, timing of auto-calibration can be driven by a variety of parameters: preset intervals (e.g., clock driven) and/or triggered by events (such as detection of a biological sample at a sensor). In some embodiments, one or more of the phases are purely clock driven, for example by a system configured to control the timing housed within a flow control device, remote analyzer, and/or other computer system. In some embodiments, one or more of the phases are driven by one or more events, including: exposure of the sensor to a biological sample (e.g., blood) exposure of sensor to a reference (e.g., calibration solution), completion of calibration measurement, completion of analyte measurement, stability of signal measurement, sensor for detecting a biological sample, and the like.

In one exemplary embodiment, calibration and measurement phases are driven by cleaning of sensor; namely, systems and methods are configured to detect when the sensor is in the biological sample and/or in the reference solution (e.g., calibration solution), wherein the system is configured to switch to appropriate phase responsive to detection of that sample/solution.

In another exemplary embodiment, an AC signal is placed on top of a DC signal (e.g., in an amperometric electrochemical analyte sensor), wherein systems and methods are configured to analyze an impedance response to the AC signal and detect a biological sample thereby.

In yet another exemplary embodiment, systems and methods are configured for analyzing the sensor's signal, wherein a change from a known reference solution (e.g., a known analyte concentration) can be detected on the signal, and the switch from the calibration phase to the measurement phase occur responsive thereto; similarly, the system can be configured to switch back to the calibration phase responsive to detection of the known signal value associated with the reference solution.

In yet another exemplary embodiment, systems and methods are configured to switch between phases responsive to one or more sensors configured to detect the biological sample and/or reference solution at a particular location.

In some embodiments, the sensor system is partially or fully controlled by a clock (e.g., predetermined time intervals), which timing can be confirmed by any of the events (e.g., triggers or sensors) described above.

In one exemplary embodiment, systems and methods are provided to enable auto-calibration of an integrated glucose sensor system with minimal user interaction. In this exemplary embodiment, the integrated sensor system is provided with the components described above, including a fluids bag, a flow control device, IV tubing, a flow control device, a remote analyzer, a local analyzer and a sensor/catheter, for example. At system start-up, a health care worker inserts the catheter and sensor into a host and injects a first reference solution (e.g., zero glucose saline solution) into the IV tubing, wherein the system is configured to allow a predetermined time period (e.g., 20 minutes) for the first reference solution to pass through the IV tubing and into the catheter. Subsequently, the health care worker couples the fluids bag to the IV tubing, wherein the fluids bag includes a second reference solution (e.g., 100 mg/dl glucose solution) configured to follow the first reference solution in the IV line. After injecting the first reference solution and coupling the second reference solution, the health care worker initiates the integrated sensor system (e.g., through the remote analyzer touch screen) after which the integrated sensor system automatically calibrates and functions for 24 hours without necessary user interface (for system calibration and/or initiation). In some embodiments, the sensor system is re-calibrated every 24 hours by injection of a new first reference solution (e.g., zero glucose saline solution).

In the above-described exemplary embodiment, the system is configured to calibrate the sensor with the first and second reference solution and using the methods described in the section entitled, "Systems and Methods for Processing Sensor Data." Additionally, the system is configured to automatically detect the difference in signal associated with the first and second reference solutions, for example, through steady state detection of a difference in signal level.

Methods of Integrated System Set-Up and Initial Use In Vivo

Referring to FIG. 6, in one exemplary embodiment, the present system is configured and arranged for continuous analyte detection in the circulatory system of a host, such as a human, and for fluid infusion. As a non-limiting example, in some embodiments, the continuous analyte sensor is a glucose sensor at least partially disposed in a fluid coupler. In this embodiment, system 600 set-up and installation includes implanting a catheter into one of the host's peripheral veins, fluidly coupling the sensor (e.g., including fluid coupler) to the implanted catheter, fluidly coupling the IV tubing and infusion solution 602a to the fluid coupler operatively connected to the sensor, to a controller and/or display (604 and/or 610), installation of the tubing into the flow control device 604, and initializing the system (e.g., turning on the flow control device). In some circumstances, an operator (e.g., a nurse, doctor or other medical caretaker) prepares a calibration solution by injecting an amount of glucose into an IV bag of infusion solution, such as but not limited to a saline hydration solution, and mixing the contents of the bag. In other circumstances, a commercially prepared calibration solution is used. In some circumstances, a medicament, nutrient or other substance may be added to the infusion solution. The bag of prepared infusion solution 602a is suspended on an IV stand 612, such as a stand that also supports the flow control device 604.

Referring to FIG. 1F, the operator implants a catheter 12 in one of the host's peripheral veins, such as a vein located in the host's forearm, using standard hospital protocol. Next, the operator grasps the fluid coupler 20, inserts analyte sensor 14 into the catheter's lumen and fluidly couples the first end 20a of the fluid coupler to the catheter's hub 18. Note that the sensor is protected by the slotted sheath 26 during insertion. Advantageously, in some embodiments, the fluid coupler and the slotted sheath are configured and arranged such that the slotted sheath prevents blood from coming out of the fluid coupler's second end, until the slotted sheath is removed (e.g., just prior to connection of the second end 20b to the IV tubing). In alternative embodiments, such as that shown in FIGS. 1F-1J, the analyte sensor is located within the fluid coupler's lumen and the second end includes a cap configured and arranged to prevent blood coming out of the second end prior to connection of the IV tubing. In some embodiments, the operator (e.g., user) sets up the flow control device, then implants the catheter and sensor and then connects the tubing to the fluid coupler. In other embodiments, the catheter and sensor are implanted prior to set-up of the flow control device with subsequent connection of the IV tubing to the fluid coupler. Either sequence of events is acceptable, as well as a matter of personal preference and/or hospital protocol.

In preferred embodiments, the IV tubing 606 is configured and arranged for installation into a flow control device 604. In some embodiments, the flow control device and tubing are configured and arranged such as is shown in FIGS. 10A-10D. However, other flow control device and/or tubing configurations are used, in some embodiments. In some embodiment, the flow control device is configured to be moved (e.g., by hand or in response to pressing a button) to the gravity flow valve position (e.g., see FIG. 10C), if it is not already in that position, such that the groove 803 is not blocked by the roller 802. In preferred embodiments, the valve is configured to automatically move to the gravity flow valve position at shut-off and/or termination of a sensor session. In other embodiments, the system is configured such that the valve moves to the gravity flow position when the system is turned on.

In preferred embodiment, the operator fluidly couples the tubing assembly 606a to the fluid reservoir and/or the fluid coupler. In some embodiments, additional lengths of IV tubing 606 are used to make these fluid connections, as is known in the art. To install the tubing assembly 606a, the operator grasp by the connector ends 606c, 606d and stretches the tubing therebetween. The operator orients the stretched tubing assembly such that its central portion 606b aligns with the valve's channel 803 and the tubing's male interconnector (e.g., connector 606d) aligns with the valve's female interconnector 809. The operator then inserts the tubing assembly into the valve channel and releases the connectors, such that the tubing assembly's central portion relaxes to a less stretched (but still stretched and linear) configuration. The operator connects the tubing assembly (e.g., via an optional length of IV tubing) to the IV solution. Then, the operator removes the protective sheath from the sensor by pulling it out of the fluid coupler by its hub 28 and connects the tubing assembly to the fluid coupler's second end (e.g., via an optional length of IV tubing).

In preferred embodiments, the system is configured such that the operator initiates system start-up after installing the sensor, the tubing, and the like, such as described above. In some embodiments, system initiation and/or start-up include, but are not limited to, turning the system on, selecting a flow profile, entering system configuration information (e.g., type of sensor, type of catheter, type of infusion solution), entering user information (e.g., patient ID, patient type, patient target analyte levels, etc.). In some embodiments, the system is configured to be initiated when the user presses a button, flips a switch and/or selects (e.g., a start-up protocol) from a menu on the user interface. In some embodiments, the system is configured to automatically receive and/or recognize at least some of the start-up information, such as via a identification information, a code and/or key in the interconnection of the tubing assembly and the flow control device, via an RFID chip in the patient arm band, via optically scanning a bar code on the patient's chart/arm band and/or on the fluid coupler and/or catheter, and the like. In some embodiments, the flow control device system electronics are configured for operator selection of a flow profile from a menu of flow profiles (e.g., 2, 3, 4, 5, 6, 7, 8, 9, 10 or more flow profiles). In preferred embodiments, the system is configured for selection of a flow profile (by the operator) at least during system start-up/initiation. However, in some further embodiments, the system electronics are configured for selection of another profile and/or modification (e.g., re-programming) of the flow profile during system use. For example, if during use of the system, infusion solution is changed from a first type to a second type (e.g., from saline to a glucose solution), the flow profile can be modified to accommodate that infusion solution change.

In some embodiments, the system is configured to begin intermittently infusing the calibration solution and drawing back samples of the host's blood (e.g., according to the flow profile), energizing the sensor and generating measurements of the calibration solution and blood, and the like, upon system initiation/start-up by the operator. For example, depending upon the flow profile specifications, the flow control device alternately infuses (e.g., at one or more rates) the calibration solution for about 0.25, 0.5, 0.75, 1.0, 1.25, 1.5, 1.75, 2.0 or more minutes, then draws back a blood sample, returns the sample to the host (e.g., reinfuse the sample), and then returns to infusing the calibration solution. Calibration measurements are taken during infusion phases of the flow profile. Blood analyte measurements are taken during drawback phases of the flow profile (e.g., when the sensor is bathed in a blood sample). In some embodiments, the sensor is a dual-electrode glucose sensor, and the system is configured to collect signal(s) from both the plus-enzyme (e.g., plus GOX) and no-enzyme working electrodes.

In some embodiments, the system is configured to follow a "break-in" procedure (also referred to as "run-in"). For example, in some embodiments, the system is configured to cycle between infusion and sample draw-back for about 0.1, 0.2, 0.3, 0.4, 0.5, 0.75, 1.0, 1.25, 1.5, 1.75 or 2-hours. In one embodiments, at about 1-hour, the processor module is configured to and/or includes programming that evaluates sensor stability (e.g., sensor break-in), such as by evaluating the rates of change of the no-enzyme waveform, the amplitude of the no-enzyme signal, and/or the like. In some embodiments, the system is configured to prompt the operator for input of a reference blood glucose value. For example, in one embodiment, the system is configured to wait about 1-hour to about 1.25-hours before prompting the operator for a reference analyte value. A reference analyte value can be obtained using any method known in the art. For example, in the case of a continuous glucose sensor, the operator can use a hand-held glucose meter to measure the host's blood glucose, and enter the measured value into the system via the user interface. In some embodiments, the processor module uses one or more entered reference values to calibrate the sensor using substantially time-corresponding sensor measurements. In some embodiments, the system is configured to utilize an entered reference value as a $b_{offset}$.

In some embodiments, the system is configured to display the host's blood glucose concentration in response to the processor module determining that break-in is complete and/or after sensor calibration. For example, if the processor module determines that the sensor signal has substantially stabilized, the system displays analyte values to the operator. If, on the other hand, the processor module determines that the sensor signal is not yet substantially stabilized, then the system does not display an analyte value to the operator. In some circumstances, the system is configured to prompt the operator to input additional reference analyte values. For example, in one embodiment, the system is configured to wait a period of time (e.g., 5, 10, 15, 20, 30, 40, 50 or 60 minutes) and then to request a reference analyte value. In a further embodiment, if the sensor signal has still not stabilized, then the system is configured to wait another period of time (e.g., 5, 10, 15, 20, 30, 40, 50 or 60 minutes) and then to request a reference analyte value. In another further embodiment, if the sensor signal has not substantially stabilized after a programmed period of time (e.g., 1.25, 1.5, 1.75, 2, 2.5, or 3-hours), then the system is configured to declare a sensor failure and to prompt the user to install a new sensor.

In preferred embodiments, the flow control device is configured to infuse the calibrant and draw-back samples according to the flow profile selected by the operator. In preferred embodiments, the sensor is configured and arranged to generate sensor data, and the processor module is configured to and/or includes programming that processes the sensor data (e.g., as described elsewhere herein), such that the analyte concentration of the host's blood is measured in real-time and/or displayed on a user interface. In preferred embodiments, the processor module is configured to and/or includes programming that intermittently calibrates (e.g., re-calibrates) the sensor.

EXAMPLES

Example 1

Glucose Sensor System Trial in Dogs

Referring now to FIG. 4, glucose sensor systems of the embodiment shown in FIG. 1 were tested in dogs. The glucose sensors were built according to the preferred embodiments described herein. Namely, a first sensor (Test 1) was built by providing a platinum wire, vapor-depositing the platinum with Parylene to form an insulating coating, helically winding a silver wire around the insulated platinum wire (to form a "twisted pair"), masking sections of the electroactive surface of the silver wire, vapor-depositing Parylene on the twisted pair, chloridizing the silver electrode to form a silver chloride reference electrode, and removing a radial window on the insulated platinum wire to expose a circumferential electroactive working electrode surface area thereon, this assembly also referred to as a "parylene-coated twisted pair assembly."

An electrode domain was formed over the electroactive surface areas of the working and reference electrodes by dip coating the assembly in an electrode solution and drying. An enzyme domain was formed over the electrode domain by subsequently dip coating the assembly in an enzyme solution and drying. A resistance domain was formed over the enzyme domain by spraying the resistance domain solution on the sensor construct.

After the sensor was constructed, it was placed in the protective sheath and then threaded through and attached to the fluid coupler.

A second sensor (Test 2) was constructed in the same manner as the first, except that the silver wire was disposed within (e.g., coiled within) the fluid coupler. Accordingly, only the platinum working electrode (a single wire) was inserted into the catheter during the experiment.

Prior to use, the sensors were sterilized using electron beam.

The forelimb of an anesthetized dog (2 years old, ~40 pounds) was cut down to the femoral artery and vein. An arterio-venous shunt was placed from the femoral artery to the femoral vein using 14 gauge catheters and ⅛-inch IV tubing. A pressurized arterial fluid line was connected to the sensor systems at all times. The test sensor systems (test 1 and test 2) included a 20 gauge×1.25-inch catheter and took measurements every 30 seconds. The catheter was aseptically inserted into the shunt, followed by insertion of the sensor into the catheter. A transcutaneous glucose sensor (control) of the type disclosed in U.S. Patent Publication No. US-2006-0155180-A1 was built and placed in the dog's abdomen according to recommended procedures. The dog was challenged with continuous incremental IV infusion of a 10% dextrose solution ("glucose challenge") until the blood glucose concentration reached about 400 mg/dL.

FIG. 4 shows the experimental results. The thick line represents data collected from the Test 1 sensor. The thin line represents data collected from the Test 2 sensor. Diamonds represent data collected from a hand-held blood glucose meter (SMBG) sampled from the dog's abdomen. Raw glucose test data (counts) are shown on the left-hand Y-axle, glucose concentrations for the "SMBG" controls are shown on the right-hand y-axle, and time is shown on the X-axle.

Each time interval on the X-axle represents 29-minutes (e.g., 10:04 to 10:33 equals 29 minutes). Immediately upon insertion into a catheter, each test sensor began collecting data with substantially no sensor equilibration time (e.g., break-in time). Each test sensor responded to the glucose challenge substantially similarly to the control sensor. For example, each device shows the glucose signal increasing from about 3200 counts at 10:33 to about 6000-6700 counts at 11:31. Then, each device showed a rapid decrease in glucose signal, to about 4700 counts at 12:00. Additionally, the response of the test sensors and the control sensor were substantially similar (e.g., the majority of the test data was substantially equivalent to the SMBG data at each time point). From these experimental show that an indwelling glucose sensor system (as described herein) in contact with the circulatory system can provide substantially continuous glucose monitoring in a clinical setting.

Example 2

Glucose Sensor System Trial in Pigs

Referring now to FIG. 5, four glucose sensor systems of the embodiment shown in FIG. 1 were tested in a pig (~104 lb), using the protocol described for Example 1, above. Glucose was continuously infused at increasing rates through a distally placed IV catheter until a readout of 300-400 mg/dl blood glucose was achieved (total 300 ml of a 10% dextrose IV solution). FIG. 5 shows the experimental results. Lines indicated the data from the four sensors (Test 1 through Test 4). Diamonds represent control measurements made with a hand-held glucose meter (SMBG). Raw glucose test data (counts) are shown on the left-hand Y-axle, glucose concentrations for the "SMBG" controls are shown on the right-hand y-axle, and time is shown on the X-axle. Test results show that though the sensors varied in sensitivity, each test sensor responded to glucose challenge substantially similarly to the control sensor (SMBG). These experimental results show that an indwelling glucose sensor system (of the preferred embodiments) in contact with the circulatory system can substantially continuously track glucose in a clinical setting.

Example 3

Glucose Sensor System with Flow Control Device Trial in Pigs

Referring now to FIG. 17, a glucose sensor was built according to the preferred embodiments described herein. Namely, a test sensor was built by providing a platinum wire, vapor-depositing the platinum with Parylene to form an insulating coating, helically winding a silver wire around the insulated platinum wire (to form a "twisted pair"), masking sections of the electroactive surface of the silver wire, vapor-depositing Parylene on the twisted pair, chloridizing the silver electrode to form a silver chloride reference electrode, and removing a radial window on the insulated platinum wire to expose a circumferential electroactive working electrode surface area thereon, this assembly also referred to as a "parylene-coated twisted pair assembly."

An electrode domain was formed over the electroactive surface areas of the working and reference electrodes by dip coating the assembly in an electrode solution and drying. An interference domain was formed over the electrode domain by subsequently dip coating the assembly in an interference domain solution and drying. An enzyme domain was formed over the interference domain by subsequently dip coating the assembly in an enzyme solution and drying. A resistance domain was formed over the enzyme domain by spraying the resistance domain solution on the sensor construct.

The test sensor was then located within a 20 gauge catheter and inserted in the femoral vein of a non-diabetic pig. The catheter was connected to an integrated sensor system 600 of the preferred embodiments. The flow control device 604 (e.g., a roller valve as depicted in FIGS. 8A-8C) was configured to move between steps one and two, as described in the section entitled "Flow Control Device Function," above. A 107-mg/dL glucose solution was used to calibrate the sensors (e.g., flows from the reservoir 602, through the tubing 606, to the catheter 12). To mimic a diabetic's hyperglycemic state, a gradual infusion of 26% dextrose was given, until the pig's blood glucose was about 600 mg/dl. Then to mimic a hypoglycemic state, 10 U Humulin N was given, until the pig's blood glucose was about 50 mg/dl. Then, the pig's blood glucose was raised to about 100 mg/dl by a second 26% dextrose infusion.

FIG. 17 is a graphical representation showing uncalibrated glucose sensor data and corresponding blood glucose values over time in a pig. Raw counts are represented on the left Y-axis. Glucose concentration is shown on the right Y-axis. Time is shown on the X-axis. Test measurements (e.g., measurements of blood glucose concentration obtained with the test sensor, raw counts) are shown as small, black dots. Control measurements (e.g., jugular vein blood samples analyzed on a Yellow Springs Instrument (YSI) glucose analyzer) are shown as diamonds.

During the experiment, the system was configured to alternate between calibration measurements (with the 107 mg/dl glucose solution) and blood glucose measurements, as described in the sections entitled "Step one: Contacting Sensor with Calibration Solution and Calibration" and "Step Two: Sample Collection and Measurement," respectively. Accordingly, as the experiment proceeded the test signal oscillated between calibration solution (107 mg/dl) and blood glucose measurements. The sensor (test) blood glucose measurement correlated tightly with the control blood glucose measurements. For example, as the pig's blood glucose concentration increased (due to infusion of glucose), so did the test measurements, reaching about 550 mg/dl at about 12:20. Similarly, as the pig's blood glucose concentration decreased (due to infusion of insulin), so did the test measurements, decreasing to about 50 mg/dl at about 14:45.

From these data, it was concluded that a glucose sensor system of the preferred embodiments (including a valve as described with reference to FIGS. 8A to 8C) accurately and sensitively measures intravenous glucose concentration over a wide dynamic range.

Example 4

Glucose Sensor System with Flow Control Device Trial in Humans

Referring now to FIG. 18, a glucose sensor, constructed as described in Example 3, and an integrated sensor system (as described in Example 3) were tested in a volunteer, diabetic host. The flow control device was configured as shown in FIGS. 8A-8C. The system was configured to alternate between a calibration phase and a blood glucose measurement phase, as described elsewhere herein. At sensor/catheter initialization, a 0 mg/dl glucose saline solution filled syringe was injected into the IV tubing and the fluids bag including 100 mg/dl glucose heparinized saline solution was subsequently coupled to the tubing. The system was then turned on (e.g., sensor initialized). The 0 mg/dl glucose saline solution passed over the sensor, after which the 100 mg/dl glucose heparinized saline solution subsequently passed over the sensor allowing for initial calibration information to be collected. The system, including a flow control device as described with reference to FIGS. 8A to 8C, then oscillated between exposure of the sensor to a blood sample and exposure of the sensor to the 100 mg/dl glucose heparinized saline solution. The sensor auto-calibrated by a combination of calibration information obtained from measurement of the 0 mg/dl-glucose and 100 mg/dl-glucose saline solutions and the step-change-response of the sensor to the blood sample, according to the methods described in the section entitled "Systems and methods for Processing Sensor Data." No external measurements (e.g., blood glucose measurements by YSI or finger stick) were used to calibrate the system in this example. During the experiment, the flow control device cycled between step one (measuring the 100 mg/dl-glucose solution) and step two (blood sample take up and measuring the blood glucose concentration), such that one cycle was completed every 5-minutes. The experiment was conducted for a period of about 2.5 days. The host followed her usual schedule of meals and insulin injections.

FIG. 18 is a graphical representation showing calibrated venous blood glucose sensor measurements (test, black dots) and corresponding control blood glucose measurements (YSI, large circles) over time in the volunteer diabetic host. Glucose concentration is shown on the Y-axis and time on the X-axis. Test measurements tracked closely with control measurements, ranging from about 350 mg/dl, at about 10:00 and about 15:30, to about 50 mg/dl, at about 11:45. From these data, it has been concluded that 1) the sensor calibration methods of the preferred embodiments accurately calibrate the sensor and 2) the glucose sensor system of the preferred embodiments accurately measures intravenous glucose concentration over a wide dynamic range, for two or more days, in humans.

Example 5

Detection of Crosstalk In Vitro

In general, crosstalk in dual-electrode sensors can be examined by recording the signal detected at each working electrode while placing them in a series of analyte solutions. This example describes one exemplary in vitro test for crosstalk on a dual-electrode analyte sensor. A variety of dual-electrode analyte sensors can be tested for crosstalk, using this method.

First, the sensor to be tested is placed in a phosphate buffered saline (PBS) for several minutes, such as until a stable signal is detected from both working electrodes. Next, the sensor is challenged with glucose solutions and optionally with one or more known noise-causing substances. For example, sensor can be placed sequentially in a series of glucose solutions (e.g., 40-mg/dl, 200-mg/dl and 400-mg/dl glucose in PBS) and the signals from the two working electrodes graphed.

If there is no crosstalk between the working electrodes, then, as the sensor is placed in solutions of increasingly higher glucose concentration, the graphed signal of the Plus GOx electrode should show corresponding signal increases, while the No GOx electrode signal should exhibit little or no change in signal. However, when the sensor is placed in a solution of a known noise-causing species (e.g., acetaminophen, ibuprofen, vitamin C, urea, and the like), both working electrodes (Plus GOx and No GOx) should exhibit an increase in signal. In some circumstances, this increase in signal is a dramatic spike in signal.

If there is crosstalk, then the signals from both electrodes should increase as the sensor is moved to solutions of increased glucose concentration. Similarly, when the sensor is placed in a solution of a known noise-causing species, both working electrodes should exhibit an increase in signal.

Example 6

Effect of Electroactive Surface Size in Dual-Electrodes In Vivo

The effect of size of the electroactive surfaces (of the working electrodes) on noise measurement was examined in non-diabetic human hosts. Sensors having electroactive surfaces of different sizes, and lacking GOx in the enzyme layer were constructed as follows. Clean, insulated Pt/Ir wires were separated into two groups. For Group 1, 0.029" of the insulation was removed from each wire (e.g., about its entire circumference), to expose electroactive surfaces. For Group 2, the same procedure was performed, except that two sequential 0.029" portions of the insulation were removed; effectively doubling the size of the Group 2 electroactive surfaces relative to those of Group 1. After exposure of the electroactive surfaces, the two groups of wires were treated identically. On each wire, a portion of the sensor's membrane was fabricated by the sequential application (and curing thereof) of electrode domain, enzyme domain and resistance domain materials. The enzyme domain material contained no active GOx, so that the sensors would be able to detect only noise (no analyte). Next, pairs of wires (e.g., two Group 1 wires or two Group 2 wires) were aligned such that the electroactive surfaces were parallel to each other, and then twisted together. An Ag/AgCl ribbon was wrapped around a portion of the twisted wires (to form the reference electrode), and then additional resistance domain material was applied to the assembly. Each host consumed 1,000-mg of acetaminophen near the end of the trial, so that the affect of a known interferent could be examined.

FIG. 19A is a graph illustrating the in vivo experimental results from implantation of a Group 1 sensor (one 0.029" electroactive surface area per electrode). The Y-axis represents raw counts and the X-axis represents time. The data collected from each electroactive surface is shown as a line (E1, No GOx and E2, No GOx). Please note that the data represents only the noise component of the signal. No analyte component was detected, due to the lack of GOx in the portions of the membrane adjacent to the electroactive surfaces. Referring now to FIG. 19A, the noise signal detected by each of the working electrodes (E1, E2) fluctuated widely throughout the implantation time. The amplitude of the noise component detected by E2 was substantially greater than the noise component detected by E1. For example, referring to the data circled by oval A, the noise signal peaks detected by E2 were substantially greater than those detected by E1. Additionally, the noise fluctuations between the two working electrodes were not always in the same direction. For example, referring to the data circled by oval B, the E2 noise signal component increased while the E1 noise signal component decreased. When the sensor was challenged with acetaminophen (drug consumption indicated by the arrow), both electrodes registered a substantial increase in noise signal, wherein the shapes of the curves were substantially similar. However, E1 detected a substantially lower total amount of noise when compared with that detected by E2; this difference in signal amplitude (in response to a non-biologic interferent) indicates that the signals (e.g., on the two working electrodes) did not have substantially similar sensitivities.

FIG. 19B is a graph illustrating the in vivo experimental results from implantation of a Group 2 sensor (two 0.029" electroactive surface areas per electrode). As described above, the Group 2 electroactive surfaces are about two-times as large as those of the Group 1 sensors. As before, the Y-axis represents raw counts and the X-axis represents time, and the data collected from each electroactive surface is shown as a line (E1, No GOx and E2, No GOx). As before, the data represents only the noise component of the signal. No analyte component was detected, due to the lack of GOx in the portions of the membrane adjacent to the electroactive surfaces. Referring now to FIG. 19B, the noise signal detected by each of the working electrodes (E1, E2). Throughout the course of the experiment (~20-hours), noise signals detected by E1 and E2 tracked very closely throughout the entire experiment. Namely, the noise signals detected by E1 and E2 were of substantially the same amplitude and followed substantially similar fluctuations, varying from about 7,000 counts (at 4:00 PM) to about 4500 counts (from about 6:30 AM to about 9:00 AM). Even when the Group 2 sensor was challenged with acetaminophen (a known non-biological interferent that should cause a false signal on the sensor), the working electrodes recorded substantially equal signal amplitudes (~6,900 counts) and followed substantially similar wave forms having substantially equivalent amplitudes; these data indicate that the two working electrodes had substantially equal sensitivities.

From these data, the inventors concluded that the electroactive surfaces of a dual-electrode glucose sensor must be sufficiently large in order for the two electrodes to detect substantially equal noise signal components. For example, in this experiment, the electroactive surfaces of the Group 1 working electrodes, which did not measure noise equivalently, were 0.029" (e.g., along the electrode's length); while electroactive surfaces of the Group 2 working electrodes, which did measure noise substantially equivalently, were two times as large (e.g., 2×0.029"=0.058" along the electrode's length) as those of the Group 1 working electrodes.

Example 7

Effect of Electroactive Surface Spacing in Dual-Electrodes In Vivo

The effect of the spacing of the electroactive surfaces (of the working electrodes) on noise measurement was examined in non-diabetic human hosts. Sensors having two different configurations were built and tested. Sensors of Configuration 1 (Config. 1) included Plus GOx and No GOx working electrodes with non-aligned (e.g., miss-aligned, skewed) electroactive surfaces. In other words, the electroactive surfaces were spaced such that, in the completed sensor, one electroactive surface would be more proximal to the sensor's tip than then other. Sensors of Configuration 2 (Config. 2) also included Plus GOx and No GOx working electrodes, except that the electroactive surfaces were closely aligned (e.g., parallel). In Config. 2, the membrane was the insulator between the two working electrodes, enabling the very close spacing (i.e., the thickness of the membrane determined the spacing between the two working electrodes, between about 0.001 inches to about 0.003 inches between the two working electrodes.)

Config. 1 sensors were fabricated as follow. For each sensor, two clean, insulated Pt/Ir wires were wound together (and an Ag/AgCl ribbon twisted there around), followed by removal of a portion of the insulating material from each wire to create the electroactive surfaces. The electroactive surfaces were offset (e.g., not next to each other) relative to the sensor's tip. The twisted wire pairs were then dipped in enzyme domain solution (including GOx) just far enough such that only the electroactive surface closest to the tip of the sensor was coated with the enzyme domain material (e.g., E1, Plus GOx). The electroactive surface farthest from the sensor tip was not coated with the enzyme domain material (e.g., E2, No GOx). After curing, resistance domain material was applied to the twisted pairs of wires.

Config. 2 sensors were fabricated as follow. Clean, insulated Pt/Ir wires were divided into two groups. Electrode and enzyme (Plus GOx) domain materials were sequentially applied to the E1, Plus GOx working electrode wires. Electrode and enzyme (No GOx) domain materials were sequentially applied to the E2, No GOx working electrode wires. Resistance domain material was applied to all wires individually (e.g., to form independent/discontinuous first and second resistance domains). After the resistance domain material was cured, one each of the E1, Plus GOx and E2, No GOx were placed together such that the wires' electroactive surfaces were aligned, and then twisted together to form a twisted pair. An Ag/AgCl ribbon was wrapped around each twisted pair (but not covering the electroactive surfaces), followed by application of a continuous resistance domain (e.g., a third resistance domain) over the sensor. The resulting sensors included a coaxial helix configuration similar to that shown in FIG. 18 of U.S. Patent Publication No. US-2008-0083617-A1, incorporated herein by reference in its entirety.

FIG. 20A is a graph illustrating the in vivo experimental results from implantation of a Config. 1 sensor (non-aligned electroactive surfaces). The Y-axis represents raw counts and the X-axis represents time. The E1, Plus GOx electrode detected both glucose and noise signal components while the E2, No GOx electrode detected only the noise signal component. Throughout most of the experiment's duration, the two working electrodes recorded signals having somewhat similar waveforms with the two lines being relatively flat with little fluctuation in amplitude (the volunteer was not diabetic, and thus would generally not have large fluctuations in glucose level). During the acetaminophen challenge, the E1, Plus GOx signal rapidly peaked at about 12,000 counts and then gradually declined, while the E2, No GOx signal peak was much lower in amplitude (~6,000 counts).

FIG. 20B is a graph illustrating the in vivo experimental results from implantation of a Config. 2 sensor (aligned electroactive surfaces). The Y-axis represents raw counts and the X-axis represents time. In general, the E1, Plus GOx electrode detected both glucose and noise signal components while the E2, No GOx electrode detected only the noise signal component. Throughout most of the experiment's duration, the two electrodes recorded signals having substantially similar waveforms; though the E1, Plus GOx electrode signal was generally higher in amplitude than that of the E2, No GOx electrode. When the sensor was challenged with acetaminophen, the signals of both working electrodes rapidly peaked at about 11,000-12,000 counts (e.g., the amplitudes of the two peaks were substantially equivalent/similar) and then gradually declined.

From these data, the inventors concluded that the electroactive surfaces of a dual-electrode glucose sensor must be sufficiently close together in order for the two electrodes to detect substantially equivalent noise signal components. Additionally, the inventors concluded that for a dual-electrode sensor including the combination of a continuous resistance domain disposed over discontinuous resistance domains (e.g., applied independently to the two working electrodes) the detected signal amplitudes more closely correspond to each other. This improves mathematical noise correction by enabling better noise signal subtraction.

Example 8

Use of Dual-Electrode Glucose Sensors in Intravenous Porcine Model

Six dual-electrode glucose sensor IV systems, including a dual-electrode glucose sensor (e.g., including a first working electrode E1 (e.g., configured to generate signals associated with both glucose and non-glucose-related species having oxidation/reduction potentials that overlap with that of glucose) and a second working electrode E2 (e.g., configured to generate signals associated with non-glucose-related species having oxidation/reduction potentials that overlap with that of glucose)) and a fluid control system (including a catheter inserted into a peripheral vein) were tested in a porcine model, as described elsewhere herein. A 100-mg/dl-glucose solution was used to calibrate and wash the dual-electrode sensor, according to procedures described elsewhere herein. To obtain an increase in serum glucose to hyperglycemic ranges, a 22.5% dextrose solution was gradually infused through the animal's left ear vein. The infusion was stopped once the blood glucose levels reached sufficiently high blood glucose values and a return to normal values was followed. Blood samples were collected in 5-minute intervals from the right jugular vein throughout the study. Plasma glucose values were determined on an YSI instrument. The study took about 4-hours.

FIG. 21A is a graph illustrating test results from an exemplary dual-electrode continuous glucose sensor coupled to a flow control system via a catheter inserted in the animal's femoral vein. The Y-axis represents glucose values (mg/dl) and the X-axis represents time. The small triangle represents glucose values provided by the dual-electrode glucose sensor system every 5 minutes, while the small diamond represents substantially time-corresponding control glucose values obtained from the YSI device.

FIG. 21B is a Clark Error Grid quantifying the clinical accuracy of the blood glucose estimates generated by the dual-electrode glucose sensor system as compared to a reference value (e.g., YSI). All values fall within area "A," which indicates that all values provided by the dual-electrode sensor are within 20% of the values provided by the YSI control test device. $R^2=0.9799$.

The dual-electrode glucose sensor tracked the animal's glucose values, from about 50-mg/dl to about 300-mg/dl over a period of about 4-hours. The signals generated by the first and second working electrodes were processed to provide the data shown in FIGS. 21A-21B. The glucose values provided by the dual-electrode sensor tracked very closely with the control measurements provided by the YSI device. Additionally, all glucose values provided by the dual-electrode glucose sensor fell within the "A" portion of the Clark Error Grid. The sensor had an MARD of 7.5% and met the FDA's ISO standard for hand-held glucose monitors (±15-mg/dl or ±20%) by 100%.

From these data, the investigators concluded that continuous IV glucose tracking (via a peripheral vein) using a dual-electrode continuous glucose sensor, including first and second working electrodes configured as described herein, coupled with a catheter and a flow control system can provide consistently accurate glucose values in vivo.

Example 9

In vivo glucose data was generated using a dual-electrode glucose sensor implanted in a host's peripheral vein, as described elsewhere herein. A flow control system, such as that described with reference to FIGS. 7-8C, was installed, including a reference glucose infusion solution (e.g., 100-mg/dl glucose). Upon initiation, the flow control device began drawing back blood samples to the glucose sensor, re-infusing the samples and infusing the reference solution, such as according to the programmed flow profile. Data were received from the plus-enzyme and no-enzyme working electrodes, such as described elsewhere herein. The signal waveforms of the non-enzyme working electrode data (e.g., second signal waveform) were evaluated to determine if the drawback/infusion was successful. For exemplary purposes, one second signal waveform (from the no-enzyme working electrode) generated during a known successful infusion and one second signal waveform generated during a known unsuccessful infusion are presented.

FIG. 22 is a graph of a second signal waveform (e.g., no-enzyme working electrode data) generated during a successful infusion of the reference solution into the host versus the adaptive calibration waveform template. Line 2202 is the adaptive calibration waveform template. Line 2204 represents the second signal waveform generated on the non-enzyme electrode during infusion of the reference solution into the host. The portion of the graph denoted by 2206 represents the data that could be used to calibrate the sensor, if the second signal waveform met at least one criterion. For example, in this experiment, the second signal waveform substantially overlapped with the adaptive waveform template. Additionally, the second signal waveform was substantially monotonic, like the adaptive waveform template. These facts indicated that the infusion was successful. The second signal waveform was integrated into the adaptive waveform template, to generate an updated adaptive waveform template. Additionally, a data value was displayed on the system's user interface.

FIG. 23 is a graph of a second signal waveform generated during an unsuccessful infusion of the reference solution into the host versus the adaptive calibration waveform template. Line 2302 represents the adaptive calibration waveform template. Line 2304 represents the second signal waveform generated on the non-enzyme electrode during the unsuccessful infusion of the reference solution into the host. The portion of the graph denoted by 2306 represents the data that could have been used to calibrate the sensor, if the second signal waveform had met at least one criterion. Lines 2302 and 2304 substantially overlapped and had a negative slope, until about 70 sample points. At about 70 sample points, line 2304 exhibited a substantial peak. A second increase began at about 110 sample points and extended to 120 sample points, when the waveform ended. During this deviation (e.g., 2306) the second signal waveform did not correlate with the adaptive template. Additionally, the second signal waveform was not monotonic. These data indicated that the infusion was not successful and the system was not reliable. The signal waveform was not integrated with the adaptive template. The signal data denoted by 2306 and corresponding generated first signal data were not used to calibrate the sensor.

Example 10

In vivo glucose data was generated using a dual-electrode glucose sensor implanted in a host's peripheral vein, as described elsewhere herein. A flow control system, such as that described with reference to FIGS. 7-8C was installed, including a reference glucose infusion solution (e.g., 100-mg/dl glucose). Upon initiation, the flow control device began drawing back blood samples to the glucose sensor, re-infusing the samples and infusing the reference solution, such as according to the programmed flow profile.

FIG. 24 is a graph of the signal generated from the plus-enzyme working electrode (black diamonds) and from the no-enzyme working electrode (black dots). Completion of sensor break-in is denoted by the dashed vertical line. The sensor was implanted in the host at about 2:00 P.M. Upon drawing-back a sample, the signal waveform increased. Upon re-infusion of the sample and infusion of the reference solution, the signal waveform decreased. Accordingly, with each cycle of sample draw-back and infusion, a signal peak and valley were generated. Upon sensor start-up, the sensor signal (e.g., baseline), on both working electrodes, started high (e.g., ~400-500 counts) and then drifted progressively downward over time (e.g., baseline drift). In this example, wherein the sensor system included a dual electrode sensor, and both electrochemical break-in (illustrated by the exponential decay during the first 30 minutes after sensor start-up) and membrane break-in (illustrated by a difference between the enzyme signal and non-enzyme signal during the first 30 minutes after sensor start-up) can be seen. After about the first 30 minutes, the sensor signal, notably the second signal waveform (e.g., no-enzyme working electrode data), stabilized.

Example 11

In vivo glucose data was generated using a dual-electrode glucose sensor implanted in a host's peripheral vein, as described elsewhere herein. A flow control system, such as that described with reference to FIGS. 7-8C were installed, including a reference glucose infusion solution (e.g., 100 mg/dL glucose). Upon initiation, the flow control device began drawing back blood samples to the glucose sensor, re-infusing the samples and infusing the reference solution, such as according to the programmed flow profile.

FIG. 25 is a graph of calculated sensor sensitivities. The Y-axis represents sensor sensitivity (in pA/mg/dL). The X-axis represents time (e.g., of sensor implantation/use). Each point represents an individual sensitivity calculation determined using a subtracted signal from the dual-electrode sensor, wherein the sensitivity was determined when the sensor was exposed to the 100 mg/dL reference solution, as described in more detail elsewhere herein. Change in calculated sensor sensitivity was evaluated over short time periods (e.g., also referred to as short-term sensitivity evaluation; every 5-minutes) throughout sensor use, and over longer time periods (e.g., also referred to as long-term sensitivity evaluation) the total change in sensor sensitivity between the calculated sensor sensitivity at t=0 and at t=1-hr, and between t=1-hr and t=2-hr). The change in sensitivity was calculated using the formula $(m_2-m_1)/m_1$. For the first hour of sensor use, when the sensor was breaking in and dramatic changes in sensitivity are observed, a change in sensitivity threshold was set at ±100% over the hour. For the second hour of sensor use, when changes in sensitivity begin to level off, the threshold was set at ±20%. For short time sensitivity evaluation, the threshold was set at a ±15% change in sensor sensitivity over 5-minutes. An example of 5 minute time period is shown at 2502. The calculated sensitivity at point 2502a was 2.2 pA/mg/dL and the calculated sensitivity at point 2502b was also 2.2 pA/mg/dL, resulting in a sensitivity change of 0% in 5-minutes. Accordingly, the change in sensitivity between these two time points was well within the ±15% per 5-minutes threshold. An example of sensitivity drift during the first hour of sensor use is denoted by 2504. At 2504a, the sensitivity was 1.5 pA/mg/dL. At 2504b, the sensitivity was about 2.2 pA/mg/dL, giving a 70% change in sensitivity over the first hour of sensor use. Accordingly, the increase in sensor sensitivity, during the first hour of sensor use, was within the ±100% threshold. Another example of sensitivity drift, during the second hour of sensor use, is denoted by 2506. For the second hour of sensor use, the threshold was set at ±20% over the second hour. Again, at 2504b, the sensitivity was about 2.2 pA/mg/dL. At point 2506a, the sensitivity was 2.4 pA/mg/dL, giving a 20% drift in sensitivity, which met the ±20% threshold.

Example 12

Pain Monitoring by Continuous Intra-Vascular Glucose Detection in the Neonatal Host A newborn infant (the host) is transferred to the newborn intensive care unit (NICU) soon after birth. When the host arrives, a nurse inserts a 24-gauge catheter into one of the host's veins. The nurse inserts a continuous glucose sensor (e.g., see FIG. 1F) into the catheter and connects the fluid coupler to the catheter's hub. The sensor is configured such that it extends into the catheter's lumen such that the electroactive surface(s) are located adjacent to the catheter's orifice. Then the nurse sets up the fluid control device (e.g., see FIG. 10A) with an infusion solution, and connects the IV tubing to the fluid coupler. The nurse initiates the system and selects a flow profile optimized for a neonatal host. For example, the flow profile directs the drawback of minimum sample volumes (e.g., about 1, 2, 3, 4 or 5-µl), return of the sample to the host, and sensor washing using minimum volumes (e.g., about 10, 20, 30, 50 or 100-µl of solution). The system begins continuously monitoring the host's blood glucose level and to display the host's blood glucose level. After a period of time, the host's blood glucose begins to rise. The host's blood glucose exceeds a first programmed range (e.g., a euglycemic range) and the processor module provides an alarm to the nurse and/or to display at least one of an instruction to the nurse, the host's glucose level, and an indication of the host's level of comfort (e.g., pain, distress), wherein the level of the comfort is associated with the host's glucose concentration. For example, the nurse is alerted that the host is beginning to become distressed and may be feeling pain. The system is configured to instruct the nurse to check the host's vital signs and to provide appropriate care for the host's observed condition. The host's blood glucose continues to increase and exceeds a second programmed range (e.g., a hyperglycemic range). The system provides an alarm, which alerts the nurse to an increase in the host's distressed condition. Additionally, the system displays at least one of updated instructions to the nurse, the host's blood glucose level, and/or an indication of the host's pain level, wherein the pain level is associated with the host's blood glucose level. Upon checking on the host, the nurse observes that the host appears to be in pain, and follows instructions displayed on the display to administer pain medication. Alternatively, the system can be configured to automatically infuse basal and/or bolus amounts of pain medication based at least in part on the measured glucose concentration. As the pain medication becomes effective, the host's blood glucose begins to return to the first programmed range. The system displays at least one of the host's blood glucose level and/or an indication of the host's comfort (e.g., pain, distress) level, wherein the indication of the host's comfort level is associated with the host's glucose level.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; U.S. Pat. No. 7,310,544; U.S. Pat. No. 7,364,592; U.S. Pat. No. 7,366,556; and U.S. Pat. No. 7,424,318.

Methods and devices that are suitable for use in conjunction with aspects of the preferred embodiments are disclosed in U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032718-A1; U.S. Patent Publication No. US-2007-0059196-A1; U.S. Patent Publication No. US-2007-0066873-A1; U.S. Patent Publication No. US-2007-0197890-A1; U.S. Patent Publication No. US-2007-0173710-A1; U.S. Patent Publication No. US-2007-0163880-A1; U.S. Patent Publication No. US-2007-0203966-A1; U.S. Patent Publication No. US-2007-0213611-A1; U.S. Patent Publication No. US-2007-0232879-A1; U.S. Patent Publication No. US-2007-0235331-A1; U.S. Patent Publication No. US-2008-0021666-A1; U.S. Patent Publication No. US-2008-0033254-A1; U.S. Patent Publication No. US-2008-0045824-A1; U.S. Patent Publication No. US-2008-0071156-A1; U.S. Patent Publication No. US-2008-0086042-A1; U.S. Patent Publication No. US-2008-0086044-A1; U.S. Patent Publication No. US-2008-0086273-A1; U.S. Patent Publication No. US-2008-0083617-A1; U.S. Patent Publication No. US-2008-0119703-A1; U.S. Patent Publication No. US-2008-0119704-A1; U.S. Patent Publication No. US-2008-0119706-A1 U.S. Patent Publication No. US-2008-0194936-A1; U.S. Patent Publication No. US-2008-0194937-A1; U.S. Patent Publication No. US-2008-0195967-A1; U.S. Patent Publication No. US-2008-0183061-A1; U.S. Patent Publication No. US-2008-0183399-A1; U.S. Patent Publication No. US-2008-0189051-A1; U.S. Patent Publication No. US-2008-0214918-A1; U.S. Patent Publication No. US-2008-0194938-A1; U.S. Patent Publication No. US-2008-0214915-A1; U.S. Patent Publication No. US-2008-0194935-A1; U.S. Patent Publication No. US-2008-0188731-A1; U.S. Patent Publication No. US-2008-0242961-A1; U.S. Patent Publication No. US-2008-0208025-A1; U.S. Patent Publication No. US-2008-0197024-A1; U.S. Patent Publication No. US-2008-0200788-A1; U.S. Patent Publication No. US-2008-0200789-A1; U.S. Patent Publication No. US-2008-0200791-A1; U.S. Patent Publication No. US-2008-0228054-A1; U.S. Patent Publication No. US-2008-0228051-A1; and U.S. Patent Publication No. US-2008-0262469-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/691,426 filed Mar. 26, 2007 and entitled "ANALYTE SENSOR"; U.S. patent application Ser. No. 12/103,594 filed Apr. 15, 2008 and entitled "BIOINTERFACE WITH MACRO- AND MICRO-ARCHITECTURE"; U.S. patent application Ser. No. 12/113,724 filed May 1, 2008 and entitled "LOW OXYGEN IN VIVO ANALYTE SENSOR"; U.S. patent application Ser. No. 12/055,098 filed Mar. 25, 2008 and entitled "ANALYTE SENSOR"; U.S. patent application Ser. No. 12/054,953 filed Mar. 25, 2008 and entitled "ANALYTE SENSOR"; U.S. patent application Ser. No. 12/055,114 filed Mar. 25, 2008 and entitled "ANALYTE SENSOR"; U.S. patent application Ser. No. 12/133,789 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,761 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/133,738 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/139,305 filed Jun. 13, 2008 and entitled "ELECTRODE SYSTEMS FOR ELECTROCHEMICAL SENSORS"; U.S. patent application Ser. No. 12/175,391 filed Jul. 17, 2008 and entitled "TRANSCUTANEOUS ANALYTE SENSOR"; U.S. patent application Ser. No. 12/182,008 filed Jul. 29, 2008 and entitled "INTEGRATED RECEIVER FOR CONTINUOUS ANALYTE SENSOR"; U.S. patent application Ser. No. 12/182,073 filed Jul. 29, 2008 and entitled "INTEGRATED RECEIVER FOR CONTINUOUS ANALYTE SENSOR"; U.S. patent application Ser. No. 12/182,083 filed Jul. 29, 2008 and entitled "INTEGRATED RECEIVER FOR CONTINUOUS ANALYTE SENSOR"; U.S. patent application Ser. No. 12/195,191 filed Aug. 20, 2008 and entitled "SYSTEM AND METHODS FOR PROCESSING ANALYTE SENSOR DATA"; U.S. patent application Ser. No. 12/195,773 filed Aug. 21, 2008 and entitled "SYSTEM AND METHODS FOR PROCESSING ANALYTE SENSOR DATA"; U.S. patent application Ser. No. 12/247,137 filed Oct. 7, 2008 and entitled "IMPLANTABLE ANALYTE SENSOR"; U.S. patent application Ser. No. 12/250,918 filed Oct. 14, 2008 and entitled "ANALYTE SENSOR"; U.S. patent application Ser. No. 12/253,125 filed Oct. 16, 2008 and entitled "SIGNAL PROCESSING FOR CONTINUOUS ANALYTE SENSOR"; U.S. patent application Ser. No. 12/253,120 filed Oct. 16, 2008 and entitled "SIGNAL PROCESSING FOR CONTINUOUS ANALYTE SENSOR"; U.S. patent application Ser. No. 12/253,064 filed Oct. 16, 2008 and entitled "SIGNAL PROCESSING FOR CONTINUOUS ANALYTE SENSOR"; U.S. patent application Ser. No. 12/252,996 filed Oct. 16, 2008 and entitled "SIGNAL PROCESSING FOR CONTINUOUS ANALYTE SENSOR"; U.S. patent application Ser. No. 12/252,967 filed Oct. 16, 2008 and entitled "SIGNAL PROCESSING FOR CONTINUOUS ANALYTE SENSOR"; U.S. patent application Ser. No. 12/252,952 filed Oct. 16, 2008 and entitled "SIGNAL PROCESSING FOR CONTINUOUS ANALYTE SENSOR"; U.S. patent application Ser. No. 12/260,017 filed Oct. 28, 2008 and entitled "SENSOR HEAD FOR USE WITH IMPLANTABLE DEVICES"; U.S. patent application Ser. No. 12/258,320 filed Oct. 24, 2008 and entitled "SYSTEMS AND METHODS FOR PROCESSING SENSOR DATA"; U.S. patent application Ser. No. 12/263,993 filed Nov. 3, 2008 and entitled "SIGNAL PROCESSING FOR CONTINUOUS ANALYTE SENSOR"; U.S. patent application Ser. No. 12/264,835 filed Nov. 4, 2008 and entitled "IMPLANTABLE ANALYTE SENSOR"; U.S. patent application Ser. No. 12/258,235 filed Oct. 24, 2008 and entitled "SYSTEMS AND METHODS FOR PROCESSING SENSOR DATA"; U.S. patent application Ser. No. 12/258,345 filed Oct. 24, 2008 and entitled "SYSTEMS AND METHODS FOR PROCESSING SENSOR DATA"; U.S. patent application Ser. No. 12/258,325 filed Oct. 24, 2008 and entitled "SYSTEMS AND METHODS FOR PROCESSING SENSOR DATA"; U.S. patent application Ser. No. 12/258,318 filed Oct. 24, 2008 and entitled "SYSTEMS AND METHODS FOR PROCESSING SENSOR DATA"; U.S. patent application Ser. No. 12/258,335 filed Oct. 24, 2008 and entitled "SYSTEMS AND METHODS FOR PROCESSING SENSOR DATA"; U.S. patent application Ser. No. 12/264,160 filed Nov. 3, 2008 and entitled "DUAL ELECTRODE SYSTEM FOR A CONTINUOUS ANALYTE SENSOR."

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An integrated sensor system for measuring an analyte in a sample of a host and for fluid infusion into the host, comprising:
   an analyte sensor configured and arranged for measuring an analyte concentration in a biological sample of a circulatory system of a host;
   a tubing assembly comprising tubing that is configured to be in fluid communication with a vascular access device configured to be in fluid communication with the circulatory system of the host;
   a flow control device configured to regulate exposure of the analyte sensor to the biological sample and to a reference solution according to a flow profile, wherein the flow control device comprises a valve, and wherein the valve is configured and arranged with a gravity flow position and a controlled flow position; and a free-flow mitigation device comprising a spring clip occluder located on the tubing assembly wherein the system is configured and arranged such that the free-flow mitigation device precludes flow responsive to at least one of power removal, loss of power to the system, and loss of power to the flow control device.

2. The system of claim 1, wherein the system is configured such that the analyte sensor is flushed by the reference solution when the valve is in the gravity flow position.

3. The system of claim 2, wherein the gravity flow position comprises a first flow rate of the solution, wherein the controlled flow position comprises a second flow rate of the solution, and wherein a ratio of the first flow rate to the second flow rate is at least about 10:1.

4. The system of claim 3, wherein the gravity flow position has a flow rate of at least about 600 ml/hr.

5. The system of claim 3, wherein the controlled flow position has a flow rate of from about 0.5 ml/hr to about 4 ml/hour.

6. The system of claim 1, wherein the valve and the tubing assembly are configured and arranged such that the tubing is in a stretched state after installation of the tubing in the valve.

7. The system of claim 1, wherein the valve is configured and arranged to preclude tubing installation when the valve is in the controlled flow position.

8. The system of claim 1, wherein the valve and tubing assembly are configured and arranged to releasably interlock such that a portion of the valve mechanically interlocks with a portion of the tubing assembly.

9. The system of claim 1, wherein the vascular access device and the tubing assembly are configured and arranged to substantially preclude rotational movement between the vascular access device and the tubing assembly when engaged.

10. The system of claim 1, wherein the system is configured for electronic control of the free-flow mitigation device.

11. The system of claim 1, further comprising an electronic solenoid associated with the flow control device, wherein the electronic solenoid provides electronic control of the free-flow mitigation device.

12. The system of claim 1, wherein the system is configured and arranged such that the free-flow mitigation device is controlled at least in part by the flow profile.

13. The system of claim 1, further comprising an intravenous bag containing a reference solution, wherein the reference solution has a known analyte concentration.

14. The system of claim 1, wherein the analyte sensor is configured to measure at least one analyte selected from the group consisting of albumin, alkaline phosphatase, alanine transaminase, aspartate aminotransferase, bilirubin, blood urea nitrogen, calcium, carbon dioxide, chloride, creatinine, glucose, gamma-glutamyl transpeptidase, hematocrit, lactate, lactate dehydrogenase, magnesium, oxygen, pH, phosphorus, potassium, sodium, total protein, uric acid, a metabolic marker and a drug.

* * * * *